US012103919B2

(12) United States Patent
Bonazzi et al.

(10) Patent No.: US 12,103,919 B2
(45) Date of Patent: Oct. 1, 2024

(54) 3-(5-OXY)-1-OXOISOINDOLIN-2-YL) PIPERIDINE-2,6-DIONE DERIVATIVES AND USES THEREOF

(71) Applicant: NOVARTIS AG, Basel (CH)

(72) Inventors: Simone Bonazzi, Cambridge, MA (US); Artiom Cernijenko, Cambridge, MA (US); Jennifer Stroka Cobb, Stow, MA (US); Janetta Dewhurst, Framingham, MA (US); John Ryan Kerrigan, Wakefield, MA (US); Gary O'Brien, Maynard, MA (US); MooJe Sung, Belmont, MA (US); Noel Marie-France Thomsen, Chelmsford, MA (US); Pamela Ting, Somerville, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/829,933

(22) Filed: Jun. 1, 2022

(65) Prior Publication Data

US 2023/0019617 A1    Jan. 19, 2023

Related U.S. Application Data

(60) Provisional application No. 63/196,422, filed on Jun. 3, 2021.

(51) Int. Cl.
| | | |
|---|---|---|
| *C07D 401/14* | (2006.01) | |
| *A61K 31/4545* | (2006.01) | |
| *A61K 31/55* | (2006.01) | |
| *A61K 45/06* | (2006.01) | |
| *C07D 405/14* | (2006.01) | |

(52) U.S. Cl.
CPC ........ *C07D 401/14* (2013.01); *A61K 31/4545* (2013.01); *A61K 31/55* (2013.01); *A61K 45/06* (2013.01); *C07D 405/14* (2013.01)

(58) Field of Classification Search
CPC ................................ C07D 401/14; A61P 7/00
See application file for complete search history.

(56) References Cited

U.S. PATENT DOCUMENTS

| | | | |
|---|---|---|---|
| 9,133,161 | B2 | 9/2015 | Traverse et al. |
| 11,566,022 | B2 | 1/2023 | Bonazzi et al. |
| 2014/0031552 | A1 | 1/2014 | Traverse et al. |
| 2017/0038387 | A1 | 2/2017 | Gandhi et al. |
| 2018/0099940 | A1 | 4/2018 | Crew et al. |
| 2018/0125821 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0237418 | A1 | 8/2018 | Crew et al. |
| 2018/0256586 | A1 | 9/2018 | Crew et al. |
| 2019/0092768 | A1 | 3/2019 | Gray et al. |
| 2019/0151295 | A1 | 5/2019 | Crew et al. |
| 2019/0192668 | A1 | 6/2019 | Mainolfi et al. |
| 2019/0276459 | A1 | 9/2019 | Crews et al. |
| 2019/0315732 | A1 | 10/2019 | Crew et al. |
| 2022/0323457 | A1* | 10/2022 | Berlin ................. C07D 401/14 |

FOREIGN PATENT DOCUMENTS

| | | |
|---|---|---|
| EP | 3202461 B1 | 12/2018 |
| EP | 2877462 B1 | 9/2019 |
| WO | 2012068512 A1 | 5/2012 |
| WO | 2014018866 A1 | 1/2014 |
| WO | 2017024019 A1 | 2/2017 |
| WO | 2018071606 A1 | 4/2018 |
| WO | 2018102067 A2 | 6/2018 |
| WO | 2018102725 A1 | 6/2018 |
| WO | 2018118598 A1 | 6/2018 |
| WO | 2018119357 A1 | 6/2018 |
| WO | 2018119441 A1 | 6/2018 |
| WO | 2018119448 A1 | 6/2018 |
| WO | 2018140809 A1 | 8/2018 |
| WO | 2019079569 A1 | 4/2019 |
| WO | 2019079701 A1 | 4/2019 |
| WO | 2019099926 A1 | 5/2019 |
| WO | 2019133531 A1 | 7/2019 |
| WO | 2019177902 A1 | 9/2019 |
| WO | 2019195609 A2 | 10/2019 |
| WO | 2020006233 A1 | 1/2020 |
| WO | 2020006262 A1 | 1/2020 |
| WO | 2020006264 A1 | 1/2020 |
| WO | 2020006265 A1 | 1/2020 |
| WO | 2020012334 A1 | 1/2020 |
| WO | 2020117759 A1 | 6/2020 |
| WO | 2021053555 A1 | 3/2021 |
| WO | 2021124172 A1 | 6/2021 |

OTHER PUBLICATIONS

Luo, et al., Syntheses of aromatic substituted 6'-thiothalidomides, Synthesis, Oct. 16, 2008, 3415-3422, 21.
Olson, et al., Pharmacological perturbation of CDK9 using selective CDK9 inhibition or degradation, Nature Chemical Biology, Feb. 2018, 163-169, 14.

* cited by examiner

*Primary Examiner* — Jeffrey S Lundgren
*Assistant Examiner* — Eric Tran
(74) *Attorney, Agent, or Firm* — Adil R. Zhugralin

(57) ABSTRACT

The present disclosure relates to compounds of formula (I) and pharmaceutical compositions and their use in reducing Widely Interspaced Zinc Finger Motifs (WIZ) expression levels, or inducing fetal hemoglobin (HbF) expression, and in the treatment of inherited blood disorders (e.g., hemoglobinopathies, e.g., beta-hemoglobinopathies), such as sickle cell disease and beta-thalassemia.

27 Claims, 1 Drawing Sheet
Specification includes a Sequence Listing.

```
                        SEQUENCE LISTING

<160> NUMBER OF SEQ ID NOS: 14

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Val Ser Gly Trp Arg Leu Phe Lys Lys Ile Ser
1               5                   10

<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ctacatttta catgatagg                                                   19

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
agcccacaat gccacggaaa t                                                21

<210> SEQ ID NO 4
<211> LENGTH: 21
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 4
gcaacatcta caccctcaaa t                                              21

<210> SEQ ID NO 5
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
tgaccgagtg gtacgtcaat g                                              21

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
agcggcagaa catcaacaaa t                                              21

<210> SEQ ID NO 7
<211> LENGTH: 67
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
agcauagcaa guuaaaauaa ggcuaguccg uuaucaacuu gaaaaagugg caccgagucg    60
gugcuuu                                                              67

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
acggaggcta agcgtcgcaa                                                20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
aacatctttc gggccgtagg                                                20
```

```
<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
gacatccgct gcgagttctg                                                   20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
tgcagcgtcc cgggcagagc                                                   20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
caagccgtgc ctcatcaaga                                                   20

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
cgggcacacc tgcggcagtt                                                   20

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
agtgggtgcg gcacttacag                                                   20
```

3-(5-OXY)-1-OXOISOINDOLIN-2-YL) PIPERIDINE-2,6-DIONE DERIVATIVES AND USES THEREOF

CLAIM OF PRIORITY

This application claims the benefit of priority to U.S. Provisional Application No. 63/196,422 filed Jun. 3, 2021, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jun. 3, 2021 is named PAT059130-US-PSP_SL.txt and is 4,096 bytes in size.

FIELD OF THE DISCLOSURE

The present disclosure relates to 3-(5-oxy)-1-oxoisoindolin-2-yl)piperidine-2,6-dione compounds and pharmaceutical compositions and their use in reducing Widely Interspaced Zinc Finger Motifs (WIZ) protein expression levels and/or inducing fetal hemoglobin (HbF) protein expression levels, and in the treatment of inherited blood disorders (hemoglobinopathies, e.g., beta-hemoglobinopathies), such as sickle cell disease and beta-thalassemia.

BACKGROUND OF THE DISCLOSURE

Sickle cell disease (SCD) is a group of severe inherited blood disorders that cause red blood cells to contort into a sickle shape. These cells can cause blockages in blood flow, leading to intense pain, organ damage and premature death. Beta thalassemias are a group of inherited blood disorders that are caused by reduced or absent synthesis of beta globin, causing anemia.

Fetal hemoglobin (HbF) induction is known to ameliorate symptoms in SCD and beta-thalassemia patients, with both genetic (single nucleotide polymorphisms in the globin control locus & BCL11A) and pharmacologic (hydroxyurea) validation in the clinic (Vinjamur, D. S., et al. (2018), *The British Journal of Haematology*, 180(5), 630-643). Hydroxyurea is the current standard of care for SCD and is thought to provide benefit via induction of HbF, but is genotoxic, causes dose-limiting neutropenia and has a response rate of less than 40%. Other mechanisms being targeted clinically and preclinically include inhibition of HDAC1/2 (Shearstone et al., 2016, *PLoS One*, 11(4), e0153767), LSD1 (Rivers et al., 2018, *Experimental Hematology*, 67, 60-64), DNMT1, PDE9a (McArthur et al., 2019, *Haematologica*. doi:10.3324/haematol.2018.213462), HRI kinase (Grevet et al., 2018, *Science*, 361(6399), 285-290) and G9a/GLP (Krivega et al., 2015, *Blood*, 126(5), 665-672; Renneville et al., 2015, *Blood*, 126(16), 1930-1939). Additionally, the immunomodulators pomalidomide and lenalidomide induce HbF ex vivo in human primary erythroid cells (Moutouh-de Parseval, L. A. et al. (2008), *The Journal of Clinical Investigation*, 118(1), 248-258) and in vivo (Meiler, S. E. et al. (2011), Blood, 118(4), 1109-1112). WIZ is ubiquitously expressed and plays a role in targeting the G9a/GLP histone methyltransferases to genomic loci to regulate chromatin structure and transcription (Bien, Chen, et al. (2015), *eLife* 2015; 4:e05606.

SUMMARY OF THE DISCLOSURE

The disclosure relates to 3-(5-oxy)-1-oxoisoindolin-2-yl) piperidine-2,6-dione compounds, which are effective in reducing WIZ protein expression levels and/or inducing fetal hemoglobin (HbF) expression, pharmaceutically acceptable salts thereof, compositions thereof, and their use in therapies for the conditions and purposes detailed above.

The disclosure provides, in a first aspect, a compound of formula (I') or a pharmaceutically acceptable salt, hydrate, solvate, prodrug, stereoisomer, or tautomer thereof, wherein:

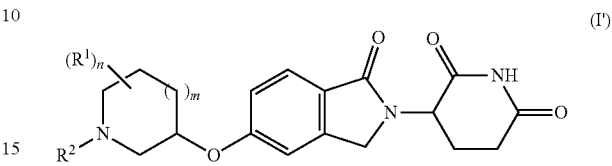

(I')

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 R' on non-adjacent carbon atoms together with the non-adjacent carbon atoms to which they are attached form a bridging ring;

$R^2$ is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, $C_1$-$C_{10}$alkyl, —$SO_2R^6$, —C(=O)—$R^{2a}$, —C(=O)—O—$R^{2a}$, and —C(=O)N$R^{2b}R^{2c}$;

wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

$R^{2a}$ is selected from $C_1$-$C_6$alkyl, and 4- to 6-membered heterocyclyl comprising 1-2 heteroatoms independently selected from N, O, and S;

$R^{2b}$ and $R^{2c}$ are each independently selected from hydrogen, and $C_1$-$C_6$alkyl;

each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

$R^6$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl;

n is 0, 1, 2, 3, 4, or 5; and m is 0, 1 or 2;

with the proviso that formula (I') does not include 3-(1-oxo-5-(pyrrolidin-3-yloxy)isoindolin-2-yl)piperidine-2,6-dione.

The disclosure provides, in a second aspect, a compound of formula (I″) or a pharmaceutically acceptable salt, hydrate, solvate, prodrug, stereoisomer, or tautomer thereof, wherein:

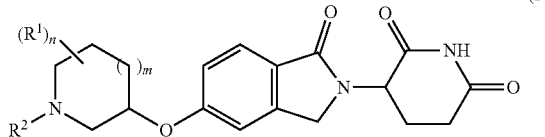

(I″)

each $R^1$ is independently selected from hydrogen, $C_1$-$C_6$alkyl hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;

$R^2$ is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, $C_1$-$C_{10}$alkyl, —$SO_2R^6$, —C(=O)—$R^{2a}$, —C(=O)—O—$R^{2a}$, and —C(=O)$NR^{2b}R^{2c}$;

wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

$R^{2a}$ is selected from $C_1$-$C_6$alkyl, and 4- to 6-membered heterocyclyl comprising 1-2 heteroatoms independently selected from N, O, and S;

$R^{2b}$ and $R^{2c}$ are each independently selected from hydrogen, and $C_1$-$C_6$alkyl;

each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

$R^6$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl;

n is 0, 1, 2, 3, 4, or 5; and m is 1 or 2.

The disclosure provides, in a third aspect, a compound of formula (I) or a pharmaceutically acceptable salt, hydrate, solvate, prodrug, stereoisomer, or tautomer thereof, wherein:

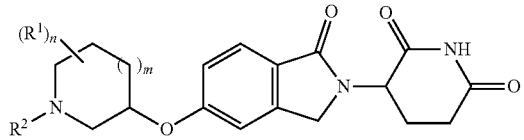

(I)

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;

$R^2$ is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, and $C_1$-$C_{10}$alkyl, wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

n is 0, 1, 2, 3 or 4; and m is 0, 1 or 2;

with the proviso that the compound of formula (I) does not include 3-(1-oxo-5-(pyrrolidin-3-yloxy)isoindolin-2-yl)piperidine-2,6-dione.

In a fourth aspect, the disclosure provides a pharmaceutical composition comprising a therapeutically effective amount of a compound of formula (I′), (I″), (I), (I-i), (IA), (IA-i), (IA-ii), (IA-iii), (IB), (IB-i), (IBA), (IB-iii), (IC), (IC-i), (IC-ii), (ID), (ID-i), or (ID-ii), or a pharmaceutically acceptable salt, hydrate, solvate, prodrug, stereoisomer, or tautomer thereof, and a pharmaceutically acceptable carrier or excipient.

In a fifth aspect, the disclosure provides a method of treating or preventing a disease or disorder in a subject in need thereof, the method comprising administering to the subject a therapeutically effective amount of a compound of formula (I′), (I″), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a sixth aspect, the disclosure provides a method of degrading WIZ protein in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a seventh aspect, the disclosure provides a method of inhibiting WIZ protein expression in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a eighth aspect, the disclosure provides a method of inhibiting, reducing, or eliminating the activity of WIZ protein or WIZ protein expression, the method comprising administering to the subject a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a ninth aspect, the disclosure provides a method of inducing or promoting fetal hemoglobin in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In an tenth aspect, the disclosure provides a method of reactivating fetal hemoglobin production or expression in a subject in need thereof, the method comprising administering to the subject a therapeutically effective amount of a compound of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a further aspect, the disclosure provides a method of increasing fetal hemoglobin expression in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a further aspect, the disclosure provides a method of treating a hemoglobinopathy, e.g., a beta-hemoglobinopathy, in a subject in need thereof, the method comprising administering to the subject a therapeutically effective amount of a compound of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a further aspect, the disclosure provides a method of treating a sickle cell disease in a subject in need thereof, the method comprising administering to the subject a therapeutically effective amount of (I'), (I"), (I), (I-i), (IA), (IA-i), (IA-ii), (IA-iii), (IB), (IB-i), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a further aspect, the disclosure provides a method of treating beta-thalassemia in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a further aspect, the disclosure provides a method of treating a disease or disorder that is affected by the modulation of WIZ protein levels comprising administering to the patient in need thereof a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a further aspect, the disclosure provides a method of treating or preventing a disorder that is affected by the reduction of WIZ protein levels, in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a further aspect, the disclosure provides a method of reducing WIZ protein levels in a subject comprising the step of administering to a subject in need thereof a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use as a medicament.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of a disease or disorder.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of a disease or disorder selected from sickle cell disease and beta-thalassemia.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in treating or preventing a disease or disorder in a subject in need thereof.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment or prevention of a disease or disorder that is affected by the reduction of WIZ protein levels.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in inhibiting WIZ protein expression in a subject in need thereof.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in degrading WIZ protein in a subject in need thereof.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in inhibiting, reducing, or eliminating the activity of WIZ protein or WIZ protein expression in a subject in need thereof.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in inducing or promoting fetal hemoglobin in a subject in need thereof.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in reactivating fetal hemoglobin production or expression in a subject in need thereof.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in increasing fetal hemoglobin production or expression in a subject in need thereof.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment or prevention of a disease or disorder that is affected by the inhibition of WIZ protein expression.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment or prevention of a disease or disorder that is affected by the degradation of WIZ protein.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of a hemoglobinopathy.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of a sickle cell disease.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of beta-thalassemia.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of a disease or disorder affected by an increase in fetal hemoglobin expression.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of a disease or disorder affected by the inhibition, reduction, or elimination of the activity of WIZ protein or WIZ protein expression.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of a disease or disorder affected by the induction or promotion of fetal hemoglobin.

In a further aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, for use in the treatment of a disease or disorder affected by the reactivation of fetal hemoglobin production or expression.

In a further aspect, the disclosure provides the use of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the manufacture of a medicament for treating a disease or disorder that is affected by the reduction of WIZ protein levels, inhibition of WIZ protein expression or degradation of WIZ protein.

In a further aspect, the disclosure provides the use of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the manufacture of a medicament for treating a disease or disorder that is affected by inducing or promoting fetal hemoglobin.

In a further aspect, the disclosure provides the use of a compound of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the manufacture of a medicament for treating a disease or disorder that is affected by reactivating fetal hemoglobin production or expression.

In a further aspect, the disclosure provides the use of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the manufacture of a medicament for treating a disease or disorder that is affected by increasing fetal hemoglobin expression.

In a further aspect, the disclosure provides the use of a compound of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the manufacture of a medicament for treating a disease or disorder that is affected by the reduction of WIZ protein levels, inhibition of WIZ protein expression or degradation of WIZ protein.

In a further aspect, the disclosure provides the use of a compound of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the manufacture of a medicament for treating a disease or disorder that is affected by inducing fetal hemoglobin.

In a further aspect, the disclosure provides the use of a compound of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the manufacture of a medicament for treating a disease or disorder that is affected by reactivating fetal hemoglobin production or expression.

In a further aspect, the disclosure provides the use of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the manufacture of a medicament for treating a disease or disorder that is affected by increasing fetal hemoglobin expression.

In a further aspect, the disclosure provides the use of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the treatment of a disease or disorder that is affected by the reduction of WIZ protein levels, inhibition of WIZ protein expression or degradation of WIZ protein.

In a further aspect, the disclosure provides the use of a compound of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, in the treatment of a disease or disorder that is affected by inducing fetal hemoglobin, reactivating fetal hemoglobin production or expression, or increasing fetal hemoglobin expression.

In a further aspect, the disclosure provides a pharmaceutical combination comprising a compound of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof, and one or more additional therapeutic agent(s).

Various aspects of the disclosure are described herein and in the claims.

Unless otherwise defined, all technical and scientific terms used herein have the same meaning as commonly understood by one of ordinary skill in the art to which this disclosure belongs. In the specification and claims, the singular forms also include the plural unless the context clearly dictates otherwise. Although methods and materials similar or equivalent to those described herein can be used in the practice or testing of the disclosure, suitable methods and materials are described below. All publications, patent applications, patents, and other references mentioned herein are incorporated by reference in their entireties for all purposes. The references cited herein are not admitted to be prior art to the claimed disclosure. In the case of conflict, the present specification, including definitions, will control. In addition, the materials, methods, and examples are illustrative only and are not intended to be limiting.

Other features and advantages of compounds, compositions, and methods disclosed herein will be apparent from the following detailed description and claims.

DETAILED DESCRIPTION OF THE DISCLOSURE

Figure 1A:
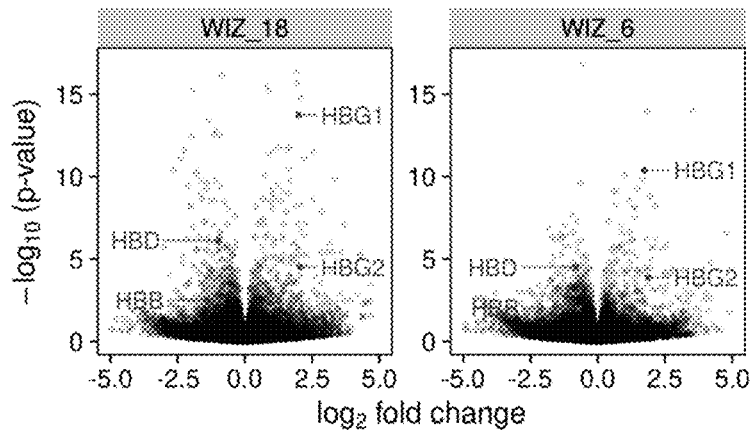
FIG. 1A depicts a volcano plot of differentially expressed genes from WIZ KO cells as compared to a scrambled gRNA control. Each dot represents a gene. HBG1/2 genes are differentially upregulated with WIZ_6 and WIZ_18 gRNA targeting WIZ KO.

The compounds disclosed herein are effective in reducing WIZ protein expression levels, or inducing fetal hemoglobin (HbF) expression. Without wishing to be bound by any theory, it is believed that the disclosed compounds may treat blood disorders, such as inherited blood disorders, e.g., sickle cell disease, and beta-thalassemia by inducing fetal hemoglobin HbF expression.

DEFINTIONS

Unless specified otherwise, the terms "compounds of the present disclosure", "compounds of the disclosure", or "compound of the disclosure" refer to compounds of formulae of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), exemplified compounds, salts thereof, particularly pharmaceutically acceptable salts thereof, hydrates, solvates, prodrugs, as well as all stereoisomers (including diastereoisomers and enantiomers), rotamers, tautomers, and isotopically labeled compounds (including deuterium substitutions), as well as inherently formed moieties.

In the groups, radicals, or moieties defined below, the number of carbon atoms is often specified preceding the group, for example, $C_1$-$C_{10}$alkyl means an alkyl group or radical having 1 to 10 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-. Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein the term "$C_1$-$C_{10}$alkyl" refers to a straight or branched hydrocarbon chain radical consisting solely of carbon and hydrogen atoms, containing no unsaturation, having from one to ten carbon atoms, and which is attached to the rest of the molecule by a single bond. The terms "$C_1$-$C_3$alkyl", "$C_1$-$C_4$alkyl", "$C_1$-$C_6$alkyl", and "$C_1$-$C_8$alkyl" are to be construed accordingly. Examples of $C_1$-$C_{10}$alkyl include, without limitations, methyl, ethyl, n-propyl, 1-methylethyl (iso propyl), n-butyl, 1-methylpropyl (sec-butyl), 2-methylpropyl (iso-butyl), 1,1-dimethylethyl (t-butyl), n-pentyl, n-hexyl, n-heptyl, 4-heptyl, n-octyl, 2-isopropyl-3-methylbutyl, n-nonyl and n-decyl.

As used herein, the term "$C_1$-$C_6$alkoxyl" refers to a radical of the formula —OR, where $R_a$ is a $C_1$-$C_6$alkyl radical as generally defined above. Examples of $C_1$-$C_6$alkoxyl include, without limitations, methoxy, ethoxy, propoxy, iso-propoxy, butoxy, iso-butoxy, tert-butoxy, sec-butoxy, pentoxy, and hexoxy.

"Alkenyl" means a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, and hexenyl. An alkenyl group can be unsubstituted or substituted and may be straight or branched. The term "$C_2$-$C_6$alkenyl" is to be construed accordingly.

Examples of $C_2$-$C_6$alkenyl include, without limitations, ethenyl (or vinyl), propenyl (e.g., prop-1-enyl, prop-2-enyl), butadienyl (e.g., buta-1,3-dienyl), butenyl (e.g., but-1-en-1-yl, but-2-en-1-yl but-3-en-1-yl), pentenyl (e.g., pent-1-en-1-yl, pent-2-en-2-yl), hexenyl (e.g., hex-1-en-2-yl, hex-2-en-1-yl), 1-ethylprop-2-enyl, 1,1-(dimethyl)prop-2-enyl, 1-ethylbut-3-enyl, and 1,1-(dimethyl)but-2-enyl.

"Alkynyl" means a straight or branched chain unsaturated hydrocarbon containing 2-12 carbon atoms. The "alkynyl" group contains at least one triple bond in the chain. The term "$C_2$-$C_6$alkynyl" is to be construed accordingly. Examples of alkynyl groups include ethynyl, propargyl, n-butynyl, isobutynyl, pentynyl, and hexynyl. An alkynyl group can be unsubstituted or substituted. Examples of "$C_2$-$C_6$alkynyl" include, without limitations, ethynyl, prop-1-ynyl, prop-2-ynyl, and but-2-ynyl.

As used herein, the term "$C_1$-$C_6$haloalkyl" refers to $C_1$-$C_6$alkyl radical, as defined above, substituted by one or more halo radicals, as defined herein. Examples of $C_1$-$C_6$haloalkyl include, without limitations, trifluoromethyl, difluoromethyl, fluoromethyl, trichloromethyl, 1,1-difluoroethyl, 2,2-difluoroethyl, 2,2,2-trifluoroethyl, 2-fluoropropyl, 3,3-difluoropropyl and 1-fluoromethyl-2-fluoroethyl, 1,3-dibromopropan-2-yl, 3-bromo-2-fluoropropyl and 1,4,4-trifluorobutan-2-yl.

As used herein, the term "$C_1$-$C_6$haloalkoxyl" means a $C_1$-$C_6$alkoxyl group as defined herein substituted with one or more halo radicals. Examples of $C_1$-$C_6$haloalkoxyl groups include, without limitations, trifluoromethoxy, difluoromethoxy, fluoromethoxy, trichloromethoxy, 1,1-difluoroethoxy, 2,2-difluoroethoxy, 2,2,2-trifluoroethoxy, 1-fluoromethyl-2-fluoroethoxy, pentafluoroethoxy, 2-fluoropropoxy, 3,3-difluoropropoxy and 3-dibromopropoxy. Preferably, the one or more halo radicals of $C_1$-$C_6$haloalkoxyl is fluoro. For example, $C_1$-$C_6$haloalkoxyl may be selected from trifluoromethoxy, difluoromethoxy, fluoromethoxy, 1,1-difluoroethoxy, 2,2-difluoroethoxy, 2,2,2-trifluoroethoxy, 1-fluoromethyl-2-fluoroethoxy, and pentafluoroethoxy.

The term "halo" means fluorine, chlorine, bromine or iodine.

As used herein, the term "cycloalkyl" means a monocyclic or polycyclic saturated or partially unsaturated carbon ring containing 3-18 carbon atoms wherein there are no delocalized pi electrons (aromaticity) shared among the ring carbon. The terms "$C_3$-$C_{11}$cycloalkyl", "$C_3$-$C_8$cycloalkyl" and "$C_3$-$C_6$cycloalkyl" are to be construed accordingly. The term polycyclic encompasses bridged (e.g., norbornane), fused (e.g., decalin) and spirocyclic cycloalkyl. Preferably, cycloalkyl, e.g., "$C_3$-$C_{11}$cycloalkyl" and "$C_3$-$C_8$cycloalkyl", is a monocyclic or spirocyclic hydrocarbon group of 3 to 11 and 3 to 8 carbon atoms, respectively.

Examples of cycloalkyl groups include, without limitations, cyclopropenyl, cyclopropyl cyclobutyl, cyclobutenyl, cyclopentyl, cyclohexyl, cycloheptanyl, cyclooctanyl, norboranyl, norborenyl, spiro[2.3]hexanyl, spiro[3.3]heptyl, spiro[3.4]octanyl, spiro[2.5]octanyl, spiro[3.5]nonanyl, spiro[4.5]decanyl, spiro[5.5]undecanyl, spiro[4.4]nonanyl, bicyclo[2.2.2]octanyl, bicyclo[2.2.2]octenyl, bicyclo[1.1.1]pentanyl and derivatives thereof.

Examples of $C_3$-$C_{11}$cycloalkyl include, without limitations, cyclopropyl, cyclobutyl, cyclopentyl, cyclohexyl, spiro[2.3]hexanyl, spiro[3.3]heptyl, spiro[3.4]octanyl, spiro[2.5]octanyl, spiro[3.5]nonanyl, spiro[4.5]decanyl, spiro[5.5]undecanyl, spiro[4.4]nonanyl, bicyclo[1.1.1]pentyl, bicyclo[2.1.1]hexyl, bicyclo[2.1.1]heptyl, bicyclo[2.2.2]octyl, and bicyclo[1.1.1]pentanyl.

Examples of $C_3$-$C_8$cycloalkyl include, without limitations, cyclopropyl, cyclobutyl, cyclopentyl, cyclohexyl, cycloheptyl, spiro[3.3]heptanyl, and cyclooctyl.

Examples of $C_3$-$C_6$cycloalkyl include, without limitations, cyclopropyl, cyclobutyl, cyclopentyl, and cyclohexyl.

"Heterocyclyl" means a saturated or partially saturated monocyclic or polycyclic ring containing carbon and at least one heteroatom selected from oxygen, nitrogen, and sulfur (O, N, and S) and wherein there are no delocalized pi electrons (aromaticity) shared among the ring carbon or heteroatoms. The terms "4- to 11-membered heterocyclyl" and "4- to 6-membered heterocyclyl" are to be construed accordingly. The heterocyclyl ring structure may be substituted by one or more substituents. The substituents can themselves be optionally substituted. The heterocyclyl may be bonded via a carbon atom or heteroatom. The term polycyclic encompasses bridged, fused and spirocyclic heterocyclyl.

Examples of heterocyclyl rings include, without limitations, oxetanyl, azetidinyl, tetrahydrofuranyl, tetrahydropyranyl, pyrrolidinyl, oxazolinyl, isoxazolinyl, oxazolidinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, dihydroisoxazolinyl, pyrrolinyl, pyrazolinyl, oxazepinyl, dithiolanyl, homotropanyl, dihydropyranyl (e.g., 3,6-dihydro-2H-pyranyl), 2-oxaspiro[3.3]heptanyl (e.g., 2-oxaspiro[3.3]heptan-6-yl), 7-oxaspiro[3.5]nonanyl (e.g., 7-oxaspiro[3.5]nonan-2-yl), 1-oxa-7-azaspiro[3.5]nonanyl, 2-azaspiro[3.3]heptanyl, 2,7-diazaspiro[3.5]nonanyl, 7-azaspiro[3.5]nonanyl, and the like.

Examples of 4- to 11-membered heterocyclyl include, without limitations, azetidinyl, pyrrolidinyl, tetrahydrofuranyl, tetrahydrothienyl, piperidinyl, piperazinyl, dihydroisoxazolinyl, tetrahydropyranyl, morpholinyl, dihydropyranyl (e.g., 3,6-dihydro-2H-pyranyl) 2-oxaspiro[3.3] heptanyl (e.g., 2-oxaspiro[3.3]heptan-6-yl), 7-oxaspiro[3.5] nonanyl (e.g., 7-oxaspiro[3.5]nonan-2-yl), 1-oxa-7-azaspiro [3.5]nonanyl, 2-azaspiro[3.3]heptanyl (e.g., 2-azaspiro[3.3] heptan-6-yl), 2,7-diazaspiro[3.5]nonanyl, and 7-azaspiro [3.5]nonanyl.

Examples of of 4- to 6-membered heterocyclyl include, without limitations, azetidinyl, pyrrolidinyl, tetrahydrofuranyl, tetrahydrothienyl, piperidinyl, piperazinyl, dihydroisoxazolinyl, tetrahydropyranyl, morpholinyl, dihydropyranyl (e.g., 3,6-dihydro-2H-pyranyl).

As used herein, the term "aryl" as used herein means monocyclic, bicyclic or polycyclic carbocyclic aromatic rings. Examples of aryl include, but are not limited to, phenyl, naphthyl (e.g., naphth-1-yl, naphth-2-yl), anthryl (e.g., anthr-1-yl, anthr-9-yl), phenanthryl (e.g., phenanthr-1-yl, phenanthr-9-yl), and the like. Aryl is also intended to include monocyclic, bicyclic or polycyclic carbocyclic aromatic rings substituted with carbocyclic aromatic rings. Examples of aryl include, without limitations, biphenyl (e.g., biphenyl-2-yl, biphenyl-3-yl, biphenyl-4-yl), phenylnaphthyl (e.g., 1-phenylnaphth-2-yl, 2-phenylnaphth-1-yl), and the like. Aryl is also intended to include partially saturated bicyclic or polycyclic carbocyclic rings with at least one unsaturated moiety (e.g., a benzo moiety). Examples include, without limitations, indanyl (e.g., indan-1-yl, indan-5-yl), indenyl (e.g., inden-1-yl, inden-5-yl), 1,2,3,4-tetrahydronaphthyl (e.g., 1,2,3,4-tetrahydronaphth-1-yl, 1,2,3,4-tetrahydronaphth-2-yl, 1,2,3,4-tetrahydronaphth-6-yl), 1,2-dihydronaphthyl (e.g., 1,2-dihydronaphth-1-yl, 1,2-dihydronaphth-4-yl, 1,2-dihydronaphth-6-yl), fluorenyl (e.g., fluoren-1-yl, fluoren-4-yl, fluoren-9-yl), and the like. Aryl is also intended to include partially saturated bicyclic or polycyclic carbocyclic aromatic rings containing one or two bridges. Examples include, without limitations, benzonorbornyl (e.g., benzonorborn-3-yl, benzonorborn-6-yl), 1,4-ethano-1,2,3,4-tetrahydronapthyl (e.g., 1,4-ethano-1,2,3,4-tetrahydronapth-2-yl, 1,4-ethano-1,2,3,4-tetrahydronapth-10-yl), and the like. The term "$C_6$-$C_{10}$aryl" is to be construed accordingly.

Examples of $C_6$-$C_{10}$aryl include, without limitations, phenyl and naphthyl. In an embodiment, $C_6$-$C_{10}$aryl is phenyl.

As used herein, the term "heteroaryl" as used herein is intended to include monocyclic heterocyclic aromatic rings containing one or more heteroatoms selected from oxygen, nitrogen, and sulfur (O, N, and S). Examples include, without limitations, pyrrolyl, furanyl, thienyl, oxazolyl, thiazolyl, imidazolyl, pyrazolyl, isothiazolyl, isooxazolyl, triazolyl, (e.g., 1,2,4-triazolyl), oxadiazolyl, (e.g., 1,2,3-oxadiazolyl, 1,2,4-oxadiazolyl, 1,2,5-oxadiazolyl, 1,3,4-oxadiazolyl), thiadiazolyl (e.g., 1,2,3-thiadiazolyl, 1,2,4-thiadiazolyl, 1,2,5-thiadiazolyl, 1,3,4-thiadiazolyl), tetrazolyl, pyranyl, pyridinyl, pyridazinyl, pyrimidinyl, pyrazinyl, 1,2,3-triazinyl, 1,2,4-triazinyl, 1,3,5-triazinyl, thiadiazinyl, azepinyl, azecinyl, and the like.

Heteroaryl is also intended to include bicyclic heterocyclic aromatic rings containing one or more heteroatoms selected from oxygen, nitrogen, and sulfur (O, N, and S). Examples include, without limitations, indolyl, isoindolyl, benzofuranyl, benzothiophenyl, indazolyl, benzopyranyl, benzimidazolyl, benzothiazolyl, benzisothiazolyl, benzoxazolyl, benzisoxazolyl, benzoxazinyl, benzotriazolyl, naphthyridinyl, phthalazinyl, pteridinyl, purinyl, quinazolinyl, cinnolinyl, quinolinyl, isoquinolinyl, quinoxalinyl, oxazolopyridinyl, isooxazolopyridinyl, pyrrolopyridinyl, furopyridinyl, thienopyridinyl, imidazopyridinyl, imidazopyrimidinyl, pyrazolopyridinyl, pyrazolopyrimidinyl, pyrazolotriazinyl, thiazolopyridinyl, thiazolopyrimidinyl, imdazothiazolyl, triazolopyridinyl, triazolopyrimidinyl, and the like.

Heteroaryl is also intended to include polycyclic heterocyclic aromatic rings containing one or more heteroatoms selected from oxygen, nitrogen, and sulfur (O, N, and S). Examples include, without limitations, carbazolyl, phenoxazinyl, phenazinyl, acridinyl, phenothiazinyl, carbolinyl, phenanthrolinyl, and the like.

Heteroaryl is also intended to include partially saturated monocyclic, bicyclic or polycyclic heterocyclyls containing one or more heteroatoms selected oxygen, nitrogen, and sulfur (O, N, and S). Examples include, without limitations, imidazolinyl, indolinyl, dihydrobenzofuranyl, dihydrobenzothienyl, dihydrobenzopyranyl, dihydropyridooxazinyl, dihydrobenzodioxinyl (e.g., 2,3-dihydrobenzo[b][1,4]dioxinyl), benzodioxolyl (e.g., benzo[d][1,3]dioxole), dihydrobenzooxazinyl (e.g., 3,4-dihydro-2H-benzo[b][1,4] oxazine), tetrahydroindazolyl, tetrahydrobenzimidazolyl, tetrahydroimidazo[4,5-c]pyridyl, tetrahydroquinolinyl, tetrahydroisoquinolinyl, tetrahydroquinoxalinyl, and the like.

The heteroaryl ring structure may be substituted by one or more substituents. The substituents can themselves be optionally substituted. The heteroaryl ring may be bonded via a carbon atom or heteroatom.

The term "5-10 membered heteroaryl" is to be construed accordingly.

Examples of 5-10 membered heteroaryl include, without limitations, indolyl, imidazopyridyl, isoquinolinyl, benzooxazolonyl, pyridinyl, pyrimidinyl, pyridinonyl, benzotriazolyl, pyridazinyl, pyrazolotriazinyl, indazolyl, benzimidazolyl, quinolinyl, triazolyl, (e.g., 1,2,4-triazolyl), pyrazolyl, thiazolyl, oxazolyl, isooxazolyl, pyrrolyl, oxadiazolyl, (e.g., 1,2,3-oxadiazolyl, 1,2,4-oxadiazolyl, 1,2,5-oxadiazolyl, 1,3,4-oxadiazolyl), imidazolyl, pyrrolopyridinyl, tetrahydroindazolyl, quinoxalinyl, thiadiazolyl (e.g., 1,2,3-thiadiazolyl, 1,2,4-thiadiazolyl, 1,2,5-thiadiazolyl, 1,3,4-thiadiazolyl), pyrazinyl, oxazolopyridinyl, pyrazolopyrimidinyl, benzoxazolyl, indolinyl, isooxazolopyridinyl, dihydropyridooxazinyl, tetrazolyl, dihydrobenzodioxinyl (e.g., 2,3-dihydrobenzo[b][1,4]dioxinyl), benzodioxolyl (e.g., benzo[d][1,3]dioxole) and dihydrobenzooxazinyl (e.g., 3,4-dihydro-2H-benzo[b][1,4]oxazine).

"Cyano" or "—CN" means a substituent having a carbon atom joined to a nitrogen atom by a triple bond, e.g., —C≡N.

As used herein, the term "$C_1$-$C_3$alkylene" refers to a straight or branched hydrocarbon chain bivalent radical consisting solely of carbon and hydrogen atoms, containing no unsaturation, having from one to three carbon atoms. The term "$C_1$-$C_2$alkylene" is to be construed accordingly.

As used herein, the term "optionally substituted" includes unsubstituted or substituted.

As used herein,

denotes the point of attachment of that particular group to the base molecule.

As used herein, the term nitrogen protecting group (abbreviated as PG) in a compound of formula (X) or (Y) or any intermediates in any of the General schemes 1 to 4 and subformulae thereof refers to a group that should protect the functional groups, concerned e.g., amino groups, against unwanted secondary reactions, such as acylations, etherifications, esterifications, oxidations, solvolysis and similar reactions. It may be removed under deprotection conditions. Depending on the protecting group employed, the skilled person would know how to remove the protecting group to obtain the free amine $NH_2$ group by reference to known procedures. These include reference to organic chemistry textbooks and literature procedures such as J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; in "The Peptides"; Volume 3 (editors: E. Gross and J. Meienhofer), Academic Press, London and New York 1981; P. J. Kocienski, "Protecting Groups", Third Edition, Georg Thieme Verlag, Stuttgart and New York 2005; and in "Methoden der organischen Chemie" (Methods of Organic Chemistry), Houben Weyl, 4th edition, Volume 15/I, Georg Thieme Verlag, Stuttgart 1974.

Preferred nitrogen protecting groups generally comprise: $C_1$-$C_6$alkyl (e.g., tert-butyl), preferably $C_1$-$C_4$alkyl, more preferably $C_1$-$C_2$alkyl, most preferably $C_1$alkyl which is mono-, di- or tri-substituted by trialkylsilyl-$C_1$-$C_7$alkoxy (e.g., trimethylsilyethoxy), aryl, preferably phenyl, or a heterocyclic group (e.g., benzyl, cumyl, benzhydryl, pyrrolidinyl, trityl, pyrrolidinylmethyl, 1-methyl-1,1-dimethylbenzyl, (phenyl)methylbenzene) wherein the aryl ring or the heterocyclic group is unsubstituted or substituted by one or more, e.g., two or three, residues, e.g., selected from the group consisting of $C_1$-$C_7$alkyl, hydroxy, $C_1$-$C_7$alkoxy (e.g., para-methoxy benzyl (PMB)), $C_2$-$C_8$alkanoyl-oxy, halogen, nitro, cyano, and $CF_3$, aryl-$C_1$-$C_2$-alkoxycarbonyl (preferably phenyl-$C_1$-$C_2$-alkoxycarbonyl (e.g., benzyloxycarbonyl (Cbz), benzyloxymethyl (BOM), pivaloyloxymethyl (POM)), $C_1$-$C_{10}$-alkenyloxycarbonyl, $C_1$-$C_6$alkylcarbonyl (e.g., acetyl or pivaloyl), $C_6$-$C_{10}$-arylcarbonyl; $C_1$-$C_6$-alkoxycarbonyl (e.g., tertbutoxycarbonyl (Boc), methylcarbonyl, trichloroethoxycarbonyl (Troc), pivaloyl (Piv), allyloxycarbonyl), $C_6$-$C_{10}$-aryl$C_1$-$C_6$-alkoxycarbonyl (e.g., 9-fluorenylmethyloxycarbonyl (Fmoc)), ally) or cinnamyl, sulfonyl or sulfenyl, succinimidyl group, silyl groups (e.g., triarylsilyl, trialkylsilyl, triethylsilyl (TES), trimethylsilylethoxymethyl (SEM), trimethylsilyl (TMS), triisopropylsilyl or tertbutyldimethylsilyl).

According to the disclosure, the preferred nitrogen protecting group (PG) can be selected from the group comprising tert-butyloxycarbonyl (Boc), benzyloxycarbonyl (Cbz), para-methoxy benzyl (PMB), methyloxycarbonyl, trimethylsilylethoxymethyl (SEM) and benzyl. The nitrogen protecting group (PG) is preferably tert-butyloxycarbonyl (Boc) or trimethylsilylethoxymethyl (SEM).

In some embodiments, the compounds of the disclosure are selective over other proteins.

As used herein, the term "therapeutic agent" in connection with methods of reducing WIZ protein expression levels and/or inducing fetal hemoglobin (HbF) expression, refers to a substance that results in a detectably lower expression of WIZ gene or WIZ protein or lower activity level of WIZ proteins as compared to those levels without such substance.

As used herein "modulator" or "degrader", means, for example, a compound of the disclosure, that effectively modulates, decreases, or reduces the levels of a specific protein (e.g., WIZ) or degrades a specific protein (e.g., WIZ). The amount of a specific protein (e.g., WIZ) degraded can be measured by comparing the amount of the specific protein (e.g., WIZ) remaining after treatment with a compound of the disclosure as compared to the initial amount or level of the specific protein (e.g., WIZ) present as measured prior to treatment with a compound of the disclosure.

As used herein "selective modulator", "selective degrader", or "selective compound" means, for example, a compound of the disclosure, that effectively modulates, decreases, or reduces the levels of a specific protein (e.g., WIZ) or degrades a specific protein (e.g., WIZ) to a greater extent than any other protein. A "selective modulator", "selective degrader", or "selective compound" can be identified, for example, by comparing the ability of a compound to modulate, decrease, or reduce the levels of or to degrade a specific protein (e.g., WIZ) to its ability to modulate, decrease, or reduce the levels of or to degrade other proteins. In some embodiments, the selectivity can be identified by measuring the $EC_{50}$ or $IC_{50}$ of the compounds. Degradation may be achieved through mediation of an E3 ligase, e.g., E3-ligase complexes comprising the protein Cereblon.

In one embodiment, the specific protein degraded is WIZ protein. In an embodiment, at least about 30% of WIZ is degraded compared to initial levels. In an embodiment, at least about 40% of WIZ is degraded compared to initial levels. In an embodiment, at least about 50% of WIZ is degraded compared to initial levels. In an embodiment, at least about 60% of WIZ is degraded compared to initial levels. In an embodiment, at least about 70% of WIZ is degraded compared to initial levels. In an embodiment, at least about 75% of WIZ is degraded compared to initial levels. In an embodiment, at least about 80% of WIZ is degraded compared to initial levels. In an embodiment, at least about 85% of WIZ is degraded compared to initial levels. In an embodiment, at least about 90% of WIZ is degraded compared to initial levels. In an embodiment, at least about 95% of WIZ is degraded compared to initial levels. In an embodiment, over 95% of WIZ is degraded compared to initial levels. In an embodiment, at least about 99% of WIZ is degraded compared to initial levels.

In an embodiment, the WIZ is degraded in an amount of from about 30% to about 99% compared to initial levels. In an embodiment, the WIZ is degraded in an amount of from about 40% to about 99% compared to initial levels. In an embodiment, the WIZ is degraded in an amount of from about 50% to about 99% compared to initial levels. In an embodiment, the WIZ is degraded in an amount of from about 60% to about 99% compared to initial levels. In an embodiment, the WIZ is degraded in an amount of from about 70% to about 99% compared to initial levels. In an embodiment, the WIZ is degraded in an amount of from about 80% to about 99% compared to initial levels. In an embodiment, the WIZ is degraded in an amount of from about 90% to about 99% compared to initial levels. In an embodiment, the WIZ is degraded in an amount of from about 95% to about 99% compared to initial levels. In an embodiment, the WIZ is degraded in an amount of from about 90% to about 95% compared to initial levels.

As used herein, the terms "inducing fetal hemoglobin", "fetal hemoglobin induction", or "increasing fetal hemoglobin expression" refer to increasing the percentage of HbF in the blood of a subject. In an embodiment, the amount of total HbF in the blood of the subject increases. In an embodiment, the amount of total hemoglobin in the blood of the subject increases. In an embodiment, the amount of HbF is increased by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of a compound disclosed herein.

In an embodiment, the total hemoglobin in the blood, e.g., the blood in a subject, is increased by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of a compound disclosed herein.

The term "a therapeutically effective amount" of a compound of the disclosure refers to an amount of the compound of the disclosure that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "a therapeutically effective amount" refers to the amount of the compound of the disclosure that, when administered to a subject, is effective to (1) at least partially alleviate, prevent and/or ameliorate a condition, or a disorder or a disease (i) mediated by WIZ, or (ii) associated with WIZ activity, or (iii) characterized by activity (normal or abnormal) of WIZ: (2) reduce or inhibit the activity of WIZ; or (3) reduce or inhibit the expression of WIZ. In another embodiment, the term "a therapeutically effective amount" refers to the amount of the compound of the disclosure that, when administered to a cell, or a tissue, or a non-cellular biological material, or a medium, is effective to at least partially reducing or inhibiting the activity of WIZ; or at least partially reducing or inhibiting the expression of WIZ.

"HBF-dependent disease or disorder" means any disease or disorder which is directly or indirectly affected by the modulation of HbF protein levels.

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a," "an," "the" and similar terms used in the context of the disclosure (especially in the context of the claims) are to be construed to cover both the singular and plural unless otherwise indicated herein or clearly contradicted by the context.

Various enumerated embodiments of the disclosure are described herein. It will be recognized that features specified in each embodiment may be combined with other specified features to provide further embodiments of the disclosure.

ENUMERATED EMBODIMENTS

Embodiment 1. A compound of formula (I') or a pharmaceutically acceptable salt, hydrate, solvate, prodrug, stereoisomer, or tautomer thereof, wherein:

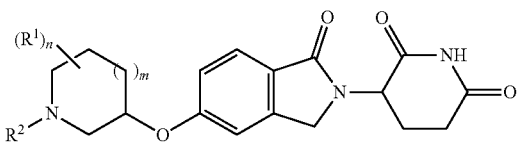

(I')

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;

$R^2$ is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, $C_1$-$C_{10}$alkyl, —$SO_2R^6$, —C(=O)—$R^{2a}$, —C(=O)—O—$R^{2a}$, and —C(=O)N$R^{2b}R^{2c}$;

wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

$R^{2a}$ is selected from $C_1$-$C_6$alkyl, and 4- to 6-membered heterocyclyl comprising 1-2 heteroatoms independently selected from N, O, and S;

$R^{2b}$ and $R^{2c}$ are each independently selected from hydrogen, and $C_1$-$C_6$alkyl;

each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each R⁵ is independently selected from —CN, $C_1$-$C_6$alkyl, $C_1$-$C_6$alkoxyl, hydroxyl, and $C_1$-$C_6$haloalkyl;

R⁶ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, e.g., R⁶ is selected from $C_3$-$C_8$cycloalkyl, and $C_1$-$C_6$alkyl;

n is 0, 1, 2, 3, 4, or 5; and m is 0, 1 or 2;

with the proviso that the compound of formula (I') does not include 3-(1-oxo-5-(pyrrolidin-3-yloxy)isoindolin-2-yl)piperidine-2,6-dione.

Embodiment 2. A compound of formula (I") or a pharmaceutically acceptable salt, hydrate, solvate, prodrug, stereoisomer, or tautomer thereof, wherein:

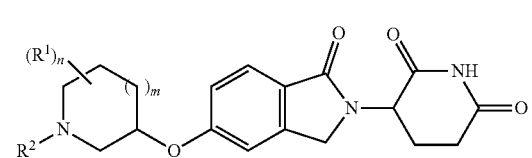

(I")

each R¹ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 R¹ on the same carbon atom together with the same carbon atom to which they are attached form a $C_3$-$C_8$cycloalkyl; or 2 R¹ on adjacent carbon atoms together with the adjacent carbon atoms to which they are attached form a $C_3$-$C_8$cycloalkyl; or 2 R¹ on non-adjacent carbon atoms together with the non-adjacent carbon atoms to which they are attached form a bridging ring;

R² is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, $C_1$-$C_{10}$alkyl, —SO$_2$R⁶, —C(=O)—R$^{2a}$, —C(=O)—O—R$^{2a}$, and —C(=O)NR$^{2b}$R$^{2c}$;

wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of R³;

R$^{2a}$ is selected from $C_1$-$C_6$alkyl, and 4- to 6-membered heterocyclyl comprising 1-2 heteroatoms independently selected from N, O, and S;

R$^{2b}$ and R$^{2c}$ are each independently selected from hydrogen, and $C_1$-$C_6$alkyl;

each R³ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of R⁴;

each R⁴ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of R⁵;

each R⁵ is independently selected from —CN, $C_1$-$C_6$alkyl, $C_1$-$C_6$alkoxyl, hydroxyl, and $C_1$-$C_6$haloalkyl;

R⁶ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, e.g., R⁶ is selected from $C_3$-$C_8$cycloalkyl, and $C_1$-$C_6$alkyl;

n is 0, 1, 2, 3, 4, or 5; and m is 1 or 2.

Embodiment 3. A compound of formula (I) or a pharmaceutically acceptable salt, hydrate, solvate, prodrug, stereoisomer, or tautomer thereof, wherein:

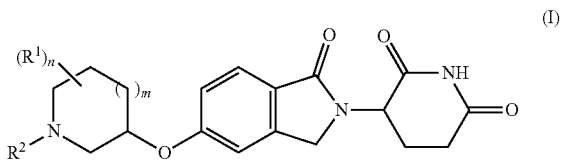

(I)

each R¹ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 R¹ on the same carbon atom together with the same carbon atom to which they are attached form a $C_3$-$C_8$cycloalkyl; or 2 R¹ on adjacent carbon atoms together with the adjacent carbon atoms to which they are attached form a $C_3$-$C_8$cycloalkyl; or 2 R¹ on non-adjacent carbon atoms together with the non-adjacent carbon atoms to which they are attached form a bridging ring;

R² is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, and $C_1$-$C_{10}$alkyl, wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of R³;

each R³ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of R⁴;

each R⁴ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of R⁵;

each R⁵ is independently selected from —CN, $C_1$-$C_6$alkyl, $C_1$-$C_6$alkoxyl, hydroxyl, and $C_1$-$C_6$haloalkyl;

n is 0, 1, 2, 3 or 4; and m is 0, 1 or 2;

with the proviso that the compound of formula (I) does not include 3-(1-oxo-5-(pyrrolidin-3-yloxy)isoindolin-2-yl)piperidine-2,6-dione.

Embodiment 4. The compound of formula (I'), (I") or (I) according to any one of the preceding Embodiments, or a pharmaceutically acceptable salt, hydrate, solvate, prodrug, stereoisomer, or tautomer thereof, wherein m is 1 or 2.

Embodiment 5. The compound of formula (I'), (I") or (I) according to any one of the preceding Embodiments, or a pharmaceutically acceptable salt, hydrate, solvate, prodrug, stereoisomer, or tautomer thereof, wherein R² is selected from C₃-C₁₁cycloalkyl, 4- to 11-membered heterocyclyl comprising 1-2 heteroatoms independently selected from N, O, and S, C₁-C₆haloalkyl, C₂-C₆alkenyl, C₂-C₆alkynyl, and C₁-C₁₀alkyl, wherein the C₃-C₁₁cycloalkyl, 4- to 11-membered heterocyclyl, C₂-C₆alkynyl, and C₁-C₁₀alkyl are each independently substituted with 0-5, e.g., 0-4, 0-3, 0-2, 0-1, occurrences of R³.

Embodiment 6. The compound of formula (I'), (I") or (I) according to any one of the preceding Embodiments, or a pharmaceutically acceptable salt, hydrate, solvate, prodrug, stereoisomer, or tautomer thereof, wherein formula (I) is formula (IA):

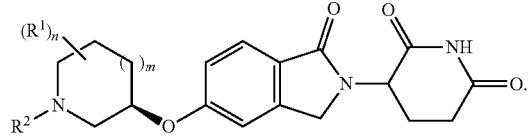
(IA)

Embodiment 7. The compound of formula (I'), (I") or (I) according to any one of Embodiments 1 to 5, or a pharmaceutically acceptable salt, hydrate, solvate, prodrug, stereoisomer, or tautomer thereof, wherein formula (I) is formula (IB):

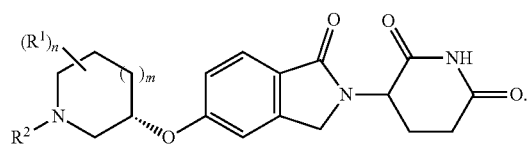
(IB)

Embodiment 8. The compound of formula (I'), (I") or (I) according to any one of Embodiments 1 to 5, or a pharmaceutically acceptable salt, hydrate, solvate, prodrug, stereoisomer, or tautomer thereof, wherein formula (I) is formula (IC):

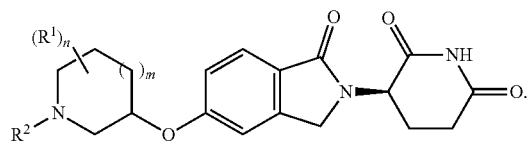
(IC)

Embodiment 9. The compound of formula (I'), (I") or (I) according to any one of Embodiments 1 to 5, or a pharmaceutically acceptable salt, hydrate, solvate, prodrug, stereoisomer, or tautomer thereof, wherein formula (I) is formula (ID):

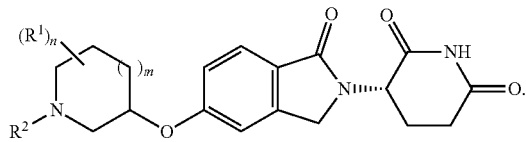
(ID)

Embodiment 10. The compound of formula (I'), (I") or (I) according to any one of Embodiments 1 to 6, and 8, or a pharmaceutically acceptable salt, hydrate, solvate, prodrug, stereoisomer, or tautomer thereof, of formula (IC-i):

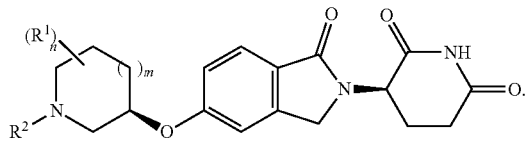
(IC-i)

Embodiment 11. The compound of formula (I'), (I") or (I) according to any one of Embodiments 1 to 5, 7, and 8, or a pharmaceutically acceptable salt, hydrate, solvate, prodrug, stereoisomer, or tautomer thereof, of formula (IC-ii):

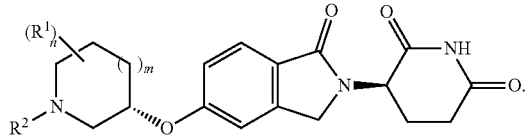
(IC-ii)

Embodiment 12. The compound of formula (I'), (I") or (I) according to any one of Embodiments 1 to 6, and 9, or a pharmaceutically acceptable salt, hydrate, solvate, prodrug, stereoisomer, or tautomer thereof, of formula (ID-i):

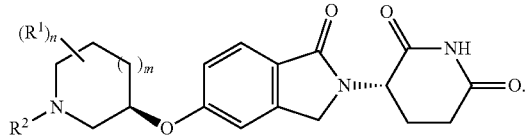
(ID-i)

Embodiment 13. The compound of formula (I'), (I") or (I) according to any one of Embodiments 1 to 5, 7, and 9, or a pharmaceutically acceptable salt, hydrate, solvate, prodrug, stereoisomer, or tautomer thereof, of formula (ID-ii):

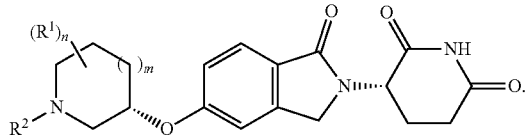
(ID-ii)

Embodiment 14. The compound of formula (I'), (I") or (I) according to any one of Embodiments 1, 2, 3, and 5 to 13, or a pharmaceutically acceptable salt, hydrate, solvate, prodrug, stereoisomer, or tautomer thereof, wherein:

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;

$R^2$ is selected from hydrogen, $C_3$-$C_{11}$cycloalkyl, $C_1$-$C_6$haloalkyl, 4- to 11-membered heterocyclyl comprising 1-2 heteroatoms independently selected from N, O, and S, $C_2$-$C_6$alkenyl, $C_2$-$C_6$alkynyl, and $C_1$-$C_{10}$alkyl, wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

each $R^3$ is independently selected from $C_1$-$C_6$alkoxyl, halo, 4- to 11-membered heterocyclyl comprising 1-2 heteroatoms independently selected from N, O, and S, and $C_3$-$C_8$cycloalkyl, wherein the 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

n is 0, 1, 2, 3, 4, or 5; and m is 0, 1 or 2, e.g., m is 1 or 2.

Embodiment 15. The compound of formula (I'), (I") or (I) according to any one of Embodiments 1, 2, 3, and 5 to 14, or a pharmaceutically acceptable salt, hydrate, solvate, prodrug, stereoisomer, or tautomer thereof, wherein:

each $R^1$ is independently selected from hydrogen, $C_1$-$C_6$alkyl, hydroxyl, halo, and $C_1$-$C_6$alkoxyl; or 2 $R^1$ on the same carbon atom together with the same carbon atom to which they are attached form a $C_3$-$C_6$cycloalkyl; or 2 $R^1$ on adjacent carbon atoms together with the adjacent carbon atoms to which they are attached form a $C_3$-$C_6$cycloalkyl; or 2 $R^1$ on non-adjacent carbon atoms together with the non-adjacent carbon atoms to which they are attached form a $C_1$-$C_3$ alkylene bridging ring;

$R^2$ is selected from hydrogen, $C_3$-$C_{11}$cycloalkyl, $C_1$-$C_6$haloalkyl, 4- to 11-membered heterocyclyl comprising 1-2 heteroatoms independently selected from N, O, and S, $C_2$-$C_6$alkenyl, $C_2$-$C_6$alkynyl, and $C_1$-$C_{10}$alkyl, wherein the $C_3$-$C_{11}$cycloalkyl, $C_2$-$C_6$alkynyl, and $C_1$-$C_{10}$alkyl are each independently substituted with 0-5 occurrences of $R^3$;

each $R^3$ is independently selected from $C_1$-$C_6$alkoxyl, halo, 4- to 11-membered heterocyclyl comprising 1-2 heteroatoms independently selected from N, O, and S, and $C_3$-$C_8$cycloalkyl, wherein the 4- to 11-membered heterocyclyl, and $C_3$-$C_8$cycloalkyl are each independently substituted with 0-3 occurrences of $R^4$;

each $R^4$ is independently selected from $C_1$-$C_{10}$alkyl, $C_1$-$C_6$alkoxyl, halo, and $C_3$-$C_8$cycloalkyl;

n is 0, 1, 2, 3, 4, or 5; and m is 0, 1 or 2, e.g., m is 1 or 2.

Embodiment 16. The compound of formula (I'), (I") or (I) according to any one of the preceding Embodiments, or a pharmaceutically acceptable salt, hydrate, solvate, prodrug, stereoisomer, or tautomer thereof, wherein:

each $R^1$ is independently selected from hydrogen, $C_1$-$C_6$alkyl, hydroxyl, fluoro, and $C_1$-$C_6$alkoxyl; or 2 $R^1$ on the same carbon atom together with the same carbon atom to which they are attached form a $C_3$-$C_6$cycloalkyl; or 2 $R^1$ on adjacent carbon atoms together with the adjacent carbon atoms to which they are attached form a $C_3$-$C_6$cycloalkyl; or 2 $R^1$ on non-adjacent carbon atoms together with the non-adjacent carbon atoms to which they are attached form a $C_1$-$C_2$ alkylene bridging ring;

$R^2$ is selected from hydrogen, $C_3$-$C_{11}$cycloalkyl, 4- to 11-membered heterocyclyl comprising 1-2 heteroatoms independently selected from N, O, and S, $C_2$-$C_6$alkynyl, and $C_1$-$C_6$alkyl, wherein the $C_3$-$C_{11}$cycloalkyl is substituted with 0-3 occurrences of $R^3$, wherein the $C_1$-$C_6$alkyl is substituted with 0-1 occurrence of $R^{3a}$, and wherein the $C_2$-$C_6$alkynyl is substituted with 0-1 occurrence of $R^{3b}$;

each $R^3$ is independently selected from $C_1$-$C_6$alkoxyl, and fluoro;

$R^{3a}$ is selected from 4- to 11-membered heterocyclyl comprising 1-2 heteroatoms independently selected from N, O, and S, and $C_3$-$C_8$cycloalkyl, wherein the 4- to 11-membered heterocyclyl, and $C_3$-$C_8$cycloalkyl are each independently substituted with 0-3 occurrences of $R^4$;

$R^{3b}$ is selected from $C_1$-$C_6$alkyl, and $C_3$-$C_8$cycloalkyl, preferably $C_3$-$C_8$cycloalkyl;

each $R^4$ is independently selected from $C_1$-$C_6$alkyl, $C_1$-$C_6$alkoxyl, fluoro, and $C_3$-$C_8$cycloalkyl;

n is 0, 1, 2 or 3; and m is 1.

Embodiment 17. The compound of formula (I'), (I") or (I) according to any one of the preceding Embodiments, or a pharmaceutically acceptable salt, hydrate, solvate, prodrug, stereoisomer, or tautomer thereof, wherein:

each $R^1$ is independently selected from hydrogen, $C_1$-$C_6$alkyl, hydroxyl, fluoro, and $C_1$-$C_6$alkoxyl; or 2 $R^1$ on the same carbon atom together with the same carbon atom to which they are attached form a $C_3$-$C_6$cycloalkyl;

$R^2$ is selected from $C_3$-$C_8$cycloalkyl, 4- to 6-membered heterocyclyl comprising 1-2 heteroatoms independently selected from N, O, and S, $C_2$-$C_6$alkynyl, and $C_1$-$C_6$alkyl, wherein the $C_3$-$C_8$cycloalkyl is substituted with 0-3 occurrences of $R^3$, wherein the $C_1$-$C_6$alkyl is substituted with 0-1 occurrence of $R^{3a}$, and wherein the $C_2$-$C_6$alkynyl is substituted with 0-1 occurrence of $R^{3b}$;

each $R^3$ is independently selected from $C_1$-$C_6$alkoxyl, and fluoro;

$R^{3a}$ is $C_3$-$C_8$cycloalkyl, wherein the $C_3$-$C_8$cycloalkyl is independently substituted with 0-3 occurrences of $R^4$;

$R^{3b}$ is selected from $C_1$-$C_6$alkyl, and $C_3$-$C_8$cycloalkyl, preferably $C_3$-$C_8$cycloalkyl;

each $R^4$ is independently selected from $C_1$-$C_6$alkyl, $C_1$-$C_6$alkoxyl, fluoro, and $C_3$-$C_8$cycloalkyl;

n is 0, 1, 2 or 3; and m is 1.

Embodiment 18. The compound of formula (I'), (I") or (I) according to any one of the preceding Embodiments, or a pharmaceutically acceptable salt, hydrate, solvate, prodrug, stereoisomer, or tautomer thereof, wherein R² is unsubstituted C₁-C₆alkyl, or —(CH₂)—R³, wherein R³ is defined according to any one of the preceding Embodiments.

Embodiment 19. The compound of formula (I'), (I") or (I) according to any one of the preceding Embodiments, or a pharmaceutically acceptable salt, hydrate, solvate, prodrug, stereoisomer, or tautomer thereof, wherein R² is unsubstituted C₁-C₆alkyl, or —(CH₂)—R³ᵃ, wherein R³ᵃ is defined according to any one of Embodiments 16 and 17.

Embodiment 20. The compound of formula (I'), (I") or (I) according to any one of the preceding Embodiments, or a pharmaceutically acceptable salt, hydrate, solvate, prodrug, stereoisomer, or tautomer thereof, wherein R² is selected from unsubstituted C₁-C₆alkyl,

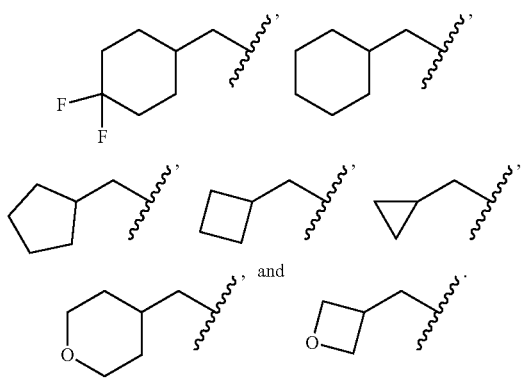

Embodiment 21. The compound of formula (I'), (I") or (I) according to any one of the preceding Embodiments, or a pharmaceutically acceptable salt, hydrate, solvate, prodrug, stereoisomer, or tautomer thereof, wherein R² is selected from methyl, ethyl, n-propyl, i-propyl, n-butyl, sec-butyl, and t-butyl.

Embodiment 22. The compound of formula (I'), (I") or (I) according to any one of the preceding Embodiments, or a pharmaceutically acceptable salt, hydrate, solvate, prodrug, stereoisomer, or tautomer thereof, wherein m is 1.

Embodiment 23. The compound of formula (I'), (I") or (I) according to any one of the preceding Embodiments, or a pharmaceutically acceptable salt, hydrate, solvate, prodrug, stereoisomer, or tautomer thereof, wherein n is 0, 1, 2 or 3, for example, n is 1.

Embodiment 24. The compound of formula (I'), (I") or (I) according to any one of the preceding Embodiments, or a pharmaceutically acceptable salt, hydrate, solvate, prodrug, stereoisomer, or tautomer thereof, wherein R¹ is selected from C₁-C₆alkyl, hydroxyl, halo, and C₁-C₆alkoxyl; or 2 R¹ on the same carbon atom together with the same carbon atom to which they are attached form a C₃-C₈cycloalkyl.

Embodiment 25. The compound of formula (I'), (I") or (I) according to any one of the preceding Embodiments, or a pharmaceutically acceptable salt, hydrate, solvate, prodrug, stereoisomer, or tautomer thereof, wherein R¹ is selected from C₁-C₄alkyl, e.g., methyl, C₁-C₄alkoxyl, e.g., methoxyl, and fluoro; or 2 R¹ on the same carbon atom together with the same carbon atom to which they are attached form a C₃-C₆cycloalkyl.

Embodiment 26. The compound of formula (I'), (I") or (I) according to any one of Embodiments 1 to 5, and 14 to 25, or a pharmaceutically acceptable salt, hydrate, solvate, prodrug, stereoisomer, or tautomer thereof, wherein formula (I) is formula (I-i), wherein:

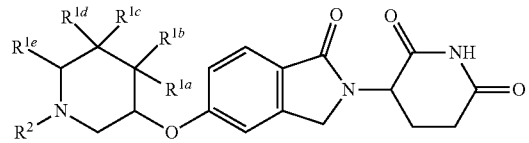

(I-i)

R¹ᵃ is independently selected from hydrogen and C₁-C₆alkyl;
R¹ᵇ is independently selected from hydrogen and C₁-C₆alkyl;
or R¹ᵃ and R¹ᵇ on the same carbon atom together with the same carbon atom to which they are attached form a C₃-C₆cycloalkyl;
R¹ᶜ is independently selected from hydrogen and C₁-C₆alkyl;
R¹ᵈ is independently selected from hydrogen, C₁-C₆alkyl, and C₁-C₆alkoxyl;
or R¹ᶜ and R¹ᵈ on the same carbon atom together with the same carbon atom to which they are attached form a C₃-C₆cycloalkyl;
R¹ᵉ is independently selected from hydrogen and C₁-C₆alkyl; and
R² is defined according to any one of the preceding Embodiments.

Embodiment 27. The compound of formula (I'), (I") or (I) according to any one of Embodiments 1 to 6, and 14 to 26, or a pharmaceutically acceptable salt, hydrate, solvate, prodrug, stereoisomer, or tautomer thereof, wherein formula (I) is formula (IA-i), wherein:

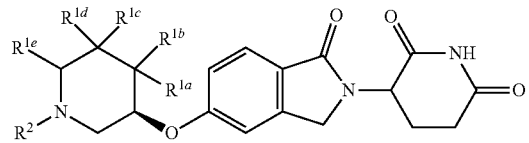

(IA-i)

R¹ᵃ is independently selected from hydrogen and C₁-C₆alkyl;
R¹ᵇ is independently selected from hydrogen and C₁-C₆alkyl;
or R¹ᵃ and R¹ᵇ on the same carbon atom together with the same carbon atom to which they are attached form a C₃-C₆cycloalkyl;
R¹ᶜ is independently selected from hydrogen and C₁-C₆alkyl;
R¹ᵈ is independently selected from hydrogen, C₁-C₆alkyl, and C₁-C₆alkoxyl;
or R¹ᶜ and R¹ᵈ on the same carbon atom together with the same carbon atom to which they are attached form a C₃-C₆cycloalkyl;
R¹ᵉ is independently selected from hydrogen and C₁-C₆alkyl; and
R² is defined according to any one of the preceding Embodiments.

Embodiment 28. The compound of formula (I'), (I") or (I) according to any one of Embodiments 1 to 6, 8, 10, and 14 to 27, or a pharmaceutically acceptable salt, hydrate, solvate, prodrug, stereoisomer, or tautomer thereof, wherein formula (I) is formula (IA-ii):

(IA-ii)

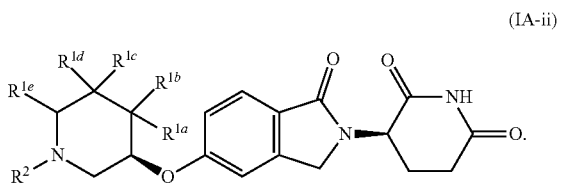

(IB-ii)

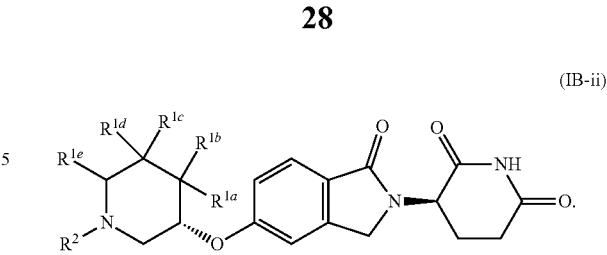

Embodiment 29. The compound of formula (I'), (I") or (I) according to any one of Embodiments 1 to 6, 9, 12, and 14 to 27, or a pharmaceutically acceptable salt, hydrate, solvate, prodrug, stereoisomer, or tautomer thereof, wherein formula (I) is formula (IA-iii):

Embodiment 32. The compound of formula (I'), (I") or (I) according to any one of Embodiments 1 to 5, 7, 9, 13, 14 to 26, and 30, or a pharmaceutically acceptable salt, hydrate, solvate, prodrug, stereoisomer, or tautomer thereof, wherein formula (I) is formula (IB-iii):

(IA-iii)

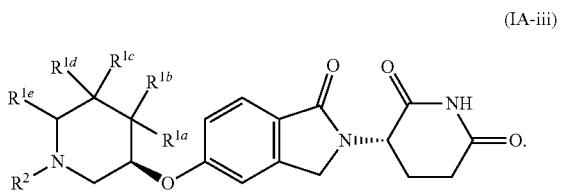

(IB-iii)

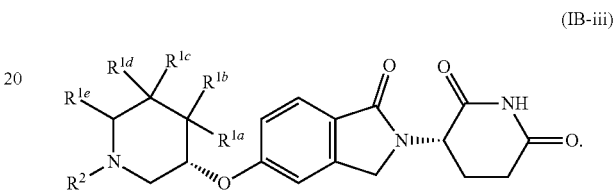

Embodiment 30. The compound of formula (I'), (I") or (I) according to any one of Embodiments 1 to 5, 7, and 14 to 26, or a pharmaceutically acceptable salt, hydrate, solvate, prodrug, stereoisomer, or tautomer thereof, wherein formula (I) is formula (IB-i), wherein:

Embodiment 33. The compound of formula (I'), (I") or (I) according to any one of Embodiments 26 to 32, or a pharmaceutically acceptable salt, hydrate, solvate, prodrug, stereoisomer, or tautomer thereof, wherein $R^{1a}$ and $R^{1b}$ are both hydrogen.

Embodiment 34. The compound of formula (I'), (I") or (I) according to any one of Embodiments 26 to 33, or a pharmaceutically acceptable salt, hydrate, solvate, prodrug, stereoisomer, or tautomer thereof, wherein $R^{1e}$ is $C_1$-$C_6$alkyl, and $R^{1a}$, $R^{1b}$, $R^{1c}$ and $R^{1d}$ are all hydrogen.

(IB-i)

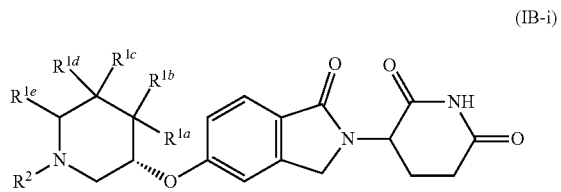

$R^{1a}$ is independently selected from hydrogen and $C_1$-$C_6$alkyl;

$R^{1b}$ is independently selected from hydrogen and $C_1$-$C_6$alkyl;

or $R^{1a}$ and $R^{1b}$ on the same carbon atom together with the same carbon atom to which they are attached form a $C_3$-$C_6$cycloalkyl;

$R^{1c}$ is independently selected from hydrogen and $C_1$-$C_6$alkyl;

$R^{1d}$ is independently selected from hydrogen, $C_1$-$C_6$alkyl, and $C_1$-$C_6$alkoxyl;

or $R^{1c}$ and $R^{1d}$ on the same carbon atom together with the same carbon atom to which they are attached form a $C_3$-$C_6$cycloalkyl;

$R^{1e}$ is independently selected from hydrogen and $C_1$-$C_6$alkyl; and $R^2$ is defined according to any one of the preceding Embodiments.

Embodiment 31. The compound of formula (I'), (I") or (I) according to any one of Embodiments 1 to 5, 7, 8, 11, 14 to 26, and 30, or a pharmaceutically acceptable salt, hydrate, solvate, prodrug, stereoisomer, or tautomer thereof, wherein formula (I) is formula (IBA):

Embodiment 35. The compound of formula (I'), (I") or (I) according to any one of Embodiments 26 to 32, or a pharmaceutically acceptable salt, hydrate, solvate, prodrug, stereoisomer, or tautomer thereof, wherein $R^{1a}$ and $R^{1b}$ are each independently selected from hydrogen and $C_1$-$C_6$alkyl, or $R^{1a}$ and $R^{1b}$ on the same carbon atom together with the same carbon atom to which they are attached form a $C_3$-$C_6$cycloalkyl, and $R^{1c}$, $R^{1d}$, and $R^{1e}$ are all hydrogen.

Embodiment 36. The compound of formula (I'), (I") or (I) according to any one of Embodiments 26 to 32, or a pharmaceutically acceptable salt, hydrate, solvate, prodrug, stereoisomer, or tautomer thereof, wherein $R^{1c}$ and $R^{1d}$ are each independently selected from hydrogen, $C_1$-$C_6$alkyl and $C_1$-$C_6$alkoxyl, e.g., $R^{1c}$ is hydrogen and $R^{1d}$ is $C_1$-$C_6$alkyl or $C_1$-$C_6$alkoxyl, or $R^{1c}$ and $R^{1d}$ on the same carbon atom together with the same carbon atom to which they are attached form a $C_3$-$C_6$cycloalkyl, and $R^{1a}$, $R^{1b}$, and $R^{1e}$ are all hydrogen.

Embodiment 37. The compound of formula (I'), (I") or (I) according to any one of the preceding Embodiments, or a pharmaceutically acceptable salt, hydrate, solvate, prodrug, stereoisomer, or tautomer thereof, wherein each $R^3$ is independently selected from 4- to 11-membered heterocyclyl comprising 1-2 heteroatoms independently selected from N, O, and S, $C_3$-$C_8$cycloalkyl, and halo, wherein the 4- to 11-membered heterocyclyl, and $C_3$-$C_8$cycloalkyl are each independently substituted with 0-2 occurrences of $R^4$, wherein each $R^4$ is independently selected from $C_1$-$C_6$alkyl, $C_1$-$C_6$alkoxyl, halo, and $C_3$-$C_8$cycloalkyl.

Embodiment 38. The compound of formula (I'), (I") or (I) according to any one of the preceding Embodiments, or a pharmaceutically acceptable salt, hydrate, solvate, prodrug, stereoisomer, or tautomer thereof, wherein each R⁴ is independently selected from $C_1$-$C_6$alkyl, and fluoro.

Embodiment 39. The compound according to any of the preceding Embodiments, wherein the glutarimide moiety of the compound of formula (I'), (I") or (I) is

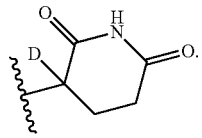 [SMILES: *C1([2H])CCC(=O)NC1=O]

Embodiment 40. The compound according to any of the preceding Embodiments, wherein the glutarimide moiety of the compound of formula (I'), (I") or (I) is

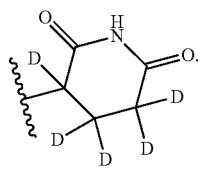 [SMILES: *C1([2H])C(=O)NC(=O)C([2H])([2H])C1([2H])[2H]]

Embodiment 41. The compound according to any of the preceding Embodiments, wherein the glutarimide moiety of the compound of formula (I'), (I") or (I) is

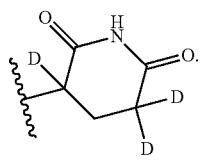 [SMILES: *C1([2H])CC([2H])([2H])C(=O)NC1=O]

Embodiment 42. The compound of formula (I'), (I") or (I) according to any one of Embodiments 1 to 3, or a pharmaceutically acceptable salt, hydrate, solvate, prodrug, stereoisomer, or tautomer thereof, selected from:

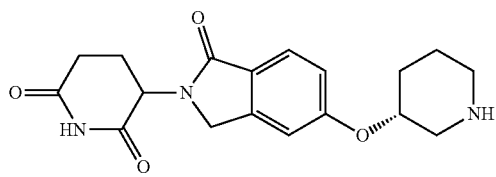

3-(1-oxo-5-(((R)-piperidin-3-yl)oxy)isoindolin-2-yl)piperidine-2,6-dione

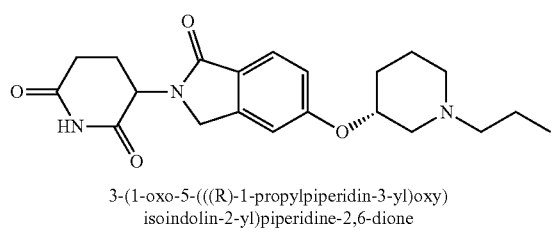

3-(1-oxo-5-(((R)-1-propylpiperidin-3-yl)oxy)isoindolin-2-yl)piperidine-2,6-dione

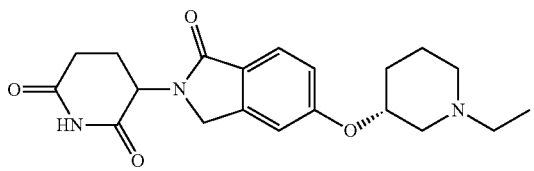

3-(5-(((R)-ethylpiperidin-3-yl)oxy)-1-oxoisoindolin-2-yl)piperidine-2,6-dione

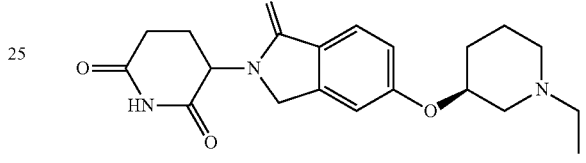

3-(5-(((R)-isopropylpiperidin-3-yl)oxy)-1-oxoisoindolin-2-yl)piperidine-2,6-dione

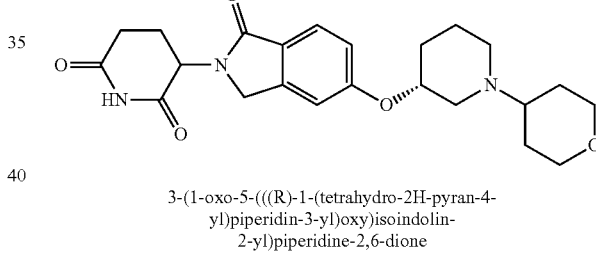

3-(5-(((S)-ethylpiperidin-3-yl)oxy)-1-oxoisoindolin-2-yl)piperidine-2,6-dione

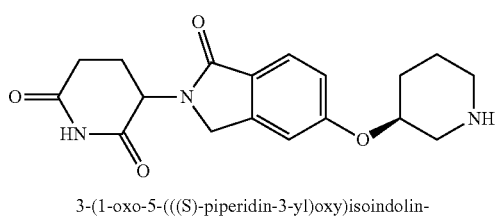

3-(1-oxo-5-(((R)-1-(tetrahydro-2H-pyran-4-yl)piperidin-3-yl)oxy)isoindolin-2-yl)piperidine-2,6-dione

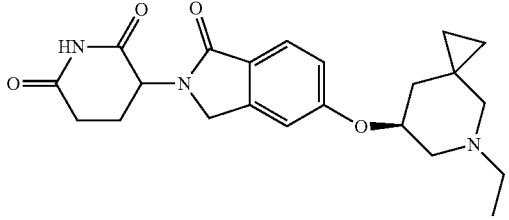

3-(1-oxo-5-(((S)-piperidin-3-yl)oxy)isoindolin-2-yl)piperidine-2,6-dione 3-(5-(((S)-5-ethyl-5-azaspiro[2.5]octan-7-yl)oxy)-1-oxoisoindolin-2-yl)piperidine-2,6-dione -continued

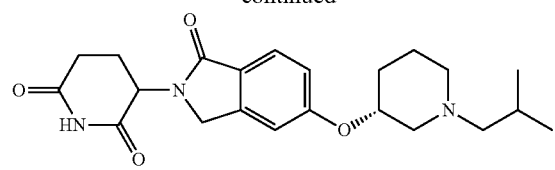

3-(5-(((R)-isobutylpiperidin-3-yl)oxy)-1-
oxoisoindolin-2-yl)piperidine-2,6-dione

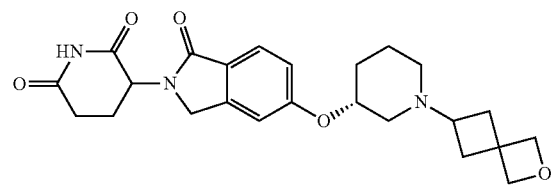

3-(5-(((R)-1-(2-oxaspiro[3.3]heptan-6-
yl)piperidin-3-yl)oxy)-1-oxoisoindolin-2-
yl)piperidine-2,6-dione

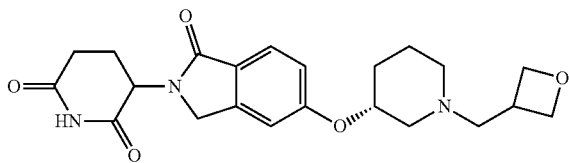

3-(5-(((R)-1-(oxetan-3-ylmethyl)piperidin-3-
yl)oxy)-1-oxoisoindolin-2-yl)piperidine-2,6-dione

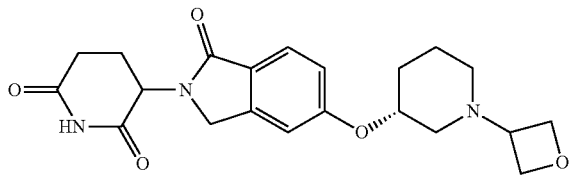

3-(5-(((R)-1-(oxetan-3-yl)piperidin-3-
yl)oxy)-1-oxoisoindolin-2-yl)
piperidine-2,6-dione

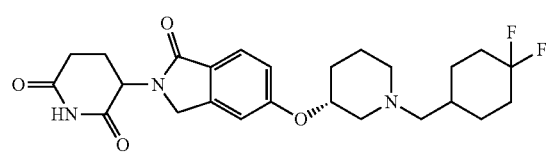

3-(5-(((R)-1-((4,4-difluorocyclohexyl)methyl)
piperidin-3-yl)oxy)-1-oxoisoindolin-2-yl)
piperidine-2,6-dione

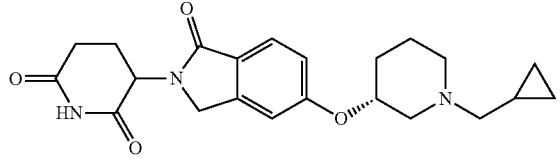

3-(5-(((R)-1-(cyclopropylmethyl)piperidin-3-
yl)oxy)-1-oxoisoindolin-2-yl)
piperidine-2,6-dione

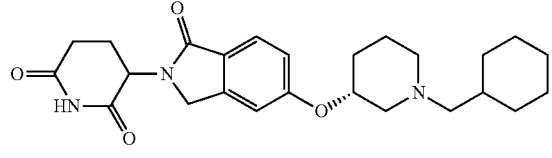

3-(5-(((R)-1-(cyclohexylmethyl)piperidin-3-
yl)oxy)-1-oxoisoindolin-2-yl)
piperidine-2,6-dione -continued

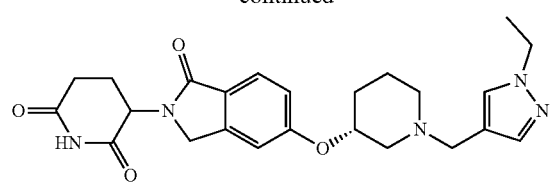

3-(5-(((R)-1-((1-ethyl-1H-pyrazol-4-yl)
methyl)piperidin-3-yl)oxy)-1-oxoisoindolin-
2-yl)piperidine-2,6-dione

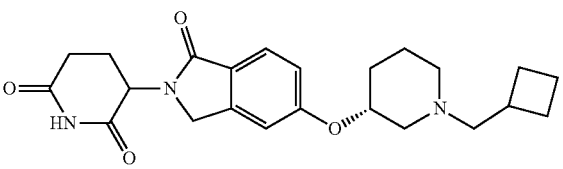

3-(5-(((R)-1-(cyclobutylmethyl)piperidin-3-
yl)oxy)-1-oxoisoindolin-2-yl)
piperidine-2,6-dione

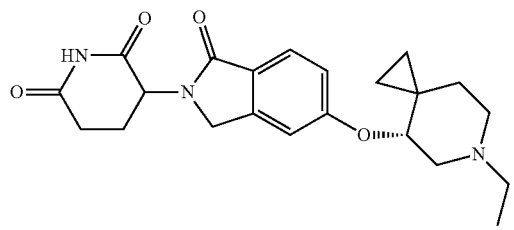

3-(5-(((R)-6-ethyl-6-azaspiro[2.5]octan-4-
yl)oxy)-1-oxoisoindolin-2-yl)
piperidine-2,6-dione

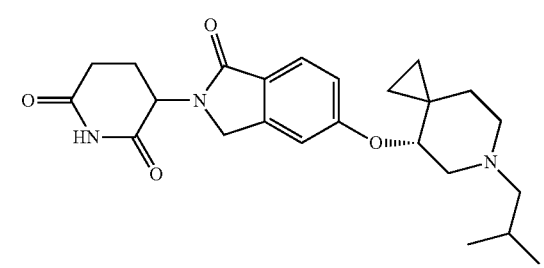

3-(5-(((R)-6-isobutyl-6-azaspiro[2.5]octan-4-
yl)oxy)-1-oxoisoindolin-2-yl)
piperidine-2,6-dione

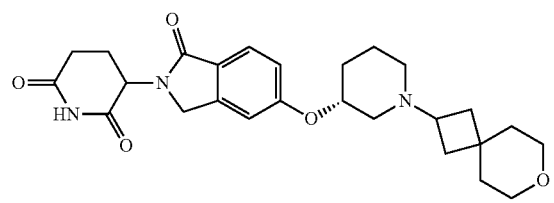

3-(5-(((R)-1-(7-oxaspiro[3.5]nonan-2-
yl)piperidin-3-yl)oxy)-1-oxoisoindolin-2-
yl)piperidine-2,6-dione

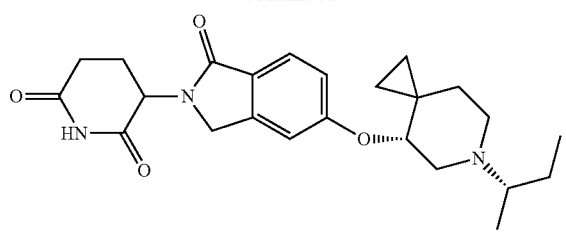

3-(5-(((R)-6-((S)-sec-butyl)-6-azaspiro[2.5]
octan-4-yl)oxy)-1-oxoisoindolin-2-yl)
piperidine-2,6-dione

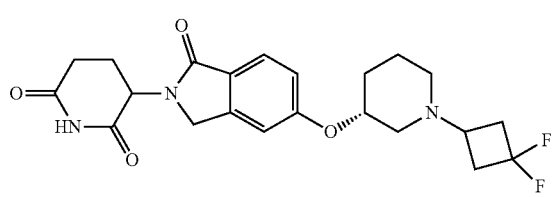

3-(5-(((R)-1-(3,3-difluorocyclobutyl)
piperidin-3-yl)oxy)-1-oxoisoindolin-2-
yl)piperidine-2,6-dione

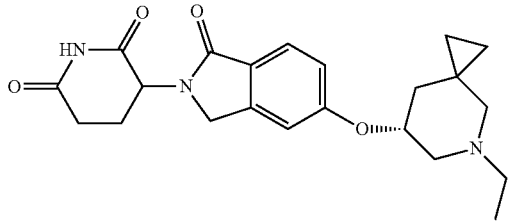

3-(5-(((R)-5-ethyl-5-azaspiro[2.5]octan-7-
yl)oxy)-1-oxoisoindolin-2-yl)
piperidine-2,6-dione

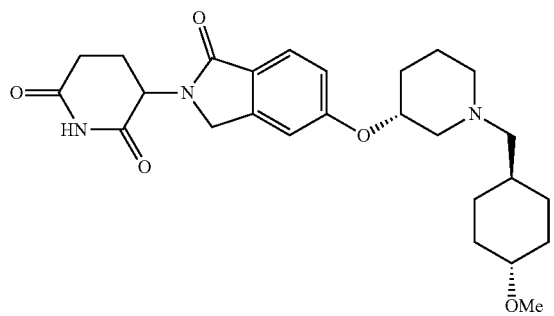

3-(5-(((R)-1-(((1r,4R)-4-methoxycyclohexyl)
methyl)piperidin-3-yl)oxy)-1-oxoisoindolin-2-
yl)piperidine-2,6-dione

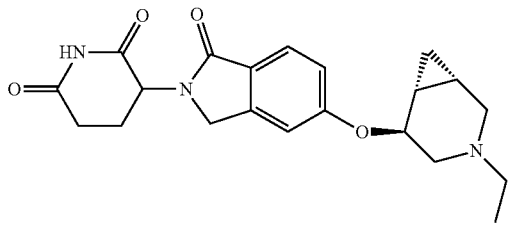

3-(5-(((1S,5S,6R)-3-ethyl-3-azabicyclo[4.1.0]
heptan-5-yl)oxy)-1-oxoisoindolin-2-yl)
piperidine-2,6-dione

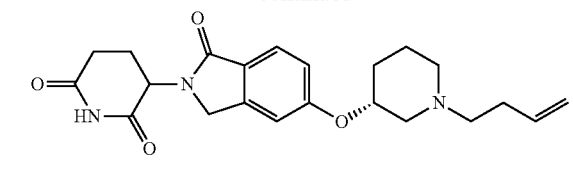

3-(5-(((R)-1-(but-3-en-1-yl)piperidin-3-yl)oxy)-
1-oxoisoindolin-2-yl)piperidine-2,6-dione

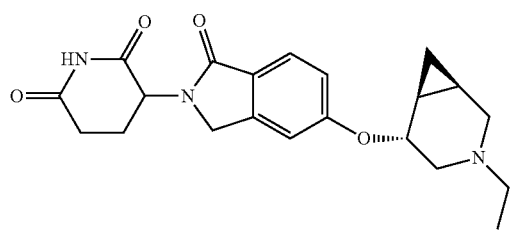

3-(5-(((1R,5R,6S)-3-ethyl-3-azabicyclo[4.1.0]
heptan-5-yl)oxy)-1-oxoisoindolin-2-yl)
piperidine-2,6-dione

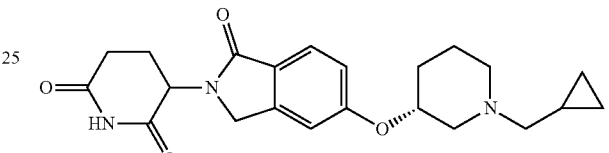

3-(5-(((R)-1-(cyclopropylmethyl)
piperidin-3-yl)oxy)-1-
oxoisoindolin-2-yl)piperidine-2,6-dione

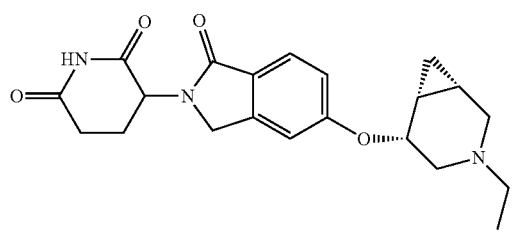

3-(5-(((1S,5S,6R)-3-ethyl-3-azabicyclo[4.1.0]
heptan-5-yl)oxy)-1-oxoisoindolin-2-yl)
piperidine-2,6-dione

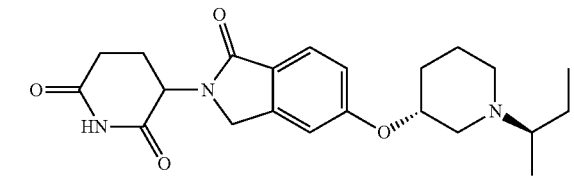

3-(5-(((R)-1-((R)-sec-butyl)piperidin-3-
yl)oxy)-1-oxoisoindolin-2-yl)
piperidine-2,6-dione

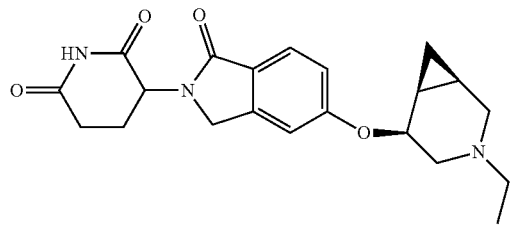

3-(5-(((1R,5S,6R)-3-ethyl-3-azabicyclo[4.1.0]
heptan-5-yl)oxy)-1-oxoisoindolin-2-yl)
piperidine-2,6-dione

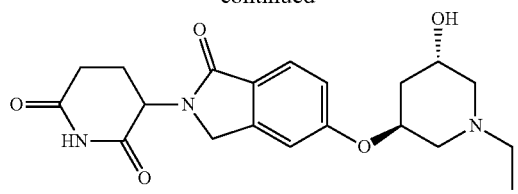

3-(5-(((3S,5S)-1-ethyl-5-hydroxypiperidin-3-yl)oxy)-1-oxoisoindolin-2-yl)piperidine-2,6-dione

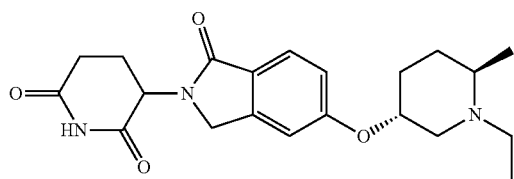

3-(5-(((3R,6R)-1-ethyl-6-methylpiperidin-3-yl)oxy)-1-oxoisoindolin-2-yl)piperidine-2,6-dione

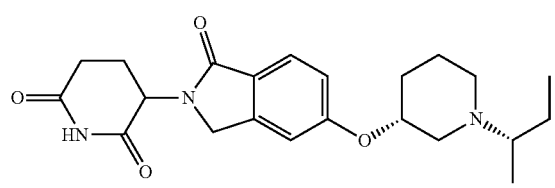

3-(5-(((R)-1-((S)-sec-butyl)piperidin-3-yl)oxy)-1-oxoisoindolin-2-yl)piperidine-2,6-dione

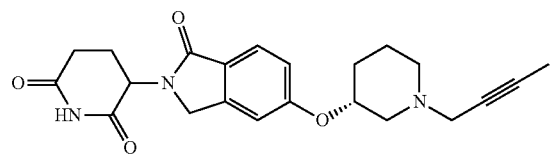

3-(5-(((R)-1-but-2-yn-1-yl)piperidin-3-yl)oxy)-1-oxoisoindolin-2-yl)piperidine-2,6-dione

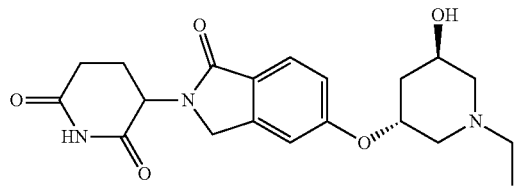

3-(5-(((3R,5R)-1-ethyl-5-hydroxypiperidin-3-yl)oxy)-1-oxoisoindolin-2-yl)piperidine-2,6-dione

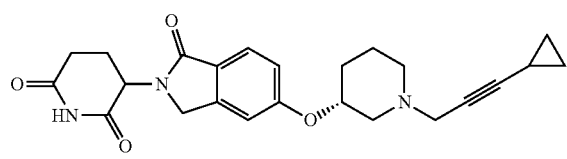

3-(5-(((R)-1-(3-cyclopropylprop-2-yn-1-yl)piperidin-3-yl)oxy)-1-oxoisoindolin-2-yl)piperidine-2,6-dione

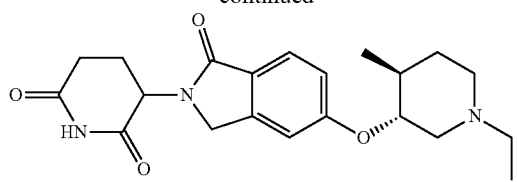

3-(5-(((3R,4S)-1-ethy-4-methylpiperidin-3-yl)oxy)-1-oxoisoindolin-2-yl)piperidine-2,6-dione

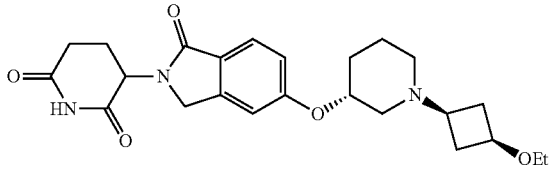

3-(5-(((R)-((1s,3S)-3-ethoxycyclobutyl)piperidin-3-yl)oxy)-1-oxoisoindolin-2-yl)piperidine-2,6-dione

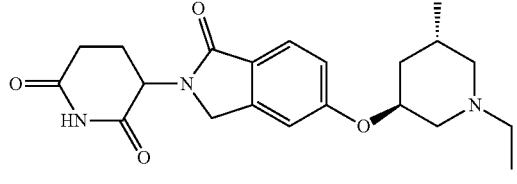

3-(5-(((3S,5S)-1-ethyl-5-methylpiperidin-3-yl)oxy)-1-oxoisoindolin-2-yl)piperidine-2,6-dione

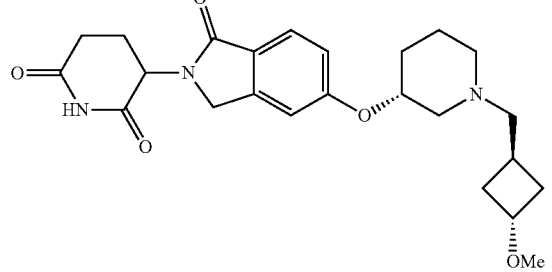

3-(5-(((R)-1-(((1r,3R)-3-methoxycyclobutyl)methyl)piperidin-3-yl)oxy)-1-oxoisoindolin-2-yl)piperidine-2,6-dione

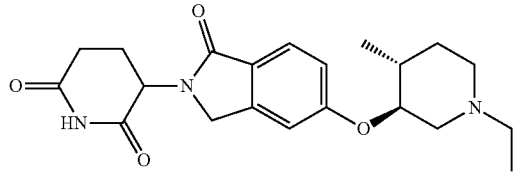

3-(5-(((3S,4R)-1-ethyl-4-methylpiperidin-3-yl)oxy)-1-oxoisoindolin-2-yl)piperidine-2,6-dione

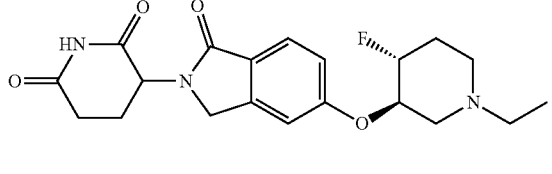

3-(5-(((3R,4R)-1-ethyl-4-fluoropiperidin-3-yl)oxy)-1-oxoisoindolin-2-yl)piperidine-2,6-dione -continued

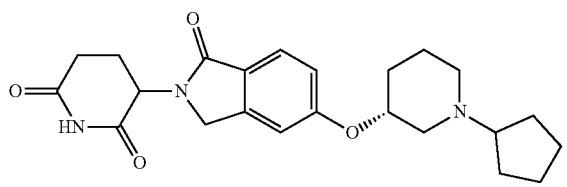

3-(5-(((R)-1-cyclopentylpiperidin-3-yl)oxy)-1-oxoisoindolin-2-yl)piperidine-2,6-dione

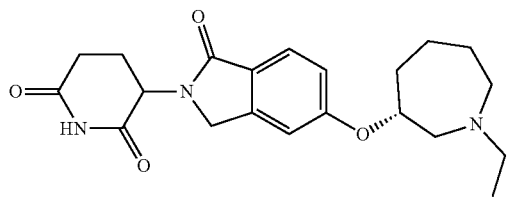

3-(5-(((R)-1-ethylazepan-3-yl)oxy)-1-oxoisoindolin-2-yl)piperidine-2,6-dione

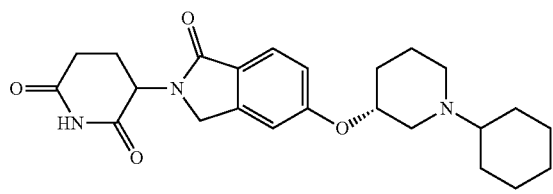

3-(5-(((R)-1-cyclohexylpiperidin-3-yl)oxy)-1-oxoisoindolin-2-yl)piperidine-2,6-dione

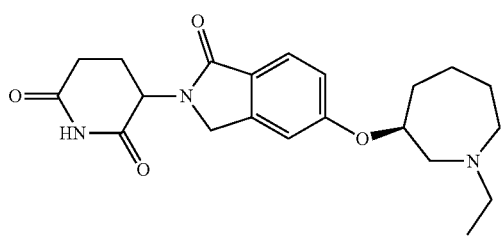

3-(5-(((S)-1-ethylazepan-3-yl)oxy)-1-oxoisoindolin-2-yl)piperidine-2,6-dione

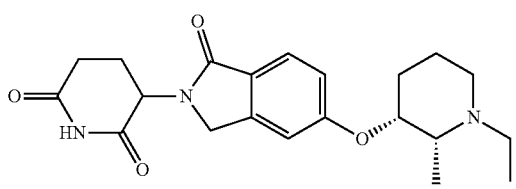

3-(5-(((2R,3R)-1-ethyl-2-methylpiperidin-3-yl)oxy)-1-oxoisoindolin-2-yl)piperidine-2,6-dione

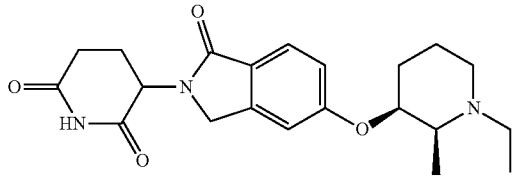

3-(5-(((2S,3S)-1-ethyl-2-methylpiperidin-3-yl)oxy)-1-oxoisoindolin-2-yl)piperidine-2,6-dione -continued

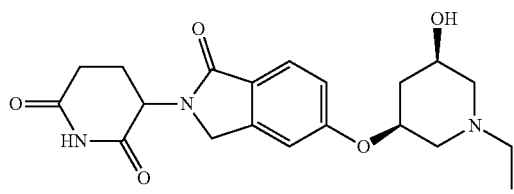

3-(5-(((3S,5R)-1-ethyl-5-hydroxypiperidin-3-yl)oxy)-1-oxoisoindolin-2-yl)piperidine-2,6-dione

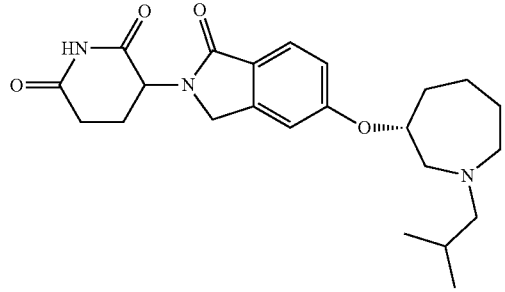

3-(5-(((R)-1-isobutylazepan-3-yl)oxy)-1-oxoisoindolin-2-yl)piperidine-2,6-dione

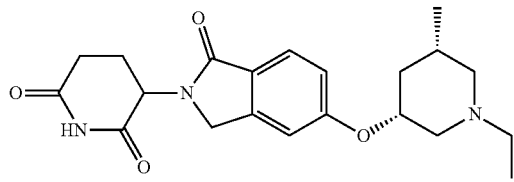

3-(5-(((3R,5S)-1-ethyl-5-methylpiperidin-3-yl)oxy)-1-oxoisoindolin-2-yl)piperidine-2,6-dione

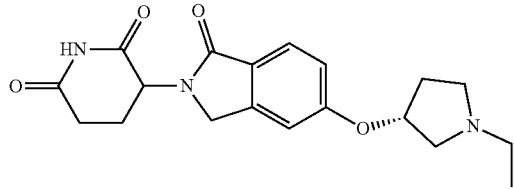

3-(5-(((R)-1-ethylpyrrolidin-3-yl)oxy)-1-oxoisoindolin-2-yl)piperidine-2,6-dione

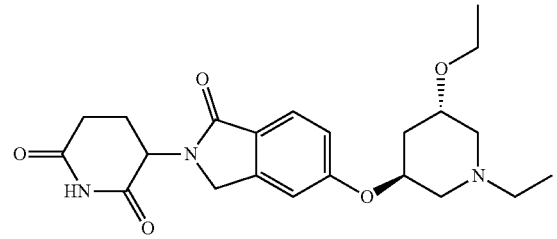

3-(5-(((3S,5S)-5-ethoxy-1-ethylpiperdin-3-yl)oxy)-1-oxoisoindolin-2-yl)piperidine-2,6-dione

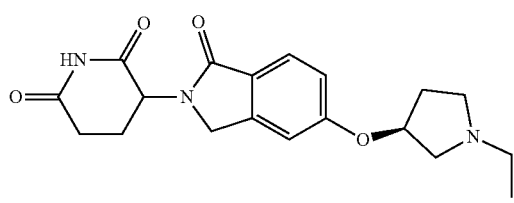

3-(5-(((S)-1-ethylpyrrolidin-3-yl)oxy)-1-oxoisoindolin-2-yl)piperidine-2,6-dione

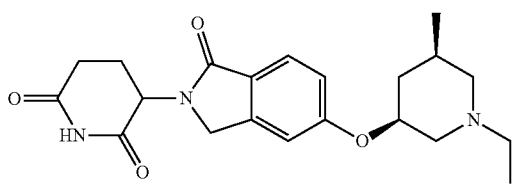

3-(5-(((3S,5R)-1-ethyl-5-methylpiperidin-3-yl)oxy)-1-oxoisoindolin-2-yl)piperidine-2,6-dione

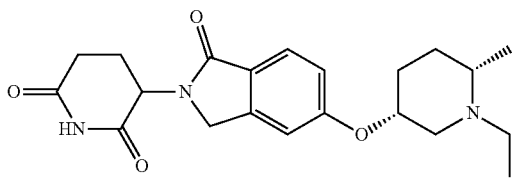

3-(5-(((3R,6S)-1-ethyl-6-methylpiperidin-3-yl)oxy)-1-oxoisoindolin-2-yl)piperidine-2,6-dione

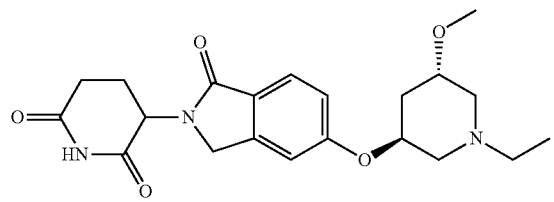

3-(5-(((3S,5S)-1-ethyl-5-methoxypiperidin-3-yl)oxy)-1-oxoisoindolin-2-yl)piperidine-2,6-dione

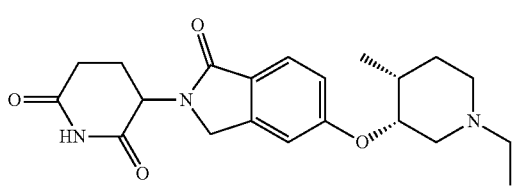

3-(5-(((3R,4R)-1-ethyl-4-methylpiperidin-3-yl)oxy)-1-oxoisoindolin-2-yl)piperidine-2,6-dione

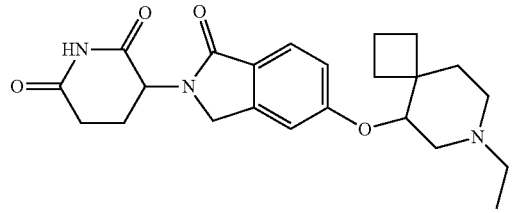

3-(5-(((R)-7-ethyl-7-azaspiro[3.5]nonan-5-yl)oxy)-1-oxoisoindolin-2-yl)piperidine-2,6-dione

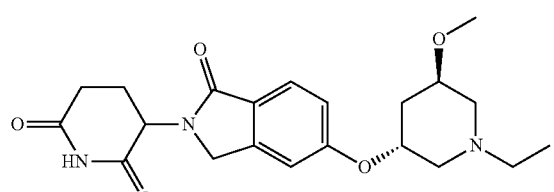

3-(5-(((3R,5R)-1-ethyl-5-methoxypiperidin-3-yl)oxy)-1-oxoisoindolin-2-yl)piperidine-2,6-dione

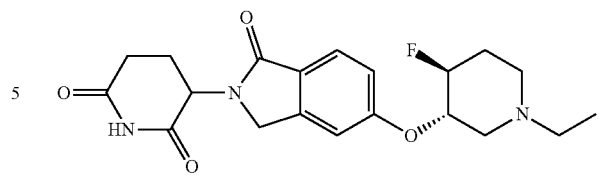

3-(5-(((3S,4S)-1-ethyl-4-fluoropiperidin-3-yl)oxy)-1-oxoisoindolin-2-yl)piperidine-2,6-dione

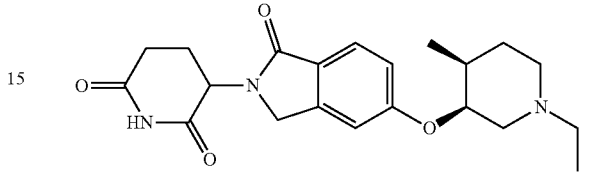

3-(5-(((3S,4S)-1-ethyl-4-methylpiperidin-3-yl)oxy)-1-oxoisoindolin-2-yl)piperidine-2,6-dione

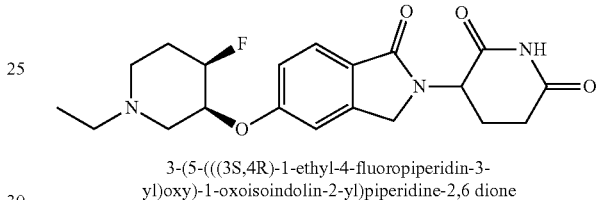

3-(5-(((3S,4R)-1-ethyl-4-fluoropiperidin-3-yl)oxy)-1-oxoisoindolin-2-yl)piperidine-2,6 dione

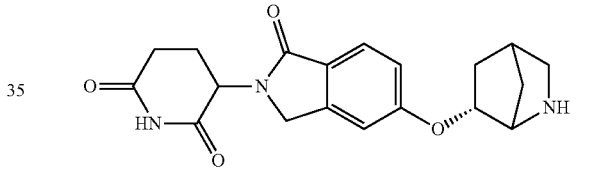

3-(5-((2-azabicyclo[2.2.1]heptan-6-yl)oxy)-1-oxoisoindolin-2-yl)piperidine-2,6-dione

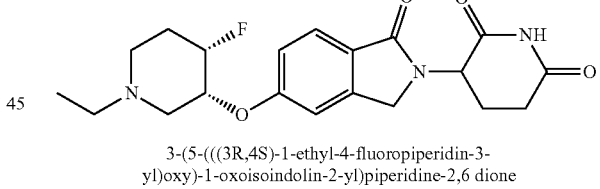

3-(5-(((3R,4S)-1-ethyl-4-fluoropiperidin-3-yl)oxy)-1-oxoisoindolin-2-yl)piperidine-2,6-dione

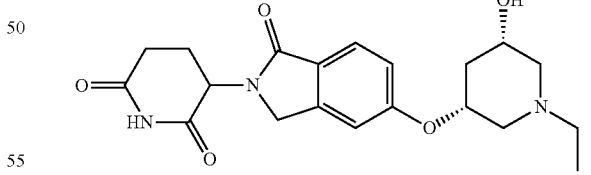

3-(5-(((3R,5S)-1-ethyl-5-hydroxypiperidin-3-oxy)-1-oxoisoindolin-2-yl)piperidine-2,6-dione

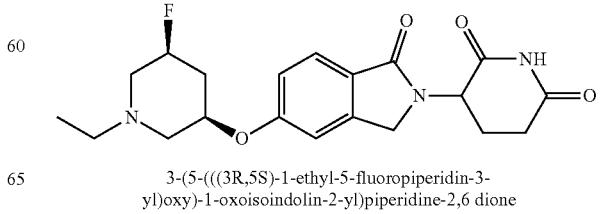

3-(5-(((3R,5S)-1-ethyl-5-fluoropiperidin-3-yl)oxy)-1-oxoisoindolin-2-yl)piperidine-2,6 dione -continued

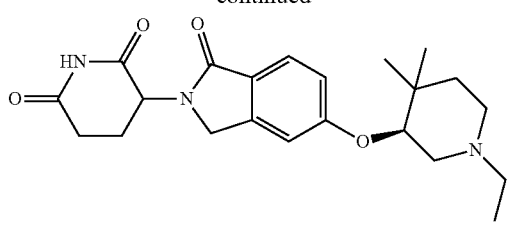

3-(5-(((S)-1-ethyl-4,4-dimethylpiperidin-3-oxy)-1-oxoisoindolin-2-yl)piperidine-2,6-dione

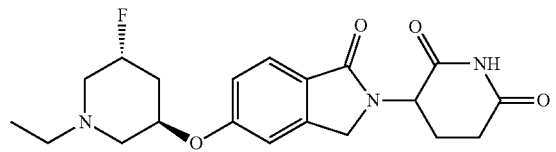

3-(5-(((3R,5R)-1-ethyl-5-fluoropiperidin-3-yl)oxy)-1-oxoisoindolin-2-yl)piperidine-2,6 dione

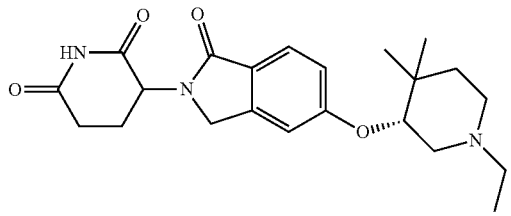

3-(5-(((R)-1-ethyl-4,4-dimethylpiperidin-3-oxy)-1-oxoisoindolin-2-yl)piperidine-2,6-dione

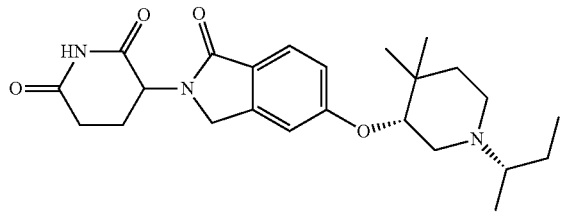

3-(5-(((R)-1-((S)-sec-butyl)-4,4-dimethylpiperidin-3-oxy)-1-oxoisoindolin-2-yl)piperidine-2,6-dione

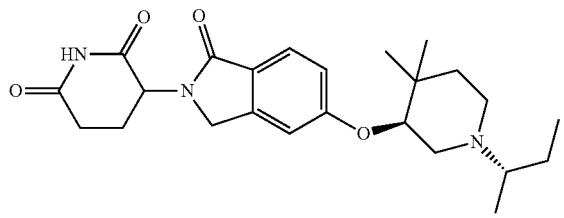

3-(5-(((S)-1-((S)-sec-butyl)-4,4-dimethylpiperidin-3-oxy)-1-oxoisoindolin-2-yl)piperidine-2,6-dione

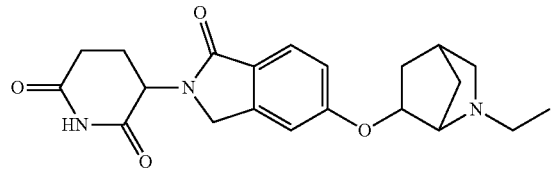

3-(5-((2-ethyl-2-azabicyclo[2.2.1]heptan-6-yl)oxy)-1-oxoisoindolin-2-yl)piperidine-2,6-dione -continued

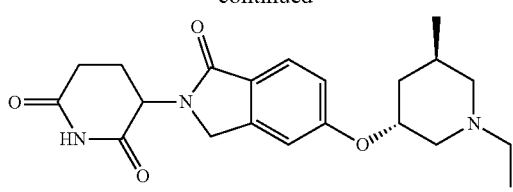

3-(5-(((3R,5R)-1-ethyl-5-methylpiperidin-3-yl)oxy)-1-oxoisoindolin-2-yl)piperidine-2,6-dione

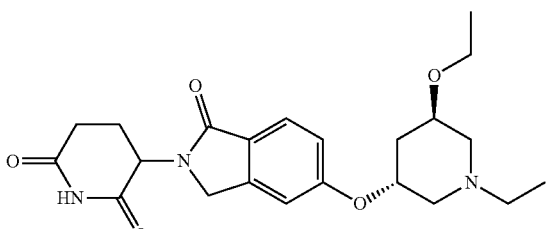

3-(5-(((3R,5R)-1-ethoxy-1-ethylpiperidin-3-yl)oxy)-1-oxoisoindolin-2-yl)piperidine-2,6-dione

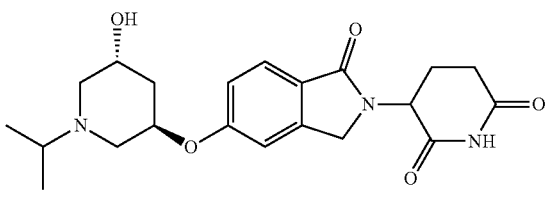

3-(5-(((3R,5R)-5-hydroxy-1-isopropylpiperidin-3-yl)oxy)-1-oxoisoindolin-2-yl)piperidine-2,6 dione

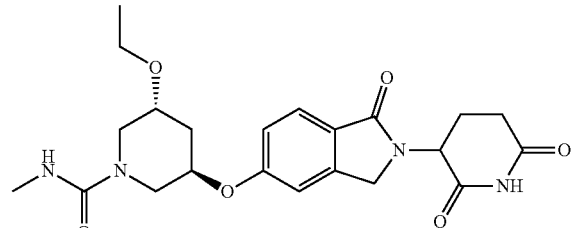

(3R,5R)-3-((2-(2,6-dioxopiperidin-3-yl)-1-oxoisoindolin-5-yl)oxy)-5-ethoxy-N-methylpiperidine-1-carboxamide

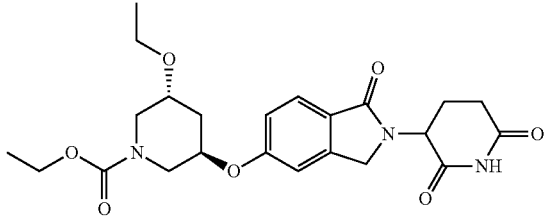

ethyl (3R,5R)-3-((2-(2,6-dioxopiperidin-3-yl)-1-oxoisoindolin-5-yl)oxy)-5-ethoxypiperidine-1-carboxylate

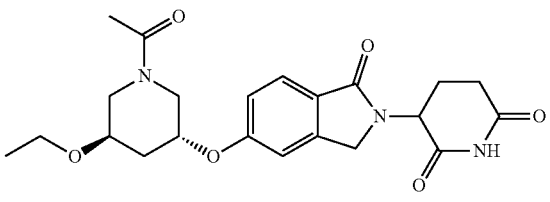

3-(5-(((3R,5R)-1-acetyl-5-ethoxypiperidin-3-yl)oxy)-1-oxoisoindolin-2-yl)piperidine-2,6 dione

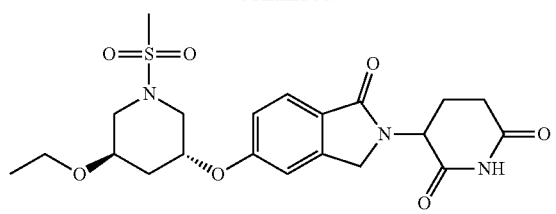

3-(5-(((3R,5R)-5-ethoxy-1-(methylsulfonyl)piperidine-3-yl)oxy)-1-oxoisoindolin-2-yl)piperidine-2,6 dione

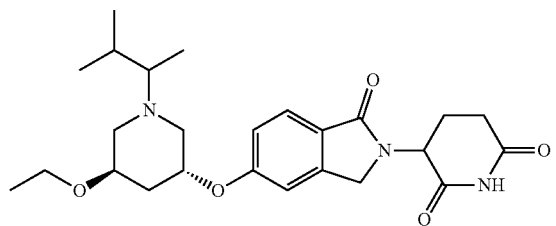

3-(5-(((3R,5R)-5-ethoxy-1-isobutylpiperidine-3-yl)oxy)-1-oxoisoindolin-2-yl)piperidine-2,6 dione

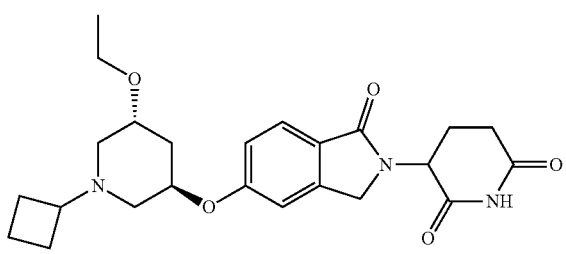

3-(5-(((3R,5R)-1-cyclobutyl-5-ethoxypiperidin-3-yl)oxy)-1-oxoisoindolin-2-yl)piperidine-2,6 dione

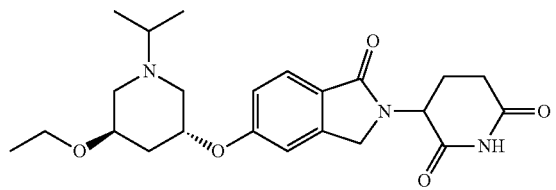

3-(5-(((3R,5R)-5-ethoxy-1-isobutylpiperidine-3-yl)oxy)-1-oxoisoindolin-2-yl)piperidine-2,6 dione

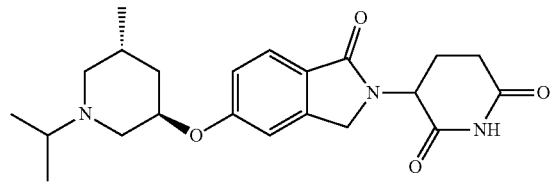

3-(5-(((3R,5R)-1-isopropyl-5-methylpiperidin-3-yl)oxy)-1-oxoisoindolin-2-yl)piperidine-2,6 dione

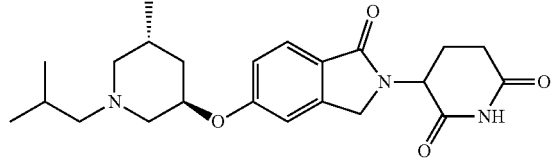

3-(5-(((3R,5R)-1-isobutyl-5-methylpiperidin-3-yl)oxy)-1-oxoisoindolin-2-yl)piperidine-2,6 dione

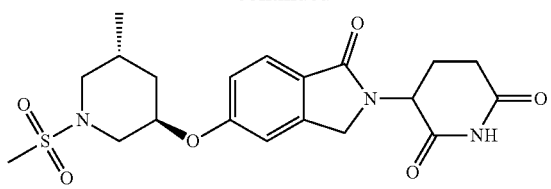

3-(5-(((3R,5R)-5-methyl-1-(methylsulfonyl)piperidin-3-yl)oxy)-1-oxoisoindolin-2-yl)piperidine-2,6 dione

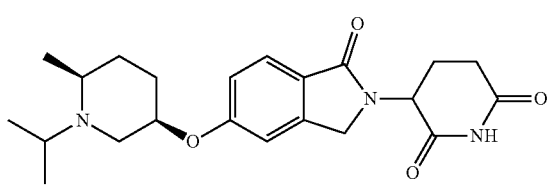

3-(5-(((3R,6S)-1-isopropyl-6-methylpiperidin-3-yl)oxy)-1-oxoisoindolin-2-yl)piperidine-2,6 dione

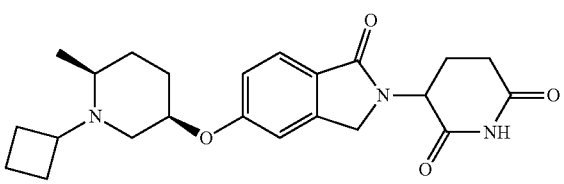

3-(5-(((3R,6S)-1-cyclobutyl-6-methylpiperidin-3-yl)oxy)-1-oxoisoindolin-2-yl)piperidine-2,6 dione

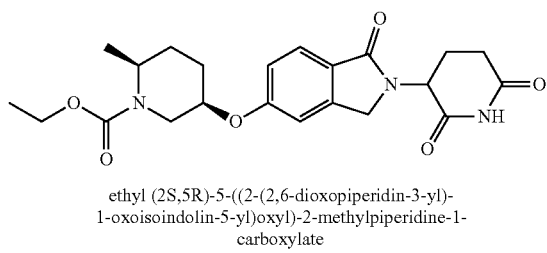

ethyl (2S,5R)-5-((2-(2,6-dioxopiperidin-3-yl)-1-oxoisoindolin-5-yl)oxy)-2-methylpiperidine-1-carboxylate

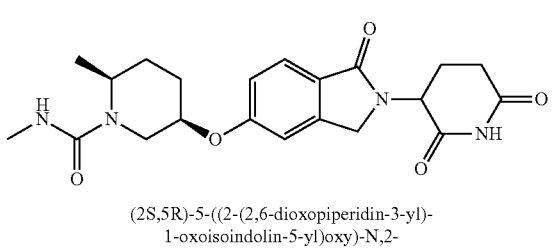

(2S,5R)-5-((2-(2,6-dioxopiperidin-3-yl)-1-oxoisoindolin-5-yl)oxy)-N,2-dimethylpiperidine-1-carboxamide

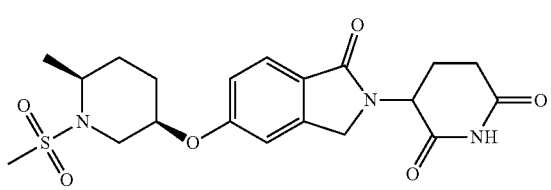

3-(5-(((3R,6S)-6-methyl-1-(methylsulfonyl)piperidin-3-yl)oxy)-1-oxoisoindolin-2-yl)piperidine-2,6-dione

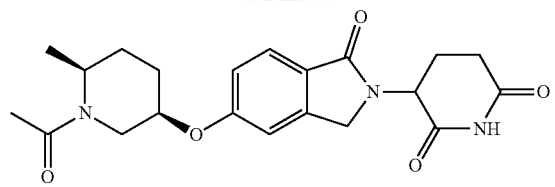

3-(5-(((3R,6S)-1-acetyl-6-methylpiperidin-3-yl)oxy)-1-oxoisoindolin-2-yl)piperidine-2,6-dione

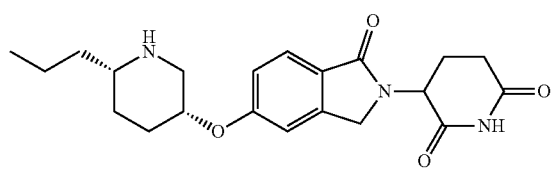

3-(1-oxo-5-(((3R,6S)-6-propylpiperidin-3-yl)oxy)-1-oxoisoindolin-2-yl)piperidine-2,6-dione

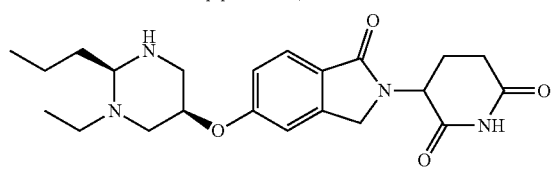

3-(5-(((3R,6S)-1-ethyl-6-propylpiperidin-3-yl)oxy)-1-oxoisoindolin-2-yl)piperidine-2,6-dione

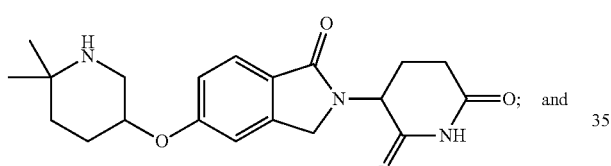

3-(5-((6,6-dimethylpiperidin-3-yl)oxy)-1-oxoisoindolin-2-yl)piperidine-2,6-dione

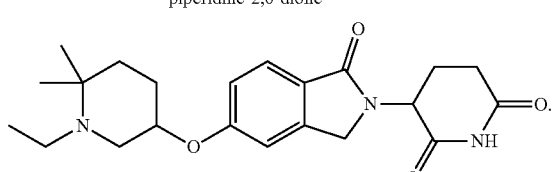

3-(5-((1-ethyl-6,6-dimethylpiperidin-3-yl)oxy)-1-oxoisoindolin-2-yl)piperidine-2,6-dione Embodiment 43. A compound of formula (I'), (I") or (I) according to any one of Embodiments 1 to 3 and 42, or a pharmaceutically acceptable salt, hydrate, solvate, prodrug, stereoisomer, or tautomer thereof, wherein the absolute configuration at the glutarimide stereocentre is S.

Embodiment 44. A compound of formula (I'), (I") or (I) according to any one of Embodiments 1 to 3 and 42, or a pharmaceutically acceptable salt, hydrate, solvate, prodrug, stereoisomer, or tautomer thereof, wherein the absolute configuration at the glutarimide stereocentre is R.

Embodiment 45. A compound of formula (I'), (I") or (I) according to any one of Embodiments 1 to 3, and 42 to 44, or a pharmaceutically acceptable salt, hydrate, solvate, prodrug, stereoisomer, or tautomer thereof, selected from:

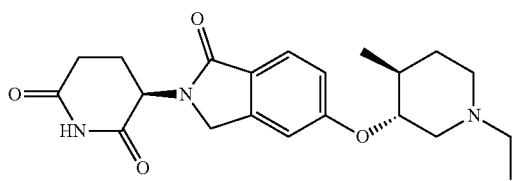

(R)-3-(5-(((3R,4S)-1-ethyl-4-methylpiperidin-3-yl)oxyl)-1-oxoisoindolin-2-yl)piperidine-2,6-dione

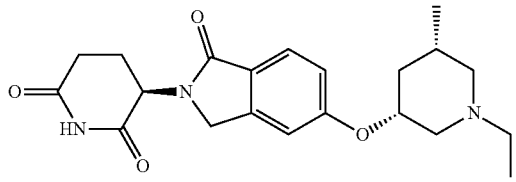

(R)-3-(5-(((3R,5S)-1-ethyl-5-methylpiperidin-3-yl)oxyl)-1-oxoisoindolin-2-yl)piperidine-2,6-dione

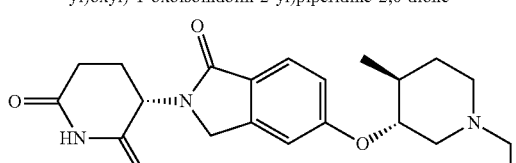

(S)-3-(5-(((3R,4S)-1-ethyl-4-methylpiperidin-3-yl)oxyl)-1-oxoisoindolin-2-yl)piperidine-2,6-dione

(S)-3-(5-(((3R,5S)-1-ethyl-5-methylpiperidin-3-yl)oxyl)-1-oxoisoindolin-2-yl)piperidine-2,6-dione

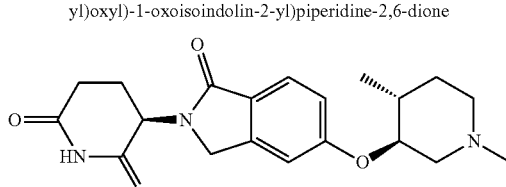

(R)-3-(5-(((3S,4R)-1-ethyl-4-methylpiperidin-3-yl)oxyl)-1-oxoisoindolin-2-yl)piperidine-2,6-dione

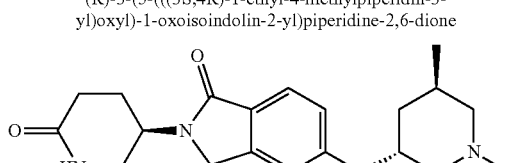

(R)-3-(5-(((3S,5R)-1-ethyl-5-methylpiperidin-3-yl)oxyl)-1-oxoisoindolin-2-yl)piperidine-2,6-dione

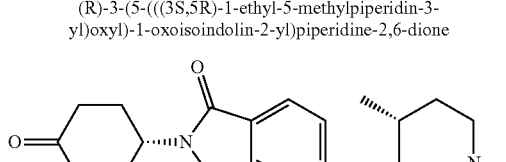

(S)-3-(5-(((3S,4R)-1-ethyl-4-methylpiperidin-3-yl)oxyl)-1-oxoisoindolin-2-yl)piperidine-2,6-dione -continued

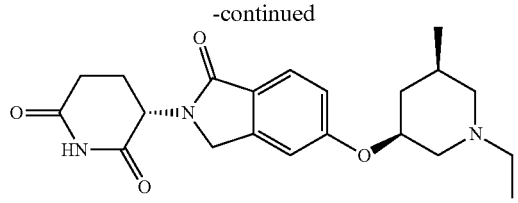

(S)-3-(5-(((3S,5R)-1-ethyl-5-methylpiperidin-3-yl)oxyl)-1-oxoisoindolin-2-yl)piperidine-2,6-dione

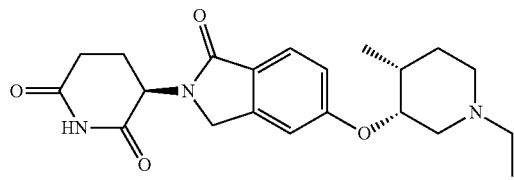

(R)-3-(5-(((3R,4R)-1-ethyl-4-methylpiperidin-3-yl)oxyl)-1-oxoisoindolin-2-yl)piperidine-2,6-dione

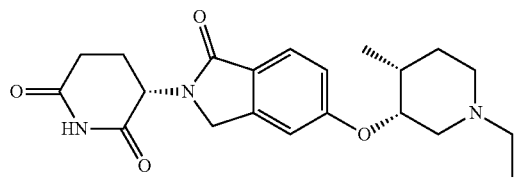

(S)-3-(5-(((3R,4R)-1-ethyl-4-methylpiperidin-3-yl)oxyl)-1-oxoisoindolin-2-yl)piperidine-2,6-dione

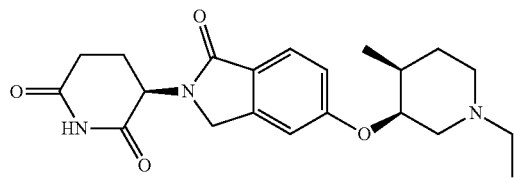

(R)-3-(5-(((3S,4S)-1-ethyl-4-methylpiperidin-3-yl)oxyl)-1-oxoisoindolin-2-yl)piperidine-2,6-dione

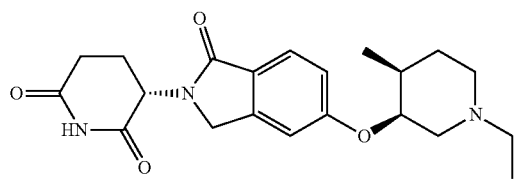

(S)-3-(5-(((3S,4S)-1-ethyl-4-methylpiperidin-3-yl)oxyl)-1-oxoisoindolin-2-yl)piperidine-2,6-dione

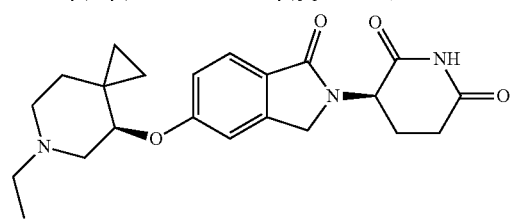

(S)-3-(5-(((R)-6-ethyl-6-azaspiro[2.5]octan-4-yl)oxy)-1-oxoisoindolin-2-yl)piperidine-2,6-dione

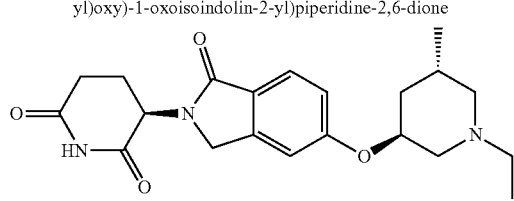

(S)-3-(5-(((3S,5S)-1-ethyl-5-methylpiperidin-3-yl)oxyl)-1-oxoisoindolin-2-yl)piperidine-2,6-dione -continued

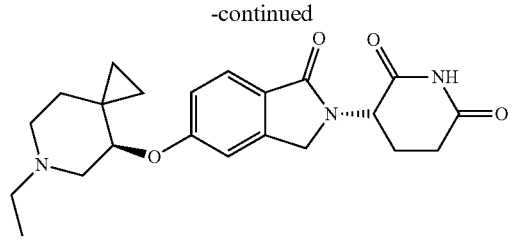

(S)-3-(5-(((R)-6-ethyl-6-azaspiro[2.5]octan-4-yl)oxy)-1-oxoisoindolin-2-yl)piperidine-2,6-dione

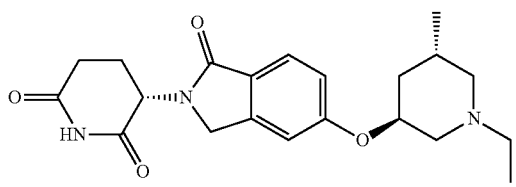

(S)-3-(5-(((3S,5S)-1-ethyl-5-methylpiperidin-3-yl)oxyl)-1-oxoisoindolin-2-yl)piperidine-2,6-dione

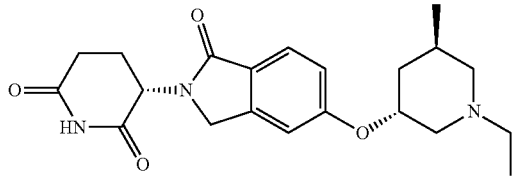

(S)-3-(5-(((3R,5R)-1-ethyl-5-methylpiperidin-3-yl)oxyl)-1-oxoisoindolin-2-yl)piperidine-2,6-dione

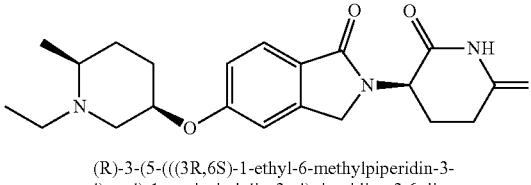

(R)-3-(5-(((3R,6S)-1-ethyl-6-methylpiperidin-3-yl)oxyl)-1-oxoisoindolin-2-yl)piperidine-2,6-dione

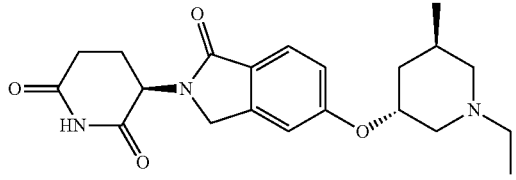

(R)-3-(5-(((3R,5R)-1-ethyl-5-methylpiperidin-3-yl)oxyl)-1-oxoisoindolin-2-yl)piperidine-2,6-dione

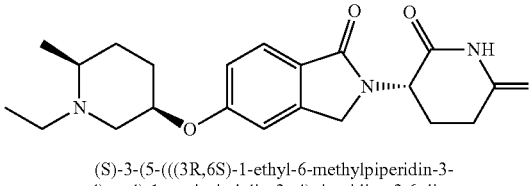

(S)-3-(5-(((3R,6S)-1-ethyl-6-methylpiperidin-3-yl)oxyl)-1-oxoisoindolin-2-yl)piperidine-2,6-dione

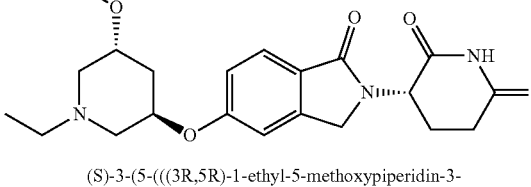

(S)-3-(5-(((3R,5R)-1-ethyl-5-methoxypiperidin-3-yl)oxyl)-1-oxoisoindolin-2-yl)piperidine-2,6-dione

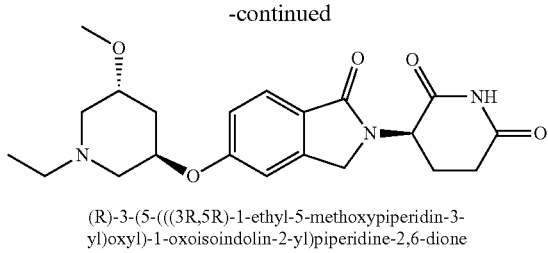

(R)-3-(5-(((3R,5R)-1-ethyl-5-methoxypiperidin-3-yl)oxy)-1-oxoisoindolin-2-yl)piperidine-2,6-dione Embodiment 46. A pharmaceutical composition comprising a therapeutically effective amount of a compound according to any one of the preceding Embodiments, or a pharmaceutically acceptable salt, hydrate, solvate, prodrug, stereoisomer, or tautomer thereof, and a pharmaceutically acceptable carrier or excipient.

Embodiment 47. A method of treating or preventing a disease or disorder in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 48. A method of degrading WIZ protein in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 49. A method of inhibiting WIZ protein expression in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 50. A method of inhibiting, reducing, or eliminating the activity of WIZ protein or WIZ protein expression, the method comprising administering to the subject a compound according to any one of Embodiments 1 to 45, or a pharmaceutically acceptable salt, hydrate, solvate, prodrug, stereoisomer, or tautomer thereof.

Embodiment 51. A method of inducing or promoting fetal hemoglobin in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 52. A method of reactivating fetal hemoglobin production or expression in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 53. A method of increasing fetal hemoglobin expression in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 54. A method of treating a hemoglobinopathy, e.g., a beta-hemoglobinopathy, in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 55. A method of treating a sickle cell disease in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 56. A method of treating beta-thalassemia in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 57. A method of treating a disease or disorder that is affected by the modulation of WIZ protein levels comprising administering to the patient in need thereof a compound according to any one of Embodiments 1 to 45, or a pharmaceutically acceptable salt, hydrate, solvate, prodrug, stereoisomer, or tautomer thereof.

Embodiment 58. A method of treating or preventing a disorder that is affected by the reduction of WIZ protein levels, in a subject in need thereof, the method comprising administering to the subject a therapeutically effective amount of a compound according to any one of Embodiments 1 to 45, or a pharmaceutically acceptable salt, hydrate, solvate, prodrug, stereoisomer, or tautomer thereof.

Embodiment 59. A method for reducing WIZ protein levels in a subject comprising the step of administering to a subject in need thereof a therapeutically effective amount of a compound according to any one of Embodiments 1 to 45, or a pharmaceutically acceptable salt, hydrate, solvate, prodrug, stereoisomer, or tautomer thereof.

Embodiment 60. A compound according to any one of Embodiments 1 to 45, or a pharmaceutically acceptable salt, hydrate, solvate, prodrug, stereoisomer, or tautomer thereof, for use as a medicament.

Embodiment 61. A compound according to any one of Embodiments 1 to 45, or a pharmaceutically acceptable salt, hydrate, solvate, prodrug, stereoisomer, or tautomer thereof, for use in the treatment of a disease or disorder selected from sickle cell disease and beta-thalassemia.

Embodiment 62. A compound according to any one of Embodiments 1 to 45, or a pharmaceutically acceptable salt, hydrate, solvate, prodrug, stereoisomer, or tautomer thereof, for use in treating or preventing a disease or disorder in a subject in need thereof.

Embodiment 63. A compound according to any one of Embodiments 1 to 45, or a pharmaceutically acceptable salt, hydrate, solvate, prodrug, stereoisomer, or tautomer thereof, for use in treating or preventing a disorder that is affected by the reduction of WIZ protein levels, in a subject in need thereof.

Embodiment 64. A compound according to any one of Embodiments 1 to 45, or a pharmaceutically acceptable salt, hydrate, solvate, prodrug, stereoisomer, or tautomer thereof, for use in inhibiting WIZ protein expression in a subject in need thereof.

Embodiment 65. A compound according to any one of Embodiments 1 to 45, or a pharmaceutically acceptable salt, hydrate, solvate, prodrug, stereoisomer, or tautomer thereof, for use in degrading WIZ protein in a subject in need thereof.

Embodiment 66. A compound according to any one of Embodiments 1 to 45, or a pharmaceutically acceptable salt, hydrate, solvate, prodrug, stereoisomer, or tautomer thereof, for use in inhibiting, reducing, or eliminating the activity of WIZ protein or WIZ protein expression in a subject in need thereof.

Embodiment 67. A compound according to any one of Embodiments 1 to 45, or a pharmaceutically acceptable salt, hydrate, solvate, prodrug, stereoisomer, or tautomer thereof, for use in inducing or promoting fetal hemoglobin in a subject in need thereof.

Embodiment 68. A compound according to any one of Embodiments 1 to 45, or a pharmaceutically acceptable salt, hydrate, solvate, prodrug, stereoisomer, or tautomer thereof, for use in reactivating fetal hemoglobin production or expression in a subject in need thereof.

Embodiment 69. A compound according to any one of Embodiments 1 to 45, or a pharmaceutically acceptable salt, hydrate, solvate, prodrug, stereoisomer, or tautomer thereof, for use in increasing fetal hemoglobin expression in a subject in need thereof.

Embodiment 70. A compound according to any one of Embodiments 1 to 45, or a pharmaceutically acceptable salt, hydrate, solvate, prodrug, stereoisomer, or tautomer thereof, for use in treating a hemoglobinopathy in a subject in need thereof.

Embodiment 71. A compound according to any one of Embodiments 1 to 45, or a pharmaceutically acceptable salt, hydrate, solvate, prodrug, stereoisomer, or tautomer thereof, for use in treating a sickle cell disease in a subject in need thereof.

Embodiment 72. A compound according to any one of Embodiments 1 to 45, or a pharmaceutically acceptable salt, hydrate, solvate, prodrug, stereoisomer, or tautomer thereof, for use in treating beta-thalassemia in a subject in need thereof.

Embodiment 73. Use of a compound according to any one of Embodiments 1 to 45, or a pharmaceutically acceptable salt, hydrate, solvate, prodrug, stereoisomer, or tautomer thereof, in the manufacture of a medicament for treating a disease or disorder that is affected by the reduction of WIZ protein levels, inhibition of WIZ protein expression or degradation of WIZ protein.

Embodiment 74. Use of a compound according to any one of Embodiments 1 to 45, or a pharmaceutically acceptable salt, hydrate, solvate, prodrug, stereoisomer, or tautomer thereof, in the manufacture of a medicament for treating a disease or disorder that is affected by inducing or promoting fetal hemoglobin.

Embodiment 75. Use of a compound according to any one of Embodiments 1 to 45, or a pharmaceutically acceptable salt, hydrate, solvate, prodrug, stereoisomer, or tautomer thereof, in the manufacture of a medicament for treating a disease or disorder that is affected by reactivating fetal hemoglobin production or expression.

Embodiment 76. Use of a compound according to any one of Embodiments 1 to 45, or a pharmaceutically acceptable salt, hydrate, solvate, prodrug, stereoisomer, or tautomer thereof, in the manufacture of a medicament for treating a disease or disorder that is affected by increasing fetal hemoglobin expression.

Embodiment 77. The use according to any one of Embodiments 73 to 76, wherein the disease or disorder is selected from sickle cell disease and beta-thalassemia.

Embodiment 78. Use of a compound according to any one of Embodiments 1 to 45, or a pharmaceutically acceptable salt, hydrate, solvate, prodrug, stereoisomer, or tautomer thereof, in the manufacture of a medicament for treating a disease or disorder that is affected by the reduction of WIZ protein levels, inhibition of WIZ protein expression or degradation of WIZ protein.

Embodiment 79. Use of a compound according to any one of Embodiments 1 to 45, or a pharmaceutically acceptable salt, hydrate, solvate, prodrug, stereoisomer, or tautomer thereof, in the manufacture of a medicament for treating a disease or disorder that is affected by inducing fetal hemoglobin.

Embodiment 80. Use of a compound according to any one of Embodiments 1 to 45, or a pharmaceutically acceptable salt, hydrate, solvate, prodrug, stereoisomer, or tautomer thereof, in the manufacture of a medicament for treating a disease or disorder that is affected by reactivating fetal hemoglobin production or expression.

Embodiment 81. Use of a compound according to any one of Embodiments 1 to 45, or a pharmaceutically acceptable salt, hydrate, solvate, prodrug, stereoisomer, or tautomer thereof, in the manufacture of a medicament for treating a disease or disorder that is affected by increasing fetal hemoglobin expression.

Embodiment 82. The use according to any one of Embodiments 78 to 81, wherein the disease or disorder is selected from sickle cell disease and beta-thalassemia.

Embodiment 83. Use of a compound according to any one of Embodiments 1 to 45, or a pharmaceutically acceptable salt, hydrate, solvate, prodrug, stereoisomer, or tautomer thereof, in the treatment of a disease or disorder that is affected by the reduction of WIZ protein levels, inhibition of WIZ protein expression or degradation of WIZ protein.

Embodiment 84. Use of a compound according to any one of Embodiments 1 to 45, or a pharmaceutically acceptable salt, hydrate, solvate, prodrug, stereoisomer, or tautomer thereof, in the treatment of a disease or disorder that is affected by inducing fetal hemoglobin, reactivating fetal hemoglobin production or expression, or increasing fetal hemoglobin expression.

Embodiment 85. The use according to any one of Embodiments 83 and 84, wherein the disease or disorder is selected from sickle cell disease and beta-thalassemia.

Embodiment 86. A pharmaceutical combination comprising a compound according to any one of Embodiments 1 to 45, or a pharmaceutically acceptable salt, hydrate, solvate, prodrug, stereoisomer, or tautomer thereof, and one or more additional therapeutic agent(s).

Embodiment 87. A compound of formula (I) or a pharmaceutically acceptable salt, hydrate, solvate, prodrug, stereoisomer, or tautomer thereof, for use as a medicament, wherein:

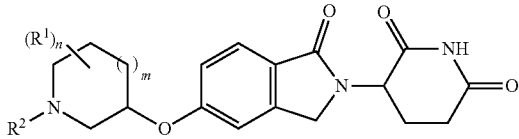

(I)

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring (e.g., $C_1$-$C_3$alkylene bridging ring);

$R^2$ is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, and $C_1$-$C_{10}$alkyl, wherein the $C_3$-$C_{11}$cycloalkyl, $C_2$-$C_6$alkynyl, and $C_1$-$C_{10}$alkyl are each independently substituted with 0-5 (or 0-4, 0-3, 0-2, 0-1) occurrences of $R^3$;

each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

n is 0, 1, 2, 3, or 4; and m is 0, 1 or 2.

Embodiment 88. A compound of formula (I), or a pharmaceutically acceptable salt, hydrate, solvate, prodrug, stereoisomer, or tautomer thereof, for use in a method defined by any one of Embodiments 61 to 72, wherein the compound of formula (I) is defined according to Embodiment 87.

Embodiment 89. A method as defined by any one of Embodiments 47 to 59, wherein the compound is defined according to Embodiment 87.

Embodiment 90. Use of a compound of formula (I), or a pharmaceutically acceptable salt, hydrate, solvate, prodrug, stereoisomer, or tautomer thereof, in a method as defined by any one of Embodiments 73 to 85, wherein the compound of formula (I) is defined according to Embodiment 87.

Depending on the choice of the starting materials and procedures, the compounds can be present in the form of one of the possible isomers or as mixtures thereof, for example as pure optical isomers, or as isomer mixtures, such as racemates and diastereomeric mixtures, depending on the number of asymmetric centres. The disclosure is meant to include all such possible isomers, including racemic mixtures, enantiomerically enriched mixtures, diastereomeric mixtures and optically pure forms. Optically active (R)- and (S)-isomers may be prepared using chiral synthons or chiral reagents, or resolved using conventional techniques. If the compound contains a disubstituted or trisubstituted cycloalkyl, the cycloalkyl substituent(s) may have a cis- or trans-configuration. The disclosure includes cis and trans configurations of substituted cycloalkyl groups as well as mixtures thereof. All tautomeric forms are also intended to be included. In particular, where a heteroaryl ring containing N as a ring atom is 2-pyridone, for example, tautomers where the carbonyl is depicted as a hydroxy (e.g., 2-hydroxypyridine) are included.

Pharmaceutically Acceptable Salts

As used herein, the terms "salt" or "salts" refers to an acid addition or base addition salt of a compound of the disclosure. "Salts" include in particular "pharmaceutically acceptable salts". The term "pharmaceutically acceptable salts" refers to salts that retain the biological effectiveness and properties of the compounds of this disclosure and, which typically are not biologically or otherwise undesirable. The compounds of the disclosure may be capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, formic acid, trifluoroacetic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the disclosure provides compounds in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the disclosure provides compounds in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Preferably, pharmaceutically acceptable salts of compounds of formulae (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), and (ID-ii) are acid addition salts.

Isotopically Labelled Compounds

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, sulfur, fluorine, chlorine and iodine, such as $^2$H, $^3$H, $^{11}$C, $^{13}$C, $^{14}$C, $^{18}$O, $^{15}$N, $^{18}$F, $^{17}$O, $^{18}$O, $^{35}$S, $^{36}$Cl, $^{123}$I, $^{124}$I, $^{125}$I respectively. The disclosure includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F compound may be particularly desirable for PET or SPECT studies. Isotopically-labeled compounds of formulae (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), and (ID-ii) can generally be prepared by conventional techniques known to those skilled in the art or by processes analogous to those described in the accompanying Examples and General Schemes (e.g., General Schemes 5a and 5b) using an appropriate isotopically-labeled reagent in place of the non-labeled reagent previously employed.

In one embodiment of any aspect of the present disclosure, the hydrogens in the compound of formula (I'), (I") or (I) are present in their normal isotopic abundances. In a another embodiment, the hydrogens are isotopically enriched in deuterium (D), and in a particular embodiment of the invention the hydrogen(s) at the glutarimide portion in compounds of Formula (I) are enriched in D, for example,

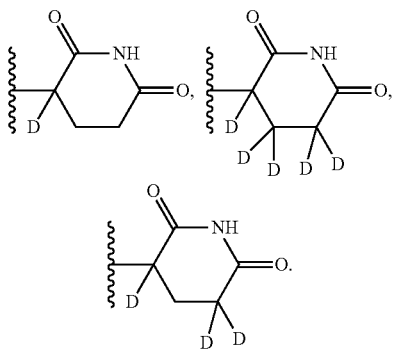

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula ((I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the disclosure include those wherein the solvent of crystallization may be isotopically substituted, e.g., D$_2$O, d$_6$-acetone, d$_6$-DMSO.

Compounds of the disclosure, e.g., compounds of formulae (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), and (ID-ii) that contain groups capable of acting as donors and/or acceptors for hydrogen bonds may be capable of forming co-crystals with suitable co-crystal formers. These co-crystals may be prepared from compounds of formulae (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), and (ID-ii) by known co-crystal forming procedures. Such procedures include grinding, heating, co-subliming, co-melting, or contacting in solution compounds of formulae (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), and (ID-ii) with the co-crystal former under crystallization conditions and isolating co-crystals thereby formed. Suitable co-crystal formers include those described in WO 2004/078163.

All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed.

Any asymmetric center (e.g., carbon or the like) of the compound(s) of the disclosure can be present in racemic or enantiomerically enriched, for example the (R)-, (S)- or (R,S)-configuration. In certain embodiments, for example, as a mixture of enantiomers, each asymmetric center is present in at least 10% enantiomeric excess, at least 20% enantiomeric excess, at least 30% enantiomeric excess, at least 40% enantiomeric excess, at least 50 enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. In certain embodiments, for example, in enantiomerically enriched form, each asymmetric center is present in at least 50% enantiomeric excess, at least 60% enantiomeric excess, at least 70% enantiomeric excess, at least 80 enantiomeric excess, at least 90% enantiomeric excess, at least 95% enantiomeric excess, or at least 99% enantiomeric excess. Thus, compounds of the disclosure can be present in a racemic mixture or in enantiomerically enriched form or in an enantiopure form or as a mixture of diastereoisomers.

In the compound formulae in any one of the aspects, Embodiments or claims of the present application the term "⟋" on a C-sp$^3$ indicates the absolute stereochemistry, either (R) or (S). In the compound formulae in any one of the aspects, Embodiments or claims of the present application the term "⟍" on a C-sp$^3$ indicates the absolute stereochemistry, either (R) or (S). In the compound formulae in any one of the aspects, Embodiments or claims of the present application the term "⟋" on a C-sp$^3$ represents a covalent bond wherein the stereochemistry of the bond is not defined. This means that the term "~" on a C-sp³ comprises an (S) configuration or an (R) configuration of the respective chiral centre or a mixture thereof. Therefore, mixtures of stereoisomers, e.g., mixtures of enantiomers, such as racemates, and/or mixtures of diastereoisomers are encompassed by the present disclosure.

Accordingly, as used herein a compound of the disclosure can be in the form of one of the possible stereoisomers, rotamers, atropisomers, tautomers or mixtures thereof, for example, as substantially pure geometric (cis or trans) stereoisomers, diastereomers, optical isomers, racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the disclosure or of intermediates can be resolved into the optical isomers (enantiomers) by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'p-toluoyl tartaric acid, mandelic acid, malic acid or camphor-10-sulfonic acid. Racemic compounds of the disclosure or racemic intermediates can also be resolved by chiral chromatography, e.g., high pressure liquid chromatography (HPLC) using a chiral adsorbent.

Furthermore, the compounds of the disclosure, including their salts, can also be obtained in the form of their hydrates, or include other solvents used for their crystallization. The compounds of the disclosure may inherently or by design form solvates with pharmaceutically acceptable solvents (including water); therefore, it is intended that the disclosure embrace both solvated and unsolvated forms. The term "solvate" refers to a molecular complex of a compound of the disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The presence of solvates can be identified by a person of skill in the art with tools such as NMR.

The compounds of the disclosure, including salts, hydrates and solvates thereof, may inherently or by design form polymorphs.

In compounds of the present disclosure, as exemplified by formula (I), the stereocenter at the 3-position of the glutarimide moiety (marked with a *) may be prone to epimerization under basic conditions.

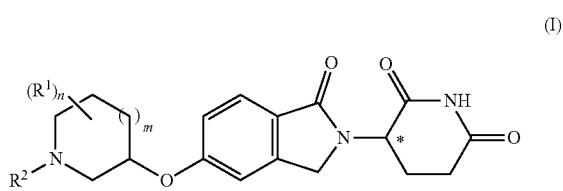

(I)

Separation of the diastereoisomers (or enantiomers as the case may be) at this position can be achieved according to known chiral separation techniques in the art, e.g., by chrial SFC. For example, separation may be carried out according to Example 65.

In one embodiment of the compounds of the present disclosure, the absolute configuration at the glutarimide stereocentre (marked with a * above) is S.

In another embodiment of the compounds of the present disclosure, the absolute configuration at the glutarimide stereocentre (marked with a * above) is R.

In one embodiment, there is provided a compound as described in any one of the Examples or according to any of Embodiments 1 to 42, wherein the absolute configuration at the glutarimide stereocentre (marked with a * above) is S.

In another embodiment, there is provided a compound as described in any one of the Examples or according to any of Embodiments 1 to 42, wherein the absolute configuration at the glutarimide stereocentre (marked with a * above) is R.

Methods of Making

The compounds of the disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art.

Generally, the compounds of formula (I'), (I"), or (I) can be prepared according to the Schemes provided infra.

General scheme 1

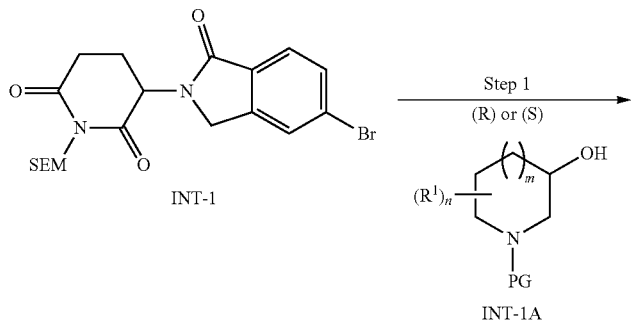

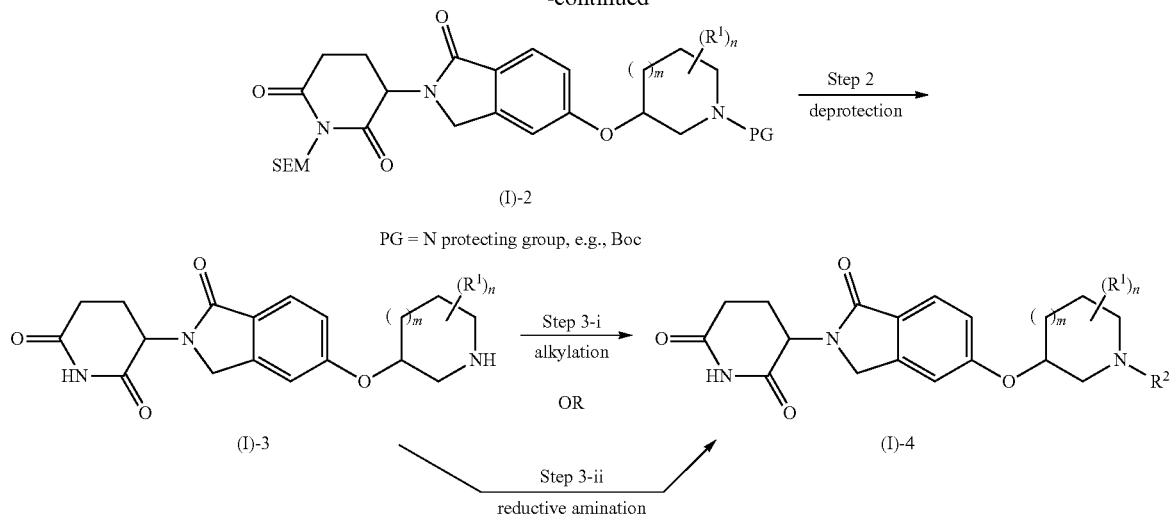

PG = N protecting group, e.g., Boc

The starting materials for the above reaction scheme are commercially available or can be prepared according to methods known to one skilled in the art or by methods disclosed herein. In general, the compounds of the disclosure are prepared in the above reaction Scheme 1 as follows:

A metallaphotoredox reaction, such as an iridium (Ir)-catalysed photoredox coupling of INT-1 with an alcohol partner of formula INT-1A in the presence of a polar solvent, such as acetonitrile (ACN) can provide the cross-coupled ether product (I)-2 in Step 1. Removal of the protecting group (e.g., Boc) under acidic conditions can provide the free amine (I)-3 (Step 2), which can then be converted to (I)-4 via an alkylation reaction (Step 3-i) with an appropriate alkyl bromide or alkyl mesylate in the presence of an amine base and polar solvent, such as diisopropylethylamine (DIPEA) and acetonitrile (ACN) or dimethylformamide (DMF), or a reductive amination (Step 3-ii) with an appropriate aldehyde in the presence of a borohydride reagent, such as sodium borohydride acetate. For Scheme 1, $R^1$, $R^2$, m and n are as defined herein, in particular according to any one of enumerated Embodiments 1 to 45.

The starting materials for the above reaction scheme are commercially available or can be prepared according to methods known to one skilled in the art or by methods disclosed herein. In general, the compounds of the disclosure, especially compounds comprising non-linear $R^1$ and/or $R^2$ groups are prepared in the above reaction Scheme 2 as follows: The compound of (I)-3 can be converted into (I)-5 via an alkylation reaction (Step 3-iii) with an appropriate non-linear alkyl iodide or mesylate in the presence of a base, such as $K_2CO_3$, and a polar solvent, such as dimethylacetamide (DMA), or (I)-6 via a reductive amination (Step 3-iv) with an appropriate ketone in the presence of a borohydride reagent, such as sodium borohydride acetate. For Scheme 2, $R^1$, $R^2$, m and n are as defined herein, in particular according to any one of enumerated Embodiments 1 to 45.

General scheme 2

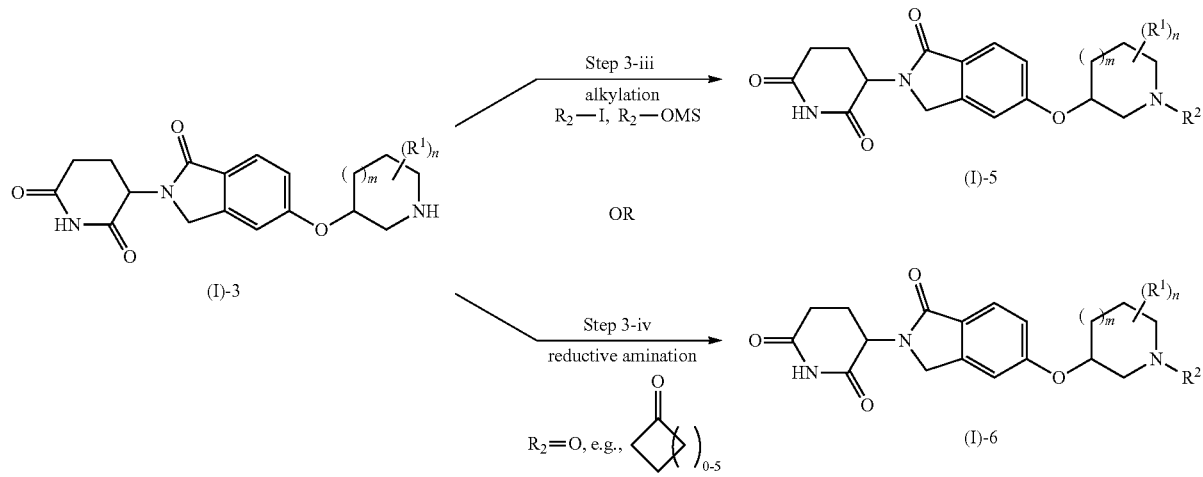

General scheme 3

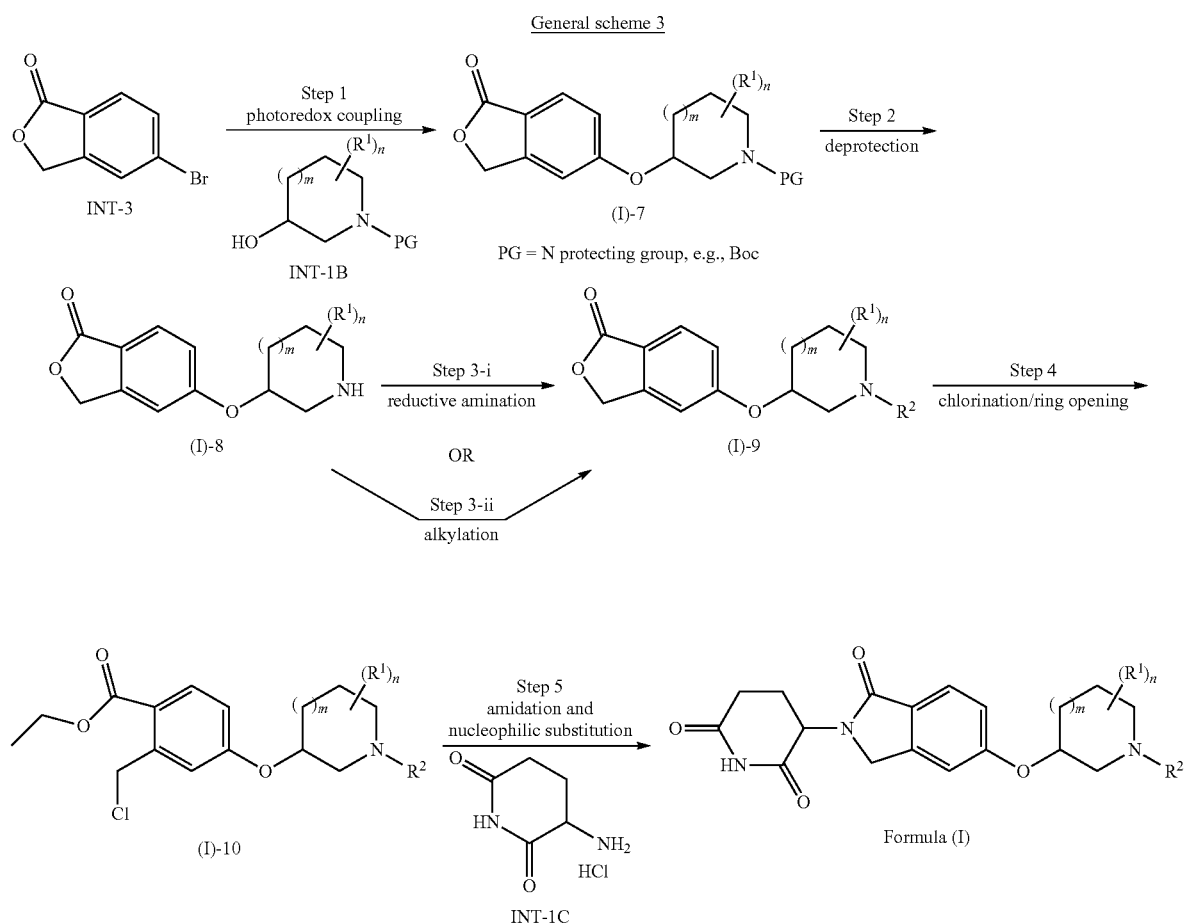

PG = N protecting group, e.g., Boc

The starting materials for the above reaction scheme are commercially available or can be prepared according to methods known to one skilled in the art or by methods disclosed herein. In general, the compounds of the disclosure are prepared in the above reaction Scheme 3 as follows:

A metallaphotoredox reaction, such as an iridium (Ir)-catalysed photoredox coupling, of (INT-3) with an alcohol partner of formula (INT-1B) in the presence of a polar solvent, such as acetonitrile (ACN) can provide the cross-coupled ether product (I)-7 in Step 1. Removal of the protecting group (e.g., Boc) under acidic conditions, can provide the free amine (I)-8 (Step 2), which can then be converted to (I)-9 via reductive amination (Step 3-i) with an appropriate aldehyde in the presence of a borohydride reagent, such as sodium borohydride acetate. Alternatively, (I)-8 may be converted into (I)-9 via an alkylation reaction (Step 3-ii) with an appropriate alkyl mesylate or halide (e.g., iodide) in the presence of an amine base and polar solvent, such as diisopropylethylamine (DIPEA) and dimethylformamide (DMF) as described in general schemes 1 and 2. Chlorination with a suitable agent, such as $SOCl_2$ and ring opening of lactone (I)-9 affords (I)-10. Subsequent ring closing by amidation and nucleophilic substitution (lectern formation) using INT-IC under basic conditions yields the final product of Formula (I), Formula (I') or Formula (I"). For Scheme 3, $R^1$, $R^2$, m and n are as defined herein, in particular according to any one of enumerated Embodiments 1 to 45.

General Schemes 4a, 4b and 4c: Deuterated Compounds of the Disclosure

Scheme 4a

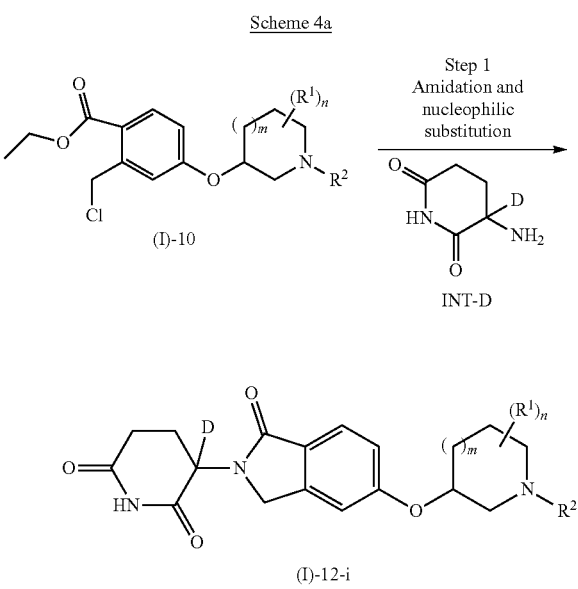

Scheme 4b

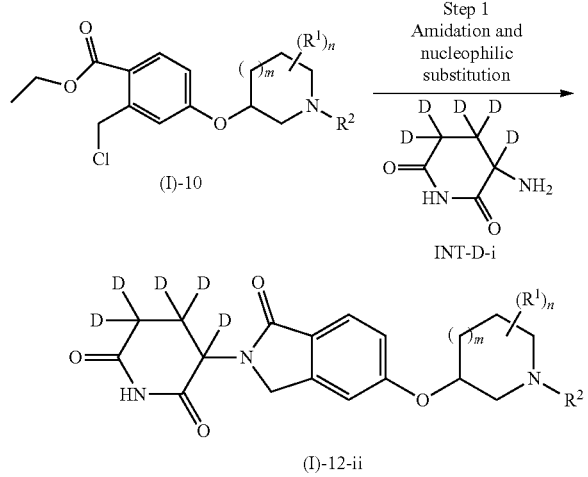

Compound (I)-10 can be prepared according to general scheme 3. Subsequent ring closing by amidation and nucleophilic substitution using deuterated INT-D (prepared according to WO 2012/068512) or deuterated INT-D-i (prepared according to WO 2012/079022) under basic conditions yields the final deuterated compounds of Formula (I), Formula (I'), or Formula (I''), i.e. (I)-12-i and (I)-12-ii, wherein $R^1$, $R^2$, m and n are as defined according to any one of enumerated Embodiments 1 to 45.

Scheme 4c

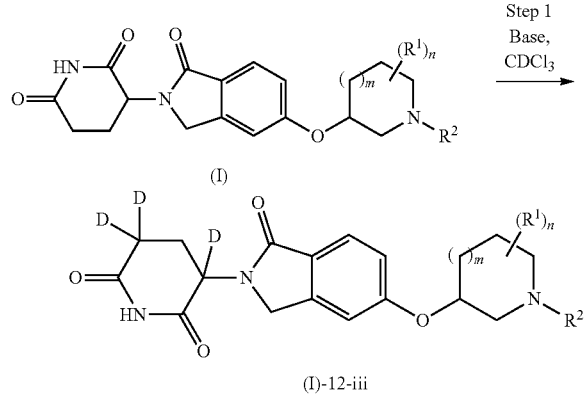

Compound (I) can be prepared according to any of general schemes 1 to 3. Base mediated hydrogen-deuterium exchange in a deuterated solvent, such as CDCl$_3$ yields the final deuterated compounds of Formula (I), Formula (I') or Formula (I''), i.e. (I)-12-iii, wherein $R^1$, $R^2$, m and n are as defined according to any one of enumerated Embodiments 1 to 45.

Thus, in an embodiment, the disclosure provides a compound of formula (I)-12-i, (I)-12-ii or (I)-12-iii, wherein $R^1$, $R^2$, m and n are as defined according to any one of enumerated Embodiments 1 to 45.

In an embodiment, there is provided a compound of formula (X') or a salt thereof, wherein:

(X')

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;

$R^{2'}$ is selected from a nitrogen protecting group, e.g., Boc, hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, $C_1$-$C_{10}$alkyl, —SO$_2$R$^6$, —C(=O)—R$^{2a}$, —C(=O)—OR$^{2a}$, and —C(=O)NR$^{2b}$R$^{2c}$;

wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

$R^{2a}$ is selected from $C_1$-$C_6$alkyl, and 4- to 6-membered heterocyclyl comprising 1-2 heteroatoms independently selected from N, O, and S;

$R^{2b}$ and $R^{2c}$ are each independently selected from hydrogen, and $C_1$-$C_6$alkyl;

each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

$R^6$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, e.g., $R^6$ is selected from $C_3$-$C_8$cycloalkyl, and $C_1$-$C_6$alkyl;

n is 0, 1, 2, 3, 4, or 5; and m is 0, 1 or 2.

In an embodiment, there is provided a compound of formula (X) or a salt thereof, wherein:

(X)

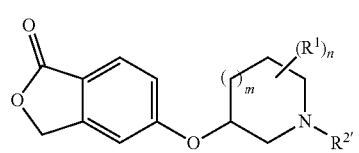

each $R^1$ is independently selected from hydrogen, $C_1$-$C_6$alkyl, hydroxyl, halo, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non adjacent carbon atoms together with the non-adjacent carbon atoms to which they are attached form a bridging ring;

$R^{2'}$ is selected from a nitrogen protecting group, e.g., Boc, hydrogen, $C_3$-$C_{11}$cycloalkyl, 4 to 11-membered heterocyclyl comprising 1-2 heteroatoms independently selected from N, O, and S, $C_1$-$C_6$haloalkyl, $C_2$-$C_6$alkenyl, and $C_1$-$C_{10}$alkyl, wherein the $C_3$-$C_{11}$cycloalkyl and $C_1$-$C_{10}$alkyl are each independently substituted with 0-5 occurrences of $R^3$;

each $R^3$ is independently selected from $C_1$-$C_6$alkoxyl, halo, $C_6$-$C_{10}$aryl, 5- to 10 membered heteroaryl comprising 1-4 heteroatoms independently selected from N, O, and S, 4- to 11-membered heterocyclyl comprising 1-2 heteroatoms independently selected from N, O, and S, $C_3$-$C_8$cycloalkyl, and $C_2$-$C_6$alkynyl, wherein the $C_2$-$C_6$alkynyl is substituted with 0-1 occurrence of $R^4$, and wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

n is 0, 1, 2, 3, or 4; and m is 0, 1 or 2.

In a further embodiment, the compound of Formula (X') or Formula (X) is of Formula (X)-i (X)-i

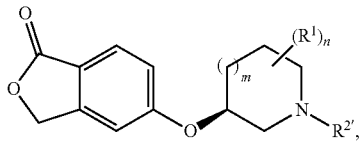

wherein $R^1$, $R^{2'}$, m and n are defined according to Formula (X') or Formula (X) above.

In a further embodiment, the compound of Formula (X') or Formula (X) is of Formula (X)-ii (X)-ii

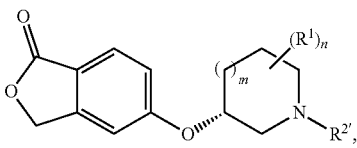

wherein $R^1$, $R^{2'}$, m and n are defined according to Formula (X') or Formula (X) above.

In a further embodiment of Formula (X'), (X), (X)-i or (X)-ii, $R^{2'}$ is selected from a nitrogen protecting group, e.g., Boc, hydrogen, and unsubstituted $C_1$-$C_{10}$alkyl.

In a further embodiment of Formula (X), there is provided a compound selected from:

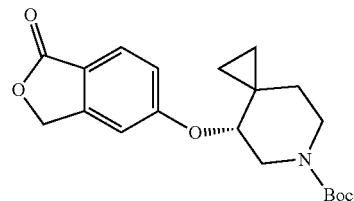

Tert-butyl (R)-4-((1-oxo-1,3-dihydroisobenzofuran-5-yl)oxy)-6-azaspiro[2.5]octane-6-carboxylate

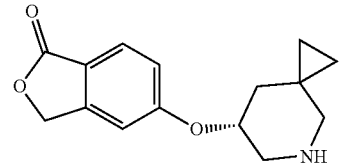

(R)-5-((5-azaspiro[2.5]octan-7-yl)oxy)isobenzofuran-1(3H)-one

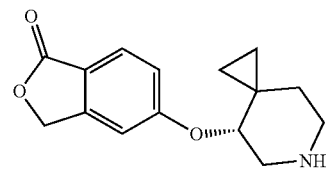

(R)-5-((6-azaspiro[2.5]octan-4-yl)oxy)isobenzofuran-1(3H)-one

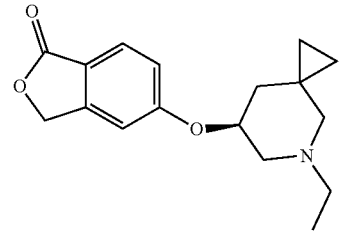

(S)-5-((5-ethyl-5-azaspiro[2.5]octan-7-yl)oxy)isobenzofuran-1(3H)-one

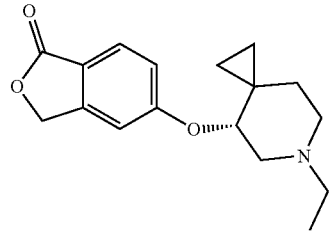

(R)-5-((6-ethyl-6-azaspiro[2.5]octan-4-yl)oxy)isobenzofuran-1(3H)-one

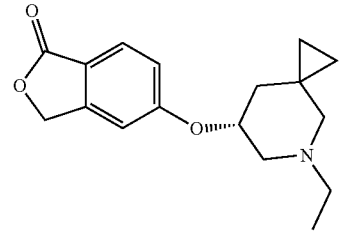

(R)-5-((5-ethyl-5-azaspiro[2.5]octan-7-yl)oxy)isobenzofuran-1(3H)-one

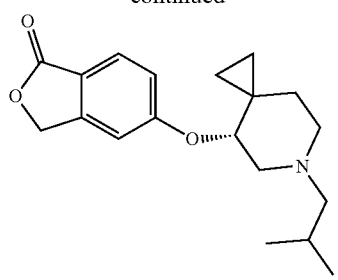

(R)-5-((6-isobutyl-6-azaspiro[2.5]octan-4-yl)oxy)isobenzofuran-1(3H)-one

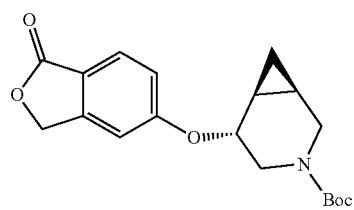

tert-butyl (1R,5R,6S)-5-((1-oxo-1,3-dihydroisobenzofuran-5-yl)oxy)-3-azabicyclo[4.1.0]heptane-3-carboxylate

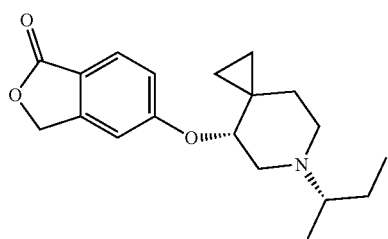

5-(((R)-6-((S)-sec-butyl)-6-azaspiro[2.5]octan-4-yl)oxy)isobenzofuran-1(3H)-one

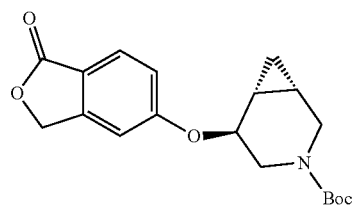

tert-butyl (1S,5S,6R)-5-((1-oxo-1,3-dihydroisobenzofuran-5-yl)oxy)-3-azabicyclo[4.1.0]heptane-3-carboxylate

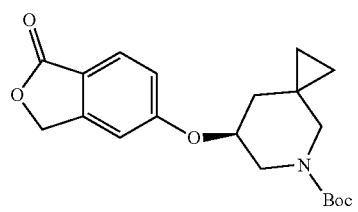

tert-butyl (S)-7-((1-oxo-1,3-dihydroisobenzofuran-5-yl)oxy)-5-azaspiro[2.5]octane-5-carboxylate

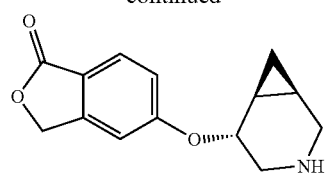

5-(((1R,5R,6S)-3-azabicyclo[4.1.0]heptane-5-yl)oxy)isobenzofuran-1(3H)-one

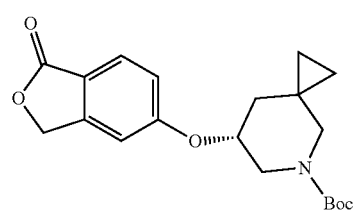

tert-butyl (R)-7-((1-oxo-1,3-dihydroisobenzofuran-5-yl)oxy)-5-azaspiro[2.5]octane-5-carboxylate

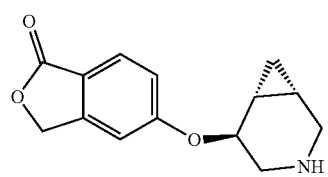

5-(((1S,5S,6R)-3-azabicyclo[4.1.0]heptane-5-yl)oxy)isobenzofuran-1(3H)-one

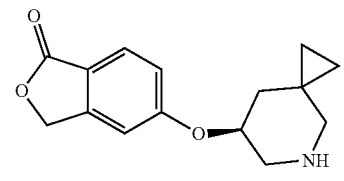

(S)-5-((5-azaspiro[2.5]octan-7-yl)oxy)isobenzofuran-1(3H)-one

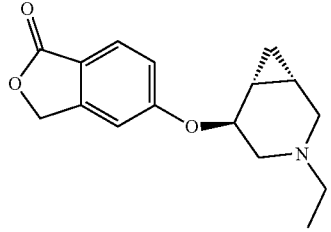

5-(((1S,5S,6R)-3-ethyl-3-azabicyclo[4.1.0]heptane-5-yl)oxy)isobenzofuran-1(3H)-one

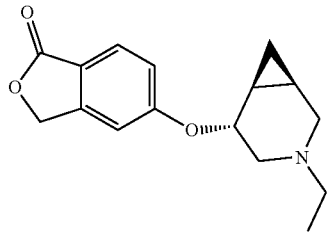

5-(((1R,5R,6S)-3-ethyl-3-azabicyclo[4.1.0]heptane-5-yl)oxy)isobenzofuran-1(3H)-one

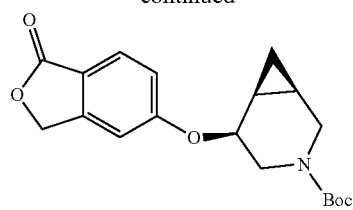

tert-butyl
(1R,5S,6S)-5-((1-oxo-1,3-
dihydroisobenzofuran-5-yl)oxy)-3-
azabicyclo[4.1.0]heptane-3-carboxylate

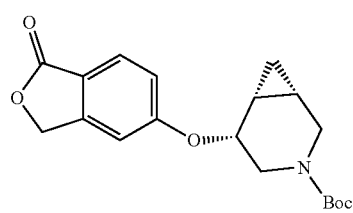

tert-butyl
(1S,5R,6R)-5-((1-oxo-1,3-
dihydroisobenzofuran-5-yl)oxy)-3-
azabicyclo[4.1.0]heptane-3-carboxylate

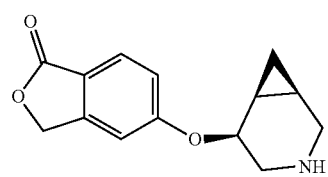

5-(((1R,5S,6S)-3-azabicyclo[4.1.0]heptan-5-
yl)oxy)isobenzofuran-1(3H)-one

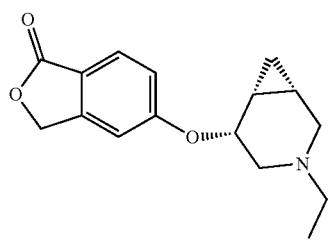

5-(((1S,5R,6R)-3-ethyl-3-
azabicyclo[4.1.0]heptan-5-
yl)oxy)isobenzofuran-1(3H)-one

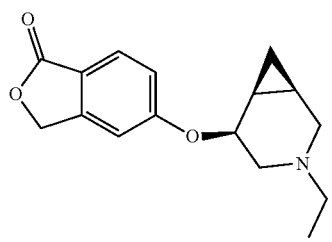

5-(((1R,5S,6S)-3-ethyl-3-
azabicyclo[4.1.0]heptan-5-
yl)oxy)isobenzofuran-1(3H)-one

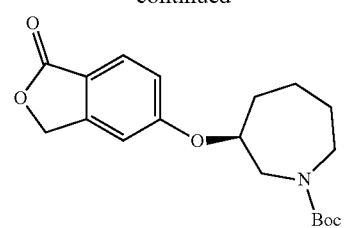

tert-butyl
(S)-3-((1-oxo-1,3-dihydroisobenzofuran-5-
yl)oxy)azepane-1-carboxylate

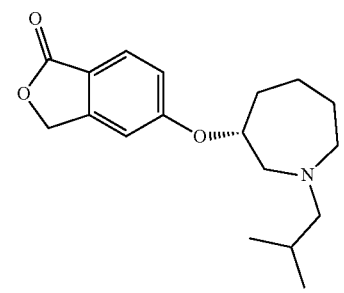

(R)-5-((1-isobutylazepan-3-
yl)oxy)isobenzofuran-1(3H)-one

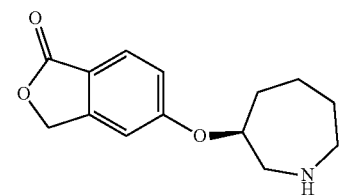

(S)-5-(azepan-3-yloxy)isobenzofuran-1(3H)-one

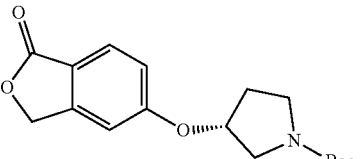

tert-butyl
(R)-3-((1-oxo-1,3-dihydroisobenzofuran-5-
yl)oxy)pyrrolidine-1-carboxylate

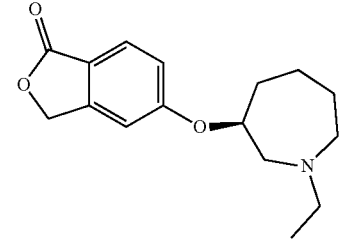

(S)-5-((1-ethylazepan-3-
yl)oxy)isobenzofuran-1(3H)-one

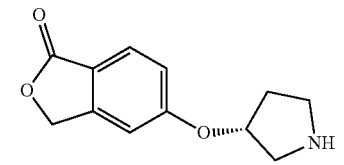

(R)-5-(pyrrolidin-3-yloxy)isobenzofuran-
1(3H)-one

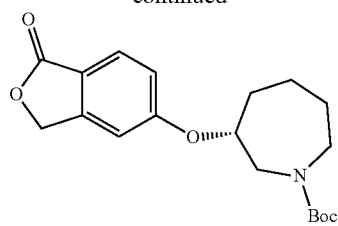

tert-butyl
(R)-3-((1-oxo-1,3-dihydroisobenzofuran-5-
yl)oxy)azepane-1-carboxylate

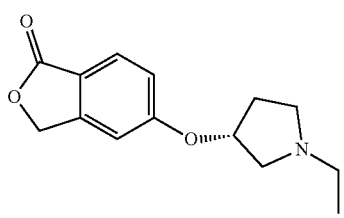

(R)-5-((1-ethylpyrrolidin-3-
yl)oxy)isobenzofuran-1(3H)-one

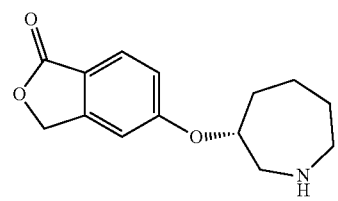

(R)-5-(azepan-3-yloxy)isobenzofuran-1(3H)-one

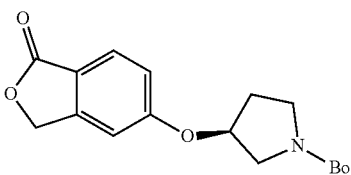

tert-butyl
(S)-3-((1-oxo-1,3-dihydroisobenzofuran-5-
yl)oxy)pyrrolidine-1-carboxylate

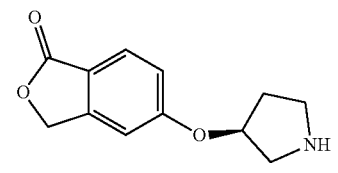

(S)-5-(pyrrolidin-3-yloxy)isobenzofuran-
1(3H)-one

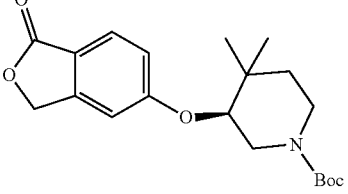

tert-butyl
(S)-4,4-dimethyl-3-((1-oxo-1,3-dihydroisobenzofuran-
5-yl)oxy)piperidine-1-carboxylate

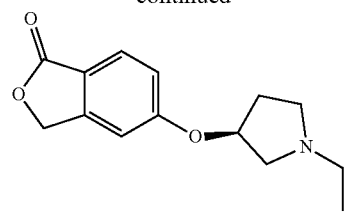

(S)-5-((1-ethylpyrrolidin-3-
yl)oxy)isobenzofuran-1(3H)-one

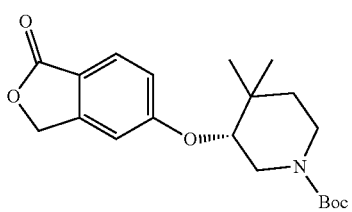

tert-butyl
(R)-4,4-dimethyl-3-((1-oxo-1,3-dihydroisobenzofuran-
5-yl)oxy)piperidine-1-carboxylate

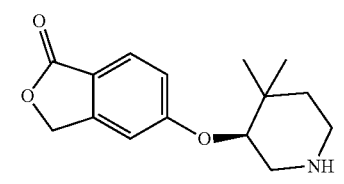

(S)-5-((4,4-dimethylpiperidin-3-
yl)oxy)isobenzofuran-1(3H)-one

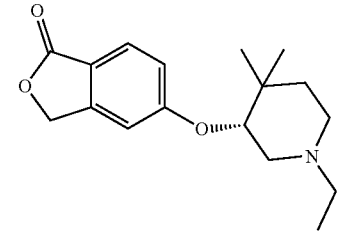

(R)-5-((1-ethyl-4,4-dimethylpiperidin-3-
yl)oxy)isobenzofuran-1(3H)-one

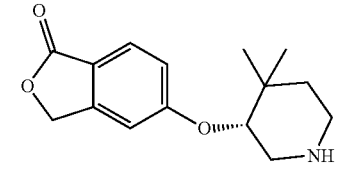

(R)-5-((4,4-dimethylpiperidin-3-
yl)oxy)isobenzofuran-1(3H)-one

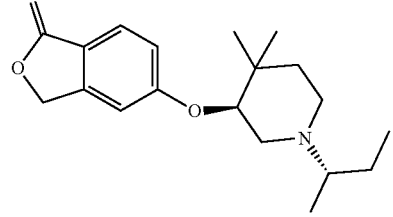

5-(((S)-1-((S)-sec-butyl)-4,4-dimethylpiperidin-
3-yl)oxy)isobenzofuran-1(3H)-one

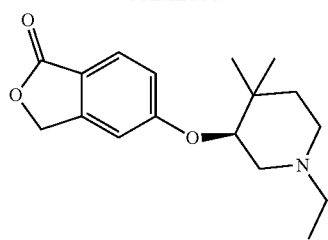

(S)-5-((1-ethyl-4,4-dimethylpiperidin-3-yl)oxy)isobenzofuran-1(3H)-one

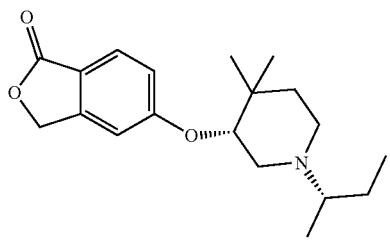

5-(((R)-1-((S)-sec-butyl)-4,4-dimethylpiperidin-3-yl)oxy)isobenzofuran-1(3H)-one

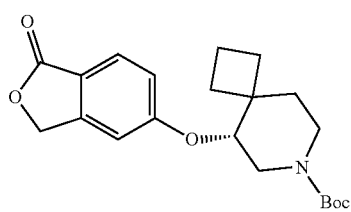

tert-butyl (R)-5-((1-oxo-1,3-dihydroisobenzofuran-5-yl)oxy)-7-azaspiro[3.5]nonane-7-carboxylate

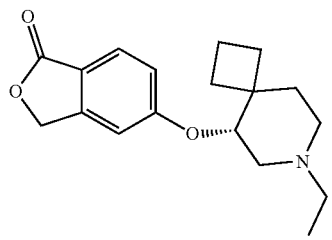

(R)-5-((7-ethyl-7-azaspiro[3.5]nonan-5-yl)oxy)isobenzofuran-1(3H)-one

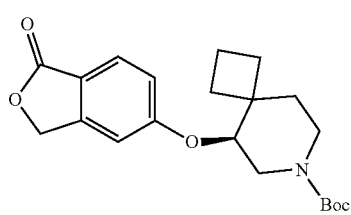

tert-butyl (S)-5-((1-oxo-1,3-dihydroisobenzofuran-5-yl)oxy)-7-azaspiro[3.5]nonane-7-carboxylate

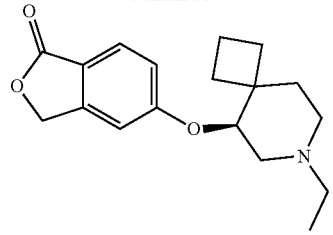

(S)-5-((7-ethyl-7-azaspiro[3.5]nonan-5-yl)oxy)isobenzofuran-1(3H)-one

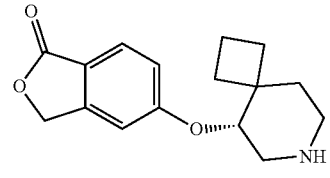

(R)-5-((7-azaspiro[3.5]nonan-5-yl)oxy)isobenzofuran-1(3H)-one

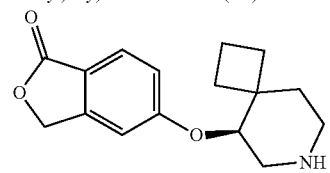

(S)-5-((7-azaspiro[3.5]nonan-5-yl)oxy)isobenzofuran-1(3H)-one

In a further embodiment, there is provided a compound of Formula (Y)

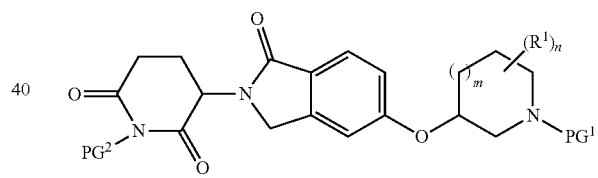

(Y)

wherein $R^1$, m and n are as defined according to Formula (X') or Formula (X) above; and
each of $PG^1$ and $PG^2$ is independently a nitrogen protecting group as defined herein.

In an embodiment, $PG^2$ is a base labile protecting group and $PG^1$ is an acid labile protecting group.

In an embodiment, $PG^2$ is the SEM protecting group (trimethylsilylethoxymethyl) and $PG^1$ is the BOC protecting group (tert-butyloxycarbonyl).

In a further embodiment, the compound of Formula (Y) is of Formula (Y)-i.

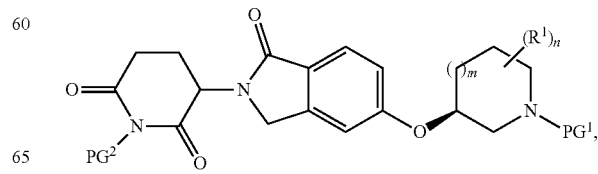

(Y)-i wherein R¹, m, n, PG¹ and PG² are defined according to Formula (Y) above.

In a further embodiment, the compound of Formula (Y) is of Formula (Y)-ii

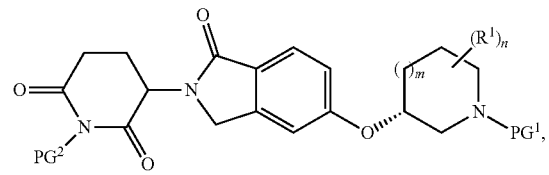

(Y)-ii wherein R¹, m, n, PG¹ and PG² are defined according to Formula (Y) above.

In a further embodiment of Formula (Y), there is provided a compound selected from:

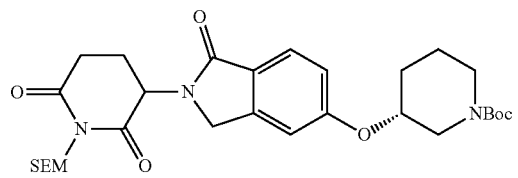

tert-butyl (3R)-3-((2-(2,6-dioxo-1-((2-(trimethylsilyl)ethoxy)methyl)piperidin-3-yl)-1-oxoisoindolin-5-yl)oxy)piperidine-1-carboxylate

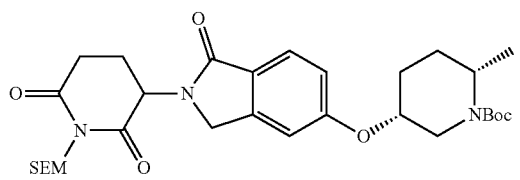

tert-butyl (2S,5R)-5-((2-(2,6-dioxo-1-((2-(trimethylsilyl)ethoxy)methyl)piperidin-3-yl)-1-oxoisoindolin-5-yl)oxy)-2-methylpiperidine-1-carboxylate

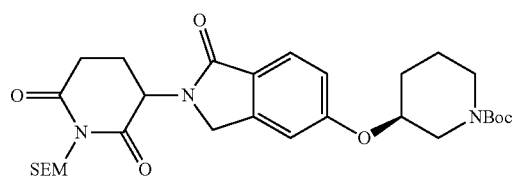

tert-butyl (3S)-3-((2-(2,6-dioxo-1-((2-(trimethylsilyl)ethoxy)methyl)piperidin-3-yl)-1-oxoisoindolin-5-yl)oxy)piperidine-1-carboxylate

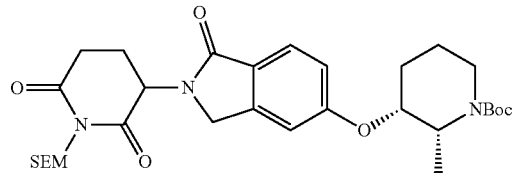

tert-butyl (2R,3R)-3-((2-(2,6-dioxo-1-((2-(trimethylsilyl)ethoxy)methyl)piperidin-3-yl)-1-oxoisoindolin-5-yl)oxy)-2-methylpiperidine-1-carboxylate -continued

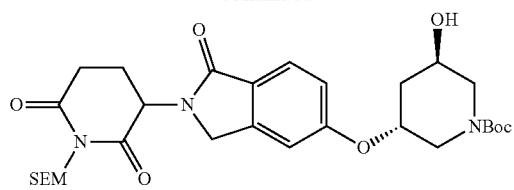

tert-butyl (3R,5R)-3-((2-(2,6-dioxo-1-((2-(trimethylsilyl)ethoxy)methyl)piperidin-3-yl)-1-oxoisoindolin-5-yl)oxy)hydroxypiperidine-1-carboxylate

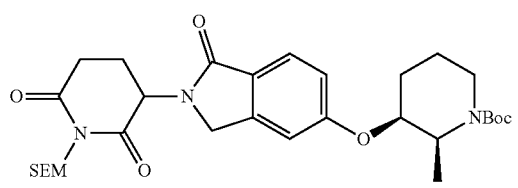

tert-butyl (2S,3S)-3-((2-(2,6-dioxo-1-((2-(trimethylsilyl)ethoxy)methyl)piperidin-3-yl)-1-oxoisoindolin-5-yl)oxy)-2-methylpiperidine-1-carboxylate

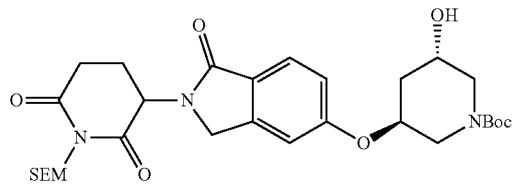

tert-butyl (3S,5S)-3-((2-(2,6-dioxo-1-((2-(trimethylsilyl)ethoxy)methyl)piperidin-3-yl)-1-oxoisoindolin-5-yl)oxy)hydroxypiperidine-1-carboxylate

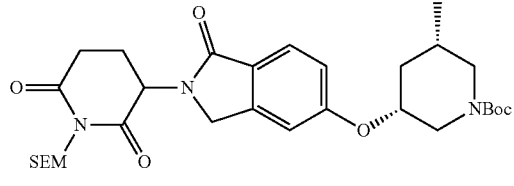

tert-butyl (3R,5S)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate

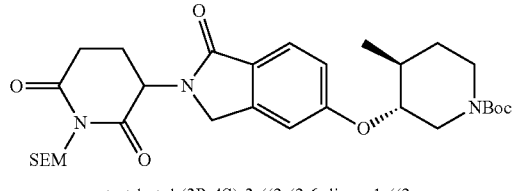

tert-butyl (3R,4S)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate

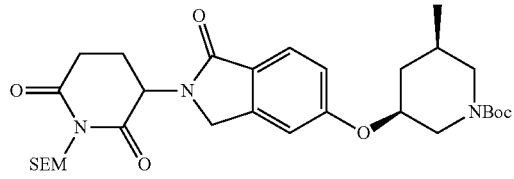

tert-butyl (3S,5R)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate

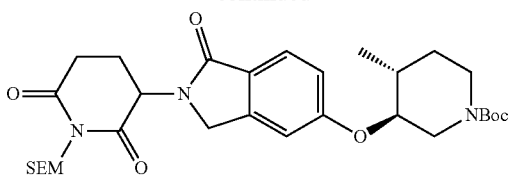

tert-butyl (3S,4R)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate

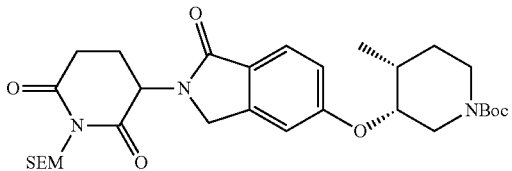

tert-butyl (3R,4R)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate

tert-butyl (3R)-3-((2-(2,6-dioxo-1-((2-(trimethylsilyl)ethoxy)methyl)piperidin-3-yl)-1-oxoisoindolin-5-yl)oxy)azepane-1-carboxylate

tert-butyl (3S,4S)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate

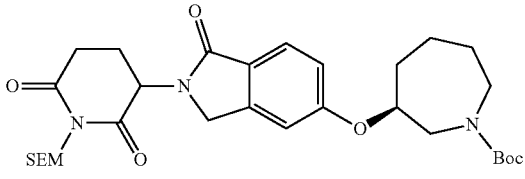

tert-butyl (3S)-3-((2-(2,6-dioxo-1-((2-(trimethylsilyl)ethoxy)methyl)piperidin-3-yl)-1-oxoisoindolin-5-yl)oxy)azepane-1-carboxylate

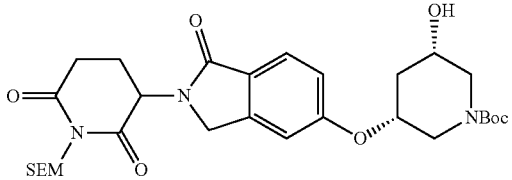

tert-butyl (3R,5S)-3-((2-(2,6-dioxo-1-((2-(trimethylsilyl)ethoxy)methyl)piperidin-3-yl)-1-oxoisoindolin-5-yl)oxy)-5-hydroxypiperidine-1-carboxylate

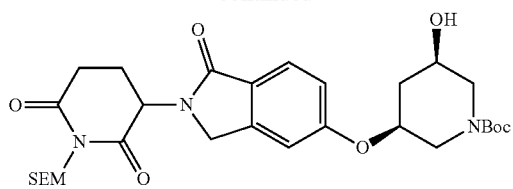

tert-butyl (3S,5R)-3-((2-(2,6-dioxo-1-((2-(trimethylsilyl)ethoxy)methyl)piperidin-3-yl)-1-oxoisoindolin-5-yl)oxy)-5-hydroxypiperidine-1-carboxylate

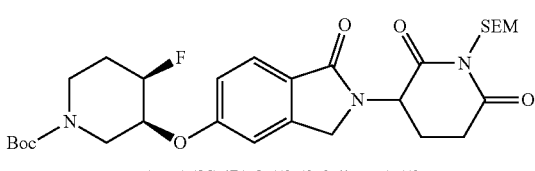

tert-butyl (3S,4R)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate

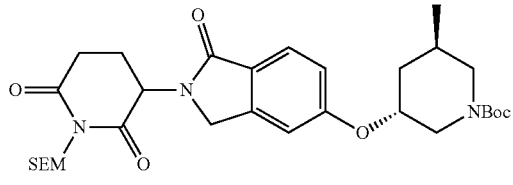

tert-butyl (3R,5R)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate

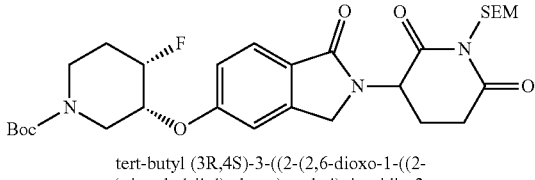

tert-butyl (3R,4S)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate

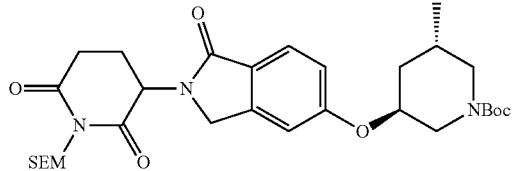

tert-butyl (3S,5S)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate

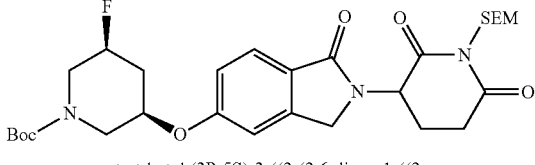

tert-butyl (3R,5S)-3-((2-(2,6-dioxo-1-((2-(trimethylsilyl)ethoxy)methyl)piperidin-3-yl)-1-oxoisoindolin-5-yl)oxy)-5-fluoropiperidine-1-carboxylate -continued

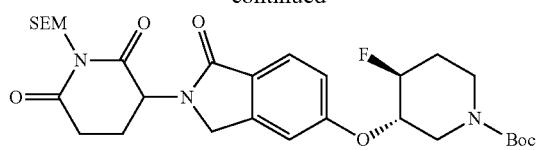

tert-butyl (3S,4S)-3-((2-(2,6-dioxo-1-((2-
(trimethylsilyl)ethoxy)methyl)piperidin-3-
yl)-1-oxoisoindolin-5-yl)oxy)-
4-fluoropiperidine-1-carboxylate

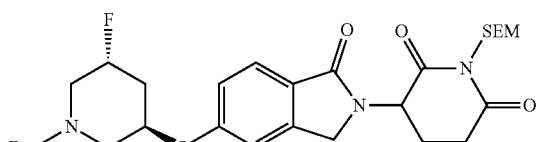

tert-butyl (3R,5R)-3-((2-(2,6-dioxo-1-((2-
(trimethylsilyl)ethoxy)methyl)piperidin-3-
yl)-1-oxoisoindolin-5-yl)oxy)-
5-fluoropiperidine-1-carboxylate

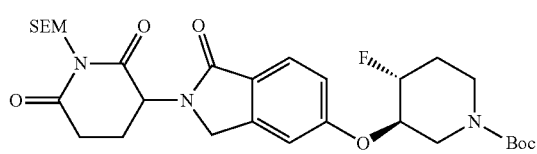

tert-butyl (3R,4R)-3-((2-(2,6-dioxo-1-((2-
(trimethylsilyl)ethoxy)methyl)piperidin-3-
yl)-1-oxoisoindolin-5-yl)oxy)-
4-fluoropiperidine-1-carboxylate

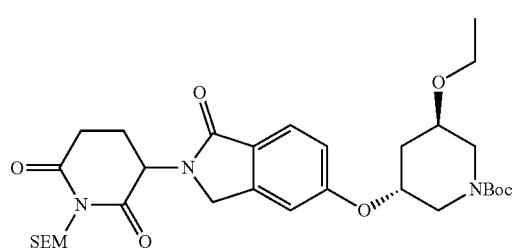

tert-butyl (3R,5R)-3-((2-(2,6-dioxo-1-((2-
(trimethylsilyl)ethoxy)methyl)piperidin-3-
yl)-1-oxoisoindolin-5-yl)oxy)-
5-ethoxypiperidine-1-carboxylate

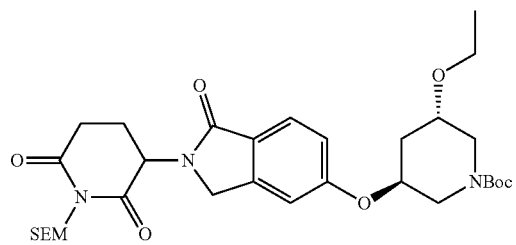

tert-butyl (3S,5S)-3-((2-(2,6-dioxo-1-((2-
(trimethylsilyl)ethoxy)methyl)piperidin-3-
yl)-1-oxoisoindolin-5-yl)oxy)-
5-ethoxypiperidine-1-carboxylate -continued

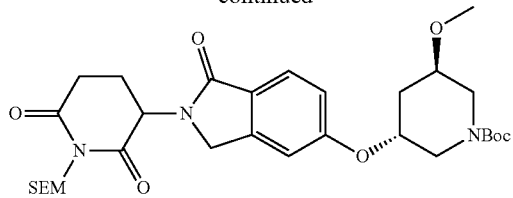

tert-butyl (3R,5R)-3-((2-(2,6-dioxo-1-((2-
(trimethylsilyl)ethoxy)methyl)piperidin-3-
yl)-1-oxoisoindolin-5-yl)oxy)-
5-methoxypiperidine-1-carboxylate

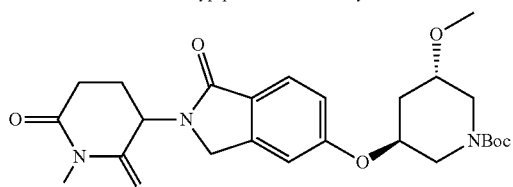

tert-butyl (3S,5S)-3-((2-(2,6-dioxo-1-((2-
(trimethylsilyl)ethoxy)methyl)piperidin-3-
yl)-1-oxoisoindolin-5-yl)oxy)-
5-methoxypiperidine-1-carboxylate

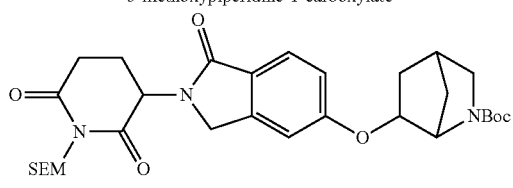

tert-butyl 6-((2-(2,6-dioxo-1-((2-
(trimethylsilyl)ethoxy)methyl)piperidin-3-
yl)-1-oxoisoindolin-5-yl)oxy)-
2-azabicyclo[2.2.1]heptane-2-carboxylate In a further aspect, the disclosure provides to a process for the preparation of a compound of formula (I'), (I''), or (I), in free form or in pharmaceutically acceptable salt form, comprising the step of:
1) coupling an aryl bromide of formula (INT-1) or formula (INT-3) with an alcohol of formula (INT-1A) or (INT-1B) under photo redox coupling conditions, to give a compound of formula (I)-2 or formula (I)-7 as defined herein.

In a further aspect, the disclosure provides a process for the preparation of a compound of formula (I'), (I'') or (I), in free form or in pharmaceutically acceptable salt form, comprising the steps of:
1) coupling an aryl bromide of formula (INT-3) with an alcohol of formula (INT-1B) under photo redox coupling conditions, to give a compound of formula (I)-7 as defined herein;
2) deprotecting a compound of formula (I)-7 to give a compound of formula (I)-8 as defined herein;
3-i) reacting a compound of formula (I)-8 under reductive amination conditions to give a compound of formula (I)-9 as defined herein; or
3-ii) reacting a compound of formula (I)-8 under alkylation conditions to give a compound of formula (I)-9 as defined herein;
4) chlorinating a compound of formula (I)-9 with a nucleophilic chlorinating reagent, such as $SOCl_2$, to give a compound of formula (I)-10 as defined herein;
5) reacting a compound of formula (I)-10 with a compound of formula (INT-1C) to give a compound of formula (I'), (I'') or (I) as defined herein;

6) optionally purifying the compound of formula (I'), (I")
or (I) as defined herein; and
7) optionally separating the resultant stereoisomers, e.g., by chromatography, e.g., by chiral chromatorgraphy.

In a further aspect, the disclosure provides a process for the preparation of a compound of formula (I'), (I"), or (I), in free form or in pharmaceutically acceptable salt form, comprising the steps of:
1) coupling an aryl bromide of formula (INT-1) with an alcohol of formula (INT-1A) under photo redox coupling conditions, to give a compound of formula (I)-2 as defined herein;
2) deprotecting a compound of formula (I)-2 to give a compound of formula (I)-3;
3-i) reacting a compound of formula (I)-3 under reductive amination conditions to give a compound of formula (I) as defined herein; or
3-ii) reacting a compound of formula (I)-3 under alkylation conditions to give a compound of formula (I'), (I") or (I) as defined herein;
4) optionally purifying the compound of formula (I'), (I") or (I) as defined herein; and
5) optionally separating the resultant stereoisomers, e.g., by chromatography, e.g., by chiral chromatorgraphy.

Photo redox coupling reaction conditions for any of the aforementioned process steps or hereinafter involve the use of an Ir(III) catalyst, such as [Ir{dF(CF$_3$)ppy}$_2${dtbbpy}] PF$_6$, a Ni(II) complex, such as [NiCl$_2$.dtbbpy], base, such as TMP, a suitable solvent, such as acetonitrile, a light source, such as a 34 W blue LED, the reaction conducted at room temperature (r.t.) for a suitable amount of time, for example 12 hours.

Reductive amination conditions for any of the aforementioned process steps or hereinafter involve the use of a corresponding aldehyde or ketone, a suitable hydride reagent, such as NaBH(OAc)$_3$, a suitable solvent, such as DMF, the reaction conducted at room temperature (r.t.).

Alkylation reaction conditions for any of the aforementioned process steps or hereinafter involve the use of a corresponding sulfonate ester, such as a corresponding mesylate, a suitable base, such as DIPEA, a suitable solvent, such as DMF, the reaction conducted at a suitable temperature, such as 100° C., under microwave.

In a further embodiment there is provided a process for the preparation of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii) in free form or in pharmaceutically acceptable salt form according to any of General Schemes 1 to 4.

Compounds of formulae (X'), (X), (X)-i, (X)-ii, (Y), (Y)-i, and (Y)-ii as defined herein are useful in the preparation of compounds of the disclosure, e.g., compounds of (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), and (ID-ii). Thus, in an aspect, the disclosure relates to a compound of formula (X'), (X), (X)-i, (X)-ii, (Y), (Y)-i, or (Y)-ii, or salts thereof. In another aspect, the disclosure relates to the use of a compound of formula (X'), (X), (X)-i, (X)-ii, (Y), (Y)-i, or (Y)-ii, or salts thereof in the manufacture of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii). The disclosure further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

PHARMACEUTICAL COMPOSITIONS

In another aspect, the disclosure provides a pharmaceutical composition comprising one or more compounds of described herein or a pharmaceutically acceptable salt, hydrate, solvate, prodrug, stereoisomer, or tautomer thereof, and one or more pharmaceutically acceptable carriers. As used herein, the term "pharmaceutical composition" refers to a compound of the disclosure, or a pharmaceutically acceptable salt thereof, together with at least one pharmaceutically acceptable carrier, in a form suitable for oral or parenteral administration. As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

In an aspect of the present disclosure, there is provided a pharmaceutical composition comprising an agent which is effective in reducing WIZ protein expression levels and/or inducing fetal hemoglobin (HbF) expression. Such compositions include, but are not limited to, small molecule compounds (e.g., small molecule compounds that can target WIZ protein for degradation, e.g., through E3 ubiquitin pathway, e.g. a compound as described herein).

In another aspect, the disclosure provides a pharmaceutical composition comprising a compound of the disclosure, or a pharmaceutically acceptable salt thereof, and a pharmaceutically acceptable carrier. In a further embodiment, the composition comprises at least two pharmaceutically acceptable carriers, such as those described herein. For purposes of the disclosure, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol;
c) binders, e.g., magnesium aluminum silicate, starch paste, gelatin, tragacanth, methylcellulose, sodium carboxymethylcellulose and/or polyvinylpyrrolidone;

d) disintegrants, e.g., starches, agar, alginic acid or its sodium salt, or effervescent mixtures; and e) absorbents, colorants, flavors and sweeteners.

In an embodiment, the pharmaceutical compositions are capsules comprising the active ingredient only.

Tablets may be either film coated or enteric coated according to methods known in the art.

Suitable compositions for oral administration include an effective amount of a compound of the disclosure in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients, which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the disclosure with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formulae (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), and (ID-ii), in free form or in pharmaceutically acceptable salt form, exhibit valuable pharmacological properties, e.g., WIZ modulating properties or WIZ degrading properties or Hbf inducing properties e.g., as indicated in the in vitro tests as provided in the examples, and are therefore indicated for therapy or for use as research chemicals, e.g., as tool compounds.

Additional properties of the disclosed compounds include having good potency in the biological assays described herein, favorable safety profile, and possess favorable pharmacokinetic properties.

Diseases and Disorders

The compounds of the disclosure can be used to treat one or more of the diseases or disorders described herein below. In one embodiment, the disease or disorder is affected by the reduction of WIZ protein expression levels and/or induction of fetal hemoglobin protein expression levels. In another embodiment, the disease or disorder is a hemoglobinopathy, e.g., beta hemoglobinopathy, including sickle cell disease (SCD) and beta-thalassemia.

Methods of Use

In an aspect of the present disclosure, there is provided a method of reducing WIZ protein expression levels and/or inducing fetal hemoglobin (HbF) expression comprising administering to a subject a therapeutically effective amount of an agent, e.g., a small molecule (e.g., a small molecule compound that can target WIZ protein for degradation, e.g., through E3 ubiquitin pathway, e.g. a compound as described herein). In an embodiment, the method of reducing WIZ protein expression levels and/or inducing fetal hemoglobin (HbF) expression is for the treatment of a hemoglobinopathy, e.g., beta hemoglobinopathy, including sickle cell disease (SCD) and beta-thalassemia.

All the aforementioned embodiments and embodiments hereinafter relating to the methods of reducing WIZ protein expression levels and/or inducing fetal hemoglobin (HbF) expression are equally applicable to:

A therapeutic agent, e.g., a small molecule (e.g., small molecule compounds that can target WIZ protein for degradation, e.g., through E3 ubiquitin pathway, e.g., a compound as described herein), for use in a method of reducing WIZ protein expression levels and/or inducing fetal hemoglobin (HbF) expression;

A therapeutic agent, e.g., a small molecule (e.g., small molecule compounds that can target WIZ protein for degradation, e.g., through E3 ubiquitin pathway, e.g., a compound as described herein), for use in the treatment of the aforementioned diseases or disorders according to the present disclosure;

Use of an agent, e.g., a small molecule (e.g. a compound as described herein), in the treatment of the aforementioned diseases or disorders according to the present disclosure; and A pharmaceutical composition comprising an agent, e.g., a small molecule (e.g., small molecule compounds that can target WIZ protein for degradation, e.g., through E3 ubiquitin pathway, e.g., a compound as described herein), for use in the treatment of the aforementioned diseases or disorders according to the present disclosure.

Having regard to their activity as WIZ modulators or degraders, compounds of formulae (I'), (I"), (I), (I-i), (IA), (IA-i), (IA-ii), (IA-iii), (IB), (IB-i), (IBA), (IB-iii), (IC), (IC-i), (IC-ii), (ID), (ID-i), and (ID-ii), in free or pharmaceutically acceptable salt form, are useful in the treatment of conditions which may be treated by modulation of WIZ protein expression levels, reduction of WIZ protein expression levels, or induction of fetal hemoglobin (HbF), such as in a blood disorder, for example an inherited blood disorder, e.g., sickle cell disease, or beta-thalassemia. In one aspect, the disclosure provides a method of treating or preventing a disease or disorder in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of treating or preventing a disorder that is affected by the reduction of WIZ protein levels, in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of inhibiting WIZ protein expression in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of degrading WIZ protein in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of inhibiting, reducing, or eliminating the activity of WIZ protein or WIZ protein expression, the method comprising administering to the subject a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of inducing or promoting fetal hemoglobin in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of reactivating fetal hemoglobin production or expression in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of increasing fetal hemoglobin expression in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of treating a hemoglobinopathy, e.g., a beta-hemoglobinopathy, in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of treating a sickle cell disease in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a method of treating beta-thalassemia in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In an embodiment, the beta-thalassemia major or intermedia is the result of homozygous null or compound heterozygous mutations resulting with beta-globin deficiency and the phenotypic complications of beta-thalassemia, whether transfusion-dependent or not.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of treating or preventing a disease or disorder in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of treating or preventing a disorder that is affected by the reduction of WIZ protein levels, in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of inhibiting WIZ protein expression in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of degrading WIZ protein in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of inhibiting, reducing, or eliminating the activity of WIZ protein or WIZ protein expression, the method comprising administering to the subject a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of inducing or promoting fetal hemoglobin in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of reactivating fetal hemoglobin production or expression in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of increasing fetal hemoglobin expression in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of treating a hemoglobinopathy, e.g., a beta-hemoglobinopathy, in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of treating a sickle cell disease in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In another aspect, the disclosure provides a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof for use in a method of treating beta-thalassemia in a subject in need thereof, the method comprising administering to the subject a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt, hydrate, solvate, prodrug, stereoisomer, or tautomer thereof.

In an embodiment, the beta-thalassemia major or intermedia is the result of homozygous null or compound heterozygous mutations resulting with beta-globin deficiency and the phenotypic complications of beta-thalassemia, whether transfusion-dependent or not.

Dosage

The pharmaceutical composition or combination of the disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated.

The above-cited dosage properties are demonstrable in vitro and in vivo tests using advantageously mammals, e.g., mice, rats, dogs, monkeys or isolated organs, tissues and preparations thereof. The compounds of the disclosure can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the disclosure can be assessed by the in vitro methods described in the Examples.

Combination Therapy

In another aspect, the disclosure provides a pharmaceutical combination comprising a compound of formula (I'), (I"), (I), (I-i), (IA), (IA-i), (IA-ii), (IA-iii), (IB), (IB-i), (IBA), (IB-iii), (IC), (IC-i), (IC-ii), (ID), (ID-i), or (ID-ii), or a pharmaceutically acceptable salt, hydrate, solvate, prodrug, stereoisomer, or tautomer thereof, and one or more additional therapeutic agent(s) for simultaneous, separate or sequential use in therapy. In an embodiment, the additional therapeutic agent is a myelosuppressive agent, such as hydroxyurea.

Combination therapy includes the administration of the subject compounds in further combination with other biologically active ingredients (such as, but not limited to, a second and different antineoplastic agent or a therapeutic agent that targets Hbf or another cancer target) and non-drug therapies (such as, but not limited to, surgery or radiation treatment). For instance, the compounds of the application can be used in combination with other pharmaceutically active compounds, preferably compounds that are able to enhance the effect of the compounds of the application.

The compound of the disclosure may be administered either simultaneously with, or before or after, one or more other therapeutic agent. The compound of the disclosure may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the disclosure. Thus, in one embodiment, the disclosure provides a combination comprising a therapeutically effective amount of a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), or a pharmaceutically acceptable salt thereof and one or more additional therapeutically active agents.

In one embodiment, the disclosure provides a product comprising a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), and at least one other therapeutic agent as a combined preparation for simultaneous, separate or sequential use in therapy. In one embodiment, the therapy is the treatment of a disease or condition modulated by WIZ. Products provided as a combined preparation include a composition comprising the compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), and the other therapeutic agent(s) together in the same pharmaceutical composition, or the compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), and the other therapeutic agent(s) in separate form, e.g., in the form of a kit.

In one embodiment, the disclosure provides a pharmaceutical composition comprising a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii), and another therapeutic agent(s). Optionally, the pharmaceutical composition may comprise a pharmaceutically acceptable carrier, as described above.

In one embodiment, the disclosure provides a kit comprising two or more separate pharmaceutical compositions, at least one of which contains a compound of formula (I'), (I"), (I), (I-i), (IA), (IA-i), (IA-ii), (IA-iii), (IB), (IB-i), (IB-ii), (IB-iii), (IC), (IC-i), (IC-ii), (ID), (ID-i), or (ID-ii). In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

In the combination therapies of the disclosure, the compound of the disclosure and the other therapeutic agent may be manufactured and/or formulated by the same or different manufacturers. Moreover, the compound of the disclosure and the other therapeutic may be brought together into a combination therapy: (i) prior to release of the combination product to physicians (e.g., in the case of a kit comprising the compound of the disclosure and the other therapeutic agent); (ii) by the physician themselves (or under the guidance of the physician) shortly before administration; (iii) in the patient themselves, e.g., during sequential administration of the compound of the disclosure and the other therapeutic agent.

PREPARATION OF COMPOUNDS

It is understood that in the following description, combinations of substituents and/or variables of the depicted formulae are permissible only if such combinations result in stable compounds.

It will also be appreciated by those skilled in the art that in the processes described below, the functional groups of intermediate compounds may need to be protected by suitable protecting groups. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; P. J. Kocienski, "Protecting Groups", Third Edition, Georg Thieme Verlag, Stuttgart and New York 2005; and in "Methoden der organischen Chemie" (Methods of Organic Chemistry), Houben Weyl, 4th edition, Volume 15/I, Georg Thieme Verlag, Stuttgart 1974.

The protecting group may also be a polymer resin, such as a Wang resin or a 2-chlorotrityl-chloride resin.

The following reaction schemes illustrate methods to make compounds of this disclosure. It is understood that one skilled in the art would be able to make these compounds by similar methods or by methods known to one skilled in the art. In general, starting components and reagents may be obtained from sources such as Sigma Aldrich, Lancaster Synthesis, Inc., Maybridge, Matrix Scientific, TCI, and Fluorochem USA, Strem, other commercial vendors, or synthesized according to sources known to those skilled in the art, or prepared as described in this disclosure.

Analytical Methods, Materials, and Instrumentation

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. Spectra are given in ppm (δ) and coupling constants, J, are reported in Hertz. Tetramethylsilane (TMS) was used as an internal standard. Chemical shifts are reported in ppm relative to dimethyl sulfoxide (δ 2.50), methanol (δ 3.31), chloroform (δ 7.26) or other solvent as indicated in NMR spectral data. A small amount of the dry sample (2-5 mg) is dissolved in an appropriate deuterated solvent (1 mL). The chemical names were generated using ChemBioDraw Ultra v12 from CambridgeSoft.

Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The sample was dissolved in a suitable solvent such as MeCN, DMSO, or MeOH and was injected directly into the column using an automated sample handler. The analysis is performed on Waters Acquity UPLC system (Column: Waters Acquity UPLC BEH C18 1.7 μm, 2.1×30 mm; Flow rate: 1 mL/min; 55° C. (column temperature); Solvent A: 0.05% formic acid in water, Solvent B: 0.04% formic acid in MeOH; gradient 95% Solvent A from 0 to 0.10 min; 95% Solvent A to 20% Solvent A from 0.10 to 0.50 min; 20% Solvent A to 5% Solvent A from 0.50 to 0.60 min; hold at 5% Solvent A from 0.6 min to 0.8 min; 5% Solvent A to 95% Solvent A from 0.80 to 0.90 min; and hold 95% Solvent A from 0.90 to 1.15 min.

ABBREVIATIONS

ACN acetonitrile
AcOH acetic acid
AIBN azobisisobutyronitrile
aq. aqueous
$B_2pin_2$ bis(pinacolato)diboron
BAST bis(2-methoxyethyl)aminosulfur trifluoride
$Boc_2O$ di-tert-butyl dicarbonate
Bn benzyl
BnBr benzyl bromide
br broad
d doublet
dd doublet of doublets
ddd doublet of doublet of doublets
ddq doublet of doublet of quartets
ddt doublet of doublet of triplets
dq doublet of quartets
dt doublet of triplets
dtbbpy 4,4'-di-tert-butyl-2,2'-dipyridyl
dtd doublet of triplet of doublets
$Cs_2CO_3$ cesium carbonate
DCE 1,2-dichloroethane
DCM dichloromethane
DHP dihydropyran
DIBAL-H diisobutylaluminium hydride
DIPEA (DIEA) diisopropylethylamine
DIPEA N,N-diisopropylethylamine
DMA N,N-dimethylacetamide
DMAP 4-dimethylaminopyridine
DME 1,2-dimethoxyethane
DMF N,N-dimethylformamide
DMP Dess-Martin periodinane or 1,1,1-Tris(acetyloxy)-1,1-dihydro-1,2-benziodoxol-3-(1H)-one
DMSO dimethylsulfoxide
$EC_{50}$ half maximal effective concentration
ELSD evaporative light scattering detector
EtOH ethanol
$Et_2O$ diethyl ether
$Et_3N$ triethylamine
EtOAc ethyl acetate
HATU 1-[bis(dimethylamino)methylene]-1H-1,2,3-triazolo[4,5-b]pyridinium 3-oxid hexafluorophosphate
HCl hydrogen chloride
hept heptet
HPLC high performance liquid chromatography
h or hr hour
HRMS high resolution mass spectrometry
g gram
g/min gram per minute
$IC_{50}$ half maximal inhibitory concentration
IPA (iPrOH) isopropyl alcohol
$Ir[(dF(CF_3)ppy)_2dtbbpy]PF_6$ [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate
$K_2CO_3$ potassium carbonate
KI potassium iodide
KOAc potassium Acetate
$K_3PO_4$ tripotassium phosphate
LCMS liquid chromatography mass spectrometry
LDA lithium diisopropylamide
m multiplet
MeCN acetonitrile
MeOH methanol
mg milligram
MHz megahertz
min minutes
mL milliliter
mmol millimole
M molar
MS mass spectrometry
NaH sodium hydride
$NaHCO_3$ sodium bicarbonate
$NaBH(OAc)_3$ sodium triacetoxyborohydride
$Na_2SO_4$ sodium sulfate
NBS N-bromosuccinimide
$NiCl_2$(glyme) Nickel(II) chloride ethylene glycol dimethyl ether complex
NMM N-methylmorpholine
NMP N-methyl-2-pyrrolidone
NMR nuclear magnetic resonance
on overnight
Pd/C palladium on carbon
$PdCl_2$(dppf)·DCM [1,1'-bis(diphenylphosphino)ferrocene]dichloropalladium(II) complex with dichloromethane
$Pd(PPh_3)_4$ tetrakis(triphenylphosphine)palladium(0)
PMB para-methoxybenzyl q quartet
qd quartet of doublets
quint quintet
quintd quintet of doublets
rbf round bottom flask
RockPhos G3 Pd [(2-di-tert-butylphosphino-3-methoxy-6-methyl-2',4',6'-triisopropyl-1,1'-biphenyl)-2-(2-aminobiphenyl)]palladium(II) methanesulfonate
rt or r.t. room temperature
Rt retention time
s singlet
i 2-(trimethylsilyl)ethoxymethyl
SnBu$_3$ tributyltin
t triplet
td triplet of doublets
tdd triplet of doublet of doublets
TBAI tetrabutylammonium iodide
TEA (NEt$_3$) triethylamine
TFA trifluoroacetic acid
TFE trifluoroethanol
TfOH triflic Acid
THF tetrahydrofuran
THP tetrahydropyran
TMP 2,2,6,6-tetramethylpiperidine
Ts tosyl
tt triplet of triplets
ttd triplet of triplet of doublets
TLC thin-layer chromatography
UPLC ultra-Performance liquid Chromatography
XPhos Pd G2 chloro(2-dicyclohexylphosphino-2',4',6'-triisopropyl-1,1'-biphenyl)[2-(2'-amino-1,1'-biphenyl)]palladium(II)
μL or uL mircolitre
ρW or uW microwave General Method I—Representative Procedure for Photoredox Catalysis with Lactone A 40 mL vial was charged with 5-bromoisobenzofuran-1(3H)-one (1 equiv), an alcohol building block (1-1.1 equiv), NiCl$_2$(glyme) (0.05 equiv), dtbbpy (0.05 equiv), and Ir[(dF(CF$_3$)ppy)$_2$dtbbpy]PF$_6$ (0.01 equiv). ACN (0.186-0.3 M) was then added, followed by 2,2,6,6-tetramethylpiperidine (1.05 equiv). The reaction flask was evacuated and backfilled with nitrogen three times. The resulting mixture was placed in PennOC m1 450 nm Photoreactor under Blue LED light at r.t. for 18 hrs. The reaction mixture was filtered, concentrated and purified by reverse phase HPLC or silica gel chromatography to afford amino-ether lactone.

General Method II—Representative Procedure for Boc Deprotection

Amino-ether lactone (1 equiv) was suspended in dioxane (0.1-25 M) and TFE (0.59-1.75 M). 4M HCl in dioxane (6 equiv) was then added and the resulting mixture was stirred at r.t. for 18-37 hrs. The reaction mixture was concentrated under reduced pressure to afford free amino-ether lactone. The obtained product was carried on to the next step without purification.

General Method III—Representative Procedure for Reductive Amination

Free amino-ether lactone (1 equiv) was suspended in DMF (0.1-0.2 M). Aldehyde (1.5 equiv) was added. The reaction stirred for 15 minutes at r.t. then NaBH(OAc)$_3$ (2 equiv) was added. The reaction stirred at r.t. for 1-18 hrs. The reaction was quenched with 50% saturated aqueous sodium bicarbonate and extracted three times with 4:1 DCM:iPrOH. The combined extracts were passed through a phase separator and concentrated onto CELITE®. The crude material was purified by silica gel chromatography to afford lactone.

General Method IV—Representative Procedure for SOCl$_2$ Lactone Opening

To a solution of lactone (1 equiv) in dichloroethane (0.1 M) and EtOH (0.1 M) stirred at 70° C. was added thionyl chloride (12 equiv) and the resulting mixture was stirred at 70° C. overnight. The reaction mixture was cooled to r.t., diluted with water and EtOAc and quenched with saturated aqueous sodium bicarbonate. The reaction mixture was extracted with EtOAc three times and the combined organic layers were passed through a phase separator and concentrated to afford α-chloro-ester. The crude material was purified by silica gel chromatography or used directly in the next step without purification.

General Method V—Representative Procedure for Lactam Ring Closing 3-aminopiperidine-2,6-dione hydrochloride (2 equiv) was dissolved in DMF (0.25 M) in a 2 mL microwave vial. DIPEA (5 equiv) was then added and the reaction was evacuated and backfilled with nitrogen three times. The resulting mixture stirred at r.t. for 15 minutes. α-chloro-ester (1 equiv) dissolved in DMF (0.17 M) and the reaction was evacuated and backfilled with nitrogen three times. The reaction stirred at 85° C. for 18 hrs and then at 150° C. for 2 hrs under microwave radiation. The reaction mixture was concentrated onto CELITE® and purified by silica gel chromatography or reverse phase HPLC to afford the lactam product.

General Method VI—Representative Procedure for Photoredox Catalysis with 3-(5-bromo-1-oxoisoindolin-2-yl)-1-((2-(trimethylsilyl)ethoxy)methyl)piperidine-2,6-dione To a capped vial, 3-(5-bromo-1-oxoisoindolin-2-yl)-1-((2-(trimethylsilyl)ethoxy)methyl)piperidine-2,6-dione (1 equiv), alcohol building block (1-1.2 equiv), dtbbpy (0.05 equiv), NiCl$_2$(glyme) (0.05 equiv), and Ir[(dF(CF$_3$)ppy)$_2$dtbbpy]PF$_6$ (0.01 equiv) were added. ACN (0.2-0.3 M) was added and the reaction was purged with nitrogen for 5-10 minutes to ensure reaction turned green. 2,2,6,6-tetramethylpiperidine (1.05-1.5 equiv) was added. The resulting mixture was placed in PennOC m1 450 nm Photoreactor under Blue LED light at r.t. for 18 hrs. The reaction mixture was filtered, concentrated and purified by reverse phase HPLC or silica gel chromatography to afford SEM protected glutarimide, Boc protected amine and isoindoline derivative.

General Method VII—Representative Procedure for Global Deprotection

To a solution of the compound containing a SEM protected glutarimide and Boc protected amine (1 equiv) in ACN (0.2-0.3 M) was added methanesulfonic acid (5-10.9 equiv). The resulting mixture was stirred at r.t. for 18 hrs and then cooled to 0° C. Triethylamine (10-15 equiv) was then added, followed by N1,N2-dimethylethane-1,2-diamine (1.6-3 equiv). The reaction mixture was then stirred at r.t. for 2-70 hrs. The reaction was quenched with basic aqueous solution, extracted with DCM and polar protic solvent, and concentrated to afford free amine or purified by silica gel chromatography to afford the free amine product.

General Method VIII—Representative Procedure for Mesylation Formation

To a solution of alcohol (1 equiv) in DCM (0.5 M) was sequentially added DIPEA (2 equiv), 1-methylimidazole (2 equiv) and methanesulfonyl chloride (1.5 equiv) dropwise. The reaction was stirred at r.t. for 18 hrs. The reaction was diluted with DCM (20 mL). The organic layer was washed with 1 M aqueous HCl three times and saturated aqueous sodium bicarbonate twice. The organic layer was passed through a phase separator and concentrated to afford the mesylate product.

General Method IX—Representative Procedure for Alkylation with Alkyl Mesylate

Piperidine (1 equiv) and mesylate (1.5 equiv) were added to a microwave vial and suspended in ACN (0.2 M). DIPEA (2 equiv) was added and the reaction was evacuated and backfilled with nitrogen three times. The reaction stirred at 140° C. for 2-10 hrs under microwave radiation. The reaction was quenched with 50% saturated aqueous sodium bicarbonate and extracted three times with 4:1 DCM:iPrOH. The organic layers were combined, passed through a phase separator and concentrated onto CELITE®. The crude material was purified by silica gel chromatography to afford alkylated piperidine compound.

General Method X—Representative Procedure for Reduction Amination

Free amino-ether lactone (1 equiv) was suspended in DMF (0.15-0.178 M). NaBH(OAc)$_3$ (2 equiv) followed by aldehyde (1.5 equiv) were added. The reaction stirred at r.t. for 1-18 hrs. The reaction was quenched with 50% saturated aqueous sodium bicarbonate and extracted three times with 4:1 DCM:iPrOH. The organic layers were combined, passed through a phase separator and concentrated onto CELITE®. The crude material was purified by silica gel chromatography to afford the lactone product.

Stereochemical Representation

The compounds of formula (I) have at least two asymmetric carbon atoms as illustrated below wherein the asymmetric carbon atoms are identified by a *:

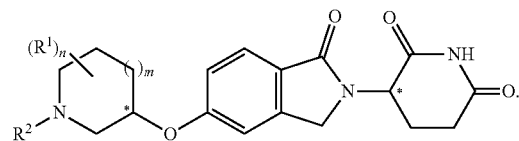

(I)

Throughout the following synthesis section describing the synthetic preparation of compounds of formula (I), compounds drawn whereby the bond from the N atom of the oxoisoindolinyl moiety to the C atom of the glutarimide moiety is depicted as flat shall be taken to mean a compound mixture which comprises both the (R) and (S) stereoisomers in relation to this stereocenter. For illustrative purposes, this can be shown by reference to Example 29:

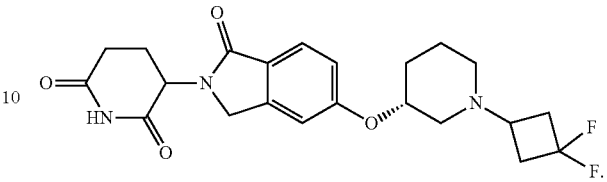

I-63

Example 29 (named as 3-(5-(((R)-1-(3,3-difluorocyclobutyl)piperidin-3-yl)oxy)-1-oxoisoindolin-2-yl)piperidine-2,6-dione) thus exists as a diastereomeric mixture of both the (R) 3-(5-(((R)-1-(3,3-difluorocyclobutyl)piperidin-3-yl)oxy)-1-oxoisoindolin-2-yl)piperidine-2,6-dione and (S)-3-(5-(((R)-1-(3,3-difluorocyclobutyl)piperidin-3-yl)oxy)-1-oxoisoindolin-2-yl)piperidine-2,6-dione.

In such cases where the compound has been separated into individual diastereomers or further mixtures of diastereomers, the stereochemical configuration of the diastereomer which is designated as (R*,S*) indicates the relative stereochemistry is known (as depicted by the wedged bonds) but not the absolute stereochemistry. Accordingly, any reference to a compound designated as (R*,S*) shall be taken to mean as either having the absolute (R,S) configuration or the (S,R) configuration. This also applies to compounds which have been synthesised from an intermediate compound whereby the relative stereochemistry is known but the absolute stereochemistry has not been determined. For illustrative purposes, this can be explained by reference to Example 55:

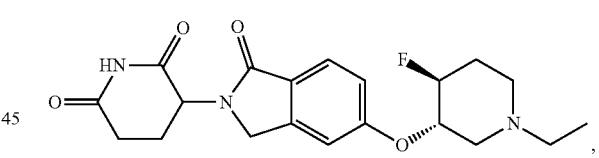

I-150 which is named as 3-(5-(((3S*,4S*)-1-ethyl-4-fluoropiperidin-3-yl)oxy)-1-oxoisoindolin-2-yl)piperidine-2,6-dione and whereby the groups attached to the 3- and 4-position of the piperidinyl moiety are represented by the wedged bonds to indicate the relative stereochemistry is known. This shall be taken to mean that the compound is either 3-(5-(((3S,4S)-1-ethyl-4-fluoropiperidin-3-yl)oxy)-1-oxoisoindolin-2-yl)piperidine-2,6-dione or 3-(5-(((3R,4R)-1-ethyl-4-fluoropiperidin-3-yl)oxy)-1-oxoisoindolin-2-yl)piperidine-2,6-dione (taking into account the flat bond to the glutarimide moiety as explained above). The same interpretation is to be applied throughout the following section for the synthesis of all compounds.

If the absolute stereochemistry of a specific chiral carbon atom in a diastereoisomeric compound or compound mixture was known the (R*,S*) designation will be replaced by the absolute (R,S) designation to indicate the compound has known absolute stereochemistry at that particular position.

Preparation of Intermediates

Preparation of rac-3-(5-bromo-1-oxoisoindolin-2-yl)piperidine-2,6-dione (INT-XX)

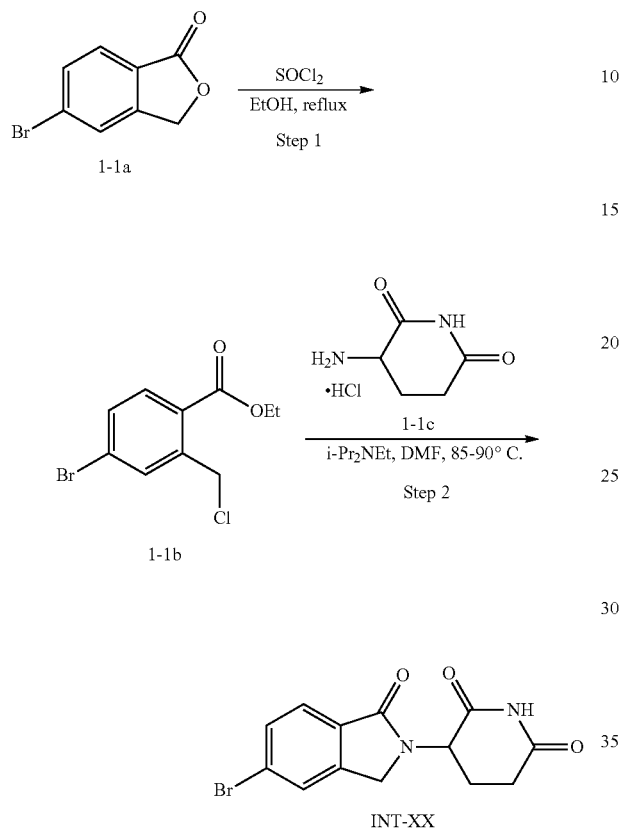

Step 1. Ethyl 4-bromo-2-(chloromethyl)benzoate (1-1b)

A stirred suspension of 5-bromophthalide 1-1a (1200 g, 5.633 mol) in EtOH (12 L) was heated to 68-72° C. SOCl$_2$ (2.40 L, 33.0 mol) was then added dropwise over a period of 7 h. The reaction mixture was concentrated under reduced pressure to about 4 L, and then water (5 L) and MTBE (5 L) were added. The resulting mixture was stirred for 40 min. The phases were separated and the aqueous phase was extracted with MTBE (1×5 L). The combined organic layers were washed with 5% aq. NaHCO$_3$ (5 L), dried over Na$_2$SO$_4$, filtered, and concentrated to dryness to afford 1-1b as a pale brown solid. MS [M+Na]$^+$=298.9. $^1$H NMR (400 MHz, Chloroform-d) δ 7.85 (d, J=8.4 Hz, 1H), 7.72 (d, J=2.0 Hz, 1H), 7.52 (dd, J=8.3, 2.0 Hz, 1H), 5.00 (s, 2H), 4.38 (q, J=7.1 Hz, 2H), 1.40 (t, J=7.1 Hz, 3H).

Step 2. 3-(5-bromo-1-oxoisoindolin-2-yl)piperidine-2,6-dione (INT-XX)

To a stirred suspension of 3-aminopiperidine-2,6-dione hydrochloride 1-1c (596.3 g, 3.623 mol) and i-Pr$_2$NEt (2.50 L, 14.3 mol) in DMF (5.0 L) was added 1-1b (1000 g, 3.623 mmol) and the resulting reaction mixture was stirred at 85-90° C. for 24 h. The reaction mixture was then allowed to cool to room temperature, water (20 L) was added, and the resulting mixture was stirred for 12 h. The formed precipitate was filtered and washed with water (5 L) and MeOH (2 L). The crude solid was slurried in MeOH (5 L) for 1 h, filtered, and washed with MeOH (2 L). The resulting solid was then taken in EtOAc (10 L) and stirred for 1 h. The obtained suspension was then filtered, washed with EtOAc (5 L), and dried under reduced pressure at 45-50° C. to afford INT-XX as an off-white solid. MS [M+1]+=323.2. $^1$H NMR (400 MHz, DMSO-d$_6$) δ 10.99 (s, 1H), 7.91-7.88 (m, 1H), 7.72 (dd, J=8.1, 1.6 Hz, 1H), 7.67 (d, J=8.0 Hz, 1H), 5.11 (dd, J=13.3, 5.1 Hz, 1H), 4.47 (d, J=17.7 Hz, 1H), 4.34 (d, J=17.7 Hz, 1H), 2.98-2.83 (m, 1H), 2.65-2.55 (m, 1H), 2.45-2.29 (m, 1H), 2.01 (dtd, J=12.7, 5.3, 2.3 Hz, 1H).

Preparation of rac-3-(5-bromo-1-oxoisoindolin-2-yl)-1-((2-(trimethylsilyl)ethoxy)methyl)piperidine-2,6-dione (INT-1)

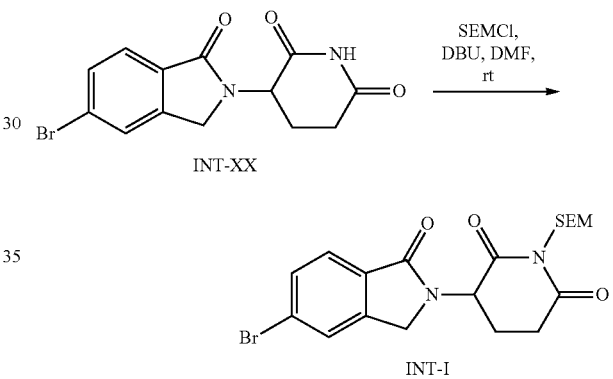

To a stirred solution of INT-XX (10.0 g, 30.9 mmol) and DBU (6.9 mL, 46 mmol) in DMF (95 mL) was added SEMCl (6.6 mL, 37 mmol) at 0° C. and the resulting reaction mixture was allowed to warm to room temperature and then stirred for 5 h. An additional portion of DBU (3.5 mL, 23 mmol) and SEMCl (3.3 mL, 19 mmol) was added and stirring was continued for an additional 2 h. The reaction mixture was then quenched with sat. aq. NH$_4$Cl (250 mL) and extracted with EtOAc (×3). The combined organic phases were dried over Na$_2$SO$_4$, filtered, and concentrated to dryness. The crude material was dissolved in minimal amount of EtOAc (~50 mL) and Et$_2$O:heptane (v/v=1:2, 400 mL) was added. The resulting cloudy solution was left standing at −5° C. overnight. The formed precipitate was filtered, washed with heptane (×3), and dried under vacuum to afford INT-1 as an off-white solid. MS [M+H]$^+$=453.4. $^1$H NMR (400 MHz, Chloroform-d) δ 7.75 (d, J=8.6 Hz, 1H), 7.66-7.61 (m, 2H), 5.37-5.09 (m, 3H), 4.48 (d, J=16.2 Hz, 1H), 4.32 (d, J=16.2 Hz, 1H), 3.74-3.50 (m, 2H), 3.11-2.98 (m, 1H), 2.94-2.83 (m, 1H), 2.33 (qd, J=13.2, 4.7 Hz, 1H), 2.24-2.15 (m, 1H), 0.97-0.90 (m, 2H), 0.00 (s, 9H).

Preparation of 3-(1-oxo-5-(((R)-piperidin-3-yl)oxy)isoindolin-2-yl)piperidine-2,6-dione (INT-2)

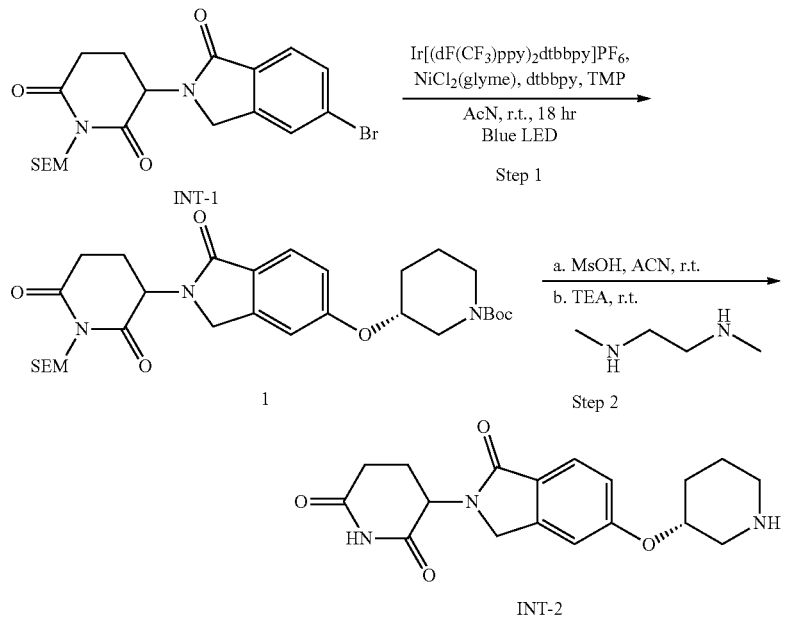

Step 1: Tert-butyl (3R)-3-((2-(2,6-dioxo-1-((2-(trimethylsilyl)ethoxy)methyl)piperidin-3-yl)-1-oxoisoindolin-5-yl)oxy)piperidine-1-carboxylate (1)

To a 40 mL vial, 3-(5-bromo-1-oxoisoindolin-2-yl)-1-((2-(trimethylsilyl)ethoxy)methyl)piperidine-2,6-dione INT-1 (4.00 g, 8.82 mmol), (R)-1-boc-3-hydroxypiperidine (1.78 g, 8.82 mmol), dtbbpy (118 mg, 0.441 mmol), NiCl$_2$(glyme) (97 mg, 0.441 mmol), and Ir[(dF(CF$_3$)ppy)$_2$dtbbpy]PF$_6$ (99 mg, 0.088 mmol) were added. ACN (29.4 mL) was added and the reaction was purged with nitrogen for 5-10 minutes to ensure reaction turned green. 2,2,6,6-tetramethylpiperidine (1.56 mL, 9.26 mmol) was added. The reaction was placed in a PennOC m1 450 nm Photoreactor under blue LED light for 18 hrs. The reaction was concentrated onto CELITE® and purified by silica gel chromatography (0-100% EtOAc in heptane) to afford tert-butyl (3R)-3-((2-(2,6-dioxo-1-((2-(trimethylsilyl)ethoxy)methyl)piperidin-3-yl)-1-oxoisoindolin-5-yl)oxy)piperidine-1-carboxylate 1 as a yellow solid. LCMS [M+H-156.3]$^+$: 418.3. $^1$H NMR (400 MHz, CDCl$_3$) δ 7.79 (dd, J=8.4, 1.8 Hz, 1H), 7.05-6.99 (m, 1H), 6.96 (s, 1H), 5.25 (d, J=9.4 Hz, 1H), 5.23-5.14 (m, 2H), 4.47-4.39 (m, 1H), 4.38-4.24 (m, 2H), 3.95 (q, J=8.6 Hz, 3H), 3.66-3.59 (m, 2H), 3.35-3.16 (m, 1H), 3.06-2.98 (m, 1H), 2.94-2.83 (m, 1H), 2.38-2.26 (m, 1H), 2.23-2.14 (m, 1H), 2.10-2.04 (m, 1H), 1.91-1.72 (m, 2H), 1.61-1.50 (m, 1H), 1.42 (s, 9H), 0.94 (dd, J=9.2, 7.3 Hz, 2H), 0.00 (s, 9H).

Step 2: 3-(1-oxo-5-(((R)-piperidin-3-yl)oxy)isoindolin-2-yl)piperidine-2,6-dione (INT-2)

To tert-butyl (3R)-3-((2-(2,6-dioxo-1-((2-(trimethylsilyl)ethoxy)methyl)piperidin-3-yl)-1-oxoisoindolin-5-yl)oxy)piperidine-1-carboxylate 1 (4.7 g, 8.2 mmol) dissolved in ACN (27 mL) was added methanesulfonic acid (5.8 mL, 89 mmol). The reaction stirred at r.t. overnight. The reaction was cooled to 0° C. and triethylamine (16.0 mL, 115 mmol) followed by N1,N2-dimethylethane-1,2-diamine (1.41 mL, 13.1 mmol) were added. The reaction stirred at r.t. for 2 hrs. The reaction was quenched with 50% saturated aqueous sodium bicarbonate and extracted three times with 4:1 DCM:iPrOH. The organic layers were combined, passed through a phase separator and concentrated. Crude material was purified by silica gel chromatography (0-100% ethanol with 1% TEA in dichloromethane) to afford 3-(1-oxo-5-(((R)-piperidin-3-yl)oxy)isoindolin-2-yl)piperidine-2,6-dione INT-2 as a cream solid. LCMS [M+H]$^+$: 344.3.

Preparation of (R)-5-((6-azaspiro[2.5]octan-4-yl)oxy)isobenzofuran-1(3H)-one (INT-20)

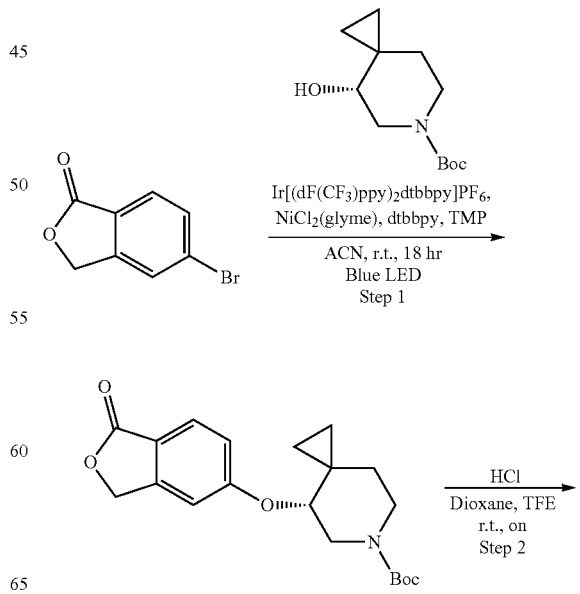

-continued

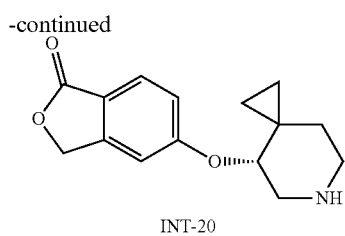

INT-20

Step 1. Tert-butyl (R)-4-((1-oxo-1,3-dihydroisobenzofuran-5-yl)oxy)-6-azaspiro[2.5]octane-6-carboxylate (19)

To a 40 mL capped vial, 5-bromoisobenzofuran-1(3H)-one (220 mg, 1.03 mmol), tert-butyl (4R)-4-hydroxy-6-azaspiro[2.5]octane-6-carboxylate (CAS #1205542-21-7) (246 mg, 1.08 mmol), dtbbpy (28 mg, 0.10 mmol), NiCl$_2$ (glyme) (23 mg, 0.10 mmol), and Ir[(dF(CF$_3$)ppy)$_2$dtbbpy] PF$_6$ (23 mg, 0.021 mmol) were added. ACN (4.4 mL) was added and the reaction was purged with nitrogen for 5-10 minutes ensuring reaction turns green. Then 2,2,6,6-tetramethylpiperidine (0.18 mL, 1.1 mmol) was added. The reaction was placed in a PennOC m1 450 nm Photoreactor under blue LED light for 18 hrs. The reaction was concentrated onto CELITE® and purified by silica gel chromatography (0-100% EtOAc in heptane) to afford product tert-butyl (R)-4-((1-oxo-1,3-dihydroisobenzofuran-5-yl)oxy)-6-azaspiro[2.5]octane-6-carboxylate 19 as a light cream solid. LCMS [M+H-tert-butyl]$^+$: 304.2. $^1$H NMR (400 MHz, CDCl$_3$) δ 7.83 (d, J=8.5 Hz, 1H), 7.02 (dd, J=8.5, 2.1 Hz, 1H), 6.91 (d, J=2.2 Hz, 1H), 5.24 (s, 2H), 4.21-3.63 (m, 3H), 3.46-3.00 (m, 2H), 1.55-0.99 (m, 11H), 0.77-0.65 (m, 1H), 0.62-0.44 (m, 3H).

Step 2: (R)-5-((6-azaspiro[2.5]octan-4-yl)oxy)isobenzofuran-1(3H)-one (INT-20)

Tert-butyl (R)-4-((1-oxo-1,3-dihydroisobenzofuran-5-yl)oxy)-6-azaspiro[2.5]octane-6-carboxylate 19 (228 mg, 0.63 mmol) was dissolved in dioxane (3.2 mL) and trifluoroethane (0.5 mL). 4M HCl in dioxane (0.95 mL, 3.8 mmol) was added and the reaction stirred at r.t. for 18 hrs. The reaction was concentrated to afford (R)-5-((6-azaspiro[2.5]octan-4-yl)oxy)isobenzofuran-1(3H)-one INT-20 as a light yellow oil. Material was used directly in the next reaction. LCMS [M+H]$^+$: 260.2.

Preparation of (R)-sec-butyl methanesulfonate (INT-27)

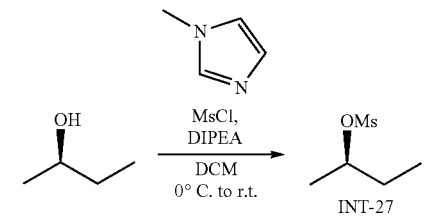

Compound INT-27 was made according to General Method VIII starting from (R)-butan-2-ol (0.2 mL, 2.177 mmol) to afford (R)-sec-butyl methanesulfonate INT-27 as an orange oil. $^1$H NMR (400 MHz, CDCl$_3$) δ 4.77 (h, J=6.3 Hz, 1H), 3.02 (s, 3H), 1.82-1.63 (m, 2H), 1.44 (d, J=6.3 Hz, 3H), 1.01 (t, J=7.4 Hz, 3H).

Preparation of Enantiomers of 5-((5-ethyl-5-azaspiro[2.5]octan-7-yl)oxy)isobenzofuran-1(3H)-one (INT-33)

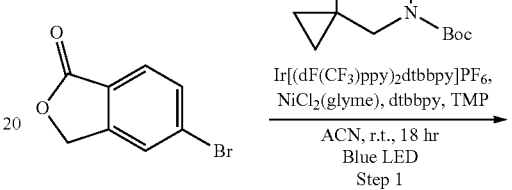

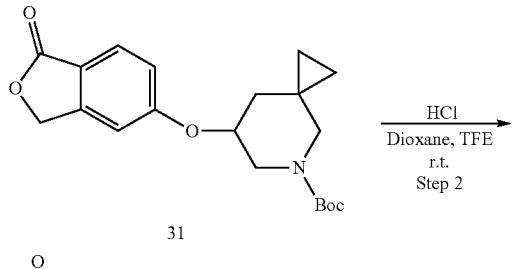

31

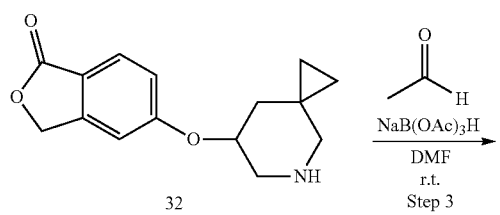

32

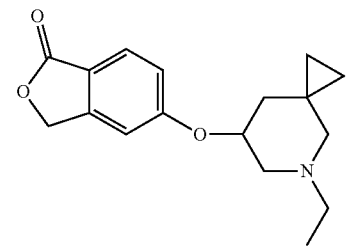

INT-33

Step 1: Tert-butyl 7-((1-oxo-1,3-dihydroisobenzofuran-5-yl)oxy)-5-azaspiro[2.5]octane-5-carboxylate (31)

Compound 31 was made according to General Method I starting from 5-bromoisobenzofuran-1(3H)-one (0.2 g, 0.939 mmol) and tert-butyl 7-hydroxy-5-azaspiro[2.5]octane-5-carboxylate (CAS #2167476-06-2) (235 mg, 1.03 mmol). The reaction was concentrated onto CELITE® and purified by silica gel chromatography (0-100% EtOAc in heptane) to afford tert-butyl 7-((1-oxo-1,3-dihydroisobenzofuran-5-yl)oxy)-5-azaspiro[2.5]octane-5-carboxylate 31 as a yellow oil. LCMS [M+H-t-butyl]$^+$: 304.3.

Step 2: 5-((5-azaspiro[2.5]octan-7-yl)oxy)isobenzofuran-1(3H)-one (32)

Tert-butyl 7-((1-oxo-1,3-dihydroisobenzofuran-5-yl)oxy)-5-azaspiro[2.5]octane-5-carboxylate 31 (271 mg, 0.754 mmol) was suspended in dioxane (7.54 mL). 4M HCl in dioxane (1.13 mL, 4.52 mmol) was added and the reaction stirred at r.t. for 18 hrs. Trifluoroethanol (2 mL) was added followed by additional 4M HCl in dioxane (1.13 mlL, 4.52 mmol). The reaction stirred at r.t. for 72 hrs. The reaction was concentrated to afford 5-((5-azaspiro[2.5]octan-7-yl)oxy)isobenzofuran-1(3H)-one 32) as a white solid. Material was used directly in the next reaction. LCMS [M+H]$^+$: 260.1.

Step 3: Enantiomers of 5-((5-ethyl-5-azaspiro[2.5]octan-7-yl)oxy)isobenzofuran-1(3H)-one (INT-33)

Compound INT-33 was made according to General Method X starting from 5-((5-azaspiro[2.5]octan-7-yl)oxy)isobenzofuran-1(3H)-one 32 (196 mg, 0.754 mmol) and acetaldehyde (63.9 µL, 1.13 mmol). The crude material was purified by silica gel chromatography (0-100% 3:1 EtOAc:EtOH with 1% TEA in heptane) to afford 5-((5-ethyl-5-azaspiro[2.5]octan-7-yl)oxy)isobenzofuran-1(3H)-one INT-33 as an orange oil. LCMS [M+H]$^+$: 288.2. $^1$H NMR (400 MHz, CDCl$_3$) δ 7.55 (d, J=8.5 Hz, 1H), 6.83-6.74 (m, 1H), 6.74-6.64 (m, 1H), 4.98 (s, 2H), 4.46-4.38 (m, 1H), 3.00-2.92 (m, 1H), 2.32-2.16 (m, 2H), 2.08 (dd, J=11.4, 1.3 Hz, 1H), 1.99-1.91 (m, 1H), 1.87-1.80 (m, 1H), 1.66-1.58 (m, 1H), 1.30-1.23 (m, 1H), 0.83 (t, J=7.2 Hz, 2H), 0.29-0.00 (m, 5H). The enantiomeric mixture of isomers was separated via chiral SFC [Column 21×250 mm Chiralpak IG; CO$_2$ Co-solvent 25% MeOH with 10 mM NH$_3$; at 80 g/min at 125 bar] to afford two single enantiomers: Peak 1: Enantiomer 1 of 5-((5-ethyl-5-azaspiro[2.5]octan-7-yl)oxy)isobenzofuran-1(3H)-one) as an orange oil; Peak 2: Enantiomer 2 of 5-((5-ethyl-5-azaspiro[2.5]octan-7-yl)oxy)isobenzofuran-1(3H)-one) as an orange oil.

Preparation of 5-(((1S,5S,6R)-3-ethyl-3-azabicyclo[4.1.0]heptan-5-yl)oxy)isobenzofuran-1(3H)-one and 5-(((1R,5R,6S)-3-ethyl-3-azabicyclo[4.1.0]heptan-5-yl)oxy)isobenzofuran-1(3H)-one

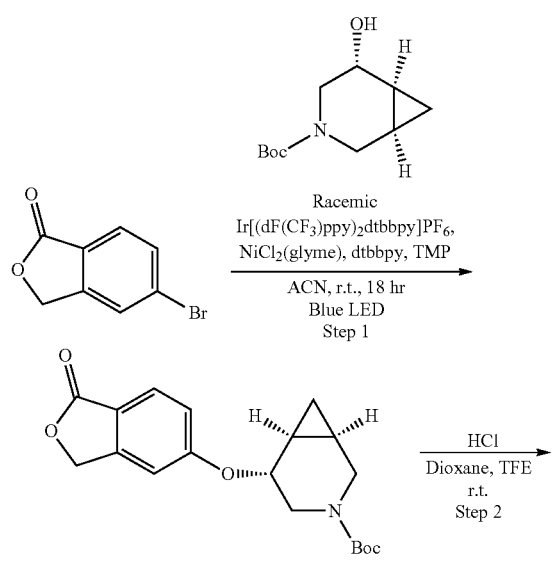

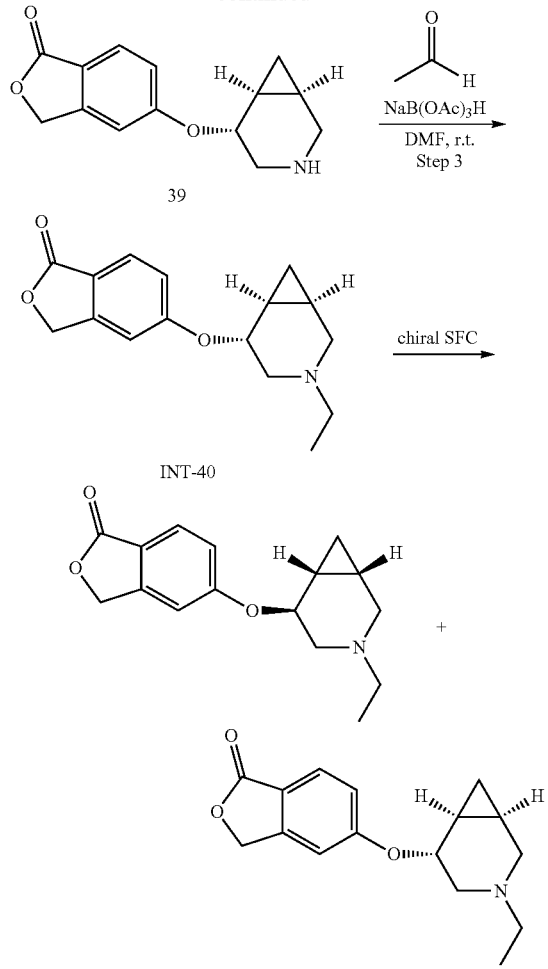

Step 1: rac-Tert-butyl (1R,5R,6S)-5-((1-oxo-1,3-dihydroisobenzofuran-5-yl)oxy)-3-azabicyclo[4.1.0]heptane-3-carboxylate (38)

To a 40 mL capped vial, 5-bromoisobenzofuran-1(3H)-one (225 mg, 1.056 mmol), rac-tert-butyl (1R,5R,6S)-5-hydroxy-3-azabicyclo[4.1.0]heptane-3-carboxylate (CAS #2305079-71-2; also referred to as 5-exo-hydroxy-3-azabicyclo[4.1.0]heptane-3-carboxylic acid tert-butyl ester) (248 mg, 1.16 mmol), dtbbpy (28 mg, 0.11 mmol), NiCl$_2$ (glyme) (23 mg, 0.11 mmol), and Ir[(dF(CF$_3$)ppy)$_2$dtbbpy]PF$_6$ (24 mg, 0.021 mmol) were added. ACN (4.5 mL) was added and the reaction was purged with nitrogen for 5-10 minutes ensuring reaction turns green. Then 2,2,6,6-tetramethylpiperidine (0.19 mL, 1.11 mmol) was added. The reaction was placed in a PennOC m1 450 nm Photoreactor under blue LED light at r.t. for 18 hrs. The reaction was concentrated onto CELITE® and purified by silica gel chromatography (0-100% EtOAc in heptane) to afford rac-tert-butyl (1R,5R,6S)-5-((1-oxo-1,3-dihydroisobenzofuran-5-yl)oxy)-3-azabicyclo[4.1.0]heptane-3-carboxylate 38 as a yellow oil. LCMS [M+H-tert-butyl]$^+$: 290.0.

Step 2: rac-5-(((1R,5R,6S)-3-Azabicyclo[4.1.0]heptan-5-yl)oxy)isobenzofuran-1(3H)-one (39)

Compound 39 was made according to General Method II starting from rac-tert-butyl (1R,5R,6S)-5-((1-oxo-1,3-dihydroisobenzofuran-5-yl)oxy)-3-azabicyclo[4.1.0]heptane-3-carboxylate 38 (224 mg, 0.65 mmol). The reaction was concentrated to afford rac-5-(((1R,5R,6S)-3-azabicyclo[4.1.0]heptan-5-yl)oxy)isobenzofuran-1(3H)-one 39 as a yellow oil. Material was used directly in the next reaction. LCMS [M+H]+: 246.2.

Step 3: 5-(((1 S,5S,6R)-3-ethyl-3-azabicyclo[4.1.0]heptan-5-yl)oxy)isobenzofuran-1(3H)-one and 5-(((1R,5R,6S)-3-ethyl-3-azabicyclo[4.1.0]heptan-5-yl)oxy)isobenzofuran-1(3H)-one Compound INT-40 was made according to General Method X starting from rac-5-(((1R,5R,6S)-3-azabicyclo[4.1.0]heptan-5-yl)oxy)isobenzofuran-1(3H)-one 39 (159 mg, 0.65 mmol) and acetaldehyde (55 µL, 0.974 mmol). The crude material was purified by silica gel chromatography (0-100% ethyl acetate in heptane) to afford rac-5-(((1R,5R,6S)-3-ethyl-3-azabicyclo[4.1.0]heptan-5-yl)oxy)isobenzofuran-1(3H)-one INT-40 as a light yellow oil. LCMS [M+H]+: 274.2. $^1$H NMR (400 MHz, CDCl$_3$) δ 7.85 (d, J=8.5 Hz, 1H), 7.13 (dd, J=8.7, 2.1 Hz, 1H), 7.05-6.98 (m, 1H), 5.28 (s, 2H), 4.66-4.38 (m, 1H), 2.87-2.79 (m, 1H), 2.77-2.65 (m, 2H), 2.36 (d, J=58.0 Hz, 3H), 1.69-1.50 (m, 1H), 1.32-1.21 (m, 1H), 1.16-1.00 (m, 3H), 0.82-0.71 (m, 1H), 0.57-0.47 (m, 1H). The enantiomeric mixture of isomers was separated via chiral SFC [Column 21×250 mm IH; CO$_2$ Co-solvent 12% MeOH with 0.5% IPA; at 80 g/min at 100 bar at 35° C.] to afford two single enantiomers: 5-(((1S*,5S*,6R*)-3-ethyl-3-azabicyclo[4.1.0]heptan-5-yl)oxy)isobenzofuran-1(3H)-one INT-40 Peak 1, Rt=2.18 mins, as a cream solid; 5-(((1R*,5R*,6S*)-3-ethyl-3-azabicyclo[4.1.0]heptan-5-yl)oxy)isobenzofuran-1(3H)-one INT-40 Peak 2, Rt=2.34 mins, as a cream solid. The absolute stereochemistry of the two enantiomers corresponding to the two product peaks was not determined.

Preparation of 5-(((1S,5R,6R)-3-ethyl-3-azabicyclo[4.1.0]heptan-5-yl)oxy)isobenzofuran-1(3H)-one and 5-(((1R,5S,6S)-3-ethyl-3-azabicyclo[4.1.0]heptan-5-yl)oxy)isobenzofuran-1(3H)-one

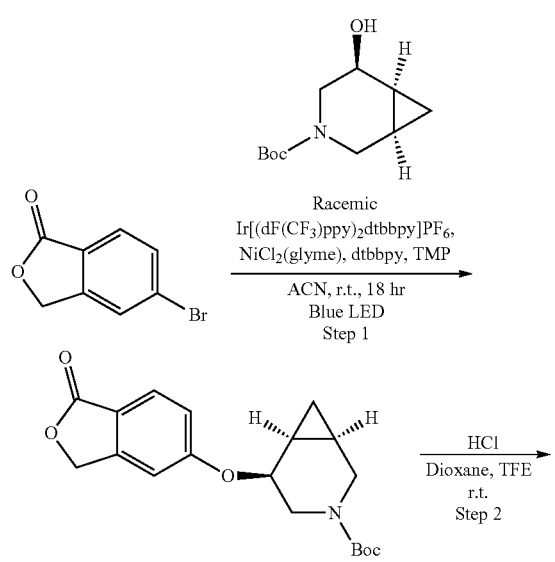

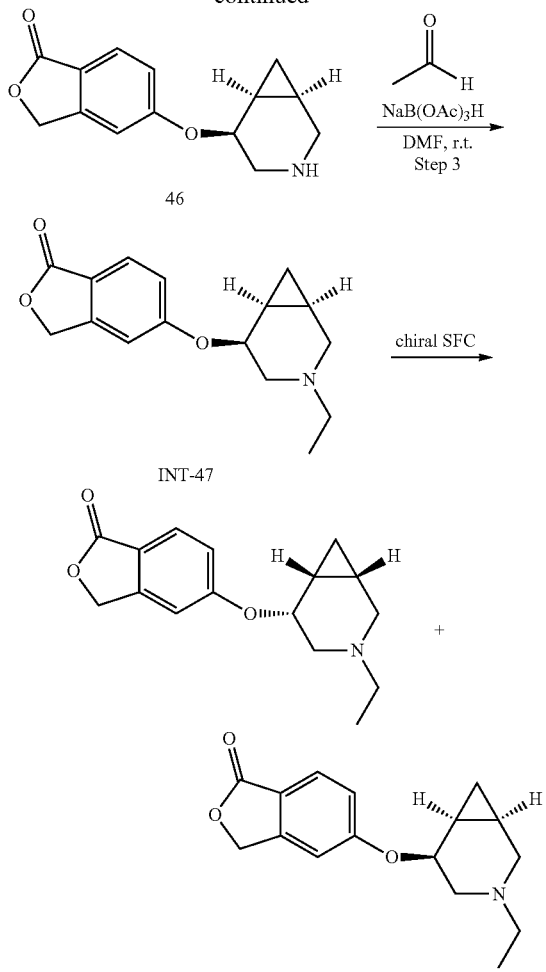

Step 1: rac-Tert-butyl (1R,5S,6S)-5-((1-oxo-1,3-dihydroisobenzofuran-5-yl)oxy)-3-azabicyclo[4.1.0]heptane-3-carboxylate (45)

To a 40 mL capped vial, 5-bromoisobenzofuran-1(3H)-one (225 mg, 1.06 mmol), rac-tert-butyl (1R,5S,6S)-5-hydroxy-3-azabicyclo[4.1.0]heptane-3-carboxylate (CAS #2305079-37-0; also referred to as 5-endo-hydroxy-3-azabicyclo[4.1.0]heptane-3-carboxylic acid tert-butyl ester) (248 mg, 1.16 mmol), dtbbpy (28 mg, 0.11 mmol), NiCl$_2$ (glyme) (23 mg, 0.11 mmol), and Ir[(dF(CF$_3$)ppy)$_2$dtbbpy]PF$_6$ (24 mg, 0.021 mmol) were added. ACN (4.5 mL) was added and the reaction was purged with nitrogen for 5-10 minutes ensuring reaction turns green. Then 2,2,6,6-tetramethylpiperidine (0.19 mL, 1.11 mmol) was added. The reaction was placed in a PennOC m1 450 nm Photoreactor under blue LED light at r.t. for 18 hrs. The reaction was concentrated onto CELITE® and purified by silica gel chromatography (0-100% EtOAc in heptane) to afford rac-tert-butyl (1R,5S,6S)-5-((1-oxo-1,3-dihydroisobenzofuran-5-yl)oxy)-3-azabicyclo[4.1.0]heptane-3-carboxylate 45 as a light yellow solid. LCMS [M+H-tert-butyl]+: 290.3.

Step 2: rac-5-(((1R,5S,6S)-3-Azabicyclo[4.1.0]heptan-5-yl)oxy)isobenzofuran-1(3H)-one (46)

Compound 46 was made according to General Method II starting from rac-tert-butyl (1R,5S,6S)-5-((1-oxo-1,3-dihydroisobenzofuran-5-yl)oxy)-3-azabicyclo[4.1.0]heptane-3-carboxylate 45 (302 mg, 0.87 mmol). Reaction was concentrated to afford rac-5-(((1R,5S,6S)-3-azabicyclo[4.1.0]heptan-5-yl)oxy)isobenzofuran-1(3H)-one 46 (214 mg, 0.874 mmol) as a yellow oil. Material was used directly in the next reaction. LCMS [M+H]$^+$: 246.2.

Step 3: 5-(((1 S,5R,6R)-3-ethyl-3-azabicyclo[4.1.0]heptan-5-yl)oxy)isobenzofuran-1(3H)-one and 5-(((1R,5S,6S)-3-ethyl-3-azabicyclo[4.1.0]heptan-5-yl)oxy)isobenzofuran-1(3H)-one Compound INT-47 was made according to General Method X starting from rac-5-(((1R,5S,6S)-3-azabicyclo[4.1.0]heptan-5-yl)oxy)isobenzofuran-1(3H)-one 46 (214 mg, 0.87 mmol) and acetaldehyde (74 µL, 1.31 mmol). The crude material was purified by silica gel chromatography (0-20% methanol in DCM) to afford rac-5-(((1R,5S,6S)-3-ethyl-3-azabicyclo[4.1.0]heptan-5-yl)oxy)isobenzofuran-1(3H)-one INT-47 as an orange oil. LCMS [M+H]$^+$: 274.2. The enantiomeric mixture of isomers was separated via chiral SFC [Column 21×250 mm IH; $CO_2$ Co-solvent 12% MeOH with 0.5% IPA; at 80 g/min at 100 bar at 35° C.] to afford two single enantiomers: 5-(((1S*,5R*,6R*)-3-ethyl-3-azabicyclo[4.1.0]heptan-5-yl)oxy)isobenzofuran-1(3H)-one INT-47 Peak 1, Rt=1.55 mins, as a brown oil; 5-(((1R*,5S*,6S*)-3-ethyl-3-azabicyclo[4.1.0]heptan-5-yl)oxy)isobenzofuran-1(3H)-one INT-47 Peak 2, Rt=1.70 mins, as a brown oil. The absolute stereochemistry of the two enantiomers corresponding to the two product peaks was not determined.

Preparation of (1r,3r)-3-ethoxycyclobutyl methanesulfonate (INT-55)

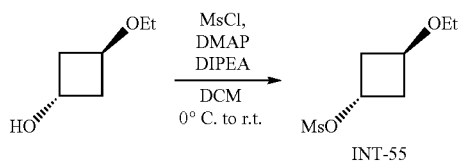

A 40 mL vial was charged (1r,3r)-3-ethoxycyclobutan-1-ol (570 mg, 4.9 mmol), DIPEA (1.3 mL, 7.4 mmol), DMAP (60 mg, 0.49 mmol) and DCM (3.0 mL). MsCl (0.42 mL, 5.4 mmol) was added and reaction stirred at 0° C. for 1 hr and r.t. for 5 hrs. The reaction was quenched with saturated aqueous $NaHCO_3$ and extracted with DCM three times. The organic layers were combined, dried over $Na_2SO_4$, filtered, and concentrated to afford (1r,3r)-3-ethoxycyclobutyl methanesulfonate INT-55 as a brown oil. Material was taken through to the next step without purification. $^1$H NMR (400 MHz, $CDCl_3$) δ 5.21 (tt, J=7.0, 5.0 Hz, 1H), 4.28-4.14 (m, 1H), 3.41 (q, J=7.0 Hz, 2H), 3.01 (s, 3H), 2.62-2.45 (m, 4H), 1.22 (t, J=7.0 Hz, 3H).

Preparation of ((1r,3r)-3-methoxycyclobutyl)methyl methanesulfonate (INT-58)

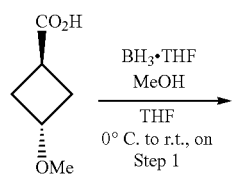

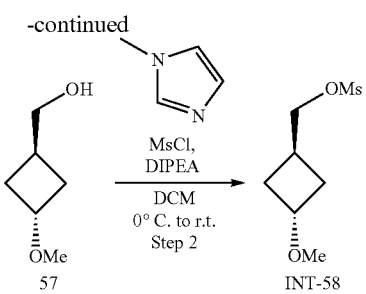

Step 1: ((1r,3r)-3-methoxycyclobutyl)methanol (57)

Trans-3-methoxycyclobutane-1-carboxylic acid (175 mg, 1.35 mmol) was dissolved in THF (4.5 mL) and cooled to 0° C. 1M borane tetrahydrofuran complex in THF (4.0 mL, 4.0 mmol) was added dropwise. The reaction stirred at r.t. for 36 hrs. The reaction was cooled to 0° C. and quenched with methanol (3.26 mL, 81 mmol) and stirred at r.t. for 2 hrs. The reaction was concentrated to dryness then redissolved in methanol (5 mL). The reaction stirred at r.t. for 18 hrs. The reaction was concentrated to afford ((1r,3r)-3-methoxycyclobutyl)methanol 57 (156 mg, 1.35 mmol) as a clear oil. Material was carried on crude to the next step.

Step 2: ((1r,3r)-3-methoxycyclobutyl)methyl methanesulfonate (INT-58)

Compound INT-58 was made according to General Method VIII starting from ((1r,3r)-3-methoxycyclobutyl)methanol 57 (156 mg, 1.345 mmol) to afford ((1r,3r)-3-methoxycyclobutyl)methyl methanesulfonate INT-58 as a light yellow oil. $^1$H NMR (400 MHz, $CD_3OD$) δ 4.26 (d, J=6.8 Hz, 2H), 4.02 (p, J=6.7 Hz, 1H), 3.24 (s, 3H), 3.09 (s, 3H), 2.67-2.57 (m, 1H), 2.23-2.10 (m, 4H).

Preparation of 7-oxaspiro[3.5]nonan-2-yl methanesulfonate (INT-60)

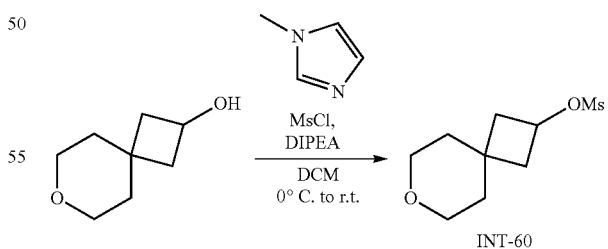

Compound INT-60 was made according to General Method VIII starting from 7-oxaspiro[3.5]nonan-2-ol (60 mg, 0.42 mmol) to afford 7-oxaspiro[3.5]nonan-2-yl methanesulfonate INT-60 as an orange oil. $^1$H NMR (400 MHz, $CDCl_3$) δ 5.05 (p, J=7.2 Hz, 1H), 3.67-3.56 (m, 4H), 3.01 (s, 3H), 2.53-2.43 (m, 2H), 2.17-2.09 (m, 2H), 1.70-1.60 (m, 4H).

Preparation of 3,3-difluorocyclobutyl methanesulfonate (INT-62)

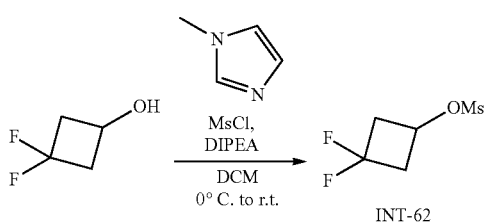

Compound INT-62 was made according to General Method VIII starting from 3,3-difluorocyclobutan-1-ol (150 mg, 1.39 mmol) to afford 3,3-difluorocyclobutyl methanesulfonate INT-62 as an orange oil. $^1$H NMR (400 MHz, CDCl$_3$) δ 5.04-4.94 (m, 1H), 3.19-3.09 (m, 2H), 3.07 (s, 3H), 3.02-2.85 (m, 2H).

Preparation of ((1r,4r)-4-methoxycyclohexyl)methyl methanesulfonate (INT-64)

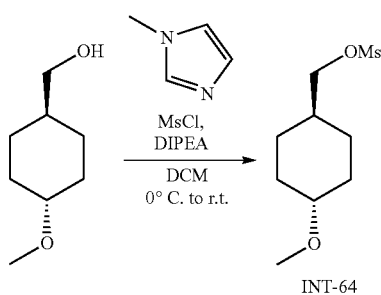

Compound INT-64 was made according to General Method VIII starting from ((1r,4r)-4-methoxycyclohexyl)methanol (250 mg, 1.73 mmol) to afford ((1r,4r)-4-methoxycyclohexyl)methyl methanesulfonate INT-64 as an orange oil. $^1$H NMR (400 MHz, CDCl$_3$) δ 4.06 (d, J=6.4 Hz, 2H), 3.37 (s, 3H), 3.17-3.06 (m, 1H), 3.02 (s, 3H), 2.18-2.09 (m, 2H), 1.94-1.85 (m, 2H), 1.82-1.70 (m, 1H), 1.31-1.18 (m, 2H), 1.16-1.04 (m, 2H).

Preparation of Cyclobutyl methanesulfonate (INT-66)

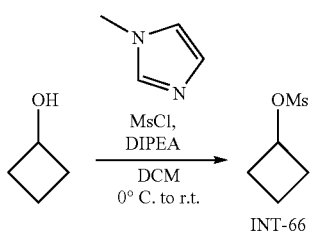

Compound INT-66 was made according to General Method VIII starting from cyclobutanol (0.2 mL, 2.55 mmol) to afford cyclobutyl methanesulfonate INT-66 as an orange oil. $^1$H NMR (400 MHz, CDCl$_3$) δ 4.99 (pd, J=7.5, 1.0 Hz, 1H), 3.00 (s, 3H), 2.48-2.26 (m, 4H), 1.95-1.82 (m, 1H), 1.71-1.56 (m, 1H).

Preparation of (S)-sec-butyl methanesulfonate (INT-68)

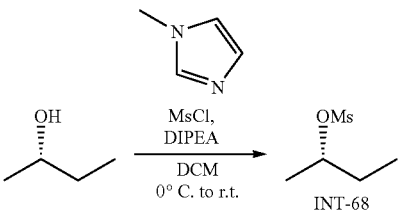

Compound INT-68 was made according to General Method VIII starting from (S)-butan-2-ol (0.2 mL, 2.17 mmol) to afford (S)-sec-butyl methanesulfonate INT-68 as an orange oil. $^1$H NMR (400 MHz, CDCl$_3$) δ 4.77 (h, J=6.3 Hz, 1H), 3.02 (s, 3H), 1.85-1.63 (m, 2H), 1.44 (d, J=6.3 Hz, 3H), 1.01 (t, J=7.4 Hz, 3H).

Preparation of rac-tert-butyl (3R,5S)-3-hydroxy-5-methylpiperidine-1-carboxylate (INT-108)

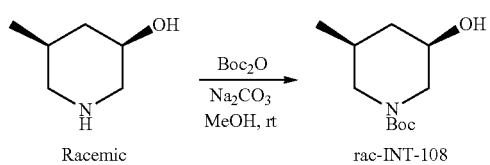

To a solution of rac-(3R,5S)-5-methylpiperidin-3-ol (245 mg, 1.62 mmol) in MeOH (2.5 mL) was added Na$_2$CO$_3$ (257 mg, 2.42 mmol) and di-tert-butyl dicarbonate (529 mg, 2.42 mmol). The reaction mixture was stirred at r.t. overnight. The reaction mixture was diluted with H$_2$O (5.0 mL) and extracted with DCM three times. The organic layers were combined, dried over Na$_2$SO$_4$, filtered, and concentrated to afford rac-tert-butyl (3R,5S)-3-hydroxy-5-methylpiperidine-1-carboxylate INT-108 as a colorless oil. Material was taken through to the next step without purification.

Preparation of enantiomers of tert-butyl 4,4-dimethyl-3-((1-oxo-1,3-dihydroisobenzofuran-5-yl)oxy)piperidine-1-carboxylate (INT-118)

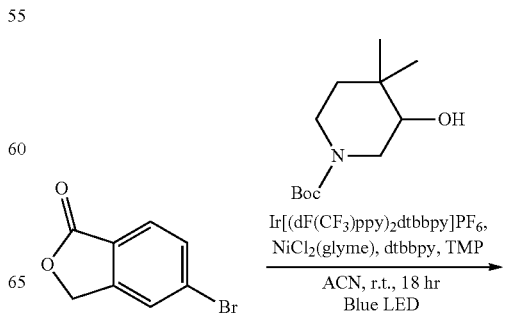

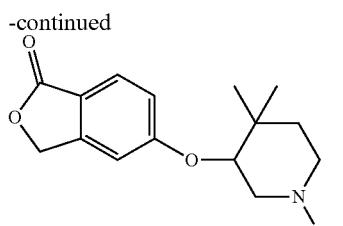

INT-118

To a 40 mL capped vial, 5-bromoisobenzofuran-1(3H)-one (0.5 g, 2.347 mmol), rac-tert-butyl 3 hydroxy-4,4-dimethylpiperidine-1-carboxylate (592 mg, 2.58 mmol), dtbbpy (63 mg, 0.235 mmol), NiCl$_2$(glyme) (52 mg, 0.235 mmol), and Ir[(dF(CF$_3$)ppy)$_2$dtbbpy]PF$_6$ (53 mg, 0.047 mmol) were added. ACN (9.99 mL) was added and the reaction was purged with nitrogen for 5-10 minutes ensuring reaction turns green. Then 2,2,6,6-tetramethylpiperidine (0.416 mL, 2.464 mmol) was added. The reaction was placed in a PennOC m1 450 nm Photoreactor under blue LED light at r.t. for 18 hrs. The reaction was concentrated onto CELITE® and purified by silica gel chromatography (0-100% EtOAc in heptane) to afford tert-butyl 4,4-dimethyl-3-((1-oxo-1,3-dihydroisobenzofuran-5-yl)oxy)piperidine-1-carboxylate INT-118 as a cream solid. LCMS [M+H-tert-butyl]$^+$: 306.2. $^1$H NMR (400 MHz, CDCl$_3$) δ 7.85 (d, J=8.5 Hz, 1H), 7.09 (dd, J=8.6, 2.1 Hz, 1H), 7.00 (s, 1H), 5.26 (s, 2H), 3.98 (dd, J=7.7, 3.4 Hz, 1H), 3.61-3.28 (m, 3H), 1.76-1.64 (m, 1H), 1.60-1.52 (m, 2H), 1.49-1.31 (m, 9H), 1.12 (s, 3H), 1.10 (s, 3H). The enantiomeric mixture of isomers was separated via chiral SFC [Column 21×250 mm ChiralPak IG; CO$_2$ Co-solvent 15% 1:1 Methanol:iPrOH; at 80 g/min at 125 bar] to afford two enantiomers: Peak 1: Enantiomer 1 of tert-butyl 4,4-dimethyl-3-((1-oxo-1,3-dihydroisobenzofuran-5-yl)oxy)piperidine-1-carboxylate (364 mg, 1.007 mmol) as a light yellow clear oil; Peak 2: Enantiomer 2 of tert-butyl 4,4-dimethyl-3-((1-oxo-1,3-dihydroisobenzofuran-5-yl)oxy)piperidine-1-carboxylate (214 mg, 0.592 mmol) as light yellow clear oil.

Preparation of 5-((4,4-dimethylpiperidin-3-yl)oxy)isobenzofuran-1(3H)-one (INT-119)

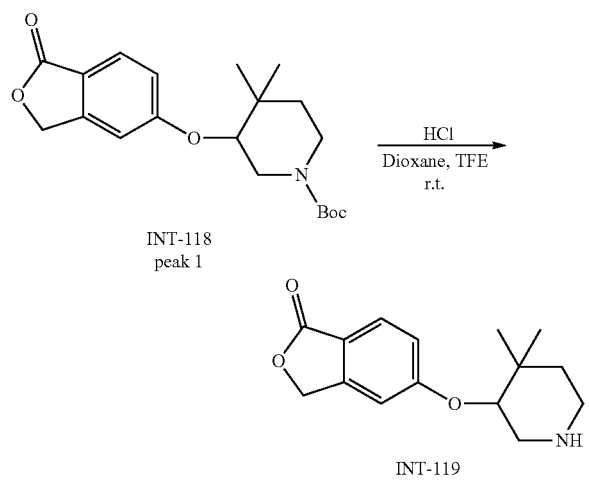

Compound INT-119 was made according to General Method II starting from Tert-butyl 4,4-dimethyl-3-((1-oxo-1,3-dihydroisobenzofuran-5-yl)oxy)piperidine-1-carboxylate INT-118 peak 1 (364 mg, 1.007 mmol). The reaction was concentrated to afford 5-((4,4-dimethylpiperidin-3-yl)oxy)isobenzofuran-1(3H)-one INT-119 as a cream solid. Material was used directly in the next reaction. LCMS [M+H]$^+$: 262.4.

Preparation of 5-((4,4-dimethylpiperidin-3-yl)oxy)isobenzofuran-1(3H)-one (INT-120)

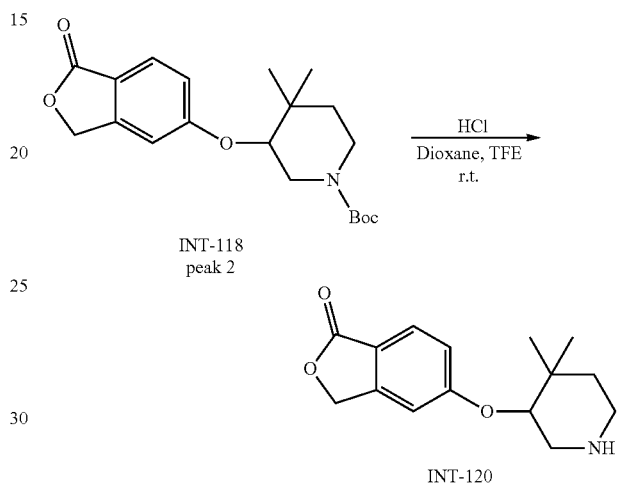

Compound INT-120 was made according to General Method II starting from Tert-butyl 4,4-dimethyl-3-((1-oxo-1,3-dihydroisobenzofuran-5-yl)oxy)piperidine-1-carboxylate INT-118 peak 2 (214 mg, 0.592 mmol). The reaction was concentrated to afford 5-((4,4-dimethylpiperidin-3-yl)oxy)isobenzofuran-1(3H)-one INT-120 as a cream solid. Material was used directly in the next reaction. LCMS [M+H]$^+$: 262.0.

Preparation of rac-tert-butyl (3R,5R)-3-hydroxy-5-methylpiperidine-1-carboxylate (INT-133)

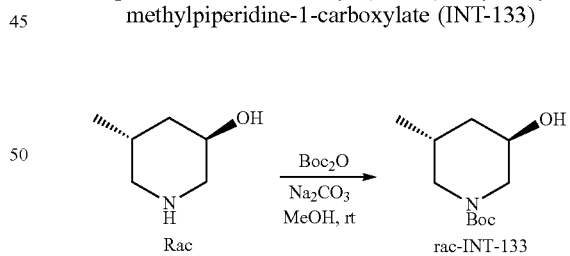

To a solution of rac-(3R,5R)-5-methylpiperidin-3-ol (251 mg, 2.2 mmol) in EtOH (6 mL), a solution of boc-anhydride (523 mg, 2.4 mmol) in EtOH (3 mL) was added via syringe. The reaction was stirred at r.t. for 20 hrs. The reaction was concentrated to afford rac-tert-butyl (3R,5R)-3-hydroxy-5-methylpiperidine-1-carboxylate INT-133 (520 mg, 2.42 mmol). Material was used directly in the next reaction without purification. $^1$H NMR (400 MHz, CDCl$_3$) δ 4.06-3.85 (m, 2H), 2.99 (dd, J=13.6, 1.9 Hz, 1H), 2.45 (s, 1H), 2.00 (dtd, J=10.7, 6.7, 3.8 Hz, 1H), 1.85 (ddt, J=13.7, 4.1, 2.1 Hz, 1H), 1.65 (d, J=25.6 Hz, 1H), 1.46 (s, 9H), 1.32-1.17 (m, 2H), 0.89 (d, J=6.7 Hz, 3H).

Preparation of rac-tert-butyl 5-hydroxy-7-azaspiro[3.5]nonane-7-carboxylate (INT-139)

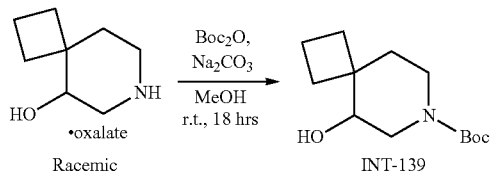

A 40 mL vial was charged with 7-azaspiro[3.5]nonan-5-ol (50 mg, 0.22 mmol), di-tert-butyl dicarbonate (57 mg, 0.26 mmol), Na$_2$CO$_3$ (27 mg, 0.26 mmol) and MeOH (1.0 mL). The reaction mixture stirred vigorously at r.t. for 18 hrs. The reaction mixture was diluted with brine and extracted with DCM four times. The organic layers were combined, passed through a phase separator and concentrated to afford tert-butyl 5-hydroxy-7-azaspiro[3.5]nonane-7-carboxylate INT-139 as a racemic mixture. Material was used directly in the next step without purification. $^1$H NMR (400 MHz, CDCl$_3$) δ 3.58 (dd, J=5.8, 2.7 Hz, 1H), 3.54-3.43 (m, 2H), 3.28 (dd, J=13.5, 2.8 Hz, 1H), 3.13 (ddd, J=13.1, 9.2, 3.5 Hz, 1H), 2.16-2.06 (m, 1H), 2.00-1.82 (m, 4H), 1.77-1.63 (m, 3H), 1.54-1.49 (m, 1H), 1.47 (s, 9H).

Preparation of Benzyl (3S,4S)-4-fluoro-3-hydroxypiperidine-1-carboxylate and benzyl (3R,4R)-4-fluoro-3-hydroxypiperidine-1-carboxylate (INT-146)

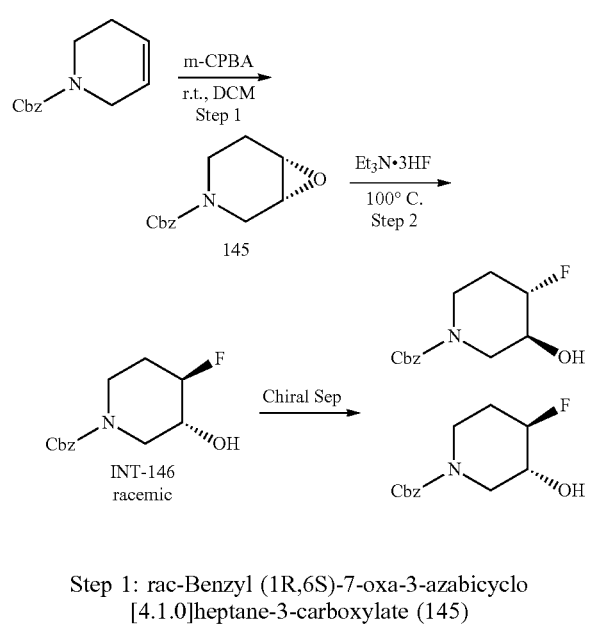

Step 1: rac-Benzyl (1R,6S)-7-oxa-3-azabicyclo[4.1.0]heptane-3-carboxylate (145)

To a suspension of benzyl 3,6-dihydropyridine-1(2H)-carboxylate (8 g, 36.8 mmol) in dry DCM (80 mL) at 0° C. under N$_2$ was added m-CPBA (9.53 g, 44.2 mmol, 85%). The reaction mixture stirred at r.t. for 12 hrs. The reaction mixture was diluted with DCM (20 mL) and washed with saturated aqueous Na$_2$S$_2$O$_3$ (2×80 mL). The organic layers were combined, washed with saturated aqueous NaHCO$_3$ (2×80 mL), brine (80 mL), dried over anhydrous Na$_2$SO$_4$, filtered, and concentrated to afford rac-benzyl (1R,6S)-7-oxa-3-azabicyclo[4.1.0]heptane-3-carboxylate 145 as yellow oil. Material was used in the next step without purification. $^1$H NMR (400 MHz, CDCl$_3$) δ 7.43-7.29 (m, 5H), 5.13 (s, 2H), 4.06-3.72 (m, 2H), 3.53 (br s, 1H), 3.34-3.16 (m, 3H), 2.19-1.84 (m, 2H)

Step 2: Benzyl (3S,4S)-4-fluoro-3-hydroxypiperidine-1-carboxylate and benzyl (3R,4R)-4-fluoro-3-hydroxypiperidine-1-carboxylate A neat mixture of rac-benzyl (1R,6S)-7-oxa-3-azabicyclo[4.1.0]heptane-3-carboxylate 145 (8 g, 34.3 mmol) and Et$_3$N·3HF (5.5 g, 34.3 mmol) stirred at 100° C. for 16 hrs. 20% BF$_3$·Et$_2$O in DCM (80 mL, 129.7 mmol) was added to reaction mixture at r.t., then the reaction mixture was diluted with saturated aqueous NaHCO$_3$ (80 mL) and extracted with DCM twice (40 mL). The organic layers were combined, washed with brine (50 mL), dried over anhydrous Na$_2$SO$_4$, filtered, and concentrated. The crude material was purified by reverse phase HPLC (20-50% ACN in water with 0.1% formic acid). The fractions containing pure product were concentrated to remove ACN and lyophilized to afford rac-benzyl (3R,4R)-4-fluoro-3-hydroxypiperidine-1-carboxylate INT-146 as yellow oil. LCMS [M+H]$^+$: 254.1. $^1$H NMR (400 MHz, DMSO-d$_6$) δ 7.45-7.26 (m, 5H), 5.46 (d, J=4.4 Hz, 1H), 4.57-4.32 (m, 1H), 3.88-3.64 (m, 2H), 3.49-3.40 (m, 1H), 3.26-2.71 (m, 2H), 2.07-1.98 (m, 1H), 1.64-1.34 (m, 1H).

The racemic mixture of isomers was further separated via chiral SFC [Column: Chiralpak AD 250×30 mm I.D; CO$_2$ Co-solvent 40% Methanol with 0.1% NH$_3$·H$_2$O; at 70 g/min at 100 bar, at 25° C.] to afford two enantiomers: INT-146 Peak 1, Rt=2.1 min, as yellow oil. LCMS [M+H]$^+$: 254.1. $^1$H NMR (400 MHz, DMSO-d6) δ 7.42-7.27 (m, 5H), 5.46 (d, J=4.8 Hz, 1H), 5.07 (s, 2H), 4.55-4.32 (m, 1H), 3.85-3.62 (m, 2H), 3.56-3.42 (m, 1H), 3.16-2.84 (m, 2H), 2.05-1.92 (m, 1H), 1.54-1.51 (m, 1H); INT-146 Peak 2, Rt=3.9 min, as yellow oil. LCMS [M+H]$^+$: 254.1. $^1$H NMR (400 MHz, DMSO-d$_6$) δ 7.42-7.27 (m, 5H), 5.46 (d, J=4.8 Hz, 1H), 5.07 (s, 2H), 4.55-4.32 (m, 1H), 3.85-3.62 (m, 2H), 3.56-3.42 (m, 1H), 3.16-2.84 (m, 2H), 2.05-1.92 (m, 1H), 1.54-1.51 (m, 1H). The absolute stereochemistry of the two enantiomers corresponding to the two product peaks was not determined.

Preparation of Benzyl (3S,4R)-4-fluoro-3-hydroxypiperidine-1-carboxylate and benzyl (3R,4S)-4-fluoro-3-hydroxypiperidine-1-carboxylate (INT-155)

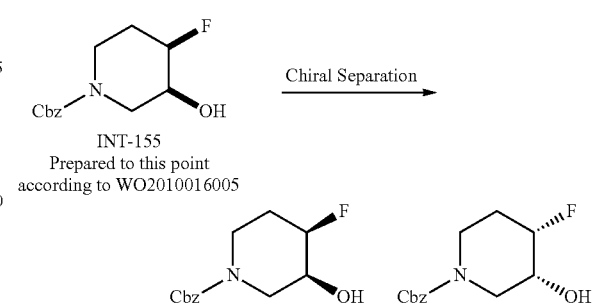

The enantiomeric mixture of INT-155 (900 mg, 3.55 mmol) was separated via chiral SFC [Column: 250 mm×30 mm, 5 um DAICEL CHIRALPAK AD-H; CO$_2$ Co-solvent 30% MeOH+0.1% NH$_3$·H$_2$O; at 60 g/min at 100 bar] to afford two enantiomers. INT-155 Peak 1, Rt=5.76 min, as colorless oil; LCMS [M+23]$^+$: 276.2. $^1$H NMR (400 MHz, CDCl$_3$) δ 7.46-7.27 (m, 5H), 5.15 (s, 2H), 4.94-4.70 (m, 1H), 3.88-3.57 (m, 3H), 3.49-3.36 (m, 2H), 2.26-2.04 (m, 2H), 1.89-1.68 (m, 1H). $^{19}$F NMR (377 MHz, CDCl$_3$) δ −201.8. INT-155 Peak 2, Rt=6.65 mins, as brown oil. LCMS [M+23]$^+$: 276.2. $^1$H NMR (400 MHz, CDCl$_3$) δ 7.52-7.29 (m, 5H), 5.16 (s, 2H), 4.93-4.74 (m, 1H), 3.95-3.57 (m, 3H), 3.50-3.35 (m, 2H), 2.23-2.04 (m, 2H), 1.94-1.68 (m, 1H). $^{19}$F NMR (377 MHz, CDCl$_3$) δ −201.8. The absolute stereochemistry of the two enantiomers corresponding to the two product peaks was not determined.

Preparation of (3R,5S)-1-benzyl-3-(benzyloxy)-5-fluoropiperidine (INT-164), (3R,5R)-1-benzyl-3-(benzyloxy)-5-fluoropiperidine (INT-165), and (2S,4R)-1-benzyl-4-(benzyloxy)-2-(fluoromethyl)pyrrolidine (165)

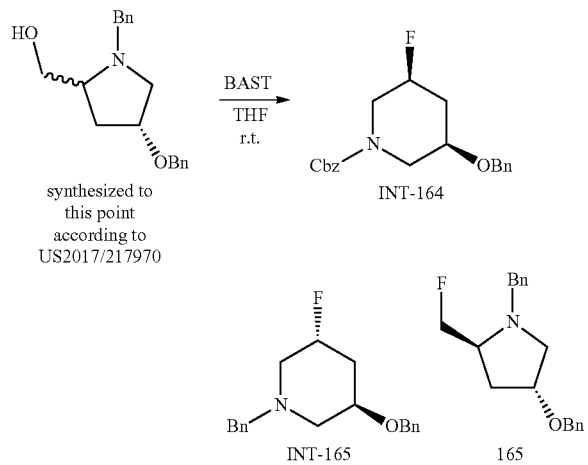

(bis-(2-methoxyethyl)amino)sulfur trufluoride (11.32 mL, 61.39 mmol) was added to a solution of ((4R)-1-benzyl-4-(benzyloxy)pyrrolidin-2-yl)methanol (17.9 g, 60.2 mmol) in THF (180 mL) at 0° C. The reaction mixture was warmed to r.t. and stirred for 3 hrs. The mixture was diluted with EtOAc (200 mL) and washed with brine (3×50 mL), dried over Na$_2$SO$_4$, filtered, and concentrated. The crude material was purified by silica gel chromatography (0-40% EtOAc in petroleum ether) and the fractions containing product were concentrated. Then resulting material was further purified by reverse phase HPLC (60-80% ACN in water with 0.05% ammonia hydroxide as modifier). Fractions containing pure product were concentrated to afford (3R,5S)-1-benzyl-3-(benzyloxy)-5-fluoropiperidine INT-164 as light yellow oil, (3R,5R)-1-benzyl-3-(benzyloxy)-5-fluoropiperidine INT-165 as light yellow oil, and (2S,4R)-1-benzyl-4-(benzyloxy)-2-(fluoromethyl)pyrrolidine 165 as light yellow oil.

(3R,5S)-1-benzyl-3-(benzyloxy)-5-fluoropiperidine INT-164: LCMS [M+H]$^+$: 300.4. $^1$H NMR (400 MHz, CDCl$_3$) δ 7.40-7.27 (m, 10H), 4.73-4.44 (m, 3H), 3.62-3.59 (m, 3H), 3.10 (br s, 2H), 2.63-2.50 (m, 1H), 2.23-1.90 (m, 2H), 1.53-1.41 (m, 1H). $^{19}$F NMR (377 MHz, CDCl$_3$) δ −183.33.

(3R,5R)-1-benzyl-3-(benzyloxy)-5-fluoropiperidine INT-165: LCMS [M+H]$^+$: 300.4. $^1$H NMR (400 MHz, CDCl$_3$) δ 7 7.27 (s, 10H), 5.01-4.81 (m, 1H), 4.54 (d, J=1.6 Hz, 2H), 3.92-3.85 (m, 1H), 3.70-3.59 (m, 2H), 2.98-2.80 (m, 2H), 2.54-2.35 (m, 1H), 2.31-2.16 (m, 2H), 1.76-1.60 (m, 1H). $^{19}$F NMR (377 MHz, CDCl$_3$) δ −182.2.

(2S,4R)-1-benzyl-4-(benzyloxy)-2-(fluoromethyl)pyrrolidine 165: LCMS [M+H]$^+$: 300.3. $^1$H NMR (400 MHz, CDCl$_3$) δ 7.41-7.28 (m, 10H), 4.67-4.34 (m, 4H), 4.17-4.00 (m, 2H), 3.71-3.44 (m, 1H), 3.15-3.11 (m, 1H), 3.08-2.87 (m, 1H), 2.54-2.36 (m, 1H), 2.27-2.23 (m, 1H), 1.89-1.75 (m, 1H).

Preparation of tert-butyl 6-hydroxy-2-azabicyclo[2.2.1]heptane-2-carboxylate and tert-butyl 5-hydroxy-2-azabicyclo[2.2.1]heptane-2-carboxylate (INT-174A and INT-174B)

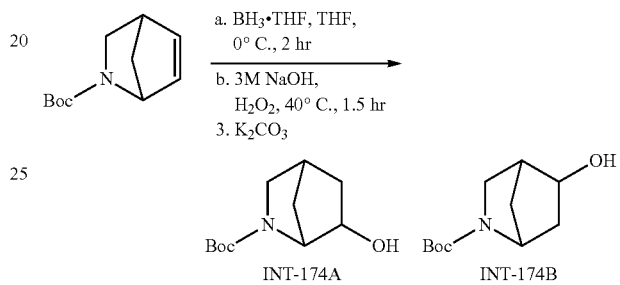

To a solution of tert-butyl 2-azabicyclo[2.2.1]hept-5-ene-2-carboxylate (2 g, 10.24 mmol) in 50 ml anhydrous THF, was cooled to 0° C. in an ice water bath. A 1 M solution of BH$_3$·THF complex (21.0 mL, 20.5 mmol) was added, and stirring was continued at 0° C. for 2 hrs. The excess BH$_3$ was destroyed by careful addition of THF-H$_2$O (a 1:1 mixture, 100 mL). A 3 M NaOH solution (3 mL, 8 mmol) was added followed by dropwise addition of 50% hydrogen peroxide (3.0 mL, 44 mmol), and the mixture was kept at 35-40° C. for 1.5 hr with stirring. After cooling to r.t., potassium carbonate (0.92 g, 6.7 mmol) was added, and the THF was removed under reduced pressure. The remaining solution was poured into an erlenmeyer flask containing methylene chloride and water. The organic layer was extracted and the aqueous layer was back extracted with more DCM. The combined organic extracts were poured through a phase separator, and concentrated to give a regioisomeric mixture of products INT-174A and INT174B as a colorless oil. This material was taken on crude through to the next step without further purification.

Preparation of Final Compounds

Example 1: 3-(5-(((R)-1-ethylpiperidin-3-yl)oxy)-1-oxoisoindolin-2-yl)piperidine-2,6-dione (I-3)

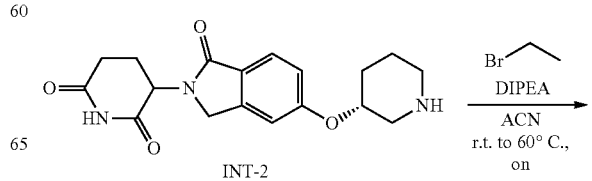

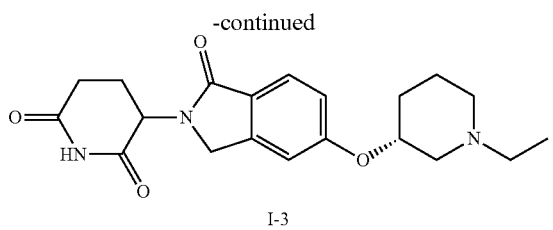

In a reaction vial with stir bar, 3-(1-oxo-5-(((R)-piperidin-3-yl)oxy)isoindolin-2-yl)piperidine-2,6-dione INT-2 (18.6 mg, 0.054 mmol) and bromoethane (7.9 mg, 0.072 mmol) were dissolved in ACN (0.5 mL). DIPEA (0.03 mL, 0.2 mmol) was added and the reaction stirred at r.t. for 1 hr then heated to 60° C. overnight. The reaction was quenched with 50% saturated aqueous sodium bicarbonate and extracted three times with 4:1 DCM:iPrOH. The organic layers were combined, passed through a phase separator and concentrated. Crude material was purified by silica gel chromatography (0-100% EtOAc:EtOH:Et$_3$N (v/v/v=75:25:1) in dichloromethane) to afford 3-(5-(((R)-1-ethylpiperidin-3-yl)oxy)-1-oxoisoindolin-2-yl)piperidine-2,6-dione I-3 as a white solid. LCMS [M+H]$^+$: 372.6. $^1$H NMR (400 MHz, DMSO-d6) δ 10.96 (s, 1H), 7.61 (d, J=8.4 Hz, 1H), 7.19 (d, J=2.1 Hz, 1H), 7.05 (dd, J=8.4, 2.2 Hz, 1H), 5.07 (dd, J=13.3, 5.1 Hz, 1H), 4.50 (dt, J=8.8, 4.6 Hz, 1H), 4.43-4.22 (m, 2H), 3.03-2.81 (m, 2H), 2.72-2.55 (m, 2H), 2.43-2.31 (m, 3H), 2.15-1.94 (m, 4H), 1.78-1.67 (m, 1H), 1.53 (dd, J=13.3, 10.0 Hz, 1H), 1.44-1.31 (m, 1H), 0.99 (t, J=7.2 Hz, 3H).

Example 2: 3-(5-(((S)-1-ethylpiperidin-3-yl)oxy)-1-oxoisoindolin-2-yl)piperidine-2,6-dione (I-6)

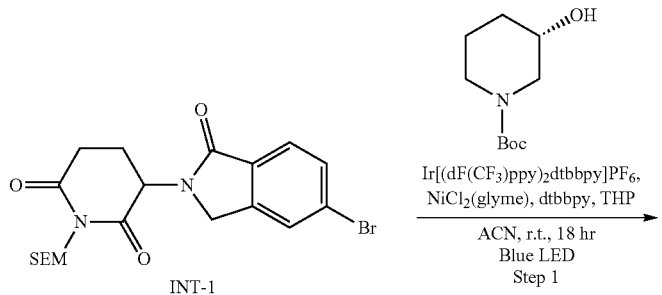

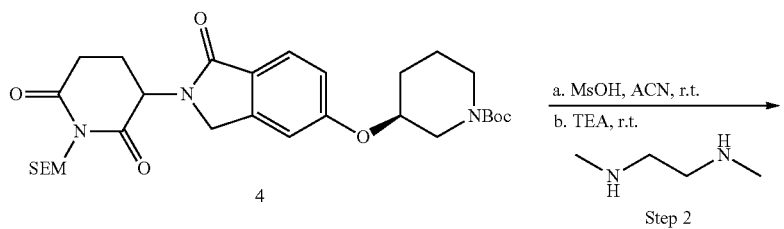

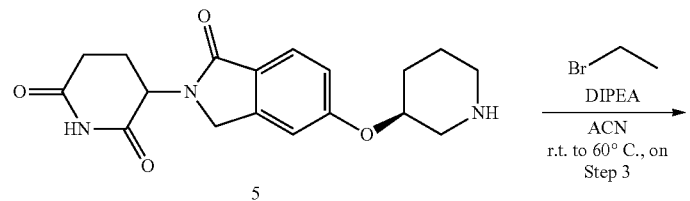

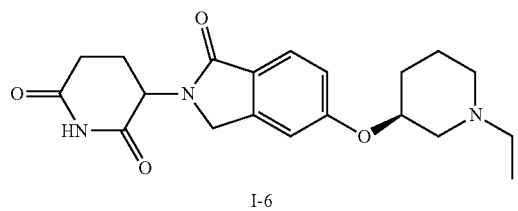

Step 1: Tert-butyl (3S)-3-((2-(2,6-dioxo-1-((2-(trimethylsilyl)ethoxy)methyl)piperidin-3-yl)-1-oxoisoindolin-5-yl)oxy)piperidine-1-carboxylate (4)

To a 40 mL vial, 3-(5-bromo-1-oxoisoindolin-2-yl)-1-((2-(trimethylsilyl)ethoxy)methyl)piperidine-2,6-dione INT-1 (220.2 mg, 0.486 mmol), tert-butyl (S)-3 hydroxypiperidine-1-carboxylate (116.4 mg, 0.578 mmol), dtbbpy (9.5 mg, 0.035 mmol), NiCl$_2$(glyme) (9.3 mg, 0.042 mmol), and Ir[(dF(CF$_3$)ppy)$_2$dtbbpy]PF$_6$ (5.7 mg, 5.1 µmol) were added. The reaction was evacuated and backfilled with nitrogen three times. ACN (2.5 mL) was added followed by 2,2,6,6-tetramethylpiperidine (0.09 mL, 0.5 mmol). The reaction was placed in PennOC m1 450 nm Photoreactor under blue LED light at r.t. for 18 hrs. The reaction was concentrated onto CELITE® and purified by silica gel chromatography (0-100% EtOAc in heptane) to afford tert-butyl (3S)-3-((2-(2,6-dioxo-1-((2-(trimethylsilyl)ethoxy)methyl)piperidin-3-yl)-1-oxoisoindolin-5-yl)oxy)piperidine-1-carboxylate 4 as a yellow foam. LCMS [M+H-156.3]$^+$: 418.2.

Step 2: 3-(1-oxo-5-(((S)-piperidin-3-yl)oxy)isoindolin-2-yl)piperidine-2,6-dione (5)

Compound 5 was made according to General Method VII starting from tert-butyl (3S)-3-((2-(2,6-dioxo-1-((2-(trimethylsilyl)ethoxy)methyl)piperidin-3-yl)-1-oxoisoindolin-5-yl)oxy)piperidine-1-carboxylate 4 (315.6 mg, 0.550 mmol). The reaction was quenched with 50% saturated aqueous sodium bicarbonate and extracted three times with 4:1 DCM:iPrOH. The organic layers were combined, passed through a phase separator and concentrated. Crude material was purified by silica gel chromatography (0-100% EtOH:Et$_3$N (v/v=100:1) in dichloromethane) to afford 3-(1-oxo-5-(((S)-piperidin-3-yl)oxy)isoindolin-2-yl)piperidine-2,6-dione 5 as a slightly off-white solid. LCMS [M+H]$^+$: 344.6. $^1$H NMR (400 MHz, DMSO-d6) δ 10.96 (s, 1H), 7.63 (d, J=8.4 Hz, 1H), 7.20 (d, J=2.2 Hz, 1H), 7.07 (dd, J=8.4, 2.2 Hz, 1H), 5.07 (dd, J=13.3, 5.1 Hz, 1H), 4.48 (s, 1H), 4.43-4.22 (m, 2H), 3.17 (d, J=12.4 Hz, 1H), 2.98-2.80 (m, 2H), 2.75-2.55 (m, 4H), 2.38 (dd, J=13.1, 4.5 Hz, 1H), 2.08-1.92 (m, 2H), 1.78-1.67 (m, 1H), 1.67-1.44 (m, 2H).

Step 3: 3-(5-(((S)-1-ethylpiperidin-3-yl)oxy)-1-oxoisoindolin-2-yl)piperidine-2,6-dione (I-6)

In a reaction vial with stir bar, 3-(1-oxo-5-(((S)-piperidin-3-yl)oxy)isoindolin-2-yl)piperidine-2,6-dione 5 (56.9 mg, 0.166 mmol) and bromoethane (22.3 mg, 0.205 mmol) were dissolved in ACN (1.0 mL). DIPEA (0.10 mL, 0.573 mmol) was added and the reaction stirred at 60° C. for 24 hrs. The reaction was quenched with 50% saturated aqueous sodium bicarbonate and extracted three times with 4:1 DCM:iPrOH. The organic layers were combined, passed through a phase separator and concentrated. Crude material was purified by silica gel chromatography (0-100% EtOAc:EtOH:Et$_3$N (v/v/v=75:25:1) in dichloromethane) to afford 3-(5-(((S)-1-ethylpiperidin-3-yl)oxy)-1-oxoisoindolin-2-yl)piperidine-2,6-dione I-6 as an off-white solid. LCMS [M+H]$^+$: 372.3. $^1$H NMR (400 MHz, DMSO-d6) δ 10.96 (s, 1H), 7.61 (d, J=8.4 Hz, 1H), 7.19 (d, J=2.2 Hz, 1H), 7.05 (dd, J=8.4, 2.2 Hz, 1H), 5.07 (dd, J=13.3, 5.1 Hz, 1H), 4.50 (tt, J=8.5, 3.9 Hz, 1H), 4.44-4.17 (m, 2H), 3.02-2.82 (m, 2H), 2.70-2.55 (m, 2H), 2.43-2.30 (m, 3H), 2.16-1.93 (m, 4H), 1.78-1.67 (m, 1H), 1.66-1.47 (m, 1H), 1.44-1.31 (m, 1H), 0.99 (t, J=7.1 Hz, 3H).

Example 3: 3-(5-(((R)-1-isobutylpiperidin-3-yl)oxy)-1-oxoisoindolin-2-yl)piperidine-2,6-dione (I-7)

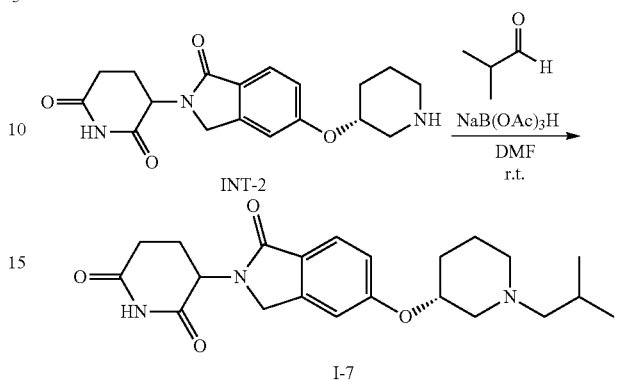

Compound I-7 was made according to General Method X starting from 3-(1-oxo-5-(((R)-piperidin-3-yl)oxy)isoindolin-2-yl)piperidine-2,6-dione INT-2 (61 mg, 0.18 mmol) and isobutanal (0.024 mL, 0.27 mmol). The crude material was purified by silica gel chromatography (0-100% EtOAc:EtOH:Et$_3$N (v/v/v=75:25:1) in heptane) to afford 3-(5-(((R)-1-isobutylpiperidin-3-yl)oxy)-1-oxoisoindolin-2-yl)piperidine-2,6-dione I-7 as a white solid. LCMS [M+H]$^+$: 400.3. $^1$H NMR (400 MHz, DMSO-d6) δ 10.89 (s, 1H), 7.54 (d, J=8.3 Hz, 1H), 7.11 (d, J=2.2 Hz, 1H), 6.97 (dd, J=8.3, 2.2 Hz, 1H), 5.00 (dd, J=13.3, 5.2 Hz, 1H), 4.48-4.37 (m, 1H), 4.31 (d, J=17.1 Hz, 1H), 4.18 (d, J=17.2 Hz, 1H), 2.89-2.78 (m, 2H), 2.58-2.48 (m, 2H), 2.37-2.25 (m, 1H), 2.06-1.86 (m, 6H), 1.72-1.60 (m, 2H), 1.55-1.41 (m, 1H), 1.35-1.24 (m, 1H), 0.77 (t, J=5.9 Hz, 6H).

Example 4: 3-(5-(((R)-1-(oxetan-3-ylmethyl)piperidin-3-yl)oxy)-1-oxoisoindolin-2-yl)piperidine-2,6-dione (I-8)

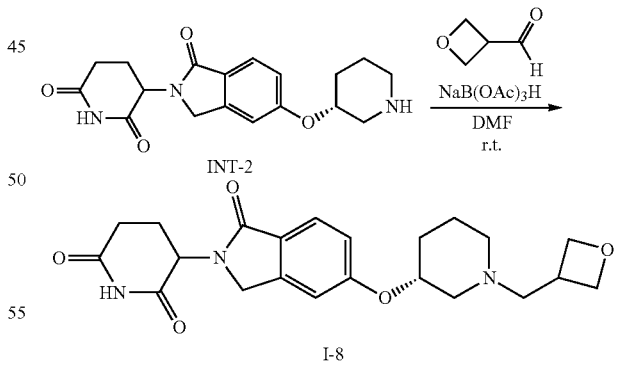

Compound I-8 was made according to General Method III starting from 3-(1-oxo-5-(((R)-piperidin-3-yl)oxy)isoindolin-2-yl)piperidine-2,6-dione INT-2 (72 mg, 0.21 mmol) and oxetane-3-carbaldehyde (27 mg, 0.32 mmol). The crude material was purified by silica gel chromatography (0-100% EtOAc:EtOH:Et$_3$N (v/v/v=75:25:1) in heptane) to afford 3-(5-(((R)-1-(oxetan-3-ylmethyl)piperidin-3-yl)oxy)-1-oxoisoindolin-2-yl)piperidine-2,6-dione I-8 as a white solid. LCMS [M+H]$^+$: 414.3. $^1$H NMR (400 MHz, DMSO-d6) δ

10.89 (s, 1H), 7.53 (d, J=8.4 Hz, 1H), 7.11 (d, J=2.2 Hz, 1H), 6.97 (dd, J=8.4, 2.1 Hz, 1H), 5.00 (dd, J=13.4, 5.1 Hz, 1H), 4.60-4.49 (m, 2H), 4.44-4.28 (m, 2H), 4.23-4.13 (m, 3H), 3.23-3.21 (m, 1H), 3.15-3.04 (m, 1H), 2.90-2.78 (m, 2H), 2.62-2.56 (m, 2H), 2.55-2.49 (m, 1H), 2.36-2.28 (m, 1H), 2.10-2.02 (m, 1H), 2.00-1.87 (m, 3H), 1.68-1.60 (m, 1H), 1.51-1.38 (m, 1H), 1.34-1.23 (m, 1H).

Example 5: 3-(5-(((R)-1-((4,4-difluorocyclohexyl)methyl)piperidin-3-yl)oxy)-1-oxoisoindolin-2-yl)piperidine-2,6-dione (I-9)

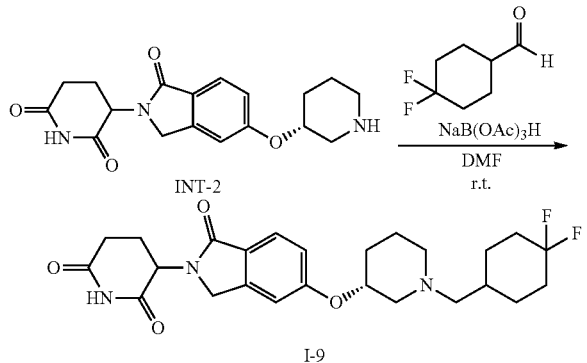

Compound I-9 was made according to General Method III starting from 1-(hydroxymethyl)-3-(1-oxo-5-(((R)-piperidin-3-yl)oxy)isoindolin-2-yl)piperidine-2,6-dione INT-2 (60 mg, 0.18 mmol) and 4,4-difluorocyclohexane-1-carbaldehyde (39 mg, 0.26 mmol). The crude material was purified by silica gel chromatography (0-100% EtOAc:EtOH:Et₃N (v/v/v=75:25:1) in heptane) to afford 3-(5-(((R)-1-((4,4-difluorocyclohexyl)methyl)piperidin-3-yl)oxy)-1-oxoisoindolin-2-yl)piperidine-2,6-dione I-9 as a white solid. LCMS [M+H]⁺: 476.4. ¹H NMR (400 MHz, DMSO-d6) δ 10.97 (s, 1H), 7.61 (d, J=8.3 Hz, 1H), 7.19 (d, J=2.2 Hz, 1H), 7.05 (dt, J=8.3, 2.2 Hz, 1H), 5.07 (dd, J=13.3, 5.1 Hz, 1H), 4.56-4.46 (m, 1H), 4.39 (dd, J=17.5, 2.4 Hz, 1H), 4.26 (d, J=17.1 Hz, 1H), 2.98-2.86 (m, 2H), 2.66-2.55 (m, 2H), 2.45-2.34 (m, 1H), 2.20-1.92 (m, 8H), 1.84-1.50 (m, 7H), 1.44-1.33 (m, 1H), 1.15-1.02 (m, 2H).

Example 6: 3-(5-(((R)-1-(cyclohexylmethyl)piperidin-3-yl)oxy)-1-oxoisoindolin-2-yl)piperidine-2,6-dione (I-10)

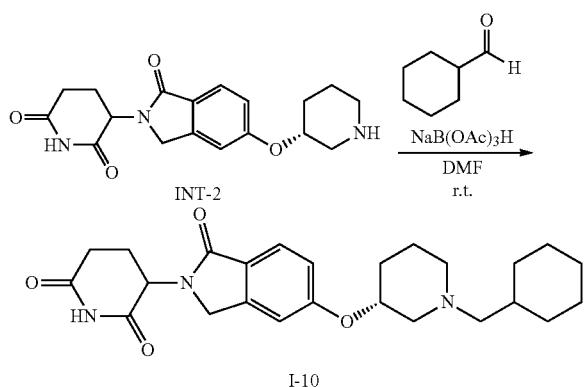

Compound I-10 was made according to General Method III starting from 1-(hydroxymethyl)-3-(1-oxo-5-(((R)-piperidin-3-yl)oxy)isoindolin-2-yl)piperidine-2,6-dione INT-2 (60 mg, 0.18 mmol) and cyclohexanecarboxaldehyde (0.032 mL, 0.26 mmol). The crude material was purified by silica gel chromatography (0-100% EtOAc:EtOH:Et₃N (v/v/v=75:25:1) in heptane) to afford 3-(5-(((R)-1-(cyclohexylmethyl)piperidin-3-yl)oxy)-1-oxoisoindolin-2-yl)piperidine-2,6-dione I-10 as a white solid. LCMS [M+H]⁺: 440.2. ¹H NMR (400 MHz, DMSO-d6) δ 10.89 (s, 1H), 7.53 (d, J=8.3 Hz, 1H), 7.11 (d, J=2.2 Hz, 1H), 6.97 (dt, J=8.5, 1.6 Hz, 1H), 5.00 (dd, J=13.3, 5.2 Hz, 1H), 4.49-4.39 (m, 1H), 4.31 (dd, J=17.1, 3.4 Hz, 1H), 4.18 (dd, J=17.1, 3.0 Hz, 1H), 2.90-2.78 (m, 2H), 2.58-2.48 (m, 2H), 2.38-2.24 (m, 1H), 2.06-1.87 (m, 6H), 1.69-1.25 (m, 9H), 1.17-1.00 (m, 3H), 0.79-0.65 (m, 2H).

Example 7: 3-(5-(((R)-1-(cyclobutylmethyl)piperidin-3-yl)oxy)-1-oxoisoindolin-2-yl)piperidine-2,6-dione (I-11)

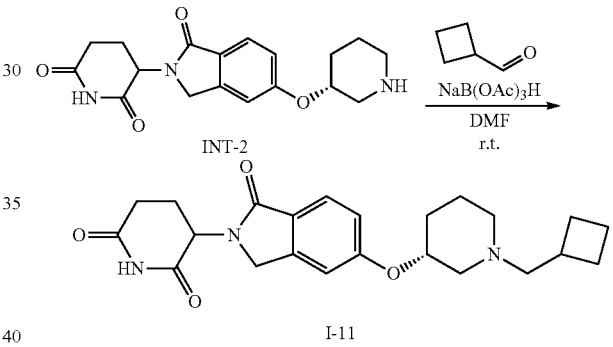

Compound I-9 was made according to General Method III starting from 1-(hydroxymethyl)-3-(1-oxo-5-(((R)-piperidin-3-yl)oxy)isoindolin-2-yl)piperidine-2,6-dione INT-2 (68 mg, 0.20 mmol) and cyclobutanecarbaldehyde (25 mg, 0.30 mmol). The crude material was purified by silica gel chromatography (0-100% EtOAc:EtOH:Et₃N (v/v/v=75:25:1) in heptane) to afford the product. The material was further purified by basic reverse phase HPLC (25-50% ACN in water with 5 mM NH₄OH as modifier). Test tubes contained 3 drops of formic acid prior to sample collection. Fractions containing desired product were combined and lyophilized to afford formate salt of 3-(5-(((R)-1-(cyclobutylmethyl)piperidin-3-yl)oxy)-1-oxoisoindolin-2-yl)piperidine-2,6-dione I-11 as a white solid. LCMS [M+H]⁺: 412.4. ¹H NMR (400 MHz, DMSO-d6) δ 10.89 (s, 1H), 8.14 (s, 1H), 7.53 (d, J=8.5 Hz, 1H), 7.11 (d, J=2.2 Hz, 1H), 6.97 (dd, J=8.3, 2.3 Hz, 1H), 5.00 (dd, J=13.3, 5.1 Hz, 1H), 4.45-4.35 (m, 1H), 4.31 (d, J=17.4 Hz, 1H), 4.18 (d, J=17.1 Hz, 1H), 2.90-2.77 (m, 2H), 2.58-2.47 (m, 2H), 2.41-2.34 (m, 1H), 2.34-2.24 (m, 3H), 2.05-1.84 (m, 6H), 1.82-1.39 (m, 6H), 1.34-1.20 (m, 1H).

Example 8: 3-(1-oxo-5-(((R)-1-propylpiperidin-3-yl)oxy)isoindolin-2-yl)piperidine-2,6-dione (I-12)

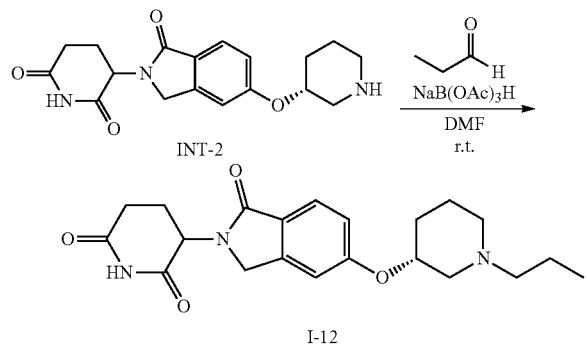

Compound I-12 was made according to General Method III starting from 1-(hydroxymethyl)-3-(1-oxo-5-(((R)-piperidin-3-yl)oxy)isoindolin-2-yl)piperidine-2,6-dione INT-2 (68 mg, 0.20 mmol) and propane (0.021 mL, 0.30 mmol). The crude material was purified by silica gel chromatography (0-100% EtOAc:EtOH:Et$_3$N (v/v/v=75:25:1) in heptane) to afford 3-(1-oxo-5-(((R)-1-propylpiperidin-3-yl)oxy)isoindolin-2-yl)piperidine-2,6-dione I-12 as a white solid. LCMS [M+H]$^+$: 386.4. $^1$H NMR (400 MHz, DMSO-d6) δ 10.89 (s, 1H), 7.54 (d, J=8.3 Hz, 1H), 7.12 (d, J=2.2 Hz, 1H), 6.97 (dd, J=8.3, 2.2 Hz, 1H), 5.00 (dd, J=13.3, 5.2 Hz, 1H), 4.47-4.36 (m, 1H), 4.31 (d, J=17.4 Hz, 1H), 4.18 (d, J=17.2 Hz, 1H), 2.93-2.78 (m, 2H), 2.59-2.48 (m, 2H), 2.37-2.16 (m, 3H), 2.07-1.87 (m, 4H), 1.70-1.61 (m, 1H), 1.54-1.42 (m, 1H), 1.41-1.25 (m, 3H), 0.76 (t, J=7.3 Hz, 3H).

Example 9: 3-(5-(((R)-1-isopropylpiperidin-3-yl)oxy)-1-oxoisoindolin-2-yl)piperidine-2,6-dione (I-13)

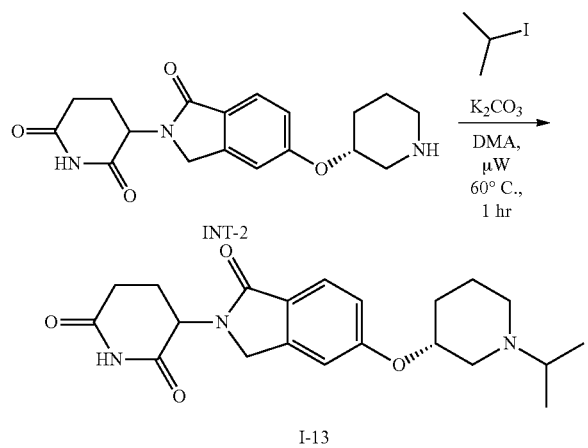

3-(1-oxo-5-(((R)-piperidin-3-yl)oxy)isoindolin-2-yl)piperidine-2,6-dione INT-2 (60 mg, 0.18 mmol) was suspended in DMA (1.75 mL). K$_2$CO$_3$ (36 mg, 0.26 mmol) was added and the reaction was evacuated and backfilled with nitrogen three times. 2-iodopropane (0.087 mL, 0.87 mmol) was added and the reaction stirred at 60° C. for 1 hr under microwave radiation. The reaction was quenched with 50% saturated aqueous sodium bicarbonate and extracted three times with 4:1 DCM:iPrOH. The organic layers were combined, passed through a phase separator, and concentrated onto CELITE®. The crude material was purified by silica gel chromatography (0-100% EtOAc:EtOH:Et$_3$N (v/v/v=75:25:1) in heptane). Pure fractions were combined, concentrated and lyophilized to afford product 3-(5-(((R)-1-isopropylpiperidin-3-yl)oxy)-1-oxoisoindolin-2-yl)piperidine-2,6-dione I-13 as a white solid. LCMS [M+H]$^+$: 386.3. $^1$H NMR (400 MHz, DMSO-d6) δ 10.97 (s, 1H), 7.61 (d, J=8.4 Hz, 1H), 7.20 (d, J=2.3 Hz, 1H), 7.05 (dd, J=8.4, 2.3 Hz, 1H), 5.07 (dd, J=13.3, 5.0 Hz, 1H), 4.56-4.44 (m, 1H), 4.39 (d, J=17.1 Hz, 1H), 4.26 (d, J=17.1 Hz, 1H), 3.31-3.27 (m, 1H), 3.01-2.84 (m, 2H), 2.65-2.56 (m, 1H), 2.44-2.35 (m, 1H), 2.31-2.24 (m, 2H), 2.18-1.94 (m, 4H), 1.79-1.71 (m, 1H), 1.62-1.52 (m, 1H), 1.49-1.32 (m, 3H), 0.84 (t, J=7.3 Hz, 3H).

Example 10: 3-(1-oxo-5-(((R)-1-(tetrahydro-2H-pyran-4-yl)piperidin-3-yl)oxy)isoindolin-2-yl)piperidine-2,6-dione (I-14)

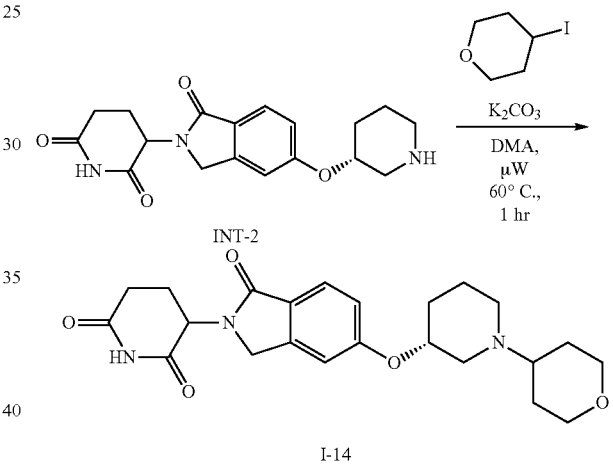

3-(1-oxo-5-(((R)-piperidin-3-yl)oxy)isoindolin-2-yl)piperidine-2,6-dione INT-2 (60 mg, 0.18 mmol) and 4-iodotetrahydro-2H-pyran (0.105 mL, 0.874 mmol) were suspended in DMA (1.75 mL). K$_2$CO$_3$ (36 mg, 0.26 mmol) was added and the reaction was evacuated and backfilled with nitrogen 3 times. The reaction stirred at 100° C. for 4 hrs under microwave radiation. The reaction was quenched with 50% saturated aqueous sodium bicarbonate and extracted three times with 4:1 DCM:iPrOH. The organic layers were combined, passed through a phase separator, and concentrated onto CELITE®. The crude material was purified by silica gel chromatography (0-100% EtOAc:EtOH:Et$_3$N (v/v/v=75:25:1) in heptane). Pure fractions were combined, concentrated and lyophilized to afford 3-(1-oxo-5-(((R)-1-(tetrahydro-2H-pyran-4-yl)piperidin-3-yl)oxy)isoindolin-2-yl)piperidine-2,6-dione I-14 as a white solid. LCMS [M+H]$^+$: 428.4. $^1$H NMR (400 MHz, DMSO-d6) δ 10.97 (s, 1H), 7.61 (d, J=8.3 Hz, 1H), 7.19 (d, J=2.4 Hz, 1H), 7.05 (dd, J=8.4, 2.2 Hz, 1H), 5.07 (dd, J=13.3, 5.0 Hz, 1H), 4.53-4.36 (m, 2H), 4.26 (d, J=17.5 Hz, 1H), 3.87 (dd, J=11.8, 3.8 Hz, 2H), 3.30-3.21 (m, 3H), 3.14-3.02 (m, 1H), 2.97-2.84 (m, 1H), 2.77-2.71 (m, 1H), 2.64-2.56 (m, 1H), 2.44-2.36 (m, 1H), 2.31-2.17 (m, 2H), 2.10-1.95 (m, 2H), 1.79-1.70 (m, 1H), 1.68-1.59 (m, 2H), 1.56-1.31 (m, 4H).

Example 11: 3-(5-(((R)-1-(2-oxaspiro[3.3]heptan-6-yl)piperidin-3-yl)oxy)-1-oxoisoindolin-2-yl)piperidine-2,6-dione (I-15)

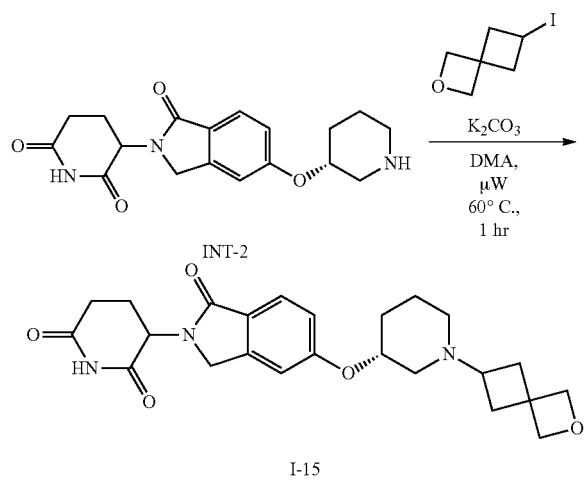

3-(1-oxo-5-(((R)-piperidin-3-yl)oxy)isoindolin-2-yl)piperidine-2,6-dione INT-2 (60 mg, 0.18 mmol) and 6-iodo-2-oxaspiro[3.3]heptane (196 mg, 0.87 mmol) were suspended in DMA (1.75 mL). $K_2CO_3$ (36 mg, 0.26 mmol) was added and the reaction was evacuated and backfilled with nitrogen 3 times. The reaction stirred at 60° C. for 1 hr then at 100° C. for 2 hrs under microwave radiation. The reaction was quenched with 50% saturated aqueous sodium bicarbonate and extracted three times with 4:1 DCM:iPrOH. The organic layers were combined, passed through a phase separator, and concentrated onto CELITE®. The crude material was purified by silica gel chromatography (0-100% EtOAc:EtOH:Et$_3$N (v/v/v=75:25:1) in heptane) to afford the product. Material was further purified by reverse phase basic HPLC (15-40% ACN in water with 5 mM NH$_4$OH as modifier). Test tubes contained 3 drops formic acid prior to sample collection. Pure fractions were combined, concentrated and lyophilized to afford formate salt of 3-(5-(((R)-1-(2-oxaspiro[3.3]heptan-6-yl)piperidin-3-yl)oxy)-1-oxoisoindolin-2-yl)piperidine-2,6-dione I-15 as a white solid. LCMS [M+H]$^+$: 440.3. $^1$H NMR (400 MHz, DMSO-d6) δ 8.25 (s, 2H), 7.54 (d, J=8.4 Hz, 1H), 7.11 (d, J=2.2 Hz, 1H), 6.97 (dd, J=8.4, 2.2 Hz, 1H), 5.00 (dd, J=13.3, 5.1 Hz, 1H), 4.48 (s, 2H), 4.45-4.27 (m, 5H), 4.18 (d, J=17.1 Hz, 1H), 2.89-2.72 (m, 2H), 2.56-2.46 (m, 2H), 2.36-2.17 (m, 3H), 1.99-1.74 (m, 6H), 1.68-1.61 (m, 1H), 1.48-1.38 (m, 1H), 1.36-1.25 (m, 1H).

Example 12: 3-(5-(((R)-1-(oxetan-3-yl)piperidin-3-yl)oxy)-1-oxoisoindolin-2-yl)piperidine-2,6-dione (I-16)

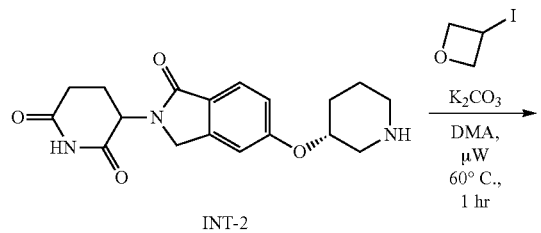

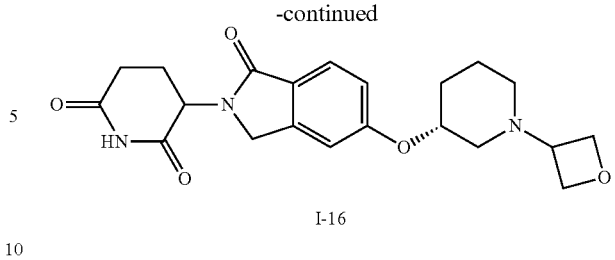

3-(1-oxo-5-(((R)-piperidin-3-yl)oxy)isoindolin-2-yl)piperidine-2,6-dione INT-2 (60 mg, 0.18 mmol) and 3-iodooxetane (0.077 mL, 0.87 mmol) were suspended in DMA (1.75 mL). $K_2CO_3$ (36 mg, 0.26 mmol) was added and the reaction was evacuated and backfilled with nitrogen 3 times. The reaction stirred at 100° C. for a total of 6 hrs under microwave radiation. The reaction was quenched with 50% saturated aqueous sodium bicarbonate and extracted three times with 4:1 DCM:iPrOH. The organic layers were combined, passed through a phase separator, and concentrated onto CELITE®. The crude material was purified by silica gel chromatography (0-100% EtOAc:EtOH:Et$_3$N (v/v/v=75:25:1) in heptane). Fractions containing desired product were combined, concentrated, and further purified by reverse phase basic HPLC (10-30% ACN in H$_2$O with 5 mM NH$_4$OH as modifier). Test tubes contained 3 drops formic acid prior to sample collection. Pure fractions were combined and lyophilized to afford formate salt of 3-(5-(((R)-1-(oxetan-3-yl)piperidin-3-yl)oxy)-1-oxoisoindolin-2-yl)piperidine-2,6-dione I-16 as a white solid. LCMS [M+H]$^+$: 400.3. $^1$H NMR (400 MHz, DMSO-d6) δ 10.78 (s, 1H), 8.25 (s, 1H), 7.54 (d, J=8.4 Hz, 1H), 7.15 (d, J=2.3 Hz, 1H), 6.99 (dd, J=8.7, 2.2 Hz, 1H), 5.00 (dd, J=13.4, 5.1 Hz, 1H), 4.51-4.42 (m, 3H), 4.39 (td, J=6.0, 2.2 Hz, 1H), 4.36-4.27 (m, 2H), 4.19 (dd, J=17.5, 2.1 Hz, 1H), 3.39 (p, J=6.3 Hz, 2H), 2.90-2.71 (m, 2H), 2.56-2.45 (m, 1H), 2.37-2.23 (m, 1H), 2.02-1.84 (m, 4H), 1.72-1.62 (m, 1H), 1.56-1.44 (m, 1H), 1.41-1.29 (m, 1H).

Example 13: 3-(5-(((R)-1-(cyclopropylmethyl)piperidin-3-yl)oxy)-1-oxoisoindolin-2-yl)piperidine-2,6-dione (I-17)

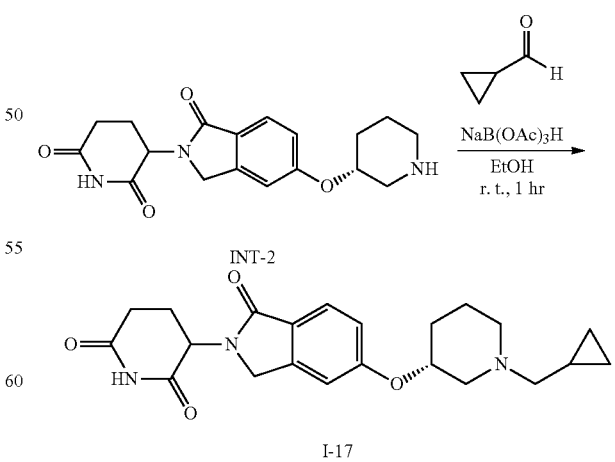

To a solution of 3-(1-oxo-5-(((R)-piperidin-3-yl)oxy)isoindolin-2-yl)piperidine-2,6-dione INT-2 (100 mg, 0.29 mmol) in EtOH (1.5 mL), sodium triacetoxyborohydride (123 mg, 0.58 mmol) was added followed by cyclopropanecarbaldehyde (0.031 mg, 0.44 mmol). The reaction stirred at r.t. for 1 hr. (SOLUTE® (HM-N Part No. 9800-5000) was added to the reaction and concentrated. The crude material was purified by silica gel chromatography (0 to 100% EtOAc:EtOH:Et$_3$N (v/v/v=75:25:1) in DCM) and concentrated. The product was diluted with 1:1 MeCN:water and lyopholized to afford 3-(5-(((R)-1-(cyclopropylmethyl)piperidin-3-yl)oxy)-1-oxoisoindolin-2-yl)piperidine-2,6-dione I-17. LCMS [M+H]$^+$: 398.3. $^1$H NMR (400 MHz, DMSO-d6) δ 10.96 (s, 1H), 7.60 (d, J=8.4 Hz, 1H), 7.19 (d, J=2.2 Hz, 1H), 7.05 (dd, J=8.4, 2.2 Hz, 1H), 5.07 (dd, J=13.3, 5.1 Hz, 1H), 4.57-4.44 (m, 1H), 4.43-4.18 (m, 2H), 3.08 (d, J=11.0 Hz, 1H), 2.90 (ddd, J=17.3, 13.6, 5.4 Hz, 1H), 2.76 (d, J=11.2 Hz, 1H), 2.63-2.54 (m, 1H), 2.44-2.29 (m, 1H), 2.23 (d, J=6.5 Hz, 2H), 2.19-1.92 (m, 3H), 1.77-1.67 (m, 1H), 1.64-1.48 (m, 1H), 1.36 (q, J=11.6, 11.0 Hz, 1H), 0.95 (m, 1H), 0.88-0.75 (m, 1H), 0.48-0.38 (m, 2H), 0.05 (d, J=4.9 Hz, 2H).

Example 14: 3-(5-(((R)-1-((1-ethyl-1H-pyrazol-4-yl)methyl)piperidin-3-yl)oxy)-1-oxoisoindolin-2-yl)piperidine-2,6-dione (I-18)

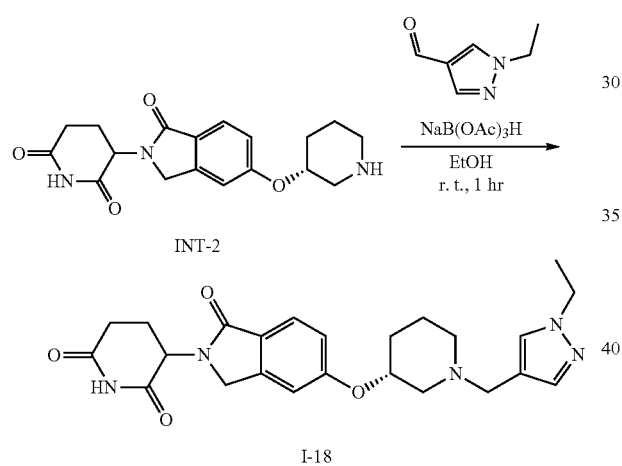

To a solution of 3-(1-oxo-5-(((R)-piperidin-3-yl)oxy)isoindolin-2-yl)piperidine-2,6-dione INT-2 (100 mg, 0.29 mmol) in EtOH (1.5 mL), sodium triacetoxyborohydride (123 mg, 0.58 mmol) was added followed by the addition of 1-ethyl-1H-pyrazole-4-carbaldehyde (54.2 mg, 0.44 mmol) in EtOH (0.5 mL). The reaction stirred at r.t. for a total of 48 hrs. (SOLUTE® (HM-N Part No. 9800-5000) was added to the reaction and the reaction was concentrated. The dry loaded crude material was purified by silica gel chromatography (0 to 100% EtOAc:EtOH:Et$_3$N (v/v/v=75:25:1) in DCM) to afford 3-(5-(((R)-1-((1-ethyl-1H-pyrazol-4-yl)methyl)piperidin-3-yl)oxy)-1-oxoisoindolin-2-yl)piperidine-2,6-dione I-18 as a colorless oil. LCMS [M+H]$^+$: 452.5. $^1$H NMR (400 MHz, DMSO-d6) δ 10.97 (s, 1H), 7.65-7.54 (m, 2H), 7.29 (d, J=1.5 Hz, 1H), 7.17 (d, J=2.2 Hz, 1H), 7.03 (dd, J=8.3, 2.2 Hz, 1H), 5.07 (dd, J=13.3, 5.1 Hz, 1H), 4.50 (dt, J=8.8, 4.6 Hz, 1H), 4.43-4.18 (m, 2H), 4.06 (q, J=7.3 Hz, 2H), 3.40 (s, 2H), 2.91 (ddd, J=17.2, 13.6, 5.2 Hz, 2H), 2.67-2.55 (m, 2H), 2.46-2.29 (m, 1H), 2.15-1.92 (m, 4H), 1.72 (dt, J=8.5, 4.3 Hz, 1H), 1.55 (ddt, J=13.5, 6.8, 3.6 Hz, 1H), 1.32 (m, 4H).

Example 15: 3-(5-(((R)-6-ethyl-6-azaspiro[2.5]octan-4-yl)oxy)-1-oxoisoindolin-2-yl)piperidine-2,6-dione (I-23)

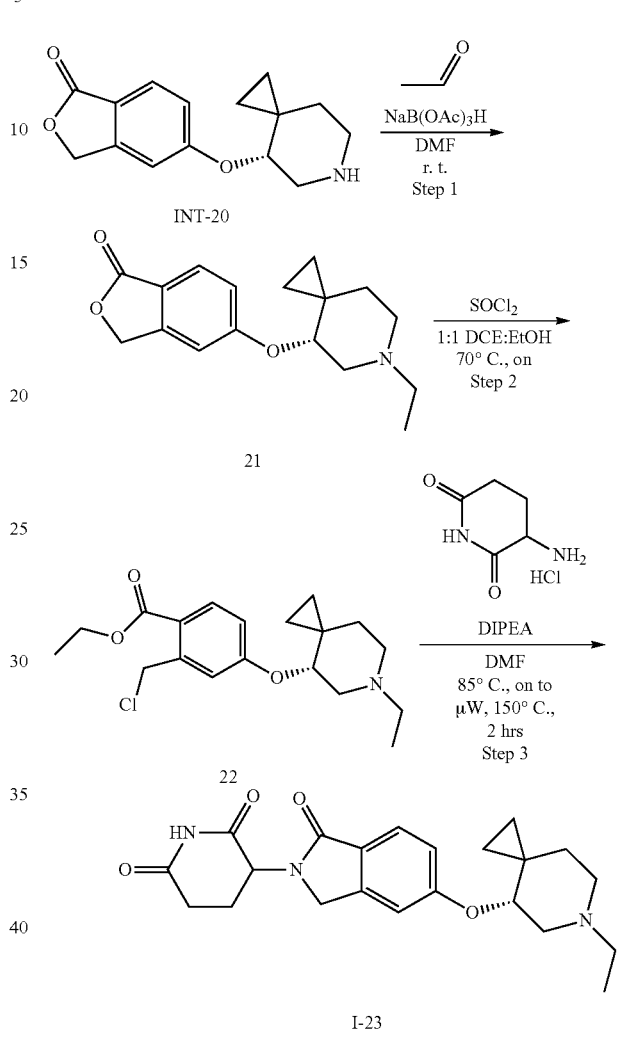

Step 1: (R)-5-((6-ethyl-6-azaspiro[2.5]octan-4-yl)oxy)isobenzofuran-1(3H)-one (21)

To a solution of (R)-5-((6-azaspiro[2.5]octan-4-yl)oxy)isobenzofuran-1(3H)-one INT-20 (164 mg, 0.63 mmol) in DMF (4.2 mL) was added sodium triacetoxyborohydride (269 mg, 1.3 mmol). Acetaldehyde (54 μL, 0.951 mmol) was added. The reaction was stirred at r.t. for 1 hr. The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% EtOAc:EtOH:Et$_3$N (v/v/v=75:25:1) in heptane) to afford (R)-5-((6-ethyl-6-azaspiro[2.5]octan-4-yl)oxy)isobenzofuran-1(3H)-one 21 as a light yellow oil. LCMS [M+H]$^+$: 288.1. 1H NMR (400 MHz, CDCl$_3$) δ 7.71 (d, J=8.5 Hz, 1H), 6.96 (dd, J=8.5, 2.2 Hz, 1H), 6.88 (d, J=2.0 Hz, 1H), 5.15 (s, 2H), 4.13 (s, 1H), 2.75-2.66 (m, 1H), 2.58-2.34 (m, 5H), 1.72-1.43 (m, 2H), 0.99 (t, J=7.2 Hz, 3H), 0.68-0.60 (m, 1H), 0.52-0.43 (m, 1H), 0.33-0.24 (m, 2H).

Step 2: Ethyl (R)-2-(chloromethyl)-4-((6-ethyl-6-azaspiro[2.5]octan-4-yl)oxy)benzoate (22)

To a solution of (R)-5-(((6-ethyl-6-azaspiro[2.5]octan-4-yl)oxy)isobenzofuran-1(3H)-one 21 (163 mg, 0.57 mmol) in dichloroethane (2.8 mL) and ethanol (2.8 mL) in a 25 mL 2 neck round bottom flask stirred at 70° C. was added thionyl chloride (0.50 mL, 6.8 mmol) dropwise. The reaction stirred at 70° C. overnight. The reaction mixture was cooled to r.t., diluted with water, and quenched with saturated sodium bicarbonate. The reaction mixture was extracted with ethyl acetate three times. The organic layers were combined, passed through a phase separator and concentrated. Crude material was purified by silica gel chromatography (0-100% EtOAc in heptane) to afford ethyl (R)-2-(chloromethyl)-4-((6-ethyl-6-azaspiro[2.5]octan-4-yl)oxy)benzoate 22 as a light yellow oil. LCMS [M+H]$^+$: 352.2.

Step 3: 3-(5-(((R)-6-ethyl-6-azaspiro[2.5]octan-4-yl)oxy)-1-oxoisoindolin-2-yl)piperidine-2,6-dione (I-23)

In a microwave vial, 3-aminopiperidine-2,6-dione hydrochloride (77 mg, 0.47 mmol) was dissolved in DMF (0.94 mL). DIPEA (0.21 mL, 1.2 mmol) was added and the reaction was evacuated and backfilled with nitrogen three times. The reaction stirred at r.t. for 15 minutes. Then ethyl (R)-2-(chloromethyl)-4-((6-ethyl-6-azaspiro[2.5]octan-4-yl)oxy)benzoate 22 (82.4 mg, 0.23 mmol) dissolved in DMF (1.4 mL) was added and the reaction was evacuated and backfilled with nitrogen three times. The reaction stirred at 85° C. overnight then microwaved at 150° C. for 2 hrs. The reaction was concentrated and purified by silica gel chromatography pushing the crude material through a plug of charcoal before reaching the silica column (0-100% EtOAc:EtOH:Et$_3$N (v/v/v=75:25:1) in heptane). Pure fractions were combined, concentrated and lyophilized to afford 3-(5-(((R)-6-ethyl-6-azaspiro[2.5]octan-4-yl)oxy)-1-oxoisoindolin-2-yl)piperidine-2,6-dione I-23 as a cream solid. LCMS [M+H]$^+$: 398.4. $^1$H NMR (400 MHz, DMSO-d6) δ 10.89 (s, 1H), 7.52 (d, J=8.5 Hz, 1H), 7.09 (d, J=2.2 Hz, 1H), 6.96 (dd, J=8.4, 2.3 Hz, 1H), 4.99 (dd, J=13.3, 5.0 Hz, 1H), 4.30 (dd, J=17.2, 6.8 Hz, 1H), 4.17 (dd, J=17.1, 6.8 Hz, 1H), 4.06 (s, 1H), 2.83 (ddd, J=17.2, 13.6, 5.4 Hz, 1H), 2.68-2.45 (m, 4H), 2.37-2.23 (m, 4H), 1.96-1.86 (m, 1H), 1.84-1.68 (m, 1H), 1.25-1.12 (m, 1H), 0.87 (td, J=7.2, 1.7 Hz, 3H), 0.57-0.48 (m, 1H), 0.48-0.38 (m, 1H), 0.31-0.20 (m, 2H).

Example 16: 3-(5-(((R)-6-isobutyl-6-azaspiro[2.5]octan-4-yl)oxy)-1-oxoisoindolin-2-yl)piperidine-2,6-dione (I-26)

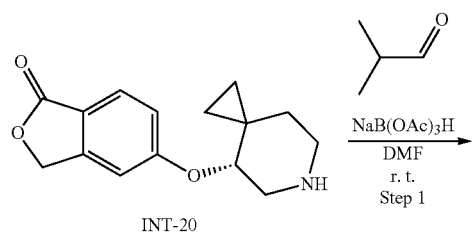

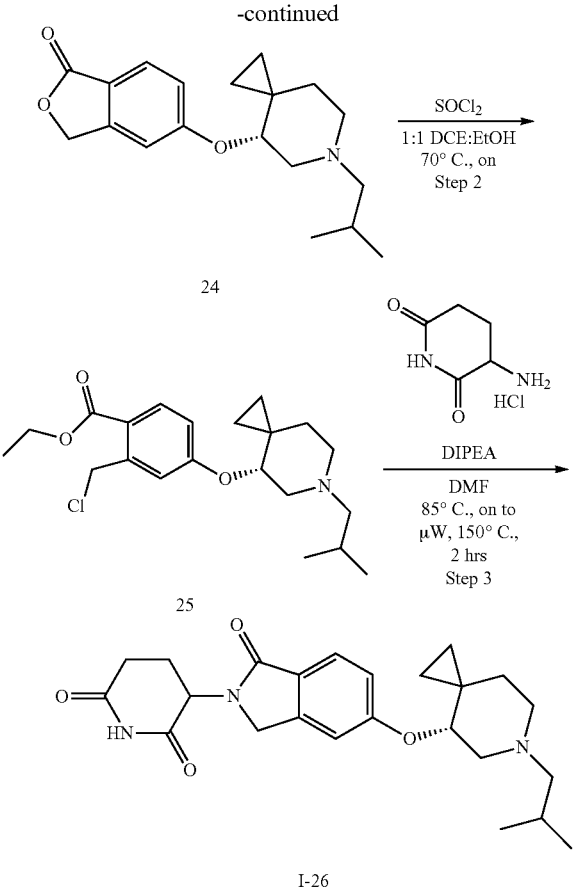

Step 1: (R)-5-((6-isobutyl-6-azaspiro[2.5]octan-4-yl)oxy)isobenzofuran-1(3H)-one (24)

Compound 24 was made according to General Method III starting from (R)-5-(((6-azaspiro[2.5]octan-4-yl)oxy)isobenzofuran-1(3H)-one INT-20 (90 mg, 0.35 mmol) and isobutanal (48 μL, 0.52 mmol). The crude material was purified by silica gel chromatography (0-100% EtOAc:EtOH:Et$_3$N (v/v/v=75:25:1) in heptane) to afford (R)-5-(((6-isobutyl-6-azaspiro[2.5]octan-4-yl)oxy)isobenzofuran-1(3H)-one 24 as a clear oil. LCMS [M+H]$^+$: 316.2.

Step 2: Ethyl (R)-2-(chloromethyl)-4-((6-isobutyl-6-azaspiro[2.5]octan-4-yl)oxy)benzoate (25)

Compound 25 was made according to General Method IV starting from (R)-5-(((6-ethyl-6-azaspiro[2.5]octan-4-yl)oxy)isobenzofuran-1(3H)-one 24 (114 mg, 0.36 mmol). Crude material was purified by silica gel chromatography (0-100% EtOAc in heptane) to afford (R)-2-(chloromethyl)-4-((6-isobutyl-6-azaspiro[2.5]octan-4-yl)oxy)benzoate 25 as a light brown oil. LCMS [M+H]$^+$: 380.3.

Step 3: 3-(5-(((R)-6-isobutyl-6-azaspiro[2.5]octan-4-yl)oxy)-1-oxoisoindolin-2-yl)piperidine-2,6-dione (I-26)

Compound I-26 was made according to General Method V starting from ethyl (R)-2-(chloromethyl)-4-((6-isobutyl-6-azaspiro[2.5]octan-4-yl)oxy)benzoate 25 (57.5 mg, 0.15 mmol). The reaction was concentrated and purified by silica gel chromatography (0-100% EtOAc:EtOH:Et₃N (v/v/v=75: 25:1) in heptane). Pure fractions were combined, concentrated and lyophilized to afford the product. Material was further purified by a second silica gel chromatography (0-100% EtOAc:EtOH:Et₃N (v/v/v=75:25:1) in heptane). Pure fractions were combined, concentrated and lyophilized to afford 3-(5-(((R)-6-isobutyl-6-azaspiro[2.5]octan-4-yl)oxy)-1-oxoisoindolin-2-yl)piperidine-2,6-dione I-26 as a white solid. LCMS [M+H]⁺: 426.3. ¹H NMR (400 MHz, DMSO-d6) δ 10.97 (s, 1H), 7.60 (d, J=8.3 Hz, 1H), 7.15 (d, J=2.2 Hz, 1H), 7.03 (dd, J=8.7, 2.1 Hz, 1H), 5.07 (dd, J=13.1, 5.1 Hz, 1H), 4.37 (dd, J=17.2, 8.9 Hz, 1H), 4.25 (dd, J=17.2, 9.1 Hz, 1H), 4.14-4.00 (m, 1H), 2.91 (ddd, J=17.4, 13.6, 5.4 Hz, 1H), 2.73-2.68 (m, 1H), 2.64-2.56 (m, 1H), 2.49-2.29 (m, 4H), 2.10-1.85 (m, 4H), 1.72-1.59 (m, 1H), 1.27-1.15 (m, 1H), 0.84-0.74 (m, 6H), 0.64-0.57 (m, 1H), 0.54-0.48 (m, 1H), 0.39-0.29 (m, 2H).

Example 17: 3-(5-(((R)-6-((S)-sec-butyl)-6-azaspiro[2.5]octan-4-yl)oxy)-1-oxoisoindolin-2-yl)piperidine-2,6-dione

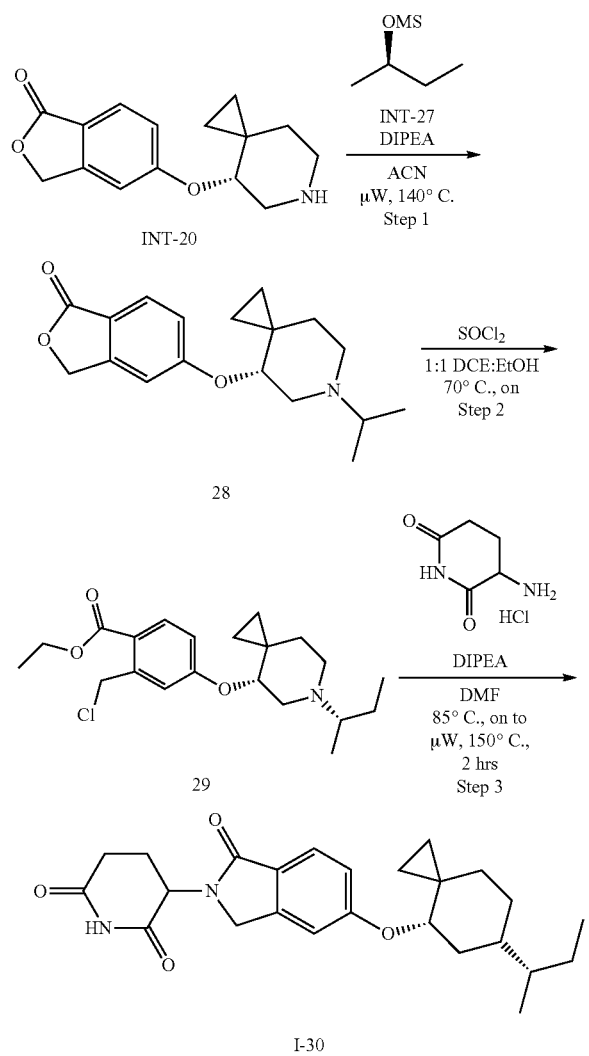

I-30

Step 1: 5-(((R)-6-((S)-sec-butyl)-6-azaspiro[2.5]octan-4-yl)oxy)isobenzofuran-1(3H)-one (28)

Compound 28 was made according to General Method IX starting from (R)-5-((6-azaspiro[2.5]octan-4-yl)oxy)isobenzofuran-1(3H)-one INT-20 (218 mg, 0.84 mmol) and (R)-sec-butyl methanesulfonate INT-27 (192 mg, 1.26 mmol). Additional (R)-sec-butyl methanesulfonate INT-27 (192 mg, 1.26 mmol) and DIPEA (293 µL, 1.68 mmol) were added. The reaction was evacuated and backfilled with nitrogen three times. The reaction stirred at 140° C. for 6 hrs under microwave radiation. The reaction was quenched with 50% saturated aqueous sodium bicarbonate and extracted three times with 4:1 DCM:iPrOH. The organic layers were combined, passed through a phase separator and concentrated onto CELITE®. The crude material was purified by silica gel chromatography (0-100% EtOAc:EtOH:Et₃N (v/v/v=75:25:1) in heptane). Pure fractions were combined, concentrated and lyophilized to afford 5-(((R)-6-((S)-sec-butyl)-6 azaspiro[2.5]octan-4-yl)oxy)isobenzofuran-1(3H)-one 28 as light orange oil and recovered starting material (R)-5-((6-azaspiro[2.5]octan-4-yl)oxy)isobenzofuran-1(3H)-one as a light orange oil. LCMS [M+H]⁺: 316.2. ¹H NMR (400 MHz, CDCl₃) δ 7.81 (d, J=8.5 Hz, 1H), 7.03 (d, J=8.7 Hz, 1H), 6.94 (s, 1H), 5.24 (s, 2H), 4.26-4.14 (m, 1H), 2.91-2.76 (m, 1H), 2.72-2.48 (m, 3H), 1.74-1.43 (m, 4H), 1.28 (s, 1H), 0.97 (d, J=6.5 Hz, 3H), 0.89 (dt, J=14.1, 7.4 Hz, 3H), 0.77-0.72 (m, 1H), 0.58-0.52 (m, 1H), 0.40-0.30 (m, 2H).

Step 2: Ethyl 4-(((R)-6-((S)-sec-butyl)-6-azaspiro[2.5]octan-4-yl)oxy)-2-(chloromethyl)benzoate (29)

Compound 29 was made according to General Method IV starting from 5-(((R)-6-((S)-sec-butyl)-6-azaspiro[2.5]octan-4-yl)oxy)isobenzofuran-1(3H)-one 28 (98.8 mg, 0.31 mmol). The crude material was purified by silica gel chromatography (0-100% EtOAc in heptane) to afford ethyl 4-(((R)-6-((S)-sec-butyl)-6-azaspiro[2.5]octan-4-yl)oxy)-2-(chloromethyl)benzoate 29 as a light orange oil. LCMS [M+H]⁺: 380.3.

Step 3: 3-(5-(((R)-6-((S)-sec-butyl)-6-azaspiro[2.5]octan-4-yl)oxy)-1-oxoisoindolin-2-yl)piperidine-2,6-dione (I-30)

Compound I-30 was made according to General Method V starting from ethyl 4-(((R)-6-((S)-sec-butyl)-6-azaspiro[2.5]octan-4-yl)oxy)-2-(chloromethyl)benzoate 29 (88.3 mg, 0.23 mmol). The reaction was concentrated and purified by silica gel chromatography pushing the crude material through a plug of charcoal before reaching the silica column (0-100% EtOAc:EtOH:Et₃N (v/v/v=75:25:1) in heptane). Fractions containing desired product were combined and concentrated. The material was further purified by basic reverse phase HPLC (35-60% ACN in water with 5 mM NH₄OH as modifier). Test tubes contained 3 drops formic acid prior to sample collection. Pure fractions were combined and lyophilized to afford formate salt 3-(5-(((R)-6-((S)-sec-butyl)-6-azaspiro[2.5]octan-4-yl)oxy)-1-oxoisoindolin-2-yl)piperidine-2,6-dione I-30 as a white solid. LCMS [M+H]⁺: 426.5. ¹H NMR (400 MHz, DMSO-d6) δ 10.89 (s, 1H), 8.10 (s, 1H), 7.52 (dd, J=8.4, 1.9 Hz, 1H), 7.06 (d, J=2.2 Hz, 1H), 6.94 (dd, J=8.5, 2.2 Hz, 1H), 4.99 (dd, J=13.4, 5.2 Hz, 1H), 4.35-4.24 (m, 1H), 4.24-4.12 (m, 1H), 4.09-3.98 (m, 1H), 3.25 (s, 3H), 2.90-2.74 (m, 1H), 2.70-2.58 (m, 1H), 2.56-2.48 (m, 2H), 2.39-2.23 (m, 2H), 1.95-1.85 (m, 1H), 1.81-1.61 (m, 1H), 1.29-1.08 (m, 2H), 0.84-

0.72 (m, 4H), 0.69 (td, J=7.4, 3.5 Hz, 2H), 0.56-0.48 (m, 1H), 0.46-0.38 (m, 1H), 0.30-0.20 (m, 2H).

Example 18: Diastereomers 3-(5-((5-ethyl-5-azaspiro[2.5]octan-7-yl)oxy)-1-oxoisoindolin-2-yl)piperidine-2,6-dione (I-35)

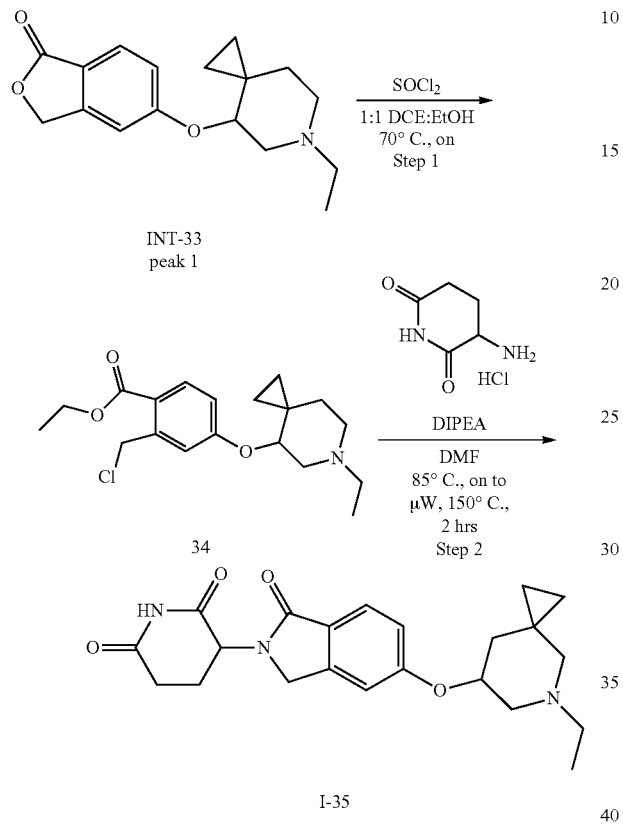

Step 1: Single Enantiomer of Ethyl 2-(chloromethyl)-4-((5-ethyl-5-azaspiro[2.5]octan-7-yl)oxy)benzoate (34)

Compound 34 was made according to General Method IV starting from 5-((5-ethyl-5-azaspiro[2.5]octan-7-yl)oxy)isobenzofuran-1(3H)-one INT-33 peak 1 (20.88 mg, 0.073 mmol). Crude material was purified by silica gel chromatography (0-100% EtOAc in heptane) to afford ethyl 2-(chloromethyl)-4-((5-ethyl-5-azaspiro[2.5]octan-7-yl)oxy)benzoate 34 as an orange oil. Material was taken through to the next step without purification. LCMS [M+H]$^+$: 352.4.

Step 2: Diastereomers 3-(5-((5-ethyl-5-azaspiro[2.5]octan-7-yl)oxy)-1-oxoisoindolin-2-yl)piperidine-2,6-dione (I-35)

Compound I-35 was made according to General Method V starting from single enantiomer of ethyl 2-(chloromethyl)-4-((5-ethyl-5-azaspiro[2.5]octan-7-yl)oxy)benzoate 34 (25.7 mg, 0.073 mmol). The reaction was concentrated and purified by reverse phase HPLC (15-40% ACN in water with 5 mM NH$_4$OH as modifier). Test tubes contained 3 drops of formic acid prior to sample collection. Fractions containing desired product were lyophilized to afford formate salt of diastereomers 3-(5-((5-ethyl-5-azaspiro[2.5]octan-7-yl)oxy)-1-oxoisoindolin-2-yl)piperidine-2,6-dione I-35 as a blueish solid. LCMS [M+H]$^+$: 398.4. $^1$H NMR (400 MHz, DMSO-d6) δ 10.97 (s, 1H), 8.26 (s, 1H), 7.61 (d, J=8.4 Hz, 1H), 7.19 (d, J=2.2 Hz, 1H), 7.03 (dd, J=8.4, 2.2 Hz, 1H), 5.07 (dd, J=13.3, 5.0 Hz, 1H), 4.67-4.53 (m, 1H), 4.39 (d, J=17.1 Hz, 1H), 4.26 (d, J=17.1 Hz, 1H), 3.12 (d, J=10.7 Hz, 1H), 2.91 (ddd, J=17.4, 13.6, 5.4 Hz, 1H), 2.64-2.55 (m, 1H), 2.43-2.33 (m, 3H), 2.24 (d, J=11.1 Hz, 1H), 2.12-1.93 (m, 3H), 1.69 (dd, J=12.4, 9.6 Hz, 1H), 1.57-1.48 (m, 1H), 0.98 (t, J=7.1 Hz, 3H), 0.49-0.28 (m, 4H).

Example 19: Diastereomers 3-(5-((5-ethyl-5-azaspiro[2.5]octan-7-yl)oxy)-1-oxoisoindolin-2-yl)piperidine-2,6-dione (I-37)

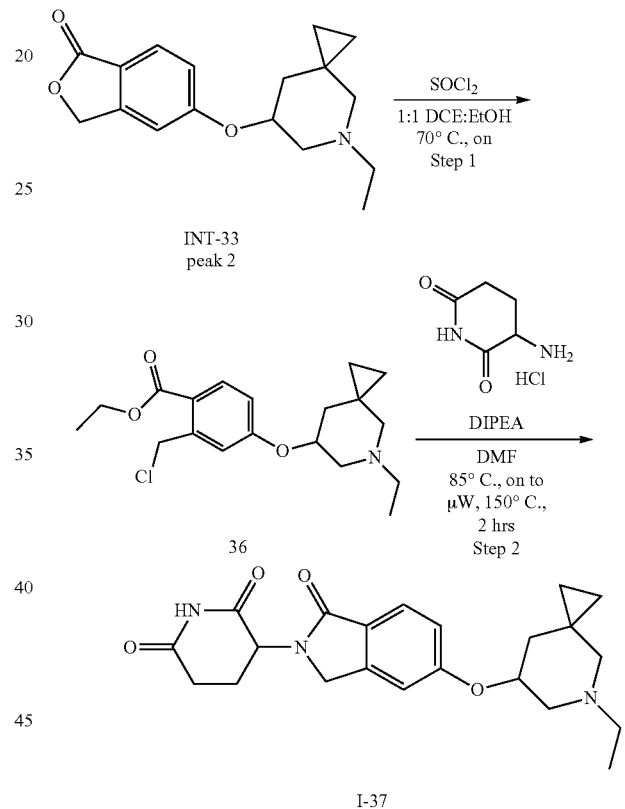

Step 1: Single Enantiomer of Ethyl 2-(chloromethyl)-4-((5-ethyl-5-azaspiro[2.5]octan-7-yl)oxy)benzoate (36)

Compound 36 was made according to General Method IV starting from 5-((5-ethyl-5-azaspiro[2.5]octan-7-yl)oxy)isobenzofuran-1(3H)-one INT-33 peak 2 (18.93 mg, 0.066 mmol) to afford single enantiomer of ethyl 2-(chloromethyl)-4-((5-ethyl-5-azaspiro[2.5]octan-7-yl)oxy)benzoate 36 as an orange oil. Material was taken through to the next step without purification. LCMS [M+H]$^+$: 352.3.

Step 2: Diastereomers 3-(5-((5-ethyl-5-azaspiro[2.5]octan-7-yl)oxy)-1-oxoisoindolin-2-yl)piperidine-2,6-dione (I-37)

Compound I-37 was made according to General Method V starting from single enantiomer of ethyl 2-(chloromethyl)-

4-((5-ethyl-5-azaspiro[2.5]octan-7-yl)oxy)benzoate 36 (23.2 mg, 0.066 mmol). The reaction was concentrated and purified by reverse phase HPLC (15-40% ACN in water with 5 mM NH$_4$OH as modifier). Test tubes contained 3 drops of formic acid prior to sample collection. Fractions containing desired product were lyophilized to afford formate salt of diastereomers 3-(5-((5-ethyl-5-azaspiro[2.5]octan-7-yl)oxy)-1-oxoisoindolin-2-yl)piperidine-2,6-dione I-37 as a blueish solid. LCMS [M+H]$^+$: 398.4. $^1$H NMR (400 MHz, DMSO-d6) δ 11.00 (s, 1H), 8.32 (s, 3H), 7.61 (d, J=8.4 Hz, 1H), 7.19 (d, J=2.2 Hz, 1H), 7.03 (dd, J=8.4, 2.3 Hz, 1H), 5.07 (dd, J=13.2, 5.1 Hz, 1H), 4.66-4.53 (m, 1H), 4.39 (d, J=17.1 Hz, 1H), 4.26 (d, J=17.2 Hz, 1H), 3.15-3.10 (m, 1H), 2.96-2.85 (m, 1H), 2.63-2.56 (m, 1H), 2.41-2.32 (m, 3H), 2.24 (d, J=11.2 Hz, 1H), 2.11-1.94 (m, 3H), 1.69 (dd, J=12.4, 9.6 Hz, 1H), 1.56-1.46 (m, 1H), 0.98 (t, J=7.3 Hz, 3H), 0.48-0.25 (m, 4H).

Example 20: 3-(5-(((1S*,5S*,6R*)-3-ethyl-3-azabicyclo[4.1.0]heptan-5-yl)oxy)-1-oxoisoindolin-2-yl)piperidine-2,6-dione (I-42)

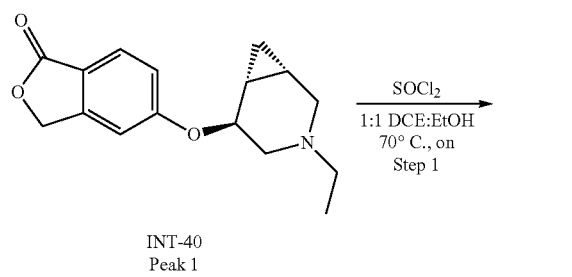

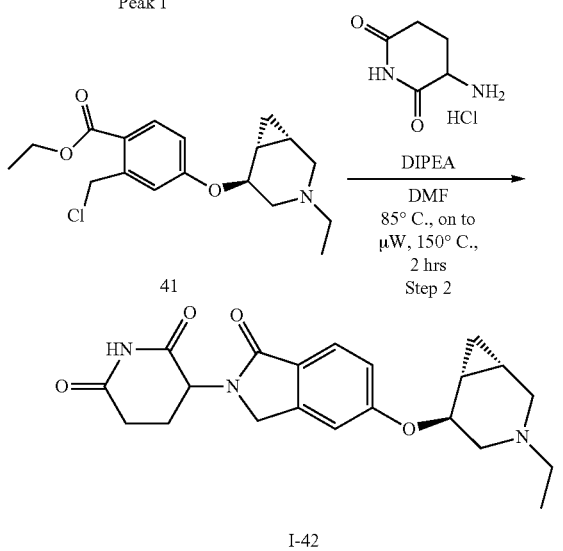

Step 1: Ethyl 2-(chloromethyl)-4-(((1S*,5S*,6R*)-3-ethyl-3-azabicyclo[4.1.0]heptan-5-yl)oxy)benzoate (41)

Compound 41 was made according to General Method IV starting from 5-(((1S*,5S*,6R*)-3-ethyl-3-azabicyclo[4.1.0]heptan-5-yl)oxy)isobenzofuran-1(3H)-one INT-40 Peak 1 (86.4 mg, 0.32 mmol) to afford ethyl 2-(chloromethyl)-4-(((1S*,5S*,6R*)-3-ethyl-3-azabicyclo[4.1.0]heptan-5-yl)oxy)benzoate 41 as a brown oil. Material was taken through to the next step without purification. LCMS [M+H]$^+$: 338.2.

Step 2: 3-(5-(((1S*,5S*,6R*)-3-ethyl-3-azabicyclo[4.1.0]heptan-5-yl)oxy)-1-oxoisoindolin-2-yl)piperidine-2,6-dione (I-42)

Compound I-42 was made according to General Method V starting from ethyl 2-(chloromethyl)-4-(((1S*,5S*,6R*)-3-ethyl-3-azabicyclo[4.1.0]heptan-5-yl)oxy)benzoate 41 (107 mg, 0.32 mmol). The reaction was concentrated and purified by silica gel chromatography pushing the crude material through a plug of charcoal before reaching the silica column (0-100% EtOAc:EtOH:Et$_3$N (v/v/v=75:25:1) in heptane). Pure fractions were combined, concentrated and lyophilized to afford 3-(5-(((1S*,5S*,6R*)-3-ethyl-3-azabicyclo[4.1.0]heptan-5-yl)oxy)-1-oxoisoindolin-2-yl)piperidine-2,6-dione I-42 as a light blue solid. LCMS [M+H]$^+$: 384.3. $^1$H NMR (400 MHz, DMSO-d6) δ 10.90 (s, 1H), 7.58 (d, J=8.4 Hz, 1H), 7.13 (s, 1H), 7.06-6.96 (m, 1H), 5.01 (dd, J=13.2, 5.0 Hz, 1H), 4.51 (s, 1H), 4.33 (dd, J=17.2, 2.9 Hz, 1H), 4.20 (d, J=17.3 Hz, 1H), 2.90-2.70 (m, 3H), 2.56-2.48 (m, 1H), 2.39-2.19 (m, 3H), 2.00-1.85 (m, 2H), 1.21-0.83 (m, 6H), 0.59 (s, 1H), 0.39 (s, 1H).

Example 21: 3-(5-(((1R*,5R*,6S*)-3-ethyl-3-azabicyclo[4.1.0]heptan-5-yl)oxy)-1-oxoisoindolin-2-yl)piperidine-2,6-dione (I-44)

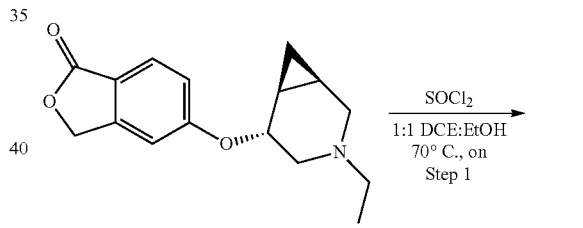

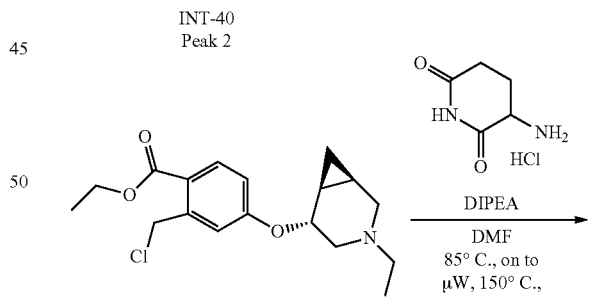

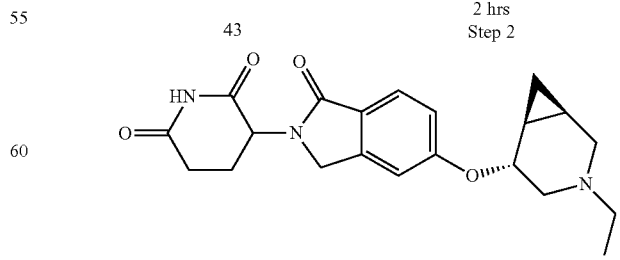

Step 1: Ethyl 2-(chloromethyl)-4-(((1R*,5R*,6S*)-3-ethyl-3-azabicyclo[4.1.0]heptan-5-yl)oxy)benzoate (43)

Compound 43 was made according to General Method IV starting from 5-(((1R*,5R*,6S*)-3-ethyl-3-azabicyclo[4.1.0]heptan-5-yl)oxy)isobenzofuran-1(3H)-one INT-40 Peak 2 (50.7 mg, 0.19 mmol) to afford ethyl 2-(chloromethyl)-4-(((1R*,5R*,6S*)-3-ethyl-3-azabicyclo[4.1.0]heptan-5-yl)oxy)benzoate 43 as a brown oil. Material was taken through to the next step without purification. LCMS [M+H]+: 338.2.

Step 2: 3-(5-(((1R*,5R*,6S*)-3-ethyl-3-azabicyclo[4.1.0]heptan-5-yl)oxy)-1-oxoisoindolin-2-yl)piperidine-2,6-dione (I-44)

Compound I-26 was made according to General Method V starting from ethyl 2-(chloromethyl)-4-(((1R*,5R*,6S*)-3-ethyl-3-azabicyclo[4.1.0]heptan-5-yl)oxy)benzoate 43 (62.5 mg, 0.19 mmol). The reaction was concentrated and purified by silica gel chromatography with the crude material passing through a plug of charcoal before going on the silica column (0-100% EtOAc:EtOH:Et$_3$N (v/v/v=75:25:1) in heptane). Pure fractions were combined, concentrated, lyophilized and further purified by reverse phase HPLC (15-40% ACN in H$_2$O with 5 mM NH$_4$OH as modifier) Test tubes contained 3 drops of formic acid prior to sample collection. Fractions containing desired product were combined and lyophilized to afford formate salt of 3-(5-(((1R*,5R*,6S*)-3-ethyl-3-azabicyclo[4.1.0]heptan-5-yl)oxy)-1-oxoisoindolin-2-yl)piperidine-2,6-dione I-44. LCMS [M+H]+: 384.3. $^1$H NMR (400 MHz, DMSO-d6) δ 10.66 (s, 1H), 8.22 (s, 1H), 7.57 (d, J=8.5 Hz, 1H), 7.12 (d, J=2.1 Hz, 1H), 7.01 (dd, J=8.7, 2.2 Hz, 1H), 5.00 (dd, J=13.4, 5.1 Hz, 1H), 4.55-4.45 (m, 1H), 4.33 (dd, J=17.1, 2.7 Hz, 1H), 4.20 (d, J=17.2 Hz, 1H), 2.91-2.70 (m, 3H), 2.57-2.48 (m, 1H), 2.41-2.14 (m, 4H), 2.00-1.87 (m, 2H), 1.16-1.07 (m, 1H), 0.99-0.84 (m, 4H), 0.63-0.53 (m, 1H), 0.38 (q, J=5.0 Hz, 1H).

Example 22 3-(5-(((1S*,5R*,6R*)-3-ethyl-3-azabicyclo[4.1.0]heptan-5-yl)oxy)-1-oxoisoindolin-2-yl)piperidine-2,6-dione (I-49)

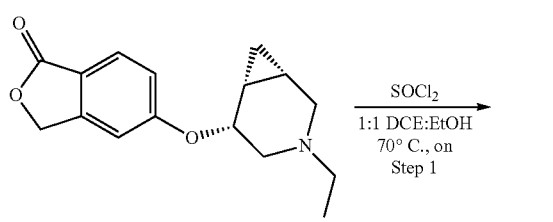

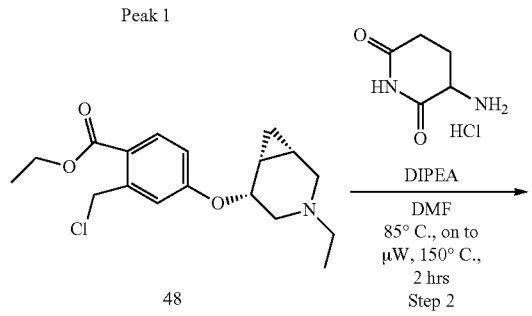

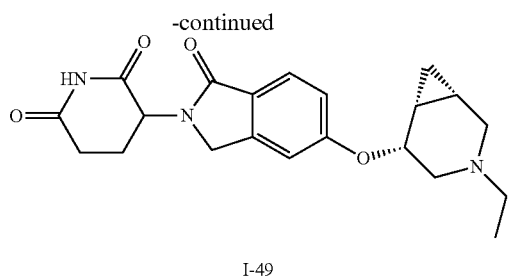

I-49

Step 1: Ethyl 2-(chloromethyl)-4-(((1S*,5R*,6R*)-3-ethyl-3-azabicyclo[4.1.0]heptan-5-yl)oxy)benzoate (48)

Compound 48 was made according to General Method IV starting from 5-(((1S*,5R*,6R*)-3-ethyl-3-azabicyclo[4.1.0]heptan-5-yl)oxy)isobenzofuran-1(3H)-one INT-47 Peak 1 (47.2 mg, 0.17 mmol) to afford ethyl 2-(chloromethyl)-4-(((1S*,5R*,6R*)-3-ethyl-3-azabicyclo[4.1.0]heptan-5-yl)oxy)benzoate 48 as a brown oil. Material was taken through to the next step without purification. LCMS [M+H]+: 338.2.

Step 2: 3-(5-(((1S*,5R*,6R*)-3-ethyl-3-azabicyclo[4.1.0]heptan-5-yl)oxy)-1-oxoisoindolin-2-yl)piperidine-2,6-dione (I-49)

Compound I-49 was made according to General Method V starting from ethyl 2-(chloromethyl)-4-(((1S*,5R*,6R*)-3-ethyl-3-azabicyclo[4.1.0]heptan-5-yl)oxy)benzoate 48 (58.4 mg, 0.17 mmol). The reaction was concentrated and purified by silica gel chromatography pushing the crude material through a plug of charcoal before reaching the silica column (0-100% EtOAc:EtOH:Et$_3$N (v/v/v=75:25:1) in heptane). Pure fractions were combined, concentrated, lyophilized and further purified by reverse phase HPLC (15-40% ACN in water with 5 mM NH$_4$OH as modifier). Test tubes contained 3 drops formic acid prior to sample collection. Pure fractions were combined and lyophilized to afford 3-(5-(((1S*,5R*,6R*)-3-ethyl-3-azabicyclo[4.1.0]heptan-5-yl)oxy)-1-oxoisoindolin-2-yl)piperidine-2,6-dione I-49 as a white solid. LCMS [M+H]+: 384.3. $^1$H NMR (400 MHz, DMSO-d6) δ 10.49 (s, 1H), 8.23 (s, 1H), 7.53 (d, J=8.5 Hz, 1H), 7.15 (d, J=2.2 Hz, 1H), 7.01 (dd, J=8.3, 2.3 Hz, 1H), 5.00 (dd, J=13.3, 5.1 Hz, 1H), 4.93-4.83 (m, 1H), 4.31 (d, J=17.1 Hz, 1H), 4.18 (d, J=17.1 Hz, 1H), 2.91-2.77 (m, 1H), 2.63 (d, J=11.0 Hz, 1H), 2.56-2.46 (m, 1H), 2.40-2.18 (m, 6H), 1.95-1.85 (m, 1H), 1.51-1.36 (m, 1H), 1.28-1.13 (m, 1H), 0.89 (t, J=7.1 Hz, 3H), 0.64-0.53 (m, 1H), 0.41-0.33 (m, 1H).

Example 23: 3-(5-(((3R,6R)-1-ethyl-6-methylpiperidin-3-yl)oxy)-1-oxoisoindolin-2-yl)piperidine-2,6-dione (I-52)

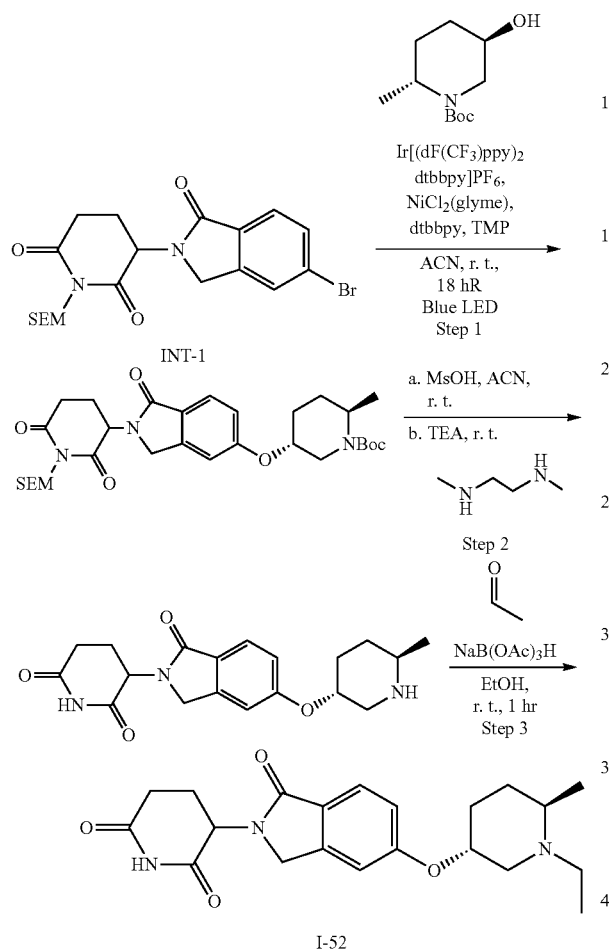

Step 1: Tert-butyl (2R,5R)-5-((2-(2,6-dioxo-1-((2-(trimethylsilyl)ethoxy)methyl)piperidin-3-yl)-1-oxoisoindolin-5-yl)oxy)-2-methyl piperidine-1-carboxylate (50)

Compound 50 was made according to General Method VI starting from 3-(5-bromo-1-oxoisoindolin-2-yl)-1-((2-(trimethylsilyl)ethoxy)methyl)piperidine-2,6-dione INT-1 (500 mg, 1.10 mmol) and tert-butyl (2R,5R)-5-hydroxy-2-methylpiperidine-1-carboxylate (237 mg, 1.10 mmol). The crude material was purified by silica gel chromatography (0 to 100% EtOAc in Heptane). Fractions containing desired product were combined and concentrated to afford tert-butyl (2R,5R)-5-((2-(2,6-dioxo-1-((2-(trimethylsilyl)ethoxy)methyl)piperidin-3-yl)-1-oxoisoindolin-5-yl)oxy)-2-methylpiperidine-1-carboxylate 50 as an off-white solid. LCMS [M−H]⁻: 586.3.

Step 2: 3-(5-(((3R,6R)-6-methylpiperidin-3-yl)oxy)-1-oxoisoindolin-2-yl)piperidine-2,6-dione (51)

Compound 51 was made according to General Method VII starting from tert-butyl (2R,5R)-5-((2-(2,6-dioxo-1-((2-(trimethylsilyl)ethoxy) methyl)piperidin-3-yl)-1-oxoisoindolin-5-yl)oxy)-2-methylpiperidine-1-carboxylate 50 (251 mg, 0.43 mmol). The reaction mixture was diluted with saturated aqueous sodium bicarbonate and extracted with 4:1 DCM:TFE three times. The organic layers were combined and concentrated. The crude material was purified by silica gel chromatography (0 to 100% EtOH:Et₃N (v/v=100:1) in EtOAc). Fractions containing desired product were combined and concentrated to afford 3-(5-(((3R,6R)-6-methylpiperidin-3-yl)oxy)-1-oxoisoindolin-2-yl)piperidine-2,6-dione 51 as a white solid. LCMS [M+H]⁺: 358.1.

Step 3: 3-(5-(((3R,6R)-1-ethyl-6-methylpiperidin-3-yl)oxy)-1-oxoisoindolin-2-yl)piperidine-2,6-dione (I-52)

To a solution of 3-(5-(((3R,6R)-6-methylpiperidin-3-yl)oxy)-1-oxoisoindolin-2-yl)piperidine-2,6-dione 51 (62 mg, 0.17 mmol) and sodium triacetoxyborohydride (55.1 mg, 0.26 mmol) in EtOH (1 mL) was added acetaldehyde (0.015 mL, 0.260 mmol) at 0° C. The reaction stirred at r.t. overnight. The reaction was concentrated and purified by silica gel chromatography (0 to 100% EtOAc:EtOH:Et₃N (v/v/v=75:25:1) in heptane). Fractions containing desired product were combined and concentrated to afford 3-(5-(((3R,6R)-1-ethyl-6-methylpiperidin-3-yl)oxy)-1-oxoisoindolin-2-yl)piperidine-2,6-dione I-52 as an off-white solid. LCMS [M+H]⁺: 386.3. ¹H NMR (400 MHz, CD₂Cl₂) δ 8.19-8.05 (m, 1H), 7.70 (d, J=8.3 Hz, 1H), 7.10-6.95 (m, 2H), 5.12 (dd, J=13.4, 5.2 Hz, 1H), 4.49 (s, 1H), 4.39-4.26 (m, 2H), 3.25-3.18 (m, 1H), 2.92-2.75 (m, 3H), 2.61 (dq, J=13.8, 7.0 Hz, 1H), 2.40-2.12 (m, 5H), 1.81-1.75 (m, 1H), 1.52-1.38 (m, 2H), 1.11 (d, J=6.2 Hz, 3H), 1.00 (t, J=7.1 Hz, 3H).

Example 24: 3-(5-(((R)-1-(but-2-yn-1-yl)piperidin-3-yl)oxy)-1-oxoisoindolin-2-yl)piperidine-2,6-dione (I-53)

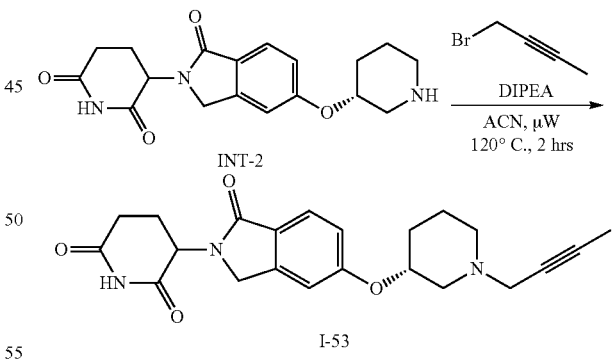

In a 2 mL microwave vial, DIPEA (51 uL, 0.291 mmol) and 1-bromo-2-butyne (17 uL, 0.189 mmol) were added to a solution of 3-(1-oxo-5-(((R)-piperidin-3-yl)oxy)isoindolin-2-yl)piperidine-2,6-dione INT-2 (50 mg, 0.15 mmol) in ACN (1 mL). The reaction stirred at 120° C. for 2 hrs under microwave radiation. The reaction was diluted with acetone and concentrated onto (SOLUTE® (HM-N Part No. 9800-5000). The crude material was purified by silica gel chromatography (0 to 100% EtOAc:EtOH:Et₃N (v/v/v=75:25:1) in DCM) to afford product that was a colorless oil that turned to a foam under high vac. The product was lyophilized to afford 3-(5-(((R)-1-(but-2-yn-1-yl)piperidin-3-yl)oxy)-1-oxoisoindolin-2-yl)piperidine-2,6-dione I-53. LCMS [M+H]+: 396.5. ¹H NMR (400 MHz, DMSO-d6) δ 10.96 (s, 1H), 7.61 (d, J=8.4 Hz, 1H), 7.19 (s, 1H), 7.05 (d, J=8.4 Hz, 1H), 5.07 (dd, J=13.3, 5.1 Hz, 1H), 4.53 (s, 1H), 4.42-4.17 (m, 2H), 3.25 (s, 2H), 3.18-2.83 (m, 2H), 2.68-2.53 (m, 2H), 2.43-2.15 (m, 3H), 1.98 (d, J=5.0 Hz, 2H), 1.79 (d, J=2.3 Hz, 4H), 1.56 (s, 1H), 1.38 (d, J=10.2 Hz, 1H).

Example 25: 3-(5-(((R)-1-(3-cyclopropylprop-2-yn-1-yl)piperidin-3-yl)oxy)-1-oxoisoindolin-2-yl)piperidine-2,6-dione (I-54)

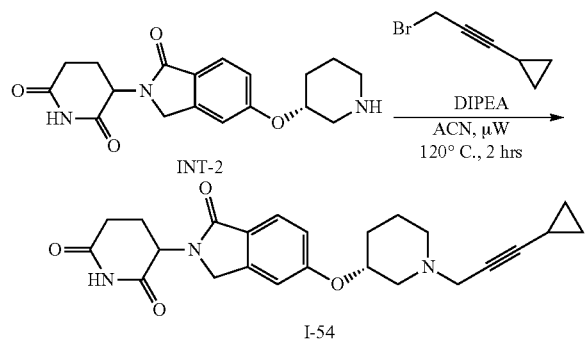

3-(1-oxo-5-(((R)-piperidin-3-yl)oxy)isoindolin-2-yl)piperidine-2,6-dione INT-2 (73 mg, 0.21 mmol) was added to a 5 mL microwave vial, followed by the addition of (3-bromoprop-1-yn-1-yl)cyclopropane (44 mg, 0.28 mmol) in ACN (2.1 mL) and DIPEA (74 uL, 0.425 mmol). The reaction stirred at 120° C. for 2 hrs under microwave radiation. The reaction was diluted with DCM and concentrated onto (SOLUTE® (HM-N Part No. 9800-5000). The crude material was purified by silica gel chromatography (0 to 100% EtOAc:EtOH:Et₃N (v/v/v=75:25:1) in DCM) to afford product. The product material was lyophilized to afford 3-(5-(((R)-1-(3-cyclopropylprop-2-yn-1-yl)piperidin-3-yl)oxy)-1-oxoisoindolin-2-yl)piperidine-2,6-dione I-54 as a fluffy white solid. LCMS [M+H]+: 422.4. ¹H NMR (400 MHz, DMSO-d6) δ 10.97 (s, 1H), 7.61 (dt, J=8.4, 3.0 Hz, 1H), 7.20 (d, J=3.8 Hz, 1H), 7.11-6.96 (m, 1H), 5.07 (d, J=13.5 Hz, 1H), 4.53 (s, 1H), 4.45-4.15 (m, 2H), 3.23 (s, 2H), 2.91 (m, 2H), 2.59 (d, J=18.7 Hz, 2H), 2.47-2.13 (m, 3H), 1.97 (d, J=11.1 Hz, 2H), 1.74 (m, 1H), 1.55 (m, 1H), 1.34 (d, J=41.6 Hz, 2H), 0.74 (dt, J=8.4, 3.0 Hz, 2H), 0.54 (dq, J=5.8, 2.9 Hz, 2H).

Example 26: 3-(5-(((R)-1-((1s,3S)-3-ethoxycyclobutyl)piperidin-3-yl)oxy)-1-oxoisoindolin-2-yl)piperidine-2,6-dione (I-56)

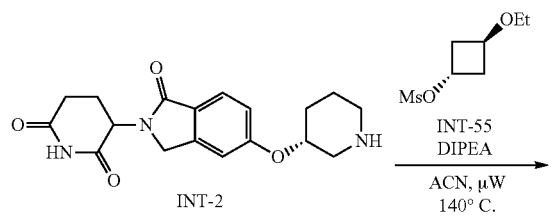

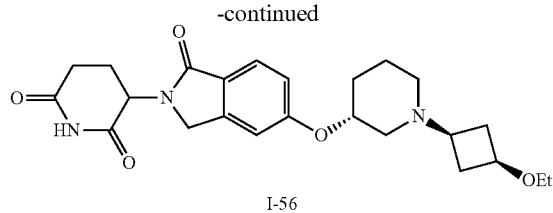

A 5 mL microwave vial was charged with 3-(1-oxo-5-(((R)-piperidin-3-yl)oxy)isoindolin-2-yl)piperidine-2,6-dione INT-2 (60 mg, 0.18 mmol), (1r,3r)-3-ethoxycyclobutyl methanesulfonate INT-55 (80 mg, 0.35 mmol), DIPEA (0.06 mL, 0.35 mmol) and ACN (0.5 mL). The reaction stirred at 140° C. for a total of 4 hrs under microwave radiation. The reaction was concentrated and purified by silica gel chromatography (0 to 100% EtOAc:EtOH:Et₃N (v/v/v=75:25:1) in heptane). Fractions containing desired product were combined and concentrated to afford 3-(5 (((R)-1-((1s,3S)-3-ethoxycyclobutyl)piperidin-3-yl)oxy)-1-oxoisoindolin-2-yl)piperidine-2,6-dione I-56 as a white solid. LCMS [M+H]+: 442.3. ¹H NMR (400 MHz, CD₂Cl₂) δ 8.04 (s, 1H), 7.71 (d, J=8.5 Hz, 1H), 7.12-6.95 (m, 2H), 5.19-5.07 (m, 1H), 4.71-4.43 (m, 1H), 4.43-4.25 (m, 2H), 3.74-3.62 (m, 1H), 3.37 (q, J=7.0 Hz, 2H), 3.07 (s, 1H), 2.94-2.66 (m, 3H), 2.53-2.28 (m, 4H), 2.24-2.15 (m, 1H), 2.13-1.94 (m, 3H), 1.91-1.74 (m, 3H), 1.14 (t, J=7.0 Hz, 3H).

Example 27: 3-(5-(((R)-1-(((1r,3R)-3-methoxycyclobutyl)methyl)piperidin-3-yl)oxy)-1-oxoisoindolin-2-yl)piperidine-2,6-dione (I-59)

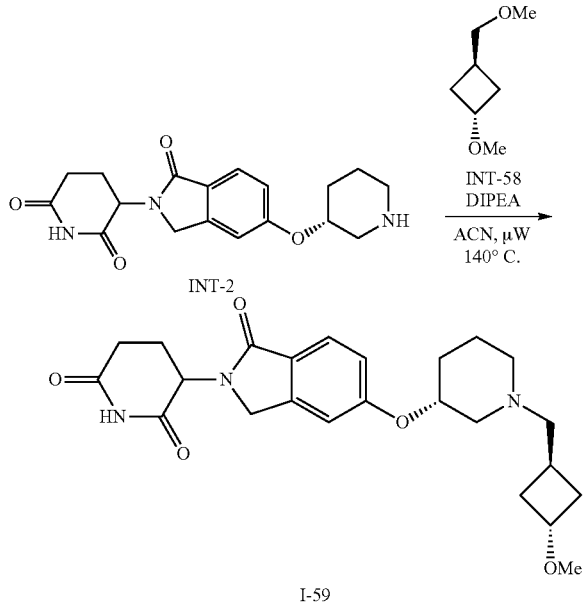

Compound I-59 was made according to General Method IX starting from 3-(1-oxo-5-(((R)-piperidin-3-yl)oxy)isoindolin-2-yl)piperidine-2,6-dione INT-2 (60 mg, 0.18 mmol) and ((1r,3r)-3-methoxycyclobutyl)methyl methanesulfonate INT-58 (51 mg, 0.26 mmol). The crude material was purified by silica gel chromatography (0-100% EtOAc:EtOH:Et₃N (v/v/v=75:25:1) in heptane). Pure fractions were combined, concentrated and lyophilized to afford 3-(5-(((R)-1-(((1r, 3R)-3-methoxycyclobutyl)methyl)piperidin-3-yl)oxy)-1-oxoisoindolin-2-yl)piperidine-2,6-dione I-59 as a white solid. LCMS [M+H]⁺: 442.5. ¹H NMR (400 MHz, DMSO-d6) δ 10.97 (s, 1H), 7.61 (d, J=8.4 Hz, 1H), 7.19 (d, J=2.2 Hz, 1H), 7.05 (dd, J=8.4, 2.3 Hz, 1H), 5.08 (dd, J=13.2, 5.1 Hz, 1H), 4.53-4.35 (m, 2H), 4.26 (d, J=17.0 Hz, 1H), 3.89 (p, J=6.2 Hz, 1H), 3.30 (s, 1H), 3.09 (s, 3H), 2.97-2.85 (m, 2H), 2.65-2.56 (m, 2H), 2.38 (q, J=4.3 Hz, 3H), 2.14-1.85 (m, 8H), 1.76-1.65 (m, 1H), 1.60-1.46 (m, 1H), 1.42-1.30 (m, 1H).

Example 28: 3-(5-(((R)-1-(7-oxaspiro[3.5]nonan-2-yl)piperidin-3-yl)oxy)-1-oxoisoindolin-2-yl)piperidine-2,6-dione (I-61)

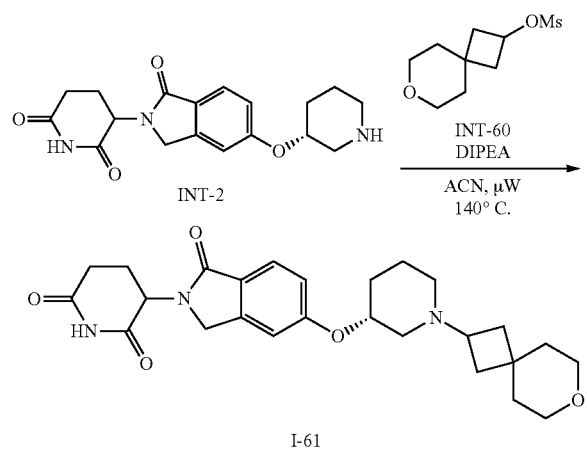

Compound I-61 was made according to General Method IX starting from 3-(1-oxo-5-(((R)-piperidin-3-yl)oxy)isoindolin-2-yl)piperidine-2,6-dione INT-2 (70 mg, 0.20 mmol) and 7-oxaspiro[3.5]nonan-2-yl methanesulfonate INT-60 (79 mg, 0.36 mmol). The crude material was purified by silica gel chromatography (0-100% EtOAc:EtOH:Et₃N (v/v/v=75:25:1) in heptane). Pure fractions were combined, concentrated and lyophilized to afford 3-(5-(((R)-1-(7 oxaspiro[3.5]nonan-2-yl)piperidin-3-yl)oxy)-1-oxoisoindolin-2-yl)piperidine-2,6-dione I-61 as a white solid. LCMS [M+H]⁺: 468.5. ¹H NMR (400 MHz, DMSO-d6) δ 10.89 (s, 1H), 7.54 (d, J=8.4 Hz, 1H), 7.12 (d, J=2.0 Hz, 1H), 6.98 (dd, J=8.3, 2.3 Hz, 1H), 5.00 (dd, J=13.4, 5.2 Hz, 1H), 4.49-4.37 (m, 1H), 4.31 (dd, J=17.2, 2.4 Hz, 1H), 4.25-4.13 (m, 1H), 3.46-3.39 (m, 2H), 3.39-3.32 (m, 2H), 3.23-3.21 (m, 1H), 2.89-2.76 (m, 2H), 2.69-2.62 (m, 1H), 2.56-2.48 (m, 2H), 2.37-2.28 (m, 1H), 2.01-1.74 (m, 6H), 1.70-1.62 (m, 1H), 1.52-1.28 (m, 7H).

Example 29: 3-(5-(((R)-1-(3,3-difluorocyclobutyl)piperidin-3-yl)oxy)-1-oxoisoindolin-2-yl)piperidine-2,6-dione (I-63)

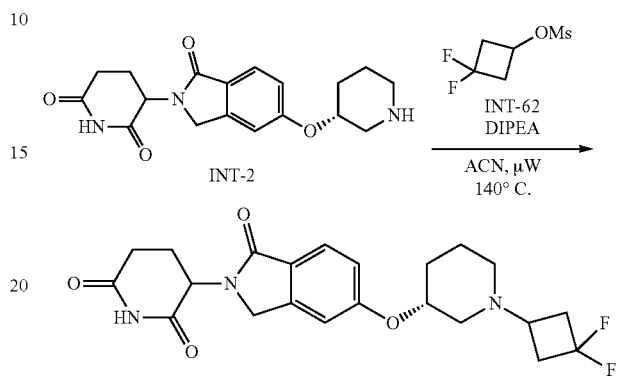

3-(1-oxo-5-(((R)-piperidin-3-yl)oxy)isoindolin-2-yl)piperidine-2,6-dione INT-2 (50 mg, 0.15 mmol) and 3,3-difluorocyclobutyl methanesulfonate INT-62 (54 mg, 0.29 mmol) were added to a 2 mL microwave vial and suspended in ACN (0.73 mL). DIPEA (0.06 mL, 0.34 mmol) was added and the reaction was evacuated and backfilled with nitrogen three times. The reaction was stirred at 140° C. for a total of 14 hrs under microwave radiation. The reaction was quenched with 50% saturated aqueous sodium bicarbonate and extracted three times with 4:1 DCM:iPrOH. The organic layers were combined, passed through a phase separator and concentrated onto CELITE®. The crude material was purified by silica gel chromatography (0-100% EtOAc:EtOH:Et₃N (v/v/v=75:25:1) in heptane). Pure fractions were combined, concentrated and lyophilized to afford 3-(5-(((R)-1-(3,3-difluorocyclobutyl)piperidin-3-yl)oxy)-1-oxoisoindolin-2-yl)piperidine-2,6-dione I-63 as a white solid. LCMS [M+H]⁺: 434.2. ¹H NMR (400 MHz, DMSO-d6) δ 10.89 (s, 1H), 7.54 (d, J=8.4 Hz, 1H), 7.14 (d, J=2.1 Hz, 1H), 6.99 (dd, J=8.4, 2.2 Hz, 1H), 5.00 (dd, J=13.3, 5.0 Hz, 1H), 4.50-4.37 (m, 1H), 4.31 (dd, J=17.2, 2.6 Hz, 1H), 4.19 (dd, J=17.4, 2.5 Hz, 1H), 2.90-2.77 (m, 2H), 2.70-2.48 (m, 5H), 2.39-2.27 (m, 3H), 2.02-1.85 (m, 4H), 1.75-1.63 (m, 1H), 1.57-1.26 (m, 2H).

Example 30: 3-(5-(((R)-1-(((1r,4R)-4-methoxycyclohexyl)methyl)piperidin-3-yl)oxy)-1-oxoisoindolin-2-yl)piperidine-2,6-dione (I-65)

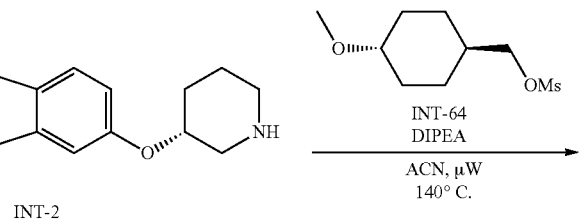

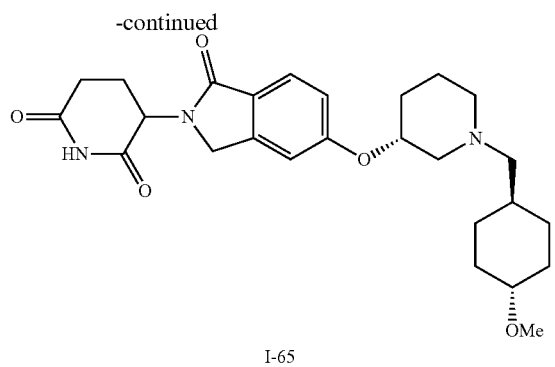

I-65

Compound I-65 was made according to General Method IX starting from 3-(1-oxo-5-(((R)-piperidin-3-yl)oxy)isoindolin-2-yl)piperidine-2,6-dione INT-2 (60 mg, 0.18 mmol) and ((1r,4r)-4-methoxycyclohexyl)methyl methanesulfonate INT-64 (58 mg, 0.26 mmol). The crude material was purified by silica gel chromatography (0-100% EtOAc:EtOH:Et$_3$N (v/v/v=75:25:1) in heptane). Pure fractions were combined, concentrated and lyophilized to afford 3-(5-(((R)-1-(((1r,4R)-4-methoxycyclohexyl)methyl)piperidin-3-yl)oxy)-1-oxoisoindolin-2-yl)piperidine-2,6-dione I-65 as a white solid. LCMS [M+H]$^+$: 470.3. $^1$H NMR (400 MHz, DMSO-d6) δ 10.97 (s, 1H), 7.62 (d, J=8.4 Hz, 1H), 7.19 (d, J=2.2 Hz, 1H), 7.05 (dd, J=8.6, 2.2 Hz, 1H), 5.08 (dd, J=13.2, 5.0 Hz, 1H), 4.54-4.46 (m, 1H), 4.39 (dd, J=17.2, 3.4 Hz, 1H), 4.26 (dd, J=17.2, 3.2 Hz, 1H), 3.22 (s, 3H), 3.07-2.96 (m, 1H), 2.96-2.84 (m, 2H), 2.67-2.56 (m, 2H), 2.45-2.33 (m, 1H), 2.16-1.93 (m, 8H), 1.82-1.67 (m, 3H), 1.61-1.33 (m, 3H), 1.13-0.96 (m, 2H), 0.90-0.78 (m, 2H).

Example 31: 3-(5-(((R)-1-(but-3-en-1-yl)piperidin-3-yl)oxy)-1-oxoisoindolin-2-yl)piperidine-2,6-dione (I-67)

(1.5 mL). DIPEA (0.10 mL, 0.58 mmol) was added and the reaction was evacuated and backfilled with nitrogen three times. The reaction stirred at 140° C. for 2 hrs under microwave radiation. The reaction was quenched with 50% saturated aqueous sodium bicarbonate and extracted three times with 4:1 DCM:iPrOH. The organic layers were combined, passed through a phase separator and concentrated onto CELITE®. The crude material was purified by silica gel chromatography (0-100% EtOAc:EtOH:Et$_3$N (v/v/v=75:25:1) in heptane). Pure fractions were combined, concentrated and lyophilized to afford 3-(5-(((R)-1-(but-3-en-1-yl)piperidin-3-yl)oxy)-1-oxoisoindolin-2-yl)piperidine-2,6-dione I-67 as a white solid and 3-(5-(((R)-1-(cyclopropylmethyl)piperidin-3-yl)oxy)-1-oxoisoindolin-2-yl)piperidine-2,6-dione I-17 as a white solid.

3-(5-(((R)-1-(but-3-en-1-yl)piperidin-3-yl)oxy)-1-oxoisoindolin-2-yl)piperidine-2,6-dione (I-67): LCMS [M+H]$^+$: 398.3. $^1$H NMR (400 MHz, DMSO-d6) δ 10.89 (s, 1H), 7.54 (d, J=8.4 Hz, 1H), 7.12 (d, J=2.3 Hz, 1H), 6.97 (dd, J=8.4, 2.3 Hz, 1H), 5.81-5.63 (m, 1H), 5.08-4.93 (m, 2H), 4.89 (dd, J=10.2, 2.0 Hz, 1H), 4.47-4.35 (m, 1H), 4.31 (d, J=17.2 Hz,

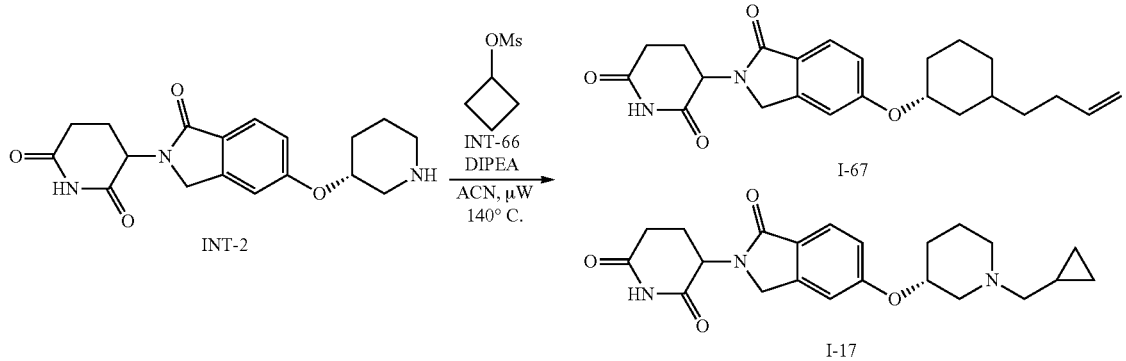

3-(1-oxo-5-(((R)-piperidin-3-yl)oxy)isoindolin-2-yl)piperidine-2,6-dione INT-2 (100 mg, 0.29 mmol) and cyclobutyl methanesulfonate INT-66 (66 mg, 0.44 mmol) were added to a 2 mL microwave vial and suspended in ACN 1H), 4.19 (d, J=17.2 Hz, 1H), 2.98-2.78 (m, 2H), 2.64-2.56 (m, 1H), 2.56-2.47 (m, 1H), 2.38-2.24 (m, 3H), 2.20-1.85 (m, 6H), 1.71-1.59 (m, 1H), 1.58-1.40 (m, 1H), 1.37-1.23 (m, 1H).

Example 32: 3-(5-(((R)-1-((R)-sec-butyl)piperidin-3-yl)oxy)-1-oxoisoindolin-2-yl)piperidine-2,6-dione (I-69)

Example 33: 3-(5-(((R)-1-((S)-sec-butyl)piperidin-3-yl)oxy)-1-oxoisoindolin-2-yl)piperidine-2,6-dione (I-70)

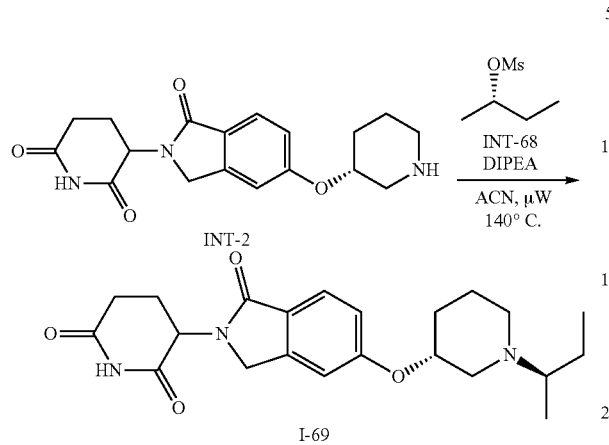

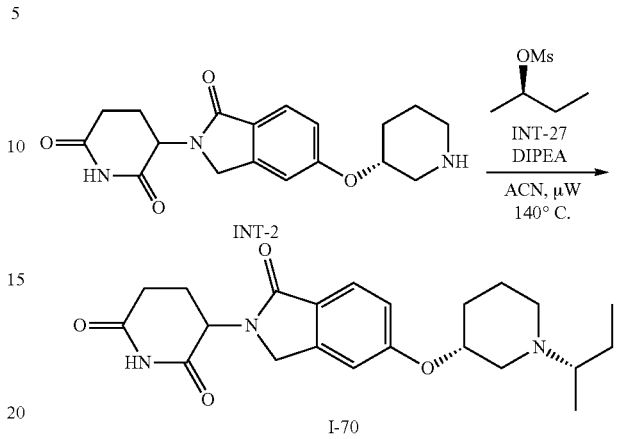

Compound I-69 was made according to General Method IX starting from 1-(hydroxymethyl)-3-(1-oxo-5-(((R)-piperidin-3-yl)oxy)isoindolin-2-yl)piperidine-2,6-dione INT-2 (100 mg, 0.29 mmol) and (S)-sec-butyl methanesulfonate INT-68 (66 mg, 0.44 mmol). The crude material was purified by silica gel chromatography (0-100% EtOAc:EtOH:Et$_3$N (v/v/v=75:25:1) in heptane). Pure fractions were combined, concentrated and lyophilized to afford 3-(5-(((R)-1-((R)-sec-butyl)piperidin-3-yl)oxy)-1-oxoisoindolin-2-yl)piperidine-2,6-dione I-69 as a white solid. LCMS [M+H]$^+$: 400.3. $^1$H NMR (400 MHz, DMSO-d6) δ 10.89 (s, 1H), 7.54 (d, J=8.3 Hz, 1H), 7.10 (dd, J=4.6, 2.2 Hz, 1H), 6.96 (dd, J=8.4, 2.3 Hz, 1H), 5.00 (dd, J=13.3, 5.2 Hz, 1H), 4.46-4.25 (m, 2H), 4.18 (d, J=17.1 Hz, 1H), 2.93-2.74 (m, 2H), 2.58-2.47 (m, 2H), 2.40-2.19 (m, 3H), 2.15-1.85 (m, 3H), 1.70-1.59 (m, 1H), 1.55-1.11 (m, 4H), 0.86-0.71 (m, 6H).

Compound I-70 was made according to General Method IX starting from 1-(hydroxymethyl)-3-(1-oxo-5-(((R)-piperidin-3-yl)oxy)isoindolin-2-yl)piperidine-2,6-dione INT-2 (100 mg, 0.29 mmol) and (R)-sec-butyl methanesulfonate INT-27 (66 mg, 0.44 mmol). The crude material was purified by silica gel chromatography (0-100% EtOAc:EtOH:Et$_3$N (v/v/v=75:25:1) in heptane). Pure fractions were combined, concentrated and lyophilized to afford 3-(5-(((R)-1-((S)-sec-butyl)piperidin-3-yl)oxy)-1-oxoisoindolin-2-yl)piperidine-2,6-dione I-70 as a white solid. LCMS [M+H]$^+$: 400.4. $^1$H NMR (400 MHz, DMSO-d6) δ 10.89 (s, 1H), 7.53 (d, J=8.3 Hz, 1H), 7.10 (dd, J=4.6, 2.2 Hz, 1H), 6.96 (dd, J=8.3, 2.1 Hz, 1H), 5.00 (dd, J=13.3, 5.0 Hz, 1H), 4.45-4.24 (m, 2H), 4.18 (d, J=17.1 Hz, 1H), 2.92-2.79 (m, 2H), 2.58-2.47 (m, 2H), 2.40-2.19 (m, 3H), 2.14-1.86 (m, 3H), 1.71-1.59 (m, 1H), 1.49-1.10 (m, 4H), 0.87-0.73 (m, 6H).

Example 34: rac-3-(5-(((3R,5R)-1-Ethyl-5-hydroxypiperidin-3-yl)oxy)-1-oxoisoindolin-2-yl)piperidine-2,6-dione (I-73)

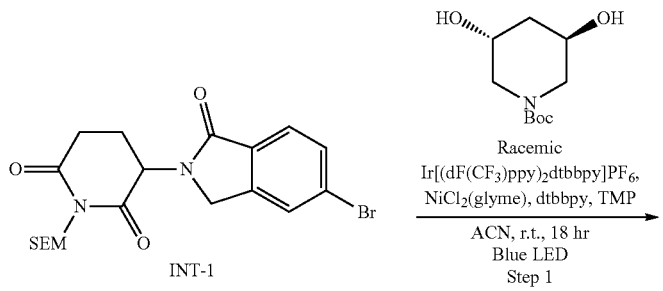

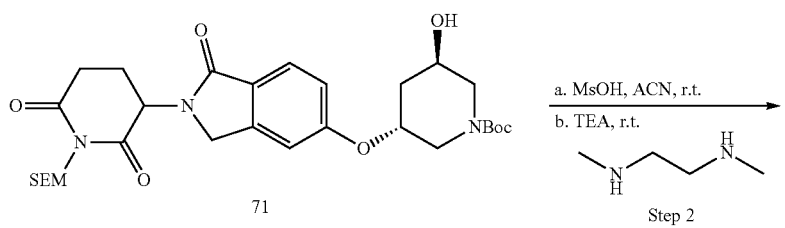

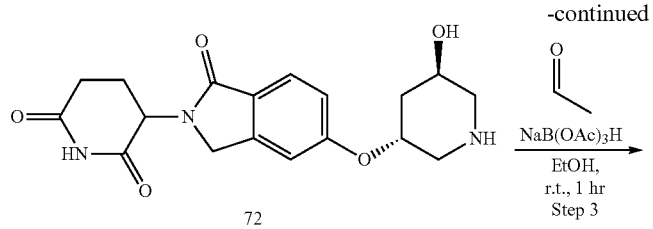 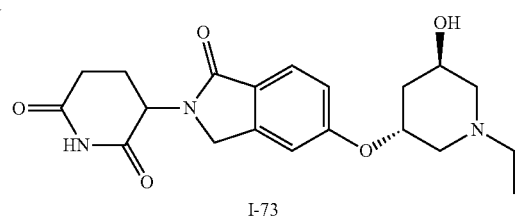

Step 1: rac-Tert-butyl (3R,5R)-3-((2-(2,6-dioxo-1-((2-(trimethylsilyl)ethoxy)methyl)piperidin-3-yl)-1-oxoisoindolin-5-yl)oxy)-5-hydroxypiperidine-1-carboxylate (71)

71 was made according to General Method VI starting from 3-(5-bromo-1-oxoisoindolin-2-yl)-1-((2-(trimethylsilyl)ethoxy)methyl)piperidine-2,6-dione INT-1 (850 mg, 1.88 mmol) rac-tert-butyl (3R,5R)-3,5-dihydroxypiperidine-1-carboxylate (489 mg, 2.25 mmol). The crude material was purified by silica gel chromatography (0 to 50% Acetone in Heptane). Fractions containing desired product were combined and concentrated to afford rac-tert-butyl (3R,5R)-3-((2-(2,6-dioxo-1-((2-(trimethylsilyl)ethoxy) methyl)piperidin-3-yl)-1-oxoisoindolin-5-yl)oxy)-5-hydroxypiperidine-1-carboxylate 71 as a pale yellow solid. LCMS [M−H]⁻: 588.3.

Step 2: rac-3-(5-(((3R,5R)-5-hydroxypiperidin-3-yl)oxy)-1-oxoisoindolin-2-yl)piperidine-2,6-dione (72)

72 was made according to General Method VII starting from 71 (453 mg, 0.77 mmol). The reaction was quenched with saturated aqueous NaHCO₃ and extracted with 4:1 DCM:EtOH three times. The organic layers were combined and concentrated to afford rac-3-(5-(((3R,5R)-5-hydroxypiperidin-3-yl)oxy)-1-oxoisoindolin-2-yl)piperidine-2,6-dione 72 (276 mg, 0.768 mmol). Material was used directly in the next reaction. LCMS [M+H]⁺: 360.2.

Step 3: rac-3-(5-(((3R,5R)-1-ethyl-5-hydroxypiperidin-3-yl)oxy)-1-oxoisoindolin-2-yl)piperidine-2,6-dione (I-73)

To a solution of rac-3-(5-(((3R,5R)-5-hydroxypiperidin-3-yl)oxy)-1-oxoisoindolin-2-yl)piperidine-2,6-dione 72 (276 mg, 0.77 mmol) and sodium triacetoxyborohydride (1.30 g, 6.14 mmol) in EtOH (5.0 mL) was added acetaldehyde (0.34 mL, 6.14 mmol) at 0° C. The reaction was stirred at r.t. for 1 hr. The reaction was concentrated and purified by silica gel chromatography (0 to 100% EtOAc:EtOH:Et₃N (v/v/v=75:25:1) in Heptane). Fractions containing desired product were combined and concentrated to afford rac-3-(5-(((3R,5R)-1-ethyl-5-hydroxypiperidin-3-yl)oxy)-1-oxoisoindolin-2-yl)piperidine-2,6-dione I-73 as a white solid. LCMS [M+H]⁺: 388.4. ¹H NMR (400 MHz, Deuterium Oxide) δ 8.43 (s, 1H), 7.74 (d, J=8.5 Hz, 1H), 7.23-7.20 (m, 1H), 7.15 (dd, J=8.5, 2.3 Hz, 1H), 5.17 (s, 1H), 5.10 (dd, J=13.3, 5.2 Hz, 1H), 4.56-4.41 (m, 2H), 4.32 (s, 1H), 3.92-3.44 (m, 2H), 3.32 (q, J=7.3 Hz, 2H), 2.98-2.79 (m, 3H), 2.49 (qd, J=12.9, 5.5 Hz, 2H), 2.23 (dtd, J=13.0, 5.2, 2.7 Hz, 1H), 1.78 (s, 1H), 1.34 (t, J=7.3 Hz, 3H).

Example 34a: tert-butyl (3R,5R)-3-((2-(2,6-dioxo-1-((2-(trimethylsilyl)ethoxy)methyl)piperidin-3-yl)-1-oxoisoindolin-5-yl)oxy)-5-hydroxypiperidine-1-carboxylate (71a)

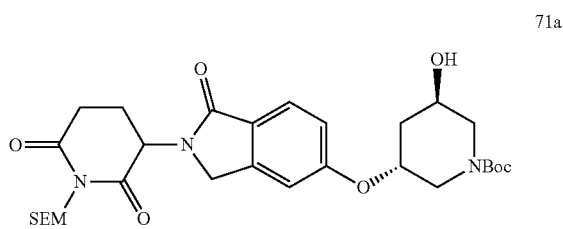 [SMILES: CC(C)(C)OC(=O)N1C[C@H](O)C[C@@H](Oc2ccc3c(c2)CN(C2CCC(=O)N(COCC[Si](C)(C)C)C2=O)C3=O)C1]

Example 34a was synthesized by analogy to the previous Example 34 starting with tert-butyl (3R,5R)-3,5-dihydroxypiperidine-1-carboxylate. LCMS [M−H]⁻: 588.3.

Example 35: rac-3-(5-(((3R,4S)-1-ethyl-4-methylpiperidin-3-yl)oxy)-1-oxoisoindolin-2-yl)piperidine-2,6-dione (I-76); (R)-3-(5-(((3R,4S)-1-ethyl-4-methylpiperidin-3-yl)oxy)-1-oxoisoindolin-2-yl)piperidine-2,6-dione, (S)-3-(5-(((3R,4S)-1-ethyl-4-methylpiperidin-3-yl)oxy)-1-oxoisoindolin-2-yl)piperidine-2,6-dione, (R)-3-(5-(((3S,4R)-1-ethyl-4-methylpiperidin-3-yl)oxy)-1-oxoisoindolin-2-yl)piperidine-2,6-dione, and (S)-3-(5-(((3S,4R)-1-ethyl-4-methylpiperidin-3-yl)oxy)-1-oxoisoindolin-2-yl)piperidine-2,6-dione

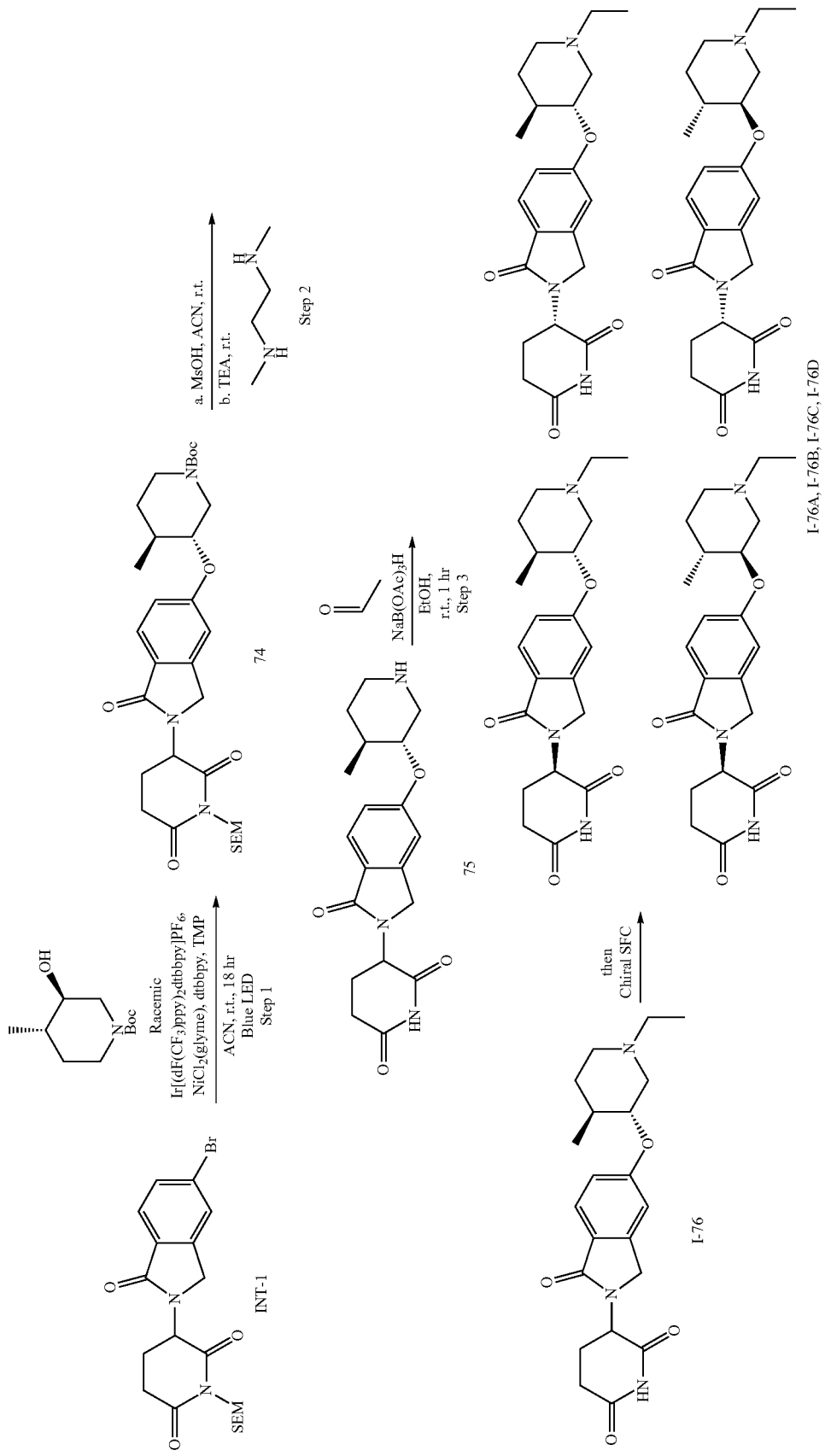

Step 1: rac-tert-butyl (3R,4S)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate (74)

74 was made according to General Method VI starting from 3-(5-bromo-1-oxoisoindolin-2-yl)-1-((2-(trimethylsilyl)ethoxy)methyl)piperidine-2,6-dione INT-1 (1.85 g, 4.08 mmol) and rac-tert-butyl (3R,4S)-3-hydroxy-4-methylpiperidine-1-carboxylate (966 mg, 4.49 mmol). The reaction mixture was filtered and concentrated to afford rac-tert-butyl (3R,4S)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate 74 as a yellow oil. Material was taken through to the next step without purification. LCMS [M−H]⁻: 586.7

Step 2: rac-3-(5-(((3R,4S)-4-methylpiperidin-3-yl)oxy)-1-oxoisoindolin-2-yl)piperidine-2,6-dione (75)

75 was made according to General Method VII starting from rac-tert-butyl (3R,4S)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate 74 (2.4 g, 4.08 mmol). The reaction was quenched with saturated aqueous NaHCO₃ and extracted with 4:1 DCM:TFE three times. The organic layers were combined, concentrated and the crude material was purified by silica gel chromatography (0 to 100% EtOAc:EtOH:Et₃N (v/v/v=75:25:1 in heptane). Fractions containing desired product were combined and concentrated to afford rac-3-(5-(((3R,4S)-4-methylpiperidin-3-yl)oxy)-1-oxoisoindolin-2-yl)piperidine-2,6-dione 75 as white solid. LCMS [M+H]⁺: 358.4.

Step 3: rac-3-(5-(((3R,4S)-1-ethyl-4-methylpiperidin-3-yl)oxy)-1-oxoisoindolin-2-yl)piperidine-2,6-dione (I-76), (R)-3-(5-(((3R,4S)-1-ethyl-4-methylpiperidin-3-yl)oxy)-1-oxoisoindolin-2-yl)piperidine-2,6-dione, (S)-3-(5-(((3R,4S)-1-ethyl-4-methylpiperidin-3-yl)oxy)-1-oxoisoindolin-2-yl)piperidine-2,6-dione, (R)-3-(5-(((3S,4R)-1-ethyl-4-methylpiperidin-3-yl)oxy)-1-oxoisoindolin-2-yl)piperidine-2,6-dione, and (S)-3-(5-(((3S,4R)-1-ethyl-4-methylpiperidin-3-yl)oxy)-1-oxoisoindolin-2-yl)piperidine-2,6-dione To a solution of rac-3-(5-(((3R,4S)-4-methylpiperidin-3-yl)oxy)-1-oxoisoindolin-2-yl)piperidine-2,6-dione 75 (350 mg, 0.979 mmol) and sodium triacetoxyborohydride (311 mg, 1.469 mmol) in EtOH (5 mL) at 0° C. was added acetaldehyde (64.7 mg, 1.469 mmol). The reaction stirred at r.t. for 2 hrs. The reaction was concentrated and purified by silica gel chromatography (0 to 100% EtOAc:EtOH:Et₃N (v/v/v=75:25:1) in Heptane). Fractions containing desired product were combined and concentrated to afford rac-3-(5-(((3R,4S)-1-ethyl-4-methylpiperidin-3-yl)oxy)-1-oxoisoindolin-2-yl)piperidine-2,6-dione I-76 as a white solid. LCMS [M+H]⁺: 386.3. ¹H NMR (400 MHz, CD₂Cl₂) δ 7.69 (d, J=8.4 Hz, 1H), 7.10 (s, 1H), 7.03 (ddd, J=8.5, 3.9, 2.2 Hz, 1H), 5.12 (ddd, J=13.4, 5.2, 3.5 Hz, 1H), 4.41-4.19 (m, 2H), 4.07 (qd, J=9.4, 4.2 Hz, 1H), 3.31-3.12 (m, 1H), 2.98-2.73 (m, 3H), 2.53-2.37 (m, 2H), 2.37-2.23 (m, 1H), 2.20-2.10 (m, 1H), 2.07-1.87 (m, 2H), 1.84-1.75 (m, 1H), 1.73-1.61 (m, 1H), 1.47-1.36 (m, 1H), 1.09-0.96 (m, 6H).

The diastereomeric mixture of isomers was separated via chiral SFC [Column 20×250 mm ChromegaChiral CC4 from ES; CO₂ Co-solvent 55% Ethanol/ACN (1:3) with 0.25% triethylamine; at 80 g/min at 100 bar, at 25° C.] to afford four stereoisomers: Peak 1 (Ex. 35A), Rt=1.74 min, as a white solid; Peak 2 (Ex. 35B), Rt=1.56 min, as a white solid. Two stereoisomers required additional separation via chiral SFC [Column 30×250 mm RegisPack from Regis Technologies; CO₂ Co-solvent 35% isopropanol with 0.25% triethylamine; at 80 g/min at 100 bar, at 25° C.] to afford two single stereoisomers: Peak 3 (Ex. 35C), Rt=2.98 mins, obtained as a white solid; Peak 4 (Ex. 35D), Rt=obtained as a white solid. The absolute stereochemistry of the four stereoisomers corresponding to the four product peaks was not determined.

Example 36: 3-(5-(((R)-1-ethylazepan-3-yl)oxy)-1-oxoisoindolin-2-yl)piperidine-2,6-dione (I-79)

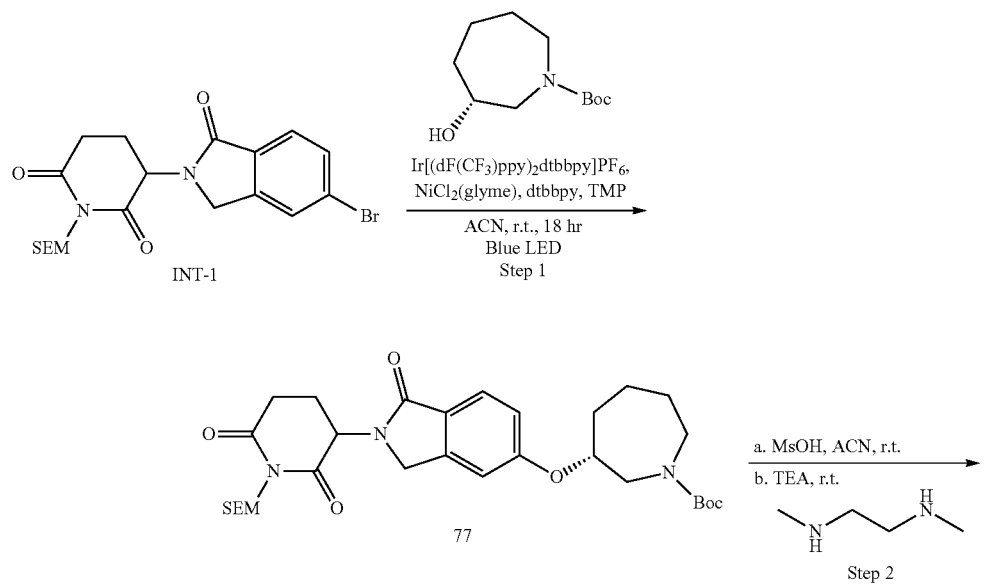

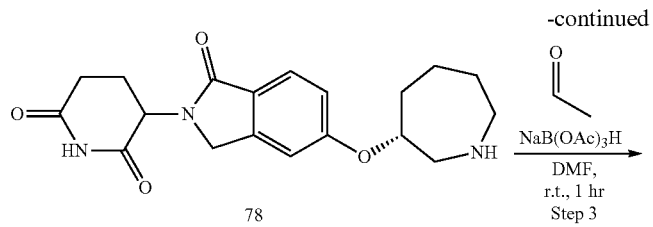

78

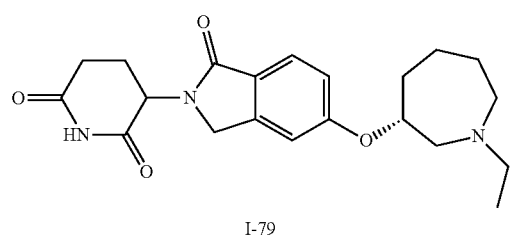

I-79

Step 1: Tert-butyl (3R)-3-((2-(2,6-dioxo-1-((2-(trimethylsilyl)ethoxy)methyl)piperidin-3-yl)-1-oxoisoindolin-5-yl)oxy)azepane-1-carboxylate (77)

Compound 77 was made according to General Method VI starting from 3-(5-bromo-1-oxoisoindolin-2-yl)-1-((2-(trimethylsilyl)ethoxy)methyl)piperidine-2,6-dione INT-1 (200 mg, 0.44 mmol) and tert-butyl (3R)-3-hydroxyazepane-1-carboxylate (104 mg, 0.49 mmol). The reaction was concentrated onto CELITE® and purified by silica gel chromatography (0-100% EtOAc in heptane) to afford tert-butyl (3R)-3-((2-(2,6-dioxo-1-((2-(trimethylsilyl)ethoxy)methyl)piperidin-3-yl)-1-oxoisoindolin-5-yl)oxy)azepane-1-carboxylate 77 as a yellow oil. LCMS [M+H-156.34]$^+$: 432.4.

Step 2: 3-(5-(((R)-azepan-3-yl)oxy)-1-oxoisoindolin-2-yl)-1-(hydroxymethyl)piperidine-2,6-dione (78)

To tert-butyl (3R)-3-((2-(2,6-dioxo-1-((2-(trimethylsilyl)ethoxy)methyl)piperidin-3-yl)-1-oxoisoindolin-5-yl)oxy)azepane-1-carboxylate 77 (44.4 mg, 0.076 mmol) dissolved in ACN (1.0 mL) was added methanesulfonic acid (0.1 mL, 1.54 mmol). The reaction stirred at r.t. for 2 hrs. The reaction was cooled to 0° C. and triethylamine (0.43 mL, 3.1 mmol) followed by N1,N2-dimethylethane-1,2-diamine (0.016 mL, 0.15 mmol) were added. The reaction stirred at r.t. for 96 hrs. The reaction was quenched with 50% saturated aqueous sodium bicarbonate and extracted with 4:1 DCM:iPrOH three times. The organic layers were combined, passed through a phase separator and concentrated to afford 3-(5-(((R)-azepan-3-yl)oxy)-1-oxoisoindolin-2-yl)piperidine-2,6-dione 78 as a yellow solid. LCMS [M+H]$^+$: 358.2.

Step 3: 3-(5-(((R)-1-ethylazepan-3-yl)oxy)-1-oxoisoindolin-2-yl)piperidine-2,6-dione (I-79)

To a solution of 3-(5-(((R)-azepan-3-yl)oxy)-1-oxoisoindolin-2-yl)-1-(hydroxymethyl)piperidine-2,6-dione 78 (28 mg, 0.078 mmol) in DMF (0.522 mL), sodium triacetoxyborohydride (50 mg, 0.24 mmol) was added followed by acetaldehyde (0.01 mL, 0.18 mmol). The reaction stirred at r.t. for 18 hrs. The reaction was quenched with 50% saturated aqueous sodium bicarbonate and extracted with 4:1 DCM: iPrOH three times. The organic layers were combined, passed through a phase separator and concentrated onto CELITE®. The crude material was purified by silica gel chromatography (0-100% EtOAc:EtOH:Et$_3$N (v/v/v=75:25:1) in heptane). Product was further purified by reverse phase HPLC (25-50% ACN in H$_2$O with 5 mM NH$_4$OH as modifier). Test tubes contained 3 drops formic acid prior to sample collection. Fractions containing pure product were combined and lyophilized to afford formate salt 3-(5-(((R)-1-ethylazepan-3-yl)oxy)-1-oxoisoindolin-2-yl)piperidine-2,6-dione I-79 as a white solid. LCMS [M+H]$^+$: 386.4. $^1$H NMR (400 MHz, DMSO-d6) δ 10.88 (s, 1H), 8.17 (s, 1H), 7.54 (d, J=8.3 Hz, 1H), 7.06 (d, J=2.2 Hz, 1H), 6.94 (dd, J=8.4, 2.2 Hz, 1H), 5.00 (dd, J=13.3, 5.1 Hz, 1H), 4.59-4.43 (m, 1H), 4.31 (dd, J=17.1, 1.9 Hz, 1H), 4.18 (d, J=17.1 Hz, 1H), 2.89-2.77 (m, 2H), 2.67-2.45 (m, 6H), 2.37-2.23 (m, 1H), 2.01-1.86 (m, 2H), 1.70-1.39 (m, 5H), 0.88 (td, J=7.0, 1.7 Hz, 3H).

Example 37: 3-(5-(((S)-1-ethylazepan-3-yl)oxy)-1-oxoisoindolin-2-yl)piperidine-2,6-dione (I-84)

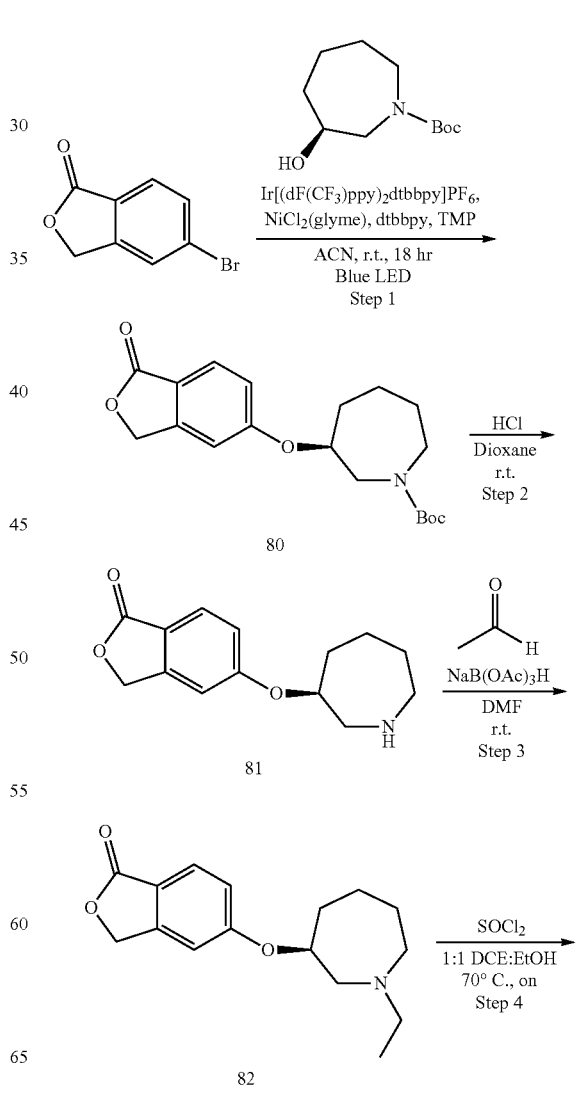

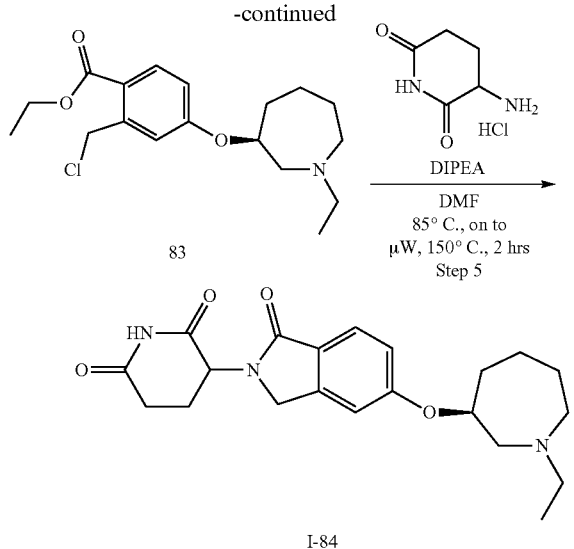

Step 1: Tert-butyl (S)-3-((1-oxo-1,3-dihydroisobenzofuran-5-yl)oxy)azepane-1-carboxylate (80)

To a 40 mL vial, 5-bromoisobenzofuranone (100 mg, 0.47 mmol), (S)-3-hydroxy-1-N-Boc-azepane (101 mg, 0.47 mmol), dtbbpy (12.6 mg, 0.047 mmol), NiCl$_2$(glyme) (10.3 mg, 0.047 mmol), and Ir[dF(CF$_3$)ppy]$_2$dtbbpy]PF$_6$ (13.1 mg, 0.012 mmol) were added. ACN (1.6 mL) was added and the reaction was purged with nitrogen for 5-10 minutes ensuring reaction turns green. Then 2,2,6,6-tetramethylpiperidine (84 µL, 0.49 mmol) was added. The reaction was placed in a PennOC m1 450 nm Photoreactor under blue LED light at r.t. for 18 hrs. The reaction was concentrated onto CELITE® and purified by silica gel chromatography (0-100% ethyl acetate in heptane) to afford tert-butyl (S)-3-((1-oxo-1,3-dihydroisobenzofuran-5-yl)oxy)azepane-1-carboxylate 80 as a yellow solid. LCMS [M+H-tert-butyl]$^+$: 292.1.

Step 2: (S)-5-(azepan-3-yloxy)isobenzofuran-1(3H)-one (81)

Tert-butyl (S)-3-((1-oxo-1,3-dihydroisobenzofuran-5-yl)oxy)azepane-1-carboxylate 80 (104 mg, 0.30 mmol) was suspended in dioxane (3.0 mL). 4 M HCl in dioxane (449 µL, 1.8 mmol) was added and the reaction stirred at r.t. for 5 hrs. The reaction was concentrated to afford (S)-5-(azepan-3-yloxy)isobenzofuran-1(3H)-one 81 as a brown semi-solid. Material was used directly in the next reaction. LCMS [M+H]$^+$: 248.2.

Step 3: (S)-5-((1-ethylazepan-3-yl)oxy)isobenzofuran-1(3H)-one (82)

Compound 82 was made according to General Method X starting from (S)-5-(azepan-3-yloxy)isobenzofuran-1(3H)-one 81 (74 mg, 0.30 mmol) and acetaldehyde (25 µL, 0.45 mmol). The crude material was purified by silica gel chromatography (0-100% EtOAc:EtOH:Et$_3$N (v/v/v=75:25:1) in heptane) to afford (S)-5-((1-ethylazepan-3-yl)oxy)isobenzofuran-1(3H)-one 82 as a brown oil. LCMS [M+H]$^+$: 276.2

Step 4: Ethyl (S)-2-(chloromethyl)-4-((1-ethylazepan-3-yl)oxy)benzoate (83)

Compound 83 was made according to General Method IV starting from (S)-5-((1-ethylazepan-3-yl)oxy)isobenzofuran-1(3H)-one 82 (7 mg, 0.025 mmol) to afford ethyl (S)-2-(chloromethyl)-4-((1-ethylazepan-3-yl)oxy)benzoate 83 as an brown oil. Material was taken through to the next step without purification. LCMS [M+H]$^+$: 340.4.

Step 5: 3-(5-(((S)-1-ethylazepan-3-yl)oxy)-1-oxoisoindolin-2-yl)piperidine-2,6-dione (I-84)

Compound I-84 was made according to General Method V starting from ethyl (S)-2-(chloromethyl)-4-((1-ethylazepan-3-yl)oxy)benzoate 83 (20 mg, 0.059 mmol). The reaction was concentrated and purified by basic reverse phase HPLC (15-40% ACN in water with 5 mM NH$_4$OH as modifier). Test tubes contained 3 drops of formic acid prior to sample collection. Fractions containing desired product were combined and concentrated to afford product as an indigo-coloured solid. The material was further purified by basic reverse phase HPLC (15-40% ACN in water with 5 mM NH$_4$OH as modifier). Test tubes contained 3 drops of formic acid prior to sample collection. Fractions containing desired product were combined and concentrated to afford 3-(5-(((S)-1-ethylazepan-3-yl)oxy)-1-oxoisoindolin-2-yl)piperidine-2,6-dione I-84 as a clear oil. LCMS [M+H]$^+$: 386.4. $^1$H NMR (400 MHz, Acetonitrile-d3) δ 8.84 (s, 1H), 7.69 (d, J=8.3 Hz, 1H), 7.20 (d, J=6.6 Hz, 1H), 7.11 (dt, J=8.4, 2.3 Hz, 1H), 5.07 (dd, J=13.4, 5.1 Hz, 1H), 4.92 (dd, J=7.0, 3.6 Hz, 1H), 4.44-4.27 (m, 2H), 3.89 (p, J=6.1 Hz, 3H), 3.32 (dd, J=13.8, 3.0 Hz, 2H), 3.26-3.19 (m, 2H), 3.11 (t, J=6.0 Hz, 2H), 2.99 (q, J=7.2 Hz, 2H), 2.86-2.79 (m, 1H), 2.74 (ddd, J=17.6, 4.8, 2.6 Hz, 1H), 2.43 (qd, J=13.2, 4.9 Hz, 1H), 2.18-2.06 (m, 2H), 1.21 (td, J=7.2, 1.2 Hz, 3H).

Example 38: 3-(5-(((R)-1-isobutylazepan-3-yl)oxy)-1-oxoisoindolin-2-yl)piperidine-2,6-dione (I-89)

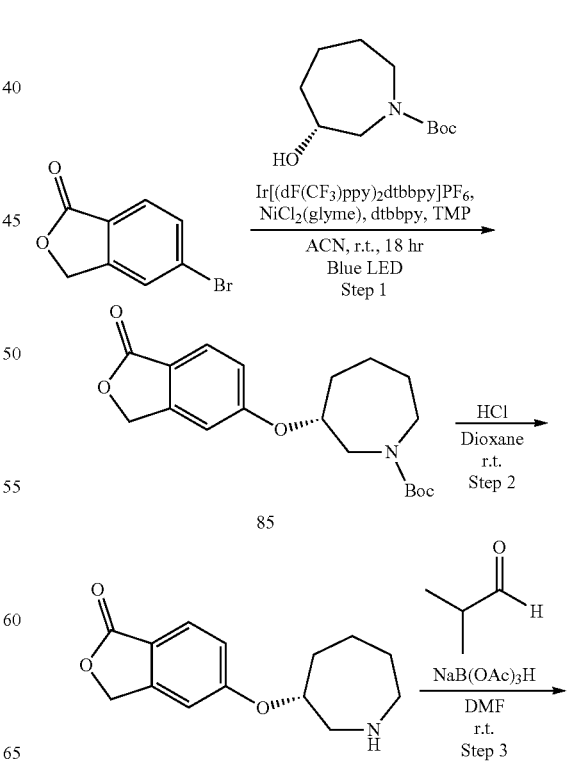

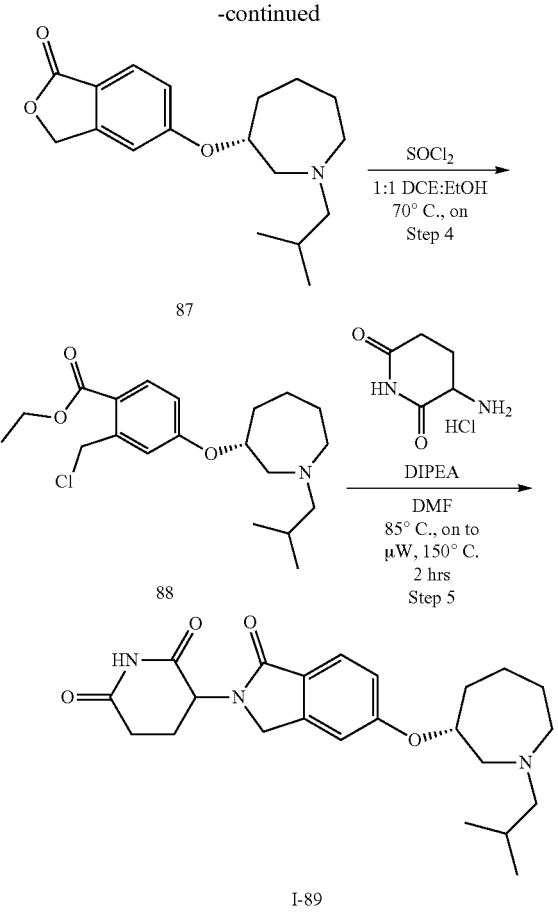

Step 1: Tert-butyl (R)-3-((1-oxo-1,3-dihydroisobenzofuran-5-yl)oxy)azepane-1-carboxylate (85)

Compound 85 was made according to General Method I starting from 5-bromoisobenzofuran-1(3H)-one (250 mg, 1.17 mmol) and tert-butyl (3R)-3-hydroxyazepane-1-carboxylate (278 mg, 1.29 mmol). The reaction was concentrated onto CELITE® and purified by silica gel chromatography (0-100% EtOAc in heptane) to afford tert-butyl (R)-3-((1-oxo-1,3-dihydroisobenzofuran-5-yl)oxy)azepane-1-carboxylate 85 as a clear oil. LCMS [M+H-tert-butyl]$^+$: 292.3.

Step 2: (R)-5-(azepan-3-yloxy)isobenzofuran-1(3H)-one (86)

Tert-butyl (R)-3-((1-oxo-1,3-dihydroisobenzofuran-5-yl)oxy)azepane-1-carboxylate 85 (305 mg, 0.88 mmol) was suspended in dioxane (4.4 mL). 4M HCl in dioxane (1.3 mL, 5.3 mmol) was added and the reaction stirred at r.t. for 72 hrs. The reaction was concentrated to afford (R)-5-(azepan-3-yloxy)isobenzofuran-1(3H)-one 86 as a clear oil. Material was used directly in the next reaction. LCMS [M+H]$^+$: 248.3.

Step 3: (R)-5-((1-isobutylazepan-3-yl)oxy)isobenzofuran-1(3H)-one (87)

Compound 87 was made according to General Method III starting from (R)-5-(azepan-3-yloxy)isobenzofuran-1(3H)-one 86 (64 mg, 0.26 mmol) and isobutanal (0.04 mL, 0.44 mmol). The crude material was purified by silica gel chromatography (0-100% EtOAc:EtOH:Et$_3$N (v/v/v=75:25:1) in heptane) to afford (R)-5-((1-isobutylazepan-3-yl)oxy) isobenzofuran-1(3H)-one 87 as a clear oil. LCMS [M+H]$^+$: 304.2.

Step 4: Ethyl (R)-2-(chloromethyl)-4-((1-isobutylazepan-3-yl)oxy)benzoate (88)

Compound 88 was made according to General Method IV starting from (R)-5-((1-isobutylazepan-3-yl)oxy)isobenzofuran-1(3H)-one 87 (30.3 mg, 0.10 mmol) to afford ethyl (R)-2-(chloromethyl)-4-((1-isobutylazepan-3-yl)oxy)benzoate 88 as a brown oil. Material was taken through to the next step without purification. LCMS [M+H]$^+$: 368.5.

Step 5: 3-(5-(((R)-1-isobutylazepan-3-yl)oxy)-1-oxoisoindolin-2-yl)piperidine-2,6-dione (I-89)

Compound I-89 was made according to General Method V starting from ethyl (R)-2-(chloromethyl)-4-((1-isobutylazepan-3-yl)oxy)benzoate 88 (36.8 mg, 0.10 mmol). The reaction was concentrated onto CELITE®. The dry loading tube was first filled with ½ inch of activated charcoal, then a filter pad, the CELITE® residue, and a second filter pad. The crude material was purified by silica gel chromatography (0-100% EtOAc:EtOH:Et$_3$N (v/v/v=75:25:1) in heptane) to afford 3-(5-(((R)-1-isobutylazepan-3-yl)oxy)-1-oxoisoindolin-2-yl)piperidine-2,6-dione I-89 as a white solid. LCMS [M+H]$^+$: 414.4. $^1$H NMR (400 MHz, DMSO-d6) δ 10.97 (s, 1H), 7.61 (d, J=8.4 Hz, 1H), 7.12 (d, J=2.3 Hz, 1H), 7.00 (dd, J=8.4, 2.2 Hz, 1H), 5.07 (dd, J=13.2, 5.0 Hz, 1H), 4.68-4.51 (m, 1H), 4.38 (dd, J=17.2, 3.3 Hz, 1H), 4.26 (dd, J=17.1, 2.0 Hz, 1H), 2.96-2.85 (m, 2H), 2.75 (dd, J=13.9, 6.6 Hz, 1H), 2.66-2.56 (m, 3H), 2.45-2.36 (m, 1H), 2.24 (d, J=7.2 Hz, 2H), 2.12-1.94 (m, 2H), 1.81-1.48 (m, 6H), 0.86 (dd, J=6.4, 2.8 Hz, 6H).

Example 39: 3-(5-(((R)-1-ethylpyrrolidin-3-yl)oxy)-1-oxoisoindolin-2-yl)piperidine-2,6-dione (I-94)

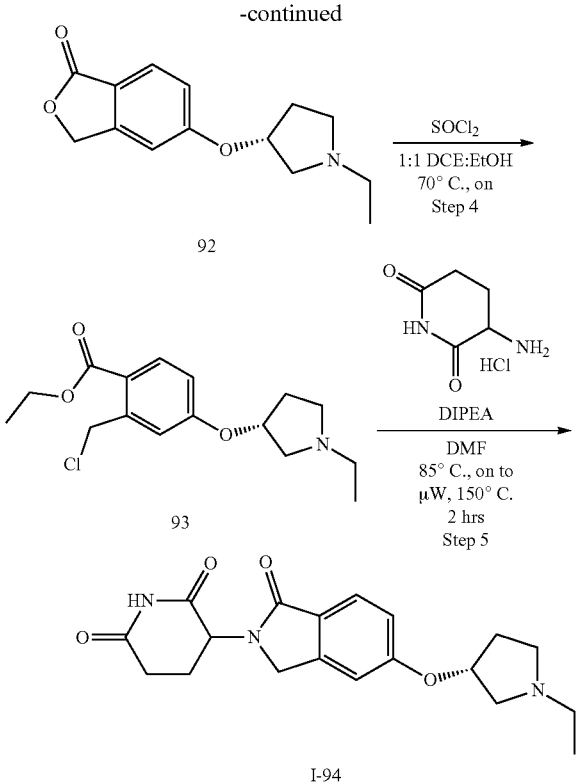

Step 1: Tert-butyl (R)-3-((1-oxo-1,3-dihydroisobenzofuran-5-yl)oxy)pyrrolidine-1-carboxylate (90)

Compound 90 was made according to General Method I starting from 5-bromoisobenzofuran-1(3H)-one (100 mg, 0.47 mmol) and (R)-1-N-Boc-3-hydroxy-pyrrolidine (97 mg, 0.52 mmol). The reaction was concentrated onto CELITE® and purified by silica gel chromatography (0-100% EtOAc in heptane) to afford tert-butyl (R)-3-((1-oxo-1,3-dihydroisobenzofuran-5-yl)oxy)pyrrolidine-1-carboxylate 90 as a yellow oil. LCMS [M+H-tert-butyl]$^+$: 264.1.

Step 2: (R)-5-(pyrrolidin-3-yloxy)isobenzofuran-1(3H)-one (91)

Tert-butyl (R)-3-((1-oxo-1,3-dihydroisobenzofuran-5-yl)oxy)pyrrolidine-1-carboxylate 90 (98 mg, 0.31 mmol) was suspended in dioxane (3.1 mL). 4M HCl in dioxane (0.46 mL, 1.84 mmol) was added and the reaction stirred at r.t. for 2 hrs. Trifluoroethanol (1 mL) was added followed by additional 4M HCl in dioxane (0.46 mL, 1.84 mmol). The reaction stirred at r.t. for 72 hrs. The reaction was concentrated to afford (R)-5-(pyrrolidin-3-yloxy)isobenzofuran-1(3H)-one 91 as a white solid. Material was used directly in the next reaction. LCMS [M+H]$^+$: 220.1.

Step 3: (R)-5-((1-ethylpyrrolidin-3-yl)oxy)isobenzofuran-1(3H)-one (92)

Compound 92 was made according to General Method X starting from (R)-5-(pyrrolidin-3-yloxy)isobenzofuran-1(3H)-one 91 (67.3 mg, 0.31 mmol) and acetaldehyde (26 µL, 0.46 mmol). The crude material was purified by silica gel chromatography (0-100% EtOAc:EtOH:Et$_3$N (v/v/v=75:25:1) in heptane) to afford (R)-5-((1-ethylpyrrolidin-3-yl)oxy)isobenzofuran-1(3H)-one 92 as a brown oil. LCMS [M+H]$^+$: 248.2. $^1$H NMR (400 MHz, CDCl$_3$) δ 7.74 (d, J=8.5 Hz, 1H), 6.92 (dd, J=8.5, 2.1 Hz, 1H), 6.78 (d, J=2.1 Hz, 1H), 5.17 (s, 2H), 4.87-4.78 (m, 1H), 2.84-2.76 (m, 3H), 2.53-2.43 (m, 2H), 2.35-2.26 (m, 1H), 2.00-1.90 (m, 1H), 1.74-1.65 (m, 1H), 1.08 (t, J=7.2 Hz, 3H).

Step 4: Ethyl (R)-2-(chloromethyl)-4-((1-ethylpyrrolidin-3-yl)oxy)benzoate (93)

Compound 93 was made according to General Method IV starting from (R)-5-((1 ethylpyrrolidin-3-yl)oxy)isobenzofuran-1(3H)-one 92 (17.5 mg, 0.071 mmol) to afford ethyl (R)-2-(chloromethyl)-4-((1-ethylpyrrolidin-3-yl)oxy)benzoate 93 as a brown oil. Material was taken through to the next step without purification. LCMS [M+H]$^+$: 312.3.

Step 5: 3-(5-(((R)-1-ethylpyrrolidin-3-yl)oxy)-1-oxoisoindolin-2-yl)piperidine-2,6-dione (I-94)

Compound I-94 was made according to General Method V starting from ethyl (R)-2 (chloromethyl)-4-((1-ethylpyrrolidin-3-yl)oxy)benzoate 93 (22 mg, 0.071 mmol). The reaction was concentrated and purified by reverse phase HPLC (10-30% ACN in water with 5 mM NH$_4$OH as modifier). Test tubes contained 3 drops of formic acid prior to sample collections. Fractions containing desired product were combined and lyophilized to afford formate salt of 3-(5-(((R)-1-ethylpyrrolidin-3-yl)oxy)-1-oxoisoindolin-2-yl)piperidine-2,6-dione I-94 as a white solid. LCMS [M+H]$^+$: 358.2. $^1$H NMR (400 MHz, DMSO-d6) δ 10.89 (s, 1H), 8.17 (s, 1H), 7.54 (d, J=8.4 Hz, 1H), 7.04 (d, J=2.2 Hz, 1H), 6.93 (dd, J=8.3, 2.4 Hz, 1H), 5.00 (dd, J=13.4, 5.1 Hz, 1H), 4.93-4.85 (m, 1H), 4.32 (d, J=17.1 Hz, 1H), 4.19 (d, J=17.2 Hz, 1H), 2.89-2.72 (m, 2H), 2.68-2.58 (m, 1H), 2.56-2.49 (m, 1H), 2.39-2.20 (m, 6H), 1.95-1.86 (m, 1H), 1.75-1.62 (m, 1H), 0.96 (t, J=7.2 Hz, 3H).

Example 40: 3-(5-(((S)-1-ethylpyrrolidin-3-yl)oxy)-1-oxoisoindolin-2-yl)piperidine-2,6-dione (I-99)

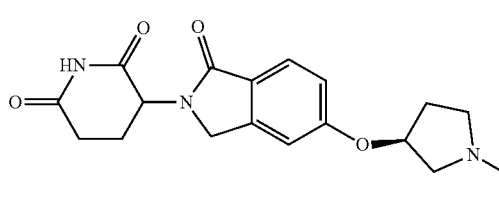

Compound I-99 was made according to the previous Example 39, except that step 1 employed (S)-1-N-boc-3-hydroxy-pyrrolidine. In the final step 5, the reaction was concentrated and purified by silica gel chromatography (0-100% EtOAc:EtOH:Et$_3$N (v/v/v=75:25:1) in heptane) to afford 3-(5-(((S)-1-ethylpyrrolidin-3-yl)oxy)-1-oxoisoindolin-2-yl)piperidine-2,6-dione I-99 as a black solid. LCMS [M+H]$^+$: 358.1. $^1$H NMR (400 MHz, CDCl$_3$) δ 7.71 (d, J=8.5 Hz, 1H), 6.89 (dd, J=8.4, 2.2 Hz, 1H), 6.82 (d, J=2.2 Hz, 1H), 5.13 (dd, J=13.2, 5.2 Hz, 1H), 4.86 (q, J=4.8, 3.0 Hz, 1H), 4.36 (dd, J=15.9, 4.7 Hz, 1H), 4.21 (d, J=15.9 Hz, 1H), 3.38 (q, J=7.3 Hz, 1H), 3.04 (dt, J=14.1, 7.1 Hz, 1H), 2.84-2.74 (m, 5H), 2.58 (ddt, J=11.4, 8.1, 3.5 Hz, 3H), 2.34-2.24 (m, 2H), 1.11 (t, J=7.2 Hz, 3H).

Example 41: 3-(5-(((3R,6S)-1-ethyl-6-methylpiperidin-3-yl)oxy)-1-oxoisoindolin-2-yl)piperidine-2,6-dione (I-102)

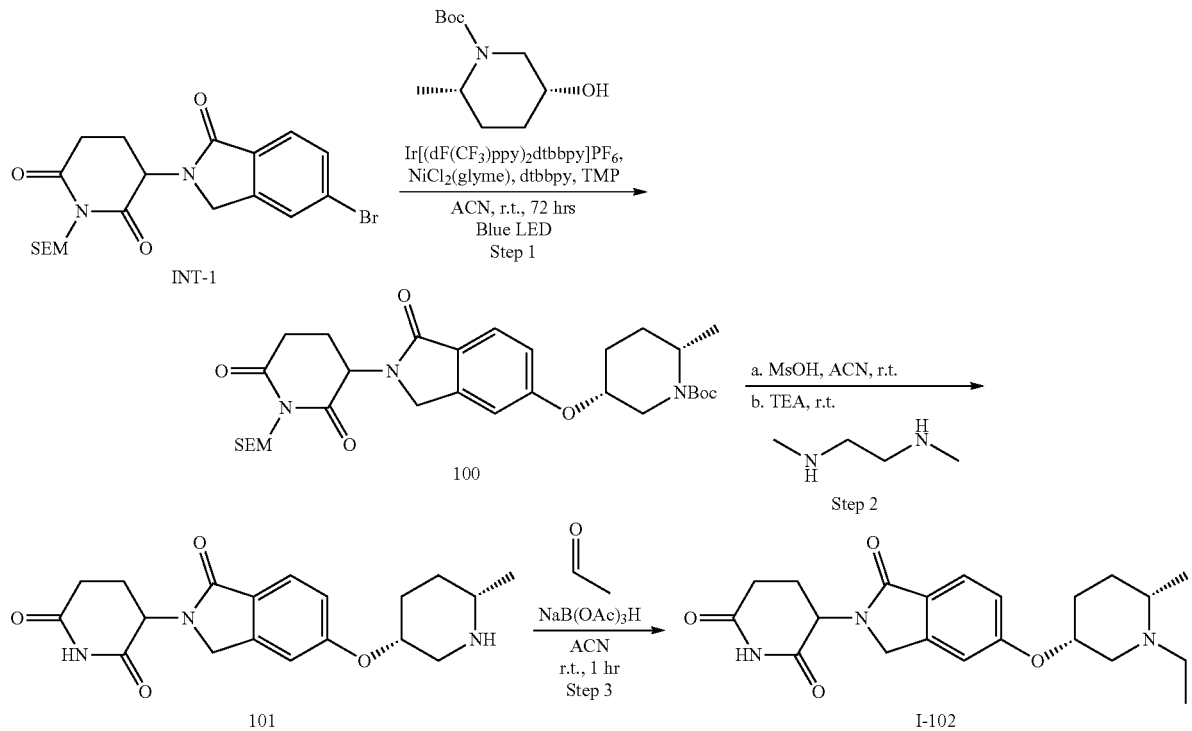

Step 1: Tert-butyl (2S,5R)-5-((2-(2,6-dioxo-1-((2-(trimethylsilyl)ethoxy)methyl)piperidin-3-yl)-1-oxoisoindolin-5-yl)oxy)-2-methylpiperidine-1-carboxylate (100)

To a 40 mL vial, 3-(5-bromo-1-oxoisoindolin-2-yl)-1-((2-(trimethylsilyl)ethoxy)methyl)piperidine-2,6-dione INT-1 (527 mg, 1.16 mmol), dtbbpy (16 mg, 0.058 mmol), NiCl₂ (glyme) (13 mg, 0.058 mmol), and Ir[(dF(CF₃)ppy)₂dtbbpy]PF₆ (13 mg, 0.012 mmol) were added. Tert-butyl (2S,5R)-5-hydroxy-2-methylpiperidine-1-carboxylate (250 mg, 1.16 mmol) in ACN (6.0 mL) was added and the reaction was purged with nitrogen for 5-10 minutes ensuring reaction turns green. Then 2,2,6,6-tetramethylpiperidine (0.206 mL, 1.2 mmol) was added. The reaction was placed in a PennOC m1 450 nm Photoreactor under blue LED light at r.t. for 72 hrs. The reaction was concentrated onto CELITE® and purified by silica gel chromatography (0-100% EtOAc in heptanes) to afford tert-butyl (2S,5R)-5-((2-(2,6-dioxo-1-((2-(trimethylsilyl)ethoxy)methyl)piperidin-3-yl)-1-oxoisoindolin-5-yl)oxy)-2-methylpiperidine-1-carboxylate 100 as a yellow foam. LCMS [M−H]⁻: 586.1.

Step 2: 3-(5-(((3R,6S)-6-methylpiperidin-3-yl)oxy)-1-oxoisoindolin-2-yl)piperidine-2,6-dione (101)

Compound 101 was made according to General Method VII starting from tert-butyl (2S,5R)-5-((2-(2,6-dioxo-1-((2-(trimethylsilyl)ethoxy)methyl)piperidin-3-yl)-1-oxoisoindolin-5-yl)oxy)-2-methylpiperidine-1-carboxylate 100 (525 mg, 0.89 mmol). The reaction was quenched with a 50% saturated aqueous sodium bicarbonate and extracted with 4:1 DCM:iPrOH three times. The organic layers were combined, passed through a phase separator and concentrated to remove DCM. A white solid crashed out of solution with remaining iPrOH. The solid was filtered to afford 3-(5-(((3R,6S)-6-methylpiperidin-3-yl)oxy)-1-oxoisoindolin-2-yl)piperidine-2,6-dione 101 as a white powder. LCMS [M+H]⁺: 358.1. ¹H NMR (400 MHz, DMSO-d6) δ 10.96 (s, 1H), 7.61 (d, J=8.4 Hz, 1H), 7.17 (d, J=2.2 Hz, 1H), 7.07 (dd, J=8.4, 2.2 Hz, 1H), 5.07 (dd, J=13.3, 5.1 Hz, 1H), 4.59-4.17 (m, 4H), 3.32 (s, 3H), 3.09 (d, J=13.7 Hz, 1H), 2.95-2.72 (m, 2H), 2.65-2.54 (m, 2H), 2.43-2.26 (m, 1H), 2.01-1.89 (m, 2H), 1.70 (t, J=13.9 Hz, 1H), 1.46-1.22 (m, 2H).

Step 3: 3-(5-(((3R,6S)-1-ethyl-6-methylpiperidin-3-yl)oxy)-1-oxoisoindolin-2-yl)piperidine-2,6-dione (I-102)

To a vial containing 3-(5-(((3R,6S)-6-methylpiperidin-3-yl)oxy)-1-oxoisoindolin-2-yl)piperidine-2,6-dione 101 (200 mg, 0.56 mmol) and ACN (4.0 mL) was added sodium triacetoxyborohydride (356 mg, 1.68 mmol) followed by acetaldehyde (63 uL, 1.12 mmol). The reaction was stirred at r.t. overnight. The reaction was quenched with saturated aqueous sodium bicarbonate and extracted with 4:1 DCM/iPrOH three times. The organics layers were combined, passed through a phase separator, and concentrated. The crude material was purified by basic reverse phase HPLC (15-40% ACN in water with 5 mM NH₄OH as modifier). Test tubes contained 3 drops formic acid prior to sample collection. Fractions containing desired product were combined and lyophilized to afford 3-(5-(((3R,6S)-1-ethyl-6-methylpiperidin-3-yl)oxy)-1-oxoisoindolin-2-yl)piperidine-2,6-dione I-102 as a white solid. LCMS [M+H]⁺: 386.3. ¹H NMR (400 MHz, DMSO-d6) δ 10.95 (s, 1H), 8.21 (s, 1H), 7.60 (d, J=8.4 Hz, 1H), 7.18 (d, J=2.2 Hz, 1H), 7.05 (dd, J=8.5, 2.2 Hz, 1H), 5.07 (dd, J=13.3, 5.1 Hz, 1H), 4.61-4.48 (m, 1H), 4.45-4.15 (m, 2H), 2.90 (ddd, J=17.3, 13.6, 5.4 Hz, 1H), 2.77-2.58 (m, 4H), 2.58-2.51 (m, 2H), 2.37 (qd, J=13.2, 4.4 Hz, 1H), 2.02-1.91 (m, 1H), 1.82-1.67 (m, 2H), 1.67-1.47 (m, 2H), 0.99 (d, J=6.4 Hz, 3H), 0.95 (s, 3H).

Example 42: 3-(5-(((R)-1-cyclopentylpiperidin-3-yl)oxy)-1-oxoisoindolin-2-yl)piperidine-2,6-dione (I-103)

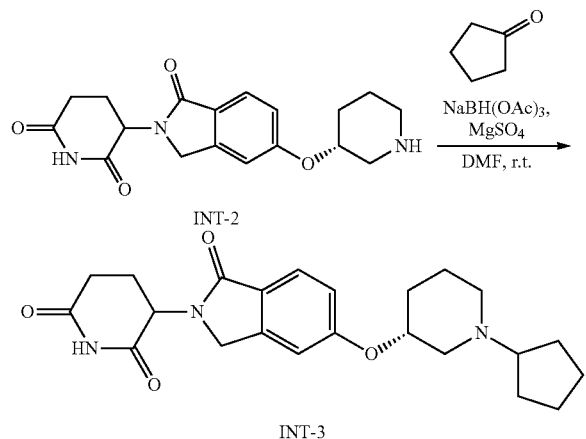

To a suspension of 3-(1-oxo-5-(((R)-piperidin-3-yl)oxy)isoindolin-2-yl)piperidine-2,6-dione INT-2 (109 mg, 0.32 mmol), MgSO₄ (76 mg, 0.64 mmol), sodium triacetoxyborohydride (101 mg, 0.48 mmol) in DMF (1.5 mL) was added cyclopentanone (0.28 mL, 3.2 mmol). The reaction was stirred at r.t. for 1 hr. The reaction was diluted with 4:1 DCM:iPrOH and washed with saturated aqueous sodium bicarbonate. The organic layer was passed through a phase separator and concentrated onto CELITE®. The crude material was purified by silica gel chromatography (0 to 100% EtOAc:EtOH:Et₃N (v/v/v=75:25:1) in DCM). Material was diluted with 1:3 ACN:water and lyophilized to afford 3-(5-(((R)-1-cyclopentylpiperidin-3-yl)oxy)-1-oxoisoindolin-2-yl)piperidine-2,6-dione I-103 as a white solid. LCMS [M+H]⁺: 412.9. ¹H NMR (400 MHz, DMSO-d6) δ 10.96 (s, 1H), 7.60 (d, J=8.4 Hz, 1H), 7.18 (s, 1H), 7.04 (d, J=8.4 Hz, 1H), 5.06 (dd, J=13.3, 5.1 Hz, 1H), 4.47 (s, 1H), 4.43-4.16 (m, 2H), 3.03 (d, J=10.7 Hz, 1H), 2.96-2.81 (m, 1H), 2.71 (m, 1H), 2.53 (m, 3H), 2.35 (dd, J=16.2, 11.7 Hz, 1H), 2.15-1.91 (m, 3H), 1.73 (m, 3H), 1.62-1.23 (m, 8H).

Example 43: 3-(5-(((R)-1-cyclohexylpiperidin-3-yl)oxy)-1-oxoisoindolin-2-yl)piperidine-2,6-dione (I-104)

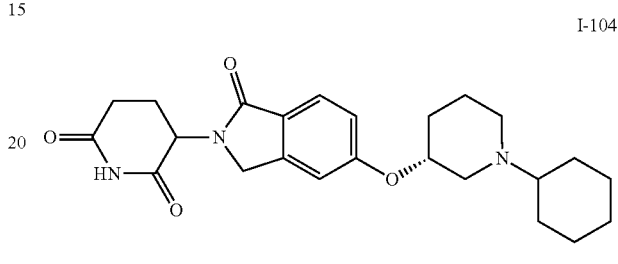

Compound I-104 was prepared in an analogous manner to previous Example 42 (I-103). The crude material was purified by silica gel chromatography (0 to 100% EtOAc:EtOH:Et₃N (v/v/v=75:25:1) in DCM) to afford product. Material was diluted with 1:3 ACN:water and lyophilized to afford 3-(5-(((R)-1-cyclohexylpiperidin-3-yl)oxy)-1-oxoisoindolin-2-yl)piperidine-2,6-dione I-104 as a white solid. LCMS [M+H]⁺: 426.5. ¹H NMR (400 MHz, DMSO-d6) δ 10.97 (s, 1H), 7.61 (d, J=8.4 Hz, 1H), 7.18 (s, 1H), 7.04 (d, J=8.5 Hz, 1H), 5.08 (dd, J=13.3, 5.1 Hz, 1H), 4.55-4.13 (m, 3H), 3.02 (s, 1H), 2.91 (ddd, J=18.0, 13.5, 5.4 Hz, 1H), 2.55 (s, 2H), 2.32 (dp, J=34.3, 12.5, 12.0 Hz, 5H), 2.12-1.91 (m, 2H), 1.72 (d, J=8.7 Hz, 4H), 1.54 (t, J=14.9 Hz, 2H), 1.34 (d, J=11.5 Hz, 1H), 1.19 (s, 4H), 1.06 (s, 1H).

Example 44: rac-3-(5-(((2R,3R)-1-ethyl-2-methylpiperidin-3-yl)oxy)-1-oxoisoindolin-2-yl)piperidine-2,6-dione (I-107)

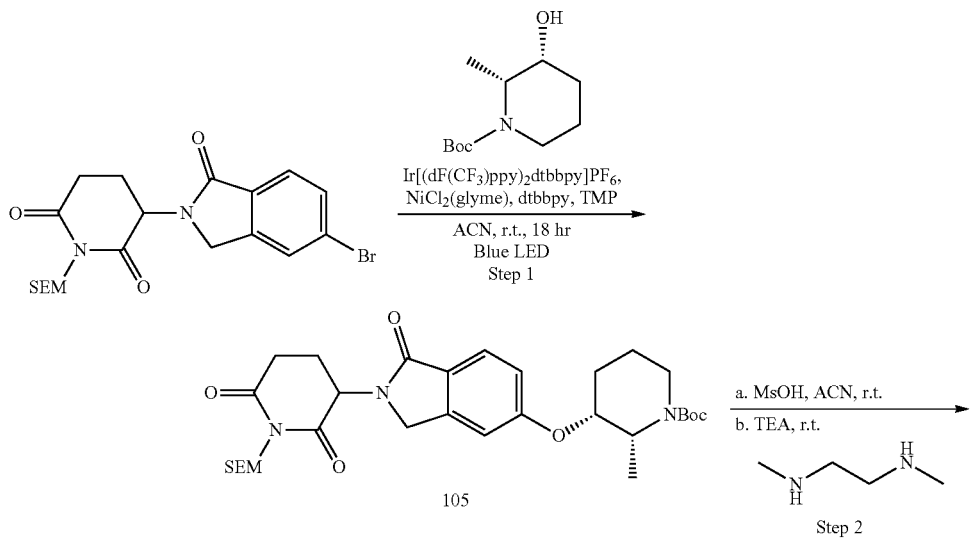

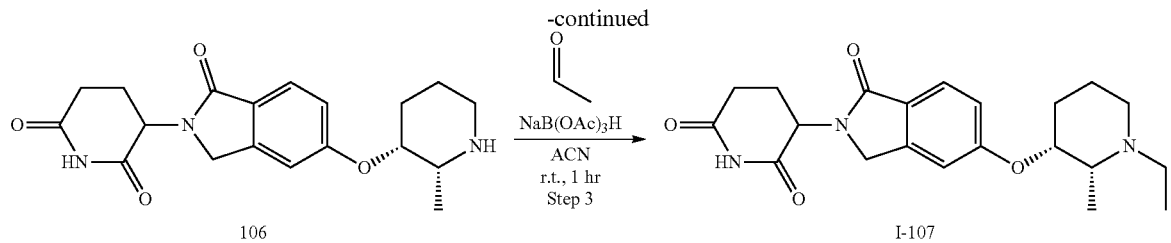

Step 1: rac-Tert-butyl (2R,3R)-3-((2-(2,6-dioxo-1-((2-(trimethylsilyl)ethoxy)methyl)piperidin-3-yl)-1-oxoisoindolin-5-yl)oxy)-2-methylpiperidine-1-carboxylate (105)

To a 40 mL vial, 3-(5-bromo-1-oxoisoindolin-2-yl)-1-((2-(trimethylsilyl)ethoxy)methyl)piperidine-2,6-dione INT-1 (500 mg, 1.1 mmol), dtbbpy (15 mg, 0.055 mmol), NiCl$_2$ (glyme) (12 mg, 0.055 mmol), and Ir[(dF(CF$_3$)ppy)$_2$dtbbpy]PF$_6$ (12 mg, 0.011 mmol) were added. rac-Tert-butyl (2R,3R)-3-hydroxy-2-methylpiperidine-1-carboxylate (237 mg, 1.1 mmol) in ACN (5.0 mL) was added and the reaction was purged with nitrogen for 5-10 minutes ensuring reaction turns green. Then 2,2,6,6-tetramethylpiperidine (0.20 mL, 1.2 mmol) was added. The reaction was placed in a PennOC m1 450 nm Photoreactor under blue LED light at r.t. for 24 hrs. The reaction was concentrated onto CELITE® and purified by silica gel chromatography (0-100% EtOAc in heptane) to afford rac-tert-butyl (2R,3R)-3-((2-(2,6-dioxo-1-((2-(trimethylsilyl)ethoxy)methyl)piperidin-3-yl)-1-oxoisoindolin-5-yl)oxy)-2-methylpiperidine-1-carboxylate 105 as a yellow foam. LCMS [M−H]$^-$: 586.5.

Step 2: rac-3-(5-(((2R,3R)-2-Methylpiperidin-3-yl)oxy)-1-oxoisoindolin-2-yl)piperidine-2,6-dione (106)

Compound 106 was made according to General Method VII starting from rac-tert-butyl (2R,3R)-3-((2-(2,6-dioxo-1-((2-(trimethylsilyl)ethoxy)methyl)piperidin-3-yl)-1-oxoisoindolin-5-yl)oxy)-2-methylpiperidine-1-carboxylate 105 (588 mg, 1.0 mmol). The reaction was quenched with a 50% saturated aqueous sodium bicarbonate and extracted with 4:1 DCM:iPrOH three times. The organic layers were combined, passed through a phase separator and concentrated onto CELITE®. The crude material was purified by silica gel chromatography (0-100% EtOH:Et$_3$N (v/v=100:1) in dichloromethane) to afford rac-3-(5-(((2R,3R)-2-methylpiperidin-3-yl)oxy)-1-oxoisoindolin-2-yl)piperidine-2,6-dione 106 as a white cream solid. LCMS [M+H]$^+$: 358.2.

Step 3: rac-3-(5-(((2R,3R)-1-Ethyl-2-methylpiperidin-3-yl)oxy)-1-oxoisoindolin-2-yl)piperidine-2,6-dione (I-107)

To a vial containing rac-3-(5-(((2R,3R)-2-methylpiperidin-3-yl)oxy)-1-oxoisoindolin-2-yl)piperidine-2,6-dione 106 (177 mg, 0.50 mmol) and ACN (4.0 mL) was added sodium triacetoxyborohydride (315 mg, 1.5 mmol) followed by acetaldehyde (60 uL, 0.99 mmol). The reaction stirred at r.t. for 1 hr. The reaction was concentrated onto CELITE® and purified by silica gel chromatography (0 to 100% EtOAc:EtOH:Et$_3$N (v/v/v=75:25:1) in DCM) to afford product. Material was diluted with 1:3 ACN:water, lyophilized and further purified by basic reverse phase HPLC (15-40% ACN in water with 5 mM NH$_4$OH as modifier). Test tubes contained 3 drops formic acid prior to sample collection. Fractions containing desired product were combined and lyophilized to afford the formate salt of rac-3-(5-(((2R,3R)-1-ethyl-2-methylpiperidin-3-yl)oxy)-1-oxoisoindolin-2-yl)piperidine-2,6-dione I-107 as a white solid. LCMS [M+H]$^+$: 386.4. $^1$H NMR (400 MHz, DMSO-d6) δ 10.97 (s, 1H), 8.26 (s, 1H), 7.61 (d, J=8.4 Hz, 1H), 7.20 (d, J=2.1 Hz, 1H), 7.06 (dd, J=8.4, 2.2 Hz, 1H), 5.07 (dd, J=13.3, 5.1 Hz, 1H), 4.53 (dt, J=8.5, 4.1 Hz, 1H), 4.46-4.19 (m, 2H), 3.14 (dd, J=6.8, 4.4 Hz, 1H), 2.91 (ddd, J=17.9, 13.5, 5.4 Hz, 1H), 2.65-2.52 (m, 2H), 2.45-2.29 (m, 4H), 2.06-1.91 (m, 1H), 1.70 (dd, J=22.3, 8.7 Hz, 3H), 1.54 (s, 1H), 1.04-0.87 (m, 6H).

Example 45: rac-3-(5-(((3R,5S)-1-ethyl-5-methylpiperidin-3-yl)oxy)-1-oxoisoindolin-2-yl)piperidine-2,6-dione (I-111); (R)-3-(5-(((3R,5S)-1-ethyl-5-methylpiperidin-3-yl)oxy)-1-oxoisoindolin-2-yl)piperidine-2,6-dione, (S)-3-(5-(((3R,5S)-1-ethyl-5-methylpiperidin-3-yl)oxy)-1-oxoisoindolin-2-yl)piperidine-2,6-dione, (R)-3-(5-(((3S,5R)-1-ethyl-5-methylpiperidin-3-yl)oxy)-1-oxoisoindolin-2-yl)piperidine-2,6-dione, and (S)-3-(5-(((3S,5R)-1-ethyl-5-methylpiperidin-3-yl)oxy)-1-oxoisoindolin-2-yl)piperidine-2,6-dione

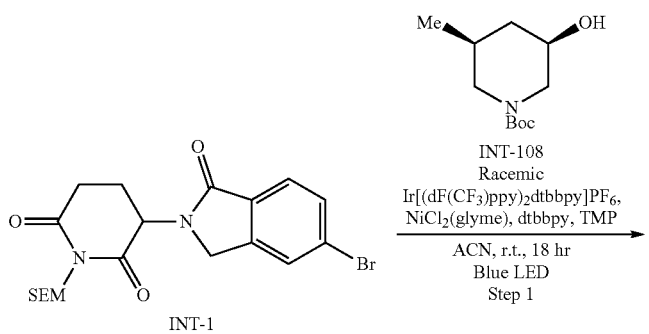

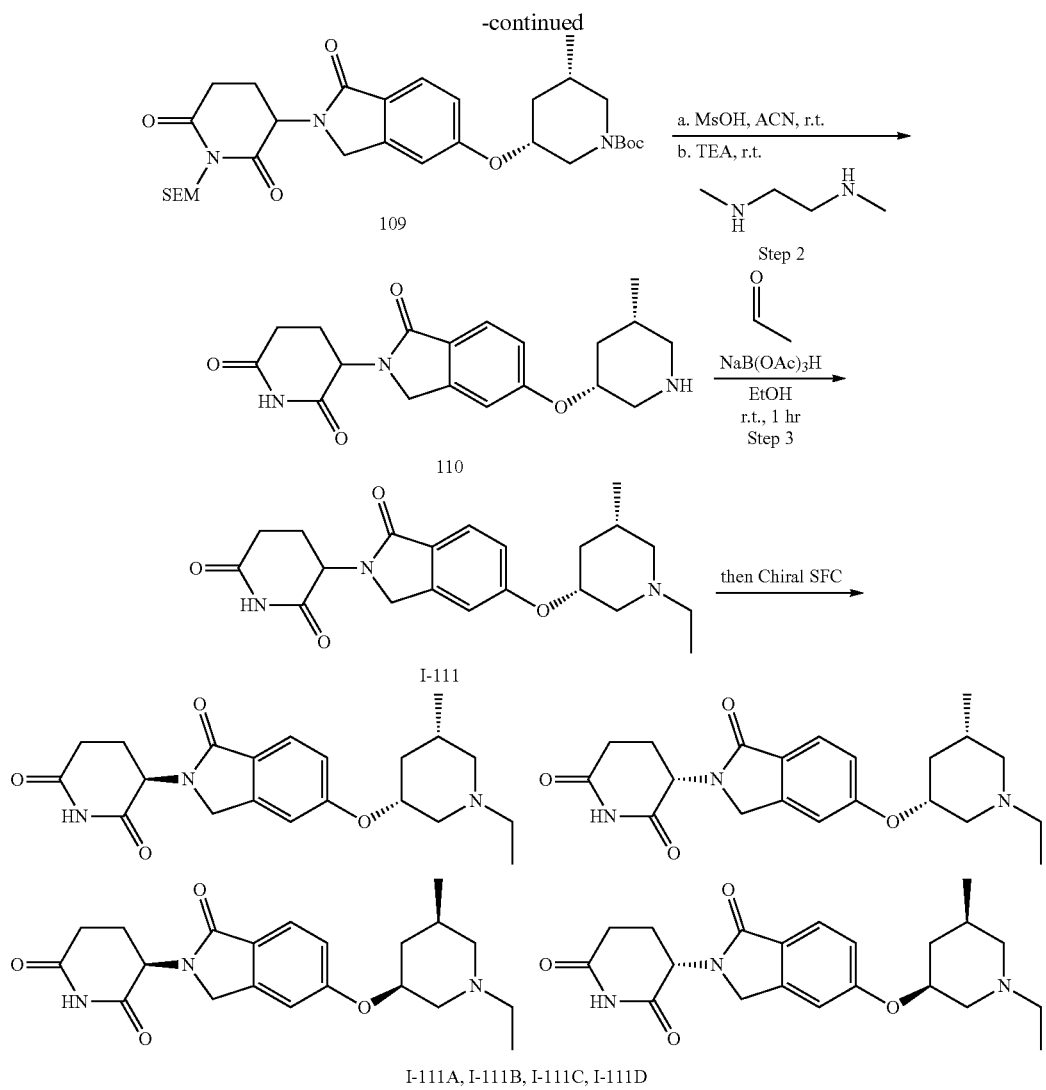

I-111A, I-111B, I-111C, I-111D

Step 1: rac-Tert-butyl (3R,5S)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate (109)

Compound 109 was made according to General Method VI starting from 3-(5-bromo-1-oxoisoindolin-2-yl)-1-((2-(trimethylsilyl)ethoxy)methyl)piperidine-2,6-dione INT-1 (750 mg, 1.65 mmol) and rac-tert-butyl (3R,5S)-3-hydroxy-5-methylpiperidine-1-carboxylate (356 mg, 1.65 mmol). The reaction was concentrated to afford rac-tert-butyl (3R,5S)-3-((2-(2,6-dioxo-1-((2-(trimethylsilyl)ethoxy) methyl)piperidin-3-yl)-1-oxoisoindolin-5-yl)oxy)-5-methylpiperidine-1-carboxylate 109 as a pale yellow solid. Material was taken through to the next step without purification. LCMS [M−H]⁻: 586.8.

Step 2: rac-3-(5-(((3R,5S)-5-methylpiperidin-3-yl)oxy)-1-oxoisoindolin-2-yl)piperidine-2,6-dione (110)

Compound 110 was made according to General Method VII starting from rac-tert-butyl (3R,5S)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate 109 (970 mg, 1.65 mmol). The reaction was quenched with saturated aqueous sodium bicarobate and extracted with 4:1 DCM:TFE three times. The organic layers were combined and concentrated to afford rac-3-(5-(((3R,5S)-5-methylpiperidin-3-yl)oxy)-1-oxoisoindolin-2-yl)piperidine-2,6-dione 110. Material was taken through to the next step without purification. LCMS [M+H]⁺: 358.3.

Step 3: rac-3-(5-(((3R,5S)-1-ethyl-5-methylpiperidin-3-yl)oxy)-1-oxoisoindolin-2-yl)piperidine-2,6-dione (I-111); (R)-3-(5-(((3R,5S)-1-ethyl-5-methylpiperidin-3-yl)oxy)-1-oxoisoindolin-2-yl)piperidine-2,6-dione, (S)-3-(5-(((3R,5S)-1-ethyl-5-methylpiperidin-3-yl)oxy)-1-oxoisoindolin-2-yl)piperidine-2,6-dione, (R)-3-(5-(((3S,5R)-1-ethyl-5-methylpiperidin-3-yl)oxy)-1-oxoisoindolin-2-yl)piperidine-2,6-dione, and (S)-3-(5-(((3S,5R)-1-ethyl-5-methylpiperidin-3-yl)oxy)-1-oxoisoindolin-2-yl)piperidine-2,6-dione To a solution of rac-3-(5-(((3R,5S)-5-methylpiperidin-3-yl)oxy)-1-oxoisoindolin-2-yl)piperidine-2,6-dione 110 (590 mg, 1.65 mmol) and sodium triacetoxyborohydride (2.8 g, 13.2 mmol) in EtOH (5.0 mL) was added acetaldehyde (0.74 mL, 13.2 mmol) at 0° C. The reaction stirred at r.t. overnight. The reaction was concentrated and purified by silica gel chromatography (0 to 100% EtOAc:EtOH:Et$_3$N (v/v/v=75: 25:1) in Heptane). Fractions containing desired product were combined and concentrated to afford rac-3-(5-(((3R, 5S)-1-ethyl-5-methylpiperidin-3-yl)oxy)-1-oxoisoindolin-2-yl)piperidine-2,6-dione I-111 as a white solid. LCMS [M+H]$^+$: 386.4. $^1$H NMR (400 MHz, CD$_2$Cl$_2$) δ 8.40 (s, 1H), 7.70 (d, J=8.4 Hz, 1H), 7.20 (dd, J=10.8, 2.2 Hz, 1H), 7.04 (ddd, J=8.1, 5.4, 2.2 Hz, 1H), 5.11 (dd, J=13.4, 5.1 Hz, 1H), 4.89-4.74 (m, 1H), 4.43-4.25 (m, 2H), 3.73-3.55 (m, 1H), 3.28-3.13 (m, 1H), 2.93-2.71 (m, 4H), 2.40-2.03 (m, 5H), 1.96 (t, J=11.5 Hz, 1H), 1.30-1.10 (m, 4H), 1.00 (d, J=6.5 Hz, 3H).

The diastereomeric mixture of isomers was further separated via a first chiral SFC [Column 20×250 mm Chromega-Chiral CC4 from ES Industries; CO$_2$ Co-solvent 60% Ethanol with 0.25% triethylamine; at 60 g/min at 100 bar, at 25° C.] then a second chiral SFC [Column 21×250 mm Chiralpak AD-H from Chiral Technologies; CO$_2$ Co-solvent 50% Ethanol with 0.25% triethylamine; at 60 g/min at 100 bar, at 25° C.] to afford four stereoisomers: Peak 1 (Ex. 45A), Rt=9.87 min, as a white solid; Peak 2 (Ex. 45B), Rt=8.80 min, as a white solid; Peak 3 (Ex. 45C), Rt=4.54 min, as a white solid; Peak 4 (Ex. 45D), Rt=6.53 min, as a white solid. The absolute stereochemistry of the four stereoisomers corresponding to the four product peaks was not determined.

Example 46: rac-3-(5-(((3R,4R)-1-ethyl-4-methylpiperidin-3-yl)oxy)-1-oxoisoindolin-2-yl)piperidine-2, 6-dione (I-114); (R)-3-(5-(((3R,4S)-1-ethyl-4-methylpiperidin-3-yl)oxy)-1-oxoisoindolin-2-yl) piperidine-2,6-dione, (S)-3-(5-(((3R,4S)-1-ethyl-4-methylpiperidin-3-yl)oxy)-1-oxoisoindolin-2-yl) piperidine-2,6-dione, (R)-3-(5-(((3S,4R)-1-ethyl-4-methylpiperidin-3-yl)oxy)-1-oxoisoindolin-2-yl) piperidine-2,6-dione, (S)-3-(5-(((3S,4R)-1-ethyl-4-methylpiperidin-3-yl)oxy)-1-oxoisoindolin-2-yl) piperidine-2,6-dione

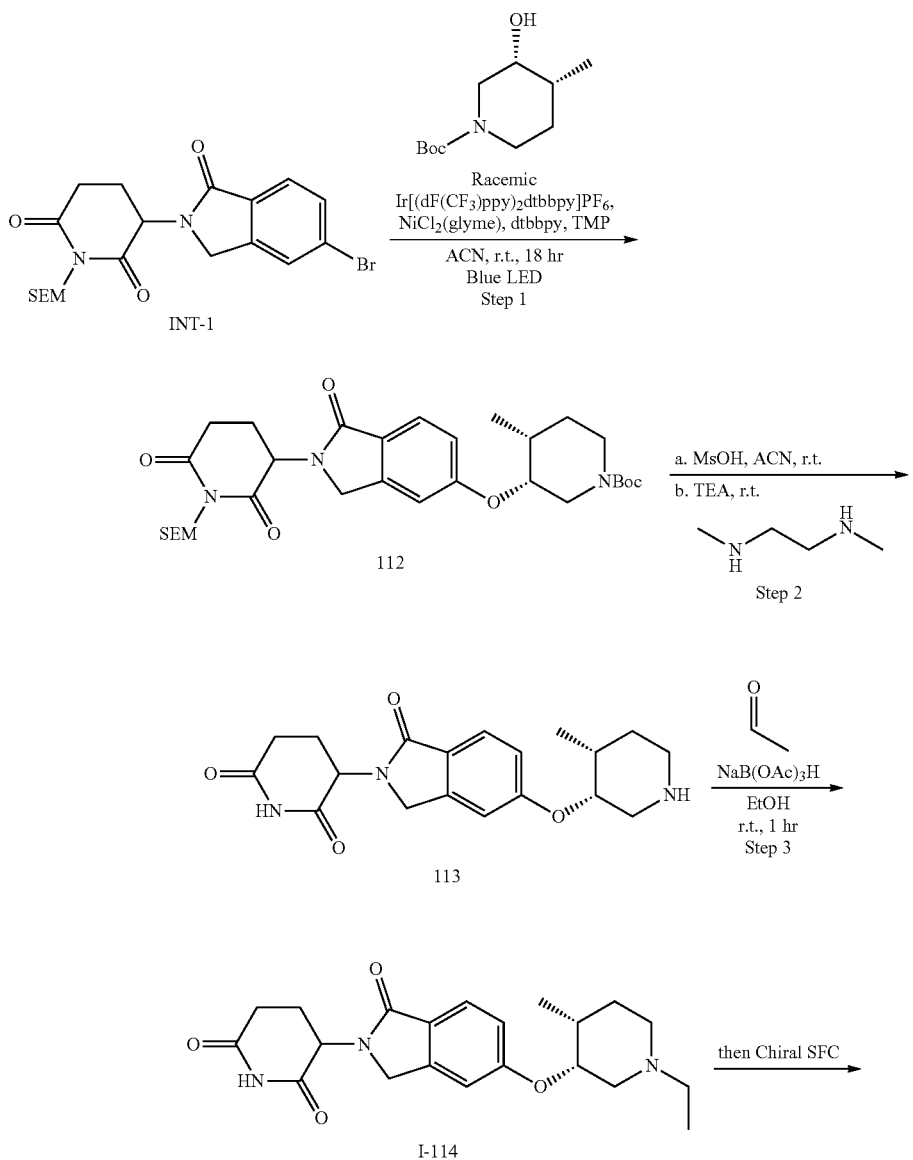

-continued

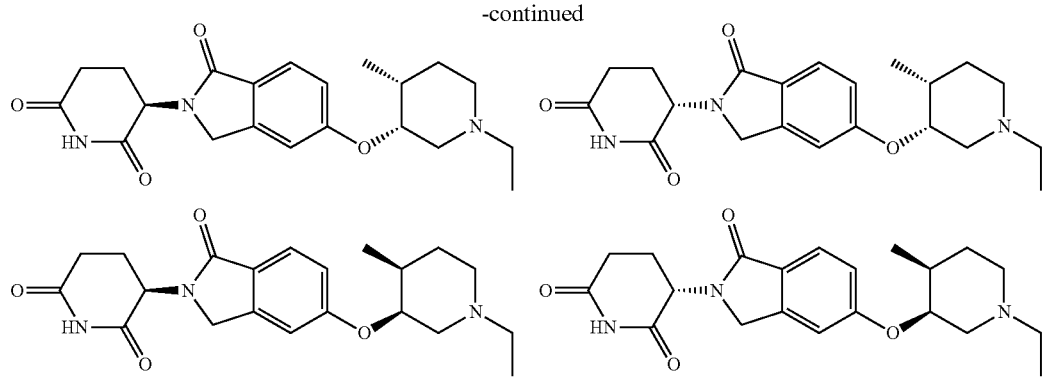

I-114A, I-114B, I-114C, I-114D

Step 1: rac-Tert-butyl (3R,4R)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate (112)

To a 40 mL vial, 3-(5-bromo-1-oxoisoindolin-2-yl)-1-((2-(trimethylsilyl)ethoxy)methyl)piperidine-2,6-dione INT-1 (527 mg, 1.16 mmol), dtbbpy (16 mg, 0.058 mmol), NiCl$_2$ (glyme) (13 mg, 0.058 mmol), and Ir[(dF(CF$_3$)ppy)$_2$dtbbpy] PF$_6$ (13 mg, 0.012 mmol) were added. Tert-butyl (3R*,4R*)-3-hydroxy-4-methylpiperidine-1-carboxylate (250 mg, 1.16 mmol) in ACN (6.0 mL) was added and the reaction was purged with nitrogen for 5-10 minutes ensuring reaction turns green. Then 2,2,6,6-tetramethylpiperidine (0.21 mL, 1.2 mmol) was added. The reaction was placed in a PennOC m1 450 nm Photoreactor under blue LED light at r.t. for 24 hrs. The reaction was concentrated onto CELITE® and purified by silica gel chromatography (0-100% EtOAc/heptane) to afford rac-tert-butyl (3R,4R)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate 112 (448 mg, 0.762 mmol) as a yellow oily foam. LCMS [M−H]$^-$: 586.4

Step 2: rac-3-(5-(((3R,4R)-4-methylpiperidin-3-yl)oxy)-1-oxoisoindolin-2-yl)piperidine-2,6-dione (113)

Compound 113 was made according to General Method VII starting from rac-tert-butyl (3R,4R)-3-((2-(2,6-dioxo-1-((2-(trimethylsilyl)ethoxy)methyl)piperidin-3-yl)-1-oxoisoindolin-5-yl)oxy)-4-methylpiperidine-1-carboxylate 112 (448 mg, 0.76 mmol). The reaction was quenched with a 50% saturated aqueous sodium bicarbonate and extracted with 4:1 DCM:iPrOH three times. The organic layers were combined, passed through a phase separator and concentrated to afford crude rac-3-(5-(((3R,4R)-4-methylpiperidin-3-yl)oxy)-1-oxoisoindolin-2-yl)piperidine-2,6-dione 113 (418 mg, 1.17 mmol). Material was taken through to the next step without purification. LCMS [M+H]$^+$: 358.3.

Step 3: rac-3-(5-(((3R,4R)-1-ethyl-4-methylpiperidin-3-yl)oxy)-1-oxoisoindolin-2-yl)piperidine-2,6-dione (I-114); (R)-3-(5-(((3R,4S)-1-ethyl-4-methylpiperidin-3-yl)oxy)-1-oxoisoindolin-2-yl)piperidine-2,6-dione, (S)-3-(5-(((3R,4S)-1-ethyl-4-methylpiperidin-3-yl)oxy)-1-oxoisoindolin-2-yl)piperidine-2,6-dione, (R)-3-(5-(((3S,4R)-1-ethyl-4-methylpiperidin-3-yl)oxy)-1-oxoisoindolin-2-yl)piperidine-2,6-dione, and (S)-3-(5-(((3S,4R)-1-ethyl-4-methylpiperidin-3-yl)oxy)-1-oxoisoindolin-2-yl)piperidine-2,6-dione To a vial containing rac-3-(5-(((3R,4R)-4-methylpiperidin-3-yl)oxy)-1-oxoisoindolin-2-yl)piperidine-2,6-dione 113 (418 mg, 1.17 mmol) and ACN (6.0 mL) was added sodium triacetoxyborohydride (744 mg, 3.51 mmol) followed by acetaldehyde (132 uL, 2.4 mmol). The reaction was stirred at r.t. for 1 hr. The reaction was concentrated onto CELITE® and purified by silica gel chromatography (0 to 100% EtOAc:EtOH:Et$_3$N (v/v/v=75:25:1) in DCM). Fractions containing desired product were combined, concentrated diluted with DMSO:H$_2$O:ACN (1:1:1). The precipitate was filtered and washed with acetone to afford rac-3-(5-(((3R,4R)-1-ethyl-4-methylpiperidin-3-yl)oxy)-1-oxoisoindolin-2-yl)piperidine-2,6-dione I-114 as a white solid. LCMS [M+H]$^+$: 386.5. $^1$H NMR (400 MHz, DMSO-d$_6$) δ 10.96 (s, 1H), 7.60 (d, J=8.4 Hz, 1H), 7.18 (s, 1H), 7.06 (dd, J=8.4, 2.2 Hz, 1H), 5.07 (dd, J=13.3, 5.1 Hz, 1H), 4.51 (s, 1H), 4.43-4.15 (m, 2H), 2.90 (ddd, J=17.7, 13.6, 5.3 Hz, 2H), 2.55 (d, J=9.4 Hz, 2H), 2.37 (dd, J=13.1, 4.4 Hz, 1H), 2.30 (q, J=7.0 Hz, 3H), 2.11 (m, 1H), 1.99-1.82 (m, 2H), 1.72-1.47 (m, 2H), 0.93 (ddd, J=13.2, 7.3, 3.9 Hz, 6H). The filtrate was purified by acidic reverse phase HPLC (2-12% ACN in water with 0.1% formic acid as modifier). Fractions containing desired product were combined, lyophilized.

The diastereomeric mixture of isomers was separated via chiral SFC [Column 2×25 mm ChromegaChiral CC4 from ES; CO$_2$ Co-solvent 70% Ethanol with 0.25% triethylamine; at 60 g/min at 100 bar, at 25° C.] to afford four stereoisomers: Peak 1 (Ex. 46A), Rt=3.2 min, as a white solid; Peak 2 (Ex. 46B), Rt=3.1 min, as a white solid. Two stereoisomers required additional separation via chiral SFC [Column 2.1× 25 cm Chiralpak AD-H from Chiral Technologies; CO$_2$ Co-solvent 50% ethanol with 0.25% triethylamine; at 70 g/min at 100 bar, at 25° C.] to afford two single stereoisomers: Peak 3 (Ex. 46C), Rt=3.5 mins, obtained as a white solid; Peak 4 (Ex. 46D), Rt=3.7 mins, obtained as a white solid. The absolute stereochemistry of the four stereoisomers corresponding to the four product peaks was not determined.

Example 47: rac-3-(5-(((3R,5S)-1-ethyl-5-hydroxypiperidin-3-yl)oxy)-1-oxoisoindolin-2-yl)piperidine-2,6-dione (I-117)

Step 2: rac-3-(5-(((3R,5S)-5-hydroxypiperidin-3-yl)oxy)-1-oxoisoindolin-2-yl)piperidine-2,6-dione (116)

Compound 116 was made according to General Method VII starting from rac-tert-butyl (3R,5S)-3-((2-(2,6-dioxo-1-((2-(trimethylsilyl)ethoxy)methyl)piperidin-3-yl)-1-oxoi-

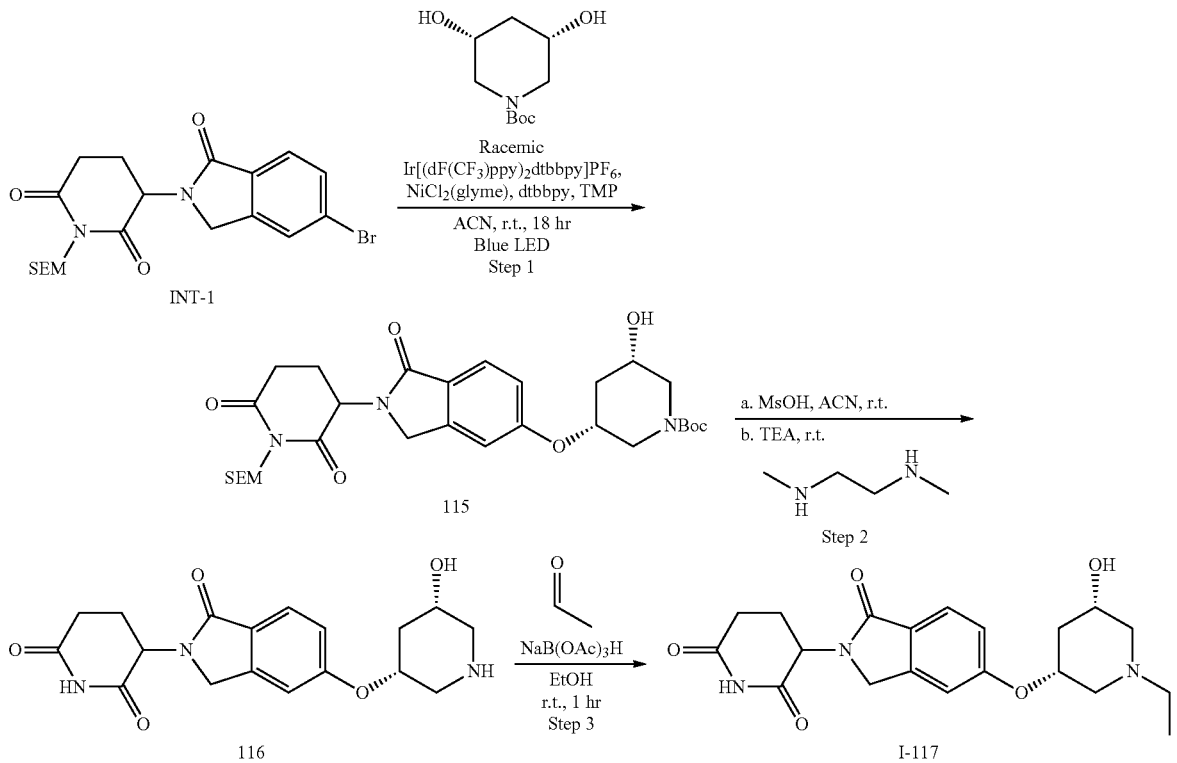

Step 1: rac-Tert-butyl (3R,5S)-3-((2-(2,6-dioxo-1-((2-(trimethylsilyl)ethoxy)methyl)piperidin-3-yl)-1-oxoisoindolin-5-yl)oxy)-5-hydroxypiperidine-1-carboxylate (115)

To a 40 mL capped vial, 3-(5-bromo-1-oxoisoindolin-2-yl)-1-((2-(trimethylsilyl)ethoxy)methyl)piperidine-2,6-dione INT-1 (500 mg, 1.1 mmol), dtbbpy (15 mg, 0.055 mmol), NiCl$_2$(glyme) (12 mg, 0.055 mmol), and Ir[(dF(CF$_3$)ppy)$_2$dtbbpy]PF$_6$ (12 mg, 0.011 mmol) were added. rac-Tert-butyl (3R,5S)-3,5-dihydroxypiperidine-1-carboxylate (240 mg, 1.1 mmol) in ACN (5.0 mL) was added and the reaction was purged with nitrogen for 5-10 minutes ensuring reaction turns green. Then 2,2,6,6-tetramethylpiperidine (0.20 mL, 1.2 mmol) was added. The reaction was placed in a PennOC ml 450 nm Photoreactor under blue LED light at r.t. for 18 hrs. The reaction was concentrated onto (SOLUTE® (HM-N Part No. 9800-5000) and purified by silica gel chromatography (0 to 100% EtOAc:EtOH:Et$_3$N (v/v/v=75:25:1) in DCM) to afford rac-tert-butyl (3R,5S)-3-((2-(2,6-dioxo-1-((2-(trimethylsilyl)ethoxy)methyl)piperidin-3-yl)-1-oxoisoindolin-5-yl)oxy)-5-hydroxypiperidine-1-carboxylate 115 as a colorless foam. LCMS [M+H-156.34]$^+$: 434.2.

soindolin-5-yl)oxy)-5-hydroxypiperidine-1-carboxylate 115 (550 mg, 0.93 mmol). The reaction was quenched with a 50% saturated sodium bicarbonate and extracted with 4:1 DCM:iPrOH three times. The organic layers were combined, passed through a phase separator and concentrated. Crude material was purified by silica gel chromatography (0-100% EtOH:Et$_3$N (v/v=100:1) in dichloromethane). Fractions containing desired product were combined, concentrated, suspended in 2:1 water:ACN and lyopholized to afford rac-3-(5-(((3R,5S)-5-hydroxypiperidin-3-yl)oxy)-1-oxoisoindolin-2-yl)piperidine-2,6-dione 116 as a white solid. LCMS [M+H]$^+$: 360.2. $^1$H NMR (400 MHz, DMSO-d6) δ 10.98 (s, 1H), 7.65 (t, J=9.0 Hz, 1H), 7.24 (d, J=11.1 Hz, 1H), 7.10 (d, J=8.2 Hz, 1H), 5.16 (d, J=39.1 Hz, 1H), 4.73-4.15 (m, 4H), 3.77 (s, 1H), 3.22-2.66 (m, 5H), 2.38-2.27 (m, 3H), 1.96 (d, J=34.9 Hz, 2H), 1.57 (d, J=11.2 Hz, 1H).

Step 3: rac-3-(5-(((3R,5S)-1-ethyl-5-hydroxypiperidin-3-yl)oxy)-1-oxoisoindolin-2-yl)piperidine-2,6-dione (I-117)

To a vial containing rac-3-(5-(((3R,5S)-5-hydroxypiperidin-3-yl)oxy)-1-oxoisoindolin-2-yl)piperidine-2,6-dione 116 (34 mg, 0.095 mmol) and ACN (2.0 mL) was added sodium triacetoxyborohydride (60 mg, 0.28 mmol) followed by acetaldehyde (11 uL, 0.19 mmol). The reaction stirred at r.t. for 1 hr. The reaction was concentrated onto CELITE® and purified by silica gel chromatography (0 to 100% EtOAc:EtOH:Et$_3$N (v/v/v=75:25:1) in DCM). The material was further purified by basic reverse phase HPLC (10-30% ACN in water with 5 mM NH$_4$OH as modifier). Test tubes contained 3 drops formic acid prior to sample collection. Fractions containing desired product were combined and lyophilized to afford rac-3-(5-(((3R,5S)-1-ethyl-5-hydroxypiperidin-3-yl)oxy)-1-oxoisoindolin-2-yl)piperidine-2,6-dione I-117 as a white solid. LCMS [M+H]$^+$: 388.5. $^1$H NMR (400 MHz, DMSO-d6) δ 10.94 (s, 1H), 8.23 (s, 1H), 7.60 (d, J=8.4 Hz, 1H), 7.20 (d, J=2.2 Hz, 1H), 7.10-6.97 (m, 1H), 5.06 (dd, J=13.3, 5.0 Hz, 1H), 4.48 (dt, J=10.3, 5.3 Hz, 1H), 4.42-4.18 (m, 2H), 3.62 (tt, J=9.7, 4.4 Hz, 1H), 3.10 (d, J=10.3 Hz, 1H), 2.90 (ddd, J=18.8, 11.8, 5.2 Hz, 2H), 2.69-2.53 (m, 1H), 2.46-2.28 (m, 4H), 2.04-1.91 (m, 1H), 1.84 (td, J=10.1, 2.8 Hz, 1H), 1.68 (t, J=10.2 Hz, 1H), 1.17 (qd, J=11.1, 2.8 Hz, 1H), 0.99 (td, J=7.1, 5.0 Hz, 4H).

Example 48: 3-(5-((1-ethyl-4,4-dimethylpiperidin-3-yl)oxy)-1-oxoisoindolin-2-yl)piperidine-2,6-dione (I-123)

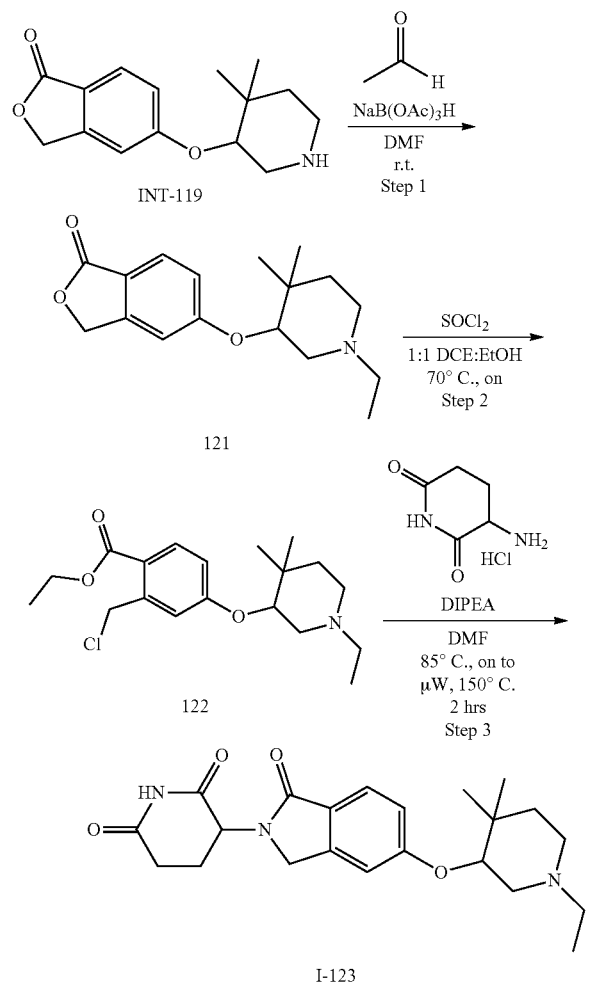

Step 1: 5-((1-ethyl-4,4-dimethylpiperidin-3-yl)oxy)isobenzofuran-1(3H)-one (121)

Compound 121 was made according to General Method X starting from single enantiomer 5-((4-dimethylpiperidin-3-yl)oxy)isobenzofuran-1(3H)-one INT-119 (0.1 g, 0.336 mmol) and acetaldehyde (0.028 mL, 0.504 mmol). The crude material was purified by silica gel chromatography (0-100% 3:1 EtOAc:EtOH with 1% TEA in heptane) to afford 5-((1-ethyl-4,4-dimethylpiperidin-3-yl)oxy)isobenzofuran-1(3H)-one 121 as a yellow oil. LCMS [M+H]$^+$: 290.1.

Step 2: Ethyl 2-(chloromethyl)-4-((1-ethyl-4,4-dimethylpiperidin-3-yl)oxy)benzoate (122)

To a solution of 5-((1-ethyl-4,4-dimethylpiperidin-3-yl)oxy)isobenzofuran-1(3H)-one 121 (0.033 g, 0.114 mmol) in dichloroethane (1.0 mL) and ethanol (1.0 mL) in a 25 mL 2 neck round bottom flask stirred at 70° C. was added thionyl chloride (0.10 mL, 1.368 mmol) dropwise. The reaction stirred at 70° C. overnight. The reaction mixture was cooled to r.t., diluted with water, and quenched with saturated sodium bicarbonate. The reaction mixture was extracted with ethyl acetate three times. The organic layers were combined, passed through a phase separator and concentrated. The crude material was purified by silica gel chromatography (0-100% EtOAc in heptane) to afford ethyl 2-(chloromethyl)-4-((1-ethyl-4,4-dimethylpiperidin-3-yl)oxy)benzoate 122 as a light orange oil. LCMS [M+H]$^+$: 354.3.

Step 3: 3-(5-((1-ethyl-4,4-dimethylpiperidin-3-yl)oxy)-1-oxoisoindolin-2-yl)piperidine-2,6-dione (I-123)

Compound I-123 was made according to General Method V starting from ethyl 2-(chloromethyl)-4-((1-ethyl-4,4-dimethylpiperidin-3-yl)oxy)benzoate 122 (22.9 mg, 0.065 mmol). The reaction was concentrated and purified by silica gel chromatography pushing the crude material through a plug of charcoal before reaching the silica column (0-100% 3:1 ethyl acetate:ethanol with 1% triethylamine in heptane). Fractions containing desired product were combined and concentrated. The material was further purified by basic reverse phase HPLC (25-50% ACN in water with 5 mM NH$_4$OH as modifier). Test tubes contained 3 drops formic acid prior to sample collection. Pure fractions were combined and lyophilized to afford formate salt 3-(5-((1-ethyl-4,4-dimethylpiperidin-3-yl)oxy)-1-oxoisoindolin-2-yl)piperidine-2,6-dione I-123 as a cream solid. LCMS [M+H]$^+$: 400.4. $^1$H NMR (400 MHz, DMSO-d6) δ 10.76 (s, 1H), 8.19 (s, 1H), 7.54 (d, J=8.3 Hz, 1H), 7.13 (d, J=2.1 Hz, 1H), 6.99 (dd, J=8.3, 2.2 Hz, 1H), 5.00 (dd, J=13.3, 5.0 Hz, 1H), 4.32 (dd, J=17.2, 6.1 Hz, 1H), 4.25-4.06 (m, 2H), 2.89-2.69 (m, 2H), 2.56-2.47 (m, 2H), 2.36-2.22 (m, 3H), 2.16-2.05 (m, 2H), 1.96-1.87 (m, 1H), 1.47-1.40 (m, 2H), 0.96-0.87 (m, 9H). Absolute stereochmistry at 3-position of the piperidine ring of I-123 was not determined.

Example 49: 3-(5-((1-ethyl-4,4-dimethylpiperidin-3-yl)oxy)-1-oxoisoindolin-2-yl)piperidine-2,6-dione (I-126)

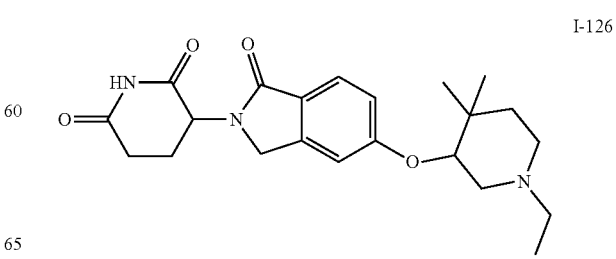

Example 49 (I-126) was synthesized by analogy to the previous Example 48 starting with single enantiomer INT-120. Absolute stereochmistry at 3-position of the piperidine ring of I-126 was not determined.

Step 1: 5-((1-ethyl-4,4-dimethylpiperidin-3-yl)oxy)isobenzofuran-1(3H)-one (124)

LCMS [M+H]$^+$: 290.1.

Step 2: 5-((1-ethyl-4,4-dimethylpiperidin-3-yl)oxy)isobenzofuran-1(3H)-one (125)

Material was used directly in the next reaction without purification. LCMS [M+H]$^+$: 354.3.

In the final step 3, the reaction was concentrated and purified by silica gel chromatography pushing the crude material through a plug of charcoal before reaching the silica column (0-100% 3:1 ethyl acetate:ethanol with 1% triethylamine in heptane). Fractions containing desired product were combined and concentrated. The material was further purified by basic reverse phase HPLC (25-50% ACN in water with 5 mM NH$_4$OH as modifier). Test tubes contained 3 drops of formic acid prior to sample collection. Pure fractions were combined and lyophilized to afford formate salt 3-(5-((1-ethyl-4,4-dimethylpiperidin-3-yl)oxy)-1-oxoisoindolin-2-yl)piperidine-2,6-dione I-126 as a white solid. LCMS [M+H]$^+$: 400.3. $^1$H NMR (400 MHz, DMSO-d6) δ 10.28 (s, 1H), 8.21 (s, 2H), 7.55 (d, J=8.5 Hz, 1H), 7.14 (d, J=2.1 Hz, 1H), 6.99 (dd, J=8.3, 2.3 Hz, 1H), 5.00 (dd, J=13.3, 5.1 Hz, 1H), 4.32 (dd, J=17.2, 6.2 Hz, 1H), 4.25-4.10 (m, 2H), 2.89-2.72 (m, 2H), 2.56-2.45 (m, 2H), 2.37-2.23 (m, 3H), 2.17-2.06 (m, 2H), 1.95-1.85 (m, 1H), 1.49-1.36 (m, 2H), 0.98-0.85 (m, 9H).

Example 50: 3-(5-((1-((S)-sec-butyl)-4,4-dimethylpiperidin-3-yl)oxy)-1-oxoisoindolin-2-yl)piperidine-2,6-dione (I-129)

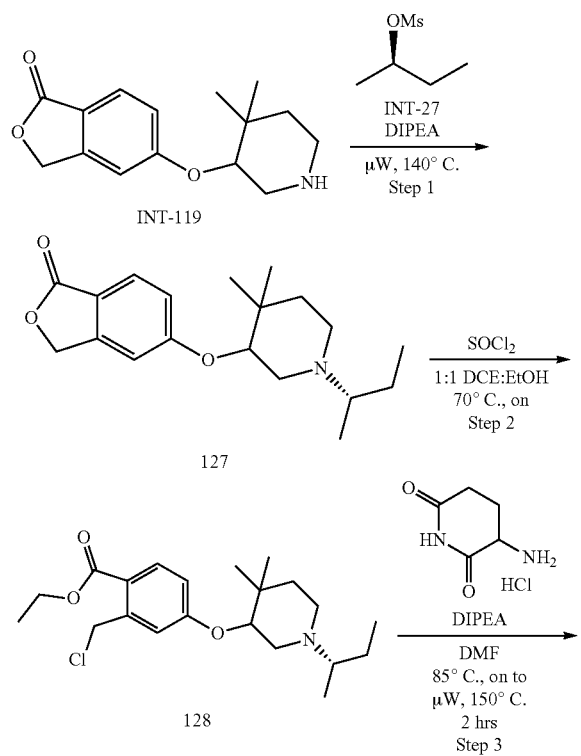

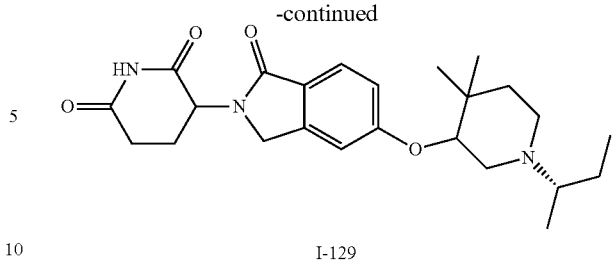

I-129

Step 1: 5-((1-((S)-sec-butyl)-4,4-dimethylpiperidin-3-yl)oxy)isobenzofuran-1(3H)-one (127)

Compound 127 was made according to General Method IX starting from single enantiomer 5-((4,4-dimethylpiperidin-3-yl)oxy)isobenzofuran-1(3H)-one INT-119 (0.1 g, 0.383 mmol) and (R)-sec-butyl methanesulfonate INT-27 (0.2 g, 1.314 mmol). The crude material was purified by silica gel chromatography (0-100% 3:1 ethyl acetate:ethanol with 1% triethylamine in heptane). Fractions containing product were combined and concentrated to afford 5-((1-((S)-sec-butyl)-4,4-dimethylpiperidin-3-yl)oxy)isobenzofuran-1(3H)-one 127 as light orange oil. LCMS [M+H]$^+$: 318.3. $^1$H NMR (400 MHz, CDCl$_3$) δ 7.73 (d, J=8.5 Hz, 1H), 7.02-6.94 (m, 1H), 6.95-6.86 (m, 1H), 5.16 (s, 2H), 4.21-3.98 (m, 1H), 2.78-2.71 (m, 1H), 2.54-2.26 (m, 4H), 1.60-1.43 (m, 3H), 1.27-1.12 (m, 1H), 0.99 (s, 3H), 0.97-0.86 (m, 6H), 0.85-0.79 (m, 3H).

Step 2: Ethyl 4-((1-((S)-sec-butyl)-4,4-dimethylpiperidin-3-yl)oxy)-2-(chloromethyl)benzoate (128)

Compound 128 was made according to General Method IV starting from 5-((1-((S)-sec-butyl)-4,4-dimethylpiperidin-3-yl)oxy)isobenzofuran-1(3H)-one 127 (0.0408 g, 0.129 mmol). Crude material was purified by silica gel chromatography (0-100% EtOAc in heptane) to afford ethyl 4-((1-((S)-sec-butyl)-4,4-dimethylpiperidin-3-yl)oxy)-2-(chloromethyl)benzoate 128 as a brown orange oil. Material was used directly in the next reaction. LCMS [M+H]$^+$: 382.2.

Step 3: 3-(5-((1-((S)-sec-butyl)-4,4-dimethylpiperidin-3-yl)oxy)-1-oxoisoindolin-2-yl)piperidine-2,6-dione (I-129)

Compound I-129 was made according to General Method V starting from ethyl 4-((1-((S)-sec-butyl)-4,4-dimethylpiperidin-3-yl)oxy)-2-(chloromethyl)benzoate 128 (49.3 mg, 0.129 mmol). The reaction was concentrated and purified by silica gel chromatography pushing the crude material through a plug of charcoal before reaching the silica column (0-100% 3:1 ethyl acetate:ethanol with 1% triethylamine in heptane). Fractions containing desired product were combined and concentrated. The material was further purified by basic reverse phase HPLC (35-60% ACN in water with 5 mM NH$_4$OH as modifier). Test tubes contained 3 drops formic acid prior to sample collection. Pure fractions were combined and lyophilized to afford formate salt 3-(5-((1-((S)-sec-butyl)-4,4-dimethylpiperidin-3-yl)oxy)-1-oxoisoindolin-2-yl)piperidine-2,6-dione I-129 as a white solid. LCMS [M+H]$^+$: 428.4. $^1$H NMR (400 MHz, DMSO-d6) δ 10.89 (s, 1H), 8.16 (s, 1H), 7.54 (d, J=8.3 Hz, 1H), 7.13-7.07 (m, 1H), 6.99-6.94 (m, 1H), 5.00 (dd, J=13.3, 5.1 Hz, 1H), 4.32 (dd, J=17.2, 4.3 Hz, 1H), 4.19 (dd, J=17.3, 3.9 Hz, 1H), 4.14-4.03 (m, 1H), 2.83 (ddd, J=17.3, 13.5, 5.4 Hz, 1H), 2.72-2.58 (m, 1H), 2.56-2.48 (m, 1H), 2.40-2.17 (m, 5H), 1.95-1.81 (m, 1H), 1.49-1.30 (m, 3H), 1.21-1.07 (m, 1H), 0.97-0.88 (m, 6H), 0.83 (d, J=6.7 Hz, 3H), 0.81-0.68 (m, 3H). Absolute stereochmistry at 3-position of the piperidine ring of I-129 was not determined.

Example 51: 3-(5-((1-((S)-sec-butyl)-4,4-dimethylpiperidin-3-yl)oxy)-1-oxoisoindolin-2-yl)piperidine-2,6-dione (I-132)

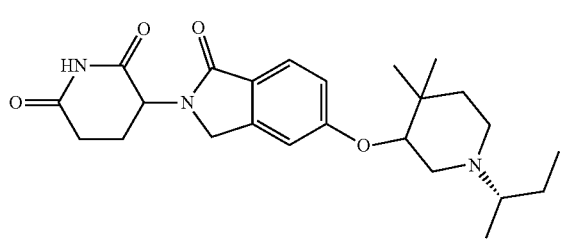

I-132

Example 51 (I-132) was synthesized by analogy to the previous Example 50 starting with single enentiomer INT-120. Absolute stereochmistry at 3-position of the piperidine ring of I-132 was not determined.

Step 1: 5-((1-((S)-sec-butyl)-4,4-dimethylpiperidin-3-yl)oxy)isobenzofuran-1(3H)-one (130)

LCMS [M+H]⁺: 318.4. ¹H NMR (400 MHz, CDCl₃) δ 7.81 (d, J=8.5 Hz, 1H), 7.10-7.03 (m, 1H), 7.00-6.94 (m, 1H), 5.24 (s, 2H), 4.24-4.10 (m, 1H), 2.85-2.76 (m, 1H), 2.60-2.33 (m, 4H), 1.64-1.47 (m, 3H), 1.35-1.21 (m, 1H), 1.07 (s, 3H), 1.03 (s, 3H), 1.00-0.95 (m, 3H), 0.94-0.87 (m, 3H).

Step 2: Ethyl 4-((1-((S)-sec-butyl)-4,4-dimethylpiperidin-3-yl)oxy)-2-(chloromethyl)benzoate (131)

Material was used directly in the next reaction. LCMS [M+H]⁺: 382.3.

In the final step 3, the material was further purified by basic reverse phase HPLC (35-60% ACN in water with 5 mM NH₄OH as modifier). Test tubes contained 3 drops formic acid prior to sample collection. Pure fractions were combined and lyophilized to afford formate salt 3-(5-((1-((S)-sec-butyl)-4,4-dimethylpiperidin-3-yl)oxy)-1-oxoisoindolin-2-yl)piperidine-2,6-dione I 132 as a white solid. LCMS [M+H]⁺: 428.5. ¹H NMR (400 MHz, DMSO-d6) δ 10.89 (s, 1H), 8.29 (s, 1H), 7.54 (d, J=8.4 Hz, 1H), 7.10 (dd, J=8.1, 2.2 Hz, 1H), 7.01-6.95 (m, 1H), 5.00 (dd, J=13.3, 5.1 Hz, 1H), 4.32 (dd, J=17.3, 5.1 Hz, 1H), 4.19 (dd, J=17.3, 5.9 Hz, 1H), 4.14-4.05 (m, 1H), 2.83 (ddd, J=17.1, 13.5, 5.4 Hz, 1H), 2.70-2.62 (m, 1H), 2.56-2.49 (m, 1H), 2.36-2.19 (m, 5H), 1.96-1.86 (m, 1H), 1.49-1.31 (m, 3H), 1.22-1.07 (m, 1H), 0.96-0.89 (m, 6H), 0.83 (d, J=6.4 Hz, 3H), 0.80-0.71 (m, 3H).

Example 52: rac-3-(5-(((3R,5R)-1-Ethyl-5-methylpiperidin-3-yl)oxy)-1-oxoisoindolin-2-yl)piperidine-2,6-dione (I-136)

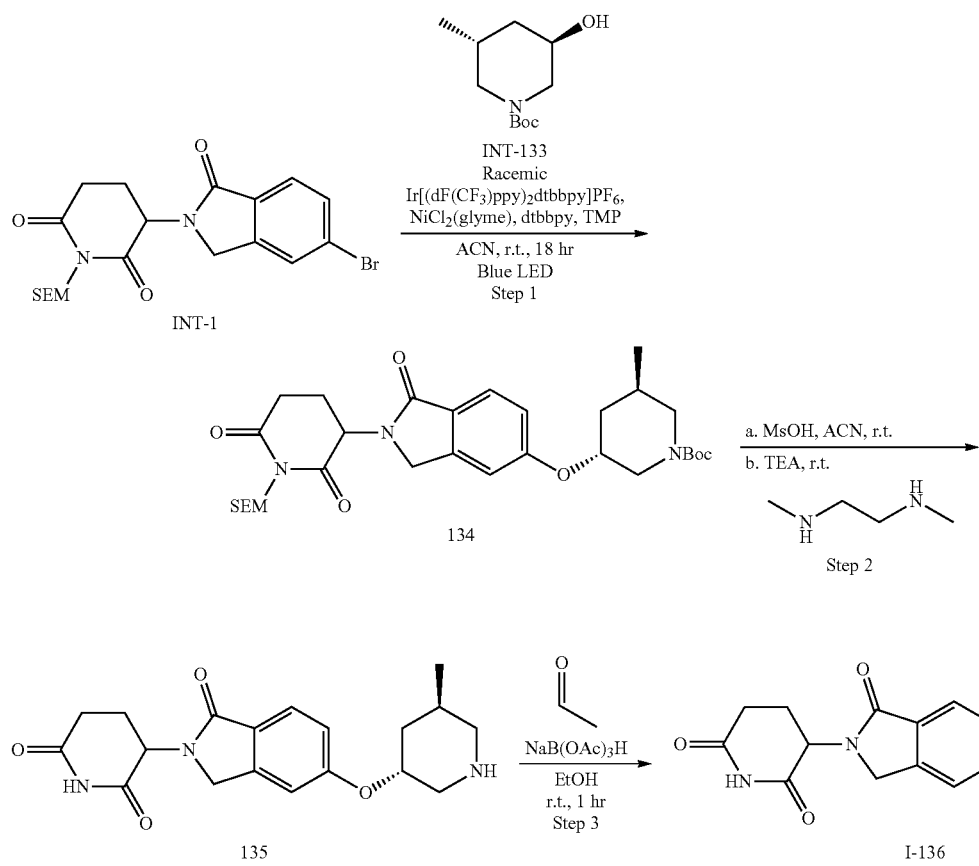

Step 1: rac-Tert-butyl (3R,5R)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate (134)

To a 40 mL capped vial, 3-(5-bromo-1-oxoisoindolin-2-yl)-1-((2-(trimethylsilyl)ethoxy)methyl)piperidine-2,6-dione INT-1 (988 mg, 2.2 mmol), dtbbpy (29.2 mg, 0.11 mmol), NiCl$_2$(glyme) (24 mg, 0.11 mmol), and Ir[(dF(CF$_3$)ppy)$_2$dtbbpy]PF$_6$ (24 mg, 0.022 mmol) were added. rac-Tert-butyl (3R,5R)-3-hydroxy-5-methylpiperidine-1-carboxylate INT-133 (469 mg, 2.2 mmol) in ACN (10.0 mL) was added and the reaction was purged with nitrogen for 5-10 minutes ensuring reaction turns green. Then 2,2,6,6-tetramethylpiperidine (0.39 mL, 2.3 mmol) was added. The reaction was placed in a PennOC m1 450 nm Photoreactor under blue LED light at r.t. for 24 hrs and 48 hrs with no LED. The reaction was concentrated onto CELITE® and purified by silica gel chromatography (0-100% EtOAc in heptane) to afford rac-tert-butyl (3R,5R)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate 134. LCMS [M−H]⁻: 586.3.

Step 2: rac-3-(5-(((3R,5R)-5-methylpiperidin-3-yl)oxy)-1-oxoisoindolin-2-yl)piperidine-2,6-dione (135)

Compound 135 was made according to General Method VII starting from rac-tert-butyl (3R,5R)-3-((2-(2,6-dioxo-1-((2-(trimethylsilyl)ethoxy) methyl)piperidin-3-yl)-1-oxoisoindolin-5-yl)oxy)-5-methylpiperidine-1-carboxylate 134 (1.11 g, 1.89 mmol). The reaction was quenched with a 50% saturated aqueous sodium bicarbonate and extracted with 4:1 DCM:iPrOH three times. The organic layers were combined, passed through a phase separator and concentrated to afford rac-3-(5-(((3R,5R)-5-methylpiperidin-3-yl)oxy)-1-oxoisoindolin-2-yl)piperidine-2,6-dione 135. Material was used directly in the next reaction without purification. LCMS [M+H]⁺: 358.2.

Step 3: rac-3-(5-(((3R,5R)-1-ethyl-5-methylpiperidin-3-yl)oxy)-1-oxoisoindolin-2-yl)piperidine-2,6-dione (I-136)

To a vial containing rac-3-(5-(((3R,5R)-5-methylpiperidin-3-yl)oxy)-1-oxoisoindolin-2-yl)piperidine-2,6-dione 135 (629 mg, 1.76 mmol) and ACN (10.0 mL) was added sodium triacetoxyborohydride (1.12 g, 5.28 mmol) followed by acetaldehyde (200 uL, 3.5 mmol). The reaction stirred at r.t. for 1 hr. The reaction was poured into saturated aqueous sodium bicarbonate and extracted with 4:1 DCM/iPrOH three times. The organics layers were combined, passed through a phase separator, and concentrated onto CELITE®. The crude material was purified by silica gel chromatography (0 to 100% EtOAc:EtOH:Et$_3$N (v/v/v=75:25:1) in DCM) to afford product. Material was dissolved in 1:1:1 DMSO:water:ACN (v/v/v=1:1:1) and further purified by basic reverse phase HPLC (15-40% ACN in water with 5 mM NH$_4$OH as modifier). Test tubes contained 3 drops formic acid prior to sample collection. Fractions containing desired product were combined and lyophilized to afford rac-3-(5-(((3R,5R)-1-ethyl-5-methylpiperidin-3-yl)oxy)-1-oxoisoindolin-2-yl)piperidine-2,6-dione I-136. LCMS [M+H]⁺: 386.3. ¹H NMR (400 MHz, DMSO-d6) δ 10.95 (s, 1H), 8.24 (s, 1H), 7.60 (d, J=8.4 Hz, 1H), 7.16 (d, J=2.2 Hz, 1H), 7.04 (dd, J=8.4, 2.2 Hz, 1H), 5.07 (dd, J=13.3, 5.1 Hz, 1H), 4.77-4.64 (m, 1H), 4.46-4.15 (m, 2H), 2.94-2.84 (m, 2H), 2.71 (d, J=10.8 Hz, 1H), 2.59 (ddd, J=17.3, 4.5, 2.4 Hz, 1H), 2.39-2.29 (m, 3H), 2.23 (d, J=12.2 Hz, 1H), 1.98 (ddd, J=9.9, 5.4, 2.7 Hz, 2H), 1.86 (d, J=13.9 Hz, 1H), 1.72 (t, J=10.1 Hz, 1H), 1.29 (t, J=12.2 Hz, 1H), 0.95 (td, J=7.2, 1.6 Hz, 3H), 0.87 (dd, J=6.8, 1.2 Hz, 3H).

Example 53: 3-(5-(((1S*,5R*,6R*)-3-ethyl-3-azabicyclo[4.1.0]heptan-5-yl)oxy)-1-oxoisoindolin-2-yl)piperidine-2,6-dione (I-138)

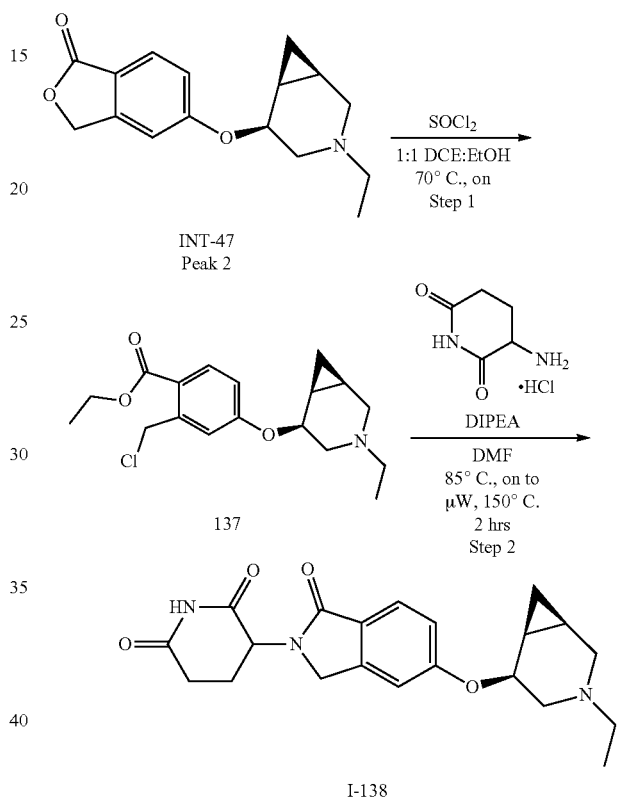

Step 1: Ethyl 2-(chloromethyl)-4-(((1R*,5S*,6S*)-3-ethyl-3-azabicyclo[4.1.0]heptan-5-yl)oxy)benzoate (137)

Compound 137 was made according to General Method IV starting from 5-(((1R*,5S*,6S*)-3-ethyl-3-azabicyclo[4.1.0]heptan-5-yl)oxy)isobenzofuran-1(3H)-one INT-47 Peak 2 (77.8 mg, 0.29 mmol). Crude material was purified by silica gel chromatography (0-100% EtOAc in heptane) to afford ethyl 2-(chloromethyl)-4-(((1R*,5S*,6S*)-3-ethyl-3-azabicyclo[4.1.0]heptan-5-yl)oxy)benzoate 137 as a brown oil. LCMS [M+H]⁺: 338.2.

Step 2: 3-(5-(((1R*,5S*,6S*)-3-ethyl-3-azabicyclo[4.1.0]heptan-5-yl)oxy)-1-oxoisoindolin-2-yl)piperidine-2,6-dione (I-138)

Compound I-138 was made according to General Method V starting from ethyl 2-(chloromethyl)-4-(((1R*,5S*,6S*)-3-ethyl-3-azabicyclo[4.1.0]heptan-5-yl)oxy)benzoate 137 (70 mg, 0.21 mmol). The reaction was concentrated and purified by silica gel chromatography pushing the crude material through a plug of charcoal before reaching the silica column (0-100% EtOAc:EtOH:Et₃N (v/v/v=75:25:1) in heptane). Pure fractions were combined, concentrated, and further purified by reverse phase HPLC (15-40% ACN in water with 5 mM NH₄OH as modifier). Test tubes contained 3 drops formic acid prior to sample collection. Pure fractions were combined and lyophilized to afford formate salt of 3-(5-(((1R*,5S*,6S*)-3-ethyl-3-azabicyclo[4.1.0]heptan-5-yl)oxy)-1-oxoisoindolin-2-yl)piperidine-2,6-dione I-138 as a white solid. LCMS [M+H]⁺: 384.2. ¹H NMR (400 MHz, DMSO-d6) δ 8.30 (s, 2H), 7.60 (d, J=8.3 Hz, 1H), 7.23 (d, J=2.0 Hz, 1H), 7.08 (dd, J=8.7, 2.4 Hz, 1H), 5.08 (dd, J=13.3, 5.0 Hz, 1H), 5.02-4.91 (m, 1H), 4.39 (d, J=17.1 Hz, 1H), 4.26 (d, J=17.0 Hz, 1H), 2.92 (ddd, J=18.0, 13.5, 5.4 Hz, 1H), 2.71 (d, J=11.0 Hz, 1H), 2.65-2.56 (m, 1H), 2.47-2.36 (m, 3H), 2.35-2.25 (m, 3H), 2.04-1.93 (m, 1H), 1.57-1.46 (m, 1H), 1.33-1.20 (m, 1H), 0.97 (t, J=7.1 Hz, 3H), 0.73-0.65 (m, 1H), 0.48-0.39 (m, 1H). The absolute stereochemistry of I-138 was not determined.

Example 54: rac-3-(5-((-7-ethyl-7-azaspiro[3.5]nonan-5-yl)oxy)-1-oxoisoindolin-2-yl)piperidine-2,6-dione (I-144)

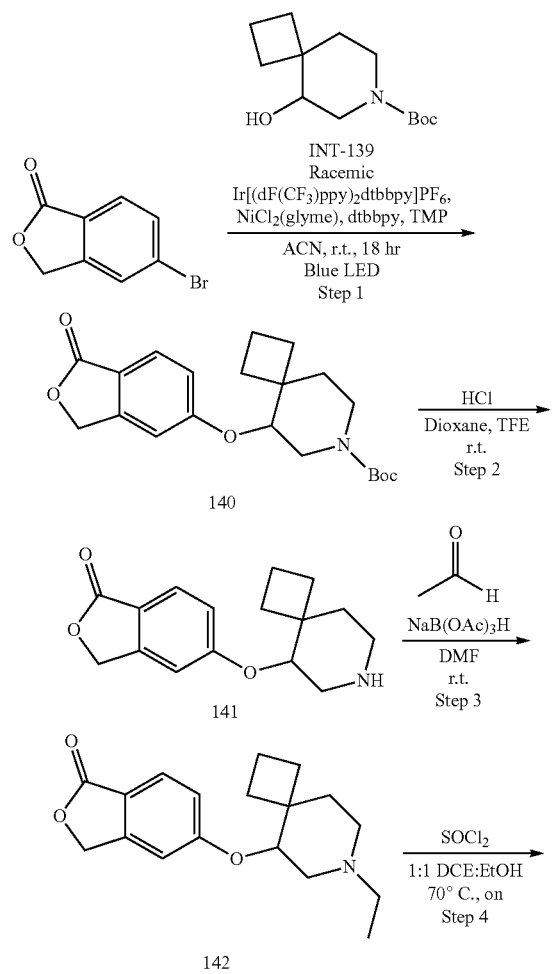

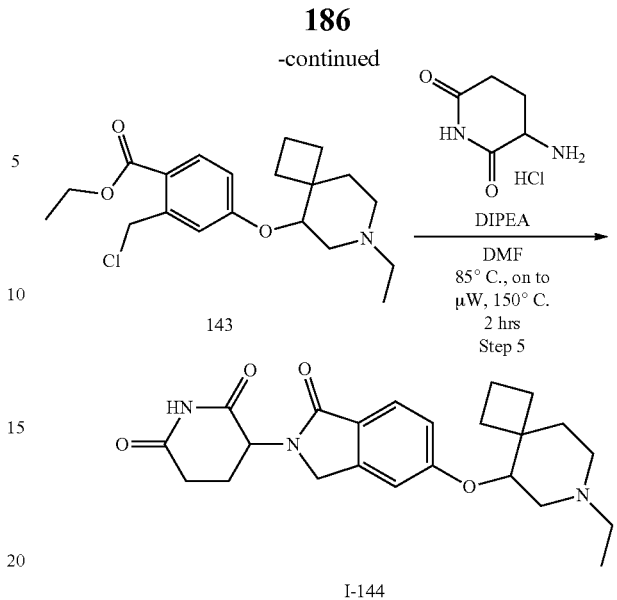

Step 1: rac-Tert-butyl 5-((1-oxo-1,3-dihydroisobenzofuran-5-yl)oxy)-7-azaspiro[3.5]nonane-7-carboxylate (140)

To a 40 mL capped vial, 5-bromoisobenzofuran-1(3H)-one (45 mg, 0.21 mmol), rac-tert-butyl 5-hydroxy-7-azaspiro[3.5]nonane-7-carboxylate (52 mg, 0.22 mmol), dtbbpy (5.7 mg, 0.021 mmol), NiCl₂(glyme) (4.6 mg, 0.021 mmol), and Ir[(dF(CF₃)ppy)₂dtbbpy]PF₆ (4.7 mg, 4.2 µmol) were added. ACN (0.9 mL) was added and the reaction was purged with nitrogen for 5-10 minutes ensuring reaction turns green. Then 2,2,6,6-tetramethylpiperidine (37 µL, 0.22 mmol) was added. The reaction was placed in a PennOC m1 450 nm Photoreactor under blue LED light at r.t. for 18 hrs. The reaction was concentrated onto CELITE® and purified by silica gel chromatography (0-100% EtOAc in heptane) to afford rac-tert-butyl 5-((1-oxo-1,3-dihydroisobenzofuran-5-yl)oxy)-7-azaspiro[3.5]nonane-7-carboxylate 140 as a light yellow solid. LCMS [M+H-tert-butyl]⁺: 318.3.

Step 2: rac-5-((7-azaspiro[3.5]nonan-5-yl)oxy)isobenzofuran-1(3H)-one (141)

Compound 141 was made according to General Method II starting from rac-tert-butyl 5-((1-oxo-1,3-dihydroisobenzofuran-5-yl)oxy)-7-azaspiro[3.5]nonane-7-carboxylate 140 (23 mg, 0.062 mmol). The reaction was concentrated to afford rac-5-((7-azaspiro[3.5]nonan-5-yl)oxy)isobenzofuran-1(3H)-one 141 as a light yellow oil. Material was used directly in the next step. LCMS [M+H]⁺: 274.1.

Step 3: rac-5-((7-ethyl-7-azaspiro[3.5]nonan-5-yl)oxy)isobenzofuran-1(3H)-one (142)

Compound 142 was made according to General Method X starting from rac-5-((7-azaspiro[3.5]nonan-5-yl)oxy)isobenzofuran-1(3H)-one 141 (17 mg, 0.062 mmol) and acetaldehyde (5.3 µL, 0.093 mmol). The crude material was purified by silica gel chromatography (0-20% methanol in DCM) to afford rac-5-((7-ethyl-7-azaspiro[3.5]nonan-5-yl)oxy)isobenzofuran-1(3H)-one 142 as a light orange solid. LCMS [M+H]⁺: 302.2.

Step 4: rac-Ethyl 2-(chloromethyl)-4-((7-ethyl-7-azaspiro[3.5]nonan-5-yl)oxy)benzoate (143)

Compound 143 was made according to General Method IV starting from rac-5-((7-ethyl-7-azaspiro[3.5]nonan-5-yl)oxy)isobenzofuran-1(3H)-one 142 (12.5 mg, 0.041 mmol) to afford rac-ethyl 2-(chloromethyl)-4-((7-ethyl-7-azaspiro[3.5]nonan-5-yl)oxy)benzoate 143 as a brown orange oil. Material was taken through to the next step without purification. LCMS [M+H]⁺: 366.3.

Step 5: rac-3-(5-((7-ethyl-7-azaspiro[3.5]nonan-5-yl)oxy)-1-oxoisoindolin-2-yl)piperidine-2,6-dione (I-144)

Compound I-144 was made according to General Method V starting from rac-ethyl 2-(chloromethyl)-4-((7-ethyl-7-azaspiro[3.5]nonan-5-yl)oxy)benzoate 143 (15 mg, 0.041 mmol). The reaction was concentrated and purified by basic reverse phase HPLC (25-50% ACN in water with 5 mM NH₄OH as modifier). Test tubes contained 3 drops formic acid prior to sample collection. Pure fractions were combined and lyophilized to afford formate salt of rac-3-(5-((7-ethyl-7-azaspiro[3.5]nonan-5-yl)oxy)-1-oxoisoindolin-2-yl)piperidine-2,6-dione I-144 as a light blue solid. LCMS [M+H]⁺: 412.2. ¹H NMR (400 MHz, DMSO-d6) δ 10.88 (s, 1H), 8.24 (s, 1H), 7.56 (d, J=8.4 Hz, 1H), 7.17 (d, J=2.2 Hz, 1H), 7.03 (dd, J=8.4, 2.2 Hz, 1H), 5.00 (dd, J=13.3, 5.0 Hz, 1H), 4.32 (dd, J=17.2, 7.3 Hz, 1H), 4.26-4.13 (m, 2H), 3.00-2.90 (m, 1H), 2.84 (ddd, J=17.3, 13.7, 5.4 Hz, 1H), 2.52 (ddd, J=17.4, 4.5, 2.4 Hz, 1H), 2.33 (td, J=13.2, 4.5 Hz, 1H), 2.27-2.17 (m, 2H), 2.11 (d, J=14.1 Hz, 2H), 1.95-1.70 (m, 4H), 1.55 (dtd, J=26.1, 9.6, 4.1 Hz, 2H), 0.91 (d, J=6.7 Hz, 4H), 0.86 (t, J=7.2 Hz, 3H).

Example 55: 3-(5-(((3S*,4S*)-1-ethyl-4-fluoropiperidin-3-yl)oxy)-1-oxoisoindolin-2-yl)piperidine-2,6-dione (I-150)

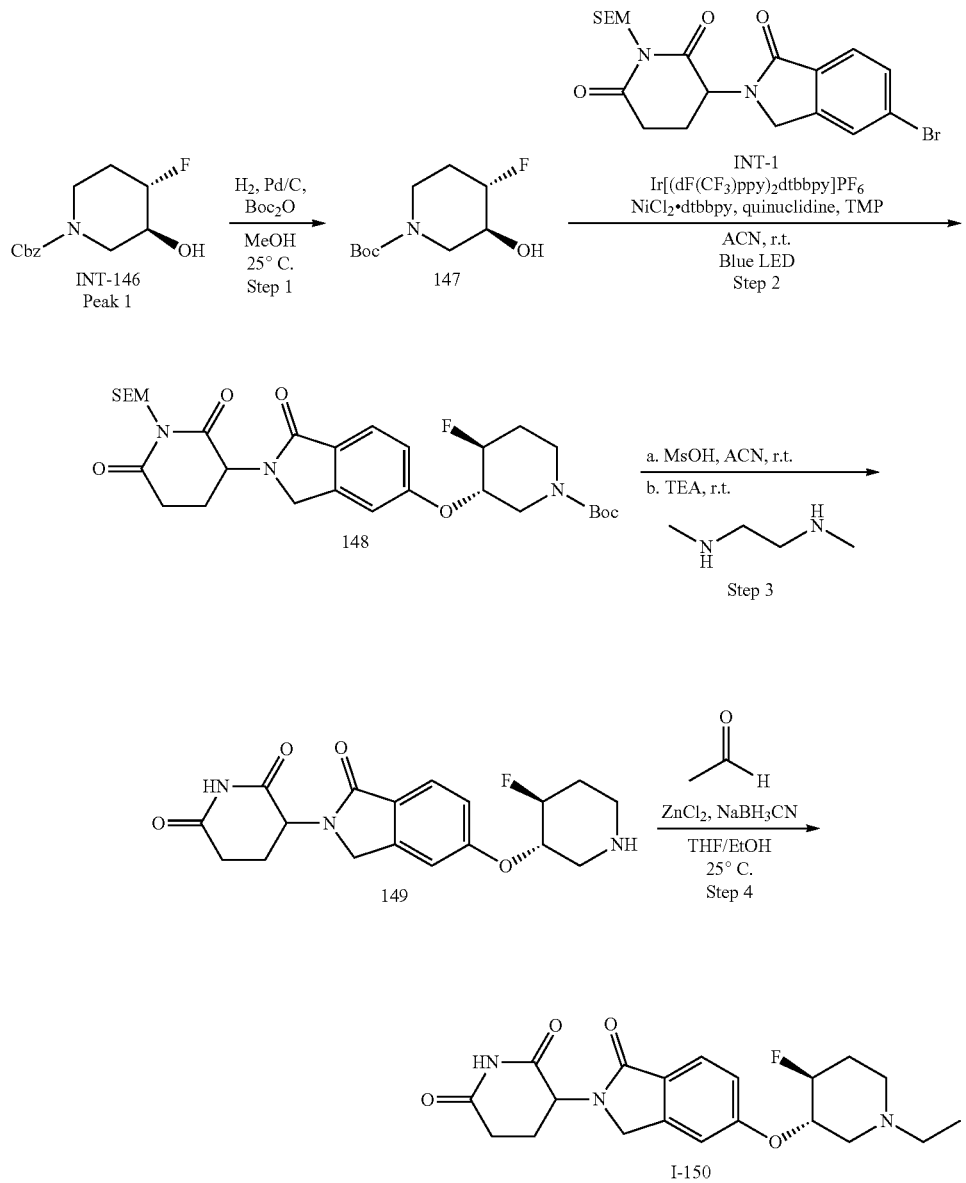

Step 1: Tert-butyl (3S*,4S*)-4-fluoro-3-hydroxypiperidine-1-carboxylate (147)

To a solution of benzyl (3S*,4S*)-4-fluoro-3-hydroxypiperidine-1-carboxylate INT-146 Peak 1 (absolute stereochemistry unknown) (230 mg, 0.91 mmol) in MeOH (2 mL) was added Boc$_2$O (218 mg, 0.23 mL, 1.0 mmol) and 10% Pd/C (50 mg, 0.047 mmol). The mixture stirred under an atmosphere of hydrogen gas at r.t. for 16 hrs. The suspension was filtered through a pad of CELITE®, the pad was washed with MeOH (3×5 mL), and the combined filtrates were concentrated. The crude material was purified by silica gel chromatography (30-55% ethyl acetate in petroleum ether) and the fractions with pure product were concentrated to afford tert-butyl (3S*,4S*)-4-fluoro-3-hydroxypiperidine-1-carboxylate 147 as a colorless oil. $^1$H NMR (400 MHz, CDCl$_3$) δ 4.60-4.41 (m, 1H), 4.00-3.72 (m, 3H), 3.11 (br s, 2H), 2.69-2.38 (m, 1H), 2.16-2.06 (m, 1H), 1.72 (br s, 1H), 1.48 (s, 9H).

Step 2: Tert-butyl (3S*,4S*)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate (148)

A mixture of 3-(5-bromo-1-oxoisoindolin-2-yl)-1-((2-(trimethylsilyl)ethoxy)methyl)piperidine-2,6-dione INT-1 (100 mg, 0.22 mmol), tert-butyl (3S*,4S*)-4-fluoro-3-hydroxypiperidine-1-carboxylate (97 mg, 0.44 mmol), Ir[dF(CF$_3$)ppy]$_2$(dtbpy)(PF$_6$) (3 mg, 0.002 mmol) and NiCl$_2$.dtbbpy (4 mg, 0.011 mmol), quinuclidine (3 mg, 0.022 mmol), TMP (62 mg, 0.44 mmol) in ACN (2.0 mL) was degassed with nitrogen gas three times. The reaction vial was sealed with parafilm, placed 2 cm away from a blue LED, and irradiated at r.t. for 16 hrs. The reaction mixture was filtered and the filter cake was washed with ACN (3×5 mL). The combined filtrates were concentrated. The crude material was purified by silica gel chromatography (20-60% EtOAc in petroleum ether) and the fractions containing pure product were concentrated to afford tert-butyl (3S*,4S*)-3-((2-(2,6-dioxo-1-((2-(trimethylsilyl)ethoxy) methyl)piperidin-3-yl)-1-oxoisoindolin-5-yl)oxy)-4-fluoropiperidine-1-carboxylate 148 as bright yellow oil. LCMS [M-27]$^+$: 564.4. $^1$H NMR (400 MHz, DMSO-d6) δ 7.66 (d, J=8.4 Hz, 1H), 7.27 (br s, 1H), 7.19-7.07 (m, 1H), 5.20-5.12 (m, 1H), 5.11-4.79 (m, 3H), 4.68-4.52 (m, 1H), 4.47-4.18 (m, 2H), 3.58-3.46 (m, 3H), 3.12-2.98 (m, 1H), 2.86-2.73 (m, 1H), 2.38-2.30 (m, 1H), 2.07 (s, 9H), 1.75 (d, J=9.6 Hz, 1H), 1.26 (br s, 5H), 0.89-0.77 (m, 2H), −0.02 (s, 9H).

Step 3: 3-(5-(((3S*,4S*)-4-fluoropiperidin-3-yl)oxy)-1-oxoisoindolin-2-yl)piperidine-2,6-dione (149)

To a mixture of tert-butyl (3S*,4S*)-3-((2-(2,6-dioxo-1-((2-(trimethylsilyl)ethoxy) methyl)piperidin-3-yl)-1-oxoisoindolin-5-yl)oxy)-4-fluoropiperidine-1-carboxylate 148 (80 mg, 0.13 mmol) in ACN (1.0 mL) was added MsOH (130 mg, 0.09 mL, 1.35 mmol). The reaction stirred at r.t. for 12 hrs. Then Et$_3$N (178 mg, 0.24 mL, 1.76 mmol) and DMEDA (20 mg, 0.02 mL, 0.23 mmol) were added and the reaction mixture stirred at r.t. for 8 hrs. The reaction mixture was concentrated, dissolved in DMSO and purified by reverse phase column chromatography (Solid phase: XB-C18, 20-35 μm, 100 Å, 0-18% acetonitrile in water with 0.1% formic acid). Fractions containing pure product were concentrated to remove ACN and then lyophilized to afford 3-(5-(((3S*,4S*)-4-fluoropiperidin-3-yl)oxy)-1-oxoisoindolin-2-yl)piperidine-2,6-dione 149 as a yellow solid. LCMS [M+H]$^+$: 362.1.

Step 4: 3-(5-(((3S*,4S*)-1-ethyl-4-fluoropiperidin-3-yl)oxy)-1-oxoisoindolin-2-yl)piperidine-2,6-dione (I-150)

To a mixture of 3-(5-(((3S*,4S*)-4-fluoropiperidin-3-yl)oxy)-1-oxoisoindolin-2-yl)piperidine-2,6-dione 149 (20 mg, 0.06 mmol) and acetaldehyde (49 mg, 0.44 mmol, 40%) in THF:EtOH (1:1, 0.5 mL) was added 2M ZnCl$_2$ in THF (0.08 mL, 0.17 mmol) and stirred at r.t. for 1 hr. NaBH$_3$CN (10 mg, 0.17 mmol) was added to the reaction mixture and the reaction mixture stirred at r.t. for 15 hrs. Additional acetaldehyde (30 mg, 0.26 mmol 40%) was added to the reaction mixture and stirred at r.t. for 16 hrs. The suspension was filtered and the filter cake was washed with ACN (3×5 mL). The combined filtrates were concentrated. The crude material was dissolved in DMSO and purified by reverse phase HPLC (1-25% ACN in water with 0.225% formic acid as modifier). The fractions containing pure product were concentrated to remove the ACN and lyophilized to afford formate salt 3-(5-(((3S*,4S*)-1-ethyl-4-fluoropiperidin-3-yl)oxy)-1-oxoisoindolin-2-yl)piperidine-2,6-dione I-150 as an off-white solid. LCMS [M+H]$^+$: 390.1. $^1$H NMR (400 MHz, ACETONITRILE-d3) δ 9.04 (br s, 1H), 8.19 (s, 1H), 7.65 (d, J=8.4 Hz, 1H), 7.20 (s, 1H), 7.11-7.00 (m, 1H), 5.04-5.95 (m, 1H), 4.82-4.59 (m, 2H), 4.40-4.23 (m, 2H), 3.32-3.22 (m, 1H), 3.02-2.93 (m, 1H), 2.87-2.68 (m, 2H), 2.61 (q, J=7.2 Hz, 2H), 2.48-2.32 (m, 3H), 2.28-2.16 (m, 1H), 2.10-1.98 (m, 1H), 1.93 (br s, 1H), 1.08 (t, J=7.2 Hz, 3H). $^{19}$F NMR (400 MHz, ACETONITRILE-d3) δ −185.5. The absolute stereochemistry at the 3- and 4-position of the piperidine ring was not determined.

Example 56: 3-(5-(((3R*,4R*)-1-ethyl-4-fluoropiperidin-3-yl)oxy)-1-oxoisoindolin-2-yl)piperidine-2,6-dione (I-154)

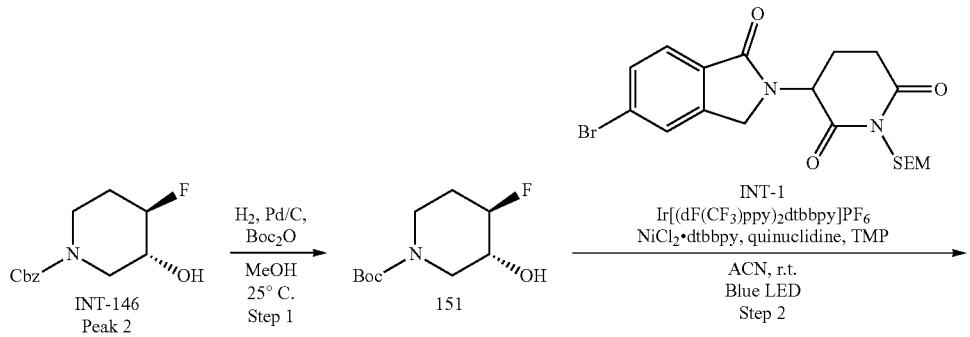

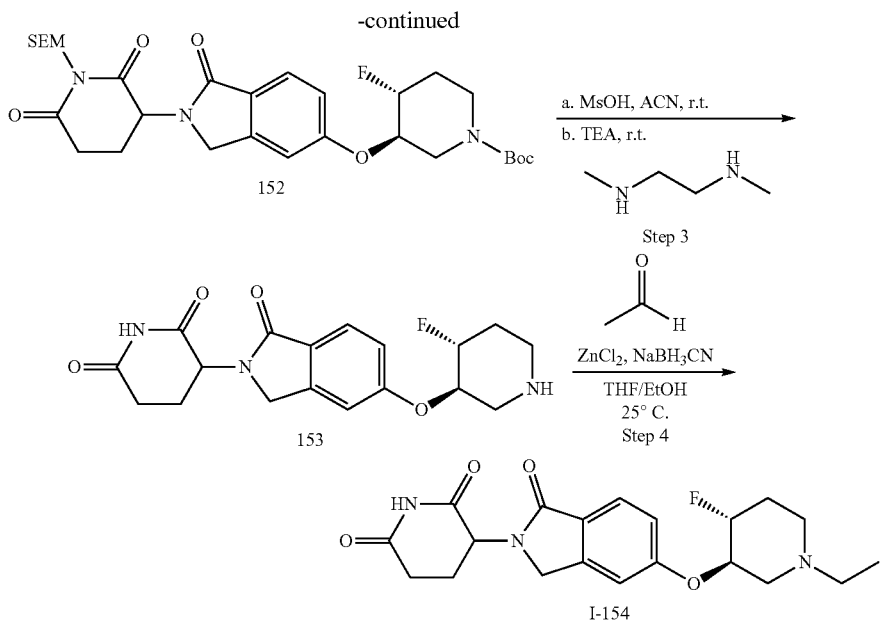

Step 1: Tert-butyl (3R*,4R*)-4-fluoro-3-hydroxypiperidine-1-carboxylate (151)

To a mixture of benzyl (3R*,4R*)-4-fluoro-3-hydroxypiperidine-1-carboxylate INT-146 peak 2 (absolute stereochemistry undetermined) (240 mg, 0.95 mmol) in MeOH (2.0 mL) was added Boc$_2$O (227 mg, 0.24 mL, 1.04 mmol) and 10% Pd/C (50 mg, 0.047 mmol). The mixture stirred under an atmosphere of hydrogen gas at r.t. for 16 hrs. The suspension was filtered through a pad of CELITE®, the pad was washed with MeOH (3×5 mL), and the combined filtrates were concentrated. The crude material was purified by silica gel chromatography (20-50% ethyl acetate in petroleum ether) and the fractions with pure product were concentrated to afford tert-butyl (3R*,4R*)-4-fluoro-3-hydroxypiperidine-1-carboxylate 151 as a colorless oil. $^1$H NMR (400 MHz, CDCl$_3$) δ 4.60-4.39 (m, 1H), 4.04-3.72 (m, 3H), 3.10 (d, J=1.6 Hz, 2H), 2.54-2.30 (m, 1H), 2.16-2.03 (m, 1H), 1.82-1.68 (m, 1H), 1.48 (s, 9H).

Step 2: Tert-butyl (3R*,4R*)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate (152)

A mixture of 3-(5-bromo-1-oxoisoindolin-2-yl)-1-((2-(trimethylsilyl)ethoxy)methyl)piperidine-2,6-dione INT-1 (100 mg, 0.22 mmol), tert-butyl (3R*,4R*)-4-fluoro-3-hydroxypiperidine-1-carboxylate 151 (73 mg, 0.33 mmol), Ir[dF(CF$_3$)ppy]$_2$(dtbpy)(PF$_6$) (3 mg, 0.002 mmol) and NiCl$_2$.dtbbpy (4 mg, 0.011 mmol), quinuclidine (2 mg, 0.022 mmol), TMP (62 mg, 0.44 mmol) in ACN (2.0 mL) was degassed three times under N$_2$. The reaction vial was sealed with parafilm, placed 2 cm away from one blue LED, and irradiated at r.t. for 16 hrs. The reaction mixture was filtered and the filter cake was washed with ACN (3×5 mL) and the combined filtrates were concentrated. The crude material was purified by reverse phase column chromatography (Solid phase: XB-C18, 20-35 μm, 100 Å, Mobile phase: 0-24% acetonitrile in water with 0.1% formic acid as modifier) and the fractions with pure product were concentrated to afford tert-butyl (3R*,4R*)-3-((2-(2,6-dioxo-1-((2-(trimethylsilyl)ethoxy) methyl)piperidin-3-yl)-1-oxoisoindolin-5-yl)oxy)-4-fluoropiperidine-1-carboxylate 152 as a white solid. LCMS [M+H-28]$^+$: 564.4.

Step 3: 3-(5-(((3R*,4R*)-4-fluoropiperidin-3-yl)oxy)-1-oxoisoindolin-2-yl)piperidine-2,6-dione (153)

MsOH (57 mg, 0.04 mL, 0.59 mmol) was added to a mixture of tert-butyl (3R*,4R*)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate 152 (30 mg, 0.059 mmol) in ACN (0.5 mL). The reaction mixture stirred at r.t. for 12 hrs. Et$_3$N (79 mg, 0.1 mL, 0.77 mmol) and DMEDA (9 mg, 0.01 mL, 0.10 mmol) were added dropwise and the mixture stirred at r.t. for 8 hrs. The reaction was concentrated to afford crude 3-(5-(((3R*,4R*)-4-fluoropiperidin-3-yl)oxy)-1-oxoisoindolin-2-yl)piperidine-2,6-dione 153. Material was taken on to the next step without purification. LCMS [M+H]$^+$: 362.1.

Step 4: 3-(5-(((3R*,4R*)-1-ethyl-4-fluoropiperidin-3-yl)oxy)-1-oxoisoindolin-2-yl)piperidine-2,6-dione (I-154)

2M ZnCl$_2$ in THF (0.2 mL, 0.42 mmol) was added to a mixture of 3-(5-(((3R*,4R*)-4-fluoropiperidin-3-yl)oxy)-1-oxoisoindolin-2-yl)piperidine-2,6-dione 153 (50 mg, 0.12 mmol) and acetaldehyde (64 mg, 0.6 mmol, 40%) in THF:EtOH (1:1, 0.5 mL) at r.t. and stirred for 1 hr. NaBH$_3$CN (26 mg, 0.42 mmol) was added and the reaction stirred at r.t. for 15 hrs. Additional acetaldehyde (64 mg, 0.6 mmol, 40%) was added and the reaction stirred at r.t. for 32 hrs. The reaction mixture was concentrated. The crude material was dissolved in DMSO and purified by reverse phase HPLC (1-25% ACN in water with 0.225% formic acid as modifier). Fractions with pure product were concentrated to afford formate salt 3-(5-(((3R*,4R*)-1-ethyl-4-fluoropiperidin-3-yl)oxy)-1-oxoisoindolin-2-yl)piperidine-2,6-dione I-154 as a yellow solid. LCMS [M+H]$^+$: 390.1 m/z. $^1$H NMR (400

MHz, DMSO-d6) δ 10.99 (br s, 1H), 8.23 (s, 1H), 7.64 (d, J=8.4 Hz, 1H), 7.29 (s, 1H), 7.13-6.50 (m, 1H), 5.09-4.95 (m, 1H), 4.81-4.58 (m, 2H), 4.46-4.25 (m, 2H), 3.15-3.09 (m, 1H), 2.97-2.88 (m, 1H), 2.87-2.80 (m, 1H), 2.65-2.60 (m, 1H), 2.42-2.35 (m, 3H), 2.17-2.05 (m, 3H), 2.04-1.97 (m, 1H), 1.86-1.74 (m, 1H), 1.00 (t, J=7.2 Hz, 3H). $^{19}$F NMR (377 MHz, DMSO-d$_6$) δ −181.9. The absolute stereochemistry at the 3- and 4-position of the piperidine ring was not determined.

Example 57: 3-(5-(((3S*,4R*)-1-ethyl-4-fluoropiperidin-3-yl)oxy)-1-oxoisoindolin-2-yl)piperidine-2,6-dione (I-159)

mg, 1.7 mmol) in MeOH (5.0 mL) at r.t. and stirred under an atmosphere of hydrogen gas for 16 hrs. The suspension was filtered through a pad of CELITE® and the filter cake was washed with MeOH (3×5 mL). The combined filtrates were concentrated. The crude material was purified by silica gel chromatography (40-60% EtOAc in petroleum ether) and the fractions containing pure product were collected and concentrated to afford tert-butyl (3S*,4R*)-4-fluoro-3-hydroxypiperidine-1-carboxylate 156 as colorless oil. $^1$H NMR (400 MHz, DMSO-d6) δ 5.17 (d, J=4.8 Hz, 1H), 4.83-4.60 (m, 1H), 3.64-3.39 (m, 3H), 3.22-3.00 (m, 2H), 1.94-1.82 (m, 1H), 1.73-1.53 (m, 1H), 1.39 (s, 9H)

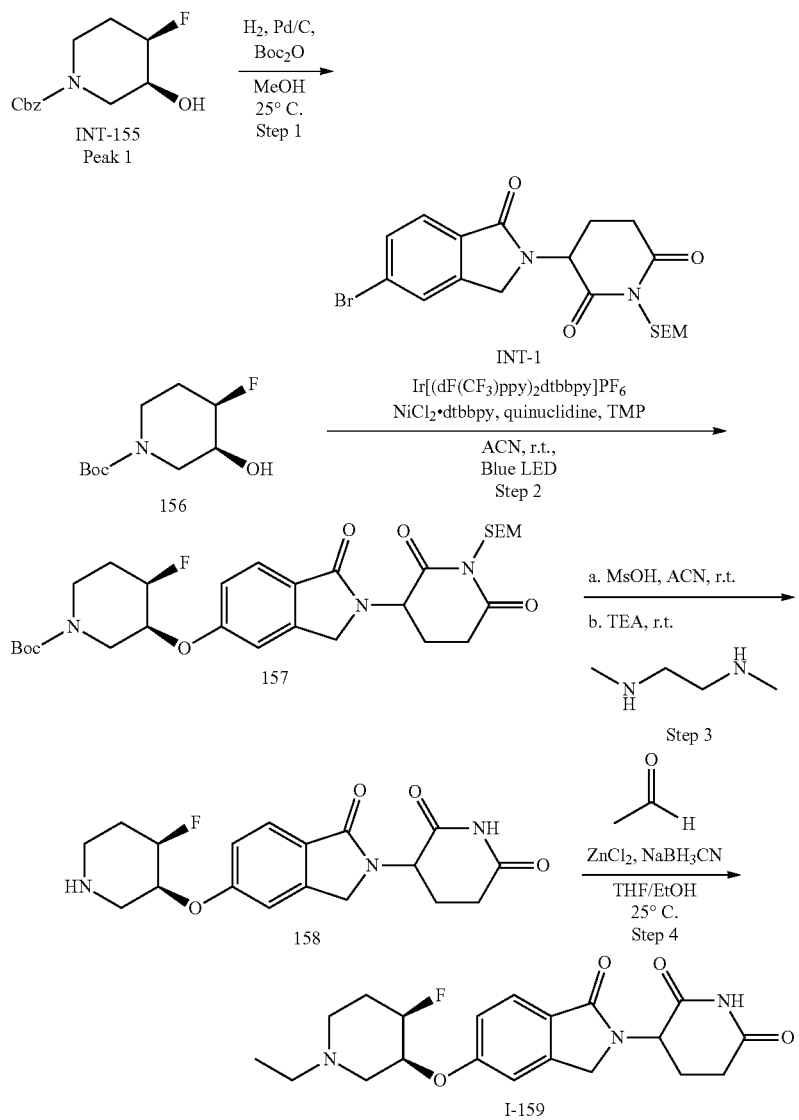

Step 1: Tert-butyl (3S*,4R*)-4-fluoro-3-hydroxypiperidine-1-carboxylate (156)

Boc$_2$O (371 mg, 0.39 mL, 1.7 mmol) and 10% Pd/C (100 mg, 0.094 mmol) were added to a solution of benzyl (3S,4R)-4-fluoro-3-hydroxypiperidine-1-carboxylate INT-155 Peak 1 (absolute stereochemistry undetermined) (430

Step 2: Tert-butyl (3S*,4R*)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate (157)

A mixture of 3-(5-bromo-1-oxoisoindolin-2-yl)-1-((2-(trimethylsilyl)ethoxy)methyl)piperidine-2,6-dione INT-1

(250 mg, 0.55 mmol), tert-butyl (3S*,4R*)-4-fluoro-3-hydroxypiperidine-1-carboxylate 156 (242 mg, 1.1 mmol), Ir[dF(CF$_3$)ppy]$_2$(dtbpy)(PF$_6$) (7 mg, 0.006 mmol), NiCl$_2$.dtbbpy (1 mg, 0.003 mmol), quinuclidine (7 mg, 0.06 mmol), TMP (155 mg, 1.1 mmol) in ACN (4.0 mL) was degassed three times under N2. The reaction vial was sealed with parafilm, placed 2 cm away from one blue LED, and irradiated at r.t. for 16 hrs. The reaction mixture was filtered and the filter cake was washed with ACN (3×5 mL). The filtrates were combined and concentrated. The crude material was purified by silica gel chromatography (0-100% EtOAc in petroleum ether) and fractions containing pure product were concentrated to afford tert-butyl (3S*,4R)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate 157 as a green oil. LCMS [M+H-28]$^+$: 564.4 m/z. $^1$H NMR (400 MHz, DMSO-d$_6$) δ 7.65 (d, J=8.4 Hz, 1H), 7.28-7.22 (m, 1H), 7.17-7.06 (m, 1H), 5.19-5.17 (m, 1H), 5.11-4.94 (m, 3H), 4.86-4.73 (m, 1H), 4.43-4.41 (m, 1H), 4.23-4.20 (m, 1H), 3.55-3.53 (m, 1H), 3.52-3.50 (m, 3H), 3.13-2.98 (m, 2H), 2.78-2.76 (m, 2H), 2.38-2.30 (m, 1H), 2.03-1.79 (m, 3H), 1.40-1.10 (m, 9H), 0.83-0.81 (m, 2H), −0.02 (s, 9H).

Step 3: 3-(5-(((3S*,4R*)-4-fluoropiperidin-3-yl)oxy)-1-oxoisoindolin-2-yl)piperidine-2,6-dione (158)

MsOH (406 mg, 0.27 mL, 4.22 mmol) was added to a solution of tert-butyl (3S*,4R*)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate 157 (250 mg, 0.42 mmol) in ACN (3.0 mL) and stirred at 40° C. for 2 hrs. Et$_3$N (556 mg, 0.76 mL, 5.5 mmol) and DMEDA (63 mg, 0.08 mL, 0.71 mmol) were added and the reaction mixture stirred at r.t. for 14 hrs. The reaction mixture was concentrated. The crude material was dissolved in DMSO and purified by reverse phase column chromatography [Column: XB-C$_{18}$ (20-35 μm, 100 Å); 0%-20% ACN in H$_2$O with 0.1% formic acid as modifier]. The fractions with pure product were concentrated to afford formate salt 3-(5-(((3S*, 4R*)-4-fluoropiperidin-3-yl)oxy)-1-oxoisoindolin-2-yl)piperidine-2,6-dione 158 as a yellow solid. LCMS [M+H]$^+$: 362.2 m/z. $^1$H NMR (400 MHz, DMSO-d$_6$) δ 10.98 (br s, 1H), 8.21 (s, 1H), 7.64 (d, J=8.4 Hz, 1H), 7.26 (s, 1H), 7.14-7.12 (m, 1H), 5.09-5.05 (m, 2H), 4.73-4.68 (m, 1H), 4.42-4.24 (m, 2H), 3.06-2.82 (m, 4H), 2.79-2.71 (m, 1H), 2.60-2.55 (m, 1H), 2.40-2.35 (m, 2H), 2.06-1.77 (m, 3H).

Step 4: 3-(5-(((3S*,4R*)-1-ethyl-4-fluoropiperidin-3-yl)oxy)-1-oxoisoindolin-2-yl)piperidine-2,6-dione (I-159)

2M ZnCl$_2$ in THF (0.37 mL, 0.74 mmol) was added to a solution of 3-(5-(((3S*,4R*)-4-fluoropiperidin-3-yl)oxy)-1-oxoisoindolin-2-yl)piperidine-2,6-dione 158 (100 mg, 0.25 mmol) and acetaldehyde (270 mg, 2.45 mmol, 40%) in THF:EtOH (1:1, 1 mL) at r.t. and stirred for 1 hr. NaBH$_3$CN (46 mg, 0.74 mmol) was added and the reaction mixture stirred at r.t. for 15 hrs. The suspension was concentrated. The crude material was dissolved in DMSO and purified by reverse phase HPLC (1-25% ACN in water with 0.225% formic acid as modifier). The fractions containing pure product were concentrated to afford formate salt 3-(5-(((3S*, 4R*)-1-ethyl-4-fluoropiperidin-3-yl)oxy)-1-oxoisoindolin-2-yl)piperidine-2,6-dione I-159 as a white solid. LCMS [M+H]$^+$: 390.1. $^1$H NMR (400 MHz, ACETONITRILE-d$_3$) δ 9.02 (br s, 1H), 8.20 (s, 1H), 7.66 (d, J=8.4 Hz, 1H), 7.18 (s, 1H), 7.10 (d, J=8.4 Hz, 1H), 5.11-4.91 (m, 2H), 4.84-4.71 (m, 1H), 4.39-4.25 (m, 2H), 3.05 (d, J=10.4 Hz, 1H), 2.86-2.70 (m, 4H), 2.67-2.55 (m, 3H), 2.45-2.34 (m, 1H), 2.23-1.98 (m, 3H), 1.10 (t, J=7.2 Hz, 3H). The absolute stereochemistry at the 3- and 4-position of the piperidine ring was not determined.

Example 58: 3-(5-(((3R*,4S*)-1-ethyl-4-fluoropiperidin-3-yl)oxy)-1-oxoisoindolin-2-yl)piperidine-2,6-dione (I-163)

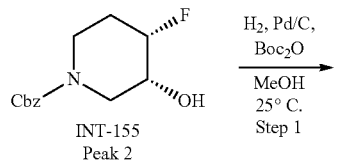

INT-155
Peak 2

H$_2$, Pd/C,
Boc$_2$O
────────→
MeOH
25° C.
Step 1

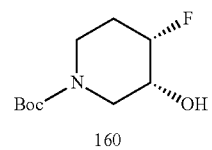

160

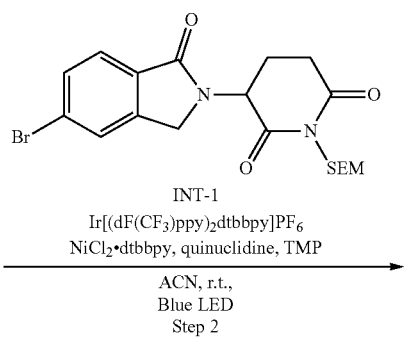

INT-1

Ir[(dF(CF$_3$)ppy)$_2$dtbbpy]PF$_6$
NiCl$_2$•dtbbpy, quinuclidine, TMP
────────────────→
ACN, r.t.,
Blue LED
Step 2

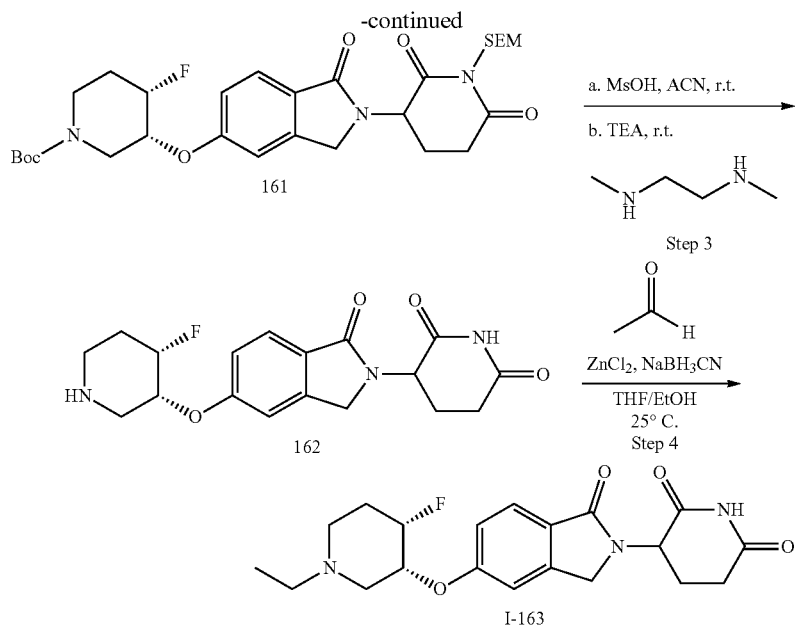

Step 1: Tert-butyl (3R*,4S*)-4-fluoro-3-hydroxypiperidine-1-carboxylate (160)

Boc₂O (389 mg, 0.41 mL, 1.78 mmol) and 10% Pd/C (100 mg, 0.094 mmol) were added to a solution of benzyl (3R,4S)-4-fluoro-3-hydroxypiperidine-1-carboxylate INT-155 Peak 2 (absolute stereochemistry undetermined) (430 mg, 1.7 mmol) in MeOH (5.0 mL) at 25° C. and stirred under an atmosphere of hydrogen gas for 16 hrs. The suspension was filtered through a pad of CELITE® and the filter cake was washed with MeOH (3×5 mL). The combined filtrates were concentrated. The crude material was purified by silica gel chromatography (40-60% EtOAc in petroleum ether) and the fractions containing pure product were collected and concentrated to afford tert-butyl (3R*,4S*)-4-fluoro-3-hydroxypiperidine-1-carboxylate 160 as a colorless oil. $^1$H NMR (400 MHz, DMSO-d6) δ 5.17 (d, J=5.2 Hz, 1H), 4.86-4.58 (m, 1H), 3.65-3.37 (m, 3H), 3.23-3.00 (m, 2H), 1.94-1.80 (m, 1H), 1.74-1.54 (m, 1H), 1.39 (s, 9H).

Step 2: Tert-butyl (3R*,4S*)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate (161)

A mixture of 3-(5-bromo-1-oxoisoindolin-2-yl)-1-((2-(trimethylsilyl)ethoxy)methyl)piperidine-2,6-dione INT-1 (260 mg, 0.57 mmol), tert-butyl (3R*,4S*)-4-fluoro-3-hydroxypiperidine-1-carboxylate 160 (250 mg, 1.15 mmol), Ir[dF(CF₃)ppy]₂(dtbpy)(PF₆) (7 mg, 0.006 mmol), NiCl₂.dtbbpy (1 mg, 0.003 mmol), quinuclidine (7 mg, 0.006 mmol), TMP (162 mg, 1.15 mmol) in ACN (4.0 mL) was degassed three times under N2. The reaction vial was sealed with parafilm, placed 2 cm away from one blue LED, and irradiated at r.t. for 16 hrs. The reaction mixture was filtered and the filter cake was washed with ACN (3×5 mL). The filtrates were combined and concentrated. The crude material was purified by silica gel chromatography (0-100% EtOAc in petroleum ether) and fractions containing pure product were concentrated to afford tert-butyl (3R*,4S*)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate as a green oil. LCMS [M-27]⁺: 564.4. $^1$H NMR (400 MHz, DMSO-d6) δ 7.66 (d, J=8.4 Hz, 1H), 7.25-7.11 (m, 1H), 7.16-7.09 (m, 1H), 5.22-5.20 (m, 1H), 5.11-4.97 (m, 3H), 4.86-4.73 (m, 1H), 4.42-4.39 (m, 1H), 4.24-4.21 (m, 1H), 3.55-3.52 (m, 3H), 3.22-2.91 (m, 2H), 2.85-2.74 (m, 1H), 2.39-2.30 (m, 1H), 2.07-2.01 (m, 2H), 1.95-1.81 (m, 1H), 1.41 (br d, J=6.8 Hz, 2H), 1.18 (t, J=7.2 Hz, 9H), 0.84-0.80 (m, 2H), 0.01-0.04 (m, 9H).

Step 3: 3-(5-(((3R*,4S*)-4-fluoropiperidin-3-yl)oxy)-1-oxoisoindolin-2-yl)piperidine-2,6-dione (162)

MsOH (422 mg, 0.29 mL, 4.4 mmol) was added to a solution of tert-butyl (3R*,4S*)-3-((2-(2,6-dioxo-1-((2-(trimethylsilyl)ethoxy)methyl)piperidin-3-yl)-1-oxoisoindolin-5-yl)oxy)-4-fluoropiperidine-1-carboxylate 161 (260 mg, 0.44 mmol) in ACN (3.0 mL) and stirred at 40° C. for 2 hrs. Et₃N (578 mg, 0.79 mL, 5.7 mmol) and DMEDA (65 mg, 0.08 mL, 0.74 mmol) were added and the reaction mixture stirred at r.t. for 14 hrs. The reaction mixture was concentrated. The crude material was dissolved in DMSO and purified by reverse phase column chromatography [Column: XB-C18 (20-35 μm, 100 Å); 0%-20% ACN in H₂O with 0.1% formic acid as modifier]. The fractions with pure product were concentrated to afford formate salt 3-(5-(((3R*,4S*)-4-fluoropiperidin-3-yl)oxy)-1-oxoisoindolin-2-yl)piperidine-2,6-dione 162 as a yellow solid. LCMS [M+H]⁺: 362.2. $^1$H NMR (400 MHz, DMSO-d₆) δ 10.98 (br s, 1H), 8.21 (s, 1H), 7.64 (d, J=8.4 Hz, 1H), 7.26 (s, 1H), 7.13-7.10 (m, 1H), 5.13-4.95 (m, 2H), 4.69-4.65 (m, 1H), 4.37-4.30 (m, 1H), 4.29 (d, J=4.0 Hz, 1H), 3.06-2.65 (m, 5H), 2.63-2.55 (m, 1H), 2.39-2.30 (m, 2H), 2.06-1.78 (m, 3H).

Step 4: 3-(5-(((3R*,4S*)-1-ethyl-4-fluoropiperidin-3-yl)oxy)-1-oxoisoindolin-2-yl)piperidine-2,6-dione (I-163)

2M ZnCl₂ in THF (0.37 mL, 0.74 mmol) was added to a solution of 3-(5-(((3R*,4S*)-4-fluoropiperidin-3-yl)oxy)-1- oxoisoindolin-2-yl)piperidine-2,6-dione 162 (100 mg, 0.25 mmol) and acetaldehyde (270 mg, 2.45 mmol, 40%) in THF:EtOH (1:1, 1 mL) at r.t. and stirred for 1 hr. NaBH₃CN (46 mg, 0.74 mmol) was added and the reaction mixture stirred at r.t. for 15 hrs. The suspension was concentrated. The crude material was dissolved in DMSO and purified by reverse phase HPLC (1-25% ACN in water with 0.225% formic acid as modifier). The fractions containing pure product were concentrated to afford formate salt 3-(5-(((3R*,4S*)-1-ethyl-4-fluoropiperidin-3-yl)oxy)-1-oxoisoindolin-2-yl)piperidine-2,6-dione I-163 as a white solid. LCMS [M+H]⁺: 390.1. ¹H NMR (400 MHz, ACETONITRILE-d₃) δ 9.08-8.80 (m, 1H), 8.15 (br s, 1H), 7.66 (d, J=8.4 Hz, 1H), 7.26-6.99 (m, 2H), 5.10-4.87 (m, 2H), 4.75-4.62 (m, 1H), 4.40-4.22 (m, 2H), 2.91 (d, J=9.6 Hz, 1H), 2.82-2.60 (m, 4H), 2.56-2.49 (m, 3H), 2.17-2.06 (m, 2H), 2.02-1.95 (m, 1H), 1.92-1.82 (m, 1H), 1.06 (t, J=7.2 Hz, 3H). The absolute stereochemistry at the 3- and 4-position of the piperidine ring was not determined.

Example 59: 3-(5-(((3R,5S)-1-ethyl-5-fluoropiperidin-3-yl)oxy)-1-oxoisoindolin-2-yl)piperidine-2,6-dione (I-169)

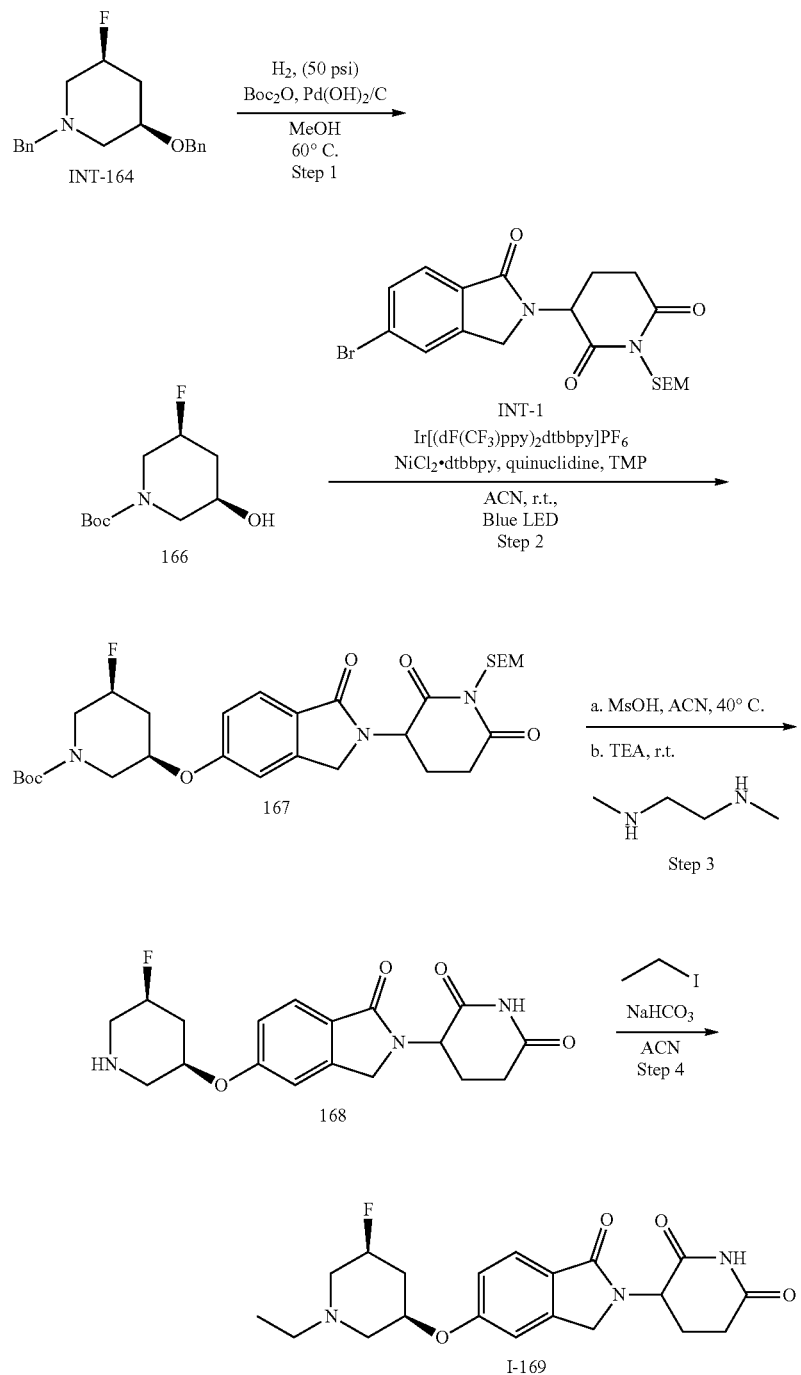

Step 1: Tert-butyl (3S,5R)-3-fluoro-5-hydroxypiperidine-1-carboxylate (166)

Boc$_2$O (1.2 g, 5.5 mmol) and 10% Pd(OH)$_2$/C (300 mg, 0.21 mmol) were added to a solution of (3R,5S)-1-benzyl-3-(benzyloxy)-5-fluoropiperidine INT-164 (1.4 g, 4.5 mmol) in MeOH (20.0 mL) at r.t. The reaction mixture stirred at 60° C. for 16 hrs under hydrogen gas (50 psi). The suspension was filtered through a pad of CELITE®, the pad was washed with MeOH (3×10 mL), and the filtrate was concentrated. The crude material was purified by silica gel chromatography (30-60% EtOAc in petroleum ether) and the fractions containing pure compound were combined and concentrated to afford tert-butyl (3S,5R)-3-fluoro-5-hydroxypiperidine-1-carboxylate 166 as a colorless oil. $^1$H NMR (400 MHz, CDCl$_3$) δ 4.91-4.61 (m, 1H), 3.85 (br s, 2H), 3.65 (br d, J=9.9 Hz, 1H), 3.54-3.27 (m, 2H), 2.41-2.23 (m, 1H), 2.16-1.99 (m, 2H), 1.48 (s, 9H). $^{19}$F NMR (377 MHz, CDCl$_3$) δ −181.4.

Step 2: Tert-butyl (3R,5S)-3-((2-(2,6-dioxo-1-((2-(trimethylsilyl)ethoxy)methyl)piperidin-3-yl)-1-oxoisoindolin-5-yl)oxy)-5-fluoropiperidine-1-carboxylate (167)

A mixture of (3S,5R)-3-fluoro-5-hydroxypiperidine-1-carboxylate 166 (387 mg, 1.8 mmol), 3-(5-bromo-1-oxoisoindolin-2-yl)-1-((2-(trimethylsilyl)ethoxy)methyl)piperidine-2,6-dione INT-1 (400 mg, 0.88 mmol), Ir[dF(CF$_3$)ppy]$_2$(dtbpy)(PF$_6$) (10 mg, 0.009 mmol) and NiCl$_2$.dtbbpy (18 mg, 0.044 mmol), quinuclidine (10 mg, 0.088 mmol), TMP (249 mg, 1.76 mmol) in ACN (8.0 mL) was degassed three times under N$_2$. The reaction vial was sealed with parafilm, placed 2 cm away from a blue LED, and irradiated at r.t. for 16 hr. The reaction mixture was filtered, the filter cake was washed with EtOAc (3×10 mL) and the combined filtrates were concentrated. The crude material was purified by silica gel chromatography (50-80% EtOAc in petroleum ether) and concentrated to to afford tert-butyl (3R,5S)-3-((2-(2,6-dioxo-1-((2-(trimethylsilyl)ethoxy)methyl)piperidin-3-yl)-1-oxoisoindolin-5-yl)oxy)-5-fluoropiperidine-1-carboxylate 167 as a bright yellow solid. $^1$H NMR (400 MHz, CDCl$_3$) δ 7.82 (d, J=8.4 Hz, 1H), 7.14-6.92 (m, 2H), 5.32-5.13 (m, 3H), 4.72-4.02 (m, 6H), 3.72-3.55 (m, 2H), 3.36-2.81 (m, 4H), 2.57-2.50 (m, 1H), 2.43-2.14 (m, 2H), 2.05-1.90 (m, 1H), 1.47 (br s, 9H), 1.00-0.90 (m, 2H), 0.01 (s, 9H). $^{19}$F NMR (377 MHz, CDCl$_3$) δ −182.6.

Step 3: 3-(5-(((3R,5S)-5-fluoropiperidin-3-yl)oxy)-1-oxoisoindolin-2-yl)piperidine-2,6-dione (168)

MsOH (568 mg, 0.38 mL, 5.9 mmol) was added to a solution of tert-butyl (3R,5S)-3-((2-(2,6-dioxo-1-((2-(trimethylsilyl)ethoxy) methyl)piperidin-3-yl)-1-oxoisoindolin-5-yl)oxy)-5-fluoropiperidine-1-carboxylate 167 (350 mg, 0.59 mmol) in ACN (2.1 mL) and stirred at 40° C. for 2 hrs. The reaction mixture was cooled to 0° C., Et$_3$N (777 mg, 1.1 mL, 7.7 mmol) was added drop wise followed by DMEDA (104 mg, 0.13 mL, 1.2 mmol). The reaction mixture stirred at r.t. for 14 hrs. The reaction mixture was concentrated and the crude material was purified by reverse phase HPLC (2-32% ACN in water with 10 mM NH$_4$HCO$_3$ as modifier). Fractions containing pure material were collected and concentrated to afford formate salt tert-butyl (3R,5S)-3-((2-(2,6-dioxo-1-((2-(trimethylsilyl)ethoxy)methyl)piperidin-3-yl)-1-oxoisoindolin-5-yl)oxy)-5-fluoropiperidine-1-carboxylate 168 as a light yellow solid. $^1$H NMR (400 MHz, DMSO-d6) δ 7.62 (d, J=8.4 Hz, 1H), 7.21 (s, 1H), 7.08-7.05 (m, 1H), 5.10-5.04 (m, 1H), 4.77-4.34 (m, 6H), 4.33-4.20 (m, 1H), 3.12-3.09 (m, 2H), 2.95-2.85 (m, 1H), 2.65-2.56 (m, 2H), 2.44-2.29 (m, 2H), 2.01-1.95 (m, 1H), 1.70-1.62 (m, 1H).

Step 4: 3-(5-(((3R,5S)-1-ethyl-5-fluoropiperidin-3-yl)oxy)-1-oxoisoindolin-2-yl)piperidine-2,6-dione (I-169)

A mixture of tert-butyl (3R,5S)-3-((2-(2,6-dioxo-1-((2-(trimethylsilyl)ethoxy)methyl)piperidin-3-yl)-1-oxoisoindolin-5-yl)oxy)-5-fluoropiperidine-1-carboxylate 168 (80 mg, 0.22 mmol), iodoethane (41 mg, 0.27 mmol) and NaHCO$_3$ (56 mg, 0.68 mmol) in ACN (1.0 mL) stirred at 80° C. for 16 hrs. The reaction mixture was concentrated and the crude material was purified by reverse phase HPLC (15-48% ACN in water with 10 mM NH$_4$HCO$_3$ as modifier). Fractions containing pure product were acidified with formic acid to pH 6 and concentrated to afford 3-(5-(((3R,5S)-1-ethyl-5-fluoropiperidin-3-yl)oxy)-1-oxoisoindolin-2-yl)piperidine-2,6-dione I-169 as an off-white solid. LCMS [M+H]$^+$: 390.3. $^1$H NMR (400 MHz, ACETONITRILE-d$_3$) δ 9.04-8.75 (m, 1H), 8.10 (s, 1H), 7.65 (d, J=8.4 Hz, 1H), 7.12 (d, J=1.6 Hz, 1H), 7.05-7.02 (m, 1H), 5.06-5.01 (m, 1H), 4.84-4.60 (m, 1H), 4.53-4.49 (m, 1H), 4.41-4.23 (m, 2H), 3.13-3.01 (m, 2H), 2.87-2.77 (m, 1H), 2.73-2.72 (m, 1H), 2.59-2.53 (m, 3H), 2.45-2.34 (m, 1H), 2.32-2.20 (m, 2H), 2.10-2.09 (m, 1H), 1.74-1.60 (m, 1H), 1.06-1.03 (m, 3H). $^{19}$F NMR (377 MHz, ACETONITRILE-d$_3$) δ −183.1.

Example 60: 3-(5-(((3R,5R)-1-ethyl-5-fluoropiperidin-3-yl)oxy)-1-oxoisoindolin-2-yl)piperidine-2,6-dione (I-173)

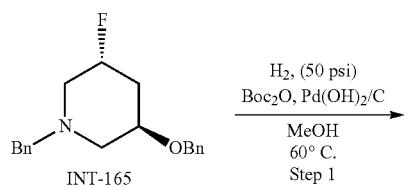

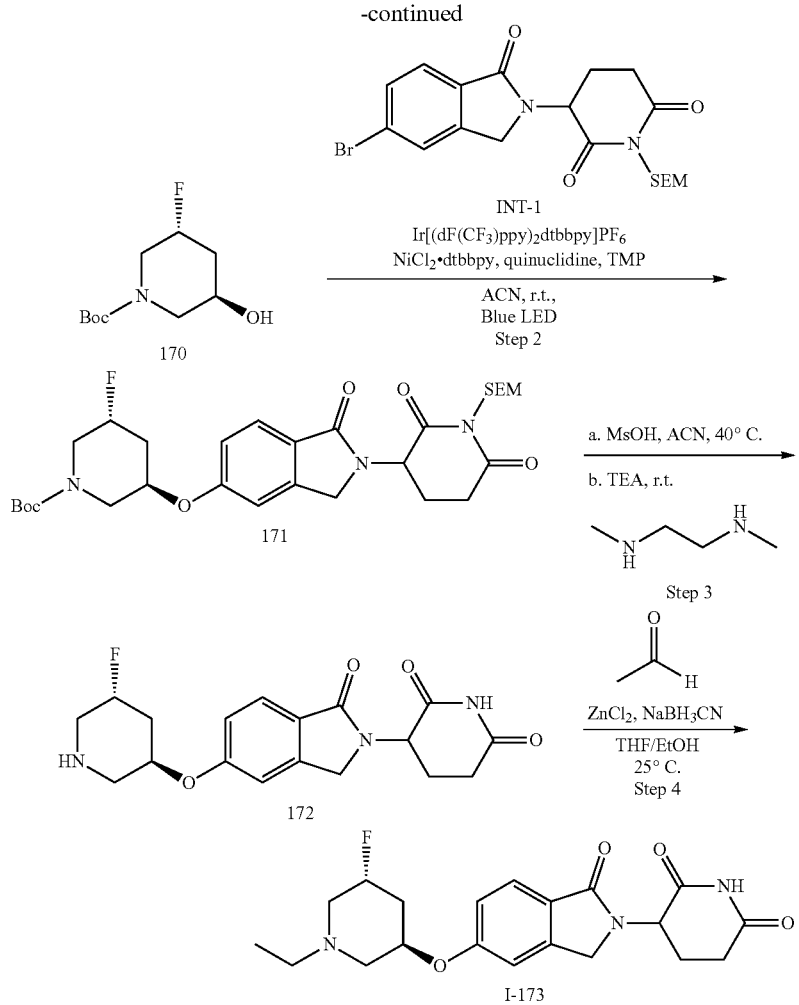

Step 1: Tert-butyl (3R,5R)-3-fluoro-5-hydroxypiperidine-1-carboxylate (170)

Boc$_2$O (1.3 g, 6.0 mmol) and 10% Pd(OH)$_2$/C (300 mg, 0.21 mmol) were added to a solution of (3R,5R)-1-benzyl-3-(benzyloxy)-5-fluoropiperidine INT-165 (1.5 g, 5.0 mmol) in MeOH (30.0 mL) at r.t. The reaction mixture stirred at 60° C. for 16 hrs under H$_2$ (50 psi). The suspension was filtered through a pad of CELITE® and the pad was washed with MeOH (3×20 mL). The filtrate was concentrated to afford tert-butyl (3R,5R)-3-fluoro-5-hydroxypiperidine-1-carboxylate as a white solid. Material was taken on crude to the next reaction without further purification. $^1$H NMR (400 MHz, DMSO-d6) δ=5.03 (s, 1H), 4.95-4.72 (m, 1H), 3.99-3.74 (m, 2H), 3.67 (s, 1H), 3.15-2.96 (m, 1H), 2.80-2.53 (m, 1H), 2.09 (s, 1H), 1.69-1.47 (m, 1H), 1.39 (s, 9H).

Step 2: tert-butyl (3R,5R)-3-((2-(2,6-dioxo-1-((2-(trimethylsilyl)ethoxy)methyl)piperidin-3-yl)-1-oxoisoindolin-5-yl)oxy)-5-fluoropiperidine-1-carboxylate (171)

A mixture of tert-butyl (3R,5R)-3-fluoro-5-hydroxypiperidine-1-carboxylate 170 (289 mg, 1.32 mmol), 3-(5-bromo-1-oxoisoindolin-2-yl)-1-((2-(trimethylsilyl)ethoxy)methyl)piperidine-2,6-dione INT-1 (300 mg, 0.66 mmol), Ir[dF(CF$_3$)ppy]$_2$(dtbpy)(PF$_6$) (7 mg, 0.006 mmol) and NiCl$_2$.dtbbpy (13 mg, 0.033 mmol), quinuclidine (7 mg, 0.066 mmol), TMP (186 mg, 1.3 mmol) in ACN (6.0 mL) was degassed three times under N$_2$. The reaction vial was sealed with parafilm, placed 2 cm away from a blue LED, and irradiated at r.t. for 16 hrs. The reaction mixture was filtered, the filter cake was washed with EtOAc (3×5 mL) and the filtrate was concentrated. The crude material was purified by silica gel chromatography (0-70% EtOAc in petroleum ether) and the fractions containing pure product were collected and concentrated to afford tert-butyl (3R,5R)-3-((2-(2,6-dioxo-1-((2-(trimethylsilyl)ethoxy)methyl)piperidin-3-yl)-1-oxoisoindolin-5-yl)oxy)-5-fluoropiperidine-1-carboxylate 171 as a bright yellow solid. LCMS [M+H]$^+$: 362.3 m/z. $^1$H NMR (400 MHz, DMSO-d6) δ 7.66 (d, J=8.0 Hz, 1H), 7.20 (br s, 1H), 7.08-7.05 (m, 1H), 5.21-5.17 (m, 1H), 5.08-5.00 (m, 3H), 4.92-4.60 (m, 2H), 4.48-4.36 (m, 1H), 4.29-4.17 (m, 1H), 3.92-3.79 (m, 1H), 3.66-3.64 (m, 1H), 3.57-3.44 (m, 3H), 3.17-2.95 (m, 2H), 2.84-2.73 (m, 1H), 2.36-2.32 (m 1H), 2.26-2.12 (m, 1H), 2.07-2.01 (m, 1H), 1.40-1.25 (m, 9H), 0.85-0.81 (m, 2H), −0.02 (s, 9H).) δ 7.66 (d, J=8.0 Hz, 1H), 7.20 (br s, 1H), 7.08-7.05 (m, 1H), 5.21-5.17 (m, 1H), 5.08-5.00 (m, 3H), 4.92-4.60 (m, 2H), 4.48-4.36 (m, 1H), 4.29-4.17 (m, 1H), 3.92-3.79 (m, 1H), 3.66-3.64 (m, 1H), 3.57-3.44 (m, 3H), 3.17-2.95 (m, 2H), 2.84-2.73 (m, 1H), 2.36-2.32 (m 1H), 2.26-2.12 (m, 1H), 2.07-2.01 (m, 1H), 1.40-1.25 (m, 9H), 0.85-0.81 (m, 2H), −0.02 (s, 9H).

Step 3: 3-(5-(((3R,5R)-5-fluoropiperidin-3-yl)oxy)-1-oxoisoindolin-2-yl)piperidine-2,6-dione (172)

MsOH (487 mg, 0.33 mL, 5.1 mmol) was added to a solution of tert-butyl (3R,5R)-3-((2-(2,6-dioxo-1-((2-(trimethylsilyl)ethoxy)methyl)piperidin-3-yl)-1-oxoisoindolin-5-yl)oxy)-5-fluoropiperidine-1-carboxylate 171 (300 mg, 0.51 mmol) in ACN (3.0 mL). The reaction stirred at 40° C. for 2 hrs. The reaction mixture was cooled to 0° C., Et₃N (667 mg, 0.92 mL, 6.6 mmol) was added dropwise followed by DMEDA (89 mg, 0.11 mL, 1.0 mmol). The reaction mixture stirred at r.t. for 14 hrs. The reaction mixture was concentrated and the crude material was purified by reverse phase HPLC (10-40% ACN in water with 10 mM NH₄HCO₃ as modifier). Fractions with pure product were collected and concentrated to afford 3-(5-(((3R,5R)-5-fluoropiperidin-3-yl)oxy)-1-oxoisoindolin-2-yl)piperidine-2,6-dione 172 as a white solid. ¹H NMR (400 MHz, DMSO-d6) δ 10.95 (s, 1H), 7.62 (d, J=8.4 Hz, 1H), 7.19 (s, 1H), 7.07-7.04 (s, 1H), 5.08-5.04 (m, 1H), 4.94-4.73 (m, 1H), 4.70-4.58 (m, 1H), 4.44-4.34 (m, 1H), 4.33-4.20 (m, 1H), 3.11-3.03 (m, 1H), 2.95-2.71 (m, 3H), 2.62-2.55 (m, 2H), 2.40-2.36 (m, 1H), 2.28-2.20 (m, 1H), 2.02-1.86 (m, 2H). ¹⁹F NMR (400 MHz, DMSO-d₆) δ 182.6.

Step 4: 3-(5-(((3R,5R)-1-ethyl-5-fluoropiperidin-3-yl)oxy)-1-oxoisoindolin-2-yl)piperidine-2,6-dione (I-173)

Acetaldehyde (107 mg, 0.97 mmol, 40%) and 2M ZnCl₂ in THF (132 mg, 0.48 mL, 0.97 mmol) were added to a solution of 3-(5-(((3R,5R)-5-fluoropiperidin-3-yl)oxy)-1-oxoisoindolin-2-yl)piperidine-2,6-dione 172 (70 mg, 0.19 mmol) in 1:1 THF/EtOH (1.0 mL) at r.t. and stirred for 1 hr. NaBH₃CN (37 mg, 0.58 mmol) was added and the mixture stirred at r.t. for 15 hrs. The reaction mixture was concentrated and the resulting crude material was purified by reverse phase HPLC (0-20% ACN in water with 0.225% formic acid as modifier). Fractions containing pure product were collected and concentrated to afford formate salt 3-(5-(((3R,5R)-1-ethyl-5-fluoropiperidin-3-yl)oxy)-1-oxoisoindolin-2-yl)piperidine-2,6-dione I-173 as an off-white solid. LCMS [M+H]⁺: 390.2. ¹H NMR (400 MHz, ACETONITRILE-d₃+D₂O) δ 8.35-8.27 (m, 1H), 7.70 (d, J=8.4 Hz, 1H), 7.13 (br s, 1H), 7.06 (d, J=8.4 Hz, 1H), 5.13-4.92 (m, 2H), 4.89-4.80 (m, 1H), 4.44-4.27 (m, 2H), 3.15-3.12 (m, 1H), 3.07-2.96 (m, 1H), 2.84-2.66 (m, 5H), 2.55-2.54 (m, 1H), 2.44-2.29 (m, 2H), 2.15-2.06 (m, 1H), 2.02-1.96 (m, 0.5H), 1.91-1.83 (m, 0.5H), 1.14-1.04 (m, 3H). ¹⁹F NMR (400 MHz, ACETONITRILE-d₃) δ 182.5.

Example 61: 3-(5-((2-azabicyclo[2.2.1]heptan-6-yl)oxy)-1-oxoisoindolin-2-yl)piperidine-2,6-dione (I-176)

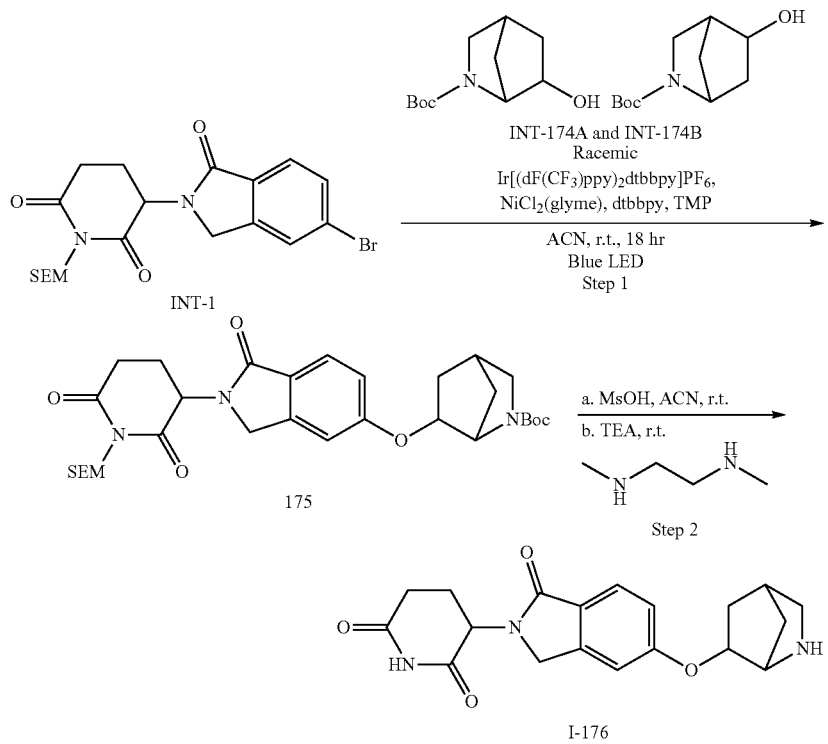

Step 1: rac-Tert-butyl 6-((2-(2,6-dioxo-1-((2-(trimethylsilyl)ethoxy)methyl)piperidin-3-yl)-1-oxoisoindolin-5-yl)oxy)-2-azabicyclo[2.2.1]heptane-2-carboxylate (175)

A racemic mixture of regioisomers tert-butyl 5-hydroxy-2-azabicyclo[2.2.1]heptane-2-carboxylate INT-174A and INT-174B (941 mg, 4.41 mmol), 3-(5-bromo-1-oxoisoindolin-2-yl)-1-((2-(trimethylsilyl)ethoxy)methyl)piperidine-2,6-dione INT-1 (2.00 g, 4.41 mmol), Ir[dF(CF₃)ppy]₂(dtbpy)

(PF₆) (0.050 g, 0.044 mmol) and NiCl₂ (glyme) (48 mg, 0.22 mmol), dttbpy (59 mg, 0.221 mmol) in ACN (20 mL) was purged with nitrogen for 10 min. Then, TMP (0.78 mL, 4.6 mmol) was added. The reaction was placed in a PennOC m1 450 nm Photoreactor under blue LED light at r.t. for 24 hrs. The reaction mixture was concentrated onto CELITE®, and purified by silica gel chromatography (0-100% EtOAc in heptanes) to afford 175 (1.8 g) that was used in the next step without further purification. LCMS [M−H]⁻: 584.4

Step 2: rac-3-(5-((2-azabicyclo[2.2.1]heptan-6-yl)oxy)-1-oxoisoindolin-2-yl)piperidine-2,6-dione (I-176))

Compound I-176 was made according to General Method VII starting from 175 (1.0 g, 1.7 mmol). The reaction was quenched with a 50% saturated aqueous sodium bicarbonate and extracted with 4:1 DCM:iPrOH three times. The organic layers were combined, passed through a phase separator and concentrated, and purified by silica gel chromatography (0-100% EtOAc:EtOH:Et3N (v/v/v=75:25:1) in DCM), then eluent was changed to (0-100% EtOH/DCM with 1% triethylamine) to afford I-176. LCMS [M+H]⁺: 356.2.

Example 62: rac-3-(5-((2-ethyl-2-azabicyclo[2.2.1]heptan-6-yl)oxy)-1-oxoisoindolin-2-yl)piperidine-2,6-dione

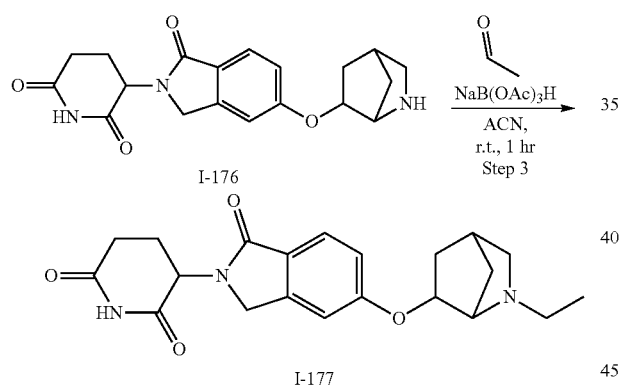

To a vial containing 3-(5-((2-azabicyclo[2.2.1]heptan-6-yl)oxy)-1-oxoisoindolin-2-yl)piperidine-2,6-dione I-176 (140 mg, 0.394 mmol) and ACN (4.0 mL) was added sodium triacetoxyborohydride (250 mg, 1.2 mmol) followed by acetaldehyde (45 uL, 0.79 mmol). The reaction stirred at r.t. for 1 hr. The reaction was poured into saturated aqueous sodium bicarbonate and extracted with 4:1 DCM/iPrOH three times. The organics layers were combined, passed through a phase separator, and concentrated. The crude material was purified by basic reverse phase HPLC (15-40% ACN in water with 5 mM NH₄OH as modifier). Test tubes contained 3 drops formic acid prior to sample collection. Fractions containing desired product were combined and lyophilized to afford I-177 rac-3-(5-((2-ethyl-2-azabicyclo[2.2.1]heptan-6-yl)oxy)-1-oxoisoindolin-2-yl)piperidine-2,6-dione LCMS [M+H]⁺: 384.3. ¹H NMR (400 MHz, DMSO-d6) δ 10.97 (s, 1H), 7.61 (d, J=8.4 Hz, 1H), 7.11 (d, J=2.2 Hz, 1H), 7.04-6.92 (m, 1H), 5.07 (dd, J=13.2, 5.1 Hz, 1H), 4.52 (d, J=6.5 Hz, 1H), 4.46-4.11 (m, 2H), 2.98-2.78 (m, 1H), 2.70-2.59 (m, 2H), 2.55 (d, J=4.3 Hz, 2H), 2.46- 2.25 (m, 4H), 1.95 (d, J=17.0 Hz, 2H), 1.52 (s, 2H), 1.42 (d, J=13.4 Hz, 1H), 1.00 (t, J=7.1 Hz, 3H).

Example 63: 3-(5-(((3R,5R)-5-ethoxy-1-ethylpiperidin-3-yl)oxy)-1-oxoisoindolin-2-yl)piperidine-2,6-dione (I-181)

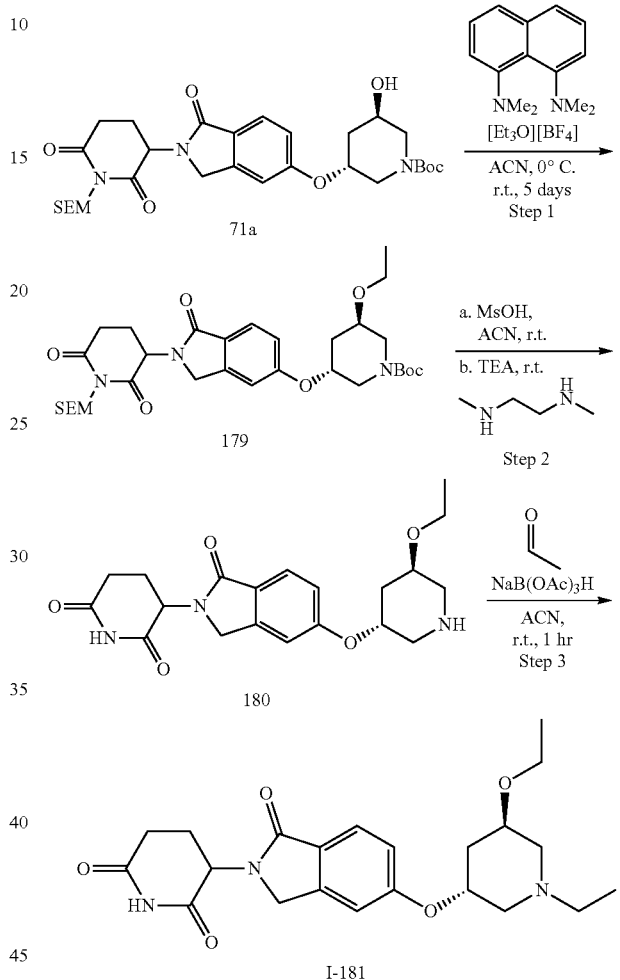

Step 1: tert-butyl (3R,5R)-3-((2-(2,6-dioxo-1-((2-(trimethylsilyl)ethoxy)methyl)piperidin-3-yl)-1-oxoisoindolin-5-yl)oxy)-5-ethoxypiperidine-1-carboxylate (179)

To a stirred solution of N¹,N¹,N⁶,N⁶-tetramethylnaphthalene-1,8-diamine (155 mg, 0.725 mmol) and tert-butyl (3R,5R)-3-((2-(2,6-dioxo-1-((2-(trimethylsilyl)ethoxy)methyl)piperidin-3-yl)-1-oxoisoindolin-5-yl)oxy)-5-hydroxypiperidine-1-carboxylate 71a (Example 34a) (225 mg, 0.382 mmol) in ACN (2 mL) was added dropwise triethyloxonium tetrafluoroborate as a 1 M solution in DCM (650 μL, 0.650 mmol) at 0° C. under positive pressure of nitrogen. After the addition was complete, the reaction was warmed to r.t. and stirred for 5 days. The reaction was filtered over CELITE® with acetone and the solvents removed under reduced pressure. This crude material 179 was taken on as is without further purification. LCMS [M+NH₄]⁻: 634.4

Step 2: 3-(5-(((3R,5R)-5-ethoxypiperidin-3-yl)oxy)-1-oxoisoindolin-2-yl)piperidine-2,6-dione (180)

Compound 180 was made according to General Method VII starting from tert-butyl (3R,5R)-3-((2-(2,6-dioxo-1-((2-(trimethylsilyl)ethoxy)methyl)piperidin-3-yl)-1-oxoisoindolin-5-yl)oxy)-5-ethoxypiperidine-1-carboxylate 179 (236 mg, 0.382 mmol). The reaction was quenched with a 50% saturated aqueous sodium bicarbonate and extracted with 4:1 DCM:iPrOH three times. The organic layers were combined, passed through a phase separator and concentrated. Material was used directly in the next reaction without purification. LCMS [M+H]$^+$: 388.3.

Step 3: 3-(5-(((3R,5R)-5-ethoxy-1-ethylpiperidin-3-yl)oxy)-1-oxoisoindolin-2-yl)piperidine-2,6-dione (I-181)

To a vial containing 3-(5-(((3R,5R)-5-ethoxypiperidin-3-yl)oxy)-1-oxoisoindolin-2-yl)piperidine-2,6-dione 180 (148 mg, 0.382 mmol) and ACN (2.0 mL) was added sodium triacetoxyborohydride (243 mg, 1.2 mmol) followed by acetaldehyde (43 μL, 0.764 mmol). The reaction was stirred at r.t. for 5 days. The reaction was poured into saturated aqueous sodium bicarbonate and extracted with 4:1 DCM/iPrOH three times. The organic layers were combined, passed through a phase separator, and concentrated onto CELITE®. The crude material was purified by silica gel chromatography (0-100% EtOAc:EtOH:Et3N (v/v/v=75:25:1) in DCM), then by basic reverse phase HPLC (15-40% ACN in water with 5 mM NH$_4$OH as modifier). Test tubes contained 3 drops formic acid prior to sample collection. Fractions containing desired product were combined and lyophilized to afford 3-(5-(((3R,5R)-5-ethoxy-1-ethylpiperidin-3-yl)oxy)-1-oxoisoindolin-2-yl)piperidine-2,6-dione I-181. LCMS [M+H]$^+$: 416.3. $^1$H NMR (400 MHz, DMSO-d6) δ 8.46-8.27 (m, 1H), 7.62 (d, J=8.4 Hz, 1H), 7.17 (d, J=2.2 Hz, 1H), 7.04 (dd, J=8.4, 2.2 Hz, 1H), 5.07 (dd, J=13.3, 5.1 Hz, 1H), 4.75 (dd, J=6.6, 3.5 Hz, 1H), 4.42-4.21 (m, 2H), 3.67 (d, J=5.4 Hz, 1H), 3.56-3.36 (m, 2H), 2.91 (ddd, J=17.3, 13.6, 5.4 Hz, 1H), 2.73-2.54 (m, 4H), 2.42-2.32 (m, 3H), 2.22 (dd, J=11.0, 7.1 Hz, 1H), 1.97 (ddd, J=11.3, 5.7, 3.0 Hz, 2H), 1.73 (t, J=10.1 Hz, 1H), 1.09 (td, J=6.9, 1.3 Hz, 3H), 0.96 (td, J=7.2, 1.5 Hz, 3H).

Example 64: 3-(5-(((3R,5R)-1-ethyl-5-methoxypiperidin-3-yl)oxy)-1-oxoisoindolin-2-yl)piperidine-2,6-dione (I-184)

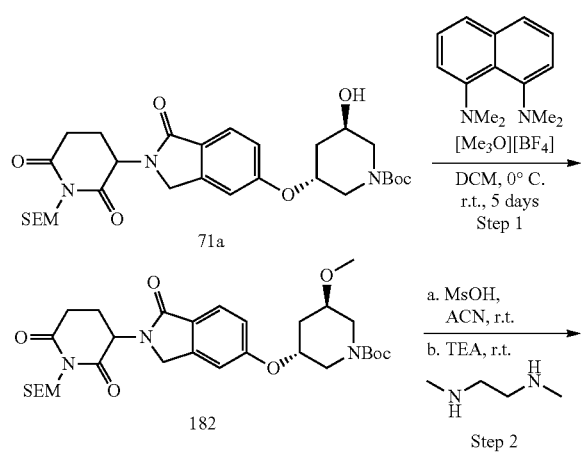

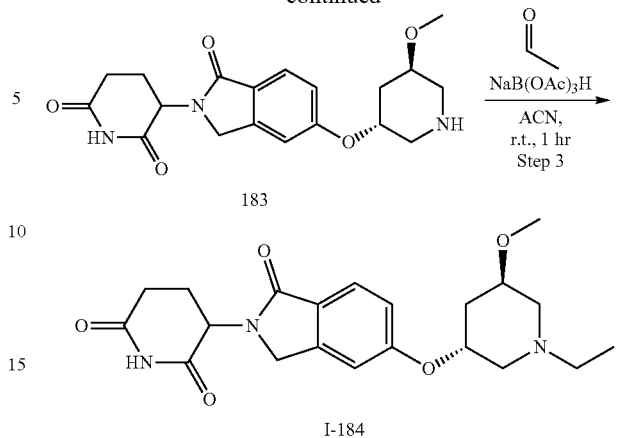

Step 1: tert-butyl (3R,5R)-3-((2-(2,6-dioxo-1-((2-(trimethylsilyl)ethoxy)methyl)piperidin-3-yl)-1-oxoisoindolin-5-yl)oxy)-5-methoxypiperidine-1-carboxylate (182)

To a stirred solution of N$^1$,N$^1$,N$^6$,N$^6$-tetramethylnaphthalene-1,8-diamine (155 mg, 0.725 mmol) and tert-butyl (3R,5R)-3-((2-(2,6-dioxo-1-((2-(trimethylsilyl)ethoxy)methyl)piperidin-3-yl)-1-oxoisoindolin-5-yl)oxy)-5-hydroxypiperidine-1-carboxylate 71a (Example 34a) (225 mg, 0.382 mmol) in DCM (3 mL) was added trimethyloxonium tetrafluoroborate (96 mg, 0.649 mmol), at 0° C. under positive pressure of nitrogen. After the addition was complete, the reaction was warmed to r.t. and stirred 24 hrs. The reaction was filtered over CELITE® with acetone and the solvents removed under reduced pressure. This crude material 182 was taken on as is without further purification. LCMS [M−H]$^-$: 602.2

Step 2: 3-(5-(((3R,5R)-5-methoxypiperidin-3-yl)oxy)-1-oxoisoindolin-2-yl)piperidine-2,6-dione (183)

Compound 183 was made according to General Method VII starting from tert-butyl (3R,5R)-3-((2-(2,6-dioxo-1-((2-(trimethylsilyl)ethoxy)methyl)piperidin-3-yl)-1-oxoisoindolin-5-yl)oxy)-5-methoxypiperidine-1-carboxylate 182 (230 mg, 0.381 mmol). The reaction was quenched with a 50% saturated aqueous sodium bicarbonate and extracted with 4:1 DCM:iPrOH three times. The organic layers were combined, passed through a phase separator and concentrated. Material was used directly in the next reaction without purification. LCMS [M+H]$^+$: 374.3.

Step 3: 3-(5-(((3R,5R)-1-ethyl-5-methoxypiperidin-3-yl)oxy)-1-oxoisoindolin-2-yl)piperidine-2,6-dione (I-184)

To a vial containing 3-(5-(((3R,5R)-5-methoxypiperidin-3-yl)oxy)-1-oxoisoindolin-2-yl)piperidine-2,6-dione 183 (142 mg, 0.380 mmol) and ACN (2.0 mL) was added sodium triacetoxyborohydride (242 mg, 1.1 mmol) followed by acetaldehyde (43 uL, 0.761 mmol). The reaction was stirred at r.t. for 5 days. The reaction was concentrated, diluted into DMSO/water/MeCN (v/v/v=1:1:1) and purified by basic reverse phase HPLC (15-40% ACN in water with 5 mM NH$_4$OH as modifier). Test tubes contained 3 drops formic acid prior to sample collection. Fractions containing desired product were combined and lyophilized to afford 3-(5-(((3R,5R)-1-ethyl-5-methoxypiperidin-3-yl)oxy)-1-oxoisoindolin-2-yl)piperidine-2,6-dione I-184. LCMS [M+H]⁺: 402.3. ¹H NMR (400 MHz, DMSO-d6) δ 8.42-8.24 (m, 1H), 7.60 (d, J=8.4 Hz, 1H), 7.15 (d, J=2.2 Hz, 1H), 7.02 (dd, J=8.4, 2.2 Hz, 1H), 5.06 (dd, J=13.2, 5.1 Hz, 1H), 4.72 (dd, J=6.3, 3.2 Hz, 1H), 4.46-4.17 (m, 2H), 3.55 (q, J=3.6 Hz, 1H), 3.24 (d, J=1.2 Hz, 3H), 2.98-2.81 (m, 1H), 2.62-2.51 (m, 3H), 2.44-2.25 (m, 5H), 2.03-1.84 (m, 2H), 1.84-1.72 (m, 1H), 0.96 (td, J=7.2, 1.5 Hz, 3H).

Alternatively, Example 64 can be synthesised according to the scheme below, whereby the ethoxyl group is replaced by the methoxyl group (e.g., using iodomethane):

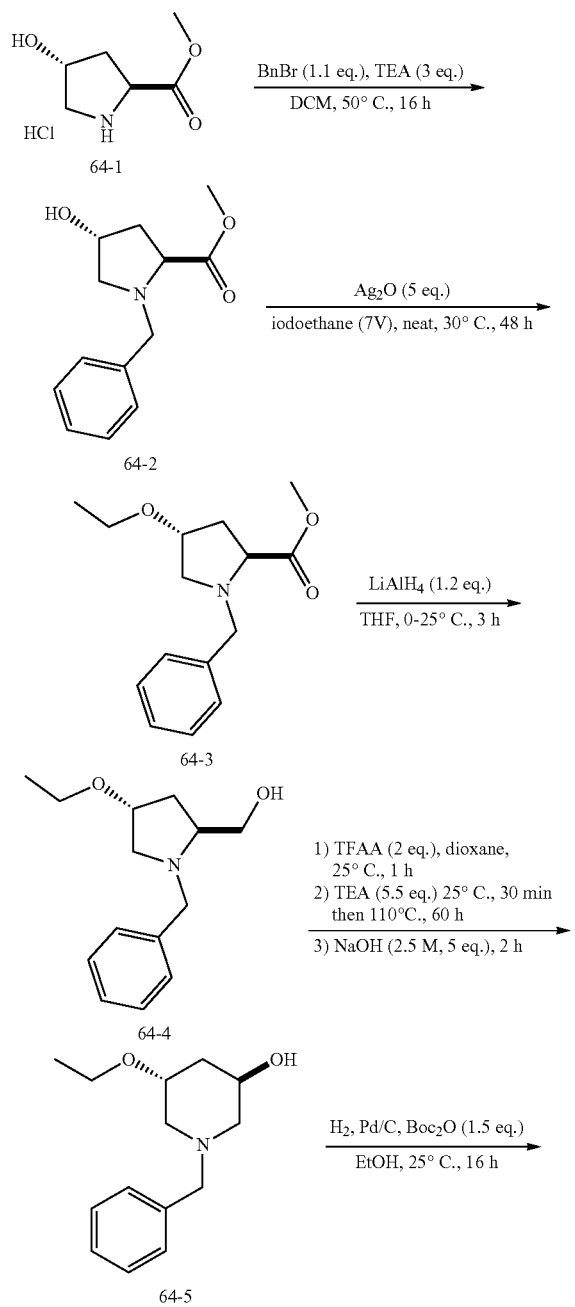

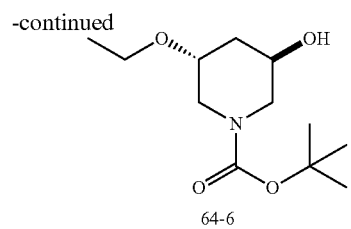

The synthesis can be carried out according to literature procedures, e.g., according to Cossy, J. et al. *Eur. J. Org. Chem.* 1999, 1693-1699. Intermediate compound 64-6 is then coupled with INT-1, e.g., according to the procedure in General Method VI. The remaining steps outlined in Example 64 can then be employed to afford 3-(5-(((3R,5R)-1-ethyl-5-methoxypiperidin-3-yl)oxy)-1-oxoisoindolin-2-yl)piperidine-2,6-dione.

Example 65-1 and 65-2: 3-(5-(((3R,5R)-1-ethyl-5-methoxypiperidin-3-yl)oxy)-1-oxoisoindolin-2-yl)piperidine-2,6-dione, Peak 1 and Peak 2

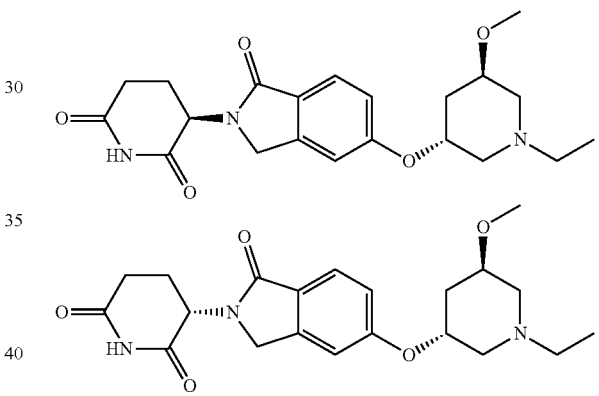

The diastereomeric mixture of I-184 (0.22 g, 0.53 mmol) was separated via chiral SFC [Column 21×250 mm: (S,S) Whelk-O1; CO₂ Co-solvent 35% ACN:IPA with 0.1% triethylamine; at 80 g/min at 125 bar at 25° C.] to afford two diastereomers. Example 65-1, Peak 1: Diastereomer 1 of 3-(5-(((3R,5R)-1-ethyl-5-methoxypiperidin-3-yl)oxy)-1-oxoisoindolin-2-yl)piperidine-2,6-dione as a white solid. Chiral SFC Rt 3.77 mins. ¹H NMR (400 MHz, DMSO) δ 10.96 (s, 1H), 7.61 (d, J=8.4 Hz, 1H), 7.16 (d, J=2.2 Hz, 1H), 7.03 (dd, J=8.4, 2.2 Hz, 1H), 5.07 (dd, J=13.3, 5.1 Hz, 1H), 4.78-4.67 (m, 1H), 4.39 (d, J=17.2 Hz, 1H), 4.26 (d, J=17.2 Hz, 1H), 3.75-3.48 (m, 1H), 3.25 (s, 3H), 2.90 (ddd, J=18.1, 13.6, 5.4 Hz, 1H), 2.75-2.54 (m, 3H), 2.48-2.27 (m, 5H), 2.05-1.85 (m, 2H), 1.85-1.73 (m, 1H), 0.97 (t, J=7.1 Hz, 3H). Example 65-2, Peak 2: Diastereomer 2 of 3-(5-(((3R,5R)-1-ethyl-5-methoxypiperidin-3-yl)oxy)-1-oxoisoindolin-2-yl)piperidine-2,6-dione as a white solid. Chiral SFC Rt 5.29 mins. ¹H NMR (400 MHz, DMSO) δ 10.96 (s, 1H), 7.61 (d, J=8.4 Hz, 1H), 7.16 (d, J=2.2 Hz, 1H), 7.03 (dd, J=8.4, 2.2 Hz, 1H), 5.07 (dd, J=13.3, 5.1 Hz, 1H), 4.78-4.67 (m, 1H), 4.39 (d, J=17.2 Hz, 1H), 4.26 (d, J=17.2 Hz, 1H), 3.75-3.48 (m, 1H), 3.25 (s, 3H), 2.90 (ddd, J=18.1, 13.6, 5.4 Hz, 1H), 2.75-2.54 (m, 3H), 2.48-2.27 (m, 5H), 2.05-1.85 (m, 2H), 1.85-1.73 (m, 1H), 0.97 (t, J=7.1 Hz, 3H). The absolute stereochemistry at the glutarimide carbon of the two stereoisomers corresponding to the two product peaks was not determined.

Example 66: 3-(5-(((3R,5R)-1-ethyl-5-hydroxypiperidin-3-yl)oxy)-1-oxoisoindolin-2-yl)piperidine-2,6-dione (I-185)

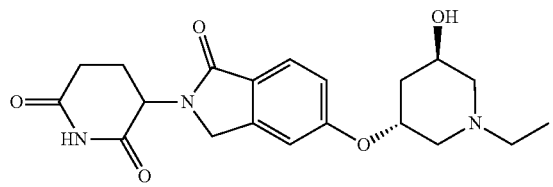

I-185

Example 66 (I-185) was Synthesized by Analogy to Example 34 Starting with Example 34a (71a)

Step 1: 3-(5-(((3R,5R)-5-hydroxypiperidin-3-yl)oxy)-1-oxoisoindolin-2-yl)piperidine-2,6-dione (186)

LCMS [M+H]$^+$: 360.2.

Step 2: 3-(5-(((3R,5R)-1-ethyl-5-hydroxypiperidin-3-yl)oxy)-1-oxoisoindolin-2-yl)piperidine-2,6-dione (I-185)

To a solution of 3-(5-(((3R,5R)-5-hydroxypiperidin-3-yl)oxy)-1-oxoisoindolin-2-yl)piperidine-2,6-dione 186 (200 mg, 0.56 mmol) and sodium triacetoxyborohydride (354 mg, 1.67 mmol) in EtOH (2 mL) and MeCN (1 mL) was added acetaldehyde (0.063 mL, 1.1 mmol). The reaction was stirred for 1 hr. The reaction was quenched with saturated aqueous sodium bicarbonate and extracted with 4:1 DCM:trifluoroethanol (3×). The reaction was concentrated and purified by reverse phase column chromatography (5-20% acetonitrile in water with 0.1% NH$_4$OH as modifier). Fractions containing desired product were combined and concentrated to afford 3-(5-(((3R,5R)-1-ethyl-5-hydroxypiperidin-3-yl)oxy)-1-oxoisoindolin-2-yl)piperidine-2,6-dione I-185 as a white solid. LCMS [M+H]$^+$: 388.4. $^1$H NMR (400 MHz, DMSO) δ 10.97 (s, 1H), 7.62 (d, J=8.4 Hz, 1H), 7.16 (d, J=2.2 Hz, 1H), 7.04 (dd, J=8.5, 2.2 Hz, 1H), 5.08 (dd, J=13.3, 5.1 Hz, 1H), 4.80 (s, 1H), 4.67 (s, 1H), 4.47-4.18 (m, 2H), 3.86 (br. s, 1H), 2.98-2.82 (m, 1H), 2.63 (d, J=12.2 Hz, 3H), 2.45-2.35 (m, 4H), 2.10 (d, J=9.1 Hz, 1H), 2.03-1.85 (m, 2H), 1.64 (t, J=11.4 Hz, 1H), 0.99-0.96 (m, 3H).

Example 67: 3-(5-(((3R,5R)-5-hydroxy-1-isopropylpiperidin-3-yl)oxy)-1-oxoisoindolin-2-yl)piperidine-2,6-dione (I-187)

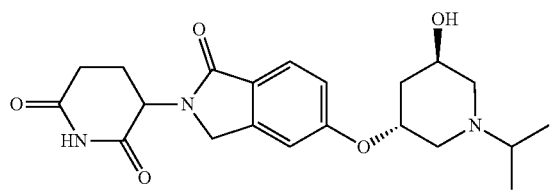

I-187

To a suspension of 3-(5-(((3R,5R)-5-hydroxypiperidin-3-yl)oxy)-1-oxoisoindolin-2-yl)piperidine-2,6-dione 186 (Example 66, Step 1) (2.41 g, 6.71 mmol), in acetone (15 mL) and DMF (5 mL) was added sodium triacetoxyborohydride (2.84 g, 13.4 mmol) followed by acetic acid (0.77 mL, 13 mmol). The reaction was stirred for 4 hours. The reaction was quenched with saturated aqueous sodium bicarbonate and extracted with 4:1 DCM:trifluoroethanol (3×). The crude material was purified by silica gel chromatography (silica saturated in Et$_3$N, 1 to 15 EtOH in DCM). Fractions containing desired product were combined and concentrated to afford 3-(5-(((3R,5R)-5-hydroxy-1-isopropylpiperidin-3-yl)oxy)-1-oxoisoindolin-2-yl)piperidine-2,6-dione (I-187) as a white solid. LCMS [M+H]+: 402.4. $^1$H NMR (400 MHz, McOD) δ 7.72 (d, J=8.5 Hz, 1H), 7.18 (s, 1H), 7.12 (dd, J=8.5, 2.2 Hz, 1H), 5.13 (dd, J=13.3, 5.2 Hz, 1H), 4.45 (d, J=7.2 Hz, 2H), 4.08 (s, 1H), 3.87 (q, J=9.2 Hz, 1H), 3.01-2.68 (m, 6H), 2.47 (td, J=13.2, 4.8 Hz, 2H), 2.24-2.10 (m, 1H), 1.99 (s, 1H), 1.86 (s, 1H), 1.07 (d, J=6.4 Hz, 6H).

Example 68: (3R,5R)-3-((2-(2,6-dioxopiperidin-3-yl)-1-oxoisoindolin-5-yl)oxy)-5-ethoxy-N-methylpiperidine-1-carboxamide (I-188)

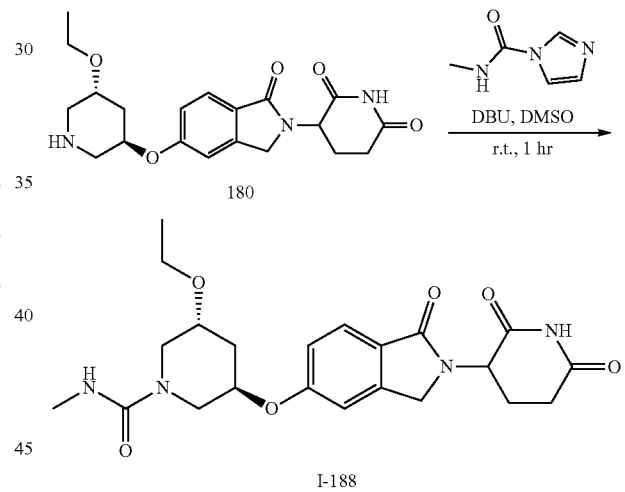

To a vial containing 3-(5-((5-ethoxypiperidin-3-yl)oxy)-1-oxoisoindolin-2-yl)piperidine-2,6-dione 180 (Example 63, Step 2) (100 mg, 0.258 mmol) and DBU (78 ul, 0.516 mmol) in DMSO (1.0 mL) was added N-methyl-1-imidazolecarboxamide (58 mg, 0.464 mmol). The reaction was stirred at r.t. for 1 hr. The reaction was was purified by reverse phase HPLC (15-35% ACN in water with 0.1% formic acid as modifier). Fractions containing desired product were combined and lyophilized to afford (3R,5R)-3-((2-(2,6-dioxopiperidin-3-yl)-1-oxoisoindolin-5-yl)oxy)-5-ethoxy-N-methylpiperidine-1-carboxamide 1-188. LCMS [M+H]$^+$: 445.3. $^1$H NMR (400 MHz, DMSO) δ 10.96 (s, 1H), 7.62 (d, J=8.4 Hz, 1H), 7.17 (s, 1H), 7.03 (d, J=8.3 Hz, 1H), 6.43 (t, J=3.9 Hz, 1H), 5.07 (dd, J=13.2, 5.0 Hz, 1H), 4.65 (s, 1H), 4.49-4.17 (m, 2H), 3.67-3.47 (m, 4H), 3.42 (ddd, J=9.3, 6.9, 2.2 Hz, 2H), 3.25 (dd, J=15.7, 9.1 Hz, 1H), 3.00-2.79 (m, 1H), 2.54 (m, 4H), 2.38 (d, J=13.1 Hz, 1H), 2.10-1.84 (m, 3H), 1.08 (td, J=7.0, 0.9 Hz, 3H).

Example 69: ethyl (3R,5R)-3-((2-(2,6-dioxopiperidin-3-yl)-1-oxoisoindolin-5-yl)oxy)-5-ethoxypiperidine-1-carboxylate (I-189)

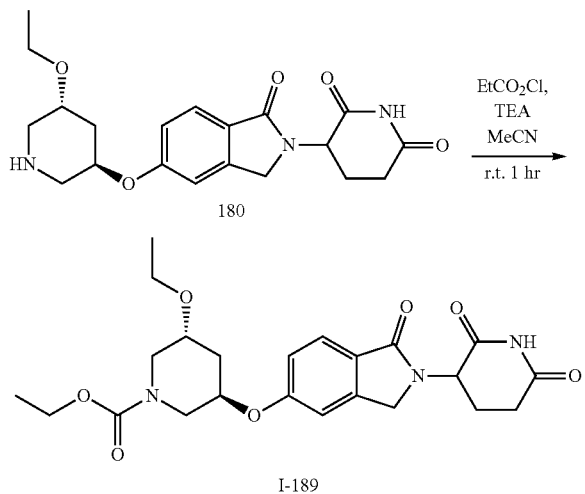

I-189

To a vial containing 3-(5-((5-ethoxypiperidin-3-yl)oxy)-1-oxoisoindolin-2-yl)piperidine-2,6-dione 180 (Example 63, Step 2) (130 mg, 0.336 mmol) and TEA (94 ul, 0.67 mmol) in ACN (2.0 mL), cooled in an ice water bath was added ethyl chloroformate (65 mg, 0.60 mmol). The reaction was stirred at r.t. for 1 hr. The reaction was poured into water and extracted with DCM three times. The organic layers were combined, passed through a phase separator, and concentrated. The crude material was purified by reverse phase HPLC (25-45% ACN in water with 0.1% formic acid as modifier, cyano 30×100 column). Fractions containing desired product were combined and lyophilized to afford ethyl (3R,5R)-3-((2-(2,6-dioxopiperidin-3-yl)-1-oxoisoindolin-5-yl)oxy)-5-ethoxypiperidine-1-carboxylate I-189. LCMS [M+H]$^+$: 460.4. $^1$H NMR (400 MHz, DMSO) δ 10.96 (s, 1H), 7.63 (d, J=8.4 Hz, 1H), 7.16 (d, J=2.2 Hz, 1H), 7.03 (d, J=8.5 Hz, 1H), 5.06 (dd, J=13.3, 5.1 Hz, 1H), 4.69 (d, J=32.1 Hz, 1H), 4.47-4.18 (m, 2H), 4.08-3.36 (m, 8H), 3.22-2.82 (m, 2H), 2.64-2.52 (m, 1H), 2.44-2.28 (m, 1H), 2.20-1.77 (m, 3H), 1.09 (t, J=7.0 Hz, 5H), 0.93 (s, 1H).

Example 70: 3-(5-(((3R,5R)-1-acetyl-5-ethoxypiperidin-3-yl)oxy)-1-oxoisoindolin-2-yl)piperidine-2,6-dione (I-190)

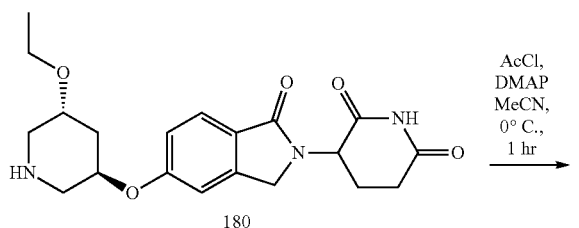

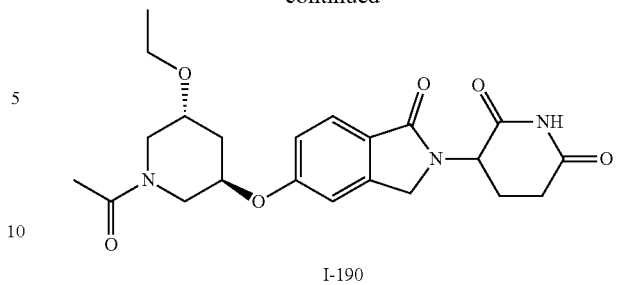

I-190

To a vial containing 3-(5-((5-ethoxypiperidin-3-yl)oxy)-1-oxoisoindolin-2-yl)piperidine-2,6-dione 180 (Example 63, Step 2) (100 mg, 0.258 mmol) and DMAP (63 mg, 0.52 mmol) in ACN (3.0 mL), cooled in an ice water bath was added acetyl chloride (27 ul, 0.39 mmol). After 1 hr, the reaction was purified by reverse phase HPLC (15-35% ACN in water with 0.1% formic acid as modifier). Fractions containing desired product were combined and lyophilized to afford 3-(5-(((3R,5R)-1-acetyl-5-ethoxypiperidin-3-yl)oxy)-1-oxoisoindolin-2-yl)piperidine-2,6-dione I-190. LCMS [M+H]+: 430.4. 1H NMR (400 MHz, McOD) δ 7.72 (dd, J=12.2, 8.3 Hz, 1H), 7.17 (d, J=2.1 Hz, 1H), 7.09 (t, J=9.4 Hz, 1H), 5.18-5.05 (m, 1H), 4.88-4.58 (m, 1H), 4.45 (dd, J=7.3, 3.3 Hz, 2H), 4.33-4.15 (m, 1H), 3.89-3.74 (m, 1H), 3.74-3.42 (m, 4H), 3.19-3.07 (m, 1H), 2.96-2.71 (m, 2H), 2.47 (dd, J=13.2, 4.7 Hz, 1H), 2.31-2.22 (m, 1H), 2.17-2.14 (m, 1H), 2.14-1.98 (m, 3H), 2.02-1.86 (m, 1H), 1.26-1.11 (m, 3H).

Example 71: 3-(5-(((3R,5R)-5-ethoxy-1-(methylsulfonyl)piperidin-3-yl)oxy)-1-oxoisoindolin-2-yl)piperidine-2,6-dione (I-191)

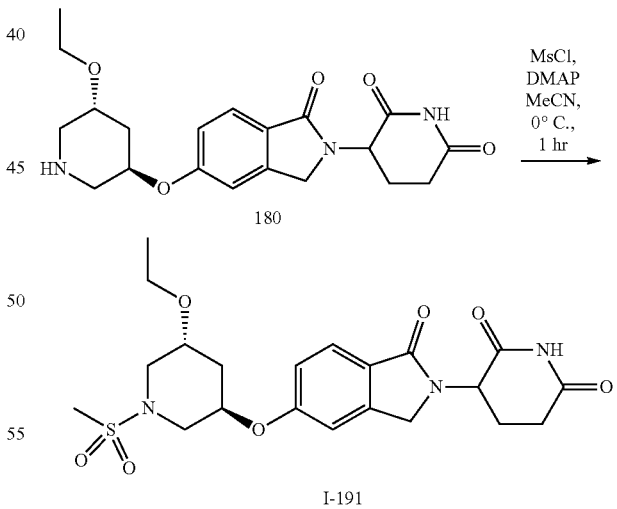

I-191

To a vial containing 3-(5-((5-ethoxypiperidin-3-yl)oxy)-1-oxoisoindolin-2-yl)piperidine-2,6-dione 180 (100 mg, 0.258 mmol) and DMAP (63 mg, 0.52 mmol) in ACN (4.0 mL), cooled in an ice water bath was added methansulfonyl chloride (24 ul, 0.31 mmol). The reaction was stirred at r.t. for 1 hr. The reaction was poured into a saturated aqueous sodium bicarbonate solution and extracted with 4:1 DCM/iPrOH three times. The organic layers were combined,

217 passed through a phase separator, and concentrated. The reaction was purified by reverse phase HPLC (5-95% ACN in water with 0.1% formic acid as modifier, 30×100 cyano column). Fractions containing desired product were combined and lyophilized to afford 3-(5-(((3R,5R)-5-ethoxy-1-(methylsulfonyl)piperidin-3-yl)oxy)-1-oxoisoindolin-2-yl)piperidine-2,6-dione I-191. LCMS [M+H]+: 466.3. $^1$H NMR (400 MHz, DMSO) δ 10.97 (s, 1H), 7.65 (d, J=8.4 Hz, 1H), 7.21 (s, 1H), 7.08 (d, J=8.5 Hz, 1H), 5.08 (dd, J=13.3, 5.1 Hz, 1H), 4.84 (m, 1H), 4.50-4.20 (m, 2H), 3.75 (m, 1H), 3.61-3.42 (m, 3H), 3.38 (d, J=4.2 Hz, 2H), 3.05 (dd, J=12.2, 7.2 Hz, 1H), 2.94 (s, 3H), 2.93-2.85 (m, 1H), 2.62 (t, J=20.5 Hz, 1H), 2.46-2.30 (m, 1H), 2.06 (d, J=11.1 Hz, 1H), 2.03-1.93 (m, 1H), 1.87 (m, 1H), 1.11 (t, J=7.0 Hz, 3H).

Example 72: 3-(5-(((3R,5R)-5-ethoxy-1-isobutylpiperidin-3-yl)oxy)-1-oxoisoindolin-2-yl)piperidine-2,6-dione (I-192)

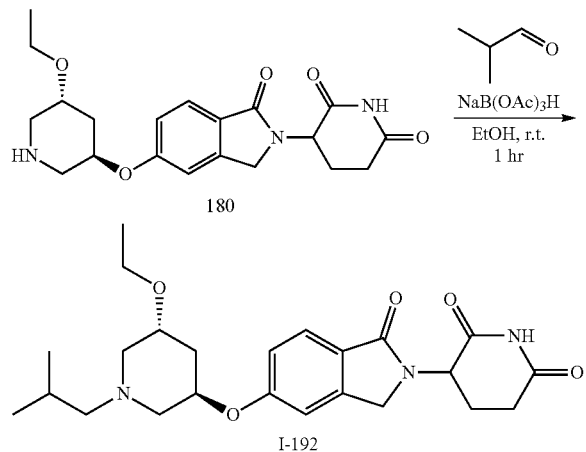

To a vial containing 3-(5-((5-ethoxypiperidin-3-yl)oxy)-1-oxoisoindolin-2-yl)piperidine-2,6-dione 180 (Example 63, Step 2) (150 mg, 0.387 mmol) and EtOH (2.0 mL) was added sodium triacetoxyborohydride (164 mg, 0.774 mmol) followed by isobutyraldehyde (42 uL, 0.58 mmol). After 15 min, an additional 1.5 eq (53 ul, 0.58 mmol) of isobutyraldehyde was added. After 1 hr, an additional 1.5 eq (53 ul, 0.58 mmol) of isobutyraldehyde was added. The reaction was poured into saturated aqueous sodium bicarbonate and extracted with 4:1 DCM/iPrOH three times. The organic layers were combined, passed through a phase separator, and concentrated. The crude material was purified by silica gel chromatography (0-100% EtOAc:EtOH:Et$_3$N (v/v/v=75:25:1) in DCM). Fractions containing desired product were concentrated. The crude oil was diluted into 2:1 water:MeCN and lyophilized to afford 3-(5-(((3R,5R)-5-ethoxy-1-isobutylpiperidin-3-yl)oxy)-1-oxoisoindolin-2-yl)piperidine-2,6-dione I-192. LCMS [M+H]+: 444.4. $^1$H NMR (400 MHz, DMSO) δ 10.96 (s, 1H), 7.60 (d, J=8.4 Hz, 1H), 7.14 (d, J=2.1 Hz, 1H), 7.01 (d, J=8.4 Hz, 1H), 5.06 (dd, J=13.3, 5.1 Hz, 1H), 4.74 (m, 1H), 4.45-4.14 (m, 2H), 3.67 (m, 1H), 3.57-3.37 (m, 2H), 3.03-2.83 (m, 1H), 2.70-2.54 (m, 3H), 2.44-2.29 (m, 2H), 2.19 (t, J=9.4 Hz, 1H), 2.06 (dd, J=7.9, 2.0 Hz, 2H), 1.97 (d, J=4.5 Hz, 1H), 1.69 (d, J=10.1 Hz, 2H), 1.08 (t, J=7.0 Hz, 3H), 0.79 (ddd, J=9.9, 6.6, 2.3 Hz, 6H).

218

Example 73: 3-(5-(((3R,5R)-1-cyclobutyl-5-ethoxypiperidin-3-yl)oxy)-1-oxoisoindolin-2-yl)piperidine-2,6-dione (I-193)

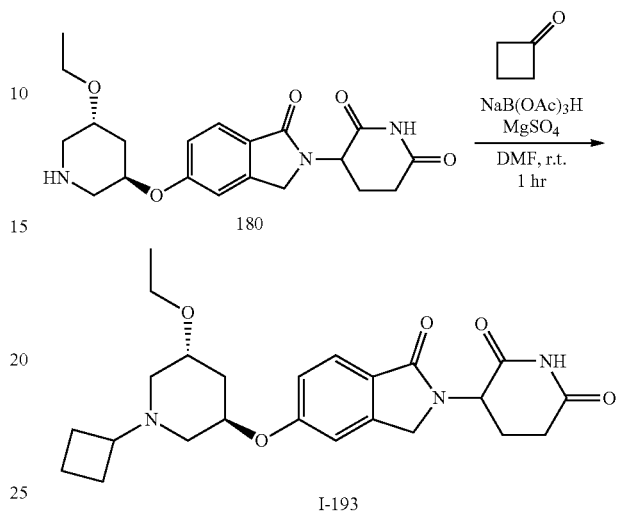

To a vial containing 3-(5-((5-ethoxypiperidin-3-yl)oxy)-1-oxoisoindolin-2-yl)piperidine-2,6-dione 180 (Example 63, Step 2) (150 mg, 0.387 mmol), MgSO4 (95.5 mg, 0.774 mmol) and DMF (2.0 mL) was added sodium triacetoxyborohydride (123 mg, 0.581 mmol) followed by cyclobutanone (290 uL, 3.87 mmol). The reaction was stirred at r.t. for 1 hr. The reaction was poured into saturated aqueous sodium bicarbonate and extracted with 4:1 DCM/TFE three times. The organic layers were combined, passed through a phase separator, and concentrated. The crude material was purified by silica gel chromatography (0-100% EtOAc:EtOH:Et$_3$N (v/v/v=75:25:1) in heptane). Fractions containing desired product were combined and concentrate, then rediluted in 2:1 water/MeCN and lyophilized to afford 3-(5-(((3R,5R)-1-cyclobutyl-5-ethoxypiperidin-3-yl)oxy)-1-oxoisoindolin-2-yl)piperidine-2,6-dione I-193. LCMS [M+H]+: 442.4. $^1$H NMR (400 MHz, DMSO) δ 10.96 (s, 1H), 7.61 (d, J=8.4 Hz, 1H), 7.16 (d, J=2.2 Hz, 1H), 7.03 (dd, J=8.5, 2.2 Hz, 1H), 5.06 (dd, J=13.3, 5.1 Hz, 1H), 4.72 (m, 1H), 4.45-4.18 (m, 2H), 3.65 (m, 1H), 3.54-3.37 (m, 2H), 2.98-2.55 (m, 3H), 2.46-2.27 (m, 3H), 2.19-1.50 (m, 11H), 1.09 (t, J=7.0 Hz, 3H).

Example 74: 3-(5-(((3R,5R)-5-ethoxy-1-isopropylpiperidin-3-yl)oxy)-1-oxoisoindolin-2-yl)piperidine-2,6-dione (I-194)

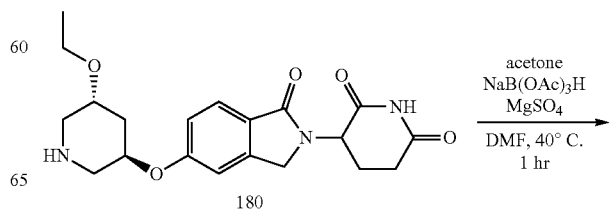

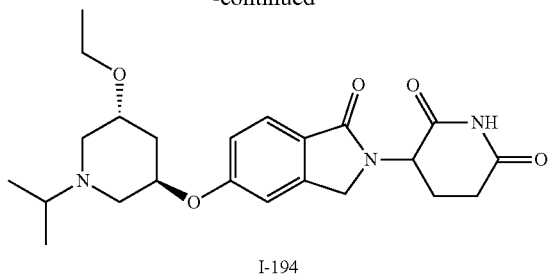

I-194

To a vial containing 3-(5-((5-ethoxypiperidin-3-yl)oxy)-1-oxoisoindolin-2-yl)piperidine-2,6-dione 180 (Example 63, Step 2) (150 mg, 0.387 mmol), MgSO4 (95.5 mg, 0.774 mmol) and DMF (2.0 mL) was added sodium triacetoxyborohydride (123 mg, 0.581 mmol) followed by acetone (284 uL, 3.87 mmol). The reaction was stirred at 40° C. for 1 hr. The reaction was poured into saturated aqueous sodium bicarbonate and extracted with 4:1 DCM/iPrOH three times. The organic layers were combined, passed through a phase separator, and concentrated. The crude material was purified by silica gel chromatography (0-100% EtOAc:EtOH:Et3N (v/v/v=75:25:1) in heptane), Fractions containing desired product were combined and concentrate, then rediluted in 2:1 water/MeCN and lyophilized to afford 3-(5-(((3R,5R)-5-ethoxy-1-isopropylpiperidin-3-yl)oxy)-1-oxoisoindolin-2-yl)piperidine-2,6-dione I-194. LCMS [M+H]$^+$: 430.2. $^1$H NMR (400 MHz, DMSO) δ 10.96 (s, 1H), 7.60 (d, J=8.4 Hz, 1H), 7.15 (d, J=2.2 Hz, 1H), 7.02 (dd, J=8.4, 2.2 Hz, 1H), 5.06 (dd, J=13.3, 5.1 Hz, 1H), 4.71 (d, J=5.5 Hz, 1H), 4.48-4.17 (m, 2H), 3.65 (m, 1H), 3.55-3.36 (m, 2H), 2.88 (q, J=5.5 Hz, 1H), 2.78-2.54 (m, 5H), 2.41-2.29 (m, 2H), 1.96 (dt, J=14.0, 5.0 Hz, 2H), 1.72 (ddd, J=12.6, 8.0, 3.6 Hz, 1H), 1.09 (t, J=7.0 Hz, 3H), 0.92 (ddd, J=10.6, 6.6, 1.6 Hz, 6H).

Example 75-1 and 75-2: 3-(5-(((3R,5R)-1-ethyl-5-methylpiperidin-3-yl)oxy)-1-oxoisoindolin-2-yl)piperidine-2,6-dione (I-202) and 3-(5-(((3R,5R)-1,5-dimethylpiperidin-3-yl)oxy)-1-oxoisoindolin-2-yl)piperidine-2,6-dione (I-203)

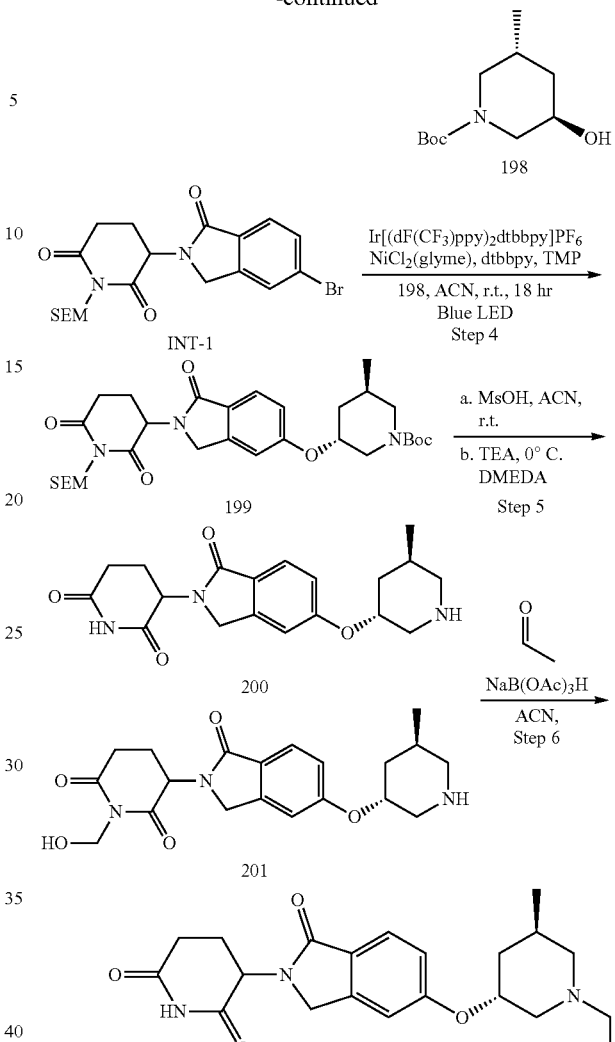

Step 1: tert-butyl (3R,5S)-3-methyl-5-((methylsulfonyl)oxy)piperidine-1-carboxylate (196)

To a solution of tert-butyl (3S,5R)-3-hydroxy-5-methylpiperidine-1-carboxylate (195) (4.03 g, 1 Eq, 18.7 mmol) in DCM (50 mL) at 0° C. were added triethylamine (2.84 g, 3.91 mL, 1.5 Eq, 28.1 mmol) and methanesulfonyl chloride (3.00 g, 2.03 mL, 1.4 Eq, 26.2 mmol). The reaction was stirred at 0° C. for 1 hr. The reaction mixture was poured into 150 ml of saturated aqueous sodium bicarbonate. The products were extracted 3× with DCM. The organic layers were passed through an isolute phase separator, and then the combined filtrate was concentrated to provide product tert-butyl (3R,5S)-3-methyl-5-((methylsulfonyl)oxy)piperidine- 1-carboxylate 196 that was used directly into the next step without further purification. $^1$H NMR (400 MHz, CDCl3) δ 4.54 (tt, J=10.6, 4.7 Hz, 1H), 4.36 (d, J=12.7 Hz, 1H), 3.98 (s, 1H), 3.04 (s, 3H), 2.68 (t, J=11.6 Hz, 1H), 2.27 (d, J=12.6 Hz, 2H), 1.71 (q, J=5.3 Hz, 1H), 1.46 (s, 9H), 1.31 (q, J=11.8 Hz, 1H), 0.95 (d, J=6.6 Hz, 3H).

Step 2: tert-butyl (3R,5R)-3-(formyloxy)-5-methylpiperidine-1-carboxylate (197)

To a solution of tert-butyl (3R,5S)-3-methyl-5-((methylsulfonyl)oxy)piperidine-1-carboxylate (196) (5.5 g, 1 Eq, 19 mmol) in Toluene (50 mL) were added potassium formate (3.2 g, 2 Eq, 37 mmol) and 1,4,7,10,13,16-hexaoxacyclooctadecane (9.9 g, 2 Eq, 37 mmol). The reaction was cooled to 23° C., then diluted with water. The products were extracted 2× with DCM. The organic layers were passed through an isolute phase separator, and the combined filtrate was concentrated. The residue was purified by flash column chromatography on silica gel (eluent: 0-50% EtOAc in heptane) to afford tert-butyl (3R,5R)-3-(formyloxy)-5-methylpiperidine-1-carboxylate 197 (1.8 g, 7.4 mmol, 39%) as a colorless oil. $^1$H NMR (400 MHz, CDCl3) δ 8.03 (s, 1H), 5.04 (s, 1H), 4.30-4.14 (m, 1H), 4.09 (s, 1H), 2.92 (dd, J=14.5, 2.0 Hz, 1H), 2.35 (s, 1H), 1.95 (ddq, J=13.2, 3.9, 1.9 Hz, 2H), 1.44 (s, 9H), 1.32 (ddd, J=15.0, 12.3, 3.0 Hz, 1H), 0.89 (d, J=6.5 Hz, 3H).

Step 3: tert-butyl (3R,5R)-3-(hydroxy)-5-methylpiperidine-1-carboxylate (198)

To a solution of tert-butyl (3R,5R)-3-(formyloxy)-5-methylpiperidine-1-carboxylate (197) (1.8 g, 1 Eq, 7.4 mmol) in MeOH (15 mL) at 23° C. was added Sodium methoxide (0.48 g, 18 mL, 0.5 molar in MeOH, 1.2 Eq, 8.9 mmol). The reaction mixture was poured into a flask containing water. The products were extracted 2× with DCM. The organic layers were passed through an isolute phase separator, and the combined filtrate was concentrated to provide tert-butyl (3R,5R)-3-hydroxy-5-methylpiperidine-1-carboxylate (198) (1.55 g, 7.1 mmol, 96%). $^1$H NMR (400 MHz, CDCl3) δ 4.01-3.82 (m, 3H), 2.98 (dd, J=13.6, 2.0 Hz, 1H), 2.45 (dd, J=13.1, 10.2 Hz, 1H), 1.99 (dtd, J=10.6, 6.8, 3.8 Hz, 1H), 1.93-1.78 (m, 2H), 1.45 (s, 9H), 1.25 (ddd, J=13.8, 11.1, 2.9 Hz, 1H), 0.88 (d, J=6.6 Hz, 3H).

Step 4: tert-butyl (3R,5R)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate (199)

tert-Butyl (3R,5R)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate (199) was synthesized by analogy to Example 52, Step 1, starting with tert-butyl (3R,5R)-3-hydroxy-5-methylpiperidine-1-carboxylate (198). Purification by silica gel chromatography (0-100% acetone in heptane) afforded tert-butyl (3R,5R)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate 199. LCMS [M–H]$^-$: 586.3.

Step 5: 3-(5-(((3R,5R)-5-methylpiperidin-3-yl)oxy)-1-oxoisoindolin-2-yl)piperidine-2,6-dione (200) and 1-(hydroxymethyl)-3-(5-(((3R,5R)-5-methylpiperidin-3-yl)oxy)-1-oxoisoindolin-2-yl)piperidine-2,6-dione (201)

To a solution of tert-butyl (3R,5R)-3-((2-(2,6-dioxo-1-((2-(trimethylsilyl)ethoxy)methyl)piperidin-3-yl)-1-oxoisoindolin-5-yl)oxy)-5-methylpiperidine-1-carboxylate (199) (12.0 g, 1 Eq, 20.3 mmol) in MeCN (60 mL) was added methanesulfonic acid (9.78 g, 6.61 mL, 5 Eq, 102 mmol) and the reaction mixture was stirred for 18 hr. The reaction was cooled to 0° C. and a stream of nitrogen gas was blown into the reaction flask while adding triethylamine (20.6 g, 28.4 mL, 10 Eq, 204 mmol) at 0° C. $N^1,N^2$-dimethylethane-1,2-diamine (DMEDA) (2.87 g, 3.49 mL, 1.6 Eq, 32.6 mmol) was rapidly added at 0° C. The reaction was stirred for 1.5 hr at 0° C. The reaction mixture was poured into saturated aqueous bicarbonate solution (400 ml) and was extracted with DCM (2×200 mL). The combined extracts were passed through a phase separator and concentrated in vacuo. The resulting precipitate was suspended in diethyl ether and filtered. The filtrate was concentrated to afford a mixture of 3-(5 (((3R,5R)-5-methylpiperidin-3-yl)oxy)-1-oxoisoindolin-2-yl)piperidine-2,6-dione (200) and 1-(hydroxymethyl)-3-(5-(((3R,5R)-5-methylpiperidin-3-yl)oxy)-1-oxoisoindolin-2-yl)piperidine-2,6-dione (201) as a beige solid (6.0 g). Material was taken through to the next step without further purification.

Step 6: 3-(5-(((3R,5R)-1-ethyl-5-methylpiperidin-3-yl)oxy)-1-oxoisoindolin-2-yl)piperidine-2,6-dione (I-202) and 3-(5-(((3R,5R)-1,5-dimethylpiperidin-3-yl)oxy)-1-oxoisoindolin-2-yl)piperidine-2,6-dione (I-203)

To a vial containing a mixture of 3-(5-(((3R,5R)-5-methylpiperidin-3-yl)oxy)-1-oxoisoindolin-2-yl)piperidine-2,6-dione (200) and 1-(hydroxymethyl)-3-(5-(((3R,5R)-5-methylpiperidin-3-yl)oxy)-1-oxoisoindolin-2-yl)piperidine-2,6-dione (201) (6.0 g) in EtOH (300 mL), cooled to 0° C. in an ice water bath, was added sodium triacetoxyborohydride (7.1 g, 34 mmol) followed by acetaldehyde (1.4 mL, 25.2 mmol) at 0° C. The reaction was stirred at 0° C. for 1 hr. The reaction was poured into saturated aqueous sodium bicarbonate and extracted with DCM three times. The organics layers were combined, and passed through a phase separator and the filtrate was concentrated. The crude material was purified by flash chromatography (0 to 100% EtOAc:EtOH:Et$_3$N (v/v/v=75:25:1) in DCM) to afford 3-(5-(((3R,5R)-1-ethyl-5-methylpiperidin-3-yl)oxy)-1-oxoisoindolin-2-yl)piperidine-2,6-dione I-202 (153 mg, 0.29 mmol) as a white solid and 3-(5-(((3R,5R)-1,5-dimethylpiperidin-3-yl)oxy)-1-oxoisoindolin-2-yl)piperidine-2,6-dione I-203. 3-(5-(((3R,5R)-1,5-dimethylpiperidin-3-yl)oxy)-1-oxoisoindolin-2-yl)piperidine-2,6-dione (I-203) was dissolved in DMSO:water:ACN (v/v/v=1:1:1) and further purified by basic reverse phase HPLC (15-40% ACN in water with 5 mM NH$_4$OH as modifier). Test tubes containing product were collected and poured into a separatory flask containing saturated aqueous sodium bicarbonate solution, extracted with 4:1 DCM/TFE and passed through an isolute phase separator and the solvents were concentrated. The crude oil was rediluted in 2:1 water/MeCN and lyophilized to afford 3-(5-(((3R,5R)-1,5-dimethylpiperidin-3-yl)oxy)-1-oxoisoindolin-2-yl)piperidine-2,6-dione I-203 (0.19 g, 0.51 mmol) as a white solid.

Example 75-1: 3-(5-(((3R,5R)-1-ethyl-5-methylpiperidin-3-yl)oxy)-1-oxoisoindolin-2-yl)piperidine-2,6-dione (I-202); LCMS [M+H]$^+$: 386.2. $^1$H NMR (400 MHz, DMSO) δ 10.95 (s, 1H), 7.60 (d, J=8.4 Hz, 1H), 7.15 (s, 1H), 7.03 (d, J=8.9 Hz, 1H), 5.06 (dd, J=13.3, 5.1 Hz, 1H), 4.70 (s, 1H), 4.51-4.14 (m, 2H), 2.98-2.82 (m, 2H), 2.68 (d, J=18.3 Hz, 1H), 2.63-2.53 (m, 1H), 2.40-2.25 (m, 3H), 2.21

(d, J=11.9 Hz, 1H), 2.03-1.91 (m, 2H), 1.86 (d, J=14.0 Hz, 1H), 1.70 (m, 1H), 1.28 (t, J=12.0 Hz, 1H), 0.94 (t, J=7.1 Hz, 3H), 0.89-0.83 (m, 3H).

Example 75-2: 3-(5-(((3R,5R)-1,5-dimethylpiperidin-3-yl)oxy)-1-oxoisoindolin-2-yl)piperidine-2,6-dione (I-203); LCMS [M+H]⁺: 372.4. ¹H NMR (400 MHz, DMSO) δ 10.95 (s, 1H), 7.60 (d, J=8.4 Hz, 1H), 7.15 (s, 1H), 7.03 (d, J=8.8 Hz, 1H), 5.06 (dd, J=13.3, 5.1 Hz, 1H), 4.71 (s, 1H), 4.47-4.13 (m, 2H), 2.98-2.73 (m, 2H), 2.61 (t, J=20.5 Hz, 2H), 2.41-2.25 (m, 1H), 2.09 (d, J=23.0 Hz, 4H), 1.97 (d, J=12.3 Hz, 2H), 1.85 (d, J=13.9 Hz, 1H), 1.66 (m, 1H), 1.24 (t, J=12.3 Hz, 1H), 0.92-0.81 (m, 3H).

Example 76-1 and 76-2: 3-(5-(((3R,5R)-1-ethyl-5-methylpiperidin-3-yl)oxy)-1-oxoisoindolin-2-yl)piperidine-2,6-dione, Peak 1 and Peak 2

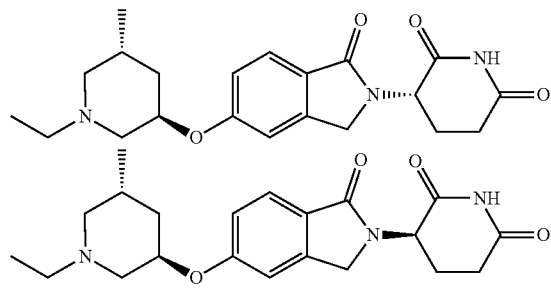

The diastereomeric mixture of 3-(5-(((3R,5R)-1-ethyl-5-methylpiperidin-3-yl)oxy)-1-oxoisoindolin-2-yl)piperidine-2,6-dione (I-202) (Example 75-1) was separated via chiral SFC [Column 21×250 mm Whelk-O1; CO₂ Co-solvent 35% IPA:ACN with 0.1% TEA; at 80 g/min at 125 bar at 25° C.] to afford the single diastereomers: Example 76-1, Peak 1: Diastereomer 1 of 3-(5-(((3R,5R)-1-ethyl-5-methylpiperidin-3-yl)oxy)-1-oxoisoindolin-2-yl)piperidine-2,6-dione as a white solid. Chiral SFC Rt 3.49 mins. ¹H NMR (400 MHz, DMSO) δ 10.96 (s, 1H), 7.60 (d, J=8.4 Hz, 1H), 7.16 (d, J=2.2 Hz, 1H), 7.04 (dd, J=8.4, 2.2 Hz, 1H), 5.07 (dd, J=13.3, 5.1 Hz, 1H), 4.71 (s, 1H), 4.44-4.21 (m, 2H), 2.97-2.81 (m, 2H), 2.75-2.65 (m, 1H), 2.63-2.56 (m, 1H), 2.41-2.28 (m, 3H), 2.23 (d, J=11.9 Hz, 1H), 2.03-1.93 (m, 2H), 1.86 (d, J=13.6 Hz, 1H), 1.71 (t, J=10.2 Hz, 1H), 1.36-1.23 (m, 1H), 0.95 (t, J=7.1 Hz, 3H), 0.87 (d, J=6.7 Hz, 3H). Example 76-1, Peak 2: Diastereomer 2 of 3-(5-(((3R,5R)-1-ethyl-5-methylpiperidin-3-yl)oxy)-1-oxoisoindolin-2-yl)piperidine-2,6-dione as a white solid. Chiral SFC Rt 5.04 mins. ¹H NMR (400 MHz, DMSO) δ 10.96 (s, 1H), 7.60 (d, J=8.4 Hz, 1H), 7.16 (d, J=2.2 Hz, 1H), 7.04 (dd, J=8.4, 2.2 Hz, 1H), 5.07 (dd, J=13.3, 5.1 Hz, 1H), 4.71 (s, 1H), 4.44-4.21 (m, 2H), 2.97-2.81 (m, 2H), 2.75-2.65 (m, 1H), 2.63-2.56 (m, 1H), 2.41-2.28 (m, 3H), 2.23 (d, J=11.9 Hz, 1H), 2.03-1.93 (m, 2H), 1.86 (d, J=13.6 Hz, 1H), 1.71 (t, J=10.2 Hz, 1H), 1.36-1.23 (m, 1H), 0.95 (t, J=7.1 Hz, 3H), 0.87 (d, J=6.7 Hz, 3H). The absolute stereochemistry at the glutarimide carbon of the two stereoisomers corresponding to the two product peaks was not determined.

Example 77: 3-(5-(((3R,5R)-1-isopropyl-5-methylpiperidin-3-yl)oxy)-1-oxoisoindolin-2-yl)piperidine-2,6-dione Formate Salt (I-204)

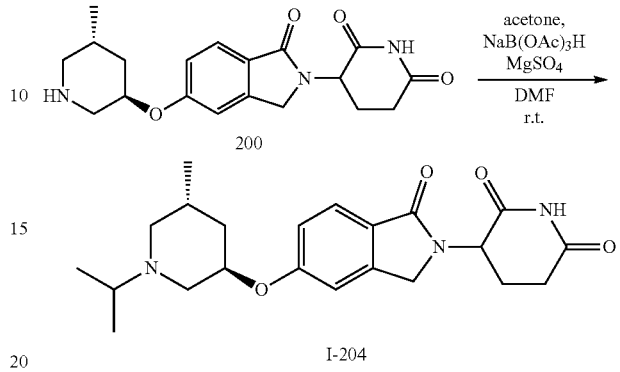

To a vial containing (200) (0.14 g, 0.38 mmol) and DMF (2 mL) was added sodium triacetoxyborohydride (0.12 g, 0.58 mmol) and MgSO₄ (95 mg, 0.77 mmol) followed by acetone (0.28 mL, 3.9 mmol). The reaction stirred at r.t. for 1 hr. The reaction was poured into saturated aqueous sodium bicarbonate and extracted with 4:1 DCM/iPrOH three times. The organics layers were combined, and passed through a phase separator and the combined filtrate was concentrated. The crude material was purified by flash chromatography (0 to 100% EtOAc:EtOH:Et3N (v/v/v=75:25:1) in DCM) to afford product. Material was dissolved in DMSO:water:ACN (v/v/v=1:1:1) and further purified by basic reverse phase HPLC (15-40% ACN in water with 5 mM NH₄OH as modifier). Test tubes contained 3 drops formic acid prior to sample collection. Fractions containing desired product were combined and lyophilized to afford 3-(5-(((3R,5R)-1-isopropyl-5-methylpiperidin-3-yl)oxy)-1-oxoisoindolin-2-yl)piperidine-2,6-dione formate salt I-204 as a white solid. LCMS [M+H]⁺: 400.3. ¹H NMR (400 MHz, DMSO) δ 8.18 (s, 1H) (formate salt), 7.59 (d, J=8.4 Hz, 1H), 7.14 (d, J=2.2 Hz, 1H), 7.02 (dd, J=8.4, 2.2 Hz, 1H), 5.06 (dd, J=13.3, 5.1 Hz, 1H), 4.68 (br. s, 1H), 4.45-4.14 (m, 2H), 2.97-2.74 (m, 2H), 2.65 (td, J=15.9, 8.4 Hz, 2H), 2.46-2.25 (m, 3H), 1.95 (t, J=10.4 Hz, 3H), 1.83 (d, J=13.1 Hz, 1H), 1.32 (m, 1H), 0.99-0.79 (m, 9H).

Example 78: 3-(5-(((3R,5R)-1-cyclobutyl-5-methylpiperidin-3-yl)oxy)-1-oxoisoindolin-2-yl)piperidine-2,6-dione Formate Salt (I-205)

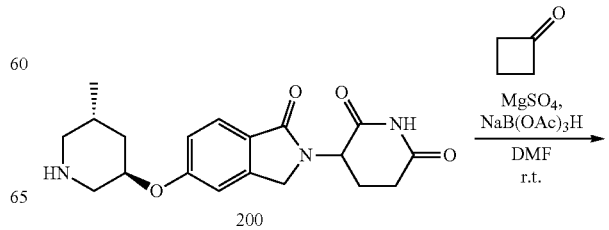

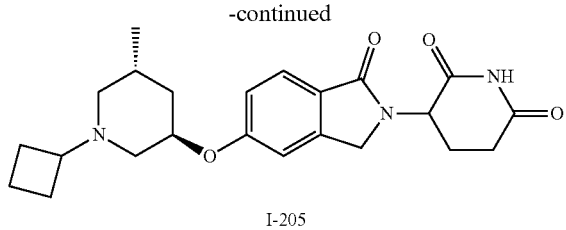

I-205

To a vial containing 3-(5-(((3R,5R)-5-methylpiperidin-3-yl)oxy)-1-oxoisoindolin-2-yl)piperidine-2,6-dione (200) (0.1 g, 0.3 mmol) and DMF (1 mL) was added sodium triacetoxyborohydride (97 mg, 0.46 mmol) and MgSO4 (75 mg, 0.61 mmol) followed by cyclobutanone (228 uL, 3.05 mmol). The reaction stirred at r.t. for 1 hr. The reaction was poured into saturated aqueous sodium bicarbonate and extracted with 4:1 DCM/iPrOH three times. The organics layers were combined, and passed through a phase separator and the combined filtrate was concentrated. The crude material was purified by flash chromatography (0 to 100% EtOAc:EtOH:Et$_3$N (v/v/v=75:25:1) in DCM) to afford product. Material was dissolved in DMSO:water:ACN (v/v/v=1:1:1) and further purified by basic reverse phase HPLC (15-40% ACN in water with 5 mM NH$_4$OH as modifier). Test tubes contained 3 drops formic acid prior to sample collection. Fractions containing desired product were combined and lyophilized to afford 3-(5-(((3R,5R)-1-cyclobutyl-5-methylpiperidin-3-yl)oxy)-1-oxoisoindolin-2-yl)piperidine-2,6-dione formate salt I-205 as a white solid. LCMS [M+H]$^+$: 412.4. $^1$H NMR (400 MHz, DMSO) δ 10.95 (s, 1H), 7.60 (d, J=8.4 Hz, 1H), 7.16 (s, 1H), 7.04 (d, J=8.7 Hz, 1H), 5.06 (dd, J=13.3, 5.1 Hz, 1H), 4.68 (m, 1H), 4.50-4.15 (m, 2H), 2.97-2.54 (m, 5H), 2.40-2.28 (m, 1H), 2.09-1.72 (m, 7H), 1.56 (dd, J=19.0, 9.3 Hz, 4H), 1.28 (t, J=13.1 Hz, 1H), 0.86 (d, J=6.7 Hz, 3H).

Example 79: 3-(5-(((3R,5R)-1-isobutyl-5-methylpiperidin-3-yl)oxy)-1-oxoisoindolin-2-yl)piperidine-2,6-dione Formate Salt (I-206)

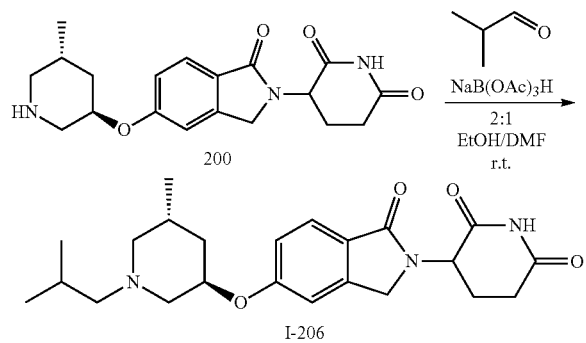

To a vial containing 3-(5-(((3R,5R)-5-methylpiperidin-3-yl)oxy)-1-oxoisoindolin-2-yl)piperidine-2,6-dione (200) (179 mg, 0.5 mmol) and EtOH (2 ml) and DMF (1 mL) was added sodium triacetoxyborohydride (212 mg, 1 mmol) followed by isobutyraldehyde (68 uL, 0.75 mmol). The reaction stirred at r.t. for 1 hr. The reaction was poured into saturated aqueous sodium bicarbonate and extracted with 4:1 DCM/TFE three times. The organics layers were combined, and passed through a phase separator and the combined filtrate was concentrated. The crude material was purified by flash chromatography (0 to 100% EtOAc:EtOH:Et$_3$N (v/v/v=75:25:1) in heptanes) to afford product. Material was dissolved in DMSO:water:ACN (v/v/v=1:1:1) and further purified by basic reverse phase HPLC (35-60% ACN in water with 5 mM NH$_4$OH as modifier). Test tubes contained 3 drops formic acid prior to sample collection. Fractions containing desired product were combined and lyophilized to afford 3-(5-(((3R,5R)-1-isobutyl-5-methylpiperidin-3-yl)oxy)-1-oxoisoindolin-2-yl)piperidine-2,6-dione formate salt I-206 as a white solid. LCMS [M+H]$^+$: 414.4. $^1$H NMR (400 MHz, DMSO) δ 10.96 (s, 1H), 7.60 (d, J=8.4 Hz, 1H), 7.15 (s, 1H), 7.03 (d, J=8.3 Hz, 1H), 5.07 (dd, J=13.2, 5.0 Hz, 1H), 4.70 (m, 1H), 4.47-4.13 (m, 2H), 2.97-2.77 (m, 2H), 2.71-2.54 (m, 2H), 2.36 (dd, J=13.5, 9.1 Hz, 2H), 2.20 (d, J=12.1 Hz, 1H), 2.00 (m, 3H), 1.90-1.62 (m, 3H), 1.33 (m, 1H), 0.89 (d, J=6.7 Hz, 3H), 0.84-0.75 (m, 6H).

Example 80: 3-(5-(((3R,5R)-5-methyl-1-(methylsulfonyl)piperidin-3-yl)oxy)-1-oxoisoindolin-2-yl)piperidine-2,6-dione (I-207)

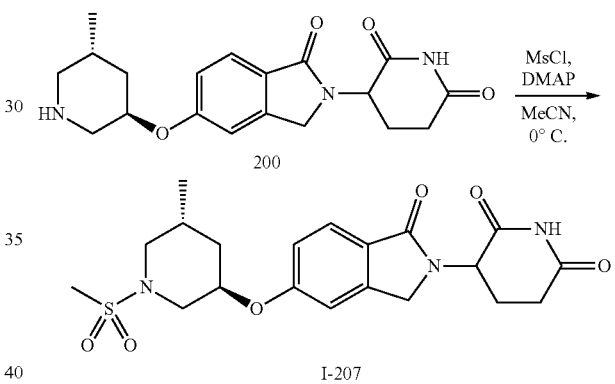

I-207

To a vial containing 3-(5-(((3R,5R)-5-methylpiperidin-3-yl)oxy)-1-oxoisoindolin-2-yl)piperidine-2,6-dione (200) (200 mg, 0.56 mmol) and DMAP (137 mg, 1.12 mmol) in ACN (3.0 mL), cooled in an ice water bath was added methansulfonyl chloride (65 ul, 0.84 mmol). The reaction was stirred at r.t. for 1 hr. The reaction was poured into water and extracted with DCM three times. The organic layers were combined, passed through a phase separator, and concentrated. The reaction was purified by reverse phase HPLC (10-30% ACN in water with 0.1% formic acid as modifier). Fractions containing desired product were combined and lyophilized to afford 3-(5-(((3R,5R)-5-methyl-1-(methylsulfonyl)piperidin-3-yl)oxy)-1-oxoisoindolin-2-yl)piperidine-2,6-dione I-207. LCMS [M+H]$^+$: 436.4. $^1$H NMR (400 MHz, DMSO) δ 10.95 (s, 1H), 7.62 (d, J=8.3 Hz, 1H), 7.21 (t, J=2.7 Hz, 1H), 7.07 (dt, J=8.3, 2.6 Hz, 1H), 5.06 (dd, J=13.2, 5.0 Hz, 1H), 4.81 (t, J=2.9 Hz, 1H), 4.48-4.22 (m, 2H), 3.79-3.65 (m, 2H), 3.54 (dd, J=11.8, 3.9 Hz, 1H), 3.05 (dd, J=13.2, 2.0 Hz, 1H), 2.89 (m, 4H), 2.60 (t, J=3.7 Hz, 1H), 2.36 (td, J=13.3, 4.6 Hz, 1H), 2.13-1.88 (m, 3H), 1.37 (td, J=12.8, 2.7 Hz, 1H), 0.88 (d, J=6.5 Hz, 3H).

Example 81: 3-(5-(((3R,6S)-1-isopropyl-6-methylpiperidin-3-yl)oxy)-1-oxoisoindolin-2-yl)piperidine-2,6-dione (I-208)

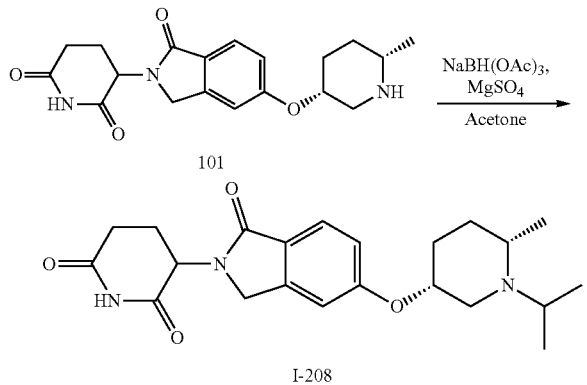

To a suspension of 3-(5-(((3R,6S)-6-methylpiperidin-3-yl)oxy)-1-oxoisoindolin-2-yl)piperidine-2,6-dione 101 (Example 41, Step 2) (98 mg, 0.27 mmol), MgSO$_4$ (66 mg, 0.55 mmol) in acetone (1.5 mL), was added sodium triacetoxyborohydride (99 mg, 0.47 mmol). The reaction was stirred at r.t. for 9 days. The reaction was diluted with 4:1 DCM:iPrOH and washed with saturated aqueous sodium bicarbonate. The organic layer was passed through a phase separator and concentrated onto Celite®. The crude material was purified by silica gel chromatography (0 to 100% EtOAc:EtOH:Et$_3$N (v/v/v=75:25:1) in DCM). Material was diluted with 1:3 ACN:water and lyophilized to afford 3-(5-(((3R,6S)-1-isopropyl-6-methylpiperidin-3-yl)oxy)-1-oxoisoindolin-2-yl)piperidine-2,6-dione I-208 as a white solid. LCMS [M+H]$^+$: 400.5. $^1$H NMR (400 MHz, DMSO) δ 10.96 (s, 1H), 7.60 (d, J=8.3 Hz, 1H), 7.16 (s, 1H), 7.04 (d, J=9.1 Hz, 1H), 5.06 (dd, J=13.3, 5.1 Hz, 1H), 4.55 (s, 1H), 4.38 (d, J=16.9 Hz, 1H), 4.25 (d, J=17.1 Hz, 1H), 3.10-2.98 (m, 1H), 2.98-2.77 (m, 2H), 2.75-2.63 (m, 1H), 2.59 (d, J=17.1 Hz, 1H), 2.47-2.28 (m, 2H), 1.97 (d, J=11.7 Hz, 1H), 1.82-1.68 (m, 2H), 1.55 (q, J=5.5 Hz, 2H), 1.02 (d, J=6.4 Hz, 3H), 0.90 (dd, J=6.6, 3.2 Hz, 3H), 0.86 (d, J=6.4 Hz, 3H).

Example 82: 3-(5-(((3R,6S)-1-cyclobutyl-6-methylpiperidin-3-yl)oxy)-1-oxoisoindolin-2-yl)piperidine-2,6-dione hydrochloride salt (I-209)

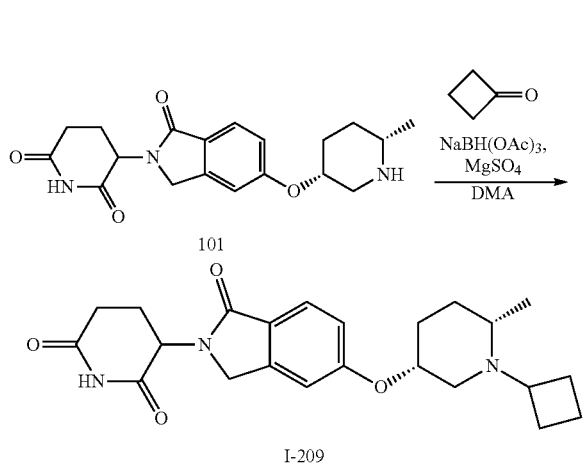

To a suspension of 3-(5-(((3R,6S)-6-methylpiperidin-3-yl)oxy)-1-oxoisoindolin-2-yl)piperidine-2,6-dione 101 (Example 41, Step 2) (98 mg, 0.27 mmol), MgSO$_4$ (66 mg, 0.55 mmol) and 1-oxocyclobutane (0.5 mL, 7.1 mmol) in DMA (1.0 mL), was added sodium triacetoxyborohydride (0.23 g, 1.1 mmol). The reaction was stirred at r.t. for 9 days. The reaction was diluted with 4:1 DCM:iPrOH and washed with saturated aqueous sodium bicarbonate. The organic layer was passed through a phase separator and concentrated onto Celite®. The crude material was purified by silica gel chromatography (0 to 100% EtOAc:EtOH:Et$_3$N (v/v/v=75:25:1) in DCM). 3-(5-(((3R,6S)-1-cyclobutyl-6-methylpiperidin-3-yl)oxy)-1-oxoisoindolin-2-yl)piperidine-2,6-dione was suspended in acetonitrile/H$_2$O (3/1 mL). 1 M aqueous HCl (1 equivalent) was then added and solvent was concentrated in vacuo to afford 3-(5-(((3R,6S)-1-cyclobutyl-6-methylpiperidin-3-yl)oxy)-1-oxoisoindolin-2-yl)piperidine-2,6-dione hydrochloride salt as a white solid (9.1 mg). The solid was dissolved into aqueous HCl (1.0 M, 210 µl, 0.210 mmol) and the solution was lyophilized overnight to provide 3-(5-(((3R,6S)-1-isopropyl-6-methylpiperidin-3-yl)oxy)-1-oxoisoindolin-2-yl)piperidine-2,6-dione hydrochloride salt I-209 (93 mg, 0.21 mmol, 76%) as a white solid. LCMS [M+H]$^+$: 412.5. $^1$H NMR (400 MHz, DMSO) δ 11.19-11.04 (m) and 9.63-9.39 (m) (1H), 10.98 (d, J=2.8 Hz, 1H), 7.68 (dd, J=8.4, 6.9 Hz, 1H), 7.37-7.08 (m, 2H), 5.15-5.03 (m, 1H), 4.98 (bs) and 4.95-4.83 (m) (1H), 4.42 (d, J=16.9 Hz, 1H), 4.29 (d, J=17.1 Hz, 1H), 3.90 (dq, J=38.2, 8.2 Hz, 1H), 3.70-3.56 (m) and 3.56-3.45 (m) (1H), 3.30-3.00 (m, 2H), 2.98-2.85 (m, 1H), 2.70-2.55 (m, 1H), 2.48-2.31 (m, 2H), 2.28-2.14 (m, 2H), 2.14-1.61 (m, 7H), 1.34 (d, J=6.5 Hz, 2H), 1.24 (d, J=6.8 Hz, 2H).

Example 83: ethyl (2S,5R)-5-((2-(2,6-dioxopiperidin-3-yl)-1-oxoisoindolin-5-yl)oxy)-2-methylpiperidine-1-carboxylate (I-210)

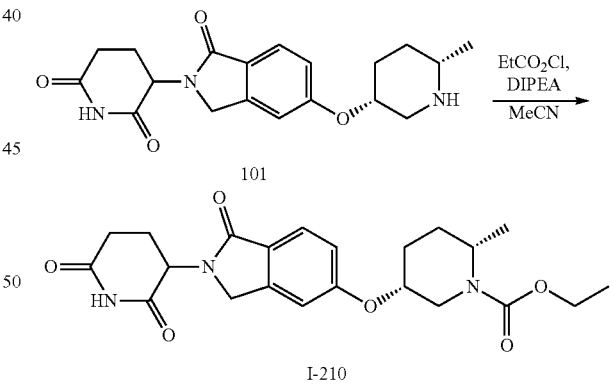

To a vial containing 3-(5-(((3R,6S)-6-methylpiperidin-3-yl)oxy)-1-oxoisoindolin-2-yl)piperidine-2,6-dione 101 (Example 41, Step 2) (130 mg, 0.36 mmol) and DIPEA (130 ul, 0.74 mmol) in ACN (2.0 mL), cooled in an ice water bath was added ethyl chloroformate (60 ul, 0.63 mmol). The reaction was stirred at r.t. for 1 hr. The reaction was quenched with 50% saturated aqueous sodium bicarbonate and extracted with 4:1 DCM/iPrOH three times. The combined organic phases were dried over anhydrous Na$_2$SO$_4$, filtered and concentrated under reduced pressure. The crude material was purified by reverse phase HPLC (5-95% ACN in water with 0.1% formic acid as modifier, cyano 30×100 column). Fractions containing desired product were combined and lyophilized to afford ethyl (2S,5R)-5-((2-(2,6-dioxopiperidin-3-yl)-1-oxoisoindolin-5-yl)oxy)-2-methylpiperidine-1-carboxylate 1-210 as a white solid. LCMS [M+H]+: 430.3. ¹H NMR (400 MHz, DMSO) δ 10.96 (s, 1H), 7.63 (d, J=8.4 Hz, 1H), 7.22 (d, J=1.9 Hz, 1H), 7.09 (dd, J=8.3, 2.2 Hz, 1H), 5.07 (dd, J=13.3, 5.1 Hz, 1H), 4.39 (dd, J=16.5, 4.8 Hz, 2H), 4.35-4.22 (m, 2H), 4.15 (d, J=12.2 Hz, 1H), 4.06 (qd, J=7.1, 4.8 Hz, 2H), 3.00-2.79 (m, 2H), 2.59 (d, J=17.0 Hz, 1H), 2.38 (qd, J=13.5, 4.7 Hz, 1H), 2.00 (t, J=15.2 Hz, 2H), 1.83-1.53 (m, 3H), 1.19 (t, J=7.1 Hz, 3H), 1.15 (d, J=6.9 Hz, 3H).

Example 84: (2S,5R)-5-((2-(2,6-dioxopiperidin-3-yl)-1-oxoisoindolin-5-yl)oxy)-N,2-dimethylpiperidine-1-carboxamide (I-211)

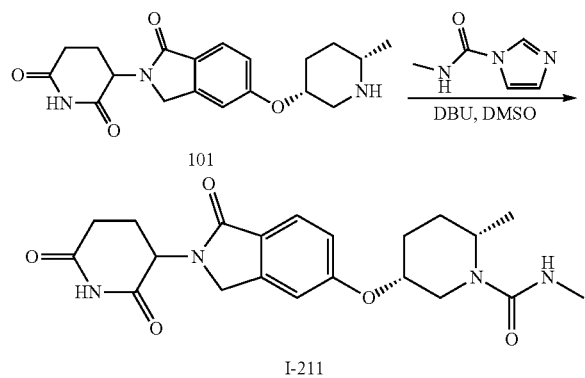

To a vial containing 3-(5-(((3R,6S)-6-methylpiperidin-3-yl)oxy)-1-oxoisoindolin-2-yl)piperidine-2,6-dione 101 (Example 41, Step 2) (75 mg, 0.21 mmol) and DBU (59 ul, 0.39 mmol) in DMSO (1.0 mL) was added N-methyl-1-imidazolecarboxamide (47 mg, 0.38 mmol). The reaction was stirred at r.t. for 1 hr. The reaction was purified by reverse phase HPLC (15-35% ACN in water with 0.1% formic acid as modifier). Fractions containing desired product were combined and lyophilized to afford (2S,5R)-5-((2-(2,6-dioxopiperidin-3-yl)-1-oxoisoindolin-5-yl)oxy)-N,2-dimethylpiperidine-1-carboxamide I-211 as a white solid. LCMS [M+H]+: 415.3. ¹H NMR (400 MHz, DMSO) δ 10.96 (s, 1H), 7.62 (d, J=8.4 Hz, 1H), 7.23 (d, J=2.2 Hz, 1H), 7.08 (dd, J=8.4, 2.2 Hz, 1H), 6.57-6.41 (m, 1H), 5.07 (dd, J=13.3, 5.1 Hz, 1H), 4.46-4.08 (m, 5H), 2.91 (ddd, J=18.1, 13.6, 5.4 Hz, 1H), 2.76-2.66 (m, 1H), 2.63-2.53 (m, 4H), 2.46-2.27 (m, 1H), 2.06-1.92 (m, 2H), 1.89-1.49 (m, 3H), 1.10 (d, J=6.8 Hz, 3H).

Example 85: 3-(5-(((3R,6S)-6-methyl-1-(methylsulfonyl)piperidin-3-yl)oxy)-1-oxoisoindolin-2-yl)piperidine-2,6-dione (I-212)

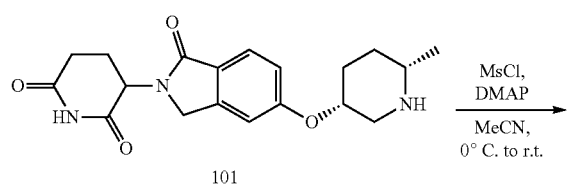

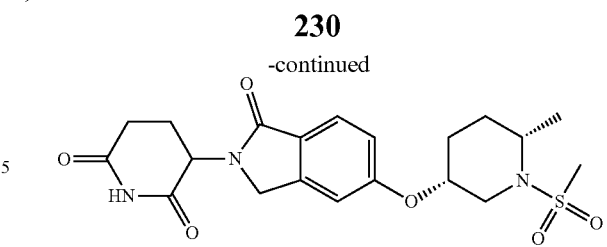

To a vial containing 3-(5-(((3R,6S)-6-methylpiperidin-3-yl)oxy)-1-oxoisoindolin-2-yl)piperidine-2,6-dione 101 (100 mg, 0.28 mmol) and DMAP (68 mg, 0.56 mmol) in ACN (4.0 mL), cooled in an ice water bath was added methansulfonyl chloride (25 ul, 0.32 mmol). The reaction was stirred at 0-5° C. for 30 min and at r.t. for 30 min. The reaction was poured into a saturated aqueous sodium bicarbonate solution and extracted with 4:1 DCM/iPrOH three times. The combined organic phases were dried over anhydrous Na₂SO₄, filtered and concentrated under reduced pressure. The reaction was purified by reverse phase HPLC (5-95% ACN in water with 0.1% formic acid as modifier, 30×100 cyano column). Fractions containing desired product were combined and lyophilized to afford 3-(5-(((3R,6S)-6-methyl-1-(methylsulfonyl)piperidin-3-yl)oxy)-1-oxoisoindolin-2-yl)piperidine-2,6-dione I-212 as a white solid. LCMS [M+H]+: 436.4. ¹H NMR (400 MHz, DMSO) δ 10.96 (s, 1H), 7.64 (d, J=8.4 Hz, 1H), 7.23 (s, 1H), 7.09 (dd, J=8.4, 2.2 Hz, 1H), 5.07 (dd, J=13.3, 5.1 Hz, 1H), 4.48 (tt, J=10.1, 4.4 Hz, 1H), 4.40 (dd, J=17.3, 3.9 Hz, 1H), 4.27 (dd, J=17.2, 5.1 Hz, 1H), 4.12-4.01 (m, 1H), 3.86-3.75 (m, 1H), 2.99 (s, 5H), 2.59 (d, J=17.2 Hz, 1H), 2.39 (qd, J=13.4, 4.8 Hz, 1H), 2.10-1.94 (m, 2H), 1.92-1.81 (m, 1H), 1.78-1.57 (m, 2H), 1.23 (d, J=6.9 Hz, 3H).

Example 86: 3-(5-(((3R,6S)-1-acetyl-6-methylpiperidin-3-yl)oxy)-1-oxoisoindolin-2-yl)piperidine-2,6-dione (I-213)

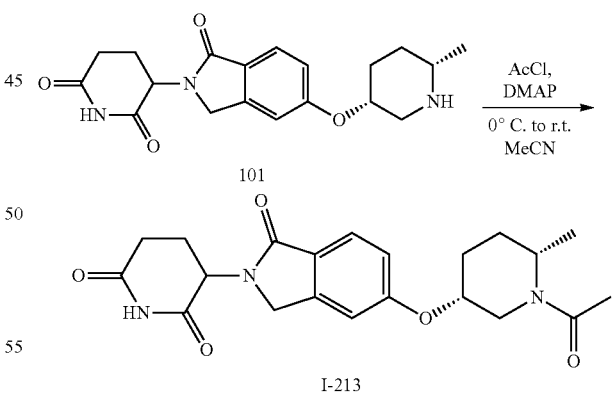

To a vial containing 3-(5-(((3R,6S)-6-methylpiperidin-3-yl)oxy)-1-oxoisoindolin-2-yl)piperidine-2,6-dione 101 (Example 41, Step 2) (100 mg, 0.28 mmol) and DMAP (68 mg, 0.56 mmol) in ACN (3.0 mL), cooled in an ice water bath was added acetyl chloride (30 ul, 0.42 mmol). The reaction was stirred at r.t. for 4 hr. The reaction was poured into a saturated aqueous sodium bicarbonate solution and extracted with 4:1 DCM/iPrOH three times. The combined organic phases were dried over anhydrous Na₂SO₄, filtered and concentrated under reduced pressure. The reaction was purified by reverse phase HPLC (5-95% ACN in water with 0.1% formic acid as modifier). Fractions containing desired product were combined and lyophilized to afford 3-(5-(((3R,6S)-1-acetyl-6-methylpiperidin-3-yl)oxy)-1-oxoisoindolin-2-yl)piperidine-2,6-dione I-213 as a white solid. LCMS [M+H]+: 400.3. ¹H NMR (400 MHz, DMSO) δ of a 1.3:1 mixture of rotamers: 10.96 (s, 1H), 7.63 (d, J=8.4 Hz, 1H), 7.27 (s) and 7.21 (s) (1H, rotamers), 7.10 (d, J=10.9 Hz, 1H), 5.07 (dd, J=13.3, 5.1 Hz, 1H), 4.75-4.67 (m) and 4.66-4.55 (m) (1H, rotamers), 4.56-4.45 (m) and 4.32-4.26 (m) (1H, rotamers), 4.39 (d, J=17.2 Hz, 1H), 4.26 (d, J=17.1 Hz, 1H), 4.19-4.08 (m) and 3.93-3.84 (m) (1H, rotamers), 3.47-3.40 (m) and 3.10 (t, J=11.9 Hz) (1H, rotamers), 2.91 (ddd, J=18.1, 13.7, 5.4 Hz, 1H), 2.59 (d, J=16.0 Hz, 1H), 2.46-2.29 (m, 1H), 2.08-1.93 (m, 5H), 1.89-1.53 (m, 3H), 1.23 (d, J=6.7 Hz) and 1.10 (d, J=7.0 Hz) (3H, rotamers).

Example 87-1 and 87-2: 3-(1-oxo-5-(((3R,6S)-6-propylpiperidin-3-yl)oxy)isoindolin-2-yl)piperidine-2,6-dione (I-221) and 3-(5-(((3R,6S)-1-ethyl-6-propylpiperidin-3-yl)oxy)-1-oxoisoindolin-2-yl)piperidine-2,6-dione (I-222)

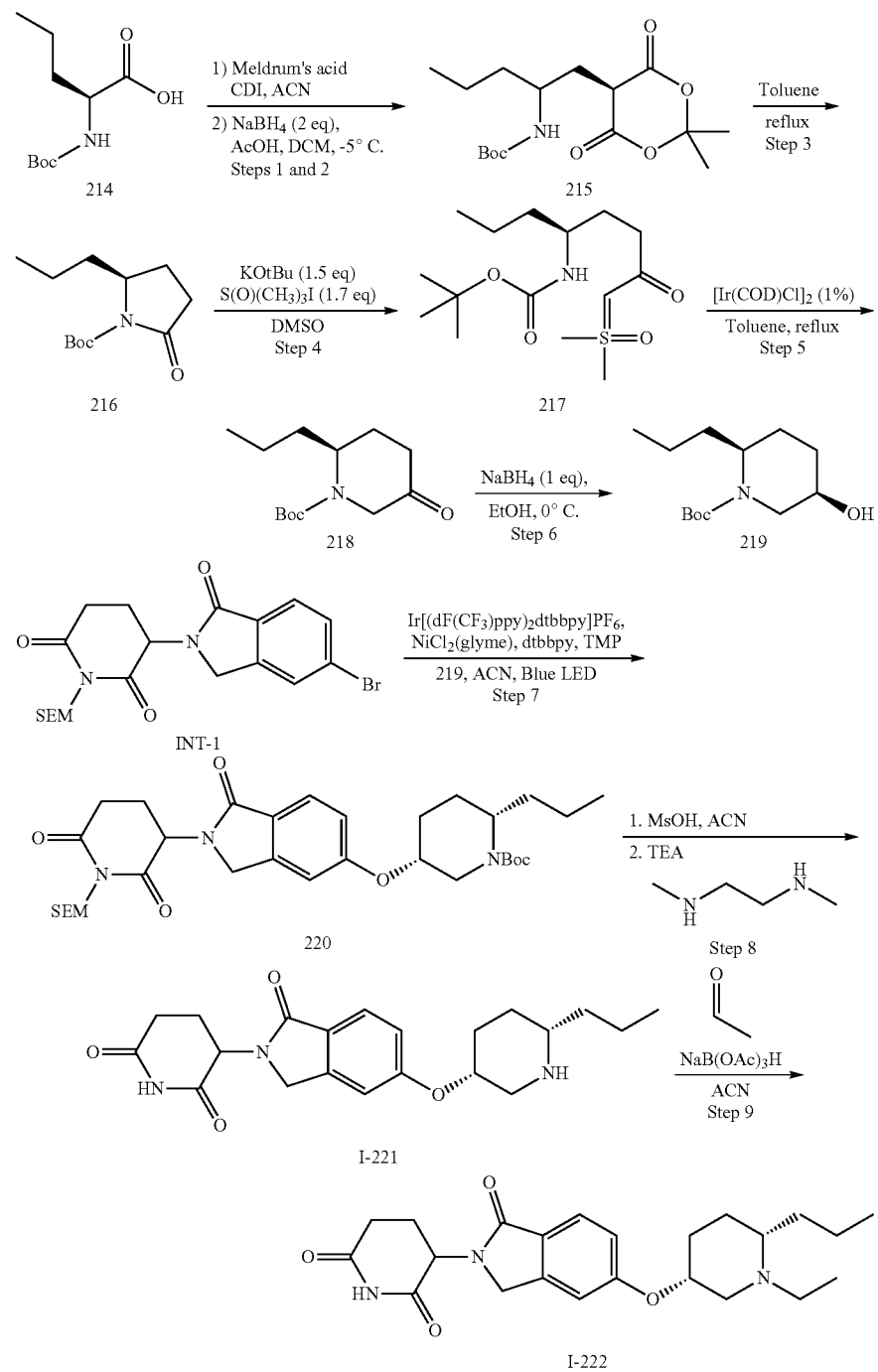

Step 1: tert-butyl (S)-(1-(2,2-dimethyl-4,6-dioxo-1,3-dioxan-5 yl)-1-oxopentan-2-yl)carbamate To CDI (15 g, 92 mmol) in acetonitrile (75 mL) was added (S)-2-((tert-butoxycarbonyl)amino)pentanoic acid (214) (20 g, 92 mmol) portion-wise over 15 minutes at 15° C. After $CO_2$ evolution ceased, 2,2-dimethyl-1,3-dioxane-4,6-dione (Meldrum's acid) (14 g, 97 mmol) was added at 15° C. and the reaction was stirred overnight at r.t. Reaction mixture was concentrated in vacuo and the crude was poured into a 1M solution of $KH_2PO_4$ (300 mL) and the aqueous phase was extracted 3× with EtOAc. Assembled organic fractions were washed with brine and dried with $Na_2SO_4$. After filtration and concentration in vacuo, tert-butyl (S)-(1-(2,2-dimethyl-4,6-dioxo-1,3-dioxan-5-yl)-1-oxopentan-2-yl)carbamate (36 g) was afforded as a yellow oil. [M−H]⁻: 342.2.

Step 2: tert-butyl (S)-(1-(2,2-dimethyl-4,6-dioxo-1,3-dioxan-5-yl)pentan-2-yl)carbamate (215)

A solution of tert-butyl (S)-(1-(2,2-dimethyl-4,6-dioxo-1,3-dioxan-5-yl)-1-oxopentan-2-yl)carbamate (16.0 g, 46.6 mmol) in DCM (250 mL) and AcOH (600 mL) was cooled to −5° C. and sodium borohydride (3.53 g, 93.2 mmol was added portion-wise over 15 minutes. The resulting solution was stirred for 3 hours at −5° C. Brine (250 ml) was slowly added to the reaction at −5° C. then water (250 ml) was added at 5° C. The two liquid phases were separated and the aqueous phase was extracted 2× with DCM. The combined organic extracts were dried over anhydrous $Na_2SO_4$ and concentrated in vacuo. tert-Butyl (S)-(1-(2,2-dimethyl-4,6-dioxo-1,3-dioxan-5-yl)pentan-2-yl)carbamate 215 (14.7 g) was afforded as a yellow oil. [M−H]⁻: 328.3.

Step 3: tert-butyl (S)-2-oxo-5-propylpyrrolidine-1-carboxylate (216)

tert-Butyl (S)-(1-(2,2-dimethyl-4,6-dioxo-1,3-dioxan-5-yl)pentan-2-yl)carbamate (215) (14.7 g, 44.6 mmol) was stirred in toluene at reflux for 3 hours. Reaction mixture was concentrated in vacuo to afford tert-butyl (S)-2-oxo-5-propylpyrrolidine-1-carboxylate 216 (10.4 g) as a yellow oil. $^1$H NMR (400 MHz, CDCl3) δ 4.17-4.05 (m, 1H), 2.65-2.50 (m, 1H), 2.42 (ddd, J=17.7, 9.5, 2.6 Hz, 1H), 2.19-2.03 (m, 1H), 1.83-1.71 (m, 2H), 1.71-1.60 (m, 1H), 1.52-1.26 (m, 11H), 1.01-0.91 (m, 3H).

Step 4: tert-butyl (S)-(8-(dimethyl(oxo)-16-sulfaneylidene)-7-oxooctan-4-yl)carbamate 2-Methylpropan-2-olate pottasium (4.21 g, 37.5 mmol) was added as a solid charge to a suspension of trimethyl(oxo)sulfonium iodide (9.35 g, 42.5 mmol) in DMSO (50 mL). The suspension was stirred for one hour, followed by addition of tert-butyl (S)-2-oxo-5-propylpyrrolidine-1-carboxylate (216) (5.68 g, 25.0 mmol) as a single solid charge, and the suspension was then aged for one hour. Water (500 mL) was added dropwise to the reaction mixture. The aqueous phase was extracted 3× with EtOAc then 3× with 9:1 EtOAc/EtOH. Assembled organic fractions were dried with $Na_2SO_4$ anh., filtered and concentrated in vacuo to afford a brown solid. The crude material was recrystallized in EtOAc and afforded tert-butyl (S)-(8-(dimethyl(oxo)-16-sulfaneylidene)-7-oxooctan-4-yl)carbamate 217 (2.85 g) as a white solid. [M+H]⁺: 320.2. $^1$H NMR (400 MHz, CDCl₃) δ 4.51-3.97 (m, 2H), 3.54 (s, 1H), 3.39 (s, 6H), 2.24 (t, J=6.4 Hz, 2H), 1.79 (s, 1H), 1.65-1.58 (m, 1H), 1.51-1.20 (m, 13H), 0.90 (t, J=7.0 Hz, 3H).

Step 5: tert-butyl (S)-5-oxo-2-propylpiperidine-1-carboxylate (218)

A suspension of tert-butyl (S)-(8-(dimethyl(oxo)-16-sulfaneylidene)-7-oxooctan-4-yl)carbamate (217) (2.75 g, 8.61 mmol) in toluene (40 mL) was degassed via nitrogen sparging for 30 minutes. The suspension was then added over 1 hour to a 80° C. degassed solution of [Ir(COD)Cl]₂ (57.8 mg, 86.1 μmol) in toluene (80 mL). The reaction mixture was aged at 80° C. for 10 hours, and then cooled to r.t. ISOLUTE® HM-N (10 g) was added to the reaction mixture and concentrated in vacuo. The crude material was purified by silica gel chromatography (5 to 100% EtOAc:EtOH (v/v=75:25) in heptane). Fractions containing desired product were combined and concentrated to afford tert-butyl (S)-5-oxo-2-propylpiperidine-1-carboxylate 218 (453 mg). [M−H]⁻: 240.2. $^1$H NMR (400 MHz, CDCl₃) δ 4.63-4.06 (m, 2H), 3.52 (d, J=18.9 Hz, 1H), 2.41 (dd, J=7.4, 5.3 Hz, 2H), 2.22 (dq, J=13.1, 6.7 Hz, 1H), 1.71-1.57 (m, 3H), 1.46 (s, 9H), 1.40-1.20 (m, 2H), 0.96 (t, J=7.3 Hz, 3H).

Step 6: tert-butyl (2S,5R)-5-hydroxy-2-propylpiperidine-1-carboxylate (219)

To a solution of tert-butyl (S)-5-oxo-2-propylpiperidine-1-carboxylate (218) (400 mg, 1.66 mmol) in EtOH (10 mL), was added sodium borohydride (94.1 mg, 2.49 mmol) at −5° C. and the mixture was stirred at this temperature for 4 hours. The reaction mixture was concentrated in vacuo and saturated aqueous NH₄Cl (30 mL) was added. The aqueous phase was extracted with DCM (4×). The combined organic fractions were dried over $Na_2SO_4$, filtered and concentrated in vacuo. The crude material was purified by silica gel chromatography (15 to 100% EtOAc in heptane). tert-butyl (2S,5R)-5-hydroxy-2-propylpiperidine-1-carboxylate 219 (190 mg) was afforded. [M-BOC]⁺: 144.2. $^1$H NMR (400 MHz, CDCl₃) δ 4.12 (q, J=7.1 Hz, 2H), 3.75-3.46 (m, 1H), 2.61-2.48 (m, 1H), 1.92-1.81 (m, 1H), 1.73-1.47 (m, 5H), 1.45 (s, 9H), 1.40-1.17 (m, 2H), 0.92 (t, J=7.2 Hz, 3H).

Step 7: tert-butyl (2S,5R)-5-((2-(2,6-dioxo-1-((2-(trimethylsilyl)ethoxy)methyl)piperidin-3-yl)-1-oxoisoindolin-5-yl)oxy)-2-propylpiperidine-1-carboxylate (220)

Compound 220 was made according to General Method VI starting from 3-(5-bromo-1-oxoisoindolin-2-yl)-1-((2-(trimethylsilyl)ethoxy)methyl)piperidine-2,6-dione INT-1 (0.37 g, 0.81 mmol) and tert-butyl (2S,5R)-5-hydroxy-2-propylpiperidine-1-carboxylate (219) (0.18 g, 0.74 mmol). The reaction mixture was cooled to room temperature, filtered and concentrated in vacuo. The crude material was purified by silica gel chromatography (1 to 10% EtOH in DCM). tert-Butyl (2S,5R)-5-((2-(2,6-dioxo-1-((2-(trimethylsilyl)ethoxy)methyl)piperidin-3-yl)-1-oxoisoindolin-5-yl)oxy)-2-propylpiperidine-1-carboxylate 220 (0.38 g) was afforded as a brown solid. LCMS [M−H]⁻: 614.2.

Step 8: 3-(1-oxo-5-(((3R,6S)-6-propylpiperidin-3-yl)oxy)isoindolin-2-yl)piperidine-2,6-dione (I-221) (Example 87-1)

Compound I-221 was made according to General Method VII starting from tert-Butyl (2S,5R)-5-((2-(2,6-dioxo-1-((2-(trimethylsilyl)ethoxy)methyl)piperidin-3-yl)-1-oxoisoindolin-5-yl)oxy)-2-propylpiperidine-1-carboxylate 220 (0.38 g, 0.61 mmol). The reaction mixture was concentrated in vacuo. The crude material was purified by silica gel chromatography (1 to 15% EtOH in DCM, 0.1% Et$_3$N modifier). Fractions containing desired product were combined and concentrated to afford 3-(1-oxo-5-(((3R,6S)-6-propylpiperidin-3-yl)oxy)isoindolin-2-yl)piperidine-2,6-dione I-221 (0.11 g) as a white solid. LCMS [M+H]$^+$: 386.3. $^1$H NMR (400 MHz, DMSO) δ 10.87 (s, 1H), 7.52 (d, J=8.4 Hz, 1H), 7.08 (d, J=2.1 Hz, 1H), 6.97 (dd, J=8.4, 2.2 Hz, 1H), 4.97 (dd, J=13.3, 5.1 Hz, 1H), 4.41 (s, 1H), 4.37-4.08 (m, 2H), 3.03 (s, 1H), 2.81 (ddd, J=18.1, 13.7, 5.4 Hz, 1H), 2.71 (d, J=13.7 Hz, 1H), 2.55-2.45 (m, 1H), 2.35-2.20 (m, 1H), 1.99-1.79 (m, 2H), 1.60 (t, J=13.4 Hz, 1H), 1.37 (d, J=13.2 Hz, 1H), 1.31-1.11 (m, 6H), 0.77 (t, J=6.9 Hz, 3H).

Step 9: 3-(5-(((3R,6S)-1-ethyl-6-propylpiperidin-3-yl)oxy)-1-oxoisoindolin-2-yl)piperidine-2,6-dione (I-222) (Example 87-2)

To a solution of 3-(1-oxo-5-(((3R,6S)-6-propylpiperidin-3-yl)oxy)isoindolin-2-yl)piperidine-2,6-dione I-221 (0.11 g, 0.27 mmol) and sodium triacetoxyborohydride (0.16 g, 0.74 mmol) in EtOH (2 mL) was added acetaldehyde (0.030 mL, 0.54 mmol) at 0° C. The reaction stirred at r.t. overnight. The reaction was concentrated and purified by silica gel chromatography (0 to 100% EtOAc:EtOH:Et$_3$N (v/v/v=75:25:1) in heptane). Fractions containing desired product were combined and concentrated to afford 3-(5-(((3R,6S)-1-ethyl-6-propylpiperidin-3-yl)oxy)-1-oxoisoindolin-2-yl)piperidine-2,6-dione I-222 (0.088 g, 0.21 mmol, 78%) as an off-white solid. LCMS [M+H]$^+$: 414.4. $^1$H NMR (400 MHz, DMSO) δ 10.96 (s, 1H), 7.60 (d, J=8.4 Hz, 1H), 7.17 (d, J=2.1 Hz, 1H), 7.04 (dd, J=8.4, 1.9 Hz, 1H), 5.06 (dd, J=13.2, 5.1 Hz, 1H), 4.53 (tt, J=5.9, 2.5 Hz, 1H), 4.38 (d, J=17.1 Hz, 1H), 4.25 (d, J=17.1 Hz, 1H), 2.90 (ddd, J=18.0, 13.5, 5.4 Hz, 1H), 2.78-2.53 (m, 6H), 2.46-2.28 (m, 1H), 2.08-1.92 (m, 1H), 1.89-1.74 (m, 1H), 1.73-1.54 (m, 3H), 1.53-1.28 (m, 3H), 1.28-1.10 (m, 1H), 0.98-0.82 (m, 6H).

Example 88-1 and 88-2: 3-(5-(((6,6-dimethylpiperidin-3-yl)oxy)-1-oxoisoindolin-2-yl)piperidine-2,6-dione (I-224) and 3-(5-((1-ethyl-6,6-dimethylpiperidin-3-yl)oxy)-1-oxoisoindolin-2-yl)piperidine-2,6-dione (I-225)

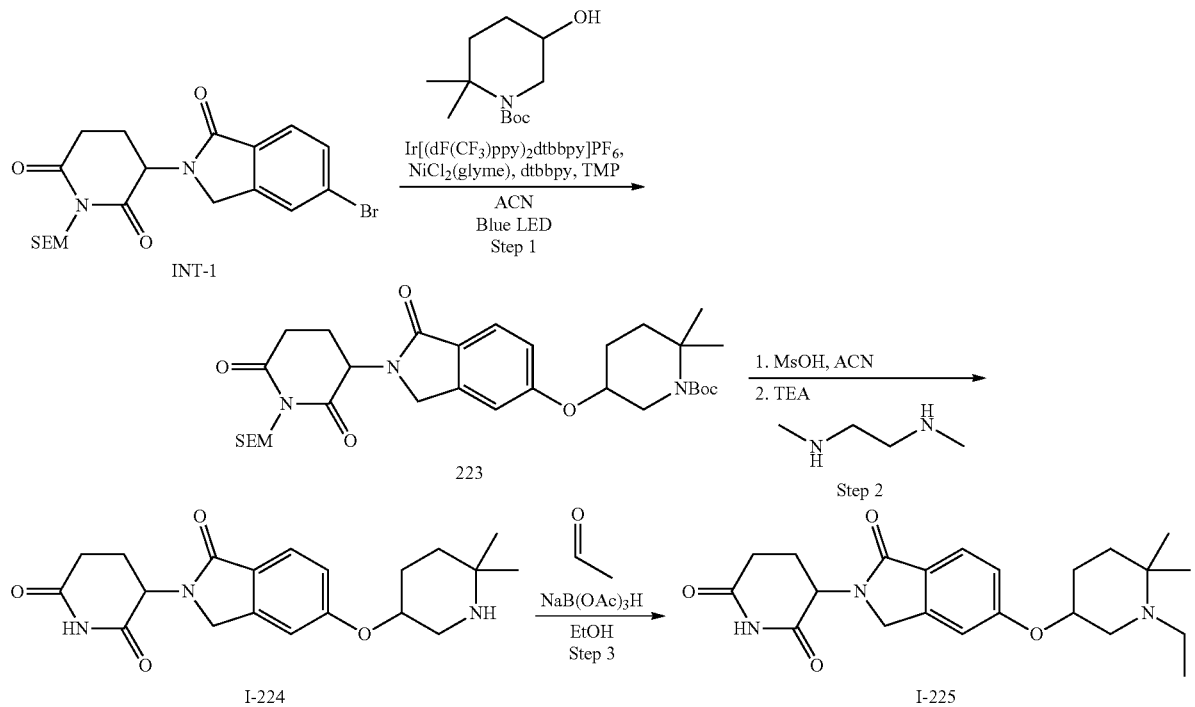

Step 1: tert-butyl 5-((2-(2,6-dioxo-1-((2-(trimethylsilyl)ethoxy)methyl)piperidin-3-yl)-1-oxoisoindolin-5-yl)oxy)-2,2-dimethylpiperidine-1-carboxylate (223)

Compound 223 was made according to General Method VI starting from 3-(5-bromo-1-oxoisoindolin-2-yl)-1-((2-(trimethylsilyl)ethoxy)methyl)piperidine-2,6-dione INT-1 (1.25 g, 2.75 mmol) and tert-butyl 5-hydroxy-2,2-dimethylpiperidine-1-carboxylate (630 mg, 2.75 mmol). The reaction mixture was cooled to room temperature, filtered and concentrated in vacuo to afford tert-butyl 5-((2-(2,6-dioxo-1-((2-(trimethylsilyl)ethoxy)methyl)piperidin-3-yl)-1-oxoisoindolin-5-yl)oxy)-2,2-dimethylpiperidine-1-carboxylate 223 (1.43 g) as an yellow oil. LCMS [M+H]$^+$: 600.5.

Step 2: 3-(5-((6,6-dimethylpiperidin-3-yl)oxy)-1-oxoisoindolin-2-yl)piperidine-2,6-dione (I-224) (Example 88-1)

Compound I-224 was made according to General Method VII starting from tert-butyl 5-((2-(2,6-dioxo-1-((2-(trimethylsilyl)ethoxy)methyl)piperidin-3-yl)-1-oxoisoindolin-5-yl)oxy)-2,2-dimethylpiperidine-1-carboxylate 223 (1.43 g, 2.38 mmol). The reaction mixture was diluted with saturated aqueous sodium bicarbonate and extracted with 4:1 DCM:TFE three times. The organic layers were combined and concentrated. The crude material was purified by silica gel chromatography (0 to 100% EtOH:Et$_3$N (v/v=100:1) in EtOAc). Fractions containing desired product were combined and concentrated to afford 3-(5-((6,6-dimethylpiperidin-3-yl)oxy)-1-oxoisoindolin-2-yl)piperidine-2,6-dione I-224 (0.56 g) as a white solid. LCMS [M+H]$^+$: 372.3. $^1$H NMR (400 MHz, DMSO) δ 10.96 (s, 1H), 7.60 (d, J=8.4 Hz, 1H), 7.18 (d, J=2.2 Hz, 1H), 7.05 (dd, J=8.4, 2.2 Hz, 1H), 5.06 (dd, J=13.3, 5.1 Hz, 1H), 4.44-4.19 (m, 3H), 2.98 (dd, J=12.8, 3.9 Hz, 1H), 2.94-2.83 (m, 1H), 2.71 (dd, J=12.9, 8.0 Hz, 1H), 2.64-2.55 (m, 1H), 2.37 (qd, J=13.1, 4.4 Hz, 1H), 2.05-1.90 (m, 2H), 1.78-1.62 (m, 1H), 1.59-1.47 (m, 1H), 1.45-1.28 (m, 1H), 1.07 (s, 3H), 1.05 (s, 3H).

Step 3: 3-(5-((1-ethyl-6,6-dimethylpiperidin-3-yl)oxy)-1-oxoisoindolin-2-yl)piperidine-2,6-dione (I-225) (Example 88-2)

To a solution of 3-(5-((6,6-dimethylpiperidin-3-yl)oxy)-1-oxoisoindolin-2-yl)piperidine-2,6-dione I-224 (479 mg, 1.29 mmol) and sodium triacetoxyborohydride (683 mg, 3.22 mmol) in EtOH (20 mL) was added acetaldehyde (0.14 mL, 2.5 mmol) at 0° C. The reaction stirred at r.t. overnight. The reaction was concentrated and purified by silica gel chromatography (0 to 100% EtOAc:EtOH:Et$_3$N (v/v/v=75:25:1) in heptane). Fractions containing desired product were combined and concentrated to afford 3-(5-((1-ethyl-6,6-dimethylpiperidin-3-yl)oxy)-1-oxoisoindolin-2-yl)piperidine-2,6-dione I-225 (0.29 g, 0.72 mmol, 56%) as an off-white solid.

LCMS [M+H]$^+$: 400.3. $^1$H NMR (400 MHz, DMSO) δ 10.96 (s, 1H), 7.60 (d, J=8.4 Hz, 1H), 7.18 (d, J=2.2 Hz, 1H), 7.04 (dd, J=8.4, 2.2 Hz, 1H), 5.06 (dd, J=13.3, 5.1 Hz, 1H), 4.45 (td, J=8.6, 4.2 Hz, 1H), 4.38 (d, J=17.2 Hz, 1H), 4.25 (d, J=17.1 Hz, 1H), 2.98-2.83 (m, 2H), 2.69-2.54 (m, 2H), 2.36 (td, J=12.3, 3.4 Hz, 2H), 2.10 (dq, J=13.5, 6.8 Hz, 1H), 2.03-1.83 (m, 2H), 1.64-1.40 (m, 3H), 1.06 (s, 3H), 0.99-0.88 (m, 6H).

BIOLOGICAL DATA

Abbreviations

BSA bovine serum albumin
Cas9 CRISPR associated protein 9
CRISPR Clustered regularly interspaced short palindromic repeats
crRNA CRISPR RNA
DMEM Dulbecco's modified eagle media
DMSO Dimethyl sulfoxide
DTT Dithiothreitol
EDTA ethylenediaminetetraacetic acid
eGFP enhanced green fluorescent protein
FACS fluorescence-activated cell sorting
FBS fetal bovine serum
FITC fluorescein
Flt3L Fms-related tyrosine kinase 3 ligand, Flt3L
HbF Fetal hemoglobin
HEPES (4-(2-hydroxyethyl)-1-piperazineethanesulfonic acid)
IMDM Iscove's modified Dulbecco's medium
KCl potassium chloride
mPB mobilized peripheral blood
PBS phosphate buffered saline
rhEPO recombinant human erythropoietin
rhIL-3 recombinant human interleukin-3
rhIL-6 recombinant human interleukin-6
rhSCF recombinant human stem cell factor
rhTPO recombinant human thrombopoietin
RNP ribonucleoprotein
shRNA short hairpin RNA
tracrRNA trans-activating crRNA
WIZ Widely-Interspaced Zinc Finger Containing Protein

MATERIALS AND METHODS

Example 89: Quantification of WIZ Protein Levels in HiBit Tag Fusion Protein Assay The HiBit system from Promega was used to develop high-throughput and quantitative assays to measure changes in WIZ protein levels in response to compounds. The HiBit tag was derived from a split Nanoluciferase and has the following protein sequence: VSGWRLFKKIS (SEQ ID NO: 1). The complementary fragment of Nanoluciferase (known as LgBit, from Promega), was added to the HiBit tag to form an active Nanoluciferase enzyme whose activity can be precisely measured. In this way, the levels of a fusion protein with the HiBit tag can be quantified in cell lysates.

Lentiviral vectors, based on the Invitrogen™ pLenti6.2/V5 DEST backbone were constructed that places the HiBit tag upstream of WIZ and expressed the fusion protein from an HSVTK promotor.

To ensure moderate and consistent expression of the HiBit-WIZ fusion protein across all cells in the population, stable cell lines were constructed from cells harboring a single copy of the construct. Lentivirus packaged with the constructs were made using the ViraPowerTMkit from Invitrogen™. 293T cells from ATCC (Catalog number: CRL-3216), were infected with the virus at low multiplicity of infection and selected by 5 µg/mL blasticidin in culture media for 2 weeks.

The levels of HiBit-WIZ tagged fusion proteins in compound-treated cell lines were measured as follows:

On day 1, cells were diluted to $1.0\times10^6$ cells/ml in normal growth medium. 20 µL of cell suspension were plated in each well of a solid white 384-well plate. Plates were incubated overnight in a 37° C. and 5% CO$_2$ humidified tissue culture incubator.

On day 2, serial dilutions of compounds were made in 384-well plates. Compound plates were set up with DMSO in columns 1, 2, 23, 24, and 10-point compound dilution series in column 3-12 and column 13-22. 10 mM stock solution of compound were placed into column 3 or 13 and a 1:5 serial dilution was carried out until there was a 10-point dilution series per compound. 50 nL of diluted compounds were transferred into the plated cells by Echo® (Labcyte) acoustic transfer. The highest concentration of compound was 25 µM. Plates were incubated overnight (about 18 hours) in a 37° C. and 5% CO$_2$ humidified tissue culture incubator.

On day 3, plates were removed from the incubator and allowed to equilibrate at room temperature for 60 minutes. HiBit substrate (Nano-Glo® HiBit Lytic Detection System, Promega Catalogue number: N3050) was added as described by the manufacturers protocols. Plates were incubated at room temperature for 30 minutes and luminescence was read using an EnVision® reader (PerkinElmer®). Data was analyzed and visualized using the Spotfire® software package.

WIZ Degradation Activity of Compounds (Table 1)

Table 1 shows WIZ degradation activity of compounds of the disclosure in the WIZ HiBit assay in 293T cells. WIZ Amax reflects the DMSO-normalized, curve-fitted percentage of WIZ-HiBit remaining at 25 uM. It was calculated by normalizing DMSO controls to 100%, parametric curve fitting of the dose response data (10-point, 5-fold), followed by calculation of response at 25 uM using the fitted equation.

TABLE 1

| Ex. No. | WIZ AC$_{50}$ (μM) | WIZ Amax | % degradation of WIZ (100 − Amax) |
|---|---|---|---|
| 1 | 0.016 | 24.04 | 75.96 |
| 2 | 0.36 | 88.89 | 11.11 |
| 3 | 0.002 | 26.79 | 73.21 |
| 4 | 0.11 | 64.40 | 35.6 |
| 5 | 0.055 | 77.26 | 22.74 |
| 6 | 0.031 | 86.71 | 13.29 |
| 7 | 0.0011 | 38.87 | 61.13 |
| 8 | 0.028 | 32.98 | 67.02 |
| 9 | 0.0042 | 28.52 | 71.48 |
| 10 | 0.033 | 45.54 | 54.46 |
| 11 | 0.11 | 56.44 | 43.56 |
| 12 | 0.13 | 68.54 | 31.46 |
| 13 | 0.014 | 27.56 | 72.44 |
| 14 | 0.057 | 40.67 | 59.33 |
| 15 | 0.0084 | 20.0 | 80 |
| 16 | 0.0025 | 40.88 | 59.12 |
| 17 | 0.014 | 27.75 | 72.25 |
| 18 | 0.02 | 61.38 | 38.62 |
| 19 | 0.012 | 37.13 | 62.87 |
| 20 | 3.75 | 75.87 | 24.13 |
| 21 | 0.0035 | 25.7 | 74.3 |
| 22 | 0.083 | 75.65 | 24.35 |
| 23 | 0.03 | 42.29 | 57.71 |
| 24 | 0.01 | 47.30 | 52.7 |
| 25 | 0.0075 | 50.21 | 49.79 |
| 26 | 0.021 | 58.9 | 41.1 |
| 27 | 0.13 | 60.26 | 39.74 |
| 28 | 0.084 | 67.1 | 32.9 |
| 29 | 0.082 | 69.01 | 30.99 |
| 30 | 0.079 | 70.76 | 29.24 |
| 31 | 0.0089 | 31.43 | 68.57 |
| 32 | 0.0017 | 19.17 | 80.83 |
| 33 | 0.0015 | 18.59 | 81.41 |
| 34 | 0.015 | 19.98 | 80.02 |
| 35 | 0.026 | 68.11 | 31.89 |
| 35A | 0.0086 | 60.81 | 39.19 |
| 35B | 0.0061 | 67.54 | 32.46 |
| 35C | 0.011 | 69.59 | 30.41 |
| 35D | 0.0063 | 62.63 | 37.37 |
| 36 | 0.057 | 32.5 | 67.5 |
| 37 | >25.0 | 103.43 | — |
| 38 | 0.025 | 35.65 | 64.35 |
| 39 | 0.21 | 47.85 | 52.15 |
| 40 | 0.77 | 73.54 | 26.46 |
| 41 | 0.00014 | 11.40 | 88.6 |
| 42 | 0.0036 | 22.9 | 77.1 |
| 43 | 0.0037 | 28.07 | 71.93 |
| 44 | 0.06 | 84.18 | 15.82 |
| 45 | 0.0076 | 56.3 | 43.7 |
| 45A | 0.040 | 48.89 | 51.11 |
| 45B | 0.044 | 67.92 | 32.08 |
| 45C | 0.049 | 66.38 | 33.62 |
| 45D | 0.051 | 48.09 | 51.91 |
| 46 | >25 | 101 | — |
| 46A | >25.00 | 109.66 | — |
| 46B | >25.00 | 110.99 | — |
| 46C | >25.00 | 105.03 | — |
| 46D | >25.00 | 110.99 | — |
| 47 | 0.088 | 77.16 | 22.84 |
| 48 | >25 | 101.5 | — |
| 49 | 0.083 | 91.37 | 8.63 |
| 50 | >25 | 97.62 | 2.38 |
| 51 | 0.200 | 87.19 | 12.81 |
| 52 | 0.0055 | 23.76 | 76.24 |
| 53 | 0.071 | 78.16 | 21.84 |
| 54 | >25.00 | 101.89 | — |
| 55 | 0.026 | 55.08 | 44.92 |
| 56 | 0.95 | 83.84 | 16.16 |
| 57 | 0.17 | 83.12 | 16.88 |
| 58 | 0.0049 | 39.27 | 60.73 |
| 59 | 0.0026 | 35.57 | 64.43 |
| 60 | 0.078 | 63.04 | 36.96 |
| 62 | 0.083 | 72.90 | 27.1 |
| 63 | 0.00012 | 20.54 | 79.46 |
| 64 | 0.0063 | 20.55 | 79.45 |
| 65-1 | 0.0014 | 18.11 | 81.89 |
| 65-2 | 0.0012 | 19.67 | 80.33 |
| 66 | 0.0333 | 19.87 | 80.13 |
| 67 | 0.0112 | 16.93 | 83.07 |
| 68 | >25 | 105.37 | — |
| 69 | >25 | 106.41 | — |
| 70 | >25 | 106.59 | — |
| 71 | 0.0453 | 39.01 | 60.99 |
| 72 | 0.0415 | 40.12 | 59.88 |
| 73 | 0.0238 | 37.20 | 62.80 |
| 74 | 0.0089 | 21.94 | 78.06 |
| 75-1 | 0.0009 | 13.40 | 86.60 |
| 75-2 | 0.0040 | 16.50 | 83.50 |
| 76-1 | 0.0016 | 13.76 | 86.24 |
| 76-2 | 0.0006 | 12.82 | 87.18 |
| 77 | 0.0011 | 13.55 | 86.45 |
| 78 | 0.0005 | 14.27 | 85.73 |
| 79 | 0.0017 | 17.29 | 82.71 |
| 80 | 0.0234 | 28.59 | 71.41 |
| 81 | 0.0020 | 10.74 | 89.26 |
| 82 | 0.0005 | 15.01 | 84.99 |
| 83 | >25 | 96.76 | 3.24 |
| 84 | 1.1735 | 81.67 | 18.33 |
| 85 | 0.0672 | 65.69 | 34.31 |
| 86 | >25 | 75.97 | 24.03 |
| 87-1 | 0.0359 | 28.58 | 71.42 |
| 87-2 | 0.0006 | 10.29 | 89.71 |
| 88-1 | 0.1345 | 50.01 | 49.99 |
| 88-2 | 0.0007 | 20.47 | 79.53 |

Example 90: Comparative WIZ AC$_{50}$ and WIZ Degradation Data (Table 2)

Table 2 shows comparative data demonstrating improved WIZ degradation. This assay produced a range of WIZ AC$_{50}$ and Amax values over several repeat runs due to normal variations in the assay. For a comparison to the compounds described in PCT/IB2020/062070, the updated arithmatic mean values are reported over the number of repeats specified below from the assay described in Example 89. Without wishing to be bound by any theory, it is hypothesized that the improved potency of compounds of formula (I) of the present disclosure is due to the confirmational restriction of the nitrogen-containing heterocyclic group bonded through oxygen to the base molecule. This increased rigidity of the chemical structures may thus lead to enhanced potency for WIZ by minimizing entropic loss.

TABLE 2

| Example Number | WIZ AC$_{50}$ (μM) | Number of Repeats |
|---|---|---|
| Example 1 | 0.016 | 3 |

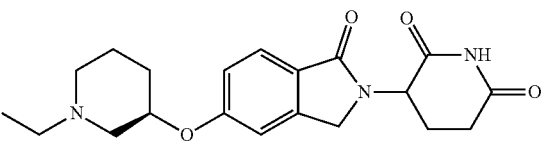 [SMILES: CCN1CCC[C@@H](Oc2ccc3c(c2)CN(C2CCC(=O)NC2=O)C3=O)C1]

3-(5-(((R)-1-ethylpiperidin-3-yl)oxy)-1-oxoisoindolin-2-yl)piperidine-2,6-dione (mixture of 2 diastereomers)

| | | |
|---|---|---|
| Example 13 | 0.021 | 3 |

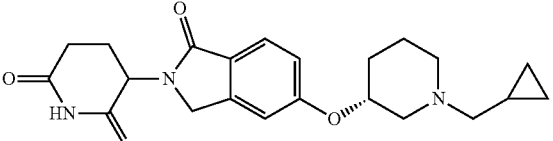

3-(5-(((R)-1-(cyclopropylmethyl)piperidin-3-yl)oxy)-1-oxoisoindolin-2-yl)piperidine-2,6-dione

| | | |
|---|---|---|
| Comparative Example 1 | 0.051 | 27 |

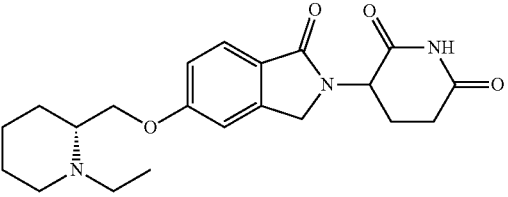 [SMILES: CCN1CCCC[C@@H]1COc1ccc2c(c1)CN(C1CCC(=O)NC1=O)C2=O]

3-(5-(((R)-1-ethylpiperidin-2-yl)methoxy)-1-oxoisoindolin-2-yl)piperidine-2,6-dione (mixture of 2 diastereomers)

| | | |
|---|---|---|
| Comparative Example 2 | 0.026 | 31 |

3-(5-(1-(1-ethylpiperidin-2-yl)ethoxy)-1-oxoisoindolin-2-yl)piperidine-2,6-dione (mixture of 2 diastereomers)

| | | |
|---|---|---|
| Comparative Example 3 | 0.032 | 1 |

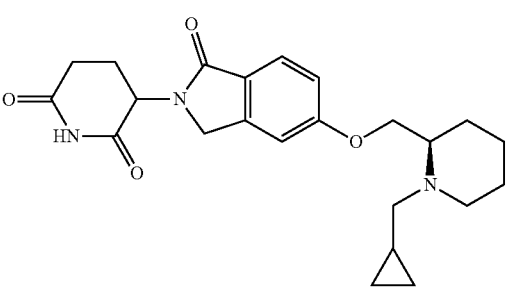 [SMILES: O=C1CCC(N2Cc3cc(OC[C@H]4CCCCN4CC4CC4)ccc3C2=O)C(=O)N1]

3-(5-(((R)-1-(cyclopropylmethyl)piperidin-2-yl)methoxy)-1-oxoisoindolin-2-yl)piperidine-2,6-dione

Example 91: Quantification of SALL4 Protein Levels in HiBiT Tag Fusion Protein Assay The HiBiT system from Promega was used to develop high-throughput and quantitative assays to measure changes in SALL4 protein levels in response to compounds. The HiBiT tag was derived from a split Nanoluciferase and has the following protein sequence: VSGWRLFKKIS (SEQ ID No: 1). The complementary fragment of Nanoluciferase (known as LgBiT, from Promega), was added to the HiBiT tag to form an active Nanoluciferase enzyme whose activity can be precisely measured. In this way, the levels of a fusion protein with the HiBiT tag can be quantified in cell lysates.

DNA constructs, based on the Invitrogen pLenti6.2/V5 DEST backbone, were constructed with the HiBiT tag upstream of SALL4 and expressed the fusion protein from a CMV promotor.

To ensure moderate and consistent expression of the HiBiT-SALL4 fusion protein across all cells in the population, stable cell lines were derived from clones. GripTite 293 MSR cells (293GT) from ThermoFisher Scientific (Catalog number: CRL-R79507), were stably transfected with prepared constructs via electroporation. Following recovery, cells were selected by 10 ug/mL blasticidin in culture media.

The levels of HiBiT-SALL4 tagged fusion proteins in compound-treated cell lines were measured as follows:

On day 1, cells were diluted to $1.0 \times 10^6$ cells/ml in normal growth medium. 20 μL of cell suspension were plated in each well of a solid white 384-well plate. Plates were incubated overnight in a 37° C. and 5% $CO_2$ humidified tissue culture incubator.

On day 2, serial dilutions of compounds were made in 384-well plates. Compound plates were set up with DMSO in columns 1, 2, 23, 24, and 10-point compound dilution series in column 3-12 and column 13-22. 10 mM stock solution of compound were placed into column 3 or 13 and a 1:5 serial dilution was carried out until there was a 10-point dilution series per compound. 100 nL of diluted compounds were transferred into the plated cells by Echo® (Labcyte) acoustic transfer. The highest concentration of compound was 50 μM. Plates were incubated overnight (18 hours) in a 37° C. and 5% CO2 humidified tissue culture incubator.

On day 3, plates were removed from the incubator and allowed to equilibrate at room temperature for 60 minutes. HiBiT substrate (Nano-Glo® HiBit Lytic Detection System, Promega Catalogue number: N3050) was added as described by the manufacturers protocols. Plates were incubated at room temperature for 30 minutes and luminescence was read using an EnVision® reader (PerkinElmer®). Data was analyzed and visualized using the Spotfire® software package.

SALL4 Degradation Activity of Comparative Compounds (Table 3)

Table 3 shows comparative data demonstrating SALL4 degradation activity of compounds of the disclosure in the SALL4 HiBiT assay in 293T cells. SALL4 Amax reflects the DMSO-normalized, curve-fitted percentage of SALL4-HiBiT remaining at 50 uM. It was calculated by normalizing DMSO controls to 100%, parametric curve fitting of the dose response data (10-point, 5-fold), followed by calculation of response at 50 uM using the fitted equation.

This assay produced a range of SALL4 $AC_{50}$ and Amax values over several repeat runs due to normal variations in the assay. For a comparison to the compounds described in PCT/IB2020/062070, the arithmatic mean values are reported over the number of repeats specified. Results from this assay indicate that compounds of formula (I) do not degrade SALL4 to the same extent as compounds described in PCT/IB2020/062070. The compounds of the present disclosure are therefore expected to have improved toxicological properties (Matyskiela, M. E., Couto, S., Zheng, X. et al. SALL4 mediates teratogenicity as a thalidomide-dependent cereblon substrate. *Nat Chem Biol* 14, 981-987 (2018); Donovan, K. A. et al. Thalidomide promotes degradation of SALL4, a transcription factor Implicated in Duane Radial Ray syndrome. *eLife* 2018; 7:e38430).

TABLE 3

| Example Number | SALL4 $AC_{50}$ (μM) | SALL4 Amax | Number of Repeats |
|---|---|---|---|
| Example 1 | 0.049 | 72.21 | 3 |
| 3-(5-(((R)-1-ethylpiperidin-3-yl)oxy)-1-oxoisoindolin-2-yl)piperidine-2,6-dione (mixture of 2 diastereomers) | | | |
| Example 13 | 0.14 | 70.82 | 3 |
| 3-(5-(((R)-1-(cyclopropylmethyl)piperidin-3-yl)oxy)-1-oxoisoindolin-2-yl)piperidine-2,6-dione | | | |
| Comparative Example 1 | 0.16 | 51.51 | 17 |

TABLE 3-continued

| Example Number | SALL4 AC$_{50}$ (μM) | SALL4 Amax | Number of Repeats |
|---|---|---|---|
| 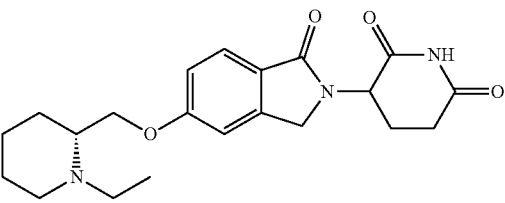 [SMILES: CCN1CCCC[C@@H]1COc1ccc2c(c1)CN(C1CCC(=O)NC1=O)C2=O]<br>3-(5-(((R)-1-ethylpiperidin-2-yl)methoxy)-1-oxoisoindolin-2-yl)piperidine-2,6-dione (mixture of 2 diastereomers)<br>Comparative Example 3 | 0.13 | 52.88 | 1 |
| 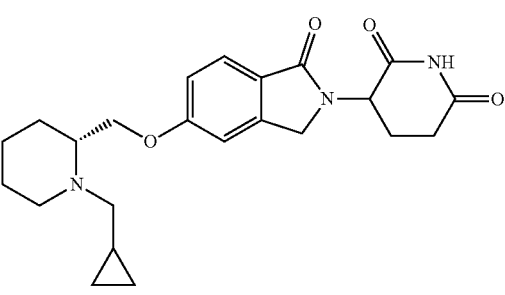 [SMILES: O=C1CCC(N2Cc3cc(OC[C@H]4CCCCN4CC4CC4)ccc3C2=O)C(=O)N1]<br>3-(5-(((R)-1-(cyclopropylmethyl)piperidin-2-yl)methoxy)-1-oxoisoindolin-2-yl)piperidine-2,6-dione | | | |

Example 92: Small Molecule HbF Induction Assay

Cryopreserved primary human CD34$^+$ hematopoietic stem and progenitor cells were obtained from AllCells, LLC. The CD34$^+$ cells were isolated from the peripheral blood of healthy donors after mobilization by administration of granulocyte colony-stimulating factor. Cells were differentiated ex vivo toward the erythroid lineage using a 2-phase culture method. In the first phase, cells were cultured in Stemspan™ Serum-Free Expansion Media (SFEM) (STEM-CELL Technologies Inc.) supplemented with rhSCF (50 ng/mL, Peprotech®, Inc.), rhIL-6 (50 ng/mL, Peprotech®, Inc.), rhIL-3 (50 ng/mL, Peprotech®, Inc.), and rhFlt3L (50 ng/mL, Peprotech®, Inc.), and 1× antibiotic-antimycotic (Life Technologies, Thermo Fisher Scientific) for 6 days at 37° C. with 5% $CO_2$. During the second phase, cells were cultured in erythroid differentiation media at 5,000 cells/mL in the presence of compound for 7 days at 37° C. with 5% 006. Erythroid Differentiation Media is comprised of IMDM (Life Technologies) supplemented with insulin (10 μg/mL. Sigma Aldrich), heparin (2 U/mL Sigma Aldrich), holo-transferrin (330 μg/mL, Sigma Aldrich), human serum AB (5%, Sigma Aldrich), hydrocortisone (1 μM, STEMCELL Technologies), rhSCF (100 ng/mL, Peprotech®, Inc.), rhIL-3 (5 ng/mL. Peprotech®, Inc.), rhEPO (3 U/mL, Peprotech®, Inc.), and 1× antibiotic-antimycotic. All compounds were dissolved and diluted into dimethylsulfoxide (DMSO) and were added to culture media for a final concentration of 0.3% DMSO for testing in a 10-point, 1:3 dilution series starting at 10 uM.

Staining and Flow Cytometry

For viability analysis, samples were washed and resuspended in phosphate-buffered saline (PBS) and stained with LIVE/DEAD™ Fixable Violet Dead Cell Stain Kit (Life Technologies, L34963) for 20 minutes. Cells were then washed again with PBS and resuspended in PBS supplemented with 2% fetal bovine serum (FBS), and 2 mM EDTA to prepare for cell surface marker analysis. Cells were labeled with allophycocyanin-conjugated CD235a (1:100, BD Biosciences, 551336) and Brilliant Violet-conjugated CD71 (1:100. BD Biosciences, 563767) antibodies for 20 minutes. For analysis of cytoplasmic Fetal Hemoglobin (HbF), cells were fixed and permeabilized using the Fixation (BioLegend®, 420801) and Permeabilization Wash (BioLegend®, 421002) Buffers according to the manufacturer's protocol. During the permeabilization step, cells were stained with phycoerythrin-conjugated or FITC-conjugated HbF-specific antibody (1:10-1:25, Invitrogen®, MHFH04-4) for 30 minutes. Stained cells were washed with phosphate-buffered saline before analysis on the FACSCanto™ II flow cytometer or LSRFortessa™ (BD Biosciences). Data analysis was performed with FlowJo™ Software (BD Biosciences), HbF Induction Activity of Compounds (Table 4)

mPB CD34+ cells were expanded for 6 days, then erythroid differentiated in the presence of compound for 7 days. Cells were fixed, stained and analyzed by flow cytometry. Table 4 shows HbF induction activity of the compounds. HbF Amax=the highest percentage of cells staining positive for HbF (% HbF+ cells) in the fitted dose-response curve. The baseline % HbF+ cells for DMSO-treated cells is approximately 30-40%.

TABLE 4

| Example Number | HbF EC50(MM) | HbF Amax |
|---|---|---|
| 1 | 0.047 | 66.5 |
| 41 | 0.025 | 73.1 |
| Comparative Example 1 | 0.087 | 64.1 |

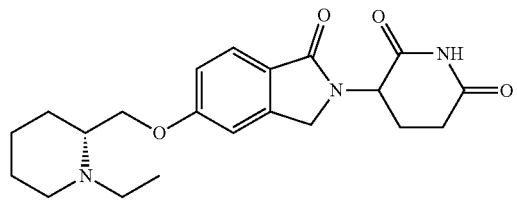 [SMILES: CCN1CCCC[C@@H]1COc1ccc2c(c1)CN(C1CCC(=O)NC1=O)C2=O]

3-(5-(((R)-1-ethylpiperidin-2-yl)methoxy)-1-oxoisoindolin-2-yl)piperidine-2,6-dione

Example 93: Cell Culture for shRNA and CRISPR Assays

HEK293T cells were maintained in DMEM high glucose complete media with sodium pyruvate, non-essential amino acids, 10% FBS, 2 mM L-glutamine, 100 U/mL pen/strep, 25 mM HEPES. Unless stated otherwise, all reagents for culturing HEK293T cells were obtained from Invitrogen™.

Mobilized peripheral blood (mPB) CD34+ cells (AllCells, LLC) were maintained in StemSpan™ serum-free expansion media (SFEM) (STEMCELL Technologies Inc.) supplemented with 50 ng/mL each of rhTPO, rhIL-6, rhFLT3L, rhSCF for 2-3 days prior to shRNA transduction or targeted ribonucleoprotein (RNP) electroporation targeting WIZ. All cytokines were obtained from Peprotech®, Inc. Cell cultures were maintained at 37° C. and 5% $CO_2$ in a humidified tissue culture incubator.

Generation of shRNA Lentiviral Clones Targeting WIZ

5'-phosphorylated sense and anti-sense complementary single-stranded DNA oligos of the respective shRNA against WIZ were synthesized by Integrated DNA Technologies, Inc. (IDT). Each DNA oligonucleotide was designed with PmeI/AscI restriction overhangs on 5'- and 3'-ends, respectively, for subsequent compatible ligation into the lentiviral vector backbone. Equimolar of each of the complementary oligonucleotides were annealed in NEB Buffer 2 (New England Biolabs® Inc.) by heating on a heating block at 98° C. for 5 minutes followed by cooling to room temperature on the bench top. Annealed double-stranded DNA oligonucleotides were ligated into pHAGE lentiviral backbone digested with PmeI/AscI using T4 DNA ligase kit (New England Biolabs). Ligation reactions were transformed into chemically competent Stbl3 cells (Invitrogen™) according to the manufacturer's protocol. Positive clones were verified using the sequencing primer (5'-ctacattttacatgatagg-3'; SEQ ID NO: 2) and plasmids were purified by Alta Biotech LLC.

Lentivirus particles for the respective shRNA constructs were generated by co-transfection of HEK293T cells with pCMV-dR8.91 and pCMV-VSV-G expressing envelope plasmid using Lipofectamine 3000 reagent in 150 mm tissue culture dish format as per manufacturer's instructions (Invitrogen™). Lentivirus supernatant was harvested 48 hours after co-transfection, filtered through a 0.45 μm filter (Millipore) and concentrated using Amicon Ultra 15 with Ultracel-100 membrane (Millipore). Infectious units of each of the lentivirus particle was determined by flow cytometry using eGFP expression as marker of transduction after serial dilution and infection of HEK293T cells.

The shRNA sequences are as follows:

```
shWIZ_#1
                               (SEQ ID NO: 3)
5'-AGCCCACAATGCCACGGAAAT-3';

shWIZ_#2
                               (SEQ ID NO: 4)
5'-GCAACATCTACACCCTCAAAT-3';

shWIZ_#4
                               (SEQ ID NO: 5)
5'-TGACCGAGTGGTACGTCAATG-3';

shWIZ_#5
                               (SEQ ID NO: 6)
5'-AGCGGCAGAACATCAACAAAT-3'.
```

Lentiviral shRNA Transduction and FACS of mPB CD34+ Cells mPB CD34+ transduction was performed on retronectin coated non-tissue culture treated 96 well-flat bottom plates (Corning, Inc.). Briefly, plates were coated with 100 μL of RetroNectin® (1 μg/mL) (TAKARABIO, Inc.), sealed and incubated at 4° C. overnight. RetroNectin® was then removed and plates were incubated with BSA (bovine serum albumin) (1%) in PBS for 30 minutes at room temperature. Subsequently, BSA (bovine serum albumin) was aspirated and replaced with 100 μL of lentiviral concentrate and centrifuged at 2000×g for 2 hours at room temperature. Next, residual supernatant was gently pipetted out and ready for transductions of mPB CD34+ cells. Ten thousand cells were plated in 150 μL of StemSpan™ Serum-free Expansion Medium (SFEM) supplemented with 50 ng/mL each of rhTPO, rhIL-6, rhFLT3L, rhSCF to initiate transduction. Cells were cultured for 72 hours prior to assessing transduction efficiencies using eGFP expression as a marker.

eGFP-positive cells were sorted on an FACSAria™ III (BD Biosciences). Briefly, the transduced mPB CD34+ cell population was washed and re-suspended with FACS buffer containing 1×Hank's buffered saline solution, EDTA (1 mM) and FBS (2%). Sorted eGFP-positive cells were used for the erythroid differentiation assay.

Targeting CRISPR Knockout of WIZ

Alt-R CRISPR-Cas9 crRNA and tracrRNA (5'-AGCAUAGCAAGUUAAAAUAAGGCUAGUCCGUUAU-CAACUUGAAAAAGUGGCACCGAGUC GGUGCUUU- 3'; SEQ ID NO: 7) were purchased from Integrated DNA Technologies, Inc. Equimolar tracrRNA was annealed with WIZ targeting crRNA (Table 3) in Tris buffer (10 mM, pH 7.5) by heating at 95° C. for 5 minutes using a polymerase chain reaction (PCR) machine (Bio-Rad) followed by cooling to room temperature on the benchtop. Subsequently, a ribonucleoprotein (RNP) complex was generated by mixing annealed tracrRNA:crRNA with 6 ug of Cas9 at 37° C. for 5 minutes in 1× buffer containing HEPES (100 mM), KCl (50 mM), $MgCl_2$ (2.5 mM), glycerol (0.03%), DTT (1 mM) and Tris pH 7.5 (2 mM).

Electroporation of the RNP complex was performed on a 4D-Nucleofector™ (Lonza) as per manufacturer's recommendation. Briefly, 50,000 mPB CD34+ cells resuspended in Primary Cell P3 Buffer with supplement (Lonza) were pre-mixed with 5 µL of RNP complex per well in nucleocuvettes and incubated for 5 minutes at room temperature. Subsequently, the mixture was electroporated using the CM-137 program. Cells were cultured for 72 hours post-RNP electroporation before initiating erythroid differentiation. The crRNA sequences are shown in Table 5 below.

TABLE 5

| Name | Sequence (5' to 3') | Target genomic region | Strand | SEQ ID NO |
|---|---|---|---|---|
| rg_0111 | ACGGAGGCTAAGCGTCGCAA | random guide, non-targeting | | 8 |
| WIZ_6 | AACATCTTTCGGGCCGTAGG | chr19:15427143-15427163 | (+) | 9 |
| WIZ_9 | GACATCCGCTGCGAGTTCTG | chr19:15427488-15427510 | (−) | 10 |
| WIZ_12 | TGCAGCGTCCCGGGCAGAGC | chr19:15425751-15425773 | (−) | 11 |
| WIZ_14 | CAAGCCGTGCCTCATCAAGA | chr19:15425571-15425593 | (−) | 12 |
| WIZ_15 | CGGGCACACCTGCGGCAGTT | chr19:15424942-15424964 | (−) | 13 |
| WIZ_18 | AGTGGGTGCGGCACTTACAG | chr19:15423169-15423191 | (−) | 14 |

Erythroid Differentiation of shRNA Transduced or RNP Electroporated mPB CD34+ Cells Erythroid differentiation was initiated by plating 8,000 RNP-electroporated or FACS sorted eGFP+ mPB CD34+ cells per well in 96-well tissue culture plate. Base differentiation media consists of IMDM (Iscove's Modified Dulbecco's Medium), human AB serum (5%), transferrin (330 µg/mL), Insulin (10 µg/mL) and Heparin (2 IU/mL). Differentiation media was supplemented with rhSCF (100 ng/mL), rhIL-3 (10 ng/mL), rhEPO (2.5 U/mL) and hydrocortisone (1 µM). After 4 days of differentiation, the cells were split (1:4) in fresh media to maintain optimal growth density. Cells were cultured for additional 3 days and utilized for assessment of fetal hemoglobin (HbF) expression.

Analysis of HbF Gene Expression by RNA-Seq

Two independent, targeted CRISPR/Cas9 knockout (KO) of WIZ were done using WIZ_6 and WIZ_18 gRNAs or a non-targeting scrambled gRNA negative control in mPB CD34+ HSCs. Cells from KO and negative control were then cultured for 7 days for erythroid differentiation and used for total RNA isolation (Zymo Research, catalogue #R1053). The quality of isolated RNA was determined before sequencing using Agilent RNA 6000 Pico Kit (Agilent, catalogue #5067-1513).

RNA sequencing libraries were prepared using the Illumina TruSeq Stranded mRNA Sample Prep protocol and sequenced using the Illumina NovaSeg6000 platform (Illumina). Samples were sequenced to a length of 2×76 basepairs. For each sample, salmon version 0.8.2 (Patro et al. 2017; doi: 10.1038/nmeth.4197) was used to map sequenced fragments to annotated transcripts in the human reference genome hg38 provided by the ENSEMBL database. Per-gene expression levels were obtained by summing the counts of transcript-level counts using tximport (Soneson et al. 2015; doi: 10.12688/f1000research.7563.1). DESeq2 was used to normalize for library size and transcript length differences, and to test for differential expression between samples treated with the gRNAs targeting WIZ and the samples treated with the scrambled gRNA controls (Love et al. 2014; doi: 10.1186/s13059-014-0550-8). Data were visualized using ggplot2 (Wickham H (2016). ggplot2: Elegant Graphics for Data Analysis. Springer-Verlag New York. ISBN 978-3-319-24277-4; https://ggplot2.tidyverse.org).

HbF Intracellular Staining

One hundred thousand cells were aliquoted into U-bottom 96-well plate and stained for 20 min in the dark with diluted LIVE/DEAD fixable violet viability dye as per manufacturer's recommendation (Invitrogen). Cells were washed with FACS staining buffer and subsequently stained with anti-CD71-BV711 (BD Biosciences) and anti-CD235a-APC (BD Biosciences) for 20 mins in the dark. After two rounds of washes with three volumes of 1×PBS, cells were fixed and permeabilized with 1× BD Cytofix/Cytoperm (BD Biosciences) for 30 minutes at room temperature in the dark. Subsequently, cells were washed twice with three volumes of 1× Perm/wash buffer (BD Biosciences). Anti-HbF-FITC (ThermoScientific) was diluted (1:25) in 1× perm/wash buffer, added to permeablized cells and incubated for 30 minutes at room temperature in the dark. Next, cells were washed twice with three volumes of 1× perm/wash buffer and analyzed by flow cytometry using LSR Fortessa (BD Biosciences). Data was analyzed with FlowJo software.

Results

WIZ KO Upregulates HBG1/2 Expression Upon Erythroid Differentiation

Targeted KO of WIZ using two independent gRNAs (WIZ_6 and WIZ_18) demonstrated upregulation of fetal hemoglobin genes (HBG1/2), as presented in FIG. 1A.

Figure 1B:
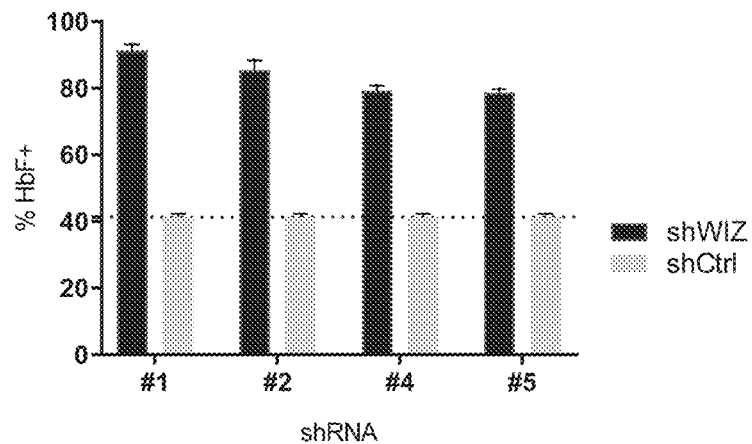
FIG. 1B depicts a bar graph showing the frequency of HbF+ cells due to shRNA– mediated loss of WIZ in human mobilized peripheral blood CD34+ derived erythroid cells.
Figure 1C:
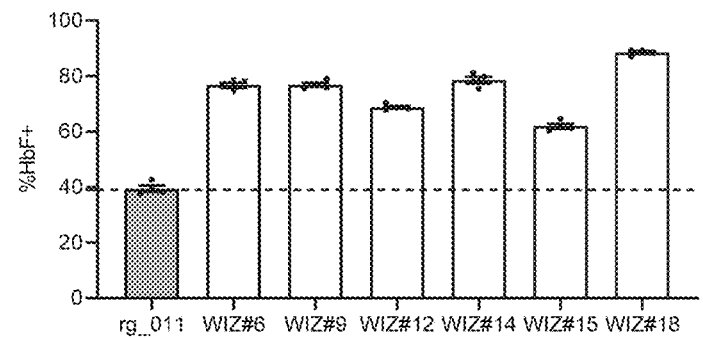
FIG. 1C depicts a bar graph showing the frequency of HbF+ cells due to CRISPR/Cas9-mediated loss of WIZ in human mobilized peripheral blood CD34+ derived erythroid cells.

Loss of WIZ Induces Fetal Hemoglobin Expression in mPB CD34+ Derived Erythroid Cells In order to validate whether WIZ is a negative regulator of HbF expression, shRNA and CRISPR-Cas9-mediated knockdown and knockout functional genetics approaches were employed. mPB CD34+ cells were treated with shRNA or CRISPR-Cas9 reagents and erythroid differentiated for 7 days prior to flow cytometry analysis. Targeted knockdown of WIZ transcript results in 78-91% HbF+ cells compared to 40% for the negative control scrambled shRNA. Error bars represent standard error of two biological replicates with three technical replicates each (FIG. 1B). CRISPR/Cas9-mediated targeted loss of WIZ results in 62-88% HbF$^+$ cells compared to 39% for random guide crRNA. Error bars represent standard error of one biological sample with four technical replicates (FIG. 1C). To summarize, the results indicate that loss of WIZ induces HbF in human primary erythroid cells. As such, the zinc finger transcription factor Widely Interspaced Zinc Finger Motifs (WIZ) was identified as a novel target for HbF induction. These data provide genetic evidence that WIZ is a regulator of fetal hemoglobin expression and represents a novel target for the treatment of sickle cell disease and beta-thalassemia.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of formula (I') or a pharmaceutically acceptable salt, hydrate, solvate, stereoisomer, or tautomer thereof, wherein:

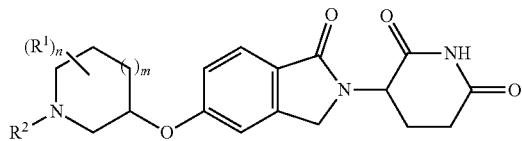

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;
$R^2$ is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, $C_1$-$C_{10}$alkyl, —$SO_2R^6$, —C(=O)—$R^{2a}$, —C(=O)—O—$R^{2a}$, and —C(=O)$NR^{2b}R^{2c}$,
wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;
$R^{2a}$ is selected from $C_1$-$C_6$alkyl, and 4- to 6-membered heterocyclyl comprising 1-2 heteroatoms independently selected from N, O, and S;
$R^{2b}$ and $R^{2c}$ are each independently selected from hydrogen, and $C_1$-$C_6$alkyl;
each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;
each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;
each $R^5$ is independently selected from —CN, $C_1$-$C_6$alkyl, $C_1$-$C_6$alkoxyl, hydroxyl, and $C_1$-$C_6$haloalkyl;
$R^6$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl;
n is 0, 1, 2, 3, 4, or 5; and
m is 0, 1 or 2;
with the proviso that the compound of formula (I') does not include 3-(1-oxo-5-(pyrrolidin-3-yloxy)isoindolin-2-yl)piperidine-2,6-dione.
2. A compound of formula (I") or a pharmaceutically acceptable salt, hydrate, solvate, stereoisomer, or tautomer thereof, wherein:

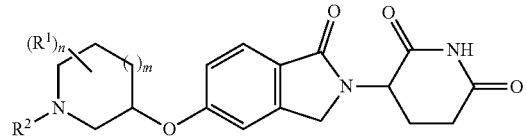

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;
$R^2$ is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, $C_1$-$C_{10}$alkyl, —$SO_2R^6$, —C(=O)—$R^{2a}$, —C(=O)—O—$R^{2a}$, and —C(=O)$NR^{2b}R^{2c}$,
wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;
$R^{2a}$ is selected from $C_1$-$C_6$alkyl, and 4- to 6-membered heterocyclyl comprising 1-2 heteroatoms independently selected from N, O, and S;
$R^{2b}$ and $R^{2c}$ are each independently selected from hydrogen, and $C_1$-$C_6$alkyl;
each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;
each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;
each $R^5$ is independently selected from —CN, $C_1$-$C_6$alkyl, $C_1$-$C_6$alkoxyl, hydroxyl, and $C_1$-$C_6$haloalkyl;
$R^6$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl;
n is 0, 1, 2, 3, 4, or 5; and
m is 1 or 2.
3. A compound of formula (I) or a pharmaceutically acceptable salt, hydrate, solvate, stereoisomer, or tautomer thereof, wherein:

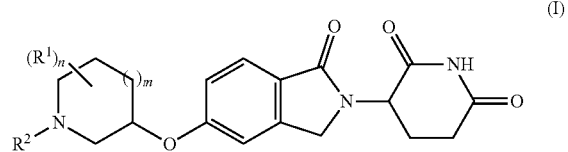

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;

$R^2$ is selected from hydrogen, $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, and $C_1$-$C_{10}$alkyl, wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

n is 0, 1, 2, 3 or 4; and m is 0, 1 or 2;

with the proviso that the compound of formula (I) does not include 3-(1-oxo-5-(pyrrolidin-3-yloxy)isoindolin-2-yl)piperidine-2,6-dione.

4. The compound of claim 1, or a pharmaceutically acceptable salt, hydrate, solvate, stereoisomer, or tautomer thereof, wherein m is 1 or 2.

5. The compound of claim 1, or a pharmaceutically acceptable salt, hydrate, solvate, stereoisomer, or tautomer thereof, wherein $R^2$ is selected from $C_3$-$C_{11}$cycloalkyl, 4- to 11-membered heterocyclyl comprising 1-2 heteroatoms independently selected from N, O, and S, $C_1$-$C_6$haloalkyl, $C_2$-$C_6$alkenyl, $C_2$-$C_6$alkynyl, and $C_1$-$C_{10}$alkyl, wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

each $R^3$ is independently selected from $C_1$-$C_6$alkoxyl, halo, $C_6$-$C_{10}$aryl, 5- to 10-membered heteroaryl comprising 1-4 heteroatoms independently selected from N, O, and S, 4- to 11-membered heterocyclyl comprising 1-2 heteroatoms independently selected from N, O, and S, and $C_3$-$C_8$cycloalkyl, wherein the $C_6$-$C_{10}$aryl, 5- to 10-membered heteroaryl, 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

n is 0, 1, 2, 3, or 4; and m is 0, 1 or 2.

6. The compound of claim 1, or a pharmaceutically acceptable salt, hydrate, solvate, stereoisomer, or tautomer thereof, wherein:

each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;

$R^2$ is selected from hydrogen, $C_3$-$C_{11}$cycloalkyl, $C_1$-$C_6$haloalkyl, 4- to 11-membered heterocyclyl comprising 1-2 heteroatoms independently selected from N, O, and S, $C_2$-$C_6$alkenyl, $C_2$-$C_6$alkynyl, and $C_1$-$C_{10}$alkyl, wherein the $C_3$-$C_{11}$cycloalkyl, 4- to 11-membered heterocyclyl, $C_2$-$C_6$alkynyl, and $C_1$-$C_{10}$alkyl are each independently substituted with 0-5 occurrences of $R^3$;

each $R^3$ is independently selected from $C_1$-$C_6$alkoxyl, halo, 4- to 11-membered heterocyclyl comprising 1-2 heteroatoms independently selected from N, O, and S, and $C_3$-$C_8$cycloalkyl, wherein the 4- to 11-membered heterocyclyl, and $C_3$-$C_8$cycloalkyl are each independently substituted with 0-4 occurrences of $R^4$;

each $R^4$ is independently selected from $C_1$-$C_{10}$alkyl, $C_1$-$C_6$alkoxyl, halo, and $C_3$-$C_8$cycloalkyl, wherein the $C_3$-$C_8$cycloalkyl is substituted with 0-3 occurrences of $R^5$;

each $R^5$ is independently selected from —CN, $C_1$-$C_6$alkyl, $C_1$-$C_6$alkoxyl, hydroxyl, and $C_1$-$C_6$haloalkyl;

n is 0, 1, 2, 3, or 4; and m is 0, 1 or 2.

7. The compound of claim 1, or a pharmaceutically acceptable salt, hydrate, solvate, stereoisomer, or tautomer thereof, wherein:

each $R^1$ is independently selected from hydrogen, $C_1$-$C_6$alkyl, hydroxyl, halo, and $C_1$-$C_6$alkoxyl; or 2 $R^1$ on the same carbon atom together with the same carbon atom to which they are attached form a $C_3$-$C_6$cycloalkyl; or 2 $R^1$ on adjacent carbon atoms together with the adjacent carbon atoms to which they are attached form a $C_3$-$C_6$cycloalkyl; or 2 $R^1$ on non-adjacent carbon atoms together with the non-adjacent carbon atoms to which they are attached form a $C_1$-$C_3$ alkylene bridging ring;

$R^2$ is selected from hydrogen, $C_3$-$C_{11}$cycloalkyl, $C_1$-$C_6$haloalkyl, 4- to 11-membered heterocyclyl comprising 1-2 heteroatoms independently selected from N, O, and S, $C_2$-$C_6$alkenyl, $C_2$-$C_6$alkynyl, and $C_1$-$C_{10}$alkyl, wherein the $C_3$-$C_{11}$cycloalkyl, $C_2$-$C_6$alkynyl, and $C_1$-$C_{10}$alkyl are each independently substituted with 0-5 occurrences of $R^3$;

each $R^3$ is independently selected from $C_1$-$C_6$alkoxyl, halo, 4- to 11-membered heterocyclyl comprising 1-2 heteroatoms independently selected from N, O, and S, and $C_3$-$C_8$cycloalkyl, wherein the 4- to 11-membered heterocyclyl, and $C_3$-$C_8$cycloalkyl are each independently substituted with 0-3 occurrences of $R^4$;
each $R^4$ is independently selected from $C_1$-$C_{10}$alkyl, $C_1$-$C_6$alkoxyl, halo, and $C_3$-$C_8$cycloalkyl;
n is 0, 1, 2, 3, or 4; and
m is 0, 1 or 2.

8. The compound of claim 1, or a pharmaceutically acceptable salt, hydrate, solvate, stereoisomer, or tautomer thereof, wherein:
each $R^1$ is independently selected from hydrogen, $C_1$-$C_6$alkyl, hydroxyl, fluoro, and $C_1$-$C_6$alkoxyl; or 2 $R^1$ on the same carbon atom together with the same carbon atom to which they are attached form a $C_3$-$C_6$cycloalkyl; or 2 $R^1$ on adjacent carbon atoms together with the adjacent carbon atoms to which they are attached form a $C_3$-$C_6$cycloalkyl; or 2 $R^1$ on non-adjacent carbon atoms together with the non-adjacent carbon atoms to which they are attached form a $C_1$-$C_2$ alkylene bridging ring;
$R^2$ is selected from hydrogen, $C_3$-$C_{11}$cycloalkyl, 4- to 11-membered heterocyclyl comprising 1-2 heteroatoms independently selected from N, O, and S, $C_2$-$C_6$alkynyl, and $C_1$-$C_6$alkyl,
wherein the $C_3$-$C_{11}$cycloalkyl is substituted with 0-3 occurrences of $R^3$, wherein the $C_1$-$C_6$alkyl is substituted with 0-1 occurrence of $R^{3a}$, and wherein the $C_2$-$C_6$alkynyl is substituted with 0-1 occurrence of $R^{3b}$;
each $R^3$ is independently selected from $C_1$-$C_6$alkoxyl, and fluoro;
$R^{3a}$ is selected from 4- to 11-membered heterocyclyl comprising 1-2 heteroatoms independently selected from N, O, and S, and $C_3$-$C_8$cycloalkyl, wherein the 4- to 11-membered heterocyclyl, and $C_3$-$C_8$cycloalkyl are each independently substituted with 0-3 occurrences of $R^4$;
$R^{3b}$ is $C_3$-$C_8$cycloalkyl;
each $R^4$ is independently selected from $C_1$-$C_6$alkyl, $C_1$-$C_6$alkoxyl, fluoro, and $C_3$-$C_8$cycloalkyl;
n is 0, 1, 2 or 3; and
m is 1.

9. The compound of claim 1, or a pharmaceutically acceptable salt, hydrate, solvate, stereoisomer, or tautomer thereof, wherein:
each $R^1$ is independently selected from hydrogen, $C_1$-$C_6$alkyl, hydroxyl, fluoro, and $C_1$-$C_6$alkoxyl; or 2 $R^1$ on the same carbon atom together with the same carbon atom to which they are attached form a $C_3$-$C_6$cycloalkyl;
$R^2$ is selected from $C_3$-$C_8$cycloalkyl, 4- to 6-membered heterocyclyl comprising 1-2 heteroatoms independently selected from N, O, and S, $C_2$-$C_6$alkynyl, and $C_1$-$C_6$alkyl,
wherein the $C_3$-$C_8$cycloalkyl is substituted with 0-3 occurrences of $R^3$, wherein the $C_1$-$C_6$alkyl is substituted with 0-1 occurrence of $R^{3a}$, and wherein the $C_2$-$C_6$alkynyl is substituted with 0-1 occurrence of $R^{3b}$;
each $R^3$ is independently selected from $C_1$-$C_6$alkoxyl, and fluoro;
$R^{3a}$ is $C_3$-$C_8$cycloalkyl, wherein the $C_3$-$C_8$cycloalkyl is substituted with 0-3 occurrences of $R^4$;
$R^{3b}$ is $C_3$-$C_8$cycloalkyl;
each $R^4$ is independently selected from $C_1$-$C_6$alkyl, $C_1$-$C_6$alkoxyl, fluoro, and $C_3$-$C_8$cycloalkyl;
n is 0, 1, 2 or 3; and
m is 1.

10. The compound of claim 1, or a pharmaceutically acceptable salt, hydrate, solvate, stereoisomer, or tautomer thereof, wherein the compound is of formula (IA) or (IB):

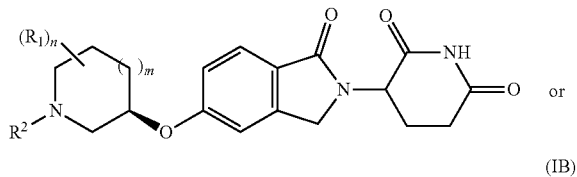

(IA)

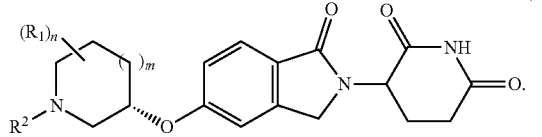

(IB)

11. The compound of claim 1, or a pharmaceutically acceptable salt, hydrate, solvate, stereoisomer, or tautomer thereof, wherein $R^2$ is unsubstituted $C_1$-$C_6$alkyl, —(CH$_2$)—$R^3$, or —(CH$_2$)—$R^{3a}$, wherein $R^{3a}$ is selected from 4- to 11-membered heterocyclyl comprising 1-2 heteroatoms independently selected from N, O, and S, and $C_3$-$C_8$cycloalkyl, wherein the 4- to 11-membered heterocyclyl, and $C_3$-$C_8$cycloalkyl are each independently substituted with 0-3 occurrences of $R^4$, and each $R^4$ is independently selected from $C_1$-$C_6$alkyl, $C_1$-$C_6$alkoxyl, fluoro, and $C_3$-$C_8$cycloalkyl.

12. The compound of claim 1, or a pharmaceutically acceptable salt, hydrate, solvate, stereoisomer, or tautomer thereof, wherein $R^2$ is selected from methyl, ethyl, n-propyl, i-propyl, n-butyl, sec-butyl, t-butyl,

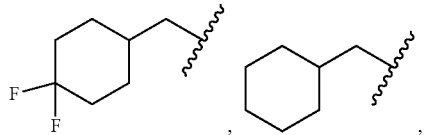

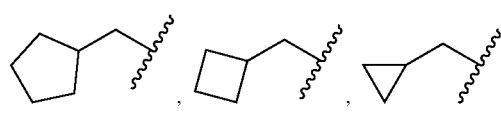

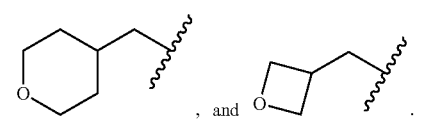

13. The compound of claim 1, or a pharmaceutically acceptable salt, hydrate, solvate, stereoisomer, or tautomer thereof, wherein $R^1$ is selected from $C_1$-$C_6$alkyl, hydroxyl, halo, and $C_1$-$C_6$alkoxyl; or 2 $R^1$ on the same carbon atom together with the same carbon atom to which they are attached form a $C_3$-$C_8$cycloalkyl.

14. The compound of claim 1, or a pharmaceutically acceptable salt, hydrate, solvate, stereoisomer, or tautomer thereof, wherein the compound is of formula (I-i), (IA-i), (IA-ii), (IA-iii), (IB-i), (IB-ii), or (IB-iii), wherein:

(I-i)

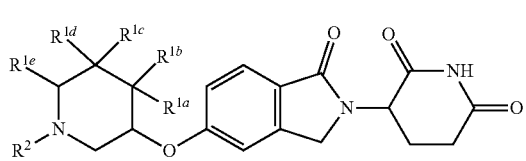

R$^{1a}$ is independently selected from hydrogen and C$_1$-C$_6$alkyl;
R$^{1b}$ is independently selected from hydrogen and C$_1$-C$_6$alkyl;
or R$^{1a}$ and R$^{1b}$ on the same carbon atom together with the same carbon atom to which they are attached form a C$_3$-C$_6$cycloalkyl;
R$^{1c}$ is independently selected from hydrogen and C$_1$-C$_6$alkyl;
R$^{1d}$ is independently selected from hydrogen, C$_1$-C$_6$alkyl, and C$_1$-C$_6$alkoxyl;
or R$^{1c}$ and R$^{1d}$ on the same carbon atom together with the same carbon atom to which they are attached form a C$_3$-C$_6$cycloalkyl; and
R$^{1e}$ is independently selected from hydrogen and C$_1$-C$_6$alkyl;

(IA-i)

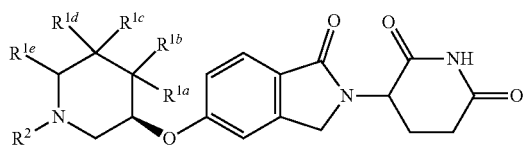

R$^{1a}$ is independently selected from hydrogen and C$_1$-C$_6$alkyl;
R$^{1b}$ is independently selected from hydrogen and C$_1$-C$_6$alkyl;
or R$^{1a}$ and R$^{1b}$ on the same carbon atom together with the same carbon atom to which they are attached form a C$_3$-C$_6$cycloalkyl;
R$^{1c}$ is independently selected from hydrogen and C$_1$-C$_6$alkyl;
R$^{1d}$ is independently selected from hydrogen, C$_1$-C$_6$alkyl, and C$_1$-C$_6$alkoxyl;
or R$^{1c}$ and R$^{1d}$ on the same carbon atom together with the same carbon atom to which they are attached form a C$_3$-C$_6$cycloalkyl; and
R$^{1e}$ is independently selected from hydrogen and C$_1$-C$_6$alkyl;

(IA-ii)

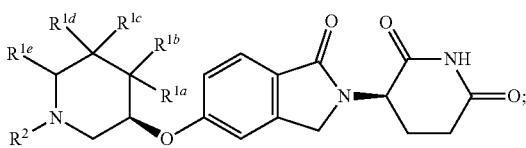

(IA-iii)

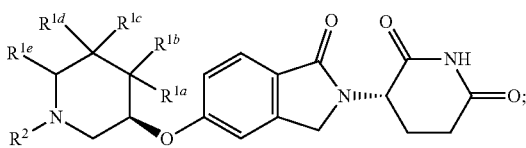

(IB-i)

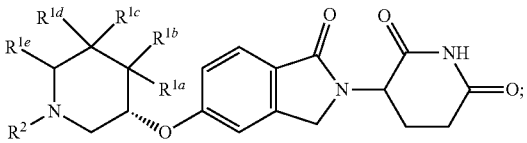

R$^{1a}$ is independently selected from hydrogen and C$_1$-C$_6$alkyl;
R$^{1b}$ is independently selected from hydrogen and C$_1$-C$_6$alkyl;
or R$^{1a}$ and R$^{1b}$ on the same carbon atom together with the same carbon atom to which they are attached form a C$_3$-C$_6$cycloalkyl;
R$^{1c}$ is independently selected from hydrogen and C$_1$-C$_6$alkyl;
R$^{1d}$ is independently selected from hydrogen, C$_1$-C$_6$alkyl, and C$_1$-C$_6$alkoxyl;
or R$^{1c}$ and R$^{1d}$ on the same carbon atom together with the same carbon atom to which they are attached form a C$_3$-C$_6$cycloalkyl; and
R$^{1e}$ is independently selected from hydrogen and C$_1$-C$_6$alkyl;

(IB-ii)

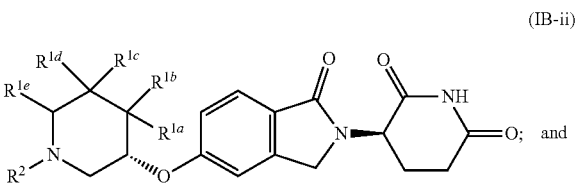 ; and (IB-iii)

15. The compound of claim 14, or a pharmaceutically acceptable salt, hydrate, solvate, stereoisomer, or tautomer thereof,
wherein
R$^{1a}$ and R$^{1b}$ are both hydrogen;
R$^{1e}$ is C$_1$-C$_6$alkyl, and R$^{1a}$, R$^{1b}$, R$^{1c}$, and R$^{1d}$ are all hydrogen;
R$^{1a}$ and R$^{1b}$ are each independently selected from hydrogen and C$_1$-C$_6$alkyl, or R$^{1a}$ and R$^{1b}$ on the same carbon atom together with the same carbon atom to which they are attached form a C$_3$-C$_6$cycloalkyl, and R$^{1c}$, R$^{1d}$, and R$^{1e}$ are all hydrogen;
R$^{1c}$ and R$^{1d}$ are each independently selected from hydrogen, C$_1$-C$_6$alkyl and C$_1$-C$_6$alkoxyl, or R$^{1c}$ and R$^{1d}$ on the same carbon atom together with the same carbon atom to which they are attached form a C$_3$-C$_6$cycloalkyl, and R$^{1a}$, R$^{1b}$, and R$^{1e}$ are all hydrogen;
each R$^3$ is independently selected from 4- to 11-membered heterocyclyl comprising 1-2 heteroatoms independently selected from N, O, and S, C$_3$-C$_8$cycloalkyl, and halo, wherein the 4- to 11-membered heterocyclyl, and C$_3$-C$_8$cycloalkyl are each independently substituted with 0-2 occurrences of R$^4$, wherein each R$^4$ is independently selected from $C_1$-$C_6$alkyl, $C_1$-$C_6$alkoxyl, halo, and $C_3$-$C_8$cycloalkyl;

or each $R^4$ is independently selected from $C_1$-$C_6$alkyl and fluoro.

16. The compound of claim 1, or a pharmaceutically acceptable salt, hydrate, solvate, stereoisomer, or tautomer thereof, wherein the compound is of formula (IC), (ID), (IC-i), (IC-ii), (ID-i), or (ID-ii):

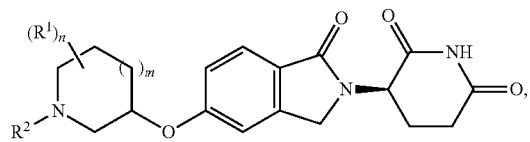
(IC)

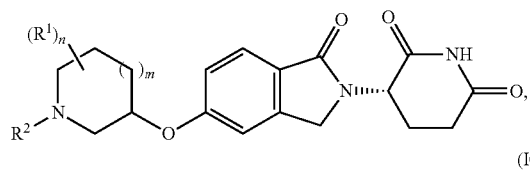
(ID)

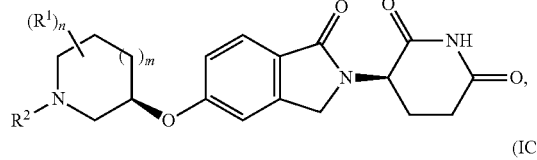
(IC-i)

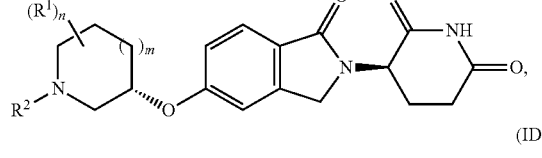
(IC-ii)

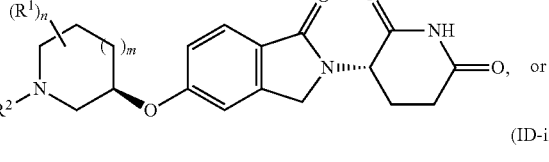
(ID-i)

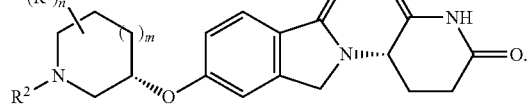
(ID-ii)

17. A compound of claim 1, or a pharmaceutically acceptable salt, hydrate, solvate, stereoisomer, or tautomer thereof, wherein the compound is selected from:

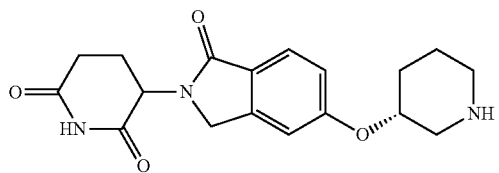

-continued

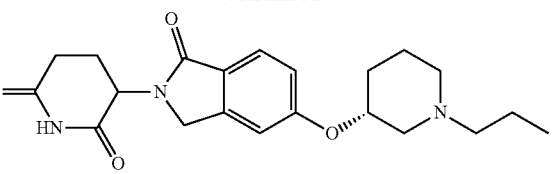

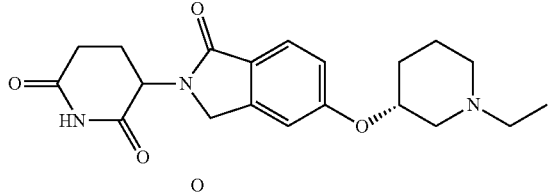

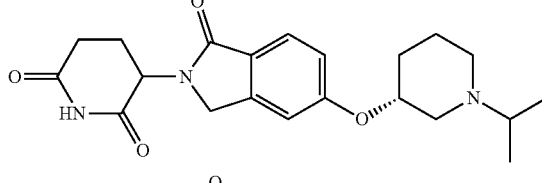

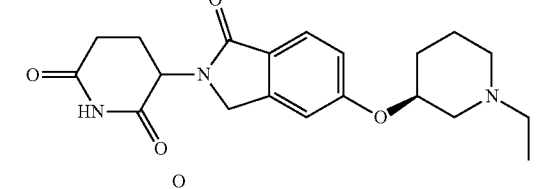

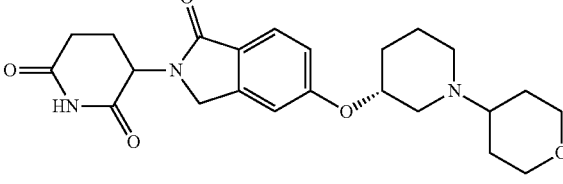

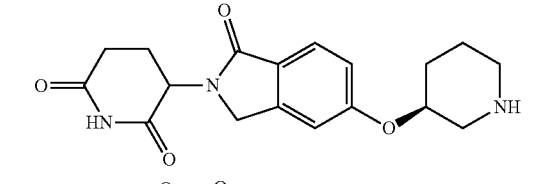

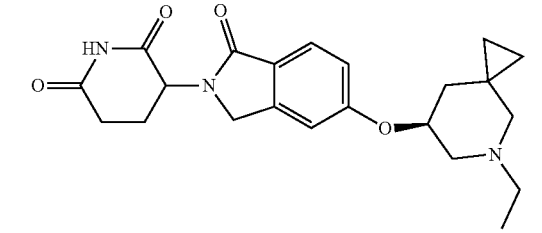

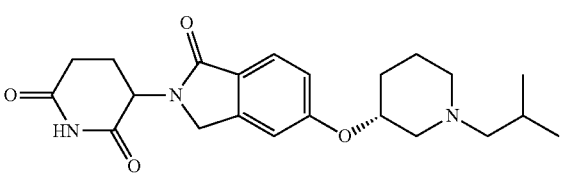

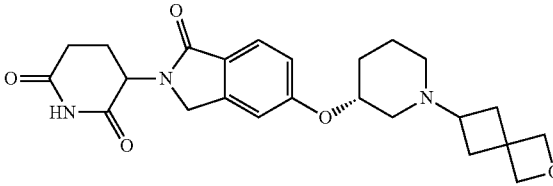

-continued
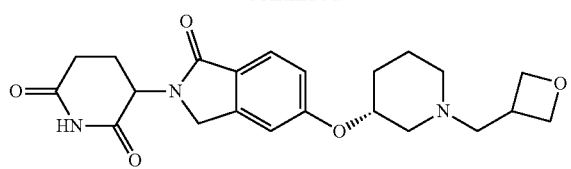
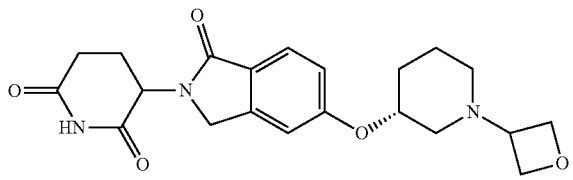
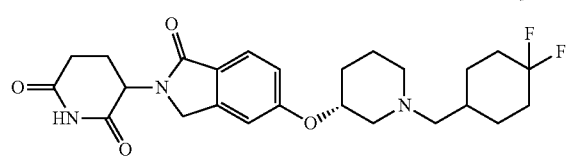
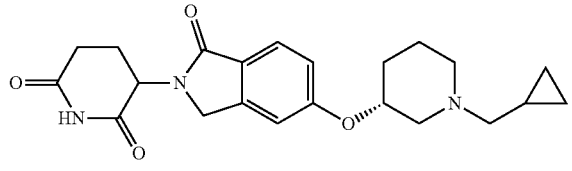
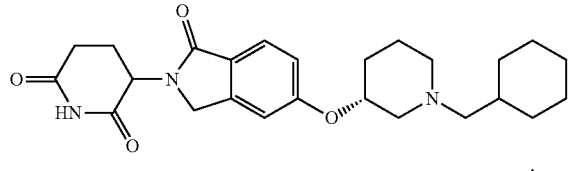
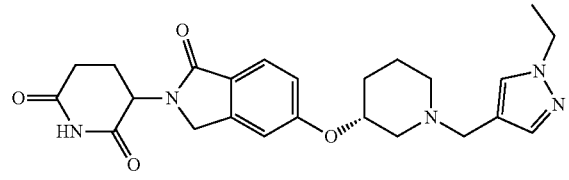
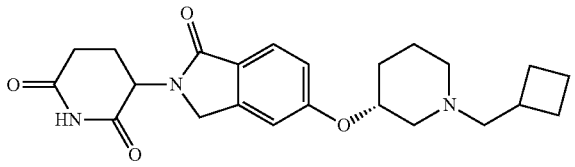
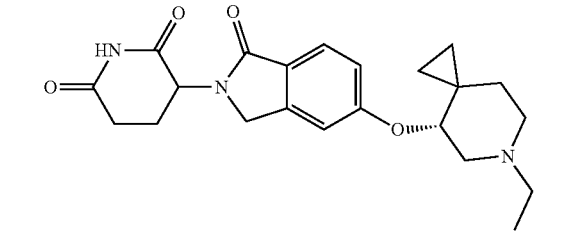
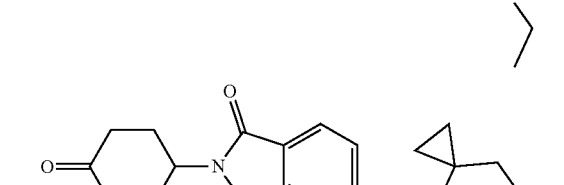
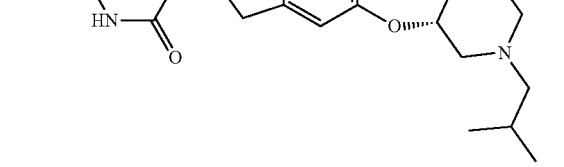
-continued
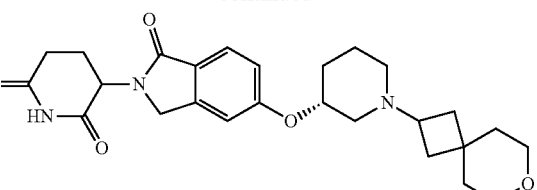
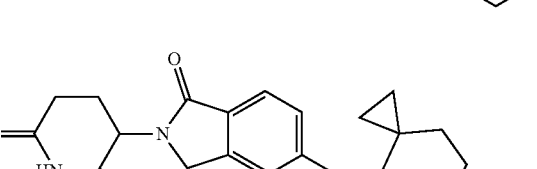
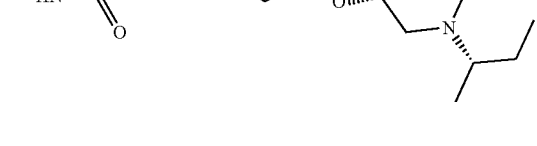
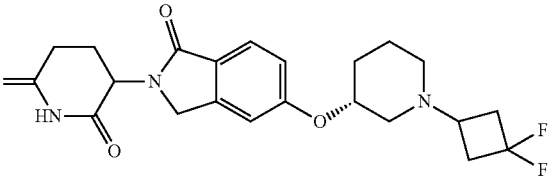
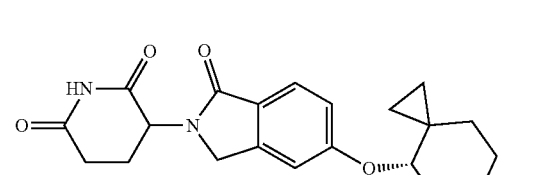
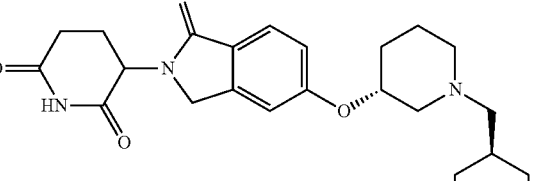
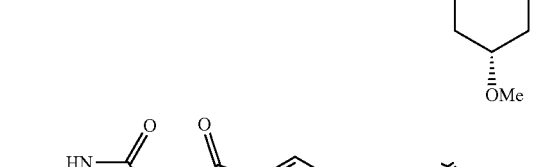
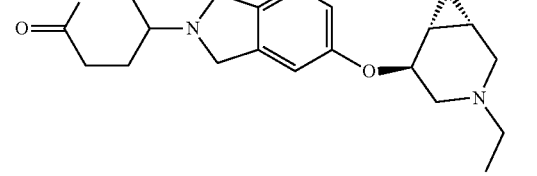
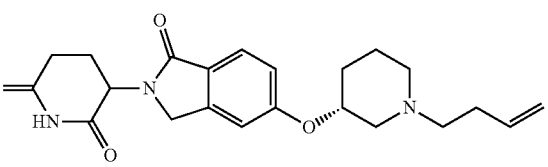

269
-continued
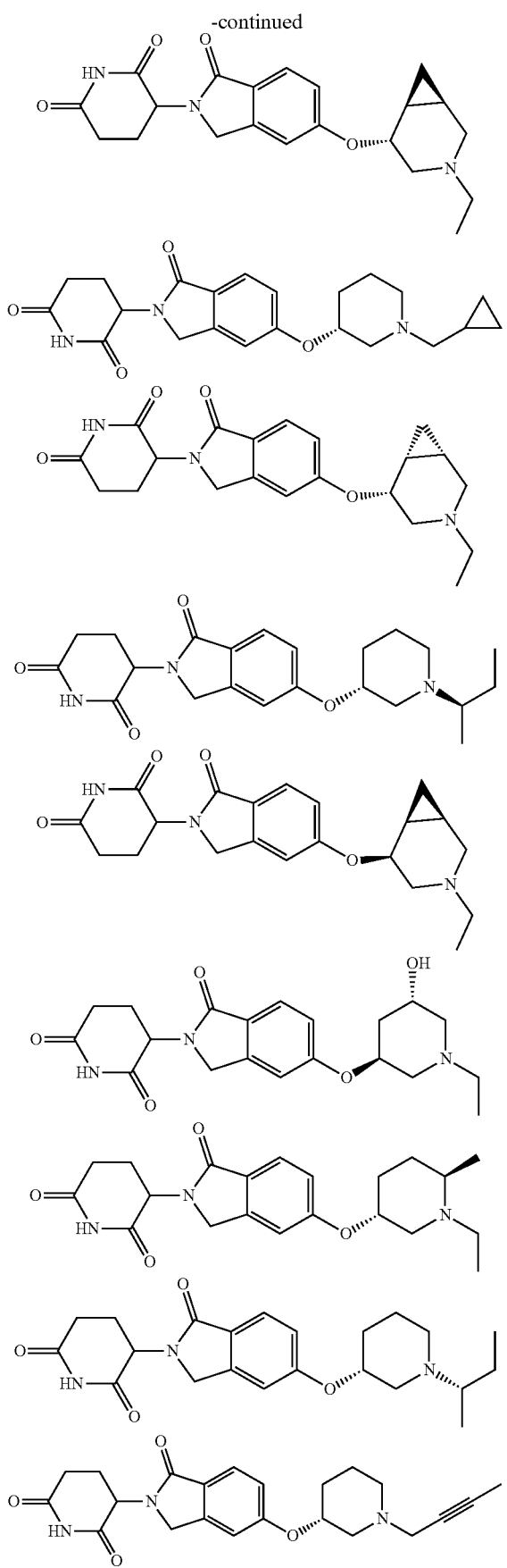
270
-continued
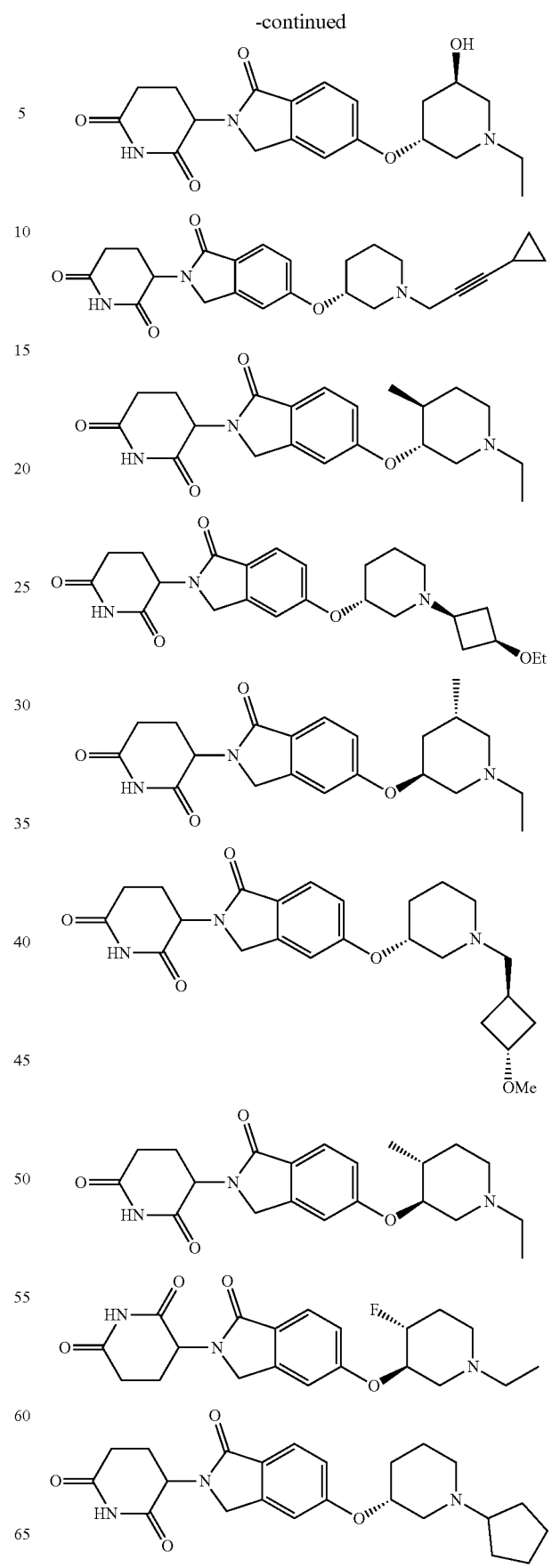

271
-continued
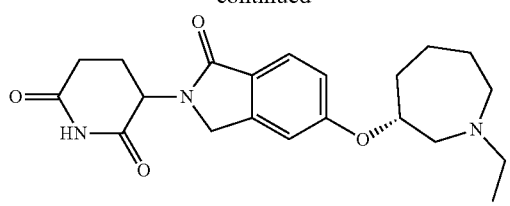
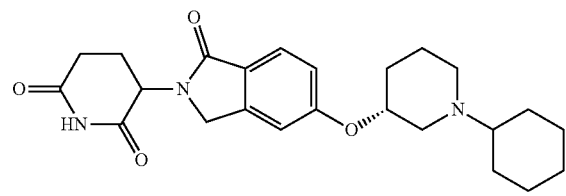
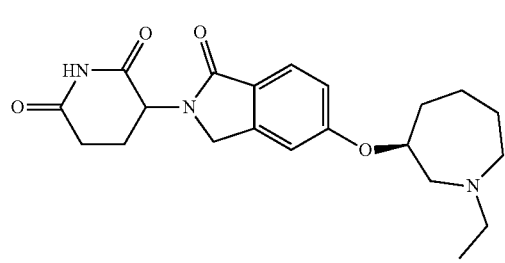
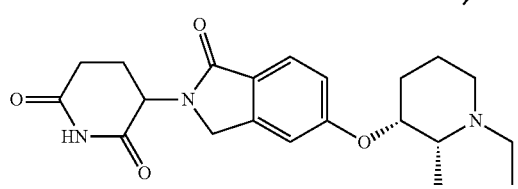
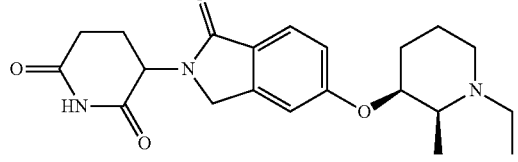
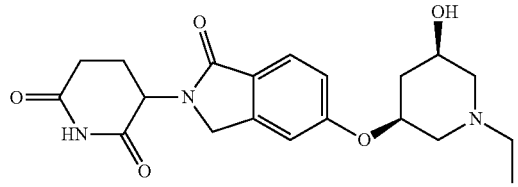
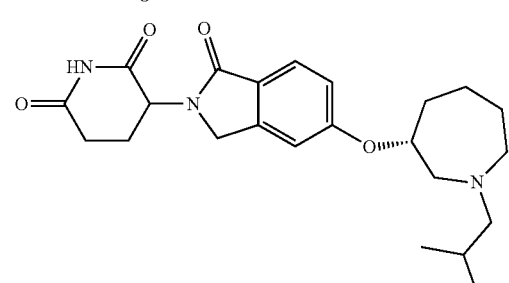
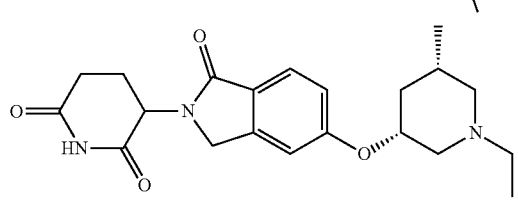
272
-continued
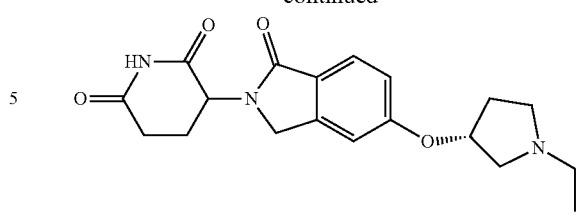
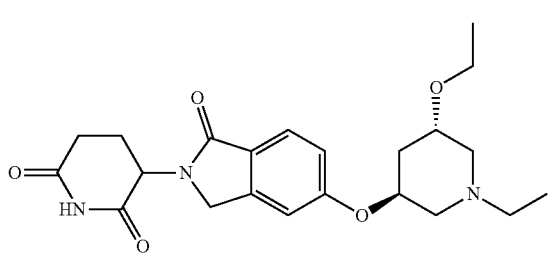
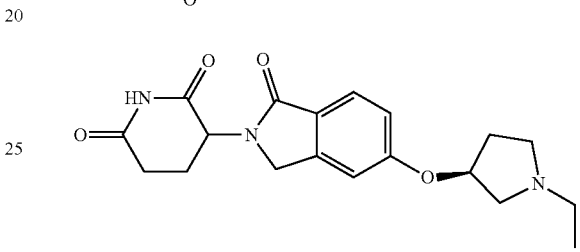
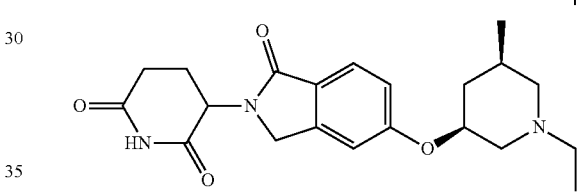
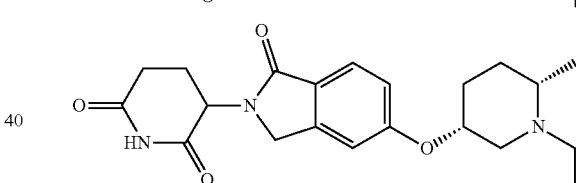
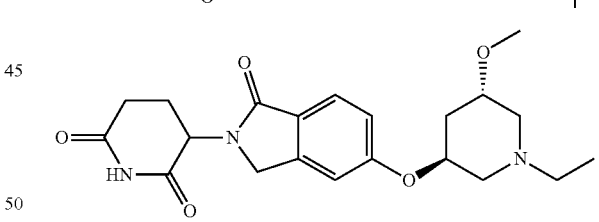
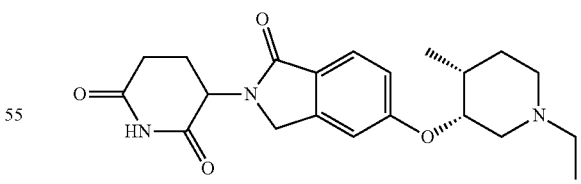
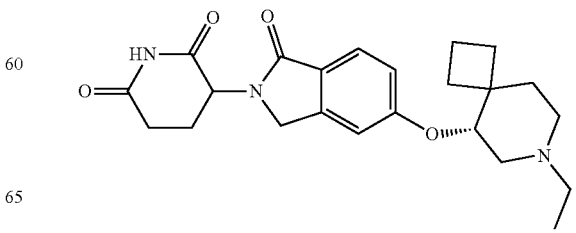

273
-continued
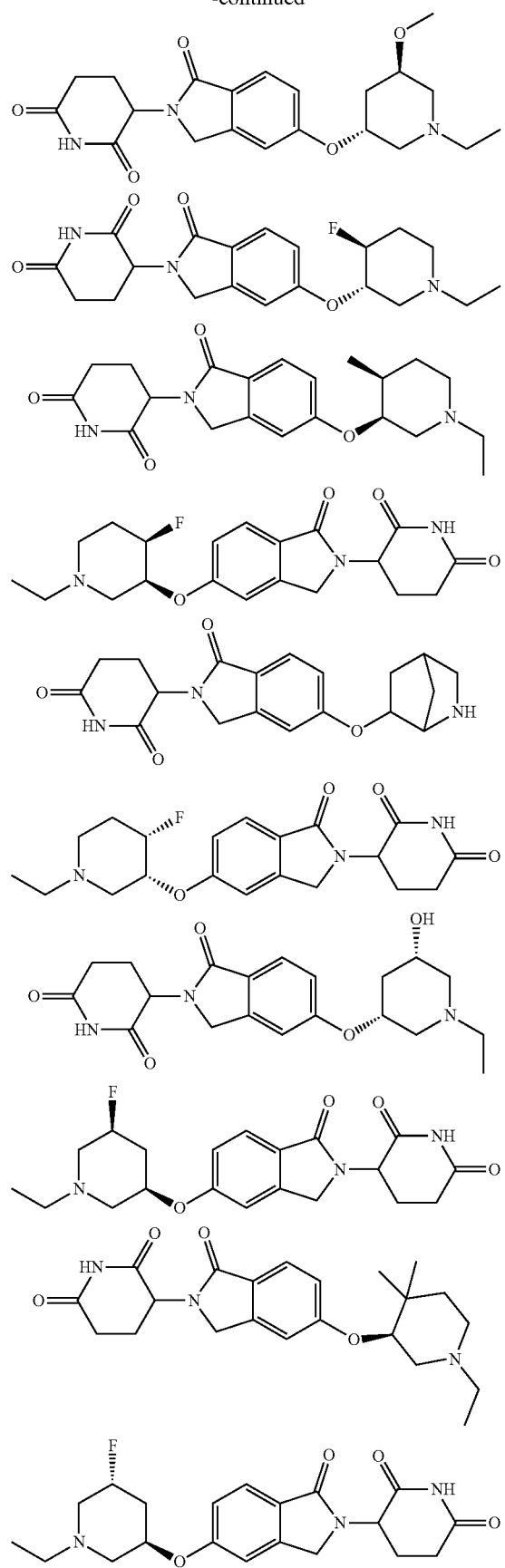
274
-continued
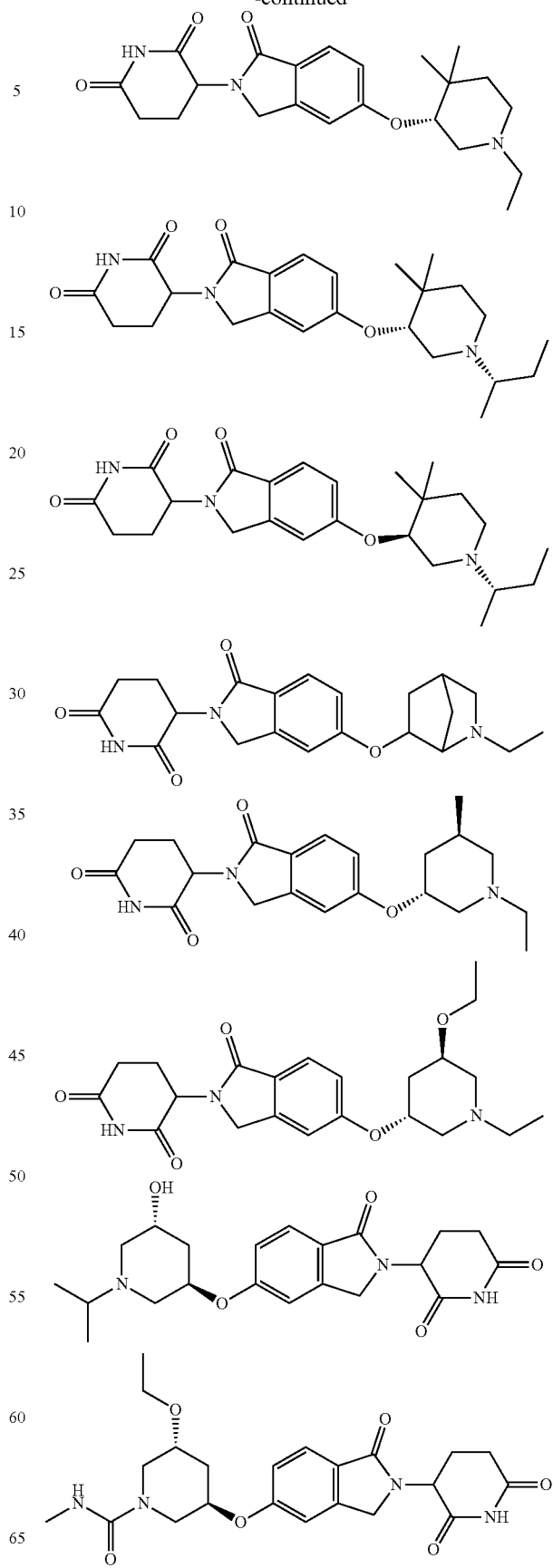

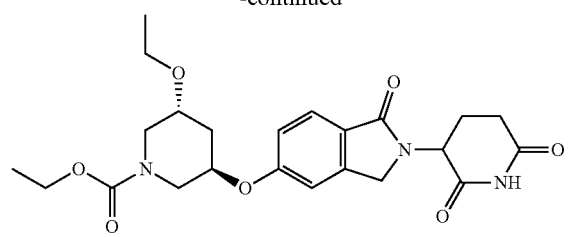
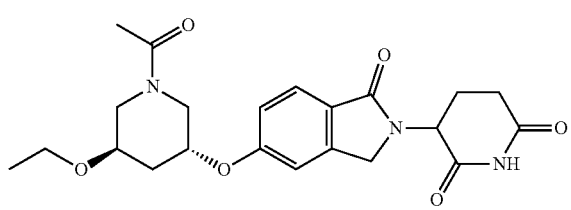
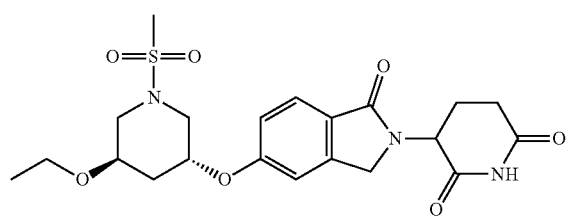
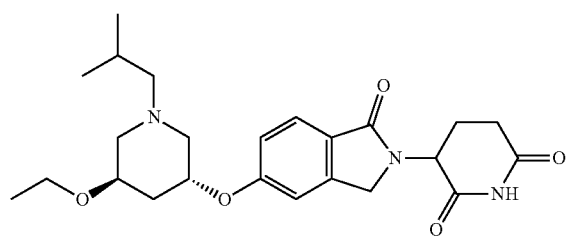
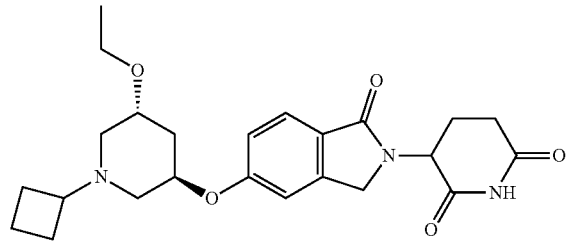
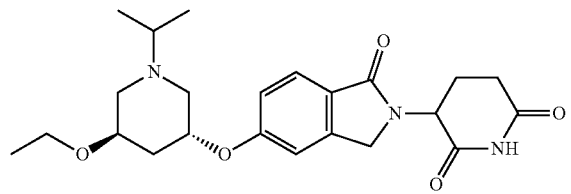
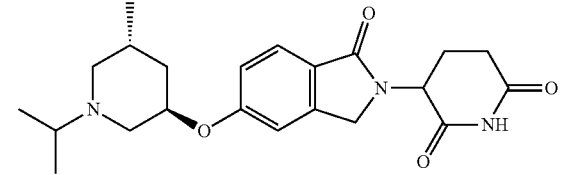
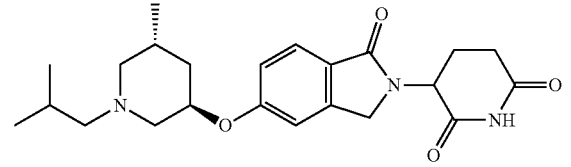
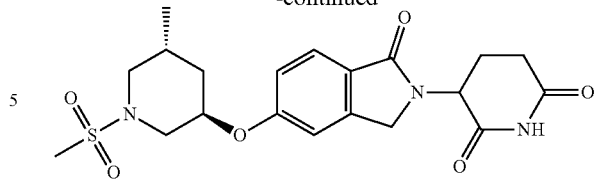
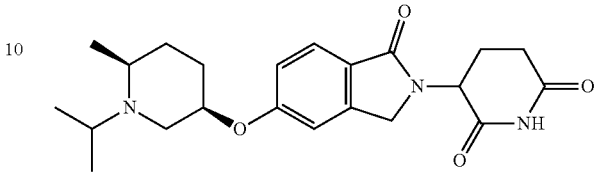
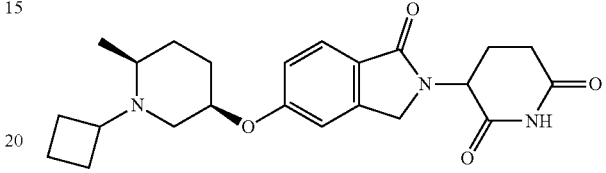
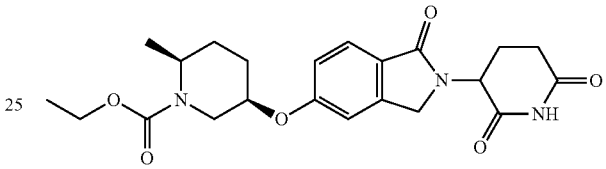
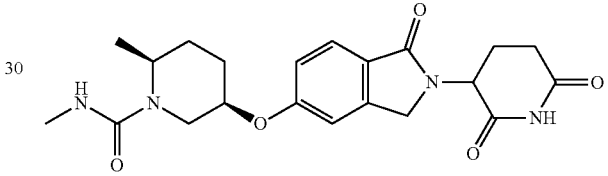
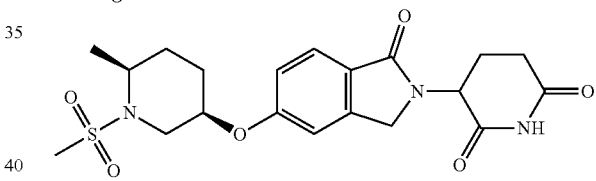
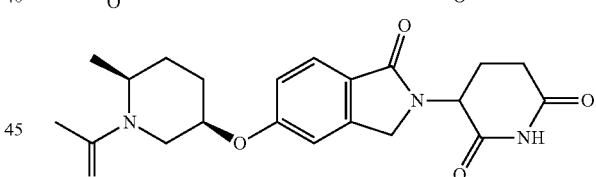
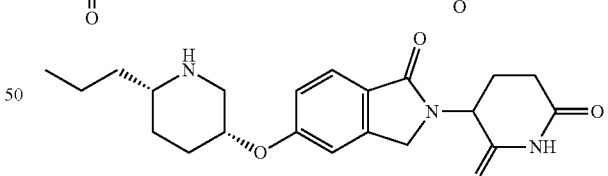
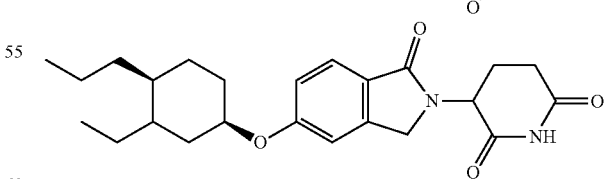
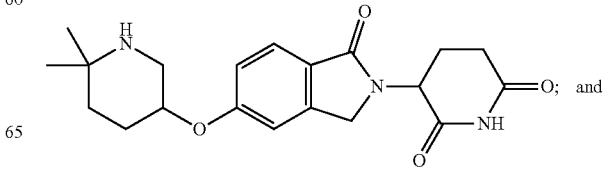

277
-continued

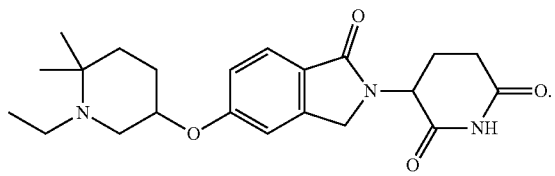

18. A compound of claim 1, or a pharmaceutically acceptable salt, hydrate, solvate, stereoisomer, or tautomer thereof, wherein the absolute configuration at the glutarimide stereocentre is S.

19. A compound of claim 1, or a pharmaceutically acceptable salt, hydrate, solvate, stereoisomer, or tautomer thereof, wherein the absolute configuration at the glutarimide stereocentre is R.

20. A compound of claim 1, or a pharmaceutically acceptable salt, hydrate, solvate, stereoisomer, or tautomer thereof, selected from:

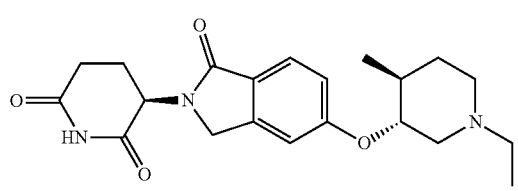

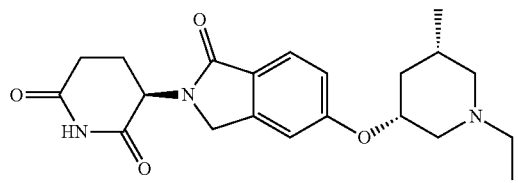

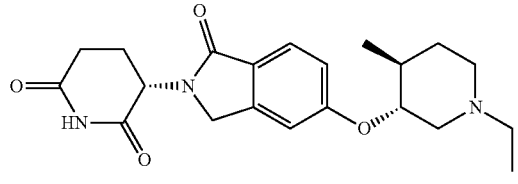

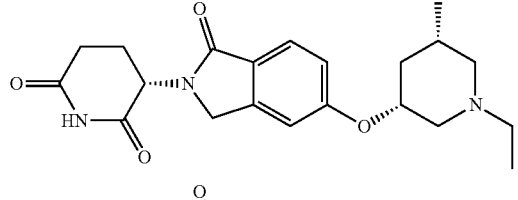

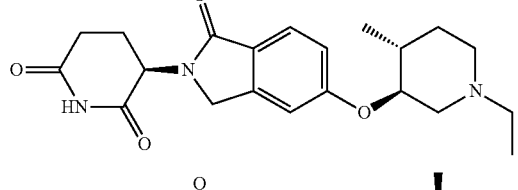

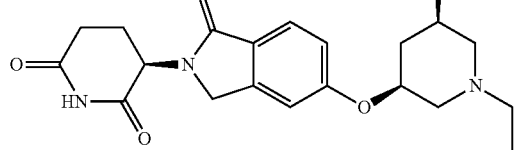

278
-continued

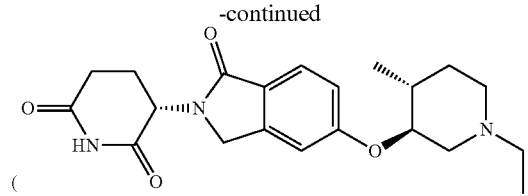

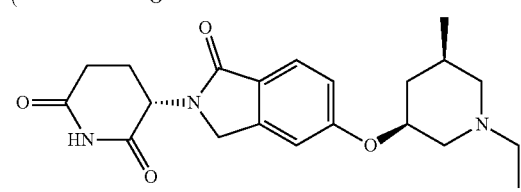

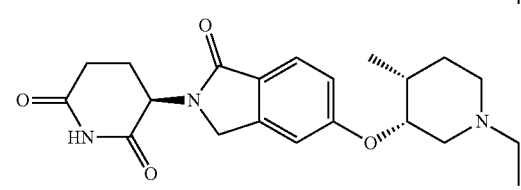

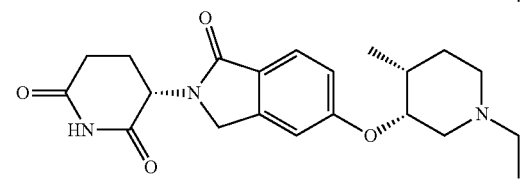

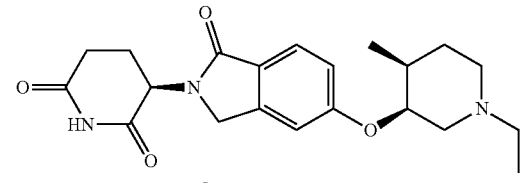

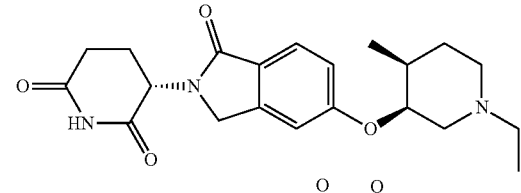

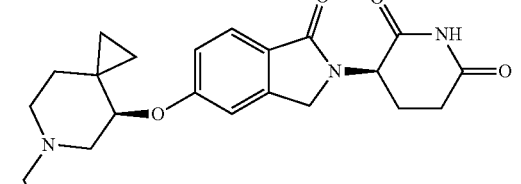

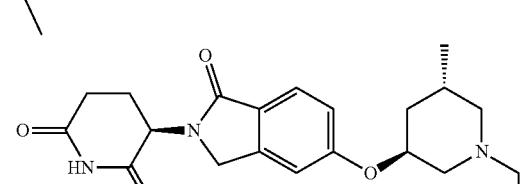

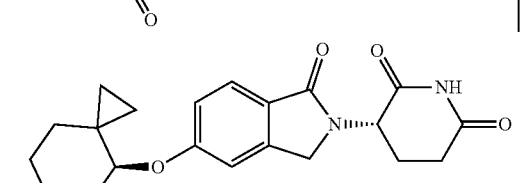

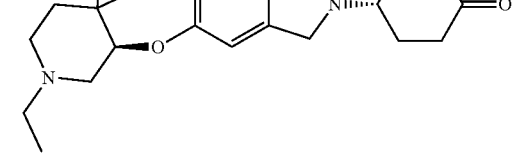

-continued

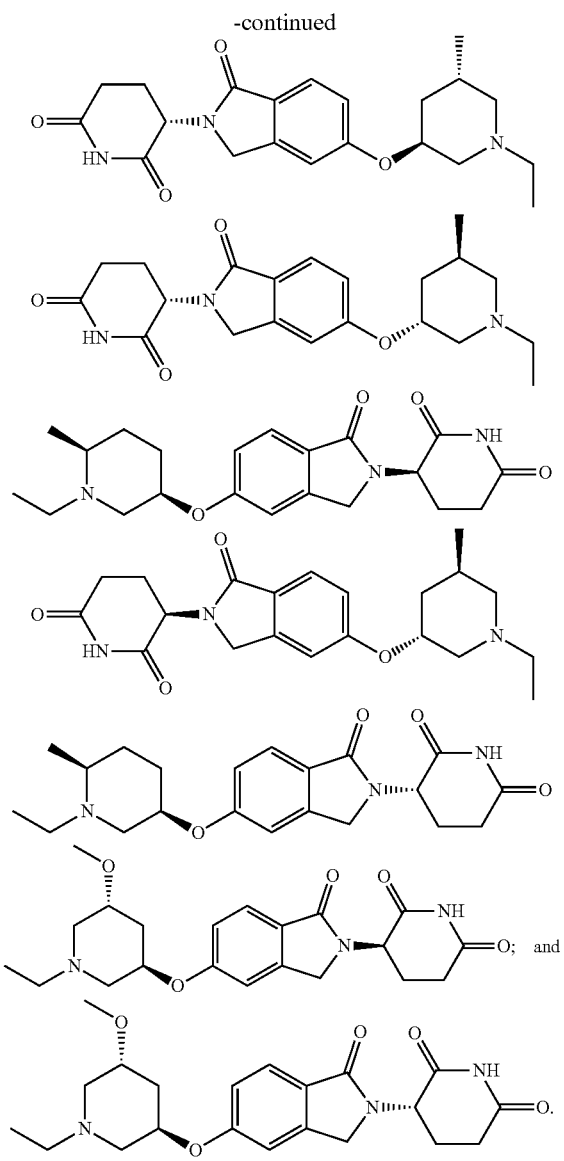

21. A pharmaceutical composition comprising a therapeutically effective amount of a compound of claim 1, or a pharmaceutically acceptable salt, hydrate, solvate, stereoisomer, or tautomer thereof, and a pharmaceutically acceptable carrier or excipient.

22. A method of degrading WIZ protein in a subject in need thereof; of inhibiting WIZ protein expression in a subject in need thereof, or of inhibiting, reducing, or eliminating the activity of WIZ protein or WIZ protein expression in a subject in need thereof, the method comprising administering to the subject a therapeutically effective amount of a compound of claim 1, or a pharmaceutically acceptable salt, hydrate, solvate, stereoisomer, or tautomer thereof.

23. A method of inducing or promoting fetal hemoglobin in a subject in need thereof; reactivating fetal hemoglobin production or expression in a subject in need thereof, or increasing fetal hemoglobin expression in a subject in need thereof, the method comprising administering to the subject a therapeutically effective amount of a compound of claim 1, or a pharmaceutically acceptable salt, hydrate, solvate, stereoisomer, or tautomer thereof.

24. A method of treating a hemoglobinopathy, sickle cell disease, or beta-thalassemia in a subject in need thereof, the method comprising administering to the subject a therapeutically effective amount of a compound of claim 1, or a pharmaceutically acceptable salt, hydrate, solvate, stereoisomer, or tautomer thereof.

25. A method of treating a disease or disorder that is affected by the modulation of WIZ protein levels in a subject in need thereof, treating or preventing a disorder that is affected by the reduction of WIZ protein levels in a subject in need thereof; or reducing WIZ protein levels in a subject in need thereof, the method comprising administering to the subject a compound of claim 1, or a pharmaceutically acceptable salt, hydrate, solvate, stereoisomer, or tautomer thereof.

26. A pharmaceutical combination comprising a compound of claim 1, or a pharmaceutically acceptable salt, hydrate, solvate, stereoisomer, or tautomer thereof, and one or more additional therapeutic agent(s).

27. A compound of Formula (Y)

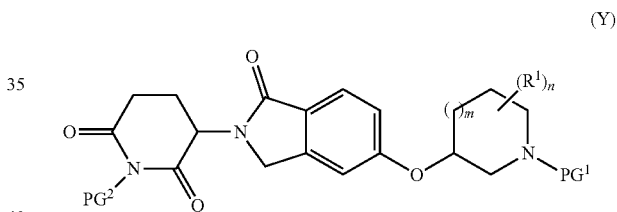

(Y)

wherein each $R^1$ is independently selected from hydrogen, $C_1$-$C_6$alkyl, hydroxyl, halo, $C_1$-$C_6$haloalkyl, $C_1$-$C_6$haloalkoxyl, and $C_1$-$C_6$alkoxyl; or 2 $R^1$ on the same carbon atom together with the same carbon atom to which they are attached form a $C_3$-$C_8$cycloalkyl; or 2 $R^1$ on adjacent carbon atoms together with the adjacent carbon atoms to which they are attached form a $C_3$-$C_8$cycloalkyl; or 2 $R^1$ on non-adjacent carbon atoms together with the non-adjacent carbon atoms to which they are attached form a bridging ring;

n is 0, 1, 2, 3, 4, or 5;

m is 0, 1 or 2; and each of $PG^1$ and $PG^2$ is independently a nitrogen protecting group.

* * * * *